(12) United States Patent
Murphy et al.

(10) Patent No.: US 7,951,383 B2
(45) Date of Patent: *May 31, 2011

(54) ATTENUATED PARAINFLUENZA VIRUS (PIV) VACCINES

(75) Inventors: Brian R. Murphy, Bethesda, MD (US); Peter L. Collins, Bethesda, MD (US); Mario H. Skiadopoulos, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 211 days.

This patent is subject to a terminal disclaimer.

(21) Appl. No.: 11/785,364

(22) Filed: Apr. 17, 2007

(65) Prior Publication Data

US 2008/0096264 A1  Apr. 24, 2008

Related U.S. Application Data

(63) Continuation-in-part of application No. 09/083,793, filed on May 22, 1998, now Pat. No. 7,208,161, and a continuation-in-part of application No. 09/458,813, filed on Dec. 10, 1999, now Pat. No. 7,314,631, which is a continuation-in-part of application No. 09/083,793, and a continuation-in-part of application No. 09/459,062, filed on Dec. 10, 1999, now Pat. No. 7,250,171, which is a continuation-in-part of application No. 09/083,793.

(60) Provisional application No. 60/047,575, filed on May 23, 1997, provisional application No. 60/059,385, filed on Sep. 19, 1997.

(51) Int. Cl.
*A61K 39/155* (2006.01)
*C12N 7/00* (2006.01)

(52) U.S. Cl. .................................... 424/211.1; 435/91.1

(58) Field of Classification Search ................ 435/320.1
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 5,716,821 A | 2/1998 | Wertz et al. | |
| 5,789,229 A | 8/1998 | Wertz et al. | |
| 5,869,036 A | 2/1999 | Belshe et al. | |
| 6,033,886 A | 3/2000 | Conzelmann | |
| 6,264,957 B1 | 7/2001 | Collins | |
| 6,410,023 B1 * | 6/2002 | Durbin et al. | 424/186.1 |
| 7,201,907 B1 * | 4/2007 | Schmidt et al. | 424/199.1 |
| 7,208,161 B1 * | 4/2007 | Murphy et al. | 424/211.1 |
| 7,250,171 B1 * | 7/2007 | Tao et al. | 424/211.1 |
| 7,314,631 B1 * | 1/2008 | Murphy et al. | 424/211.1 |
| 7,622,123 B2 * | 11/2009 | Skiadopoulos et al. | 424/199.1 |

FOREIGN PATENT DOCUMENTS

| | | |
|---|---|---|
| EP | 0 440 219 A1 | 8/1991 |
| EP | 0 702 085 A1 | 3/1996 |
| WO | WO 92/01471 | 2/1992 |
| WO | WO 93/14207 | 7/1993 |
| WO | WO 93/21310 | 10/1993 |
| WO | WO 97/06270 | 2/1997 |
| WO | WO 97/11093 | 3/1997 |
| WO | WO 97/12032 | 4/1997 |
| WO | WO 97/20468 | 6/1997 |
| WO | WO 98/02530 | 1/1998 |
| WO | WO 98/43668 | 10/1998 |
| WO | WO 98/53078 | 11/1998 |
| WO | WO 99/02657 | 1/1999 |
| WO | WO 99/15631 | 4/1999 |
| WO | WO 99/24564 | 5/1999 |
| WO | WO 00/61611 | 10/2000 |
| WO | WO 00/61737 | 10/2000 |
| WO | WO 01/04271 | 1/2001 |
| WO | WO 01/04321 | 1/2001 |
| WO | WO 01/04335 | 1/2001 |

OTHER PUBLICATIONS

Tao et al. J. Virol. Apr. 1998, vol. 72, No. 4, pp. 2955-2961.*
Matsuoka et al. J. Virol. 1991, vol. 181, pp. 403-407.*
Stokes et al. Virus Research 1993, vol. 30, No. 1, pp. 43-52.*
Evans et al. Nature 1985, vol. 314, No. 11, pp. 548-550.*
NCBI Accession No. U51116 submitted on Mar. 11, 1997.*
Skiadopoulos et al. Virology Jul. 1999, vol. 260, pp. 125-135.*
Bailly et al., "A Recombinant Human Parainfluenza Virus Type 3 (PIV3) in Which the Nucleocapsid N Protein Has Been Replaced", Journal Virology, vol. 74, No. 7, 3188-3195 (2000).
Baron et al., "Rescue of Rinderpest Virus From Cloned Cdna", Journal Virology, vol. 71, No. 2, 1265-1271 (1997).
Bellini et al., "Measles Virus P Gene Codes for Two Proteins", Journal Virology, vol. 53, No. 3, 908-919 (1985).
Belshe et al., "Cold Adaptation of Parainfluenza Virus Type 3", Journal Medical Virology, vol. 10(4), 235-242 (1982).
Belshe et al., "Comparison of Enzyme-Linked Immunosorbent Assay and Neutralization Techniques for Measurement of Antibody", Infect and Immun. vol. 37, 160-165 (1982).
Blumberg et al., "Measles Virus L Protein Evidences Elements of Ancestral RNA Polymerase," Virology, 164:487-497, 1988.
Buchholz et al., "Chimeric Bovine Respiratory Syncytial Virus With Glycoprotein Gene Substitutions," Journal Virology, vol. 74, No. 3, 1187-1199 (2000).
Buchholz et al., "Generation of Bovine Respiratory Syncytial Virus (BRSV) from cDNA," Journal Virology, vol. 73, No. 1, 251-259 (1999).
Bukreyev et al., "Recombinant Respiratory Syncytial virus from which the Entire SH Gene has been Deleted Grows Efficiently in Cell Culture and Exhibits Site-Specific Attenuation in the Respiratory Tract of the Mouse," J. Virol. 71:8973-8982, 1997.

(Continued)

Primary Examiner — Bao Li
(74) Attorney, Agent, or Firm — Woodcock Washburn LLP

(57) ABSTRACT

The invention provides isolated nucleic acids encoding recombinant genomes or antigenomes of Human Parainfluenza Viruses that are useful as vaccines. The recombinant genomes or antigenomes can be incorporated into expression vectors for production of recombinant viruses in vitro. The invention also provides recombinant Human Parainfluenza viruses having one or more mutations that attenuate replication of the virus in a host.

2 Claims, 70 Drawing Sheets

OTHER PUBLICATIONS

Figure 1:
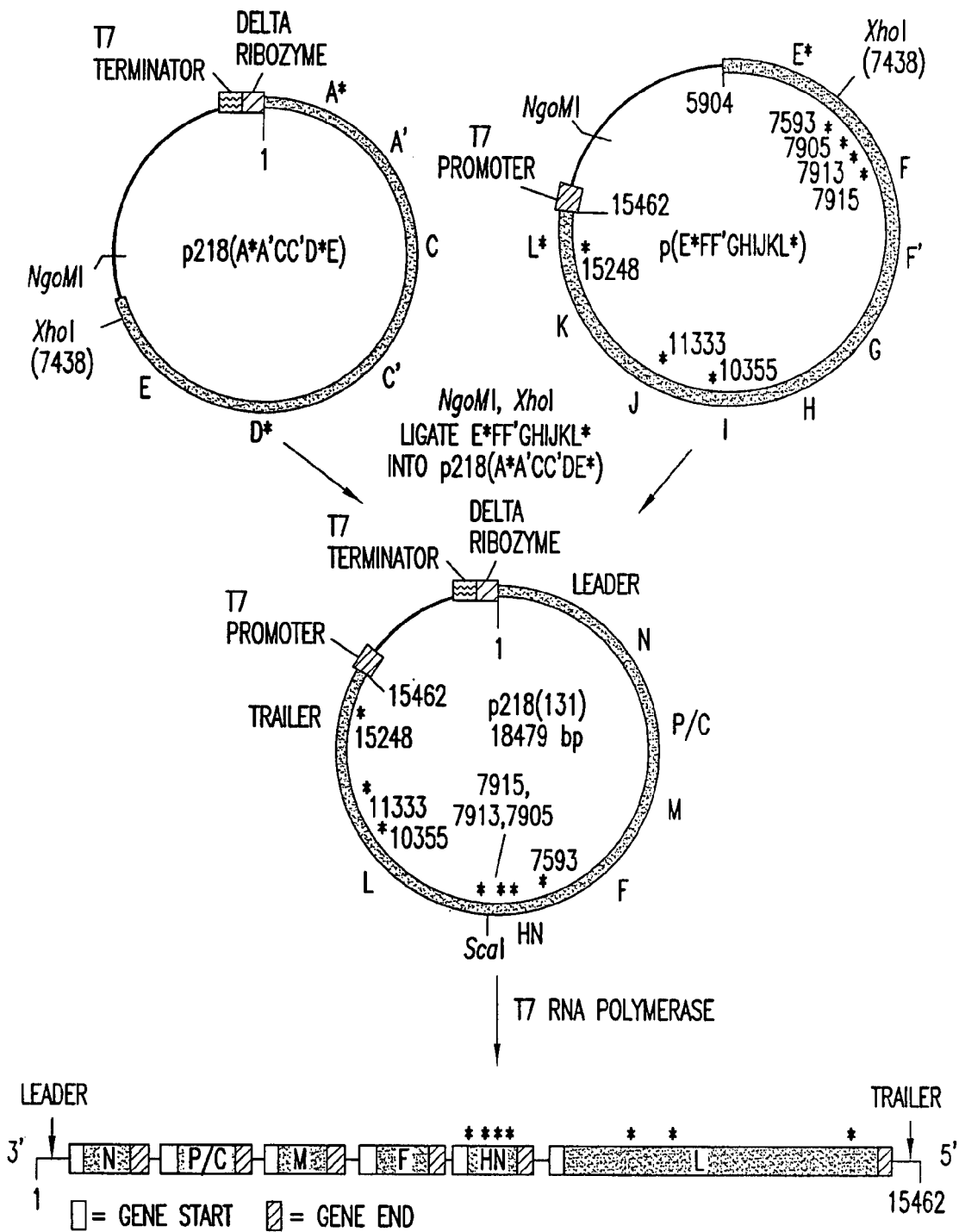

Bukreyev et al., "Interferon Gamma Expressed by a Recombinant Respiratory Syncytial Virus Attenuates Virus Replication in Mice," Proc. Natl. Acad. Sci. USA, vol. 96, 2367-2372 (1999).

Bukreyev et al., "Recovery of Infectious Respiratory Syncytial Virus Expressing an Additional, Foreign Gene," Journal Virology, vol. 70, No. 10, 6634-6641 (1996).

Cadd et al., "The Sendai Paramyxiovirus Accessory C Proteins Inhibit Viral Genome Amplification in Promoter-Specific Fashion," J. Virol 70: 5067-74, 1996.

Cahour et al., "Growth-Restricted Dengue Virus Mutants Containing Deletions in the 5 Noncoding Region of the RNA Genome," Virology, vol. 207, 68-76 (1995).

Cattaneo et al., "Measles Virus Editing Provides Additional Cytosine-Rich Protein," Cell, vol. 56, 759-764, (1989).

Cheng et al., "Effective Amplification of Long Targets From Cloned Inserts," Proc. Natl. Acad. Sci. USA, vol. 91, 5695-5699 (1994).

Clarke et al., "Rescue of Mumps Virus From cDNA," J Virology, vol. 74, No. 10, 4831-4838 (2000).

Clements et al., "Comparison of Virologic—Immunologic Resp. of Volunteers to Live Avian-Human Influenza A H3N2 Reassortant," Journal Clinical Microbiology, vol. 27, No. 1, 219-222 (1989).

Clements et al., "Evaluation of Bovine Cold-Adapted Human, and Wild Type Human Parainfluenza Type 3 Viruses in Adult Volunteers," J. Clinical Microbiology, vol. 29, 1175-1182 (1991).

Clements et al., "Use of Single-Gene Reassortant Viruses to Study Role of A nain Influenza A Virus," Journal Clinical Microbiology, vol. 30, No. 3, 655-662 (1992).

Clements-Mann et al., "Safety and Immunogenicity of Live Attenuated Human-Bovine (UK) Reassortant Rotavirus Vaccines VP7 Specificity," Vaccine vol. 17, 2715-2725 (1999).

Collins et al., "Parainfluenza Viruses," Fields Virology 3rd ed., Lippincott-Raven Publishers, Philadelphia 1205-1241, (1996).

Collins et al., "Rescue of a 7502-Nucleotide (49.3% of Full-Length) Synthetic Analog of Respiratory Syncytial Virus Genomic RNA," Virology 195:252-256, 1993.

Collins et al., "Rescue of Synthetic Analogs of Respiratory Syncytial Virus Genomic RNA and Effect of Truncations and Mutations on the Expression of a Foreign Reporter Gene," Proc. Natl. Acad. Sci. USA, 88:9663-9667, 1991.

Collins et al., "Production of Infectious Human Respiratory Syncytial Virus From Cloned cDNA," Pro. Natl. Acad. Sci., vol. 92, 11563-11567 (1995).

Connors et al., "A Cold-Passaged Attenuated Strain of Human Respiratory Syncytial Virus Contains Mutations in the F and L Genes," Virology 208:478-484, 1995.

Conzelmann et al., "Rescue of Synthetic Genomic RNA Analogs of Rabies Virus by Plasmid-Encoded Proteins," J. Virol. 68: 713-719, 1994.

Conzelmann et al., "Genetic Manipulation of Non-Segmented Negative-Strand RNA Viruses," Journal General Virology, vol. 77, 381-389 (1996).

Cook et al., "Antigenic Relationships Among the "Newer" Myxoviruses (Parainfluenza)," Amer. Jour. Hyq. 69:250, 1959.

Cook et al., "In Vivo Antigenic Studies of Parainfluenza Viruses," American Journal of Hygiene, vol. 77, 150-159 (1962).

Corsoro and Pearson, "Enhancing the Efficiency of DNA Mediated Gene Transfer in Mammalian Cells," Somatic Cell Genetics, vol. 7, No. 5, 603-616 (1981).

Crookshanks et al., "Evaluation of Cold-Adapted and Temperature-Sensitive Mutants of Parainfluenza Virus Type 3," Journal Medical Virology, vol. 13, 243-249 (1984).

Crowe et al., "A Further Attenuated Derivative of a Cold-Passaged Temperature-Sensitive Mutant of Human Respiratory Syncytial Virus Retains Immunogenicity and Protective Efficacy Against Wild-Type Challenge in Seronegative Chimpanzees," Vaccine 12:783-790, 1994.

Crowe et al., "Acquisition of the $ts$ Phenotype by a Chemically Mutagenized Cold-Passaged Human Respiratory Syncytial Virus Vaccine Candidate Results from the Acquisition of a Single Mutation in the Polymerase (L) Gene," Virus Genes 13: 269-273, 1996.

Crowe et al., "Cold-Passaged, Temperature-Sensitive Mutants of Human Respiratory Syncytial Virus (RSV)," Vaccine, vol. 13, No. 9, 847-855 (1995).

Curran et al., "The Sendai Virus Nonstructural C Proteins Specifically Inhibit Viral mRNA Synthesis," Virology 189: 647-656, 1992.

Curran et al., "Sendai Virus P Gene Produces Multiple Proteins From Overlapping Open Reading Frames, Enzyme," vol. 44, 244-249 (1990).

Delenda et al., "Normal Cellular Replication of Sendai Virus Without Trans-Frame, Nonstructural V Protein," Virology, vol. 228, 55-62 (1997).

Delenda et al., "Sendai Viruses With Altered P, V, and W Protein Expression," Virology, vol. 242, 327-337 (1998).

Deng et al, "Localization of a Domain on the Paramyxovirus Attachment Protein Required for the Promotion of Cellular Fusion," Virology, vol. 209, 457-469 (1995).

Dimock et al., "Rescue of Synthetic analogs of Genomic RNA and Replicative-Intermediate RNA of Human Parainfluenza Virus Type 3," Journal Virology, vol. 67, No. 5, 2772-2778 (1993).

Durbin et al., "Mini. Protein Requirements for Transcription, RNA Replication of Minigenome of Human Parainfluenza Virus Type 3 and Evaluation of the Rule of Six," Virology, vol. 234, 74-83 (1997).

Durbin et al., "Mutations in C, D, and V Open Reading Frames of Human Parainfluenza Virus Type 3 Attenuate Replication in Rodents and Primates," Virology, vol. 261, 319-330 (1999).

Durbin et al., "Recovery of Infections Human Parainfluenza Virus Type 3 from cDNA," Virology, vol. 235, 323-332 (1997).

Emerson et al., "A Simian Strain of Hepatitis A Virus, AGM-27, Functions As An Attenuated Vaccine for Chimpanzees," Journal Infectious Diseases, vol. 173, 592-597 (1996).

Escoffier et al., "Nonstructural C Protein is Required for Efficient Measles Virus Replication in Human Peripheral Blood Cells," J Virol. 73:1695-8, 1999.

Finke et al. "Ambisense Gene Expression for Recombinant Rabies Virus: Random Packaging of Positive- and Negative-Strand Ribonucleoprotein Complexes into Rabies Virions," J. Virol. 71:7281-7288, 1997.

Firestone et al., "Nucleotide Sequence Analysis of the Respiratory Syncytial Virus Subgroup A Cold-Passaged ($cp$) Temperature Sensitive ($ts$) $cpts$-248/404 Live Attenuated Virus Vaccine Candidate," Virology 225:419-422, 1996.

Flexner et al., "Prevention of vaccinia virus infection in immunodeficient mice by vector-directed IL-2 expression," Nature 33:259-262,1987.

Frank et al. "Comparison of Different Tissue Cultures for Isolation and Quantitation of Influenza and Parainfluenza Viruses," J. Clin. Microbiol. 10:32-6(1979).

Fuerst et al., "Eukaryotic transient-expression system based on recombinant vaccinia virus that synthesizes bacteriophage T7 RNA polymerase," Proc. Natl. Acad. Sci. USA 83:8122-8126, 1986.

Galinski et al., "Molecular Cloning and Sequence Analysis of Human Parainfluenza 3 Virus mRNA Encoding the P and C Proteins," Virology 155:46-60, 1986.

Galinski et al., "Molecular Cloning and Sequence Analysis of Human Parainfluenza 3 Virus mRNA Encoding the L Protein," Virology 165:499-510, 1988.

Galinski et al., "RNA Editing in the Phosphoprotein Gene of the Human Parainfluenza Virus Type 3," Virology 186:543-550, 1992.

Galinski, "Annotated Nucleotide and Protein Sequences for Selected Paramyxoviridae," In the Paramyxoviruses, Kingsbury D.W., Ed., 537-568, Plenum Press, New York, 1991.

Garcin et al., "A Point Mutation in the Sendai Virus Accessory C Proteins Attenuates Virulence for Mice, but Not Virus Growth in Cell Culture," Virology 238:424-431, 1997.

Garcin et al., "A Highly Recombinogenic System for Recovery of Infectious Sendai Paramyxovirus for cDNA," EMBO Journal, vol. 14, No. 24, 6087-6094 (1995).

Graham et al., "A New Technique for the Assay of Infectivity of Human Adenovirus 5 DNA, Virology," vol. 52, 456-467 (1973).

Gromeier et al., "Dual Stem Loops within the Poliovirus Internal Ribosomal Entry Site Control Neurovirulence," Journal of Virology, vol. 73, No. 2, 958-964 (1999).

Grosfeld et al., "RNA Replication by Respiratory Syncytial Virus (RSV) Is Directed by N, P, and L Proteins," Journal of Virology, vol. 69, No. 9, 5677-5686 (1995).

Haas et al., "Codon Usage Limitation in the Expression of HIV-1 Envelope Glycoprotein," Current Biology, vol. 6, No. 3, 315-324 (1996).

Hall et al., "Cold Passaged Human Parainfluenza Type 3 Viruses Contain ts and Non ts Mutations Leading to Attenuation in Rhesus Monkeys," Virus Research, vol. 22, 173-184 (1992).

Hasan et al., "Creation of an Infectious Recombinant Sendai Virus Expressing the Firefly Luciferase Gene from the 3' Proximal First Locus," J. Gen. Virol. 78:2813-20, 1997.

Hawley-Nelson et al., "A New Higher Efficiency Polyatomic Liposome Transfection Reagent," Focus, vol. 15, No. 3, 73-79 (1993).

He et al., "Recovery of Infectious SV5 From Cloned DNA and Expression of a Foreign Gene," Virology, vol. 237, 249-260 (1997).

He et al., "The Paramyxovirus SV5 Small Hydrophobic (SH) Protein Is Not Essential for virus Growth in Tissue Culture Cells," Virol. vol. 250 30-40 (1998).

Heikkinen et al., "Prevalence of Various Respiratory Viruses in the Middle Ear During Acute Ottitis Media," New England Journal of Medicine, vol. 340, 260-264 (1999).

Hoffman et al., "An Infectious Clone of Human Parainfluenza Virus Type 3," Journal Virology, vol. 71, No. 6, 4272-4277 (1997).

Hurwitz et al., "Intranasal Sendai Virus Vaccine Protects African Green Monkeys From Infection With Human Parainfluenza Virus Type One," Vaccine, vol. 15, No. 5, 533-540 (1997).

Itoh et al., "Isolation of an Avirulent Mutant of Sendai Virus with Two Amino Acid Mutations from a Highly Virulent Field Strain Through Adaptation to LLC-MK$_2$ Cells," J. Gen Virol. 78:3207-3215, 1997.

Jin et al., "Recombinant Human Respiratory Syncytial Virus (RSV) from cDNA and Construction of Subgroup A and B Chimeric RSV," Virology, vol. 251, 206-214 (1998).

Johnson et al., "Specific Targeting to CD4+ Cells of Recombinant Vesicular Stomatitis Viruses Encoding Human Immunodeficiency Virus Envelope Proteins," J. Virol. 71:5060-5068, 1997.

Juhasz et al., "The Temperature-Sensitive (ts) Phenotype of a Cold-Passaged (cp) Live Attenuated Respiratory Syncytial Virus," Journal of Virology, vol. 71, No. 8, 5814-5819 (1997).

Kahn et al., "Recombinant Vesicular Stomatitis Virus Expressing Respiratory Syncytial Virus (RSV) Glycoproteins: RSV Fusion Protein Can Mediate Infection and Cell Fusion," Virology 254:81-91, 1999.

Kapikian et al., "Update on Jennerian and Modified Jennerian Approach to Vaccination of Infants and Young Children . . . ," Genetically Engineered Vaccines, vol. 327, 59-69 (1992).

Karron et al., "A Live Human Parainfluenza Type 3 Virus Vaccine is Attenuated and Immunogenic in Healthy Infants and Children," J. Inf. Dis. 172:1445-1450, 1995.

Karron et al., "A Live Attenuated Bovine Parainfluenza Virus Type 3 Vaccine Is Safe, Infectious, Immunogenic, and Phenotypically Stable in Infants and Children," Journal of Infectious Diseases, vol. 171, 1107-1104 (1995).

Karron et al., "Evaluation of a Live Attenuated Bovine Parainfluenza Type 3 Vaccine in Two to Six Month Old Infants," Pediatric Infectious Diseases Journal, vol. 15, 650-654 (1996).

Kast et al., "Protection against lethal Sendai virus infection by in vivo priming of virus-specific cytotoxic T lymphocytes with a free synthetic peptide," Proc. Natl. Acad.Sci.USA 88:2283-2287,1991.

Kato et al., "Importance of Cysteine Rich Carboxyl Terminal Half of V Protein for Sendai Virus Pathogenesis," Journal Virology, vol. 71, No. 10, 7266-7272 (1997).

Kato et al., "Initiation of Sendai Virus Multiplication From Transfected cDNA or RNA with Negative or Positive Sense," Genes to Cells, vol. 1, 569-579 (1996).

Kato et al., "The Paramyxovirus Sendai Virus V Protein Encodes a Luxury Function Required for Viral Pathogenesis," EMBO Journal, vol. 16, No. 3, 578-587 (1997).

Kozak et al, "At Least Six Nucleotides Preceding the AUG Initiator Codon Enhance Translation in Mammalian Cells," Journal Molecular Biology, vol. 196, 947-950 (1987).

Kretzschmar et al., "Normal Replication of Vesicular Stomatitis Virus Without C Proteins," Virology, vol. 216, 309-316 (1996).

Kunkel et al., "Rapid and Efficient Site-Specific Mutagenesis Without Phenotypic Selection," Proc. Natl. Acad. Sci., vol. 82, 488-492 (1985).

Kuo et al., "Effect of Mutations in the Gene-Start and Gene-End Sequence Motifs on Transcription of Monocistronic and Dicistronic Minigenomes of Respiratory Syncytial Virus," J. Virol. 70:6892-6901, 1996.

Kurotani et al., "Sendai Virus C Proteins are Categorically Nonessential Gene Products but Silencing Their Expression Severely Impairs Viral Replication and Pathogenesis," Genes to Cells 3:111-124, 1998.

Lamb et al., "In the Paramyxoviruses," D. Kingsbury, ed., 181-214, Plenum Press, New York, 1991.

Latorre et al., The Various Sendai Virus C Proteins are Not Functionally Equivalent and Exert both Positive and Negative Effects on Viral FNA Accumulation During the Course of Infection, J. Virol. 72:5984-5993, 1998.

Lawson et al., "Recombinant Vesicular Stomatitis Viruses From DNA," Proc. Natl. Acad. Sci., vol. 92, 4477-4481 (1995).

Liston et al., "Ribosomal Frameshifting During Translation of Measles Virus P Protein mRNA Is Capable of Directing Synthesis," Journal Virology, vol. 69, No. 11, 6742-6750 (1995).

Mallipeddi et al., "Sequence Comparison Between the Phosphoprotein mRNAs of Human and Bovine Respiratory Syncytial Viruses Identifies a Divergent Domain in the Predicted Protein," J. Gen. Virol. 73:2441-2444, 1992.

Mallipeddi et al., "Sequence Variability of the Glycoprotein Gene of Bovine Respiratory Syncytial Virus," J. Gen. Virol. 74:2001-2004, 1993.

Marx et al., "Pediatric Hospitalizations for Croup," Journal Infectious Diseases, vol. 176, 1423-1427 (1997).

Matsuoka et al., "The P Gene of Human Parainfluenza Virus Type 1 Encodes P and C Proteins But Not a Cysteine Rich V Protein," Journal Virology, vol. 65, No. 6, 3406-3410 (1991).

Mebatsion et al., "Highly Stable Expression of a Foreign Gene from Rabies Virus Vectors," Proc. Natl. Acad. Sci. U S A 93:7310-7314,1996.

Men et al., "Dengue Type 4 Virus Mutants Containing Deletions in the 3 Noncoding Region of the RNA," Journal of Virology, vol. 70, No. 6, 3930-3937 (1996).

Mink et al., "Nucleotide Sequences of the 3' Leader and 5' Trailer Regions of Human Respiratory Syncytial Virus Genomic RNA," Virology 185:615-624, 1991.

Moriya et al., "Large Quantity Production with Extreme Convenience of Human SDF-la by a Sendai Virus Vector," FEBS Lett. 425:105-111, 1998.

Murphy et al., "Enhanced pulmonary histopathology is observed in cotton rats immunized with formalin-inactivated respiratory syncytial virus (RSV) or purified F glycoprotein and challenged with RSV 3-6 months after immunization," Vaccine 8(5):497-502, 1990.

Murphy et al., "Failure of Attenuated Temperature-Sensitive Influenza A (H3N2) Virus to Induce Heterologous Interference in Humans to Parainfluenza Type 1 Virus," Infect.Immun.12:62-8,1975.

Murphy et al., "Current Approaches to the Development of Vaccines Effective Against Parainfluenza," Virus Research, vol. 11, 1-15 (1988).

Murphy et al., "Dose Response of Influenza A Washington 897 80 (H3N2) Avian-Human Reassortant Virus in Adult Volunteers," Journal Infectious Diseases, vol. 152, No. 1, 225-229 (1985).

Muster et al., "An Influenza A Virus Containing Influenza B Virus 5 and 3 Noncoding Regions on the Neuraminidase Gene Is Attenuated in Mice," Proc. Natl. Acad. Sci., vol. 88, 5177-5181 (1991).

Needleman and Wunsch, "A General Method Applicable to the Search for Similarities in the Amino Acid Sequence of Two Proteins," Journal of Molecular Biology, vol. 48 (1970).

Neumann et al., "Gene Transfer Into Mouse Lymoa Cells by Electroporation in High Electric Fields," EMBO J. vol. 1, No. 7, 841-845 (1982).

Palese et al., "Negative Strand RNA Viruses Genetic Engineering and Applications," Proc. Natl. Acad. Sci., vol. 93, 11354-11358 (1996).

Park et al., "In Vivo Model for Pseudo-Templated Transcription in Sendai Virus," Journal Virology, vol. 66, No. 12, 7033-7039 (1992).

Pastey et al. "Nucleotide Sequence Analysis of the Non-Structural NS1(1C) and NS2 (1B) Protein Genes of Bovine Respiratory Syncytial Virus," J. of Gen. Virol. 76:193-197, 1995.
Pastey et al., "Structure and Sequence Comparison of Bovine Respiratory Syncytial Virus Fusion Protein," Virus Res. 29: 195-202, 1993.
Pearson et al., "Improved Tools for Biological Sequence Comparison," Proc. Natl. Acad. Sci. USA, vol. 85, 2444-2448 (1988).
Peeters et al., "Rescue of Newcastle Disease Virus From Cloned cDNA . . . ," Journal of Virology, vol. 73 (1999).
Pelet et al., "The P Gene of Bovine Parainfluenza Virus 3 Expresses All Three Reading Frames from a Single MRNA Edition Site," EMBO Journal, vol. 10, No. 2, 443-448 (1991).
Perez-Schael et al., "Efficacy of Rhesus Rotavirus Based Quadrivalent Vaccine in Infants and Young Children in Venezuela," New England of Journal Medicine, vol. 337, No. 17, 1181-1187 (1997).
Perrotta et al., "A Pseudoknot-Like Structure Required for Efficient Self-Cleavage of Hepatitis Delta Virus RNA," Nature, vol. 350, 434-436 (1991).
Radecke (Radicle) et al., "The Nonstructural C Protein Is Not Essential for Multiplication of Edmonston B Strain Measles Virus in Cultured Cells," Virology, vol. 217, 418-421 (1996).
Radecke et al., "Rescue of Measles Viruses from Cloned DNA," EMBO Journal, vol. 14, 5773-5784 (1995).
Randhawa et al., "Nucleotide Sequences of Genes Encoding the Putative Attachment Glycoprotein (G) of Mouse and Tissue Culture Passaged Strains of Pneumonia," Virology, vol. 207 240-245 (1995).
Ray et al., "Temperature-Sensitive Phenotype of Human Parainfluenza Virus Type 3 Candidate Vaccine Strain (cp45) Correlates with a Defect in the L Gene," J. Virol. 70:580-584, 1996.
Ray et al., "Human Parainfluenza Virus Induces a Type Specific Protective Immune Response, Journal Infectious Diseases," vol. 162, 746-749 (1990).
Roberts et al., "Recovery of Negative Strand RNA Viruses From Plasmid DNAs," Virology 247, 1-6 (1998).
Roberts et al., "Attenuated Vesicular Stomatitis Viruses as Vaccine Vectors," J. Virol. 73:3723-3732, 1999.
Roberts et al., "Vaccination with a Recombinant Vesicular Stomatitis Virus Expressing an Influenza Virus Hamagglutinin Provides Complete Protection from Influenza Virus Challenge," J. Virol. 72:4704-4711, 1998.
Sakaguchi et al., "Expression of the HN, F, NP and M Proteins of Sendai Virus by Recombinant Vaccinia Viruses and Their Contribution to Protective Immunity Against Sendai Virus Infections in Mice," J. Gen. Virol. 74:479-484, 1993.
Sakai et al., "Accommodation of Foreign Genes into the Sendai Virus Genome: Sizes of Inserted Genes and Viral Replication," FEBS Letters 456:221-226, 1999.
Sanchez et al., "Cloning and Gene Assignment of mRNAs of Human Parainfluenza Virus 3," Virology, vol. 147, 177-186 (1985).
Schnell et al., "Foreign Glycoproteins Expressed from Recombinant Vesicular Stomatitis Viruses are Incorporated Efficiently into Virus Particles," Proc. Natl. Acad. Sci. USA 93:11359-11365, 1996.
Schneider et al., "Recombinant Measles Viruses Defective for RNA Editing," Virology, vol. 227, 314-322 (1997).
Schnell et al., "Construction of a Novel Virus that Targets HIV-1-Infected Cells and Controls HIV-1 Infection," Cell 90:849-857, 1997.
Schnell et al., "The Minimal Conserved Transcription Stop-Start Signal Promotes Stable Expression of a Foreign Gene in Vesicular Stomatitis Virus," J. Virol. 70:2318-2323, 1996.
Schnell et al., "Infectious Rabies Viruses from Cloned cDNA," EMBO Journal, vol. 13, No. 18, 4195-4203 (1994).
Singh et al., "A Recombinant Measles Virus Expressing Biologically Active Human Interleukin-12," J. Gen. Virol. 80:101-106, 1999.
Singh et al., "A Recombinant Measles Virus expressing Hepatitis B Virus Surface Antigen Induces Humoral Immune Responses in Genetically Modified Mice," J. Virol. 73:4823-4828, 1999.
Skiadopoulos et al., "Generation of Parainfluenza Virus Type 1 Vaccine Candidate by Replacing HN and F Glycoproteins . . . ," Vaccine, vol. 18, 503-510 (1999).
Skiadopoulos et al., "Identification of Mutations Contributing to Temperature Sensitive Cold Adapted . . . ," Journal Virology, vol. 73, No. 2, 1374-1381 (1999).
Skiadopoulos et al., "Three Amino Acid Substitutions in L Protein of Human Parainfluenza Virus Type 3 cp45 Live Attenuated Vaccine . . . ," Journal Virology, vol. 72, No. 3, 1762-1768 (1998).
Smith & Waterman, "Comparison of Biosequences," Advanced Applied Mathematics, vol. 2, 482-489 (1981).
Snyder et al., "Evaluation of Live Avian Human Reassortant Influenza A H2N2 and H1N1 Virus Vaccines," Journal Clinical Micro., vol. 23, No. 5, 852-857 (1986).
Spielhofer et al., "Chimeric Measles Viruses with a Foreign Envelope," J. Virol. 72:2150-2159, 1998.
Sprent et al., "Generalization of the Sign Test, Applied Nonparametric Statistical Method," 123-126, Chapman and Hall, London, 1989.
Spriggs et al., "Sequence Analysis of P and C Protein Genes of Human Parainfluenza Virus Type 3," Journal General Virology, vol. 67, 2705-2719 (1986).
Steinhoff et al., "A Mallard 6750 78 Avian Human by Not A Ann Arbor 6 60 Cold Adapted Influenza," Journal Infectious Diseases, vol. 163, 1023-1028 (1991).
Stokes et al., "The Complete Nucleotide Sequence of Two Cold-Adapted, Temperature-Sensitive Attenuated Mutant Vaccine Viruses ($cp12$ and $cp45$) Derived from the JS Strain and Human Parainfluenza Virus Type 3 (PIV3)," Virus Res. 30:43-52, 1993.
Stokes et al., "The Complete Nucleotide Sequence of JS Strain of Human Parainfluenza Virus Type 3," Virus Research, vol. 25, 91-103 (1992).
Suzu et al., "Nucleotide Sequence of Bovine Parainfluenza 3 Virus Genome, Nucleic Acids Research," vol. 15, No. 7, 2945-2958 (1987).
Tanabayashi et al., "Functional Interaction of Paramyxovirus Glycoproteins," Journal Virology, vol. 70, No. 9, 6112-6118 (1996).
Tao et al., "A Live Attenuated Chimeric Recombinant Parainfluenza Virus (PIV) Encoding the Internal Proteins of PIV Type 3 . . . ," Vaccine, vol. 17, 1100-1108 (1999).
Tao et al., "Recovery of a Fully Viable Chimeric Human Parainfluenza Virus (PIV) Type 3 . . . ," Journal Virology, vol. 72, No. 4, 2955-2961 (1998).
Teng et al., "Altered Growth Characteristics of Recombinant Respiratory Syncytial Viruses," Journal Virology, vol. 73, No. 1, 466-473 (1999).
Teng et al., "Identification of Respiratory Syncytial virus Proteins Required for Formation and Passage," Journal Virology, vol. 72, No. 7, 5707-5716 (1998).
Thomas et al., "Two mRNAs That Differ by Two Nontemplated Nucleotides," Cell, vol. 54, 891-902 (1988).
Thomson et al., "Recombinant Polyepitope Vaccines for the Delivery of Multiple CD8 Cytotoxic T Cell Epitopes," J. Immunol. 157:822,1996.
Valsamakis et al., "Recombinant Measles Viruses with Mutations in the C, V, or F Gene Have Altered Growth Phenotypes In Vivo," Journal Virology, vol. 72, No. 10, 7754-7761 (1998).
van Wyke Coelingh et al., "Antigenic Variation in the Hemagglutinin-Neuraminidase Protein of Human Parainfluenza Type 3 Virus," Virology 143(2):569-582,1985.
Van Wyke Coelingh et al., "Antigenic and Structural Properties of Hemagglutinin-Neuraminidase Glycoprotein of Human Parainfluenza Virus Type 3: Sequence Analysis of Variants Selected with Monoclonal Antibodies which Inhibit Infectivity, Hemagglutination, and Neuraminidase Activities," J. Virol. 61:1473-1477, 1987.
van Wyke Coelingh et al., "Antibody Responses of Humans and Nonhuman Primates to Individual Antigenic Sites," Journal Virology, vol. 64, No. 8, 3833-3843 (1990).
Van Wyke Coelingh et al., "Attenuation of Bovine Parainfluenza Virus Type 3 in Nonhuman Primates, Journal Infectious Diseases," vol. 157, No. 4, 655-662 (1988).
van Wyke Coelingh et al., "Conserved Epitopes on Hemagglutinin-Neuraminidase Proteins of Human and Bovine Parainfluenza Type 3 Viruses," Journal Virology, vol. 60, No. 1, 90-96 (1986).
Vidal et al., "Editing of Sendai Virus PC mRNA by G Insertion Occurs During mRNA Synthesis Via a Virus Encoded Activity," Journal Virology, vol. 64, No. 1, 239-246 (1990).

Wathen et al., "Characterization of a Novel Human Respiratory Syncytial Virus Chimeric FG Glycoprotein Expressed Using a Baculovirus Vector," J. Gen. Virol. 70:2625-2635, 1989.

Whelan et al., "Efficient Recovery of Infectious Vesicular Stomatitis Virus Entirely from cDNA Clones," Proc. Natl. Acad. Sci., vol. 92, 8388-8392 (1995).

Whitehead et al., "A Single Nucleotide Substitution in Transcription Start Signal of M2 Gene . . . ," Virology, vol. 247, 232-239 (1998).

Whitehead et al., "Recombinant Respiratory Syncytial Virus (RSV) Bearing a Set of Mutations . . . ," Journal Virology, vol. 72, No. 5, 4467-4471 (1998).

Whitehead et al., "Recombinant Respiratory Syncytial Virus Bearing a Deletion of Either the NS2 or SH Gene . . . ," Journal Virology, vol. 73, No. 4, 3438-3442 (1999).

Wigler et al., "Biochemical Transfer of Single Copy Eukaryotic Genes Using Total Cellular DNA As Donor," Cell, vol. 14, 725-731 (1978).

Wyatt et al., "Replication Deficient Vaccinia Virus Encoding Bacteriophage T7 RNA, Virology," vol. 210, 202-205 (1995).

Yu et al., "Sendai Virus-Based Expression of HIV-1 gp 120: Reinforcement by the V(-) Version," Genes to Cells 2:457-466, 1997.

Zamora et al., "Gene Junction Sequences of Bovine Respiratory Syncytial Virus," Virus Res. 24:115-121, 1992.

Zamora et al., "Sequence Analysis of M2 mRNA of Bovine Respiratory Syncytial Virus Obtained from an F-M2 Dicistronic mRNA Suggests Structural Homology with that of Human Respiratory Syncytial Virus," J. Gen Virol. 73:737-741, 1992.

Zimmerman et al., "The Poly(C) Region Affects Progression of Encephalomyocarditis Virus," Journal Virology, vol. 71, No. 5, 4145-4149 (1997).

Crowe et al, "Current Approaches to the Development of Vaccines Against Disease Caused by Respiratory Syncytial Virus," Vaccine vol. 13 No. 4 415-421 (1995).

Kunkel et al., "Rapid and Efficient Site-Specific Mutagenesis Without Phenotypic Selection," Methods Enzymol. vol. 154 367-383 (1987).

Kretzschmar et al., "High-Efficiency Incorporaion of Functional Influenza Virus Glycoproteins into Recombinant Vesicular Stomatitis Viruses," J. Virol. vol. 71, pp. 5982-5989 (1997).

* cited by examiner

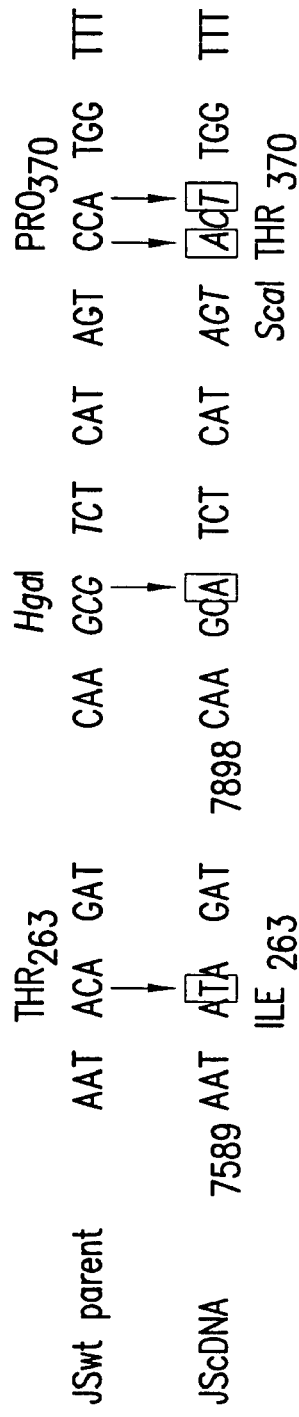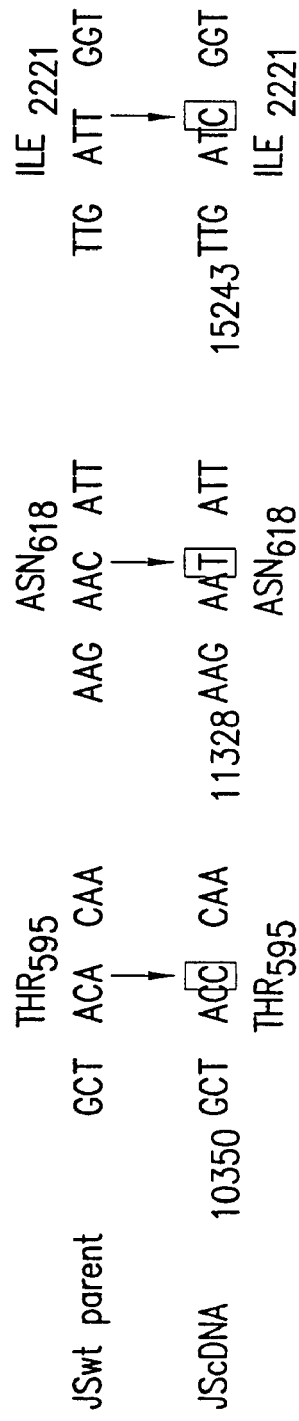
FIG.2

SCHEMATIC REPRESENTATION OF RECOMBINANT PIV3 VIRUSES BEARING MUTATI

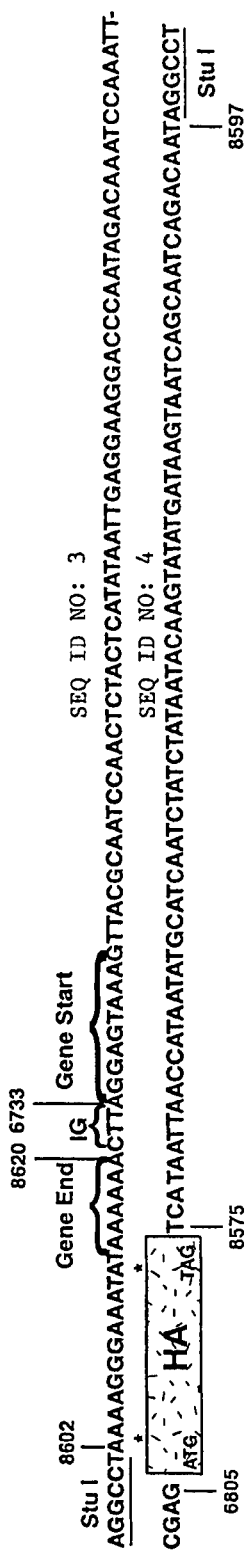
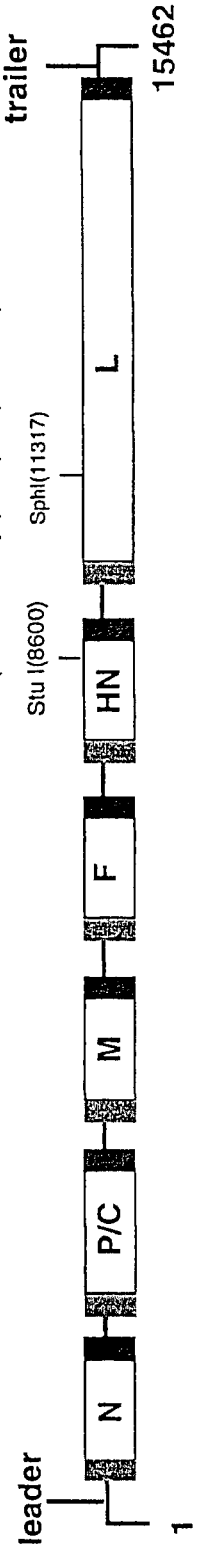
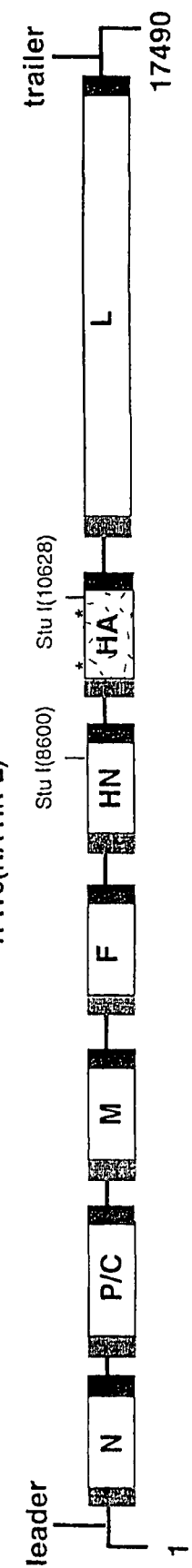
FIG. 20B

FIG.21

FIG.25A gene unit insertion

FIG.25B

HN gene 3' non-coding region insertion

| Construct | Mean peak titer ($\log_{10} TCID_{50}/ml$)[a] | Reduction in titer at 39°[c] ($\log_{10} TCID_{50}/ml$)[b] |
|---|---|---|
| rHPIV3 wt | 9.4 | 0.3 |
| rHPIV3 1HN$_{N-P}$ | 7.4 | 0.7 |
| rHPIV3 1HN$_{P-M}$ | 7.9 | 2.3 |
| rHPIV3 2HN$_{N-P}$ | 7.9 | 0.3 |
| rHPIV3 2HN$_{P-M}$ | 9.2 | 0.5 |
|

FIG. 32

FIG.33

Genetic structures of PIV3-2 chimeric viruses compared with rPIV3 parent and rPIV3-1

FIG.39A

Chimeric PIV3-2 F and HN constructs with transmembrane and cytoplasmic domains derived from PIV3 F and HN

FIG.39B

Chimeric PIV3-2 F and HN constructs with cytoplasmic domain derived from PIV3 F and HN

FIG.39C

Cloning of BPIV3 strain Ka or strain SFN coding region into HPIV3 context

41A. Mutagenesis to create restriction sites at start and stop codons of N

```
    HPIV3 N                                    BPIV3 N
    pUC119JSN                              pBS-KaN or pBS-SFN
CAAAAATGTTG    GCAACTAATCGA        CAAAAATGTTG    GCAACTAATCGA
       ↓                                  ↓
    HPIV3 N                                    BPIV3 N
TAACCATGGTGA      GCACTTAAGCAC      TAACCATGGTGA      GCACTTAAGCAC
 NcoI   pUC119JSN-NcoI/AflII  AflII   NcoI  pUC119KaN-NcoI/AflII  AflII
                                          or pUC119SFN-NcoI/AflII
         ↓                                       ↓
   NcoI AflII digestion                  NcoI AflII digestion
```

41B.

```
                                      BPIV3 N coding

NcoI              AflII
   ─┤ ├─            ─┤ ├─
              ↓
   NcoI              AflII
   ─┤    BPIV3 N    ├─
   pUC119B/HKaN-NcoI/AflII or
   pUC119B/HSFN-NcoI/AflII
```

41C. Mutagenesis to restore start and stop codon context

Legend
▒ BPIV3 sequence
☐ HPIV3 sequence

```
    NcoI                AflII
TAACCATGGTGA         GCACTTAAGCAC
      ↓                    ↓
CAAAAATGTTGA         GCAACTAGTCGA

─┤  BPIV3 N  ├─
    ↓                       ↓
   MluI   pUC119B/HKaN or  EcoRI
          pUC119B/HSFN
```

FIG.41

Cloning of BPIV3 N coding region into HPIV3 antigenomic cDNA

Legend:
- ☐ HPIV3 sequence
- ▦ BPIV3 Ka sequence
- ☐ BPIV3 SF sequence
- ▨ plasmid sequence

FIG.42

Nucleotide sequences of HPIV3, BPIV3 and chimeric viruses around the start (A) and stop (B) codons of the N gene 43A.
```
rJS   GGAACTCTATAATTTCAAAAATGTTGAGCCTATTTGATAC
cKa   GGAACTCTATAATTTCAAAAATGTTGAGTCTATTCGACAC
cSF   GGAACTCTATAATTTCAAAAATGTTGAGTCTATTCGACAC
Ka    GAAATCCTAAGACTGTAATCATGTTGAGTCTATTCGACAC
SF    GAAATCCTAAGACTGTAATCATGTTGAGTCTATTCGACAC
```

43B.
```
rJS   TTAACGCATTTGGAAGCAACTAATCGAATCAACATTTTAA
cKa   TCAGTGCATTCGGAAGCAACTAGTCGAATCAACATTTTAA
cSF   TCAGTGCATTCGGAAGCAACTAGTCGAATCAACATTTTAA
Ka    TCAGTGCATTCGGAAGCAACTAGTCACAAAGAGATGACCA
SF    TCAGTGCATTCGGAAGCAACTAGTCACAAAGAGATGACCA
```

FIG.43

Confirmation of identity of potential BPIV3/HPIV3 chimeras by TaqI digestion

```
ACCAAACAAG AGAAGAGACT TGCTTGGGAA TATTAATTCA AATAAAAATT      50
AACTTAGGAT TAAAGAACTT TACCGAAAGG TAAGGGGAAA GAAATCCTAA     100
GACTGTAATC ATGTTGAGTC TATTCGACAC ATTCAGTGCG CGTAGGCAGG     150
AGAACATAAC GAAATCAGCT GGTGGGGCTG TTATTCCCGG GCAAAAAAAC     200
ACTGTGTCTA TATTTGCTCT TGGACCATCA ATAACAGATG ACAATGATAA     250
AATGACATTG GCTCTTCTCT TTTTGTCTCA TTCTTTAGAC AATGAAAAGC     300
AGCATGCGCA AAGAGCTGGA TTTTTAGTTT CTCTGTTATC AATGGCTTAT     350
GCCAACCCAG AATTATATTT AACATCAAAT GGTAGTAATG CAGATGTTAA     400
ATATGTTATC TACATGATAG AGAAGACCC AGGAAGACAG AAATATGGTG     450
GGTTTGTCGT CAAGACTAGA GAGATGGTTT ATGAAAAGAC AACTGATTGG     500
ATGTTCGGGA GTGATCTTGA GTATGATCAA GACAATATGT TGCAAAATGG     550
TAGAAGCACT TCTACAATCG AGGATCTTGT TCATACTTTT GGATATCCAT     600
CGTGTCTTGG AGCCCTTATA ATCCAAGTTT GGATAATACT TGTTAAGGCT     650
ATAACCAGTA TATCAGGATT GAGGAAAGGA TTCTTTACTC GGTTAGAAGC     700
ATTTCGACAA GATGGAACAG TTAAATCCAG TCTAGTGTTG AGCGGTGATG     750
CAGTAGAACA AATTGGATCA ATTATGAGGT CCCAACAGAG CTTGGTAACA     800
CTCATGGTTG AAACACTGAT AACAATGAAC ACAGGCAGGA ATGATCTGAC     850
AACAATAGAA AAGAATATAC AGATTGTAGG AAACTACATC AGAGATGCAG     900
GTCTTGCTTC ATTTTCAAC ACAATCAGAT ATGGCATTGA GACTAGAATG     950
GCAGCTCTAA CTCTGTCTAC CCTTAGACCG GATATCAACA GACTCAAGGC    1000
ACTGATCGAG TTATATCTAT CAAAGGGGCC ACGTGCTCCT TTTATATGCA    1050
TTTTGAGAGA TCCCGTGCAT GGTGAGTTTG CACCAGGCAA CTATCCTGCC    1100
CTCTGGAGTT ATGCGATGGG TGTAGCAGTT GTACAAAACA AGGCCATGCA    1150
ACAGTATGTA ACAGGAAGGT CTTATCTGGA TATTGAAATG TTCCAACTTG    1200
GTCAAGCAGT GGCACGTGAT GCCGAGTCGC AGATGAGTTC AATATTAGAG    1250
GATGAACTGG GGTCACACA AGAAGCCAAG CAAAGCTTGA AGAAACACAT    1300
GAAGAACATC AGCAGTTCAG ATACAACCTT TCATAAGCCT ACAGGGGGAT    1350
CAGCCATAGA AATGGCGATA GATGAAGAAG CAGGGCAGCC TGAATCCAGA    1400
GGAGATCAGG ATCAAGGAGA TGAGCCTCGG TCATCCATAG TTCCTTATGC    1450
ATGGGCAGAC GAAACCGGGA ATGACAATCA AACTGAATCA ACTACAGAAA    1500
TTGACAGCAT CAAAACTGAA CAAAGAAACA TCAGAGACAG GCTGAACAAA    1550
AGACTCAACG AGAAAAGGAA ACAGAGTGAC CGAGATCAA CTGACATCAC    1600
AAACAACACA AATCAAACTG AAATAGATGA TTTGTTCAGT GCATTCGGAA    1650
GCAACTAGTC ACAAAGAGAT GACCACTATC ACCAGCAACA AGTAAGAAAA    1700
ACTTAGGATT AATGGAAATT ATCCAATCCA GAGACGGAAG GACAAATCCA    1750
GAATCCAACC ACAACTCAAT CAACCAAAGA TTCATGGAAG ACAATGTTCA    1800
AAACAATCAA ATCATGGATT CTTGGGAAGA GGGATCAGGA GATAAATCAT    1850
CTGACATCTC ATCGGCCCTC GACATCATTG AATTCATACT CAGCACCGAC    1900
TCCCAAGAGA ACACGGCAGA CAGCAATGAA ATCAACACAG GAACCACAAG    1950
ACTTAGCACG ACAATCTACC AACCTGAATC CAAAACAACA GAAACAAGCA    2000
AGGAAAATAG TGGACCAGCT AACAAAAATC GACAGTTTGG GGCATCACAC    2050
GAACGTGCCA CAGAGACAAA AGATAGAAAT GTTAATCAGG AGACTGTACA    2100
GGGAGGATAT AGGAGAGGAA GCAGCCCAGA TAGTAGAACT GAGACTATGG    2150
TCACTCGAAG AATCTCCAGA AGCAGCCCAG ATCCTAACAA TGGAACCCAA    2200
ATCCAGGAAG ATATTGATTA CAATGAAGTT GGAGAGATGG ATAAGGACTC    2250
TACTAAGAGG GAAATGCGAC AATTTAAAGA TGTTCCAGTC AAGGTATCAG    2300
GAAGTGATGC CATTCCTCCA ACAAACAAG ATGGAGACGG TGATGATGGA    2350
```

FIG.46A

| | | | | |
|---|---|---|---|---|
| AGAGGCCTGG | AATCTATCAG | TACATTTGAT | TCAGGATATA | CCAGTATAGT | 2400
| GACTGCCGCA | ACACTAGATG | ACGAAGAAGA | ACTCCTTATG | AAGAACAACA | 2450
| GGCCAAGAAA | GTATCAATCA | ACACCCCAGA | ACAGTGACAA | GGGAATTAAA | 2500
| AAAGGGGTTG | GAAGGCCAAA | AGACACAGAC | AAACAATCAT | CAATATTGGA | 2550
| CTACGAACTC | AACTTCAAAG | GATCGAAGAA | GAGCCAGAAA | ATCCTCAAAG | 2600
| CCAGCACGAA | TACAGGAGAA | CCAACAAGAC | CACAGAATGG | ATCCCAGGGG | 2650
| AAGAGAATCA | CATCCTGGAA | CATCCTCAAC | AGCGAGAGCG | GCAATCGAAC | 2700
| AGAATCAACA | AACCAAACCC | ATCAGACATC | AACCTCGGGA | CAGAACCACA | 2750
| CAATGGGACC | AAGCAGAACA | ACCTCCGAAC | CAAGGATCAA | GACACAAAAG | 2800
| ACGGATGGAA | AGGAAAGAGA | GGACACAGAA | GAGAGCACTC | GATTTACAGA | 2850
| AAGGGCGATT | ACATTATTAC | AGAATCTTGG | TGTAATCCAA | TCTGCAGCAA | 2900
| AATTAGACCT | ATACCAAGAC | AAGAGAGTTG | TGTGTGTGGC | GAATGTCCTA | 2950
| AACAATGCAG | ATACTGCATC | AAAGATAGAC | TTCCTAGCAG | GTTTGATGAT | 3000
| AGGAGTGTCA | ATGGATCATG | ATACCAAATT | AAATCAGATT | CAGAACGAGA | 3050
| TATTAAGTTT | GAAAACTGAT | CTTAAAAAGA | TGGATGAATC | ACATAGAAGA | 3100
| CTAATTGAGA | ATCAAAAGA | ACAATTATCA | CTGATCACAT | CATTAATCTC | 3150
| AAATCTTAAA | ATTATGACAG | AGAGGAGG | GAAGAAGGAC | CAACCAGAAC | 3200
| CTAGCGGGAG | GACATCCATG | ATCAAGACAA | AAGCAAAAGA | AGAGAAAATA | 3250
| AAGAAAGTCA | GGTTTGACCC | TCTTATGGAA | ACACAGGGCA | TCGAGAAAAA | 3300
| CATCCCTGAC | CTCTATAGAT | CAATAGAGAA | AACACCAGAA | AACGACACAC | 3350
| AGATCAAATC | AGAAATAAAC | AGATTGAATG | ATGAATCCAA | TGCCACTAGA | 3400
| TTAGTACCTA | GAAGAATAAG | CAGTACAATG | AGATCATTAA | TAATAATCAT | 3450
| TAACAACAGC | AATTTATCAT | CAAAAGCAAA | GCAATCATAC | ATCAACGAAC | 3500
| TCAAGCTCTG | CAAGAGTGAC | GAGGAAGTGT | CTGAGTTGAT | GGACATGTTC | 3550
| AATGAGGATG | TCAGCTCCCA | GTAAACCGCC | AACCAAGGGT | CAACACCAAG | 3600
| AAAACCAATA | GCACAAAACA | GCCAATCAGA | GACCACCCCA | ATACACCAAA | 3650
| CCAATCAACA | CATAACAAAG | ATCTCCAGAT | CATAGATGAT | TAAGAAAAAC | 3700
| TTAGGATGAA | AGGACTAATC | AATCCTCCGA | ACAATGAGC | ATCACCAACT | 3750
| CCACAATCTA | CACATTCCCA | GAATCCTCTT | TCTCCGAGAA | TGGCAACATA | 3800
| GAGCCGTTAC | CACTCAAGGT | CAATGAACAG | AGAAAGGCCA | TACCTCATAT | 3850
| TAGGGTTGTC | AAGATAGGAG | ATCCGCCCAA | ACATGGATCC | AGATATCTGG | 3900
| ATGTCTTTTT | ACTGGGCTTC | TTTGAGATGG | AAAGGTCAAA | AGACAGGTAT | 3950
| GGGAGCATAA | GTGATCTAGA | TGATGATCCA | AGTTACAAGG | TTTGTGGCTC | 4000
| TGGATCATTG | CCACTTGGGT | TGGCTAGATA | CACCGGAAAT | GATCAGGAAC | 4050
| TCCTACAGGC | TGCAACCAAG | CTCGATATAG | AAGTAAGAAG | AACTGTAAAG | 4100
| GCTACGGAGA | TGATAGTTTA | CACTGTACAA | ACATCAAAC | CTGAACTATA | 4150
| TCCATGGTCC | AGTAGATTAA | GAAAAGGGAT | GTTATTTGAC | GCTAATAAGG | 4200
| TTGCACTTGC | TCCTCAATGT | CTTCCACTAG | ATAGAGGGAT | AAAATTCAGG | 4250
| GTGATATTTG | TGAACTGCAC | AGCAATTGGA | TCAATAACTC | TATTCAAAAT | 4300
| CCCTAAGTCC | ATGGCATTGT | TATCATTGCC | TAATACAATA | TCAATAAATC | 4350
| TACAAGTACA | TATCAAAACA | GGAGTTCAGA | CAGATTCCAA | AGGAGTAGTT | 4400
| CAGATTCTAG | ATGAAAAGG | TGAAAAATCA | CTAAATTTCA | TGGTTCATCT | 4450
| CGGGTTGATC | AAAAGGAAGA | TGGGCAGAAT | GTACTCAGTT | GAATATTGTA | 4500
| AGCAGAAGAT | CGAGAAGATG | AGATTATTAT | TCTCATTGGG | ATTAGTTGGA | 4550
| GGGATCAGCT | TCCACGTCAA | CGCAACTGGC | TCTATATCAA | AGACATTAGC | 4600
| AAGTCAATTA | GCATTCAAAA | GAGAAATCTG | CTATCCCCTA | ATGGATCTGA | 4650
| ATCCACACTT | AAATTCAGTT | ATATGGGCAT | CATCAGTTGA | AATTACAAGG | 4700

FIG.46B

```
GTAGATGCAG TTCTCCAGCC TTCATTACCT GGCGAATTCA GATACTACCC    4750
AAACATCATA GCAAAGGGG  TCGGGAAAAT CAGACAGTAA AATCAACAAC    4800
CCTGATATCC AACATTGCAA ATCAGGCTAC CCACAGGAGA AAAATCAAAA    4850
ACTTAGGATC AAAGGGATCA CCACGAACCC CGGAAAACAG CCAAACAAAC    4900
CAACACACAA ATCACAGACA AAAGGAGAA  GGCACTGCAA AGACCGAGAA    4950
AAAACAGAAC GCACACAACC AAGCAGAGAA AAGCCAAAGC CCGCCATTCA    5000
CAAACACACC AACAATCCTG CAAACAAGCA CCAAAACAGA GGTCAAAAGA    5050
CAAAGAGCAC CAGATATGAC CATCACAACC ACAATCATAG CCATATTACT    5100
AATACCCCCA TCATTTGTC  AAATAGACAT AACAAAACTG CAACGTGTAG    5150
GTGTGTTAGT CAACAATCCT AAAGGCATGA AGATTTCACA AAATTTCGAA    5200
ACGAGATACC TGATATTAAG TTTGATACCC AAAATAGAGA ATTCACACTC    5250
ATGTGGGGAT CAACAGATAA ACCAATACAA GAAGTTATTG GATAGATTGA    5300
TAATTCCTCT ATATGATGGA TTAAAATTAC AAAAAGATGT AATAGTAGTA    5350
AGTCATGAAA CCCACAACAA TACTAATCTT AGGACAAAAC GATTCTTTGG    5400
AGAGATAATT GGGACAATTG CGATAGGGAT AGCCACTTCA GCACAAATCA    5450
CCGCAGCAGT CGCTCTTGTC GAAGCTAAAC AGGCAAAGTC AGACATAGAA    5500
AAACTCAAAG AGGCTATAAG AGACACAAAC AAGGCAGTAC AATCGATTCA    5550
AAGTTCTGTA GGTAACCTAA TTGTTGCAGT TAAATCAGTT CAAGACTATG    5600
TCAACAATGA AATTATACCT TCAATCACAA GATTAGGCTG TGAAGCAGCA    5650
GGGTTACAAT TGGGAATTGC ATTGACACAA CATTACTCAG AATTAACAAA    5700
TATATTTGGT GATAATATAG GAACACTGAA AGAAAAAGGG ATAAAATTAC    5750
AAGGGATAGC ATCATTATAT CACACAAACA TAACGGAAAT ATTTACTACT    5800
TCAACAGTTG ACCAATATGA TATTTATGAC CTATTATTCA CTGAGTCAAT    5850
CAAGATGAGA GTGATAGATG TTGATTTGAG TGATTACTCA ATTACTCTTC    5900
AAGTTAGACT TCCTTTATTA ACTAAACTAT CAAATACTCA AATTTATAAA    5950
GTAGATTCTA TATCATACAA CATCCAGGGC AAAGAGTGG  ATATTCCTCT    6000
TCCCAATCAC ATCATGACAA AAGGGGCTTT TCTAGGTGGT GCTGATATTA    6050
AAGAATGCAT AGAGGCATTC AGCAGTTATA TATGTCCTTC TGATCCAGGT    6100
TACATATTAA ATCACGAGAT AGAGAATTGT TTATCAGGGA ACATAACACA    6150
GTGTCCTAAG ACTGTTGTTA CATCAGATGT GGTACCACGA TACGCGTTTG    6200
TGAATGGTGG ATTAATTGCA AACTGCATAA CAACTACATG TACATGCAAT    6250
GGAATTGACA ATAGAATTAA TCAATCACCT GATCAAGGAA TTAAGATCAT    6300
AACACATAAA GAATGCCAGG TAATAGGTAT AAACGGAATG TTATTCAATA    6350
CTAATAGAGA AGGGACATTA GCAACTTATA CATTTGATGA CATCATATTA    6400
AATAACTCTG TTGCACTTAA TCCAATTGAT ATATCTATGG AACTCAACAA    6450
GGCAAAACTA GAATTAGAAG AATCGAAGGA ATGGATAAAG AAATCAAATC    6500
AAAAGTTAGA TTCCGTTGGA AGTTGGTATC AATCTAGTGC AACAATCACC    6550
ATAATCATAG TGATGATAAT AATTCTAGTT ATAATCAATA TAACAATTAT    6600
TGTAGTCATA ATCAAATTCC ATAGAATTCA GGGGAAAGAT CAAAACGACA    6650
AAAACAGTGA GCCGTATATA CTGACAAATA GACAATAAGA CTATACACGA    6700
TCAAATATAA AAAGTACAAA AAACTTAGGA CAAAGTTGT  CAACACAGC    6750
AGCACCGAAT AGACCAAAAG GCAGCGCAGA GGCGACACCA AACTCAAAAA    6800
TGGAATATTG GAAACACACA AACAGCATAA ATAACACCAA CAATGAAACC    6850
GAAACAGCCA GAGGCAAACA TAGTAGCAAG GTTACAAATA TCATAATGTA    6900
CACCTTCTGG ACAATAACAT TAACAATATT ATCAGTCATT TTTATAATGA    6950
TATTGACAAA CTTAATTCAA GAGAACAATC ATAATAAATT AATGTTGCAG    7000
GAAATAAGAA AAGAATTCGC GGCAATAGAC ACCAAGATTC AGAGGACTTC    7050
```

FIG.46C

```
GGATGACATT GGAACCTCAA TACAGTCAGG AATAAATACA AGACTTCTCA    7100
CAATTCAGAG TCATGTTCAA AACTATATCC CACTATCATT AACACAACAA    7150
ATGTCAGATC TCAGAAAATT TATCAATGAT CTAACAAATA AAGAGAACA     7200
TCAAGAAGTG CCAATACAGA GAATGACTCA TGATAGAGGT ATAGAACCCC    7250
TAAATCCAAA CAAGTTCTGG AGGTGTACAT CTGGTAACCC ATCTCTAACA    7300
AGTAGTCCTA AGATAAGGTT AATACCAGGA CCAGGTTTAT TAGCAACATC    7350
TACTACAGTA AATGGCTGTA TTAGAATTCC ATCGTTAGTA ATCAATCATC    7400
TAATCTATGC TTACACCTCT AATCTTATTA CCCAGGGCTG TCAAGATATA    7450
GGGAAATCTT ACCAAGTACT ACAAATAGGG ATAATTACTA TAAATTCGGA    7500
CCTAGTACCT GATTTAAACC CCAGAGTCAC ACATACATTT AATATTGATG    7550
ATAATAGAAG ATCTTGCTCT CTGGCACTAT TGAATACAGA TGTTTATCAG    7600
TTATGCTCAA CACCAAAAGT TGATGAAAGA TCCGATTATG CATCAACAGG    7650
TATTGAGGAT ATTGTACTTG ACATTGTCAC TAATAATGGA TTAATTATAA    7700
CAACAAGGTT TACAAATAAT AATATAACTT TTGATAAACC GTATGCAGCA    7750
TTGTATCCAT CAGTGGGACC AGGAATCTAT TATAAGGATA AGTTATATT     7800
TCTCGGATAT GGAGGTCTAG AGCATGAAGA AAACGGAGAC GTAATATGTA    7850
ATACAACTGG TTGTCCTGGC AAAACACAGA GAGACTGTAA TCAGGCTTCT    7900
TATAGCCCAT GGTTCTCAAA TAGGAGAATG GTAAACTCTA TTATTGTTGT    7950
TGATAAAGGC ATAGATGCAA CTTTTAGCTT GAGGGTGTGG ACTATTCCAA    8000
TGAGCCAAAA TTATTGGGGA TCAGAAGGAA GATTACTTTT ATTAGGTGAC    8050
AGAATATACA TATATACTAG ATCCACAAGT TGGCACAGTA AATTACAGTT    8100
AGGGGTAATT GATATTTCTG ATTATACTAA TATAAGAATA AATTGGACTT    8150
GGCATAATGT ACTATCACGG CCAGGGAATG ATGAATGTCC ATGGGGTCAT    8200
TCATGCCCAG ACGGATGTAT AACAGGAGTT TACACTGATG CATATCCGCT    8250
AAACCCATCG GGGAGTGTTG TATCATCAGT AATTCTTGAT TCACAAAAGT    8300
CTAGAGAAAA CCCAATCATT ACTTACTCAA CAGCTACAAA TAGAATAAAT    8350
GAATTAGCTA TATATAACAG AACACTTCCA GCTGCATATA CAACAACAAA    8400
TTGTATCACA CATTATGATA AAGGGTATTG TTTTCATATA GTAGAAATAA    8450
ATCACAGAAG TTTGAATACG TTTCAACCTA TGTTATTCAA AACAGAAGTT    8500
CCAAAAAACT GCAGCTAAAT TGATCATCGC ATATCGGATG CAAGATGACA    8550
TTAAAAGAGA CCACCAGACA GACAACACAG GAGACGATGC AAGATATAAA    8600
GAAATAATAA AAAACTTAGG AGAAAAGTGT GCAAGAAAAA TGGACACCGA    8650
GTCCACAGC GGCACAACAT CTGACATTCT GTACCTGAA TGTCACCTCA      8700
ATTCTCCTAT AGTTAAAGGA AAGATAGCAC AACTGCATAC AATAATGAGT    8750
TTGCCTCAGC CCTACGATAT GGATGATGAT TCAATACTGA TTATTACTAG    8800
ACAAAAAATT AAACTCAATA AATTAGATAA AGACAACGG TCAATTAGGA     8850
AATTAAGATC AGTCTTAATG GAAAGAGTAA GTGATCTAGG TAAATATACC    8900
TTTATCAGAT ATCCAGAGAT GTCTAGTGAA ATGTTCCAAT TATGTATACC    8950
CGGAATTAAT AATAAAATAA ATGAATTGCT AAGTAAAGCA AGTAAAACAT    9000
ATAATCAAAT GACTGATGGA TTAAGAGATC TATGGGTTAC TATACTATCG    9050
AAGTTAGCAT CGAAAAATGA TGGAAGTAAT TATGATATCA ATGAAGATAT    9100
TAGCAATATA TCAAATGTTC ACATGACTTA TCAATCAGAC AAATGGTATA    9150
ATCCATTCAA GACATGGTTT ACTATTAAGT ATGACATGAG AAGATTACAA    9200
AAAGCCAAAA ATGAGATTAC ATTCAATAGG CATAAAGATT ATAATCTATT    9250
AGAAGACCAA AAGAATATAT TGCTGATACA TCCAGAACTC GTCTTAATAT    9300
TAGATAAACA AAATTACAAT GGGTATATAA TGACTCCTGA ATTGGTACTA    9350
ATGTATTGTG ATGTAGTTGA AGGGAGGTGG AATATAAGTT CATGTGCAAA    9400
```

FIG.46D

```
ATTGGATCCT AAGTTACAAT CAATGTATTA TAAGGGTAAC AATTTATGGG      9450
AAATAATAGA TGGACTATTC TCGACCTTAG GAGAAAGAAC ATTTGACATA      9500
ATATCACTAT TAGAACCACT TGCATTATCG CTCATTCAAA CTTATGACCC      9550
GGTTAAACAG CTCAGGGGGG CTTTTTTAAA TCACGTGTTA TCAGAAATGG      9600
AATTAATATT TGCAGCTGAG TGTACAACAG AGGAAATACC TAATGTGGAT      9650
TATATAGATA AAATTTAGA TGTGTTCAAA GAATCAACAA TAGATGAAAT       9700
AGCAGAAATT TTCTCTTTCT TCCGAACTTT TGGACACCCT CCATTAGAGG      9750
CGAGTATAGC AGCAGAGAAA GTTAGAAAGT ATATGTATAC TGAGAAATGC      9800
TTGAAATTTG ATACTATCAA TAAATGTCAT GCTATTTTTT GTACAATAAT      9850
TATAAATGGA TATAGAGAAA GACATGGTGG TCAATGGCCT CCAGTTACAT      9900
TACCTGTCCA TGCACATGAA TTTATCATAA ATGCATACGG ATCAAATTCT      9950
GCCATATCAT ATGAGAATGC TGTAGATTAT TATAAGAGCT TCATAGGAAT     10000
AAAATTTGAC AAGTTTATAG AGCCTCAATT GGATGAAGAC TTAACTATTT     10050
ATATGAAAGA TAAAGCATTA TCCCCAAAGA ATCAAACTG GGACACAGTC      10100
TATCCAGCTT CAAACCTGTT ATACCGCACT AATGTGTCTC ATGATTCACG     10150
AAGATTGGTT GAAGTATTTA TAGCAGATAG TAAATTTGAT CCCCACCAAG     10200
TATTAGATTA CGTAGAATCA GGATATTGGC TGGATGATCC TGAATTTAAT     10250
ATCTCATATA GTTAAAAGA GAAAGAAATA AAACAAGAAG GTAGACTTTT      10300
TGCAAAAATG ACATACAAGA TGAGGGCTAC ACAAGTATTA TCAGAAACAT     10350
TATTGGCGAA TAATATAGGG AAATTCTTCC AAGAGAATGG GATGGTTAAA     10400
GGAGAAATTG AATTACTCAA GAGACTAACA ACAATATCTA TGTCTGGAGT     10450
TCCGCGGTAT AATGAGGTAT ACAATAATTC AAAAGTCAC ACAGAAGAAC      10500
TTCAAGCTTA TAATGCAATT AGCAGTTCCA ATTTATCTTC TAATCAGAAG     10550
TCAAAGAAGT TTGAATTTAA ATCTACAGAT ATATACAATG ATGGATACGA     10600
AACCGTAAGC TGCTTCTTAA CGACAGATCT TAAAAAATAT TGTTTAAATT     10650
GGAGGTATGA ATCAACAGCT TTATTCGGTG ATACTTGTAA TCAGATATTT     10700
GGGTTAAAGG AATTATTTAA TTGGCTGCAC CCTCGCCTTG AAAAGAGTAC     10750
AATATATGTT GGAGATCCTT ATTGCCCGCC ATCAGATATT GAACATTTAC     10800
CACTTGATGA CCATCCTGAT TCAGGATTTT ATGTTCATAA TCCTAAAGGA     10850
GGAATAGAAG GGTTTTGCCA AAAGTTATGG ACACTCATAT CTATCAGTGC     10900
AATACATTTA GCAGCTGTCA AAATCGGTGT AAGAGTTACT GCAATGGTTC     10950
AAGGGGATAA TCAAGCCATA GCTGTTACCA CAAGAGTACC TAATAATTAT     11000
GATTATAAAG TTAAGAAAGA GATTGTTTAT AAAGATGTGG TAAGATTTTT     11050
TGATTCCTTG AGAGAGGTGA TGGATGATCT GGGTCATGAG CTCAAACTAA     11100
ATGAAACTAT AATAAGTAGT AAAATGTTTA TATATAGCAA AAGGATATAC     11150
TATGACGGAA GAATCCTTCC TCAGGCATTA AAAGCATTGT CTAGATGTGT     11200
TTTTTGGTCT GAAACAATCA TAGATGAGAC AAGATCAGCA TCCTCAAATC     11250
TGGCTACATC GTTTGCAAAG GCCATTGAGA ATGGCTACTC ACCTGTATTG     11300
GGATATGTAT GCTCAATCTT CAAAAATATC CAACAGTTGT ATATAGCGCT     11350
TGGAATGAAT ATAAACCCAA CTATAACCCA AAATATTAAA GATCAATATT     11400
TCAGGAATAT TCATTGGATG CAATATGCCT CCTTAATCCC TGCTAGTGTC     11450
GGAGGATTTA ATTATATGGC CATGTCAAGG TGTTTTGTCA GAAACATTGG     11500
AGATCCTACA GTCGCTGCGT TAGCCGATAT TAAAAGATTT ATAAAAGCAA     11550
ATTTGTTAGA TCGAGGTGTC CTTTACAGAA TTATGAATCA AGAACCAGGC     11600
GAGTCTTCTT TTTTAGACTG GGCCTCAGAT CCCTATTCAT GTAACTTACC     11650
ACAATCTCAA AATATAACCA CCATGATAAA GAATATAACT GCAAGAAATG     11700
TACTACAGGA CTCACCAAAC CCATTACTAT CTGGATTATT TACAAGTACA     11750
```

FIG.46E

```
ATGATAGAAG AGGATGAGGA ATTAGCTGAG TTCCTAATGG ACAGGAGAAT    11800
AATCCTCCCA AGAGTTGCAC ATGACATTTT AGATAATTCT CTTACTGGAA    11850
TTAGGAATGC TATAGCTGGT ATGTTGGATA CAACAAAATC ACTAATTCGA    11900
GTAGGGATAA GCAGAGGAGG ATTAACCTAT AACTTATTAA GAAAGATAAG    11950
CAACTATGAT CTTGTACAAT ATGAGACACT TAGTAAAACT TTAAGACTAA    12000
TAGTCAGTGA CAAGATTAAG TATGAAGATA TGTGCTCAGT AGACCTAGCC    12050
ATATCATTAA GACAAAAAAT GTGGATGCAT TTATCAGGAG GAAGAATGAT    12100
AAATGGACTT GAAACTCCAG ATCCTTTAGA GTTACTGTCT GGAGTAATAA    12150
TAACAGGATC TGAACATTGT AGGATATGTT ATTCAACTGA AGGTGAAAGC    12200
CCATATACAT GGATGTATTT ACCAGGCAAT CTTAATATAG GATCAGCTGA    12250
GACAGGAATA GCATCATTAA GGGTCCCTTA CTTTGGATCA GTTACAGATG    12300
AGAGATCTGA AGCACAATTA GGGTATATCA AAATCTAAG CAAACCAGCT     12350
AAGGCTGCTA TAAGAATAGC AATGATATAT ACTTGGGCAT TTGGGAATGA    12400
CGAAATATCT TGGATGGAAG CATCACAGAT TGCACAAACA CGTGCAAACT    12450
TTACATTGGA TAGCTTAAAG ATTTTGACAC CAGTGACAAC ATCAACAAAT    12500
CTATCACACA GGTTAAAAGA TACTGCTACT CAGATGAAAT TTTCTAGTAC    12550
ATCACTTATT AGAGTAAGCA GGTTCATCAC AATATCTAAT GATAATATGT    12600
CTATTAAAGA AGCAAATGAA ACTAAAGATA CAAATCTTAT TTATCAACAG    12650
GTAATGTTAA CAGGATTAAG TGTATTTGAA TATCTATTTA GGTTAGAGGA    12700
GAGTACAGGA CATAACCCTA TGGTCATGCA TCTACATATA GAGGATGGAT    12750
GTTGTATAAA AGAGAGTTAC AATGATGAGC ATATCAATCC GGAGTCTACA    12800
TTAGAGTTAA TCAAATACCC TGAGAGTAAT GAATTTATAT ATGATAAGGA    12850
CCCTTTAAAG GATATAGATC TATCAAAATT AATGGTTATA AGAGATCATT    12900
CTTATACAAT TGACATGAAT TACTGGATG ACACAGATAT TGTACATGCA     12950
ATATCAATAT GTACTGCAGT TACAATAGCA GATACAATGT CGCAGCTAGA    13000
TCGGGATAAT CTTAAGGAGC TGGTTGTGAT TGCAAATGAT GATGATATTA    13050
ACAGTCTGAT AACTGAATTT CTGACCCTAG ATATACTAGT GTTTCTCAAA    13100
ACATTTGGAG GGTTACTCGT GAATCAATTT GCATATACCC TTTATGGATT    13150
GAAAATAGAA GGAAGGGATC CCATTTGGGA TTATATAATG AGAACATTAA    13200
AAGACACCTC ACATTCAGTA CTTAAAGTAT TATCTAATGC ACTATCTCAT    13250
CCAAAAGTGT TTAAGAGATT TTGGGATTGT GGAGTTTTGA ATCCTATTTA    13300
TGGTCCTAAT ACTGCTAGTC AAGATCAAGT TAAGCTTGCT CTCTCGATTT    13350
GCGAGTACTC CTTGGATCTA TTTATGAGAG AATGGTTGAA TGGAGCATCA    13400
CTTGAGATCT ATATCTGTGA TAGTGACATG GAAATAGCAA ATGACAGAAG    13450
ACAAGCATTT CTCTCAAGAC ATCTTGCCTT TGTGTGTTGT TTAGCAGAGA    13500
TAGCATCTTT TGGACCAAAT TTATTAAATC TAACATATCT AGAGAGACTT    13550
GATGAATTAA AACAATACTT AGATCTGAAC ATCAAAGAAG ATCCTACTCT    13600
TAAATATGTG CAAGTATCAG GACTGTTAAT TAAATCATTC CCCTCAACTG    13650
TTACGTATGT AAGGAAAACT GCGATTAAGT ATCTGAGGAT TCGTGGTATT    13700
AATCCGCCTG AAACGATTGA AGATTGGGAT CCCATAGAAG ATGAGAATAT    13750
CTTAGACAAT ATTGTTAAAA CTGTAAATGA CAATTGCAGT GATAATCAAA    13800
AGAGAAATAA AAGTAGTTAT TTCTGGGGAT TAGCTCTAAA GAATTATCAA    13850
GTCGTGAAAA TAAGATCCAT AACGAGTGAT TCTGAAGTTA ATGAAGCTTC    13900
GAATGTTACT ACACATGGAA TGACACTTCC TCAGGAGGA AGTTATCTAT     13950
CACATCAGCT GAGGTTATTT GGAGTAAACA GTACAAGTTG TCTTAAAGCT    14000
CTTGAATTAT CACAAATCTT AATGAGGGAA GTTAAAAAG ATAAAGATAG     14050
ACTCTTTTTA GGAGAAGGAG CAGGAGCTAT GTTAGCATGT TATGATGCTA    14100
```

FIG.46F

```
CACTCGGTCC TGCAATAAAT TATTATAATT CTGGTTTAAA TATTACAGAT    14150
GTAATTGGTC AACGGGAATT AAAAATCTTC CCATCAGAAG TATCATTAGT    14200
AGGTAAAAAA CTAGGAAATG TAACACAGAT TCTTAATCGG GTGAGGGTGT    14250
TATTTAATGG GAATCCCAAT TCAACATGGA TAGGAAATAT GGAATGTGAG    14300
AGTTTAATAT GGAGTGAATT AAATGATAAG TCAATTGGTT TAGTACATTG    14350
TGACATGGAG GGAGCGATAG GCAAATCAGA AGAAACTGTT CTACATGAAC    14400
ATTATAGTAT TATTAGGATT ACATATTTAA TCGGGGATGA TGATGTTGTC    14450
CTAGTATCAA AAATTATACC AACTATTACT CCGAATTGGT CTAAAATACT    14500
CTATCTATAC AAGTTGTATT GGAAGGATGT AAGTGTAGTG TCCCTTAAAA    14550
CATCCAATCC TGCCTCAACA GAGCTTTATT TAATTTCAAA AGATGCTTAC    14600
TGTACTGTAA TGGAACCCAG TAATCTTGTT TTATCAAAAC TTAAAAGGAT    14650
ATCATCAATA GAAGAAAATA ATCTATTAAA GTGGATAATC TTATCAAAAA    14700
GGAAGAATAA CGAGTGGTTA CAGCATGAAA TCAAGAAGG AGAAAGGGAT     14750
TATGGGATAA TGAGGCCATA TCATACAGCA CTGCAAATTT TTGGATTCCA    14800
AATTAACTTA AATCACTTAG CTAGAGAATT TTTATCAACT CCTGATTTAA    14850
CCAACATTAA TAATATAATT CAAAGTTTTA CAAGAACAAT TAAAGATGTT    14900
ATGTTCGAAT GGGTCAATAT CACTCATGAC AATAAAAGAC ATAAATTAGG    14950
AGGAAGATAT AATCTATTCC CGCTTAAAAA TAAGGGGAAA TTAAGATTAT    15000
TATCACGAAG ATTAGTACTA AGCTGGATAT CATTATCCTT ATCAACCAGA    15050
TTACTGACGG GCCGTTTTCC AGATGAAAAA TTTGAAAATA GGGCACAGAC    15100
CGGATATGTA TCATTGGCTG ATATTGATTT AGAATCCTTA AAGTTATTAT    15150
CAAGAAATAT TGTCAAAAAT TACAAGAAC ACATAGGATT AATATCATAC     15200
TGGTTTTTGA CCAAAGAGGT CAAAATACTA ATGAAGCTTA TAGGAGGAGT    15250
CAAACTACTA GGAATTCCTA AACAGTACAA AGAGTTAGAG GATCGATCAT    15300
CTCAGGGTTA TGAATATGAT AATGAATTTG ATATTGATTA ATACATAAAA    15350
ACATAAAATA AAACACCTAT TCCTCACCCA TTCACTTCCA ACAAAATGAA    15400
AAGTAAGAAA AACATGTAAT ATATATATAC CAAACAGAGT TTTTCTCTTG    15450
TTTGGT                                                    15456
```

FIG.46G

```
ACCAAACAAG AGAAGAGACT TGCTTGGGAA TATTAATTCA AATAAAAATT      50
AACTTAGGAT TAAAGAACTT TACCGAAAGG TAAGGGGAAA GAAATCCTAA     100
GACTGTAATC ATGTTGAGTC TATTCGACAC ATTCAGTGCG CGTAGGCAGG     150
AGAACATAAC AAAATCAGCT GGTGGGGCTG TTATTCCCGG GCAAAAAAAC     200
ACTGTGTCTA TATTTGCTCT TGGACCATCA ATAACAGATG ACAATGACAA     250
AATGACATTG GCTCTTCTCT TTTTGTCTCA TTCTTTAGAC AATGAAAAGC     300
AGCATGCGCA AAGAGCTGGA TTTTAGTTT CTCTGTTATC AATGGCTTAT      350
GCCAACCCAG AATTATATTT AACATCAAAT GGTAGTAATG CAGATGTTAA     400
ATATGTCATC TACATGATAG AGAAAGACCC AGGAAGACAG AAATATGGTG     450
GGTTTGTCGT CAAGACTAGA GAGATGGTTT ATGAAAAGAC AACTGACTGG     500
ATGTTTGGGA GTGATCTTGA GTATGATCAA GACAATATGT TGCAAAATGG     550
TAGAAGCACT TCTACAATCG AGGATCTTGT TCATACTTTT GGATATCCAT     600
CGTGTCTTGG AGCCCTTATA ATCCAGGTTT GGATAATACT TGTTAAGGCT     650
ATAACCAGTA TATCAGGATT GAGGAAAGGA TTCTTTACTC GGTTAGAAGC     700
ATTTCGACAA GATGGAACAG TTAAATCCAG TCTAGTGTTG AGCGGTGATG     750
CAGTAGAACA AATTGGATCA ATTATGAGGT CCCAACAGAG CTTGGTAACA     800
CTCATGGTTG AAACACTGAT AACAATGAAC ACAGGCAGGA ATGACCTGAC     850
AACAATAGAA AAGAATATAC AGATTGTAGG AAACTACATC AGAGATGCAG     900
GTCTTGCTTC ATTTTCAAC ACAATCAGAT ATGGCATTGA GACTAGAATG       950
GCAGCTCTAA CTCTGTCTAC CCTTAGACCG GACATCAACA GACTCAAGGC    1000
ACTGATAGAG CTATATCTAT CAAAGGGGCC ACGTGCTCCT TTTATATGCA    1050
TTTTGAGAGA TCCTGTGCAT GGTGAGTTTG CACCAGGCAA CTATCCTGCC    1100
CTCTGGAGTT ATGCGATGGG TGTAGCAGTT GTACAAAACA AGGCCATGCA    1150
ACAGTATGTA ACAGGAAGGT CCTATCTGGA TATTGAAATG TTCCAACTGG    1200
GTCAAGCAGT GGCACGTGAC GCCGAGTCGC AGATGAGTTC AATATTAGAG    1250
GATGAACTGG GGTCACACA AGAAGCCAAG CAAAGCTTGA AGAAACACAT      1300
GAAGAACATC AGCAGTTCAG ATACAACCTT CTATAAGCCT ACAGGGGGAT    1350
CAGCCATAGA AATGGCAATA GATGAGGAAG CAGAGCAGCC CGAATCCAGA    1400
GGAGACCAAG ACCAAGGAGA TGAACCTCGG TCATCCATAG TTCCTTATGC    1450
ATGGGCAGAC GAAACCGGGA ATGACAACCA AACTGAATCA ACCACAGAAA    1500
TTGACAGCAT CAAAACTGAA CAAAGAAACA TCAGAGACAG GCTGAACAAA    1550
AGACTCAACG AGAAAAGGAA ACAGAGTAAC CCGGGATCAA CTGACATCAC    1600
AAACAACACA AATCAAACTG AAATAGATGA TTTATTCAGT GCATTCGGAA    1650
GCAACTAGTC ACAAAGAGAT GACCACCATC ATCAGCAACA AGTAAGAAAA    1700
ACTTAGGATT AATGGAAATT ATCCAATCCG GAGACGGAAG GACAAATCCA    1750
GAATCCAACC ACAACTCAAT CAACCAAAGA TTCATGGAAG ACAATGTTCA    1800
AAACAATCAA ATCATGGATT CTTGGGAAGA GGGATCAGGA GATAAATCAT    1850
CTGACATCTC ATCGGCCCTC GACATCATTG AATTCATACT CAACACCGAC    1900
TCCCAAGAGA ACACGGCAGA CAGCAATGAA ATCAACACAG GAGCCACAAG    1950
ACTTAGCACG ACAATCTACC AACTTGAGTC CAAAACAACA GAAACAAGCA    2000
AGGAAAATAG TGGACCAGCT AACAAAAATC GACAGTTTGG GGCATCACAC    2050
GAACGTGCCA CAGAGACAAA AGATAGAAAT GTTAATCAGA AGACTGTACA    2100
GGGAGGATAT AGGAGAGGAA GCAGCCCAGA TAGTAGAACT GAGACTATGG    2150
TCACTCGAGG AATCTCCAGA AGCAGCCCAG ATCCTAACAA TGGAACCCAA    2200
ATCCAGGAAG ATATTGATTA CAATGAAGTT GGAGAGATGG ATAAGGACTC    2250
TACTAAGAGG GAAATGCGAC AATTTAAAGA TGTTCCAGTC AAGGTATCAG    2300
GAAGTGATGC CATTCCTCCA ACAAAACAAG ATGGAGACGG TGATGATGGA    2350
```

FIG.47A

```
AGAGGCCTGG AATCTATCAG TACATCTGAT TCAGGATATA CCAGTATAGT    2400
GACTGCCGCA ACACTAGATG ACGAAGAAGA ACTCCTTATG AAGAACAACA    2450
GGCCAAGAAA GTATCAATCA ACACCCCAGA ACAGTGACAA GGGAATTAAA    2500
AAAGGGAGTG GAAGGCCAAA AGACACAGAC AAACAATCAC CAATATTGGA    2550
CTACGAACTC AACTCCAAAG GATCGAAGAA GAGCCAGAAA ATCCTCAAAG    2600
CCAGCACGAA TACAGGAGAA CCAACAAGAT CACAGAGTGG ATCCCAGGGG    2650
AAGAGAATCA CATCCTGGAA CATCCTCAAC AGCGAGAGCG GCAATCGAGC    2700
AGAATCAACA AACCAAACCC ATCAGACATC AATCTCGGGA CAGAACCACA    2750
CAATGGGACC AAGCAGAACA ACCTCAGAAC CAAGGACCAA GACACAAAAG    2800
ACGGATGGAA AGGAAAGAGA GGACACAGAA GAGAGCACTC GATTTACAGA    2850
AAGGGCGATT ACATTATTAC AGAATCTTGG TGTAATCCAA TCTGCAGCAA    2900
AATTAGACCT ATACCAAGAC AAGAGAGTTG TGTGTGTGGC GAATGTCCTA    2950
AACAATGCAG ATACTGCATC AAAGATAGAC TTCCTAGCAG GTTTGATGAT    3000
AGGAGTGTCA ATGGATCATG ATGTCAAATT AAATCAGATT CAGAACGAGA    3050
TATTAAGTTT AAAAACTGAT CTTAAGAAGA TGGATGAATC ACATAGAAGA    3100
CTAATTGAGA ATCAAAAAGA ACAATTATCA CTGATCACAT CATTAATCTC    3150
AAATCTTAAA ATCATGACAG AGAGGAGG GAAGAAGGAC CAACCAGAAC      3200
CTAGCGGGAG GACATCCATG ATCAAGACAA AGGCAAAGA AGAGAGAATA     3250
AAGAAAGTCA GGTTTGACCC TCTTATGGAA ACACAGGGCA TCGAGAAAAA    3300
CATCCCTGAC CTCTACAGAT CAATAGAGAA ACACCAGAA AACGACACAC     3350
AGATCAAATC AGAAATAAAC AGATTGAATG ATGAATCCAA TGCCACTAGA    3400
TTAGTACCTA GAAGAATAAG CAGTACAATG AGATCACTAA TAATAATCAT    3450
CAACAACAGC AATTTATCAT CAAAAGCAAA GCAATCATAC ATCAACGAAC    3500
TCAAGCTCTG CAAGAGTGAT GAGGAAGTGT CTGAGTTGAT GGACATGTTC    3550
AATGAGGATG TCAGCTCCCA GTAAACCGCC AACCAAGGGT CAACACCAAG    3600
AAAACCAACA GCACAAAACA GCCAATAAGA GACCATCCCA ACACACCGAA    3650
CCAATCAACA CATAACAAAG ATCTTTAGAT CATAGATGAC TAAGAAAAAC    3700
TTAGGATGAA AGGACTGATC AATCCTCCAA AACAATGAGC ATCACCAGCT    3750
CCACAATCTA CACATTCCCA GAATCCTCTT TCTCCGAGAA TGGCAACATA    3800
GAGCCGTTAC CACTCAAGGT CAATGAACAG AGAAAGGCCA TACCTCATAT    3850
TAGGGTTGTC AAGATAGGAG ATCCGCCCAA ACATGGATCC AGATATCTGG    3900
ATGTCTTTTT ACTGGGCTTC TTTGAAATGG AAAGGTCAAA AGACAGGTAT    3950
GGGAGCATAA GTGATCTAGA TGATGATCCA AGTTACAAGG TTTGTGGCTC    4000
TGGATCATTG CCACTTGGGT TGGCTAGATA CACTGGAAAT GATCAGGAAC    4050
TCCTACAGGC TGCAACCAAG CTCGATATAG AAGTAAGAAG AACTGTAAAG    4100
GCTACGGAGA TGATAGTTTA CACTGTGCAA AACATCAAAC CTGAACTATA    4150
TCCATGGTCC AGTAGATTAA GAAAAGGGAT GTTATTTGAC GCTAACAAGG    4200
TTGCACTTGC TCCTCAATGT CTTCCACTAG ATAGAGGGAT AAAATTCAGG    4250
GTGATATTTG TGAACTGCAC AGCAATTGGA TCAATAACTC TATTCAAAAT    4300
CCCCAAGTCC ATGGCATTGT TATCATTGCC TAATACAATA TCAATAAATC    4350
TACAAGTACA TATCAAAACA GGAATTCAGA CAGATTCCAA AGGAGTAGTT    4400
CAGATTCTAG ATGAAAAGG TGAAAAATCA CTAAATTTCA TGGTTCATCT    4450
CGGGTTGATC AAAAGGAAGA TGGGTAGAAT GTACTCAGTT GAATATTGTA    4500
AGCAGAAGAT TGAGAAGATG AGATTATTAT TCTCATTGGG ATTAGTTGGA    4550
GGGATCAGCT TCCACGTCAA CGCAACTGGC TCTATATCAA AGACATTAGC    4600
AAGTCAATTA GCATTTAAAA GAGAAATCTG CTATCCCCTA ATGGATCTGA    4650
ATCCACACTT AAATTTAGTT ATATGGGCAT CATCAGTTGA AATTACAAGA    4700
```

FIG.47B

```
GTAGATGCAA TTCTCCAGCC TTCATTACCT GGCGAATTCA GATACTACCC  4750
AAACATCATA GCAAAGGGG  TCGGGAAAAT CAGACAGTAA AACCAACAAC   4800
CCTGACATCC AACACTGCAA ATCAGGCTAC CCACAGGAGA AAAATCAAAA  4850
ACTTAGGATC AAAGGGATCA CCACAAACCC CGGGAAACAG CCAAACCAAC  4900
CAACACACAA ATCACAGACA AAAGGAAAA  GGCACTGCAA AGACCGAGAA   4950
CAAGCAGAAC GCACACAACC AAGCAGAGGA AAGCCAAAGC CCGCCATTCA  5000
CAAACACACC AACAATCCTA CAAACAAGCA CCAAAATAGA GGTCAAAAGA  5050
CAAAGAGCAT CAGATATGAC CATCACAACC ATAATCATAG CCATACTACT  5100
AATACCCCTA TCATTCTGTC AAATAGACAT AACAAAACTG CAACGTGTAG  5150
GTGTATTAGT CAACAATCCC AAAGGCATGA AATTTCACA  AAATTTGAA    5200
ACGAGATACC TGATATTAAG TCTGATACCC AAAATAGAGA ATTCACACTC  5250
ATGTGGGGAT CAACAGATAA ACCAATACAA GAAGTTATTG GATAGATTGA  5300
TAATTCCTCT ATATGATGGA TTAAAATTAC AAAAAGATGT AATAGTAGTA  5350
AGTCATGAAA CCCATAATAA TACTAATCTT AGGACAAAAC GATTCTTTGG  5400
AGAGATAATT GGGACAATTG CGATAGGGAT AGCCACCTCA GCGCAAATCA  5450
CCGCAGCAGT CGCTCTTGTC GAAGCTAAAC AGGCAAGGTC AGACATAGAA  5500
AAACTCAAAG AAGCTATAAG AGACACAAAC AAGGCAGTAC AATCGATTCA  5550
AGTTCTGTA  GGTAACCTAA TTGTTGCAGT TAAATCAGTT CAAGACTATG  5600
TCAACAATGA AATTGTACCT TCAATCACAA GATTAGGCTG TGAAGCAGCA  5650
GGGTTACAAT GGGAATTGC  ACTGACACAA CATTACTCAG AATTAACAAA   5700
TATATTTGGT GATAATATAG GAACACTGAA AGAAAAGGG  ATAAAATTAC   5750
AGGGGATAGC ATCGTTATAT CATACAAACA TAACAGAAAT ATTTACTACT  5800
TCAACAGTTG ACCAATATGA TATTTATGAC CTATTATTCA CTGAATCAAT  5850
CAAGATGAGA GTGATAGATG TTGATTTGAG TGATTACTCA ATTACTCTTC  5900
AAGTTAGACT TCCTTTATTA ACTAAACTAT CAAATACTCA GATTTATAAA  5950
GTAGATTCTA TATCATACAA CATCCAGGGC AAAGAGTGGT ATATTCCTCT  6000
TCCCAATCAC ATCATGACAA AAGGGGCTTT TCTAGGTGGT GCTGATATTA  6050
AAGAATGCAT AGAGGCATTC AGCAGTTATA TATGTCCTTC TGATCCAGGT  6100
TATATATTAA ATCACGAGAT AGAGAATTGT TTATCAGGA  ACATAACACA   6150
GTGTCCTAAG ACTGTTGTTA CATCAGATGT GGTACCACGA TACGCGTTTG  6200
TGAATGGTGG ATTAATTGCA AACTGCATAA CAACTACATG TACATGCAAT  6250
GGAATTGACA ATAGAATTAA TCAATCACCT GATCAAGGAA TTAAGATCAT  6300
AACACATAAA GAATGCCAGG TAATAGGTAT AAACGGAATG TTATTCAATA  6350
CTAATAGAGA AGGGACATTA GCAACTTATA CATTTGATGA CATTATATTA  6400
AATAACTCTG TTGCACTTAA TCCAATTGAT ATATCTATGG AACTTAACAA  6450
GGCAAAACTA GAATTAGAAG AATCGAAGGA ATGGATAAAG AAATCAAATC  6500
AAAAGTTAGA TTCCGTTGGA AGTTGGTATC AATCTAGTGC AACAATCACC  6550
ATAATCATAG TGATGATAAT AATTCTATTT ATAATCAATA TAACAATTAT  6600
TGTAGTCATA ATCAAATTCT ATAGAATTAA GGGGGAAAAT CAAAACGACA  6650
AAAACAGTGA GCCGTATATA CTGACAAATA GACAATAAGA CTATACACGA  6700
TCAAATATAG AAAGTACAAA AAACTTAGGA ACAAGTTGT  TCAACACAGC   6750
AGCAGCGAAC AGACCCAAAG GCAGCGCAGA GGCGACACCG AACCCAAAAA  6800
TGGAATATTG GAAACACACA AACAGCACAA AAAACACCAA CAATGAAACC  6850
GAAACAACCA GAGGCAAACA CAGTAGCAAG GTTACAAATA TCATAATGTA  6900
CACCTTCTGG ACAATAACAT CAACAATATT ATTAGTCATT TTTATAATGA  6950
TATTGACAAA CTTAATTCAA GAGAACAATC ATAATAAATT AATGTTGCAG  7000
GAAATAAGAA AAGAATTCGC GGCAATAGAC ACCAAGATTC AGAGGACCTC  7050
```

FIG.47C

```
GGATGACATT GGAACCTCAA TACAGTCAGG AATAAATACA AGACTTCTCA    7100
CAATTCAGAG TCATGTTCAA AACTATATCC CACTATCACT AACACAACAA    7150
ATGTCAGATC TCAGAAAATT TATCAATGAT CTAACAAATA AAGAGAACA     7200
TCAAGAAGTG CCAATACAGA GAATGACTCA TGATAGAGGT ATAGAACCCC    7250
TAAATCCAGA CAAGTTCTGG AGGTGTACAT CTGGTAACCC ATCTCTAACA    7300
AGTAGTCCTA AGATAAGGTT AATACCAGGG CCAGGTTTAT TAGCAACATC    7350
TACTACAGTA AATGGCTGTA TTAGAATCCC ATCGTTAGCA ATCAATCATT    7400
TAATCTACGC TTACACCTCT AATCTTATCA CCCAGGGCTG TCAAAATATA    7450
GGGAAATCTT ACCAAGTACT ACAAATAGGG ATAATTACTA TAAATTCGGA    7500
CCTAGTACCT GATTTAAATC CCAGAGTCAC ACATACATTT AATATTGATG    7550
ATAATAGGAA ATCTTGCTCT CTGGCACTAT TGAATACAGA TGTTTATCAG    7600
TTATGCTCAA CACCAAAAGT TGATGAGAGA TCCGATTATG CATCAACAGG    7650
TATTGAGGAT ATTGTACTTG ACATTGTCAC TAATAATGGA TTAATTATAA    7700
CAACAAGGTT TACAAATAAT AATATAACTT TTGATAAACC GTATGCAGCA    7750
TTGTATCCAT CAGTAGGACC AGGAATCTAT TATAAGGGTA AGTTATATT     7800
TCTCGGATAT GGAGGTCTAG AGCATGAAGA AAACGGAGAC GTAATATGTA    7850
ATACAACTGG TTGTCCTGGC AAAACACAGA GAGACTGTAA TCAGGCTTCT    7900
TATAGCCCAT GGTTCTCAAA TAGGAGAATG GTAAACTCTA TTATTGTTGT    7950
TGATAAAGGC ATAGATGCAA CTTTTAGCTT GAGGGTGTGG ACTATTCCAA    8000
TGAGCCAAAA TTATTGGGGA TCAGAAGGAA GATTACTTTT ATTAGGTGAC    8050
AGAATATACA TATATACTAG ATCCACAAGT TGGCACAGTA AATTACAGTT    8100
AGGGGTAATT GATATTCTG ATTATAATAA TATAAGAATA AATTGGACTT     8150
GGCATAATGT ACTATCACGG CCAGGAAATG ATGAATGTCC ATGGGGTCAT    8200
TCATGCCCAG ACGGATGTAT AACAGGAGTT TACACTGATG CATATCCGCT    8250
AAACCCATCG GGGAGTGTTG TATCATCAGT AATTCTTGAC TCACAAAAGT    8300
CTAGAGAAAA CCCAATCATT ACCTACTCAA CAGCTACAAA TAGAATAAAT    8350
GAATTAGCTA TATATAACAG AACACTTCCA GCTGCATATA CAACAACAAA    8400
TTGTATCACA CATTATGATA AAGGGTATTG TTTTCATATA GTAGAAATAA    8450
ATCACAGAAG TTTGAATACG TTTCAACCTA TGTTATTCAA AACAGAAGTT    8500
CCAAAAAACT GCAGCTAAAT TGATCATCGC ATATCGGATG CCAGATGACA    8550
TTAAAGAGA CCACCAGACA GACAACACAG GAGATGATGC AAGATATAAA     8600
GGAATAATAA AAAACTTAGG AGAAAAGTGT GCAAGAAAAA TGGACACTGA    8650
ATCCCACAGC GGCACAACAT CTGACATTCT GTACCCTGAA TGTCACCTCA    8700
ATTCTCCTAT AGTTAAAGGA AAAATAGCAC AACTGCATAC AATAATGAGT    8750
TTGCCCCAAC CCTACGATAT GGATGATGAT TCAATACTGA TTATTACTAG    8800
ACAAAAAATC AAACTCAATA AATTAGATAA AGACAACGG TCAATTAGGA     8850
AATTAAGATC AGTCTTAATG GAAAGAGTAA ATGATCTTGG TAAATACACC    8900
TTTATCAGAT ATCCAGAAAT GTCTAGTGAA ATGTTCCAAT TATGTATACC    8950
CGGAATTAAT AATAAAATAA ATGAATTGCT AAGTAAAGCA AGTAAAACAT    9000
ATAATCAAAT GACTGATGGA TTAAGAGATC TATGGGTTAC TGTACTATCG    9050
AAGTTAGCAT CGAAAATGA TGGAAGTAAT TATGATATCA ATGAAGATAT     9100
TAGCAATATA TCAAATGTTC ACATGACTTA CCAATCAGAC AAATGGTATA    9150
ATCCATTCAA GACATGGTTT ACTATTAAGT ATGACATGAG GAGATTACAA    9200
AAAGCCAAAA ATGAGATTAC ATTCAATAGG CATAAAGATT ATAATCTATT    9250
AGAAGACCAA AAGAATATAT TGCTGATACA TCCAGAACTC GTCTTAATAT    9300
TAGATAAACA AAATTACAAT GGGTATATAA TGACTCCTGA ATTGGTACTA    9350
ATGTATTGTG ATGTAGTTGA AGGGAGGTGG AATATAAGTT CATGTGCAAA    9400
```

FIG.47D

```
ATTGGATCCT AAATTACAAT CAATGTATTA TAAAGGTAAC AATTTATGGG    9450
AAATAATAGA TGGACTATTC CTGACCTTAG GAGAAAGAAC ATTTGACATA    9500
ATATCACTAT TAGAACCGCT TGCATTATCG CTCATTCAAA CTCATGACCC    9550
GGTTAAACAG CTCAGAGGGG CTTTTTTAAA TCACGTGTTA TCAGAAATGG    9600
AATCAATATT CGCAGCTGAG TGTACAACAG AGGAAATACC TAATGTGGAT    9650
TATATAGATA AAATTTTAGA TGTATTCAAA GAATCAACAA TAGATGAAAT    9700
AGCAGAAATT TTCTCTTTCT TCCGAACTTT TGGACACCCT CCATTAGAGG    9750
CGAGTATAGC AGCAGAGAAA GTTAGAAAGT ATATGTACAC TGAGAAATGT    9800
TTGAAATTTG ATACTATCAA TAAATGTCAT GCTATTTTTT GTACAATAAT    9850
TATAAATGGA TATAGAGAAA GACATGGTGG TCAATGGCCT CCAGTTACAT    9900
TACCTATTCA TGCACATGAA TTTATCATAA ATGCGTACGG ATCAAATTCT    9950
GCCATATCAT ATGAAAATGC TGTAGATTAT TATAAGAGCT TCATAGGAAT   10000
AAAATTTGAC AAGTTTATAG AGCCTCAATT GGATGAAGAC TTAACTATTT   10050
ATATGAAAGA TAAAGCATTA TCCCAAAGA AATCTAACTG GACACAGTC    10100
TATCCAGCTT CAAACCTGTT ATACCGCACT AATGTGTCTC ATGATTCACG   10150
AAGATTGGTT GAAGTATTTA TAGCAGATAG TAAATTTGAT CCCCACCAAG   10200
TATTAGATTA CGTAGAATCA GGATATTGGC TAGATGATCC TGAATTTAAT   10250
ATCTCATATA GTTTAAAAGA GAAAGAAATA AAACAAGAAG GTAGACTTTT   10300
TGCAAAAATG ACATACAAGA TGAGAGCTAC ACAAGTATTA TCAGAAACAT   10350
TATTGGCGAA TAATATAGGG AAATTCTTCC AAGAGAATGG GATGGTTAAA   10400
GGAGAAATTG AATTACTCAA GAGACTGACA ACAATATCTA TGTCTGGGGT   10450
TCCGCGGTAT AATGAGGTAT ACAATAATTC AAAAAGTCAC ACAGAGGAAC   10500
TTCAAGCTTA TAATGCAATT AGCAGTTCCA ATTTATCTTC TAATCAGAAG   10550
TCAAAGAAGT TTGAATTTAA ATCAACAGAT ATATACAATG ATGGATACGA   10600
AACCGTAAGC TGCTTCTTAA CGACAGATCT TAAAAAATAT TGTTTAAATT   10650
GGAGGTATGA ATCAACAGCT TTATTCGGTG ATACTTGTAA TCAGATATTT   10700
GGGTTAAAGG AATTATTTAA TTGGCTGCAC CCTCGCCTTG AAAAGAGTAC   10750
AATATATGTT GGAGATCCTT ATTGCCCGCC ATCAGATATT GAACATTTAC   10800
CACTTGATGA CCATCCTGAT TCAGGATTTT ATGTTCATAA TCCTAAAGGA   10850
GGAATAGAAG GGTTTTGCCA AAAGTTATGG ACACTCATAT CTATCAGTGC   10900
CATACATTTA GCAGCTGTCA AAATCGGTGT AAGAGTTACT GCAATGGTTC   10950
AAGGGGATAA TCAAGCCATA GCTGTTACCA CCAGAGTACC TAATAATTAT   11000
GATTATAAGG TTAAGAAAGA GATTGTTTAT AAAGATGTGG TAAGATTTTT   11050
TGATTCTTTG AGAGAGGTTA TGGATGATCT GGGTCATGAG CTCAAACTAA   11100
ATGAAACTAT AATAAGTAGT AAAATGTTTA TATATAGCAA AAGGATATAC   11150
TATGACGGAA GAATCCTTCC TCAGGCGTTA AAAGCATTGT CTAGATGTGT   11200
TTTTTGGTCT GAAACAATCA TAGATGAGAC AAGATCAGCA TCCTCAAATC   11250
TGGCGACATC GTTTGCAAAG GCCATTGAGA ATGGCTACTC ACCTGTATTG   11300
GGATATGTAT GCTCAATCTT CAAAAATATC CAACAGTTGT ATATAGCACT   11350
TGGAATGAAT ATAAATCCAA CTATAACCCA AAATATTAAA GATCAATATT   11400
TCAGGAATAT TCATTGGATG CAATATGCAT CTCTAATCCC TGCTAGTGTC   11450
GGAGGATTTA ATTATATGGC CATGTCAAGG TGTTTTGTCA GAAACATTGG   11500
AGATCCTACA GTCGCTGCAT TAGCTGATAT TAAAAGATTT ATAAAAGCAA   11550
ATTTGTTAGA TCGAGGTGTC CTTTACAGAA TTATGAATCA GGAACCAGGC   11600
GAGTCCTCCT TTTTAGACTG GGCTTCAGAC CCCTATTCAT GTAACTTACC   11650
ACAATCTCAA AATATAACCA CCATGATAAA GAATATAACT GCAAGAAATG   11700
TACTACAGGA CTCACCAAAC CCATTACTAT CTGGATTATT TACAAGTACA   11750
```

FIG.47E

```
ATGATAGAAG AGGATGAGGA ATTAGCTGAG TTCCTAATGG ACAGGAGAAT    11800
AATTCTCCCA AGGGTTGCGC ATGACATTTT AGATAATTCT CTTACTGGAA    11850
TTAGGAATGC TATAGCTGGT ATGTTGGATA CAACAAAATC ACTAATTCGA    11900
GTAGGGATAA ACAGAGGAGG ATTAACCTAT AACTTATTAA GAAAGATAAG    11950
CAACTATGAT CTTGTACAAT ATGAGACACT TAGTAAAACT TTAAGACTAA    12000
TAGTCAGTGA CAAGATTAAG TATGAAGATA TGTGCTCAGT AGACCTAGCC    12050
ATATCATTAA GACAAAAAAT GTGGATGCAT TTATCAGGAG GAAGAATGAT    12100
AAATGGACTT GAAACTCCAG ATCCTTTAGA GTTACTGTCT GGAGTAATAA    12150
TAACAGGATC TGAGCATTGT AGGATATGTT ATTCAACTGA AGGTGAAAGC    12200
CCATATACAT GGATGTATTT ACCAGGCAAT CTTAATATAG GATCAGCTGA    12250
AACAGGAATA GCATCATTAA GGGTCCCTTA CTTGGATCA GTTACGGATG     12300
AGAGATCTGA AGCACAATTG GGTATATCA AAAATCTAAG CAAACCAGCT     12350
AAGGCTGCTA TAAGAATAGC AATGATATAT ACTTGGGCAT TGGGAATGA     12400
CGAAATATCT TGGATGGAAG CATCACAGAT TGCACAAACA CGTGCGAACT    12450
TTACATTAGA TAGCTTAAAG ATTTTGACAC CAGTGACAAC ATCAACAAAT    12500
CTATCACATA GGTTAAAAGA TACTGCTACT CAGATGAAAT TTTCTAGTAC    12550
ATCACTTATT AGAGTAAGCA GGTTCATCAC AATATCTAAT GATAATATGT    12600
CTATTAAAGA GGCAAATGAA ACTAAGATA CAAATCTTAT TTATCAACAG     12650
GTAATGTTAA CAGGGTTAAG TGTATTTGAA TATCTATTTA GGTTAGAGGA    12700
GAGTACAGGA CATAACCCTA TGGTCATGCA TCTACATATA GAGGATGGAT    12750
GTTGTATCAA AGAGAGTTAC AATGATGAGC ATATCAATCC GGAGTCTACA    12800
TTAGAGTTAA TTAAATACCC TGAGAGTAAT GAATTTATAT ATGATAAGGA    12850
CCCTTTAAAG GATATAGATC TATCAAAATT AATGGTTATA AGAGATCATT    12900
CTTATACAAT TGACATGAAT TACTGGGACG ACACAGATAT TGTACATGCA    12950
ATATCAATAT GTACTGCAGT TACAATAGCA GATACAATGT CGCAGCTAGA    13000
TCGGGATAAT CTTAAGGAGC TGGTTGTAAT TGCAAATGAT GATGATATTA    13050
ACAGTCTGAT AACTGAATTT CTGACCCTAG ATATACTAGT GTTTCTCAAA    13100
ACATTTGGAG GGTTACTCGT GAATCAATTT GCATATACCC TTTATGGATT    13150
GAAAATAGAA GGAAGGGATC CCATTTGGGA TTATATAATG AGAACATTAA    13200
AAGACACCTC ACATTCAGTA CTTAAGTAT TATCTAATGC ACTATCTCAT     13250
CCAAAAGTGT TAAGAGATT TTGGGATTGT GGAGTTTTGA ATCCTATTTA     13300
TGGTCCTAAT ACTGCTAGTC AGGACCAAGT TAAGCTTGCT CTCTCAATTT    13350
GCGAGTACTC CTTGGATCTA TTTATGAGAG AATGGCTGAA TGGAGCATCA    13400
CTTGAGATCT ATATCTGTGA TAGTGACATG GAAATAGCAA ATGATAGAAG    13450
ACAAGCATTT CTCTCAAGAC ACCTTGCCTT TGTGTGTTGT TTAGCAGAGA    13500
TAGCATCTTT TGGACCAAAT TTATTAAATC TAACATATCT AGAGAGACTT    13550
GACGAATTAA AACAATACTT GGATCTGAAC ATCAAAGAAG ATCCTACTCT    13600
TAAATATGTG CAAGTATCAG GACTGTTAAT TAAATCATTC CCCTCAACTG    13650
TTACGTATGT GAGGAAAACT GCGATTAAGT ATCTGAGGAT TCGTGGCATT    13700
AATCCGCCTG AAACGATTGA AGATTGGGAT CCCATAGAAG ATGAGAATAT    13750
CTTAGACAAT ATTGTTAAAA CTGTAAATGA CAATTGCAGT GATAATCAAA    13800
AGAGAAATAA AAGTAGTTAT TTCTGGGGAT TAGCTCTAAA GAATTATCAA    13850
GTCGTAAAAA TAAGATCCAT AACGAGTGAT TCTGAAGTTA ATGAAGCTTC    13900
GAATGTTACT ACACATGGAA TGACACTTCC TCAGGGAGGA AGTTATCTAT    13950
CACATCAGCT GAGGTTATTT GGAGTAAACA GTACAAGTTG TCTGAAAGCT    14000
CTTGAATTGT CACAAATTTT AATGAGGGAA GTTAAAAAG ATAAAGATAG     14050
ACTCTTTTTA GGAGAAGGAG CAGGAGCTAT GTTAGCATGT TATGATGCTA    14100
```

FIG.47F

```
CACTCGGTCC TGCAATAAAT TATTACAATT CTGGTTTAAA TATTACAGAT    14150
GTAATTGGTC AACGGGAATT AAAAATCTTC CCATCAGAAG TATCATTAGT    14200
AGGTAAAAAA CTAGGAAATG TAACACAGAT TCTTAATCGG GTGAGGGTGT    14250
TATTTAATGG GAATCCCAAT TCAACATGGA TAGGAAATAT GGAATGTGAG    14300
AGTTTAATAT GGAGTGAATT AAATGATAAG TCAATTGGTT TAGTACATTG    14350
TGACATGGAG GGAGCAATAG GCAAATCAGA AGAAACTGTT TTACATGAAC    14400
ATTATAGTAT TATTAGGATT ACATATTTAA TTGGGGATGA TGATGTTGTT    14450
CTAGTATCAA AAATTATACC AACTATTACT CCGAATTGGT CTAAAATACT    14500
CTATCTATAC AGGTTGTATT GGAAGGATGT GAGTGTAGTG TCCCTTAAAA    14550
CATCCAATCC TGCCTCAACA GAGCTTTATT TAATTTCAAA GGATGCTTAC    14600
TGTACTGTAA TGGAACCCAG TAATCTTGTT TTATCAAAAC TTAAAAGGAT    14650
ATCATCAGTA GAAGAAAATA ATCTATTAAA ATGGATAATC TTATCAAAAA    14700
GGAAGAACAA CGAATGGTTA CAGCATGAAA TCAAAGAAGG AGAAAGGGAT    14750
TATGGGATAA TGAGGCCATA TCATACAGCA CTGCAAATTT TTGGATTCCA    14800
AATTAACTTA AATCACTTAG CTAAAGAATT TTTATCAACT CCTGATTTAA    14850
CCAACATTAA TAATATAATT CAAAGTTTTA CAAGAACAAT TAAAGATGTT    14900
ATGTTCGAAT GGGTCAATAT CACTCATGAC AATAAAAGAC ATAAATTAGG    14950
AGGAAGATAT AATCTATTCC CGCTTAAAAA TAAGGGGAAG TTAAGATTAC    15000
TATCACGAAG ATTAGTACTA AGCTGGATAT CATTATCTTT ATCAACCAGA    15050
TTACTGACAG GCCGTTTCCC AGATGAAAAA TTTGAAAATA GGGCACAGAC    15100
CGGATATGTA TCATTGGCTG ATACTGATTT AGAATCTTTA AAGTTATTAT    15150
CAAGAAATAT TGTCAAAAGT TACAAAGAAC ACATAGGATT AATATCATAC    15200
TGGTTTTTAA CCAAGAGGT CAAAATACTA ATGAAACTTA TAGGGGAGT    15250
CAAACTACTA GGAATTCCCA AACAGTACAA AGAGTTAGAG GATCGATCAT    15300
TTCAGGGTTA TGAATATGAT AATGAATTTG ATATTGATTA ATACATAAAA    15350
ACAAAAAATA AAACACCTAA TCCTCTCCCA TTCACTTCCA ACAAAATGAA    15400
AAGTAAGAAA AACATATAAT ATACATATAC CAAACAGAGT TTTTCTCTTG    15450
TTTGGT                                                    15456
```

ATTENUATED PARAINFLUENZA VIRUS (PIV) VACCINES

RELATED APPLICATIONS

This application is a Continuation-In-Part of application Ser. No. 09/083,793 filed on May 22, 1998 and issued as U.S. Pat. No. 7,208,161 on Apr. 24, 2001, which is a continuation-in-part application of, and claims the benefit under Title 35 of U.S. Provisional Application No. 60/047,575, filed May 23, 1997, and U.S. Provisional Application No. 60/059,385, filed Sep. 19, 1997.

This application is also a Continuation-In-Part of application Ser. No. 09/458,813 filed on Dec. 10, 1999 and issued as U.S. Pat. No. 7,314,631 on Jan. 1, 2008, which is a continuation-in-part application of, and claims the benefit under Title 35 of, U.S. patent application Ser. No. 09/083,793, filed May 22, 1998 now U.S. Pat. No. 7,208,161 which is a continuation-in-part of U.S. Provisional Application No. 60/047,575, filed May 23, 1997, now abandoned, and U.S. Provisional Application No. 60/059,385, filed Sep. 19, 1997, now abandoned, and also a Continuation-In-Part of U.S. application Ser. No. 09/459,062 filed on Dec. 10, 1999, and issued as U.S. Pat. No. 7,250,171 on July 31, 2007, which is a continuation-in-part application of, and claims the benefit under Title 35 of, U.S. patent application Ser. No. 09/083,793, filed May 22, 1998 which is a continuation-in-part of U.S. Provisional Application No. 60/047,575, filed May 23, 1997, now abandoned, and U.S. Provisional Application No. 60/059,385, filed Sep. 19, 1997, now abandoned.

The entire contents of all of the above applications are hereby incorporated by reference in their entirety and priority of each is claimed under 35 U.S.C. §120.

BACKGROUND OF THE INVENTION

Human parainfluenza viruses (HPIV), HPIV1, HPIV2, and HPIV3 are significant causes of bronchiolitis, croup and pneumonia in infants and children. Karron et al., J. Infect. Dis. 172: 1445-50 (1995); Collins et al. "Parainfluenza Viruses", p. 1205-1243. In B. N. Fields et al., eds., Fields Virology, 3rd ed, vol. 1. Lippincott-Raven Publ., Philadelphia (1996); Murphy et al., Virus Res. 11:1-15 (1988). Infections by these viruses result in substantial morbidity in children less than 3 years of age, and are responsible for approximately 20% of hospitalizations among young infants and children for respiratory tract infections.

Despite considerable efforts to develop effective vaccine therapies against HPIV, no approved vaccine agents have yet been achieved for any HPIV strain, nor for ameliorating HPIV related illnesses. To date, only two live attenuated PIV vaccine candidates have received particular attention. One of these candidates is a bovine PIV (BPIV) strain that is antigenically related to HPIV3, and which has been shown to protect animals against HPIV3. BPIV3 is attenuated, genetically stable and immunogenic in human infants and children (Karron et al., J. Inf. Dis. 171:1107-14 (1995a); Karron et al., J. Inf. Dis. 172:1445-1450, (1995b)). A second PIV3 vaccine candidate, JS cp45 is a cold-adapted mutant of the JS wild-type (wt) strain of HPIV3 (Karron et al., (1995b), supra; Belshe et al., J. Med. Virol. 10:235-42 (1982)). This live, attenuated, cold-passaged (cp) PIV3 vaccine candidate exhibits temperature-sensitive (ts), cold-adaptation (ca), and attenuation (att) phenotypes which are stable after viral replication in vivo. The cp45 virus is protective against human PIV3 challenge in experimental animals and is attenuated, genetically stable, and immunogenic in seronegative human infants and children (Hall et al., Virus Res. 22:173-184 (1992); Karron et al., (1995b), supra.

HPIV3 is a member of the Paramyxovirus genus of the Paramyxovirus family, order Mononegavirales. Its genome is a single strand of negative-sense RNA 15462 nucleotides (nt) in length (Galinski et al., Virology 165: 499-510, (1988); Stokes et al., Virus Res. 25:91-103 (1992)) and encodes at least eight proteins (Collins et al., supra, (1996); Galinski, supra, (1991); Spriggs and Collins, J. Gen. Virol. 67: 2705-2719, (1986)). Three of these proteins are associated with the RNA genome to form the nucleocapsid; namely the nucleocapsid protein N, phosphoprotein P, and large polymerase subunit L. Three additional proteins are associated with the envelope, namely the matrix protein M, taught to mediate viral attachment and release, the hemagglutinin-neuraminidase protein HN, and the fusion protein F. Two other proteins, HN and F, represent the neutralizing and protective antigens of PIVs (Collins et al. In Fields Virology, 3rd ed., 1:1205-43 (1996)). Significant sequence divergence in these two protective antigens among different PIVs is the basis for the type specificity of protective immunity against these pathogens (id.).

Another protein of PIV, the C protein, is encoded by an overlapping open reading frame (ORF) of the P protein mRNA (Spriggs and Collins, 1986), and the D protein is generated by RNA editing of the P cistron (Galinski et al. Virology 186:543-50 (1992)). The P mRNA also contains an internal ORF which has the potential to encode a cystein-rich domain called V. The V ORF is also found in other paramyxoviruses and typically is accessed by RNA editing, but this is not the case with PIV. Presently, it is not known whether the PIV V ORF is expressed.

The viral genome of PIV also contains extragenic leader and trailer regions, possessing promoters required for viral replication and transcription. Thus, the PIV genetic map is represented as 3' leader-N-P/C/D-M-F-HN-L-trailer. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination.

Identification of attenuating mutations in cp45 and other PIV3 vaccine candidates is of interest for a variety of reasons. In particular, it will be useful to understand the genetic basis of attenuation and to characterize the molecular virology and pathogenesis of attenuated HPIV3 strains to provide clinically acceptable vaccines for use against these and other paramyxoviruses, especially HPIV1 and HPIV2 which together account for an additional 7% of pediatric hospital admissions. To achieve these and related goals, a method for producing virus with a wt phenotype from cDNA is needed to determine which mutation(s) in the cp45 virus specify the ts, ca and att phenotypes and which gene(s) of the BPIV3 specify the attenuation phenotype.

The complete nucleotide sequences of the prototype PIV3 strain, and of the JS wt HPIV3 and cp45 strains have been determined (Stokes et al., supra., (1992); Stokes et al., Virus Res. 30: 43-52 (1993)). From these studies, the cp45 strain was shown to possess at least seventeen nucleotide substitutions compared to the parental JS wt HPIV3 strain, eight of which are correlated with changes to viral proteins. However, it has not been previously shown which of these identified mutations specify desired, e.g., ts, ca, and att, phenotypes. Recently, growth of cp45 at nonpermissive temperatures was reported to be complemented by coexpression of a cDNA clone of the L gene of the 47885 wt PIV3 strain (Ray et al., J. Virol. 70:580-584 (1996)), suggesting that the L gene may contain one or more mutations which contribute to the ts phenotype of cp45. However, the results of this study are complicated by the fact that the 47885 strain is not isogenic with the JS parent of cp45 (for example, the two viruses are 4% different at the nucleotide level, and the L proteins differ at 41 amino acid positions (Stokes et al., supra, (1992); published erratum appears in Virus Res. 27:96 (1993); Virus Res. 25:91-103. Also, this method of complementation does not provide a clear measurement of the relative contribution of the L gene mutation(s) to the overall ts phenotype of cp45.

Rescue and analysis of attenuating mutations in PIV3 and other RNA viruses require effective methods to manipulate cDNAs for the particular viruses of interest. Despite previous advancements identifying cDNAs for PIV, manipulation of the genomic RNA of this and other negative-sense RNA viruses has proven difficult. One major obstacle in this regard is that the naked genomic RNA of these viruses is noninfectious.

Successful methods for direct genetic manipulation of non-segmented negative strand RNA viruses have only recently begun to be developed (for reviews, see Conzelmann, J. Gen. Virol. 77:381-89 (1996); Palese et al., Proc. Natl. Acad. Sci. U.S.A. 93:11354-58, (1996)). Functional nucleocapsids have been successfully generated from the intracellular coexpression of separately transfected plasmids bearing the T7 RNA polymerase promoter and encoding either genomic or antigenomic RNA and the N, P, and L proteins. The intracellular cDNA expression is driven by T7 RNA polymerase which is produced by co-infecting with a vaccinia recombinant virus. This approach was first used to determine the transcription and replication requirements of cDNA-encoded minireplicons. Some success has been achieved in the application of these general methods to rescue infectious rabies virus, vesicular stomatitis virus (VSV), measles virus, and Sendai virus from cDNA-encoded antigenomic RNA in the presence of the nucleocapsid N, phosphoprotein P, and large polymerase subunit L (Garcin et al., EMBO J. 14:6087-6094 (1995); Lawson et al., Proc. Natl. Acad. Sci. U.S.A. 92:4477-81 (1995); Radecke et al., EMBO J. 14:5773-5784 (1995); Schnell et al., EMBO J. 13:4195-203 (1994); Whelan et al., Proc. Natl. Acad. Sci. U.S.A. 92:8388-92 (1995)). Respiratory synctial virus (RSV) has also been recovered from cDNA encoded antigenome but this required the transfection of an additional plasmid encoding the M2 ORF 1 transcription elongation factor (Collins et al., 1995).

Rescue of infectious PIV virus and other Mononegavirales members is complicated by virtue of their non-segmented negative-strand RNA genome. The genomic ribonucleoprotein complexes (RNPs) of segmented genome viruses, such as influenza, are generally small in size and loosely structured, and can be assembled in vitro from RNA and required viral proteins. However, PIV and other Mononegavirales members feature much larger and more tightly structured RNPs, which tend to be refractory to functional association in vitro. Furthermore, the coding potential of HPIV3 P mRNA is complicated by cotranscriptional "RNA editing" (Galinski et al., Virology 186: 543-50 (1992)). The resultant shifts in reading frame can access internal ORFs which are expressed as chimeras fused to the N-terminal part of P. In addition, HPIV3 appears to differ from most other paramyxoviruses which express a chimeric V protein, as noted above. The corresponding set of proteins from HPIV3 editing has not yet been identified, and the internal V ORF of HPIV3 is separated from the editing site by numerous translational stop codons (Galinski et al. (1992, supra). Yet another complicating factor is that editing by BPIV3 and HPIV3 produces a novel chimeric protein D, in which the upstream half of P is fused to a domain encoded by a second internal ORF (Pelet et al., EMBO J. 10: 443-448 (1991); Galinski et al., supra, (1992)). The D protein does not have a counterpart in other paramyxoviruses.

In view of the foregoing, an urgent need exists in the art for tools and methods to engineer safe and effective vaccines to alleviate the serious health problems attributable to PIV, particularly illnesses among infants and children attributable to HPIV3. Quite surprisingly, the present invention satisfies these and other related needs.

Human parainfluenza virus type 3 (HPIV3) is a common cause of serious lower respiratory tract infection in infants and children less than one year of age. It is second only to respiratory syncytial virus (RSV) as a leading cause of hospitalization for viral lower respiratory tract disease in this age group (Collins et al., in B. N. Fields Virology, p. 1205-1243, 3rd ed., vol. 1., Knipe et al., eds., Lippincott-Raven Publishers, Philadelphia, 1996; Crowe et al., Vaccine 13:415-421, 1995; Marx et al., J. Infect. Dis. 176:1423-1427, 1997, all incorporated herein by reference). Infections by this virus result in substantial morbidity in children less than 3 years of age. HPIV1 and HPIV2 are the principal etiologic agents of laryngotracheobronchitis (croup) and also can cause severe pneumonia and bronchiolitis (Collins et al., 1996, supra). In a long term study over a 20 year period, HPIV1, HPIV2, and HPIV3 were identified as etiologic agents for 6.0, 3.2, and 11.5%, respectively, of hospitalizations for respiratory tract disease accounting in total for 18% of the hospitalizations, and, for this reason, there is a need for an effective vaccine (Murphy et al., Virus Res. 11:1-15, 1988). The parainfluenza viruses have also been identified in a significant proportion of cases of virally-induced middle ear effusions in children with otitis media (Heikkinen et al., N. Engl. J. Med. 340:260-264, 1999, incorporated herein by reference). Thus, there is a need to produce a vaccine against these viruses that can prevent the serious lower respiratory tract disease and the otitis media that accompanies these HPIV infections. HPIV1, HPIV2, and HPIV3 are distinct serotypes that do not elicit significant cross-protective immunity. The major protective antigens of PIVs are the hemeagglutinin (HN) and fusion (F) glycoproteins, which mediate viral attachment, penetration and release. Protection against reinfection is mediated primarily by virus-neutralizing antibodies.

Despite considerable efforts to develop effective vaccine therapies against HPIV, no approved vaccine agents have yet been achieved for any HPIV serotype, nor for ameliorating HPIV related illnesses. To date, only two live attenuated PIV vaccine candidates have received particular attention. One of these candidates is a bovine PIV (BPIV3) strain that is antigenically related to HPIV3 and which has been shown to protect animals against HPIV3. BPIV3 is attenuated, genetically stable and immunogenic in human infants and children (Karron et al., J. Inf. Dis. 171:1107-14 (1995a); Karron et al., J. Inf. Dis. 172:1445-1450, (1995b)). A second PIV3 vaccine candidate, JS cp45, is a cold-adapted mutant of the JS wildtype (wt) strain of HPIV3 (Karron et al., (1995b), supra; Belshe et al., J. Med. Virol. 10:235-42 (1982)). This live, attenuated, cold-passaged (cp) PIV3 vaccine candidate exhibits temperature-sensitive (ts), cold-adaptation (ca), and attenuation (att) phenotypes which are stable after viral replication in vivo. The cp45 virus is protective against human PIV3 challenge in experimental animals and is attenuated, genetically stable, and immunogenic in seronegative human infants and children (Hall et al., Virus Res. 22:173-184 (1992); Karron et al., (1995b), supra The most promising prospects to date are live attenuated vaccine viruses since these have been shown to be efficacious in non-human primates even in the presence of passively transferred antibodies, an experimental situation that simulates that present in the very young infant who possesses maternally acquired antibodies (Crowe et al., Vaccine 13:847-855, 1995; Durbin et al., J Infect Dis 179:1345-1351, 1999). Two live attenuated PIV3 vaccine candidates, a temperature-sensitive (ts) derivative of the wild type PIV3 JS strain (designated PIV3 cp45) and a bovine PIV3 (BPIV3) strain, are undergoing clinical evaluation (Karron et al., Pediatr Infect Dis J 15:650-654, 1996; Karron et al., J Infect Dis 171:1107-1114, 1995a; Karron et al., J Infect Dis 172, 1445-1450, 1995b). The live attenuated PIV3 cp45 vaccine candidate was derived from the JS strain of HPIV3 via serial passage in cell culture at low temperature and has been found to be protective against HPIV3 challenge in experimental animals and to be satisfactorily attenuated, genetically stable, and immunogenic in seronegative human infants and children (Belshe et al, J. Med. Virol. 10:235-242, 1982; Belshe et al., Infect Immun 37:160-5, 1982; Clements et al., J. Clin. Microbiol. 29:1175-82, 1991; Crookshanks et al., J. Med. Virol 13:243-9, 1984; Hall et al., Virus Res. 22:173-184, 1992; Karron et al., J. Infect. Dis. 172, 1445-1450, 1995b). Because these PIV3 candidate vaccine viruses are biologically derived, there is no proven methods for adjusting the level of attenuation should this be found necessary from ongoing clinical trials.

To facilitate development of PIV vaccine candidates, recombinant DNA technology has recently made it possible to recover infectious negative-stranded RNA viruses from cDNA (for reviews, see Conzelmann, J. Gen. Virol. 77:381-89 (1996); Palese et al., Proc. Natl. Acad. Sci. U.S.A. 93:11354-58, (1996)). In this context, recombinant rescue has been reported for infectious respiratory syncytial virus (RSV), rabies virus (RaV), simian virus 5 (SV5), rinderpest virus, Newcastle disease virus (NDV), vesicular stomatitis virus (VSV), measles virus (MeV), and Sendai virus (SeV) from cDNA-encoded antigenomic RNA in the presence of essential viral proteins (see, e.g., Garcin et al., EMBO J. 14:6087-6094 (1995); Lawson et al., Proc. Natl. Acad. Sci. U.S.A. 92:4477-81 (1995); Radecke et al., EMBO J. 14:5773-5784 (1995); Schnell et al., EMBO J. 13:4195-203 (1994); Whelan et al., Proc. Natl. Acad. Sci. U.S.A. 92:8388-92 (1995); Hoffman et al., J. Virol. 71:4272-4277 (1997); Kato et al., Genes to Cells 1:569-579, 1996, Roberts et al., Virology 247:1-6, 1998; Baron et al., J. Virol. 71:1265-1271, 1997; International Publication No. WO 97/06270; Collins et al., Proc. Natl. Acad. Sci. USA 92:11563-11567, 1995; U.S. patent application Ser. No. 08/892,403, filed Jul. 15, 1997 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); U.S. patent application Ser. No. 09/291,894, filed on Apr. 13, 1999; U.S. Provisional Patent Application Ser. No. 60/129,006, filed Apr. 13, 1999; U.S. Provisional Patent Application Ser. No. 60/143,097, filed by Bucholz et al. on Jul. 9, 1999; Juhasz et al., J. Virol. 71:5814-5819, 1997; He et al. Virology 237:249-260, 1997; Peters et al. J. Virol. 73:5001-5009, 1999; Whitehead et al., Virology 247:232-239, 1998a; Whitehead et al., J. Virol. 72:4467-4471, 1998b; Jin et al. Virology 251:206-214, 1998; Bucholz et al. J. Virol. 73:251-259, 1999; Whitehead et al., J. Virol. 73:3438-3442, 1999, and Clarke et al., J. Virol. 74:4831-4838, 2000; each incorporated herein by reference in its entirety for all purposes).

In more specific regard to the instant invention, a method for producing HPIV with a wt phenotype from cDNA was recently developed for recovery of infectious, recombinant HPIV3 JS strain (see, e.g., Durbin et al., Virology 235:323-332, 1997; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, these disclosures allow for genetic manipulation of viral cDNA clones to determine the genetic basis of phenotypic changes in biological mutants, e.g., which mutations in the HPIV3 cp45 virus specify its ts, ca and att phenotypes, and which gene(s) or genome segment(s) of BPIV3 specify its attenuation phenotype. Additionally, these and related disclosures render it feasible to construct novel PIV vaccine candidates having a wide range of different mutations and to evaluate their level of attenuation, immunogenicity and phenotypic stability (see also, U.S. Provisional Patent Application Ser. No. 60/143,134, filed by Bailly et al. on Jul. 9, 1999; and U.S. patent application Ser. No. 09/350,821, filed by Durbin et al. on Jul. 9, 1999; each incorporated herein by reference).

Thus, infectious wild type recombinant PIV3, (r)PIV3, as well as a number of ts derivatives, have now been recovered from cDNA, and reverse genetics systems have been used to generate infectious virus bearing defined attenuating mutations and to study the genetic basis of attenuation of existing vaccine viruses. For example, the three amino acid substitutions found in the L gene of cp45, singularly or in combination, have been found to specify the ts and attenuation phenotypes. Additional ts and attenuating mutations are present in other regions of the PIV3 cp45. In addition a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., J Virol 72:1762-8, 1998; Tao et al., J Virol 72:2955-2961, 1998; Tao et al., Vaccine 17:1100-1108, 1999, incorporated herein by reference). rPIV3-1.cp45L was attenuated in hamsters and induced a high level of resistance to challenge with PIV1. Yet another recombinant chimeric virus, designated rPIV3-1.cp45, has been produced that contains 12 of the 15 cp45 mutations, i.e., excluding the mutations that occur in HN and F. This recombinant vaccine candidate is highly attenuated in the upper and lower respiratory tract of hamsters and induces a high level of protection against HPIV1 infection (Skiadopoulos et al., Vaccine In press, 18:503-510, 1999).

A number of studies have focused on the possible use of viral vectors to express foreign antigens toward the goal of developing vaccines against a pathogen for which other vaccine alternatives are not proved successful. In this context, a number of reports suggest that foreign genes may be successfully inserted into a recombinant negative strand RNA virus genome or antigenome with varying effects (Bukreyev et al., J. Virol. 70:6634-41, 1996; Bukreyev et al., Proc. Natl. Acad. Sci. USA 96:2367-72, 1999; Finke et al. J. Virol. 71:7281-8, 1997; Hasan et al., J. Gen. Virol. 78:2813-20, 1997; He et al., Virology 237:249-60, 1997; Jin et al., Virology 251:206-14, 1998; Johnson et al., J. Virol. 71:5060-8, 1997; Kahn et al., Virology 254:81-91, 1999; Kretzschmar et al., J. Virol. 71:5982-9, 1997; Mebatsion et al., Proc. Natl. Acad. Sci. USA 93:7310-4, 1996; Moriya et al., FEBS Lett. 425:105-11, 1998; Roberts et al., J. Virol. 73:3723-32, 1999; Roberts et al., J. Virol. 72:4704-11, 1998; Roberts et al., Virology 247:1-6, 1998; Sakai et al., FEBS Letter 456:221-226, 1999; Schnell et al., Proc. Natl. Acad. Sci. USA 93:11359-65, 1996a; Schnell et al., J. Virol. 70:2318-23, 1996b; Schnell et al., Cell 90:849-

57, 1997; Singh et al., J. Gen. Virol. 80:101-6, 1999; Singh et al., J. Virol. 73:4823-8, 1999; Spielhofer et al., J. Virol. 72, 2150-9, 1998; Yu et al., Genes to Cells 2:457-66 et al., 1999; U.S. Provisional Patent Application Ser. No. 60/143,425, filed on Jul. 13, 1999, each incorporated herein by reference). When inserted into the viral genome under the control of viral transcription gene-start and gene-end signals, the foreign gene may be transcribed as a separate mRNA and yield significant protein expression. Surprisingly, in some cases foreign sequence has been reported to be stable and capable of expressing functional protein during numerous passages in vitro.

However, to successfully develop vectors for vaccine use, it is insufficient to simply demonstrate a high, stable level of protein expression. For example, this has been possible since the early-to-mid 1980s with recombinant vaccinia viruses and adenoviruses, and yet these vectors have proven to be disappointments in the development of vaccines for human use. Similarly, most nonsegmented negative strand viruses which have been developed as vectors do not possess properties or immunization strategies amenable for human use. Examples in this context include vesicular stomatitis virus, an ungulate pathogen with no history of administration to humans except for a few laboratory accidents; Sendai virus, a mouse pathogen with no history of administration to humans; simian virus 5, a canine pathogen with no history of administration to humans; and an attenuated strain of measles virus which must be administered systemically and would be neutralized by measles-specific antibodies present in nearly all humans due to maternal antibodies and widespread use of a licensed vaccine. Furthermore, some of these prior vector candidates have adverse effects, such as immunosupression, which are directly inconsistent with their use as vectors. Thus, one must identify vectors whose growth characteristics, tropisms, and other biological properties make them appropriate as vectors for human use. It is further necessary to develop a viable vaccination strategy, including an immunogenic and efficacious route of administration.

Among a host of human pathogens for which a vector-based vaccine approach may be desirable is the measles virus. A live attenuated vaccine has been available for more than three decades and has been largely successful in eradicating measles disease in the United States. However, the World Health Organization estimates that more than 45 million cases of measles still occur annually, particularly in developing countries, and the virus contributes to approximately one million deaths per year.

Measles virus is a member of the Morbillivirus genus of the Paramyxoviridae family (Griffin et al., In "Fields Virology", B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). It is one of the most contagious infectious agents known to man and is transmitted from person to person via the respiratory route (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267-1312. Lippincott-Raven Publishers, Philadelphia, 1996). The measles virus has a complex pathogenesis, involving replication in both the respiratory tract and various systemic sites (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267-1312. Lippincott-Raven Publishers, Philadelphia, 1996).

Although both mucosal IgA and serum IgG measles virus-specific antibodies can participate in the control of measles virus, the absence of measles virus disease in very young infants possessing maternally-acquired measles virus-specific antibodies identifies serum antibodies as a major mediator of resistance to disease (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267-1312. Lippincott-Raven Publishers, Philadelphia, 1996). The two measles virus glycoproteins, the hemagglutinin (HA) and fusion (F) proteins, are the major neutralization and protective antigens (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267-1312. Lippincott-Raven Publishers, Philadelphia, 1996).

The currently available live attenuated measles vaccine is administered by a parenteral route (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267-1312. Lippincott-Raven Publishers, Philadelphia, 1996). Both the wild type measles virus and the vaccine virus are very readily neutralized by antibodies, and the measles virus vaccine is rendered non-infectious by even very low levels of maternally-acquired measles virus-specific neutralizing antibodies (Halsey et al., N. Engl. J. Med. 313:544-9, 1985; Osterhaus et al., Vaccine 16:1479-81, 1998). Thus, the vaccine virus is not given until the passively-acquired maternal antibodies have decreased to undetectable levels. In the United States, measles virus vaccine is not given until 12 to 15 months of age, a time when almost all children are readily infected with the measles virus vaccine. In the developing world, measles virus continues to have a high mortality rate, especially in children within the latter half of the first year of life (Gellin et al., J. Infect. Dis. 170, S3-14, 1994; Taylor et al., Am. J. Epidemiol. 127:788-94, 1988). This occurs because the measles virus, which is highly prevalent in these regions, is able to infect that subset of infants in whom maternally-acquired measles virus-specific antibody levels have decreased to a non-protective level. Therefore, there is a need for a measles virus vaccine that is able to induce a protective immune response even in the presence of measles virus neutralizing antibodies with the goal of eliminating measles virus disease occurring within the first year of life as well as that which occurs thereafter. Given this need, there have been numerous attempts to develop an immunization strategy to protect infants in the latter half of the first year of life against measles virus, but none of these strategies has been effective to date.

The first strategy for developing an early measles vaccine involved administration of the licensed live attenuated measles virus vaccine to infants about six months of age by one of the following two methods (Cutts et al., Biologicals 25, 323-38, 1997). In one general protocol, the live attenuated measles virus was administered intranasally by drops (Black et al., New Eng. J. Med. 263, 165-169; 1960; Kok et al., Trans. R. Soc. Trop. Med. Hyg. 77:171-6, 1983; Simasathien et al., Vaccine 15:329-34, 1997) or into the lower respiratory tract by aerosol (Sabin et al., J. Infect. Dis. 152:1231-7, 1985), to initiate an infection of the respiratory tract. In a second protocol, the measles virus was given parenterally but at a higher dose than that employed for the current vaccine. The administration of vaccines that can replicate on mucosal surfaces has been successfully achieved in early infancy for both live attenuated poliovirus and rotavirus vaccines (Melnick et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 655-712. 2 vols. Lippencott-Raven Publishers, Philadelphia, 1996; Perez-Schael et al., N. Engl. J. Med. 337, 1181-7, 1997), presumably because passively-acquired IgG antibodies have less access to mucosal surfaces than they do to systemic sites of viral replication. In this situation, the live attenuated poliovirus vaccine viruses are able to infect the mucosal surface of the gastrointestinal tract or the respiratory tract of young infants, including those with maternal antibodies, resulting in the induction of a protective immune response.

Therefore, a plausible method is to immunize via the respiratory tract of the young infant with the live attenuated measles virus vaccine, since this is the natural route of infection with the measles virus. However, the live attenuated measles virus that is infectious by the parenteral route was inconsistently infectious by the intranasal route (Black et al., New Eng. J. Med. 263:165-169, 1960; Cutts et al., Biologicals 25, 323-38, 1997; Kok et al., Trans. R. Soc. Trop. Med. Hyg. 77:171-6, 1983; Simasathien et al., Vaccine 15:329-34, 1997), and this decreased infectivity was especially apparent for the Schwartz stain of measles virus vaccine which is the current vaccine strain. Presumably, during the attenuation of this virus by passage in tissue culture cells of avian origin, the virus lost a significant amount of infectivity for the upper respiratory tract of humans. Indeed, a hallmark of measles virus biology is that the virus undergoes rapid changes in biological properties when grown in vitro. Since this relatively simple route of immunization was not successful, a second approach was tried involving administration of the live virus vaccine by aerosol into the lower respiratory tract (Cutts et al., Biologicals 25, 323-38, 1997; Sabin et al., J. Infect. Dis. 152:1231-7, 1985).

Infection of young infants by aerosol administration of measles virus vaccine was accomplished in highly controlled experimental studies, but it has not been possible to reproducibly deliver a live attenuated measles virus vaccine in field settings by aerosol to the young uncooperative infant (Cutts et al., Biologicals 25, 323-38, 1997). In another attempt to immunize six-month old infants, the measles vaccine virus was administered parenterally at a 10- to 100-fold increased dose (Markowitz et al., N. Engl. J. Med. 322:580-7, 1990). Although high-titer live measles vaccination improved seroconversion in infants 4-6 months of age, there was an associated increase in mortality in the high-titer vaccine recipients later in infancy (Gellin et al., J. Infect. Dis. 170:S3-14, 1994; Holt et al., J. Infect. Dis. 168:1087-96, 1993; Markowitz et al., N. Engl. J. Med. 322:580-7, 1990) and this approach to immunization has been abandoned.

A second strategy previously explored for a measles virus vaccine was the use of an inactivated measles virus vaccine, specifically, a formalin inactivated whole measles virus or a subunit virus vaccine prepared from measles virus (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267-1312. Lippincott-Raven Publishers, Philadelphia, 1996). However, the clinical use of the vaccines in the 1960's revealed a very serious complication, namely, that the inactivated virus vaccines potentiated disease rather than prevented it (Fulginiti et al., JAMA 202:1075-80, 1967). This was first observed with formalin-inactivated measles virus vaccine (Fulginiti et al., JAMA 202:1075-80, 1967). Initially, this vaccine prevented measles, but after several years vaccinees lost their resistance to infection. When subsequently infected with naturally circulating measles virus, the vaccinees developed an atypical illness with accentuated systemic symptoms and pneumonia (Fulginiti et al., JAMA 202:1075-80, 1967; Nader et al., J. Pediatr. 72:22-8, 1968; Rauh et al., Am. J. Dis. Child 109: 232-7, 1965). Retrospective analysis showed that formalin inactivation destroyed the ability of the measles fusion (F) protein to induce hemolysis-inhibiting antibodies, but it did not destroy the ability of the HA (hemagglutinin or attachment) protein to induce neutralizing antibodies (Norrby et al., J. Infect. Dis. 132:262-9, 1975; Norrby et al., Infect. Immun. 11:231-9, 1975). When the immunity induced by the HA protein had waned sufficiently to permit extensive infection with wild type measles virus, an altered and sometimes more severe disease was seen at the sites of measles virus replication (Bellanti, Pediatrics 48:715-29, 1971; Buser, N. Engl. J. Med. 277:250-1, 1967). This atypical disease is believed to be mediated in part by an altered cell-mediated immune response in which Th-2 cells were preferentially induced leading to heightened disease manifestations at the sites of viral replication (Polack et al., Nat. Med. 5:629-34, 1999). Because of this experience with nonliving measles virus vaccines and also because the immunogenicity of such parenterally-administered vaccines can be decreased by passively-transferred antibodies, there has been considerable reluctance to evaluate such vaccines in human infants. It should be noted that disease potentiation appears to be associated only with killed vaccines.

Yet another strategy that has been explored for developing a vaccine against measles for use in young infants has been the use of viral vectors to express a protective antigen of the measles virus (Drillien et al., Proc. Natl. Acad. Sci. USA 85:1252-6, 1988; Fooks et al., J. Gen. Virol. 79:1027-31, 1998; Schnell et al., Proc. Natl. Acad. Sci. USA 93:11359-65, 1996a; Taylor et al., Virology 187:321-8, 1992; Wild et al., Vaccine 8:441-2, 1990; Wild et al., J. Gen. Virol. 73:359-67, 1992). A variety of vectors have been explored including poxviruses such as the replication-competent vaccinia virus or the replication-defective modified vaccinia virus Ankara (MVA) stain. Replication-competent vaccinia recombinants expressing the F or HA glycoprotein of measles virus were efficacious in immunologically naive vaccinees. However, when they were administered parenterally in the presence of passive antibody against measles virus, their immunogenicity and protective efficacy was largely abrogated (Galletti et al., Vaccine 13, 197-201, 1995; Osterhaus et al., Vaccine 16:1479-81, 1998; Siegrist et al., Vaccine 16:1409-14, 1998; Siegrist et al., Dev. Biol. Stand. 95:133-9, 1998).

Replication-competent vaccinia recombinants expressing the protective antigens of RSV have also been shown to be ineffective in inducing a protective immune response when they are administered parenterally in the presence of passive antibody (Murphy et al., J. Virol. 62:3907-10, 1988a), but they readily protected such hosts when administered intranasally. Unfortunately, replication -competent vaccinia virus recombinants are not sufficiently attenuated for use in immunocompromised hosts such as persons with human immunodeficiency virus (HIV) infection (Fenner et al., World Health Organization, Geneva, 1988; Redfield et al., N. Engl. J. Med. 316, 673-676, 1987), and their administration by the intranasal route even to immunocompetent individuals would be problematic. Therefore they are not being pursued as vectors for use in human infants, some of whom could be infected with HIV.

The MVA vector, which was derived by more than 500 passages in chick embryo cells (Mayr et al., Infection 3:6-14, 1975; Meyer et al., J. Gen. Virol. 72:1031-1038, 1991), has also been evaluated as a potential vaccine vector for the protective antigens of several paramyxoviruses (Durbin et al., J. Infect. Dis. 179:1345-51, 1999a; Wyatt et al., Vaccine 14, 1451-1458, 1996). MVA is a highly attenuated host range mutant that replicates well in avian cells but not in most mammalian cells, including those obtained from monkeys and humans (Blanchard et al., J. Gen. Virol. 79:1159-1167, 1998; Carroll et al., Virology 238:198-211, 1997; Drexler et al., J. Gen. Virol. 79, 347-352, 1998; Sutter et al., Proc. Natl. Acad. Sci. U.S.A. 89:10847-10851, 1992). Avipox vaccine vectors, which have a host range restriction similar to that of MVA, also have been constructed that express measles virus protective antigens (Taylor et al., Virology 187, 321-8, 1992). MVA is non-pathogenic in immunocompromised hosts and has been administered to large numbers of humans without incident (Mayr et al., Zentralbl Bakteriol [B] 167, 375-90, 1978; Stickl et al., Dtsch. Med. Wochenschr. 99:2386-92, 1974; Werner et al., Archives of Virology 64, 247-256, 1980). Unfortunately, both the immunogenicity and efficacy of MVA expressing a paramyxovirus protective antigen were abrogated in passively-immunized rhesus monkeys whether delivered by a parenteral or a topical route (Durbin et al., Virology 235:323-332, 1999). The immunogenicity of DNA vaccines expressing measles virus protective antigens delivered parenterally was also decreased in passively-immunized hosts (Siegrist et al., Dev. Biol. Stand. 95:133-9, 1998). Replication-defective vectors expressing measles virus protective antigens are presently being evaluated, including adenovirus-measles virus HA recombinants (Fooks et al., J. Gen. Virol. 79:1027-31, 1998). In this context, MVA recombinants expressing parainfluenza virus antigens, unlike replication-competent vaccinia virus recombinants, lacked protective efficacy when given by a mucosal route to animals with passively-acquired antibodies, and it is unlikely that they, or the similar avipox vectors, can be used in infants with maternally-acquired measles virus antibodies.

Based on the reports summarized above, it appears unlikely that a replication-competent or replication-defective poxvirus vector, or a DNA vaccine, expressing a measles virus protective antigen will be satisfactorily immunogenic or efficacious in infants possessing passively-acquired maternal measles virus-specific antibodies.

A recently developed replication-competent virus vector expressing measles virus HA that replicates in the respiratory tract of animal hosts has been developed, namely, vesicular stomatitis virus (VSV), a rhabdovirus which naturally infects cattle but not humans (Roberts et al., J. Virol. 73:3723-32, 1999; Schnell et al., Proc. Natl. Acad. Sci. USA 93:11359-65. 1996a). Since VSV is an animal virus that can cause disease in humans, development of this recombinant for use in humans will require that a VSV backbone that is satisfactorily attenuated in human infants be first identified (Roberts et al., J. Virol. 73:3723-32, 1999), but such clinical studies have not been initiated.

Although there have been numerous advances toward development of effective vaccine agents against PIV and other pathogens, including measles, there remains a clear need in the art for additional tools and methods to engineer safe and effective vaccines to alleviate the serious health problems attributable to these pathogens, particularly among young infants. Among the remaining challenges in this context is the need for additional tools to generate suitably attenuated, immunogenic and genetically stable vaccine candidates for use in diverse clinical settings against one or more pathogens. To facilitate these goals, existing methods for identifying and incorporating attenuating mutations into recombinant vaccine strains and for developing vector-based vaccines and immunization methods must be expanded. Surprisingly, the present invention fulfills these needs and provides additional advantages as described herein below.

SUMMARY OF THE INVENTION

The present invention further provides novel tools and methods for introducing defined, predetermined structural and phenotypic changes into infectious PIV. In one embodiment of the invention, an isolated polynucleotide molecule is provided which comprises an operably linked transcriptional promoter, a polynucleotide sequence encoding a PIV genome or antigenome, and a transcriptional terminator.

The PIV genome or antigenome can be a human or non-human PIV sequence, or a recombinantly modified version thereof. In one embodiment, the polynucleotide sequence encodes a chimeric genome or antigenome comprising a human PIV sequence recombinantly joined with a nonhuman PIV sequence, such as a gene or gene segment from bovine PIV (BPIV). In additional examples, the polynucleotide encodes a chimera of sequences from a nonhuman PIV and at least one other PIV of human or nonhuman origin.

In other embodiments, the invention provides an isolated infectious PIV particle comprising a recombinant PIV (rPIV) genome or antigenome. The isolated infectious PIV particle can be a viral or subviral particle. As used herein, subviral particle refers to any infectious PIV particle which lacks a structural element, eg., a gene segment, gene, protein, or protein functional domain, which is present in a complete virus (eg., an assembled virion including a complete genome or antigenome, nucleocapsid and envelope). Thus, one example of a subviral particle of the invention is an infectious nucleocapsid containing a genome or antigenome, and the products of N, P, and L genes. Other subviral particles are produced by partial or complete deletions or substitutions of non-essential genes and/or their products (eg., F, HN, M, or C), among other non-essential structural elements.

The isolated infectious PIV particle is preferably a human PIV, more preferably human PIV3 (HPIV3). The invention also provides isolated, infectious particles from bovine or murine PIV (BPIV or MPIV), as well as particles comprising chimeric sequences from two or more different PIV genomes, for example particles incorporating polynucleotide sequences from HPIV3 and HPIV1, from HPIV3 and HPIV2 sequences, or comprised of HPIV3 and BPIV sequences.

In related aspects of the invention, isolated, infectious PIV particles are provided which incorporate nucleotide sequences from HPIV3 joined to at least one sequence from a heterologous PIV, such as HPIV1, HPIV2, BPIV or MPIV. For example, entire genes of HPIV3 may be replaced by counterpart genes from other forms of PIV, such as the HN and/or F glycoprotein genes of PIV1 or PIV2. Alternatively, a selected gene segment, for example a cytoplasmic tail, transmembrane domain or ectodomain of HN or F of HPIV1 or HPIV2, can be substituted for a corresponding gene segment in a counterpart HPIV3 gene to yield constructs encoding chimeric proteins, e.g. fusion proteins having a cytoplasmic tail and/or transmembrane domain of PIV3 fused to an ectodomain of PIV1 or PIV2. Alternatively, genes or gene segments from one PIV can be added (i.e., without substitution) within a heterologous PIV background to create novel immunogenic properties within the resultant clone.

Other modifications can be produced by introducing into a PIV genome or antigenome a nucleotide insertion, rearrangement, deletion or substitution selected to encode a desired phenotypic alteration, such as one that results in attenuation, temperature-sensitivity, cold-adaptation, small plaque size, host range restriction, improved growth in vitro. or a change in an immunogenic epitope of PIV. In one aspect of the invention, mutations occurring in biologically derived, attenuated PIV are identified and introduced individually or in combination into a full-length PIV clone. Typically these mutations are single amino acid changes displayed by biologically derived mutant viruses over a wild-type PIV, for example changes exhibited by PIV mutants having ts, ca or att phenotypes. These changes from biologically derived mutant PIV are incorporated into a recombinant PIV clone to specify desired characteristics in the resultant virus. Exemplary mutations include amino acid changes which specify an attenuated phenotype in the HPIV3 strain JS cp45. Among these exemplary mutations are mutations occurring within the PIV polymerase gene L specifying ts, ca or att phenotypes, for example amino acid substitutions occurring at Tyr942, Leu992, and/or Thr1558 of the JS wild type PIV strain. In more detailed aspects, attenuated PIV recombinants are described wherein Tyr942 is replaced by His, Leu992 is replaced by Phe, and/or Thr1558 is replaced by Ile.

Also provided within the invention are recombinant PIV having multiple, phenotype-specifying mutations introduced in selected combinations into the genome or antigenome of an infectious clone to yield desired characteristics including attenuation, temperature sensitivity, cold-adaptation, small plaque size, host range restriction, etc. For example, PIV clones are provided which incorporate at least two separate mutations adopted from a biologically derived PIV mutant, e.g., two ts mutations from HPIV3 JS cp45. Multiply attenuated viruses are thus obtained by selecting mutations from a "menu" of identified lesions and introducing these mutations in various combinations to calibrate a vaccine virus to selected levels of attenuation, immunogenicity and stability.

In additional embodiments, the invention provides for supplementation of one or more mutations adopted from biologically derived PIV, e.g., ts, ca or att mutations, with additional types of mutations involving the same or different genes. Target genes for mutation in this context include the nucleocapsid protein N, phosphoprotein P, large polymerase subunit L, matrix protein M, hemagglutinin-neuraminidase protein HN, fusion protein F and the C, D and V ORF products. In preferred aspects, attenuating mutations adopted from biologically derived PIV are incorporated within a chimeric PIV recombinant, e.g., a PIV recombinant having nucleotide sequences from both HPIV3 and HPIV1, or from both HPIV and BPIV viruses.

In other embodiments, the invention provides methods for producing an infectious PIV particle, e.g, a viral or subviral particle, from one or more isolated polynucleotide molecules encoding a PIV genome or antigenome (see also copending U.S. provisional patent application No. 60/047,575, filed May 23, 1997, incorporated herein by reference in its entirety). To produce an infectious PIV particle according to these methods, an expression vector comprising an isolated polynucleotide molecule encoding a PIV genome or antigenome is coexpressed in a cell or cell-free system with an expression vector comprising one or more isolated polynucleotide molecules encoding N, P, and L proteins of a PIV, whereby an infectious PIV particle is produced.

The PIV genome or antigenome and the N, P, and L proteins may be coexpressed by a single expression vector, or by separate expression vectors. In alternate embodiments, the N, P, and L proteins are each encoded on separate expression vectors.

Within the aforementioned methods, the polynucleotide molecule encoding the PIV genome or antigenome may correspond to a genomic or antigenomic sequence of human, bovine or murine PIV. Alternatively, the PIV encoding polynucleotide may be a chimera of a human PIV genomic or antigenomic sequence and at least one non-human PIV genomic or antigenomic sequence. In additional methods for producing infectious PIV, the polynucleotide encoding the PIV genome or antigenome is a chimera of two or more human PIV genomes, for example a polynucleotide containing sequences from HPIV3 joined to sequences from one or more related forms of human PIV, such as human PIV1 or human PIV2. Individual genes of human PIV3 may be substituted by counterpart genes from heterologous PIV, for example the HN and F glycoprotein genes of PIV1 or PIV2, to yield a modified genome or antigenome encoding a chimeric PIV. Alternatively, a selected, heterologous gene segment, such as a cytoplasmic tail, transmembrane domain or ectodomain of HN or F of HPIV1 or HPIV2, can be substituted for a counterpart gene segment in a different PIV type or different gene, e.g., HN or F of HPIV3, to yield constructs encoding chimeric proteins, e.g. fusion proteins having a cytoplasmic tail and/or transmembrane domain of PIV3 fused to an ectodomain of PIV1 or PIV2.

In yet additional methods for producing infectious PIV, the PIV genome or antigenome is modified to yield a chimera of a human PIV genomic or antigenomic sequence and at least one non-human PIV sequence, for example a polynucleotide containing sequences from both human and bovine PIV.

In other methods for producing infectious PIV, the PIV genome or antigenome is modified by a nucleotide insertion, rearrangement, deletion or substitution selected to encode a desirable phenotypic alteration, such as one that results in attenuation, temperature-sensitivity, cold-adaptation, small plaque size, host range restriction, or a change in an immunogenic epitope of PIV. Alternatively, the polynucleotide molecule encoding the PIV genome or antigenome can be modified to encode non-PIV molecules, e.g., a cytokine, a T-helper epitope, a restriction site marker, or a protein of a different microbial pathogen (e.g., virus, bacterium or fungus) capable of eliciting a protective immune response in the intended host. In one embodiment, the PIV genome or antigenome is modified to encode protein from a human RSV or from measles virus.

In other embodiments of the invention a cell or cell-free expression system (e.g., a cell-free lysate) is provided which incorporates an expression vector comprising an isolated polynucleotide molecule encoding a PIV genome or antigenome, and an expression vector comprising one or more isolated polynucleotide molecules encoding N, P, and L proteins of a PIV. Upon expression, the genome or antigenome and N, P, and L proteins combine to produce an infectious PIV particle, such as a viral or subviral particle. The isolated polynucleotide molecules encoding the PIV genome or antigenome and the one or more isolated polynucleotide molecules encoding N, P, and L proteins of PIV can be expressed by a single vector, or the genome and one or more of the N, P, and L proteins can be incorporated into two or more separate vectors.

The present invention provides chimeric parainfluenza viruses (PIVs) that are infectious in humans and other mammals and are useful in various compositions to generate desired immune responses against one or more PIVs, or against a PIV and one or more additional pathogens in a host susceptible to infection therefrom. In preferred aspects, the invention provides novel methods for designing and producing attenuated, chimeric PIVs that are useful as vaccine agents for preventing and/or treating infection and related disease symptoms attributable to PIV and one or more additional pathogens. Included within these aspects of the invention are novel, isolated polynucleotide molecules and vectors incorporating such molecules that comprise a chimeric PIV genome or antigenome including a partial or complete PIV vector genome or antigenome combined or integrated with one or more heterologous genes or genome segments that encode single or multiple antigenic determinants of a heterologous pathogen or of multiple heterologous pathogens. Also provided within the invention are methods and compositions incorporating a chimeric PIV for prophylaxis and treatment of infection by both a selected PIV and one or more heterologous pathogens, e.g., a heterologous PIV or a non-PIV pathogen such as a measles virus.

The invention thus involves methods and compositions for developing live vaccine candidates based on chimeras that employ a parainfluenza virus or subviral particle that is recombinantly modified to incorporate one or more antigenic determinants of a heterologous pathogen(s). Chimeric PIVs of the invention are constructed through a cDNA-based virus recovery system. Recombinant chimeric PIVs made from cDNA replicate independently and are propagated in a similar manner as biologically-derived viruses. The recombinant viruses are engineered to incorporate nucleotide sequences from both a vector (i.e., a "recipient" or "background") PIV genome or antigenome, and one or more heterologous "donor" sequences encoding one or more antigenic determinants of a different PIV or heterologous pathogen—to produce an infectious, chimeric virus or subviral particle. In this manner, candidate vaccine viruses are recombinantly engineered to elicit an immune response against one or more PIVs or a polyspecific response against a selected PIV and a non-PIV pathogen in a mammalian host susceptible to infection therefrom. Preferably the PIV and/or non-PIV pathogen(s) from which the heterologous sequences encoding the antigenic determinant(s) are human pathogens and the host is a human host. Also preferably, the vector PIV is a human PIV, although non-human PIVs, for example a bovine PIV (BPIV), can be employed as a vector to incorporate antigenic determinants of human PIVs and other human pathogens. Chimeric PIVs according to the invention may elicit an immune response against a specific PIV, e.g., HPIV1, HPIV2, HPIV3, or a polyspecific immune response against multiple PIVs, e.g., HPIV1 and HPIV2. Alternatively, chimeric PIVs of the invention may elicit a polyspecific immune response against one or more PIVs and a non-PIV pathogen such as measles virus.

Exemplary chimeric PIV of the invention incorporate a chimeric PIV genome or antigenome as described above, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components.

Chimeric PIV of the invention include a partial or complete "vector" PIV genome or antigenome derived from or patterned after a human PIV or non-human PIV combined with one or more heterologous gene(s) or genome segment(s) of a different PIV or other pathogen to form the chimeric PIV genome or antigenome. In preferred aspects of the invention, chimeric PIV incorporate a partial or complete human PIV vector genome or antigenome combined with one or more heterologous gene(s) or genome segment(s) from a second human PIV or a non-PIV pathogen such as measles virus.

The PIV "vector" genome or antigenome typically acts as a recipient or carrier to which are added or incorporated one or more "donor" genes or genome segments of a heterologous pathogen. Typically, polynucleotides encoding one or more antigenic determinants of the heterologous pathogen are added to or substituted within the vector genome or antigenome to yield a chimeric PIV that thus acquires the ability to elicit an immune response in a selected host against the heterologous pathogen. In addition, the chimeric virus may exhibit other novel phenotypic characteristics compared to one or both of the vector PIV and heterologous pathogens. For example, addition or substitution of heterologous genes or genome segments within a vector PIV strain may additionally, or independently, result in an increase in attenuation, growth changes, or other desired phenotypic changes as compared with a corresponding phenotype of the unmodified vector virus and/or donor. In one aspect of the invention, chimeric PIVs are attenuated for greater efficacy as a vaccine candidate by incorporation of large polynucleotide inserts which specify the level of attenuation in the resulting chimeric virus dependent upon the size of the insert.

Preferred chimeric PIV vaccine candidates of the invention bear one or more major antigenic determinants of a human PIV, e.g., of HPIV1, HPIV2 or HPIV3, and thus elicit an effective immune response against the selected PIV in human hosts. The antigenic determinant which is specific for a selected human PIV may be encoded by the vector genome or antigenome, or may be inserted within or joined to the PIV vector genome or antigenome as a heterologous polynucleotide sequence from a different PIV. The major protective antigens of human PIVs are their HN and F glycoproteins, although other proteins can also contribute to a protective or therapeutic immune response. In this context, both humoral and cell mediated immune responses are advantageously elicited by representative vaccine candidates within the invention. Thus, polynucleotides encoding antigenic determinants that may be present in the vector genome or antigenome, or integrated therewith as a heterologous gene or genome segment, may encode one or more PIV N, P, C, D, V, M, F, HN and/or L protein(s) or selected immunogenic fragment(s) or epitope(s) thereof from any human PIV.

In addition to having one or more major antigenic determinants of a selected human PIV, preferred chimeric PIV vaccine viruses of the invention bear one or more major antigenic determinants of a second human PIV or of a non-PIV pathogen. In exemplary aspects, the chimeric PIV includes a vector genome or antigenome that is a partial or complete human PIV (HPIV) genome or antigenome, for example of HPIV3, and further includes one or more heterologous gene(s) or genome segment(s) encoding antigenic determinant(s) of at least one heterologous PIV, for example HPIV1 and/or HPIV2. Preferably, the vector genome or antigenome is a partial or complete HPIV3 genome or antigenome and the heterologous gene(s) or genome segment(s) encoding the antigenic determinant(s) is/are of one or more heterologous HPIV(s). In alternative embodiments, one or more genes or genome segments encoding one or more antigenic determinants of HPIV1 may be added to or substituted within the partial or complete HPIV3 genome or antigenome. Preferably, the antigenic determinant(s) of HPIV1 is/are selected from HPIV1 HN and F glycoproteins or comprise one or more antigenic domains, fragments or epitopes of the HN and/or F glycoproteins. In various exemplary embodiments, both of the HPIV1 genes encoding the HN and F glycoproteins are substituted for counterpart HPIV3 HN and F genes in the HPIV3 vector genome or antigenome. These constructs yield chimeric PIVs that elicit a mono- or polyspecific immune response in humans to HPIV3 and/or HPIV1.

In additional exemplary embodiments, one or more genes or genome segments encoding one or more antigenic determinants of HPIV2 is/are added to, or incorporated within, a partial or complete HPIV3 genome or antigenome, yielding a new or additional immunospecificity of the resultant chimera against HPIV2 alone, or against HPIV3 and HPIV2. In more detailed aspects, one or more HPIV2 genes or genome segments encoding one or more HN and/or F glycoproteins or antigenic domains, fragments or epitopes thereof is/are added to or incorporated within the partial or complete HPIV3 vector genome or antigenome.

In yet additional aspects of the invention, multiple heterologous genes or genome segments encoding antigenic determinants of multiple heterologous PIVs are added to or incorporated within a partial or complete PIV vector genome or antigenome, preferably an HPIV vector genome or antigenome. In one preferred embodiment, heterologous genes or genome segments encoding antigenic determinants from both HPIV1 and HPIV2 are added to or incorporated within a partial or complete HPIV3 vector genome or antigenome. In more detailed aspects, one or more HPIV1 genes or genome segments encoding one or more HN and/or F glycoproteins (or antigenic domains, fragments or epitopes thereof) and one or more HPIV2 genes or genome segments encoding HN and/or F glycoproteins, antigenic domains, fragments or epitopes, is/are added to or incorporated within the partial or complete HPIV3 vector genome or antigenome. In one example, both HPIV1 genes encoding HN and F glycoproteins are substituted for counterpart HPIV3 HN and F genes to form a chimeric HPIV3-1 vector genome or antigenome, which is further modified by addition or incorporation of one or more genes or gene segments encoding single or multiple antigenic determinants of HPIV2. This is readily achieved within the invention, for example, by adding or substituting a transcription unit comprising an open reading frame (ORF) of an HPIV2 HN within the chimeric HPIV3-1 vector genome or antigenome. Following this method, specific constructs exemplifying the invention are provided which yield chimeric PIVs having antigenic determinants of both HPIV1 and HPIV2, as exemplified by the vaccine candidates rPIV3-1.2HN and rPIV3-1 cp45.2HN described herein below.

In alternative aspects of the invention, chimeric PIVs of the invention are based on a human PIV vector genome or antigenome which is employed as a recipient for incorporation of major antigenic determinants from a non-PIV pathogen. Pathogens from which one or more antigenic determinants may be adopted into the chimeric PIV vaccine candidate include, but are not limited to, measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. This assemblage of pathogens that may be thus targeted for vaccine development according to the methods of the invention is exemplary only, and those skilled in the art will understand that the use of PIV vectors for carrying antigenic determinants extends broadly to a large host of additional pathogens.

This, in various alternative aspects of the invention, a human PIV genome or antigenome can be employed as a vector for incorporation of one or more major antigenic determinants from a wide range of non-PIV pathogens. Representative major antigens that can be incorporated within chimeric PIVs of the invention include, but are not limited to the measles virus HA and F proteins; the F, G, SH and M2 proteins of subgroup A and subgroup B respiratory syncytial virus, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G Protein, Epstein Barr Virus gp350 protein; filovirus G protein, bunyavirus G protein, flavivirus E and NS1 proteins, and alphavirus E protein.

Various human PIV vectors can be employed to carry heterologous antigenic determinants of non-PIV pathogens to elicit one or more specific humoral or cell mediated immune responses against the antigenic determinant(s) carried by the chimeric vaccine virus and hence elicit an effective immune response against the wild-type "donor" pathogen in susceptible hosts. In preferred embodiments, one or more heterologous genes or genome segments from the donor pathogen is joined to or inserted within a partial or complete HPIV3 genome or antigenome. Alternatively, the heterologous gene or genome segment may be incorporated within a chimeric HPIV vector genome or antigenome, for example a partial or complete HPIV3 genome or antigenome bearing one or more genes or genome segments of a heterologous PIV. For example, the gene(s) or genome segment(s) encoding the antigenic determinant(s) of a non-PIV pathogen may be combined with a partial or complete chimeric HPIV3-1 vector genome or antigenome, e.g., as described above having one or both HPIV1 genes encoding HN and F glycoproteins substituted for counterpart HPIV3 HN and F genes. Alternatively, the gene(s) or genome segment(s) encoding the antigenic determinant(s) of a non-PIV pathogen may be combined with a partial or complete chimeric genome or antigenome that incorporates single or multiple antigenic determinants of HPIV2, e.g., an HPIV2 HN gene, within an HPIV1 or HPIV3 vector genome or antigenome, or a chimeric HPIV3-1 vector genome or antigenome as described above. The heterologous gene(s) or genome segment(s) encoding one or more measles antigenic determinant(s) may be combined with any of the PIV vectors or chimeric PIV vectors disclosed herein. In the examples provided herein, the vector genome or antigenome is a partial or complete HPIV3 genome or antigenome, or a chimeric HPIV genome or antigenome comprising a partial or complete HPIV3 genome or antigenome having one or more genes or genome segments encoding antigenic determinant(s) of a heterologous HPIV added or incorporated therein. In one such chimeric construct, a transcription unit comprising an open reading frame (ORF) of a measles virus HA gene is added to a HPIV3 vector genome or antigenome at various positions, yielding exemplary chimeric PIV/measles vaccine candidates rPIV3(HA HN-L), rPIV3(HA N-P), rcp45L(HA N-P), rPIV3(HA P-M), or rcp45L(HA P-M).

To construct chimeric PIV clones of the invention, a heterologous gene or genome segment of a donor PIV or non-PIV pathogen may be added or substituted at any operable position in the vector genome or antigenome. Often, the position of a gene or gene segment substitution will correspond to a wild-type gene order position of a counterpart gene or genome segment within the partial or complete PIV vector genome or antigenome. In other embodiments, the heterologous gene or genome segment is added or substituted at a position that is more promoter-proximal or promotor-distal compared to a wild-type gene order position of a counterpart gene or genome segment within the background genome or antigenome, to enhance or reduce expression, respectively, of the heterologous gene or genome segment. In more detailed aspects of the invention, a heterologous genome segment, for example a genome segment encoding an immunogenic ectodomain of a heterologous PIV or non-PIV pathogen, can be substituted for a corresponding genome segment in a counterpart gene in the PIV vector genome or antigenome to yield constructs encoding chimeric proteins, e.g. fusion proteins having a cytoplasmic tail and/or transmembrane domain of one PIV fused to an ectodomain of another PIV or non-PIV pathogen. In alternate embodiments, a chimeric PIV genome or antigenome may be engineered to encode a polyspecific chimeric glycoprotein in the recombinant virus or subviral particle having immunogenic glycoprotein domains or epitopes from two different pathogens. In yet additional embodiments, heterologous genes or genome segments from one PIV or non-PIV pathogen can be added (i.e., without substitution) within a PIV vector genome or antigenome to create novel immunogenic properties within the resultant clone. In these cases, the heterologous gene or genome segment may be added as a supernumerary gene or genome segment, optionally for the additional purpose of attenuating the resultant chimeric virus, in combination with a complete PIV vector genome or antigenome. Alternatively, the heterologous gene or genome segment may be added in conjunction with deletion of a selected gene or genome segment in the vector genome or antigenome.

In preferred embodiments of the invention, the heterologous gene or genome segment is added at an intergenic position within the partial or complete PIV vector genome or antigenome. Alternatively, the gene or genome segment can be inserted within other noncoding regions of the genome, for example, within 5' or 3' noncoding regions or in other positions where noncoding nucleotides occur within the vector genome or antigenome. In some instances, it may be desired to insert the heterologous gene or genome segment at a noncoding site corresponding to or overlapping a cis-acting regulatory sequence within the vector genome or antigenome, e.g., within a sequence required for efficient replication, transcription, and/or translation. These regions of the vector genome or antigenome represent target sites for disruption or modification of regulatory functions associated with introduction of the heterologous gene or genome segment.

For the preferred purpose of constructing candidate vaccine viruses for clinical use, it is often desirable to adjust the attenuation phenotype of chimeric PIV of the invention by introducing additional mutations that increase or decrease the level of attenuation in the recombinant virus. Therefore, in additional aspects of the invention, attenuated, chimeric PIVs are produced in which the chimeric genome or antigenome is further modified by introducing one or more attenuating mutations that specify an attenuating phenotype in the resultant virus or subviral particle. These attenuating mutations may be generated de novo and tested for attenuating effects according to well known rational design mutagenesis strategies. Alternatively, the attenuating mutations may be identified in existing biologically derived mutant PIV or other viruses and thereafter incorporated into a chimeric PIV of the invention.

Preferred attenuating mutations in the latter context are readily identified and incorporated into a chimeric PIV, either by inserting the mutation within the vector genome or antigenome by cloning or mutagenizing the vector genome or antigenome to contain the attenuating mutation. Preferably, attenuating mutations are engineered within the vector genome or antigenome and are imported or copied from biologically derived, attenuated PIV mutants. These are recognized to include, for example, cold passaged (cp), cold adapted (ca), host range restricted (hr), small plaque (sp), and/or temperature sensitive (ts) PIV mutants. In exemplary embodiments, one or more attenuating mutations present in the well characterized JS HPIV3 cp45 mutant strain are incorporated within chimeric PIV of the invention, preferably including one or more mutations identified in the polymerase L protein, e.g., at a position corresponding to Tyr942, Leu992, or Thr1558 of JS cp45. Alternatively or additionally, attenuating mutations present in the JS HPIV3 cp45 mutant strain are introduced in the N protein of chimeric PIV clones, for example which encode amino acid substitution(s) at a position corresponding to residues Val96 or Ser389 of JS cp45. Yet additional useful attenuating mutations encode amino acid substitution(s) in the C protein, e.g., at a position corresponding to Ile96 of JS cp45. Other mutations identified in PIV3 JS cp45 that can be adopted to adjust attenuation of a chimeric PIV of the invention are found in the F protein, e.g., at a position corresponding to Ile420 or Ala450 of JS cp45, and in the HN protein, e.g., at a position corresponding to residue Val384 of JS cp45.

Attenuating mutations from biologically derived PIV mutants for incorporation into chimeric PIV of the invention also include mutations in noncoding portions of the PIV genome or antigenome, for example in a 3' leader sequence. Exemplary mutations in this context may be engineered at a position in the 3' leader of a recombinant virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45.

From PIV3 JS cp45 and other biologically derived PIV mutants, a large "menu" of attenuating mutations is provided, each of which mutations can be combined with any other mutation(s) for finely adjusting the level of attenuation in chimeric PIV vaccine candidates of the invention. In exemplary embodiments, chimeric PIVs are constructed which include one or more, and preferably two or more, mutations of HPIV3 JS cp45. Thus, chimeric PIVs of the invention selected for vaccine use often have two and sometimes three or more attenuating mutations from biologically derived PIV mutants or like model sources to achieve a satisfactory level of attenuation for broad clinical use. Preferably, these attenuating mutations incorporated within recombinant chimeric PIVs of the invention are stabilized by multiple nucleotide substitutions in a codon specifying the mutation.

Additional attenuating mutations can be readily adopted or engineered within chimeric PIVs of the invention that are identified in other viruses, particularly other nonsegmented negative stranded RNA viruses. This is accomplished by mapping a mutation identified in a heterologous negative stranded RNA virus to a corresponding, homologous site in a PIV vector genome or antigenome (or heterologous insert in the PIV chimera) and mutating the existing sequence in the "recipient" to the mutant genotype (either by an identical or conservative mutation), as described in U.S. Provisional Patent Application Ser. No. 60/129,006, filed on Apr. 13, 1999, incorporated herein by reference.

In yet additional aspects of the invention, chimeric PIVs, with or without attenuating mutations modeled after biologically derived attenuated mutant viruses, are constructed to have additional nucleotide modification(s) to yield a desired phenotypic, structural, or functional change. Typically, the selected nucleotide modification will be made within the partial or complete PIV vector genome, but such modifications can be made as well within any heterologous gene or genome segment that contributes to the chimeric clone. These modifications preferably specify a desired phenotypic change, for example a change in growth characteristics, attenuation, temperature-sensitivity, cold-adaptation, plaque size, host range restriction, or immunogenicity. Structural changes in this context include introduction or ablation of restriction sites into PIV encoding cDNAs for ease of manipulation and identification.

In preferred embodiments, nucleotide changes within the genome or antigenome of a chimeric PIV include modification of a viral gene by partial or complete deletion of the gene or reduction or ablation (knock-out) of its expression. Target genes for mutation in this context include any of the PIV genes, including the nucleocapsid protein N, phosphoprotein P, large polymerase subunit L, matrix protein M, hemagglutinin-neuraminidase protein HN, fusion protein F, and the products of the C, D and V open reading frames (ORFs). To the extent that the recombinant virus remains viable and infectious, each of these proteins can be selectively deleted, substituted or rearranged, in whole or in part, alone or in combination with other desired modifications, to achieve novel deletion or knock out mutants. For example, one or more of the C, D, and/or V genes may be deleted in whole or in part, or its expression reduced or ablated (e.g., by introduction of a stop codon, by a mutation in an RNA editing site, by a mutation that alters the amino acid specified by an initiation codon, or by a frame shift mutation in the targeted ORF(s)). In one embodiment, a mutation can be made in the editing site that prevents editing and ablates expression of proteins whose mRNA is generated by RNA editing (Kato et al., EMBO 16:578-587, 1997 and Schneider et al., Virology 227:314-322, 1997, incorporated herein by reference). Alternatively, one or more of the C, D, and/or V ORF(s) can be deleted in whole or in part to alter the phenotype of the resultant recombinant clone to improve growth, attenuation, immunogenicity or other desired phenotypic characteristics (see, U.S. patent application Ser. No. 09/350,821, filed by Durbin et al. on Jul. 9, 1999, incorporated herein by reference).

Alternative nucleotide modifications in chimeric PIV of the invention include a deletion, insertion, addition or rearrangement of a cis-acting regulatory sequence for a selected gene in the recombinant genome or antigenome. In one example, a cis-acting regulatory sequence of one PIV gene is changed to correspond to a heterologous regulatory sequence, which may be a counterpart cis-acting regulatory sequence of the same gene in a different PIV, or a cis-acting regulatory sequence of a different PIV gene. For example, a gene end signal may be modified by conversion or substitution to a gene end signal of a different gene in the same PIV strain. In other embodiments, the nucleotide modification may comprise an insertion, deletion, substitution, or rearrangement of a translational start site within the recombinant genome or antigenome, e.g., to ablate an alternative translational start site for a selected form of a protein.

In addition, a variety of other genetic alterations can be produced in a chimeric PIV genome or antigenome, alone or together with one or more attenuating mutations adopted from a biologically derived mutant PIV. For example, genes or genome segments from non-PIV sources may be inserted in whole or in part. In one such aspect, the invention provides methods for attenuating chimeric PIV vaccine candidates based on host range effects due to the introduction of one or more gene(s) or genome segment(s) from, e.g., a non-human PIV into a human PIV vector-based chimeric virus. For example, host range attenuation can be conferred on a HPIV-vector based chimeric construct by introduction of nucleotide sequences from a bovine PIV (BPIV) (see, e.g., (e.g., as disclosed in U.S. Provisional Application Ser. No. 60/143,134 filed on Jul. 9, 1999, incorporated herein by reference). These effects are attributed to structural and functional divergence between the vector and donor viruses and provide a stable basis for attenuation. For example, between HPIV3 and BPIV3 the percent amino acid identity for each of the N proteins is 86%, for P is 65%, M 93%, F 83%, HN 77%, and L 91%. All of these proteins are therefore candidates for introduction into a HPIV vector to yield an attenuated chimeric virus which cannot readily be altered by reversion. In exemplary embodiments, the vector genome or antigenome is an HPIV3 genome or antigenome and the heterologous gene or genome segment is a N ORF derived from a selected BPIV3 strain.

In yet additional aspects of the invention, the order of genes can be changed to cause attenuation or reduce or enhance expression of a particular gene. Alternatively, a PIV genome promoter can be replaced with its antigenome counterpart to yield additional desired phenotypic changes. Different or additional modifications in the recombinant genome or antigenome can be made to facilitate manipulations, such as the insertion of unique restriction sites in various intergenic regions or elsewhere. Nontranslated gene sequences can be removed to increase capacity for inserting foreign sequences.

In yet additional aspects, polynucleotide molecules or vectors encoding the chimeric PIV genome or antigenome can be modified to encode non-PIV sequences, e.g., a cytokine, a T-helper epitope, a restriction site marker, or a protein or immunogenic epitope of a microbial pathogen (e.g., virus, bacterium or fungus) capable of eliciting a protective immune response in an intended host. In one such embodiment, chimeric PIVs are constructed that incorporate a gene encoding a cytokine to yield novel phenotypic and immunogenic effects in the resulting chimera.

In addition to providing chimeric PIV for vaccine use, the invention provides related cDNA clones and vectors which incorporate a PIV vector genome or antigenome and heterologous polynucleotide(s) encoding one or more heterologous antigenic determinants, wherein the clones and vectors optionally incorporate mutations and related modifications specifying one or more attenuating mutations or other phenotypic changes as described above. Heterologous sequences encoding antigenic determinants and/or specifying desired phenotypic changes are introduced in selected combinations, e.g., into an isolated polynucleotide which is a recombinant cDNA vector genome or antigenome, to produce a suitably attenuated, infectious virus or subviral particle in accordance with the methods described herein. These methods, coupled with routine phenotypic evaluation, provide a large assemblage of chimeric PIVs having such desired characteristics as attenuation, temperature sensitivity, altered immunogenicity, cold-adaptation, small plaque size, host range restriction, genetic stability, etc. Preferred vaccine viruses among these candidates are attenuated and yet sufficiently immunogenic to elicit a protective immune response in the vaccinated mammalian host.

In related aspects of the invention, compositions (e.g., isolated polynucleotides and vectors incorporating a chimeric PIV-encoding cDNA) and methods are provided for producing an isolated infectious chimeric PIV. Included within these aspects of the invention are novel, isolated polynucleotide molecules and vectors incorporating such molecules that comprise a chimeric PIV genome or antigenome. Also provided is the same or different expression vector comprising one or more isolated polynucleotide molecules encoding N, P, and L proteins. These proteins can alternatively be expressed directly from the genome or antigenome cDNA. The vector(s) is/are preferably expressed or coexpressed in a cell or cell-free lysate, thereby producing an infectious chimeric parainfluenza virus particle or subviral particle.

BPIV3, which is antigenically-related to HPIV3, offers an alternative approach to the development of a live attenuated virus vaccine for HPIV1, HPIV2, and HPIV3. The first vaccine used in humans, live vaccinia virus believed to be of bovine origin, was developed by Jenner almost 200 years ago for the control of smallpox. During the ensuing two centuries, vaccinia virus was successful in controlling this disease and played an essential role in the final eradication of smallpox. In this "Jennerian" approach to vaccine development, an antigenically-related animal virus is used as a vaccine for humans. Animal viruses that are well adapted to their natural host often do not replicate efficiently in humans and hence are attenuated. At present, there is a lack of a thorough understanding regarding the genetic basis for this form of host range restriction. Evolution of a virus in its mammalian or avian host results in significant divergence of nucleotide (nt) and amino acid sequences from that of the corresponding sequences in the related human virus. This divergent sequence, consisting of a large number of sequence differences, specifies the host range attenuation phenotype. Having an attenuation phenotype which is based on numerous sequence differences is a desirable property in a vaccine virus since it should contribute to the stability of the attenuation phenotype of the animal virus following its replication in humans.

The recently licensed quadrivalent rotavirus is an example of the Jennerian approach to vaccine development in which a nonhuman rotavirus strain, the rhesus rotavirus (RRV), was found to be attenuated in humans and protective against human serotype 3 to which it is antigenically highly related (Kapikian et al., Adv. Exp. Med. Biol. 327:59-69, 1992). Since there was a need for a multivalent vaccine that would induce resistance to each of the four major human rotavirus serotypes, the Jennerian approach was modified by constructing three reassortant viruses using conventional genetic techniques of gene reassortment in tissue culture. Each single gene reassortant virus contained 10 RRV genes plus a single human rotavirus gene that coded for the major neutralization antigen (VP7) of serotype 1, 2, or 4. The intent was to prepare single gene substitution RRV reassortants with the attenuation characteristics of this simian virus and the neutralization specificity of human rotavirus serotype 1, 2, or 4. The quadrivalent vaccine based on the host range restriction of the simian RRV in humans provided a high level of efficacy against human rotavirus infection in infants and young children (Perez-Schael et al., N. Engl. J. Med. 337:1181-1187, 1997). However, the vaccine virus retains mild reactogenicity in older seronegative infants lacking maternal antibody, therefore a second generation Jennerian vaccine, based on the UK strain of bovine rotavirus, is being developed to replace the RRV vaccine (Clements-Mann et al., Vaccine 17:2715-2725, 1999).

The Jennerian approach also is being explored to develop vaccines for parainfluenza type 1 virus and for hepatitis A virus which are attenuated and immunogenic in non-human primates (Emerson et al., J. Infect. Dis. 173:592-597, 1996; Hurwitz et al., Vaccine 15:533-540, 1997). The Jennerian approach was used for the development of a live attenuated vaccine for influenza A virus but it failed to produce a consistently attenuated vaccine for use in humans (Steinhoff et al., J. Infect. Dis. 163:1023-1028, 1991). As another example, reassortant viruses that contain two gene segments encoding the hemagglutinin and neuraminidase surface glycoproteins from a human influenza A virus and the six remaining gene segments from an avian influenza A virus were attenuated in humans (Clements et al., J. Clin. Microbiol. 27:219-222, 1989; Murphy et al., J. Infect. Dis. 152:225-229, 1985; and Snyder et al., J. Clin. Microbiol. 23:852-857, 1986). This indicated that one or more of the six gene segments of the avian virus attenuated the avian-human influenza A viruses for humans. The genetic determinants of this attenuation were mapped using reassortant viruses possessing a single gene segment from an attenuating avian influenza A virus and the remaining genes from a human strain. It was shown that the nonstructural (NS), polymerase (PB1, PB2) and M genes contributed to the attenuation phenotype of avian influenza A viruses in humans (Clements et al., J. Clin. Microbiol. 30:655-662, 1992).

In another study, the severe host range restriction of bovine respiratory syncytial virus (BRSV) for replication in chimpanzees was only slightly alleviated by replacement of the BRSV F and G glycoproteins with their HRSV counterparts. This indicated that F and G are involved in this host range restriction, but that one or more additional bovine RSV genes are also involved (Buchholz et al., J. Virol. 74:1187-1199, 2000). This illustrates that more than one gene can contribute in unpredictable ways to the host range restriction phenotype of a mammalian or avian virus in primates.

The instant invention provides a new basis for attenuating a wild type or mutant parental virus for use as a vaccine against HPIV, in which attenuation is based completely or in part on host range effects, while at least one or more of the major neutralization and protective antigenic determinant(s) of the chimeric virus is homologous to the virus against which the vaccine is directed. The HN and F proteins of BPIV3 are each approximately 80% related by amino acid sequence to their corresponding HPIV3 proteins (Suzu et al., Nucleic Acids Res. 15:2945-2958, 1987, incorporated herein by reference) and 25% related by antigenic analysis (Coelingh et al., J. Virol. 64:3833-3843, 1990; Coelingh et al., J. Virol. 60:90-96, 1986; van Wyke Coelingh et al., J. Infect. Dis. 157:655-662, 1988, each incorporated herein by reference). Previous studies indicated that two strains of BPIV3, the Kansas (Ka) strain and the Shipping Fever (SF) prototype strain, were attenuated for the upper and lower respiratory tract of rhesus monkeys, and one of these, the Ka strain, was attenuated in chimpanzees (van Wyke Coelingh et al., 1988, supra, incorporated herein by reference). Immunization of nonhuman primates with the Ka virus induced antibodies reactive with HPIV3 and induced resistance to the replication of the human virus in the upper and the lower respiratory tract of monkeys (id.) Subsequent evaluation of the Ka strain in humans indicated that the virus was satisfactorily attenuated for seronegative infants, and it retained the attenuation phenotype following replication in fully susceptible infants and children (Karron et al., 1996, supra; and Karron et al., 1995a, supra; each incorporated herein by reference). Its major advantages therefore were that it was satisfactorily attenuated for fully susceptible seronegative infants and children, and its attenuation phenotype was stable following replication in humans.

However, the level of serum hemagglutination-inhibiting antibodies reactive with HPIV3 induced in seronegative vaccinees who received 105.0 tissue culture infectious dose50 (TCID)50 of the Ka strain of BPIV3 was 1:10.5, which was three-fold lower than similar vaccinees who received a live attenuated HPIV3 vaccine (Karron et al., 1995a, supra; and Karron et al., 1995b, supra; each incorporated herein by reference). This lower level of antibodies to the human virus induced by BPIV3 reflected in large part the antigenic divergence between HPIV3 and BPIV3 (Karron et al., 1996, supra; and Karron et al., 1995a, supra; each incorporated herein by reference). Studies to determine the efficacy of the Ka vaccine candidate against HPIV3 in humans have not been performed, but it is likely that this reduced level of antibodies reactive with HPIV3 will be reflected in a reduced level of protective efficacy.

Although it is clear that BPIV3 has host range genes that restrict replication in the respiratory tract of rhesus monkeys, chimpanzees and humans, it remains unknown which of the bovine proteins or noncoding sequences contribute to this host range restriction of replication. It is possible that any of the BPIV3 proteins or noncoding sequences may confer a host range phenotype. It is not possible to determine in advance which genes or genome segments will confer an attenuation phenotype. This can only be accomplished by systematic substitution of BPIV3 coding and non-coding sequences for their HPIV3 counterparts and by evaluation of the recovered HPIV3/BPIV3 chimeric viruses in seronegative rhesus monkeys or humans.

Despite the numerous advances toward development of effective vaccine agents against PIV serotypes 1, 2, and 3, there remains a clear need in the art for additional tools and methods to engineer safe and effective vaccines to alleviate the serious health problems attributable to PIV, particularly illnesses among infants and children due to infection by HPIV. Among the remaining challenges in this context is the need for additional tools to generate suitably attenuated, immunogenic and genetically stable vaccine candidates for use in diverse clinical settings. To facilitate these goals, existing methods for identifying and incorporating attenuating mutations into recombinant vaccine strains must be expanded. Furthermore, it is recognized that methods and compositions for designing vaccines against human PIV can be implemented as well to design novel vaccine candidates for veterinary use. Surprisingly, the present invention fulfills these needs and provides additional advantages as described hereinbelow.

The present invention also provides human-bovine chimeric parainfluenza viruses (PIVs) that are infectious and attenuated in humans and other mammals. In related aspects, the invention provides novel methods for designing and producing attenuated, human-bovine chimeric PIVs that are useful in various compositions to generate a desired immune response against PIV in a host susceptible to PIV infection. Included within these aspects of the invention are novel, isolated polynucleotide molecules and vectors incorporating such molecules that comprise a chimeric PIV genome or antigenome including a partial or complete human or bovine PIV "background" genome or antigenome combined or integrated with one or more heterologous gene(s) or genome segment(s) of a different PIV virus. Also provided within the invention are methods and compositions incorporating human-bovine chimeric PIV for prophylaxis and treatment of PIV infection.

The invention thus involves a method for developing live attenuated PIV vaccine candidates based on chimeras between HPIVs and BPIV3. Chimeras are generated using a cDNA-based virus recovery system. Recombinant viruses made from cDNA replicate independently and are propagated in the same manner as if they were biologically-derived viruses. Chimeric human-bovine PIV of the invention are recombinantly engineered to incorporate nucleotide sequences from both human and bovine PIV strains to produce an infectious, chimeric virus or subviral particle. In this manner, candidate vaccine viruses are recombinantly engineered to elicit an immune response against PIV in a mammalian host susceptible to PIV infection, including humans and non-human primates. Human-bovine chimeric PIV according to the invention may be engeneered to elicit an immune response to a specific PIV, e.g., HPIV3, or a polyspecific response against multiple PIVs, e.g., HPIV1 and HPIV3. Additional chimeric viruses can be designed in accordance with the teachings herein which serve as vectors for antigens of non-PIV pathogens, for example respiratory syncytial virus (RSV) or measles virus.

Exemplary human-bovine chimeric PIV of the invention incorporate a chimeric PIV genome or antigenome comprising both human and bovine polynucleotide sequences, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components.

Chimeric human-bovine PIV of the invention include a partial or complete "background" PIV genome or antigenome derived from or patterned after a human or bovine PIV strain or subgroup virus combined with one or more heterologous gene(s) or genome segment(s) of a different PIV strain or subgroup virus to form the human-bovine chimeric PIV genome or antigenome. In preferred aspects of the invention, chimeric PIV incorporate a partial or complete human PIV background genome or antigenome combined with one or more heterologous gene(s) or genome segment(s) from a bovine PIV.

The partial or complete background genome or antigenome typically acts as a recipient backbone or vector into which are imported heterologous genes or genome segments of the counterpart, human or bovine PIV. Heterologous genes or genome segments from the counterpart, human or bovine PIV represent "donor" genes or polynucleotides that are combined with, or substituted within, the background genome or antigenome to yield a human-bovine chimeric PIV that exhibits novel phenotypic characteristics compared to one or both of the contributing PIVs. For example, addition or substitution of heterologous genes or genome segments within a selected recipient PIV strain may result in an increase or decrease in attenuation, growth changes, altered immunogenicity, or other desired phenotypic changes as compared with a corresponding phenotype(s) of the unmodified recipient and/or donor.

Genes and genome segments that may be selected for use as heterologous substitutions or additions within human-bovine chimeric PIV of the invention include genes or genome segments encoding a PIV N, P, C, D, V, M, F, SH (where appropriate), HN and/or L protein(s) or portion(s) thereof. In addition, genes and genome segments encoding non-PIV proteins, for example, an SH protein as found in mumps and SV5 viruses, may be incorporated within human-bovine PIV of the invention. Regulatory regions, such as the extragenic 3' leader or 5' trailer regions, and gene-start, gene-end, intergenic regions, or 3' or 5' non-coding regions, are also useful as heterologous substitutions or additions.

Preferred human-bovine chimeric PIV vaccine candidates of the invention bear one or more of the major antigenic determinants of HPIV3 in a background which is attenuated by the substitution or addition of one or more BPIV3 genes or genome segments. The major protective antigens of PIVs are their HN and F glycoproteins, although other proteins can also contribute to a protective immune response. In certain embodiments, the background genome or antigenome is an HPIV genome or antigenome, e.g., an HPIV3, HPIV2, or HPIV1 background genome or antigenome, to which is added or into which is substituted one or more BPIV gene(s) or genome segment(s), preferably from BPIV3. In one exemplary embodiment described below, an ORF of the N gene of a BPIV3 is substituted for that of an HPIV. Alternatively, the background genome or antigenome may be a BPIV genome or antigenome which is combined with one or more genes or genome segments encoding a HPIV3, HPIV2, or HPIV1 glycoprotein, glycoprotein domain or other antigenic determinant.

In accordance with the methods of the invention, any BPIV gene or genome segment, singly or in combination with one or more other BPIV genes, can be combined with HPIV sequences to give rise to a human-bovine chimeric PIV vaccine candidate. Any HPIV, including different strains of a particular HPIV serotype, e.g., HPIV3 will be a reasonable acceptor for attenuating BPIV gene(s). In general, the HPIV3 gene(s) or genome segment(s) selected for inclusion in a human-bovine chimeric PIV for use as a vaccine against human PIV will include one or more of the HPIV protective antigens such as the HN or F glycoproteins.

In exemplary aspects of the invention, human-bovine chimeric PIV bearing one or more bovine gene(s) or genome segment(s) exhibits a high degree of host range restriction, e.g., in the respiratory tract of mammalian models of human PIV infection such as non-human primates. In exemplary embodiments a human PIV is attenuated by the addition or substitution of one or more bovine gene(s) or genome segment(s) to a partial or complete human, e.g., HPIV3, PIV background genome or antigenome. In one example, the HPIV3 N gene is substituted by the BPIV3 N gene to yield a novel human-bovine chimeric PIV vaccine candidate.

Preferably, the degree of host range restriction exhibited by human-bovine chimeric PIV vaccine candidates of the invention is comparable to the degree of host range restriction exhibited by the respective BPIV parent or "donor" strain. Preferably, the restriction should have a true host range phenotype, i.e., it should be specific to the host in question and should not restrict replication and vaccine preparation in vitro in a suitable cell line. In addition, human-bovine chimeric PIV bearing one or more bovine gene(s) or genome segment(s) elicit a high level of resistance in hosts susceptible to PIV infection. Thus, the invention provides a new basis for attenuating a live virus vaccine against PIV, one which is based on host range effects due to the introduction of one or more gene(s) or genome segment(s) from a heterologous PIV, e.g., between HPIV3 and BPIV3.

In related aspects of the invention, human-bovine chimeric PIV incorporates one or more heterologous gene(s) that encode an HPIV HN and/or F glycoprotein(s). Alternatively, the chimeric PIV may incorporate one or more genome segment(s) encoding an ectodomain (and alternatively a cytoplasmic domain and/or transmembrane domain), or immunogenic epitope of an HPIV HN and/or F glycoprotein(s). These immunogenic proteins, domains and epitopes are particularly useful within human-bovine chimeric PIV because they generate novel immune responses in an immunized host. In particular, the HN and F proteins, and immunogenic domains and epitopes therein, provide major protective antigens.

In certain embodiments of the invention, addition or substitution of one or more immunogenic gene(s) or genome segment(s) from a human PIV subgroup or strain to or within a bovine background, or recipient, genome or antigenome yields a recombinant, chimeric virus or subviral particle capable of generating an immune response directed against the human donor virus, including one or more specific human PIV subgroups or strains, while the bovine backbone confers an attenuated phenotype making the chimera a useful candidate for vaccine development. In one exemplary embodiment, one or more human PIV glycoprotein genes, e.g., HN and/or F, are added to or substituted within a partial or complete bovine genome or antigenome to yield an attenuated, infectious human-bovine chimera that elicits an anti-human PIV immune response in a susceptible host.

In alternate embodiments, human-bovine chimeric PIV additionally incorporate a gene or genome segment encoding an immunogenic protein, protein domain or epitope from multiple human PIV strains, for example two HN or F proteins or immunogenic portions thereof each from a different HPIV, e.g., HPIV1 or HPIV2. Alternatively, one glycoprotein or immunogenic determinant may be provided from a first HPIV, and a second glycoprotein or immunogenic determinant may be provided from a second HPIV by substitution without the addition of an extra glycoprotein- or determinant-encoding polynucleotide to the genome or antigenome. Substitution or addition of HPIV glycoproteins and antigenic determinants may also be achieved by construction of a genome or antigenome that encodes a chimeric glycoprotein in the recombinant virus or subviral particle, for example having an immunogenic epitope, antigenic region or complete ectodomain of a first HPIV fused to a cytoplasmic domain of a heterologous HPIV. For example, a heterologous genome segment encoding a glycoprotein ectodomain from a HPIV1 or HPIV2 HN or F glycoprotein may be joined with a genome segment encoding a corresponding HPIV3 HN or F glycoprotein cytoplasmic/endodomain in the background genome or antigenome.

In alternate embodiments a human-bovine chimeric PIV genome or antigenome may encode a substitute, extra, or chimeric glycoprotein or antigenic determinant thereof in the recombinant virus or subviral particle, to yield a viral recombinant having both human and bovine glycoproteins, glycoprotein domains, or immunogenic epitopes. For example, a heterologous genome segment encoding a glycoprotein ectodomain from a human PIV HN or F glycoprotein may be joined with a genome segment encoding a corresponding bovine HN or F glycoprotein cytoplasmic/endodomain in the background genome or antigenome. Alternatively, the human PIV HN or F glycoprotein or parts thereof may be joined with a genome segment encoding an HN or F glycoprotein or parts thereof from another PIV strain or serotype.

Thus, according to the methods of the invention, human-bovine chimeric PIV may be constructed by substituting the heterologous gene or genome segment for a counterpart gene or genome segment in a partial PIV background genome or antigenome. Alternatively, the heterologous gene or genome segment may be added as a supernumerary gene or genome segment in combination with a complete (or partial if another gene or genome segment is deleted) PIV background genome or antigenome. For example, two human PIV HN or F genes or genome segments can be included, one each from HPIV2 and HPIV3.

Often, a heterologous gene or genome segment is added near an intergenic position within a partial or complete PIV background genome or antigenome. Alternatively, the gene or genome segment can be placed in other noncoding regions of the genome, for example, within the 5' or 3' noncoding regions or in other positions where noncoding nucleotides occur within the partial or complete genome or antigenome. In one aspect, noncoding regulatory regions contain cis-acting signals required for efficient replication, transcription, and translation, and therefore represent target sites for modification of these functions by introducing a heterologous gene or genome segment or other mutation as disclosed herein.

In more detailed aspects of the invention, attenuating mutations are introduced into cis-acting regulatory regions to yield, e.g., (1) a tissue specific attenuation (Gromeier et al., J. Virol. 73:958-964, 1999; Zimmermann et al., J. Virol. 71:4145-4149, 1997), (2) increased sensitivity to interferon (Zimmermann et al., 1997, supra), (3) temperature sensitivity (Whitehead et al., 1998a, supra), (4) a general restriction in level of replication (Men et al., J. Virol. 70:3930-3937, 1996; Muster et al., Proc. Natl. Acad. Sci. USA 88:5177-5181, 1991), and/or (5) host specific restriction of replication (Cahour et al., Virology 207:68-76, 1995). These attenuating mutations can be achieved in various ways to produce an attenuated human-bovine chimeric PIV of the invention, for example by point mutations, swaps of sequences between related viruses, or nucleotide deletions.

In yet additional alternative methods provided herein, a heterologous gene or genome segment may be added or substituted at a position corresponding to a wild-type gene order position of a counterpart gene or genome segment within the partial or complete PIV background genome or antigenome. In other embodiments, the heterologous gene or genome segment is added or substituted at a position that is more promoter-proximal or promotor-distal compared to a wild-type gene order position of a counterpart gene or genome segment within the background genome or antigenome, to enhance or reduce expression, respectively, of the heterologous gene or genome segment.

In general aspects of the invention, bovine genes or genome segments may be added to or substituted within a human PIV background to form an attenuated, human-bovine chimeric PIV. Alternatively, the chimera may be comprised of one or more human gene(s) or genome segment(s) added to or substituted within a bovine PIV background to form an attenuated PIV vaccine candidate. In this context, a chimeric PIV genome or antigenome is formed of a partial or complete bovine PIV background genome or antigenome combined with a heterologous gene or genome segment from a human PIV. In preferred aspects, one or more bovine PIV gene(s) or genome segment(s) is substituted for a counterpart gene(s) or genome segment(s) within a human PIV background genome or antigenome. In alternate embodiments, one or more human PIV glycoprotein genes, e.g., HN and/or F or a genome segment encoding a cytoplasmic domain, transmembrane domain, ectodomain or immunogenic epitope of a human PIV glycoprotein gene is substituted for a counterpart gene or genome segment within the bovine PIV background genome or antigenome. For example, both human PIV glycoprotein genes HN and F may be substituted to replace counterpart HN and F glycoprotein genes in a bovine PIV background genome or antigenome.

In a parallel fashion, the chimeric human-bovine PIV of the invention can be readily designed as "vectors" to incorporate antigenic determinants from different pathogens, including more than one PIV strain or group (e.g., both human PIV3 and human PIV1), respiratory syncytial virus (RSV), measles and other pathogens (see, e.g., U.S. Provisional Patent Application Ser. No. 60/170,195, filed Dec. 10, 1999 by Murphy et al., incorporated herein by reference).

In more detailed aspects of the invention, human-bovine chimeric PIV are comprised of a partial or complete BPIV background genome or antigenome combined with one or more heterologous gene(s) or genome segment(s) from a human PIV. Within these aspects, one or more of the HPIV glycoprotein genes HN and F, or one or more genome segments encoding a cytoplasmic domain, transmembrane domain, ectodomain or immunogenic epitope of the HN and/or F genes, may be added to a BPIV background genome or antigenome or substituted for one or more counterpart genes or genome segments within the BPIV background genome or antigenome to yield the chimeric construct. Often, both HPIV glycoprotein genes HN and F will be substituted to replace counterpart HN and F glycoprotein genes in the BPIV background genome or antigenome, as exemplified by the recombinant chimeric virus rBPIV3-FHHNH described below. This is a desirable construct because it combines the antigenic determinants of the human PIV with the host range restricting elements of the bovine PIV.

In combination with the host range phenotypic effects provided in the human-bovine chimeric PIV of the invention, it is often desirable to adjust the attenuation phenotype by introducing additional mutations that increase or decrease attenuation of the chimeric virus. Thus, in additional aspects of the invention, attenuated, human-bovine chimeric PIV are produced in which the chimeric genome or antigenome is further modified by introducing one or more attenuating mutations specifying an attenuating phenotype in the resultant virus or subviral particle. These can include mutations in RNA regulatory sequences or in encoded proteins. These attenuating mutations may be generated de novo and tested for attenuating effects according to a rational design mutagenesis strategy. Alternatively, the attenuating mutations may be identified in existing biologically derived mutant PIV and thereafter incorporated into a human-bovine chimeric PIV of the invention.

Introduction of attenuating and other desired phenotype-specifying mutations into chimeric bovine-human PIV of the invention may be achieved by transferring a heterologous gene or genome segment, e.g., a gene encoding an L protein or portion thereof, into a bovine or human PIV background genome or antigenome. Alternatively, the mutation may be present in the selected background genome or antigenome, and the introduced heterologous gene or genome segment may bear no mutations or may bear one or more different mutations. Typically, the human or bovine background or "recipient" genome or antigenome is modified at one or more sites corresponding to a site of mutation in a heterologous virus (e.g., a heterologous bovine or human PIV or a non-PIV negative stranded RNA virus) to contain or encode the same or a conservatively related mutation (e.g., a conservative amino acid substitution) as that identified in the donor virus (see, PCT/US00/09695 filed Apr. 12, 2000 and its priority U.S. Provisional Patent Application Ser. No. 60/129,006, filed Apr. 13, 1999, incorporated herein by reference). In one exemplary embodiment, a bovine background or "recipient" genome or antigenome is modified at one or more sites corresponding to a site of mutation in HPIV3 JS cp45, as enumerated below, to contain or encode the same or a conservatively related mutation as that identified in the cp45 "donor."

Preferred mutant PIV strains for identifying and incorporating attenuating mutations into bovine-human chimeric PIV of the invention include cold passaged (cp), cold adapted (ca), host range restricted (hr), small plaque (sp), and/or temperature sensitive (ts) mutants, for example the JS HPIV3 cp 45 mutant strain. In exemplary embodiments, one or more attenuating mutations occur in the polymerase L protein, e.g., at a position corresponding to Tyr942, Leu992, or Thr1558 of JS wild type HPIV3. Alternatively, attenuating mutations in the N protein may be selected and incorporated in a human-bovine chimeric PIV, for example which encode amino acid substitution(s) at a position corresponding to residues Val96 or Ser389 of JS. Alternative or additional mutations may encode amino acid substitution(s) in the C protein, e.g., at a position corresponding to Ile96 of JS and in the M protein, e.g., at a position corresponding to Pro199 (for example a Pro199 to Thr mutation). Yet additional mutations for adjusting attenuation of a human-bovine chimeric PIV of the invention are found in the F protein, e.g., at a position corresponding to Ile420 or Ala450 of JS, and in the HN protein, e.g., at a position corresponding to residue Val384 of JS.

Attenuating mutations from biologically derived PIV mutants for incorporation into human-bovine chimeric PIV of the invention also include mutations in noncoding portions of the PIV genome or antigenome, for example in a 3' leader sequence. Exemplary mutations in this context may be engineered at a position in the 3' leader of a recombinant virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45.

From JS cp45 and other biologically derived PIV and non-PIV mutants, a large "menu" of attenuating mutations is provided, each of which mutations can be combined with any other mutation(s) for adjusting the level of attenuation in a recombinant PIV bearing a genome or antigenome that is a chimera of human and bovine gene(s) or genome segment(s). For example, mutations within recombinant PIV of the invention include one or more, and preferably two or more, mutations of JS cp45. Desired human-bovine chimeric PIV of the invention selected for vaccine use often have at least two and sometimes three or more attenuating mutations to achieve a satisfactory level of attenuation for broad clinical use. Preferably, recombinant human-bovine chimeric PIV incorporate one or more attenuating mutation(s) stabilized by multiple nucleotide substitutions in a codon specifying the mutation.

Additional mutations which can be adopted or transferred to human-bovine chimeric PIV of the invention may be identified in non-PIV nonsegmented negative stranded RNA viruses and incorporated in PIV mutants of the invention. This is readily accomplished by mapping the mutation identified in a heterologous negative stranded RNA virus to a corresponding, homologous site in a recipient PIV genome or antigenome and mutating the existing sequence in the recipient to the mutant genotype (either by an identical or conservative mutation), as described in PCT/US00/09695 filed Apr. 12, 2000 and its priority U.S. Provisional Patent Application Ser. No. 60/129,006, filed Apr. 13, 1999, incorporated herein by reference.

In addition to recombinant human-bovine chimeric PIV, the invention provides related cDNA clones, vectors and particles, each of which incorporate HPIV and BPIV sequences and, optionally, one or more of the additional, phenotype-specific mutations set forth herein. These are introduced in selected combinations, e.g., into an isolated polynucleotide which is a recombinant cDNA genome or antigenome, to produce a suitably attenuated, infectious virus or subviral particle upon expression, according to the methods described herein. This process, coupled with routine phenotypic evaluation, provides human-bovine chimeric PIV having such desired characteristics as attenuation, temperature sensitivity, altered immunogenicity, cold-adaptation, small plaque size, host range restriction, genetic stability, etc. In particular, vaccine candidates are selected which are attenuated and yet are sufficiently immunogenic to elicit a protective immune response in the vaccinated mammalian host.

In yet additional aspects of the invention, human-bovine chimeric PIV, with or without additional mutations adopted, e.g., from a biologically derived attenuated mutant virus, are constructed to have additional nucleotide modification(s) to yield a desired phenotypic, structural, or functional change. Typically, the selected nucleotide modification will specify a phenotypic change, for example a change in growth characteristics, attenuation, temperature-sensitivity, cold-adaptation, plaque size, host range restriction, or immunogenicity. Structural changes in this context include introduction or ablation of restriction sites into PIV encoding cDNAs for ease of manipulation and identification.

In preferred embodiments, nucleotide changes within the genome or antigenome of a human-bovine chimeric PIV include modification of a viral gene by partial or complete deletion of the gene or reduction or ablation (knock-out) of its expression. These modifications can be introduced within the human or bovine background genome or antigenome, or may be introduced into the chimeric genome or antigenome by incorporation within the heterologous gene(s) or genome segment(s) added or substituted therein. Target genes for mutation in this context include any of the PIV genes, including the nucleocapsid protein N, phosphoprotein P, large polymerase subunit L, matrix protein M, hemagglutinin-neuraminidase protein HN, small hydrophobic SH protein, where applicable, fusion protein F, and the products of the C, D and V open reading frames (ORFs). To the extent that the recombinant virus remains viable and infectious, each of these proteins can be selectively deleted, substituted or rearranged, in whole or in part, alone or in combination with other desired modifications, to achieve novel deletion or knock out mutants. For example, one or more of the C, D, and/or V genes may be deleted in whole or in part, or its expression reduced or ablated (e.g., by introduction of a stop codon, by a mutation in an RNA editing site, by a mutation that alters the amino acid specified by an initiation codon, or by a frame shift mutation in the targeted ORF(s). In one embodiment, a mutation can be made in the editing site that prevents editing and ablates expression of proteins whose mRNA is generated by RNA editing (Kato et al., EMBO J. 16:578-587, 1997a and Schneider et al., Virology 227:314-322, 1997, each incorporated herein by reference). Alternatively, one or more of the C, D, and/or V ORF(s) can be deleted in whole or in part to alter the phenotype of the resultant recombinant clone to improve growth, attenuation, immunogenicity or other desired phenotypic characteristics (see, U.S. patent application Ser. No. 09/350,821, filed by Durbin et al. on Jul. 9, 1999, incorporated herein by reference).

Alternative nucleotide modifications in human-bovine chimeric PIV of the invention include a deletion, insertion, addition or rearrangement of a cis-acting regulatory sequence for a selected gene in the recombinant genome or antigenome. As with other such modifications described herein, these modifications can be introduced within the human or bovine background genome or antigenome, or may be introduced into the chimeric genome or antigenome by incorporation within the heterologous gene(s) or genome segment(s) added or substituted therein. In one example, a cis-acting regulatory sequence of one PIV gene is changed to correspond to a heterologous regulatory sequence, which may be a counterpart cis-acting regulatory sequence of the same gene in a different PIV, or a cis-acting regulatory sequence of a different PIV gene. For example, a gene end signal may be modified by conversion or substitution to a gene end signal of a different gene in the same PIV strain. In other embodiments, the nucleotide modification may comprise an insertion, deletion, substitution, or rearrangement of a translational start site within the recombinant genome or antigenome, e.g., to ablate an alternative translational start site for a selected form of a protein.

In addition, a variety of other genetic alterations can be produced in a human-bovine chimeric PIV genome or antigenome, alone or together with one or more attenuating mutations adopted from a biologically derived mutant PIV. For example, genes or genome segments from non-PIV sources may be inserted in whole or in part. Alternatively, the order of genes can be changed, or a PIV genome promoter replaced with its antigenome counterpart. Different or additional modifications in the recombinant genome or antigenome can be made to facilitate manipulations, such as the insertion of unique restriction sites in various non-coding regions or elsewhere. Nontranslated gene sequences can be removed to increase capacity for inserting foreign sequences.

In yet additional aspects, polynucleotide molecules or vectors encoding the human-bovine chimeric PIV genome or antigenome can be modified to encode non-PIV sequences, e.g., a cytokine, a T-helper epitope, a restriction site marker, or a protein or immunogenic epitope of a microbial pathogen (e.g., virus, bacterium, parasite, or fungus) capable of eliciting a protective immune response in an intended host. In one such embodiment, human-bovine chimeric PIV are constructed that incorporate a gene or genome segment from a respiratory syncytial virus (RSV), for example a gene encoding an antigenic protein (e.g., an F or G protein), immunogenic domain or epitope of RSV.

In related aspects of the invention, compositions (e.g., isolated polynucleotides and vectors incorporating a PIV-encoding cDNA) and methods are provided for producing an isolated infectious human-bovine chimeric PIV. Included within these aspects of the invention are novel, isolated polynucleotide molecules and vectors incorporating such molecules that comprise a human-bovine chimeric PIV genome or antigenome. Also provided is the same or different expression vector comprising one or more isolated polynucleotide molecules encoding N, P, and L proteins. These proteins also can be expressed directly from the genome or antigenome cDNA. The vector(s) is/are preferably expressed or coexpressed in a cell or cell-free lysate, thereby producing an infectious human-bovine chimeric PIV viral particle or subviral particle.

The above methods and compositions for producing chimeric PIV yield infectious viral or subviral particles, or derivatives thereof. An infectious virus is comparable to the authentic PIV particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, and L proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell-free lysate containing an expression vector which comprises an isolated polynucleotide molecule comprising a chimeric PIV genome or antigenome as described above, and an expression vector (the same or different vector) which comprises one or more isolated polynucleotide molecules encoding the N, P, and L proteins of PIV. One or more of these proteins also can be expressed from the genome or antigenome cDNA. Upon expression the genome or antigenome and N, P and L proteins combine to produce an infectious chimeric parainfluenza virus or subviral particle.

The human-bovine chimeric PIVs of the invention are useful in various compositions to generate a desired immune response against PIV in a host susceptible to PIV infection. Human-bovine chimeric PIV recombinants are capable of eliciting a protective immune response in an infected mammalian host, yet are sufficiently attenuated so as not to cause unacceptable symptoms of severe respiratory disease in the immunized host. In addition, the human-bovine chimeric PIV recombinants should replicate with sufficient efficiency in vitro to make vaccine preparation feasible. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated chimeric parainfluenza virus or subviral particle as described above. In preferred embodiments, the vaccine is comprised of a chimeric PIV having at least one, and preferably two or more additional mutations or other nucleotide modifications as described above to achieve a suitable balance of attenuation and immunogenicity. The vaccine can be formulated in a dose of 103 to 107 PFU of attenuated virus. The vaccine may comprise attenuated chimeric PIV that elicits an immune response against a single PIV strain or against multiple PIV strains or groups. In this regard, chimeric PIV can be combined in vaccine formulations with other PIV vaccine strains, or with other viral vaccine viruses such as RSV.

In related aspects, the invention provides a method for stimulating the immune system of an individual to elicit an immune response against one or more PIVs, or against PIV in a mammalian subject. The method comprises administering a formulation of an immunologically sufficient amount a chimeric PIV in a physiologically acceptable carrier and/or adjuvant. In one embodiment, the immunogenic composition is a vaccine comprised of a chimeric PIV having at least one, and preferably two or more attenuating mutations or other nucleotide modifications specifying a desired phenotype and/or level of attenuation as described above. The vaccine can be formulated in a dose of 103 to 107 PFU of attenuated virus. The vaccine may comprise an attenuated chimeric PIV that elicits an immune response against a single PIV, against multiple PIVs, e.g., HPIV1 and HPIV3, or against one or more PIV(s) and a non-PIV pathogen such as measles or RSV. In this context, chimeric PIVs can elicit a monospecific immune response or a polyspecific immune response against multiple PIVs, or against one or more PIV(s) and a non-PIV pathogen. Alternatively, chimeric PIV having different immunogenic characteristics can be combined in a vaccine mixture or administered separately in a coordinated treatment protocol to elicit more effective protection against one PIV, against multiple PIVs, or against one or more PIV(s) and a non-PIV pathogen such as measles or RSV. Preferably the immunogenic compositions of the invention are administered to the upper respiratory tract, e.g., by spray, droplet or aerosol. Preferably the immunogenic composition is administered to the upper respiratory tract, e.g., by spray, droplet or aerosol.

RSV and PIV3 cause significant amount of illness within the first four months of life, whereas most of the illness caused by PIV1 and PIV2 occurs after six months of age (Collins et al., In Fields Virology, Vol. 1, pp. 1205-1243, Lippincott-Raven Publishers, Philadelphia, 1996; Reed et al., J. Infect. Dis. 175:807-13, 1997). A preferred immunization sequence employing live attenuated RSV and PIV vaccines is to administer RSV and PIV3 as early as one month of age (e.g., at one and two months of age) followed by a bivalent PIV1 and PIV2 vaccine at four and six months of age. It is thus desirable to employ the methods of the invention to administer multiple PIV vaccines, including one or more chimeric PIV vaccines, coordinately, e.g., simultaneously in a mixture or separately in a defined temporal sequence (e.g., in a daily or weekly sequence), wherein each vaccine virus preferably expresses a different heterologous protective antigen. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

Figure 5A:
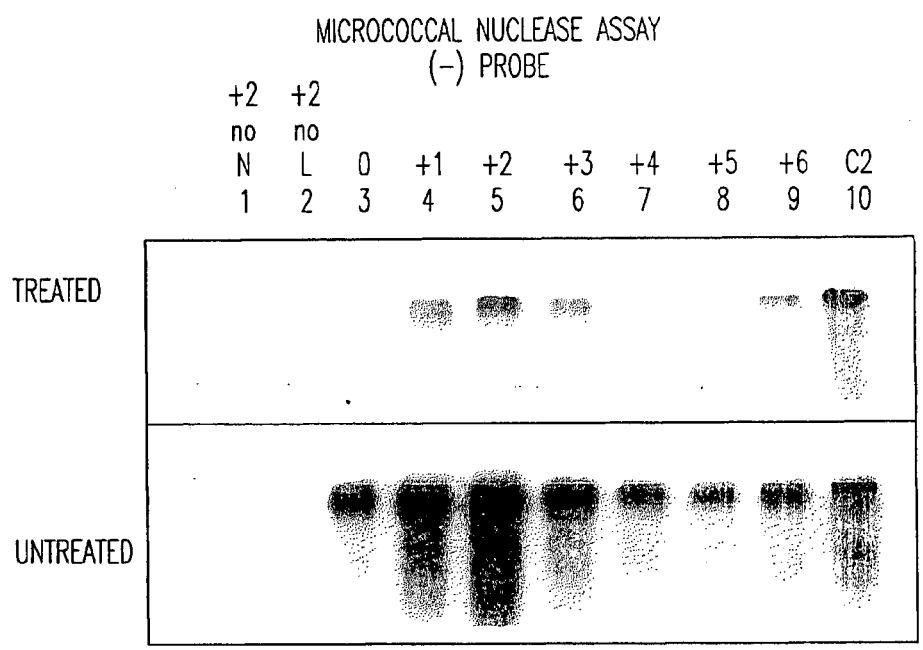
Figure 5B:
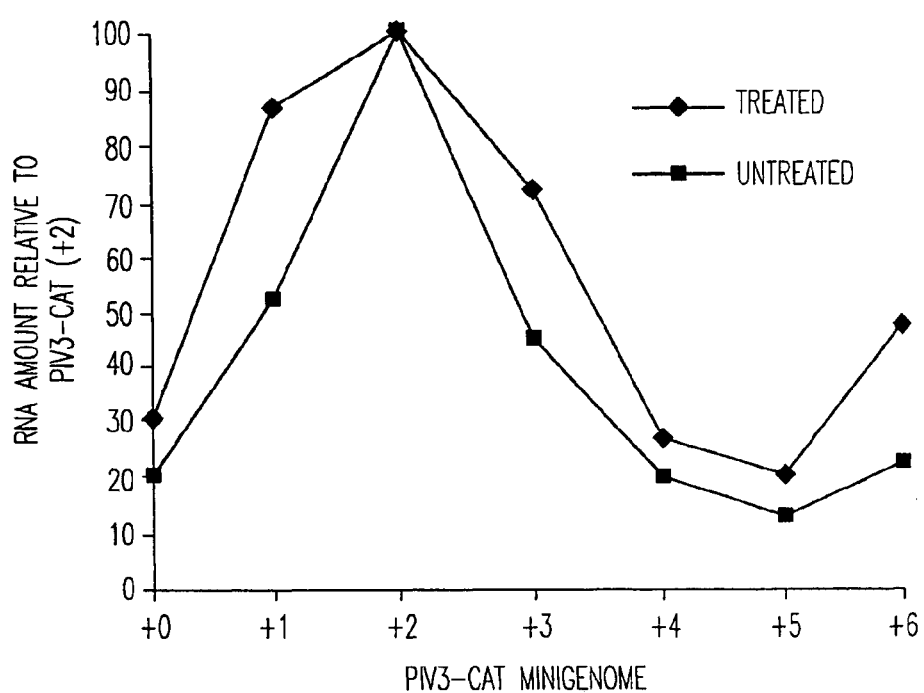
Figure 6A:
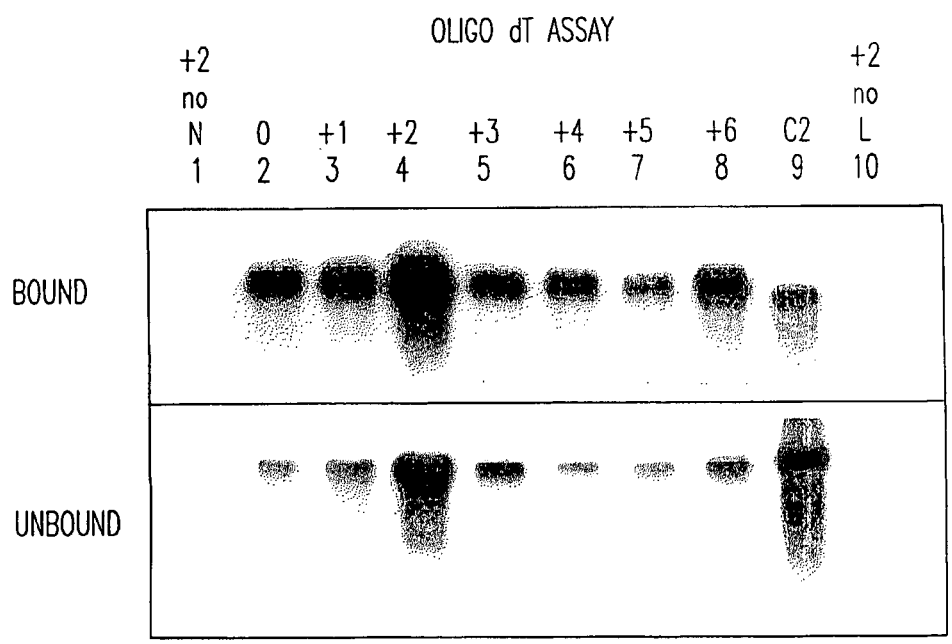
Figure 6B:
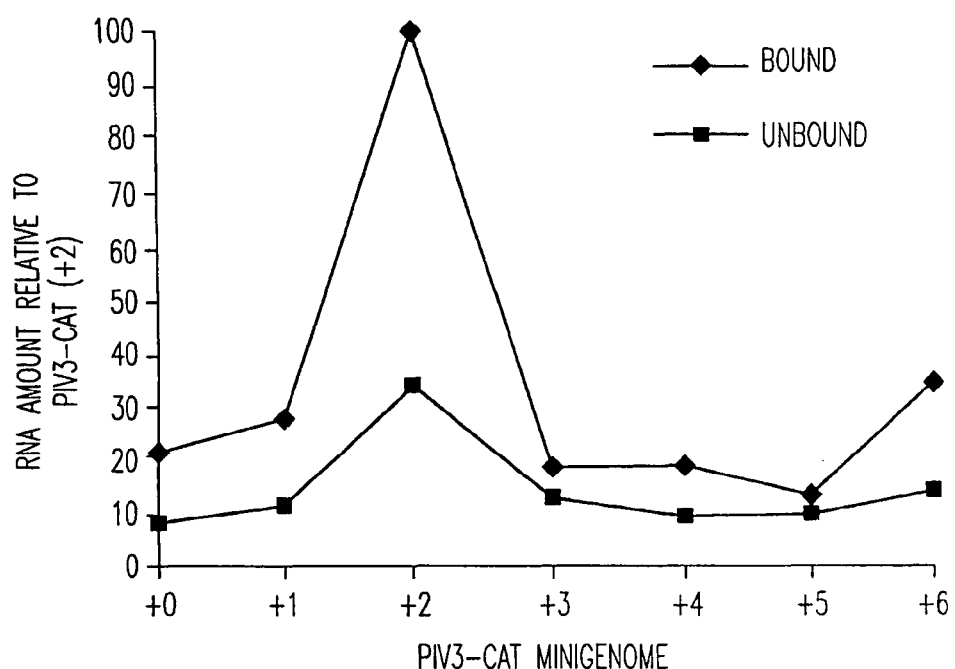

Importantly, the presence of multiple PIV serotypes and their unique epidemiology with PIV3 disease occurring at an earlier age than that of PIV1 and PIV2 makes it desirable to sequentially immunize an infant with different PIV vectors each expressing the same heterologous antigenic determinant such as the measles virus HA. This sequential immunization permits the induction of the high titer of antibody to the heterologous protein that is characteristic of the secondary antibody response. In one embodiment, early infants (e.g. 2-4 month old infants) can be immunized with an attenuated chimeric virus of the invention, for example a chimeric HPIV3 expressing the measles virus HA protein and also adapted to elicit an immune response against HPIV3, such as rcp45L(HA P-M). Subsequently, e.g., at four months of age the infant is again immunized but with a different, secondary vector construct, such as the rPIV3-1 cp45L virus expressing the measles virus HA gene and the HPIV1 antigenic determinants as the functional, obligate glycoproteins of the vector. Following the first vaccination, the vaccinee will elicit a primary antibody response to both the PIV3 HN and F proteins and to the measles virus HA protein, but not to the PIV1 HN and F protein. Upon secondary immunization with the rPIV3-1 cp45L expressing the measles virus HA, the vaccinee will be readily infected with the vaccine because of the absence of antibody to the PIV1 HN and F proteins and will develop both a primary antibody response to the PIV1 HN and F protective antigens and a high titered secondary antibody response to the heterologous measles virus HA protein. A similar sequential immunization schedule can be developed where immunity is sequentially elicited against HPIV3 and then HPIV2 by one or more of the chimeric vaccine viruses disclosed herein, simultaneous with stimulation of an initial and then secondary, high titer protective response against measles or another non-PIV pathogen. This sequential immunization strategy, preferably employing different serotypes of PIV as primary and secondary vectors, effectively circumvents immunity that is induced to the primary vector, a factor ultimately limiting the usefulness of vectors with only one serotype. The success of sequential immunization with rPIV3 and rPIV3-1 virus vaccine candidates as described above has been demonstrated. (Tao et al., Vaccine 17:1100-8, 1999).

BRIEF DESCRIPTION OF THE DRAWINGS

FIG. 1 illustrates construction of the plasmid p218(131), encoding a complete copy of HPIV3 genomic RNA. The diagram of p218(A*A'CC'D*E) (top left) illustrates the location of the T7 terminator and delta ribozyme adjacent to nucleotide 1 of the HPIV3 genome. The top right diagram of p(E*FF'GHIJKL*) illustrates the locations of the 7 sequencing markers (asterisk), see FIG. 2 below, and the T7 promoter adjacent to nucleotide 15462 of HPIV3. The 15 overlapping clones used to construct the full length genomic cDNA are indicated by letters on the outside of the two plasmids. The unique restriction sites NgoMI and XhoI were used to clone p218(131) which encodes the complete negative-sense genomic RNA of HPIV3 illustrated at the bottom. The location of each sequencing marker in p218(131) differentiating recombinant JS from JS wt is indicated by an asterisk.

FIG. 2 depicts sequence markers in cDNA encoded genomic RNA of the HN (1) and L(2) genes of HPIV3. Sequences are negative sense, mutations are boxed.

1) A non-coding nt substitution at 7903 removes a Hga I site from JS wt. Nucleotide substitutions in JS cDNA at 7913 and 7915 create a Sca I site and change amino acid 370 from proline to threonine, ablating the antibody epitope recognized by mAb 170/7 and 423/6. Also, the HN gene was found to contain an additional point mutation at nt 7593 which had not been recognized previously. This results in a threonine to isoleucine change at amino acid position 263 in the HN protein.

2) The three incidental non-coding mutations in the L gene of JS cDNA that occurred during plasmid construction or assembly are boxed.

FIG. 3 includes a diagram (not to scale) of the PIV3-CAT cDNA (top, drawn as a circular plasmid) and the encoded minigenome RNA (bottom, drawn as a single strand of negative-sense RNA, 3' to 5').

Plasmid: The T7 promoter is shown as a black arrow pointing in the direction of transcription. Positions are shown for the delta ribozyme, the T7 transcriptional terminator, the inserted vaccinia virus transcriptional terminators (T7CT and T5AT), restriction enzyme sites, and the coding sequence for the various domains of the encoded minigenome.

Minigenome RNA: The 5' (right hand) end of the minigenome is defined by the promoter for T7 RNA polymerase, which contributes an extension of two nonviral G residues. These are not included in length calculations. The 3' end is defined by the ribozyme and is free of any heterologous nucleotides. PIV3-specific regions are shown as open boxes. The CAT ORF is shaded and the negative-sense complements of the translational initiation (UAC) and termination (AUU) codons are shown. Nucleotide positions are indicated according to the shortest, 898-nucleotide minigenome. Nucleotide lengths of specific regions are given in parentheses. The sequence of positions 90 to 124 (3' to 5', negative-sense) is shown at the bottom; PIV3-specific sequence is underlined, the complement of a vaccinia virus transcriptional terminator is overlined, the complement of the XbaI site is italicized, and the complement of the translational start codon for the CAT ORF is in bold. The site where 0 to 6 G residues were inserted, resulting in PIV3-CAT 0 to +6, is indicated. Abbreviations: GS, transcriptional gene-start motif; GE, transcriptional gene-end termination/polyadenylation motif; NT, nontranslated gene sequence.

FIG. 4 depicts expression of CAT enzyme by minigenomes PIV3-CAT 0 to +6. Cells were transfected with plasmids encoding the indicated PIV3-CAT minigenome and the N, P and L proteins, and were infected simultaneously with vaccinia virus recombinant vTF7-3 expressing T7 RNA polymerase. Lysates were prepared 48 h post-infection, and samples representing 3000 cells were analyzed for CAT activity. Activities are expressed relative to the +2 minigenome, which is a multiple of six, as 100. Samples in which the L plasmid was omitted did not have CAT activity detectable under these conditions.

FIGS. 5A and 5B depict synthesis of mini-antigenomic RNA by PIV3-CAT minigenomes 0 to +6. Cells were transfected and infected as described for FIG. 4, except for controls in which N plasmid (lane 1) or L plasmid (lane 2) was omitted. The PIV3-CAT minigenome plasmid which was transfected in each case is indicated. Cell lysates were prepared at 48 h post-transfection: one aliquot was treated with micrococcal nuclease (treated) and the second was mock-treated (untreated), followed by processing for RNA purification. The RNAs were analyzed by Northern blot hybridization with a negative-sense CAT riboprobe. As a marker and control for nuclease treatment, the RSV-CAT C2 minigenome (Grosfeld et al., J. Virol. 69:5677-5686 (1995), incorporated herein by reference in its entirety) was complemented by the RSV N, P and L proteins and was processed in parallel (Lane 10). Autoradiograms of the hybridized blots are shown in FIG. 5A. FIG. 5B shows phosphorimager analysis in which the amount of hybridization relative to the +2 minigenome was calculated separately for the treated and untreated samples.

FIGS. 6A and 6B depict synthesis of polyadenylated mRNA by PIV3-CAT minigenomes 0 to +6. Using aliquots of cells from the same experiment as shown in FIGS. 5A and 5B, total intracellular RNA was harvested at 48 h post-transfection and fractionated by oligo(dT) chromatography into bound and unbound fractions, which were analyzed by Northern blot hybridization with a negative-sense CAT riboprobe. FIG. 6A shows autoradiograms of the hybridized blots. FIG. 6B shows the phosphorimager analysis in which the amount of hybridization was normalized relative to the bound RNA fraction of the +2 minigenome, this was calculated separately for the bound and unbound fractions.

Figure 7A:
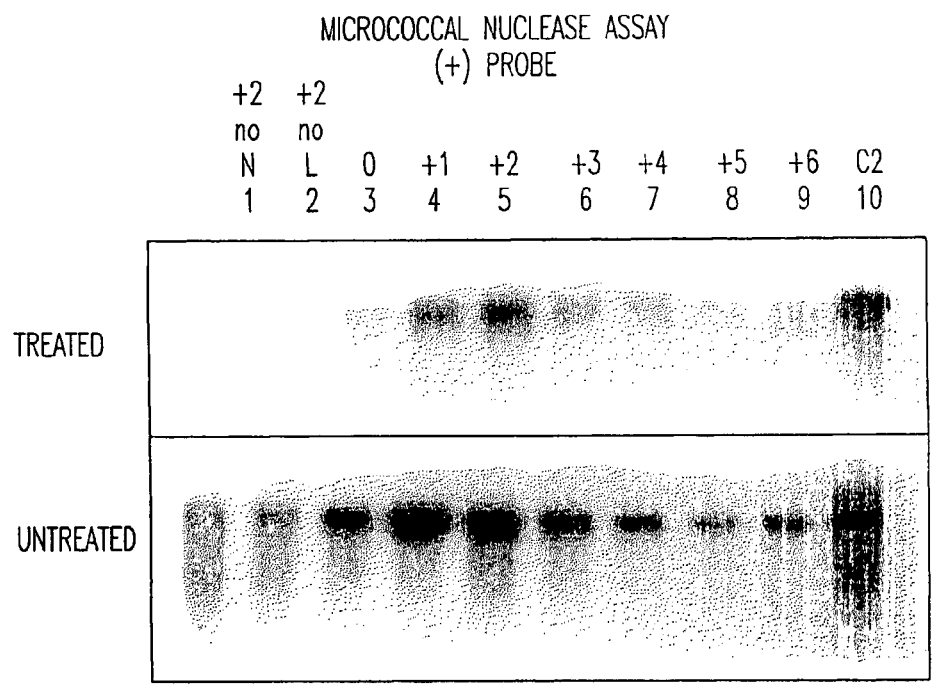
Figure 7B:
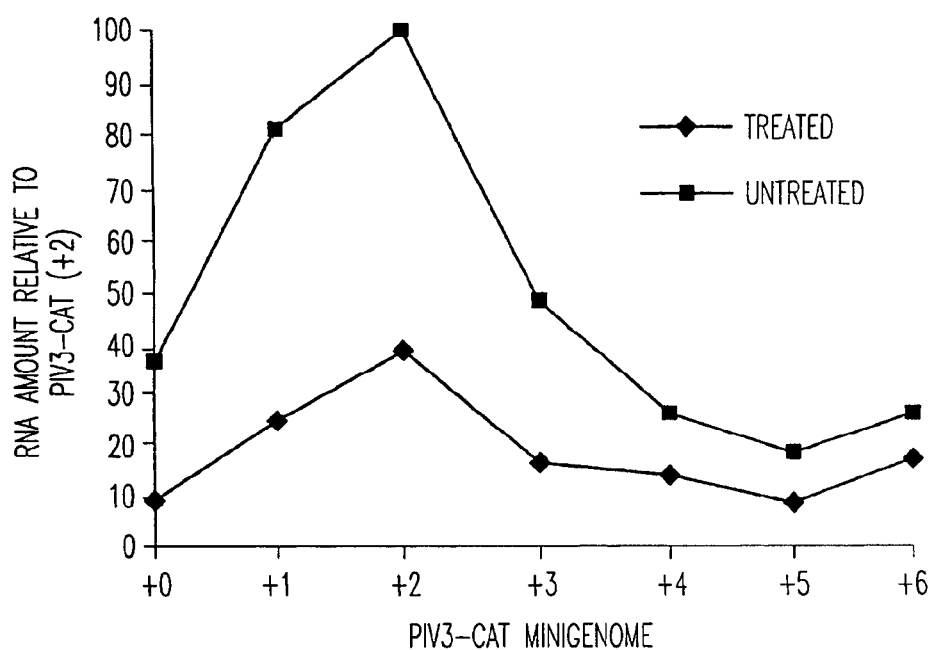

FIGS. 7A and 7B depict accumulation of intracellular minigenome in response to plasmid encoding PIV3-CAT minigenomes 0 to +6. This is a continuation of the experiment shown in FIGS. 5A and 5B. Thus, cells which had been transfected with plasmids encoding a minigenome and the N, P and L proteins and infected with vTF7-3 were harvested 48 h post-transfection and cell lysates were prepared. One aliquot of lysate was treated with micrococcal nuclease (treated) and the other was mock-treated (untreated), followed by processing for RNA purification. The RNAs were analyzed by Northern blot hybridization with a positive-sense CAT riboprobe, whereas in FIG. 5A the riboprobe was negative-sense. FIG. 7A shows autoradiograms of the hybridized blots. FIG. 7B shows phosphorimager analysis in which the amount of hybridization relative to the +2 minigenome was calculated separately for the treated and untreated samples.

Figure 8:
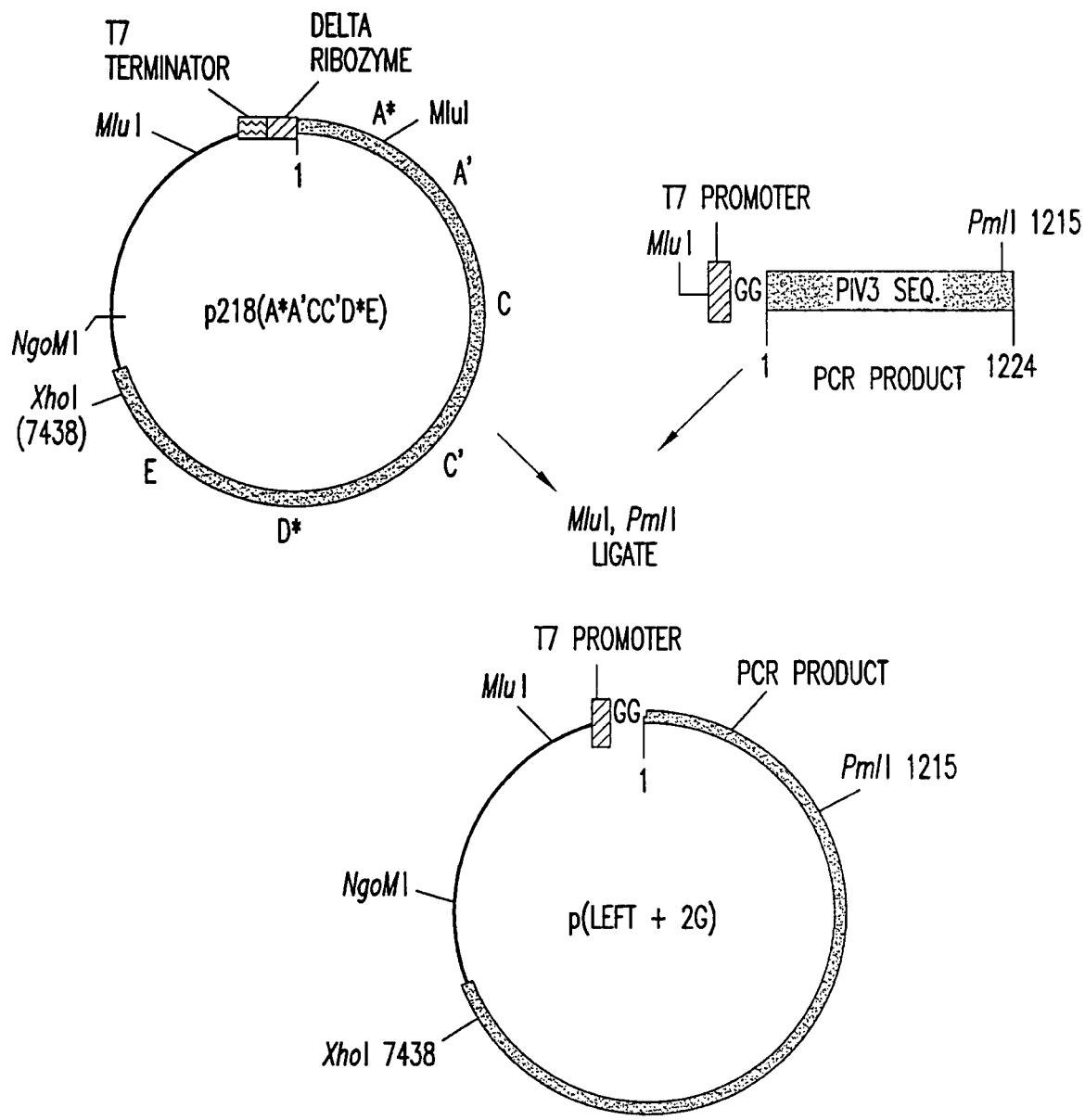
Figure 9:
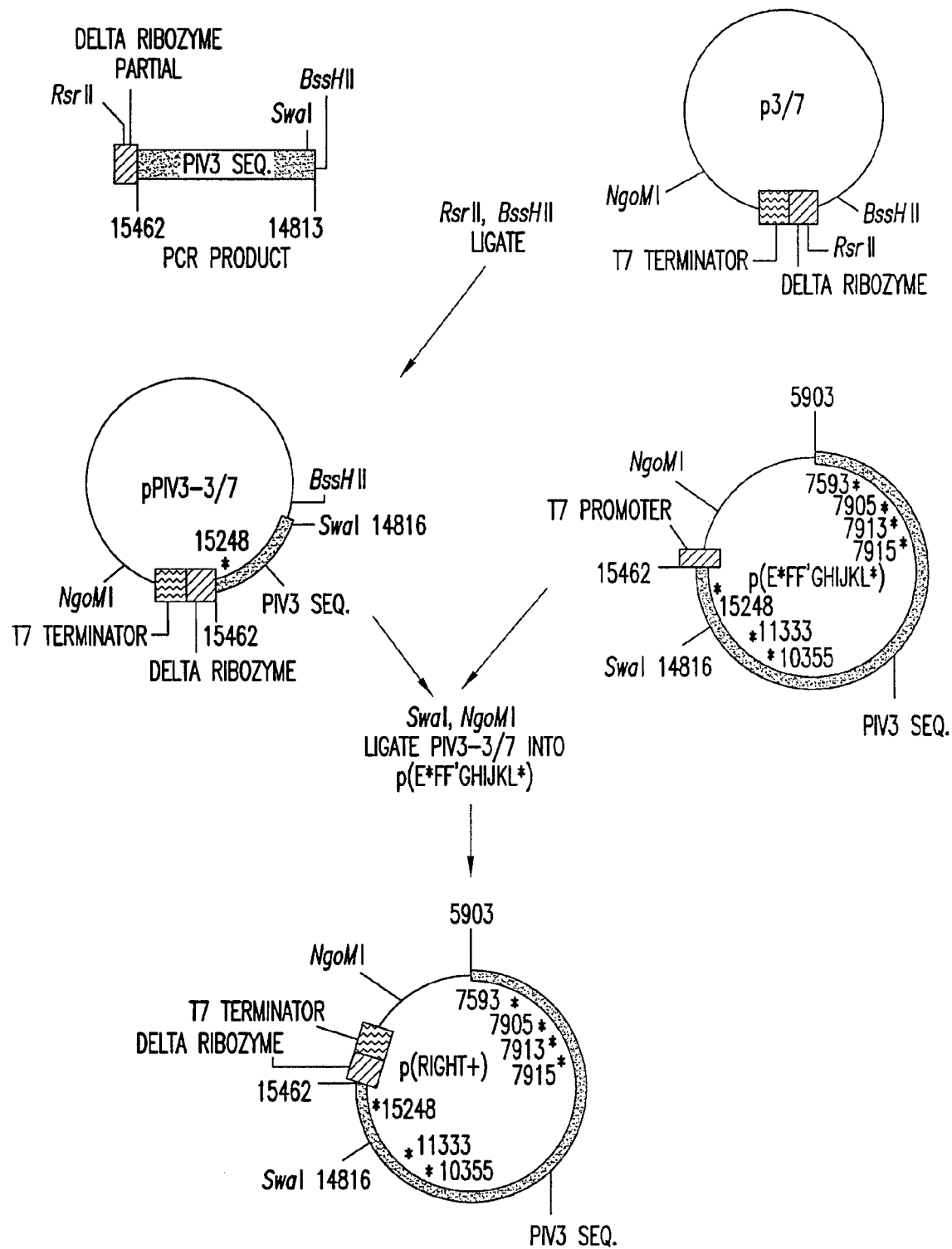
Figure 10:
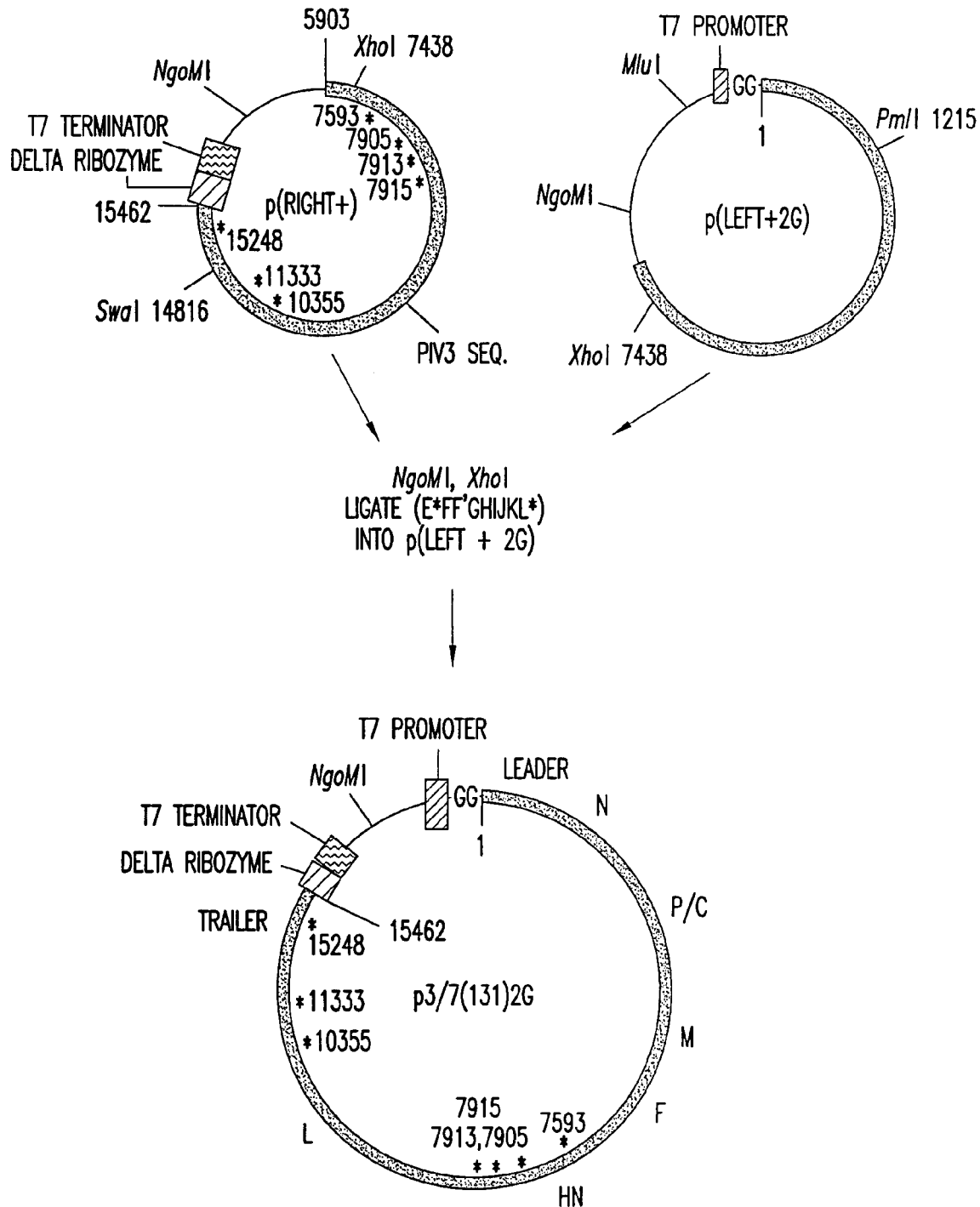

FIGS. 8-10 illustrate construction of p3/7(131)2G. p3/7 (131)2G encodes a complete positive-sense HPIV3 antigenome and contains two G residues between the T7 promoter and nucleotide 1 of the antigenome. The construction involved modification separately of the left and right halves of cDNA 218(131) encoding the negative-sense genome. Using the same strategy, a second cDNA, p3/7(131) was constructed which is identical to p3/7(131)2G except that the two G residues were omitted.

FIG. 8 depicts construction of p(Left+2G), performed by replacing the ribozyme and T7 transcription terminator of p218(A*A'CC'D*E) with a T7 promoter including two G residues. p218 (A*A'CC'D*E) was used as the template in a PCR that amplified the left-hand 1224 nucleotides of the HPIV3 genome (black rectangle labeled "PIV3seq.") using a left hand PCR primer that introduced the T7 promoter. This PCR fragment was cloned into the MluI-PmlI window of p218(A*A'CC'D*E), resulting in p(Left+2G).

FIG. 9 depicts construction of p(Right+), performed by replacing the T7 promoter of p(E*FF'GHIHKL*) with a ribozyme and T7 terminator placed adjacent to PIV3 nucleotide 15642 in the positive-sense (antigenome) strand. p(E*FF'GHIHKL*) was used as a template in a PCR that amplified the right-hand 649 nucleotides of the HPIV3 genome (black rectangle labeled "PIV3 seq.") using a mutagenic oligonucleotide that added part of the delta ribozyme (including a naturally-occurring RsrII site). This PCR product was cloned into the RsrII-BssHII window of p3/7 to yield pPIV3-3/7, thus reconstructing a complete ribozyme flanked by the T7 terminator. The SwaI-NgoMI fragment of pPIV3-3/7 was cloned into the SwaI-NgoMI windows of p(E*FF'GHIHKL*), resulting in p(Right+). The locations of the seven sequence markers are indicated with asterisks.

FIG. 10 depicts construction of p3/7(131)2G. The NgoMI-XhoI fragment of p(Right+) was cloned into the NgoMI-XhoI window of p(Left+2G), resulting in p3/7(131)2G. The positions of HPIV3 genes are indicated (not to scale). The locations of sequence markers are indicated with asterisks.

Figure 11:
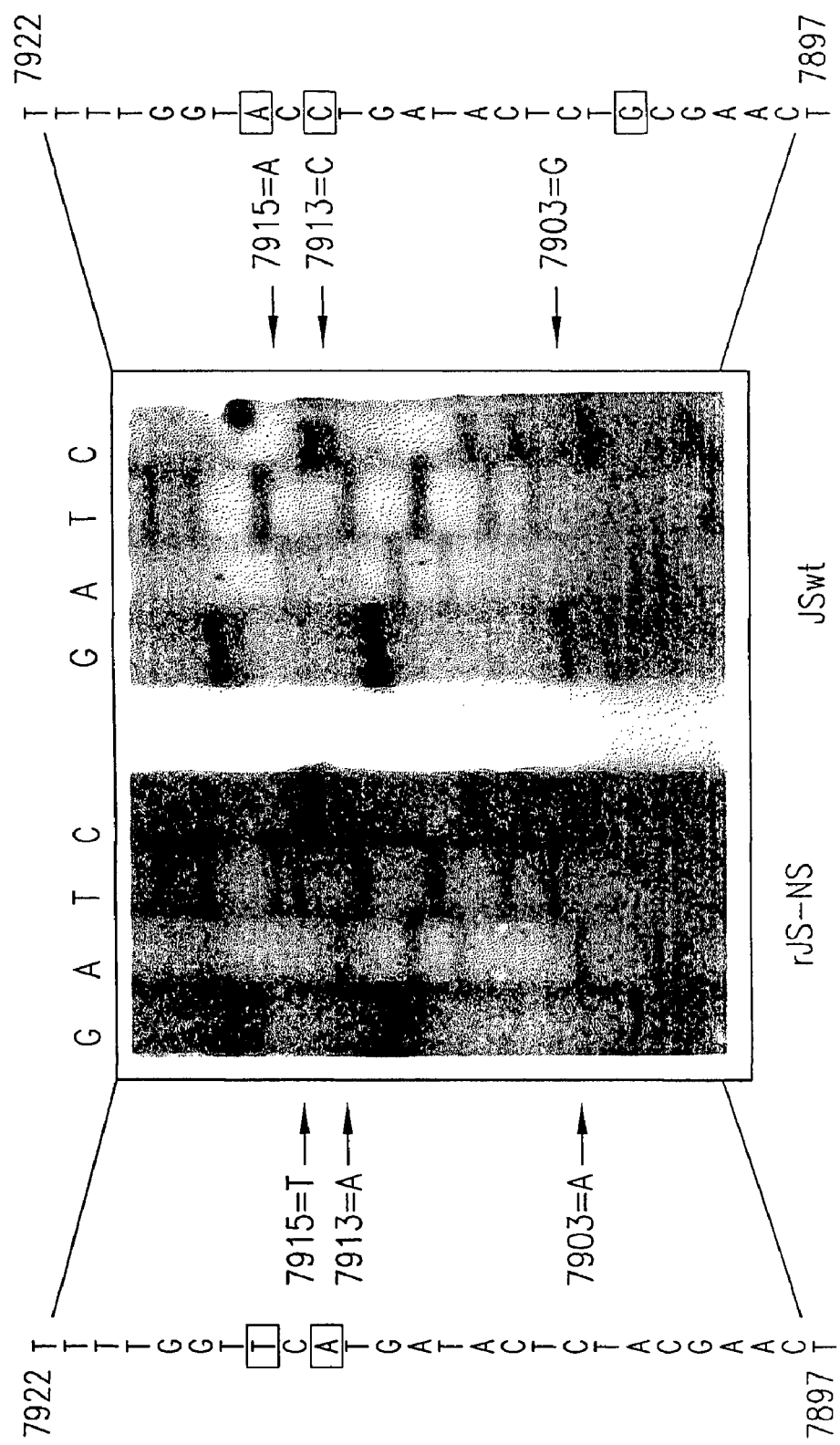

FIG. 11 shows sequence confirmation of a negative sense recombinant PIV3. A 1379 bp fragment (nucleotides 7334-8713) spanning the mutations at 7903, 7913, and 7915 was generated by RT-PCR of RNA from infected cells and then analyzed by cycle-sequencing. The mutations differentiating recombinant PIV from JS wt are indicated by arrows. The complete sequence from nt 7897 to 7922 is shown in the margin next to each gel, with the three nucleotide differences indicated in bold.

Figure 12:
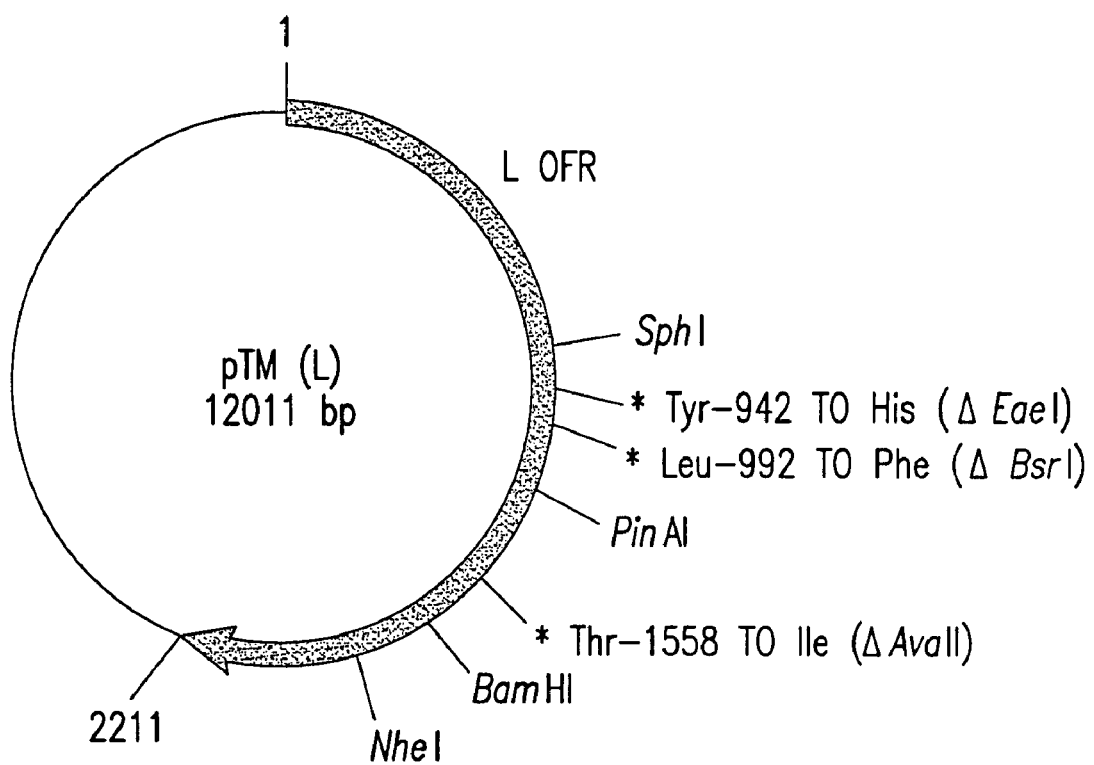

FIG. 12 provides a map of plasmid pTM(L)942/992/1558, which contains the PIV3 L cDNA with amino acid substitutions at positions 942, 992, and 1558 in the L protein sequence. The relative position of each of coding change is indicated, together with the aa difference and the naturally-occurring restriction site which was deliberately ablated as a marker. Restriction sites used for cloning (SphI, PinAI, BamHI and NheI) are indicated. The arrow shows the direction of the L protein coding sequence and is numbered according to amino acid position.

Figure 13:
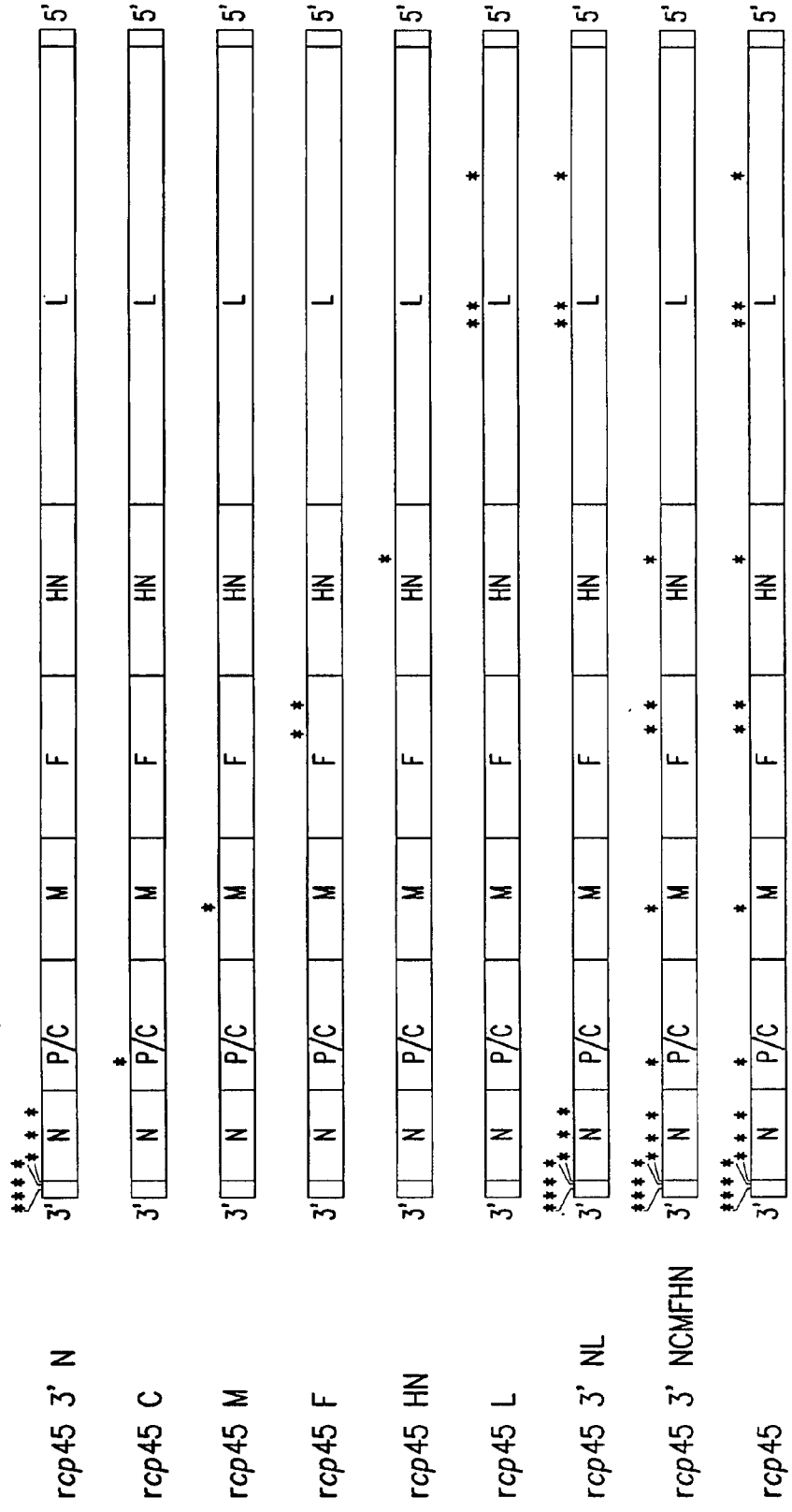

FIG. 13 is a schematic representation of recombinant PIV3 viruses bearing representative mutations within the invention.

Figure 14:
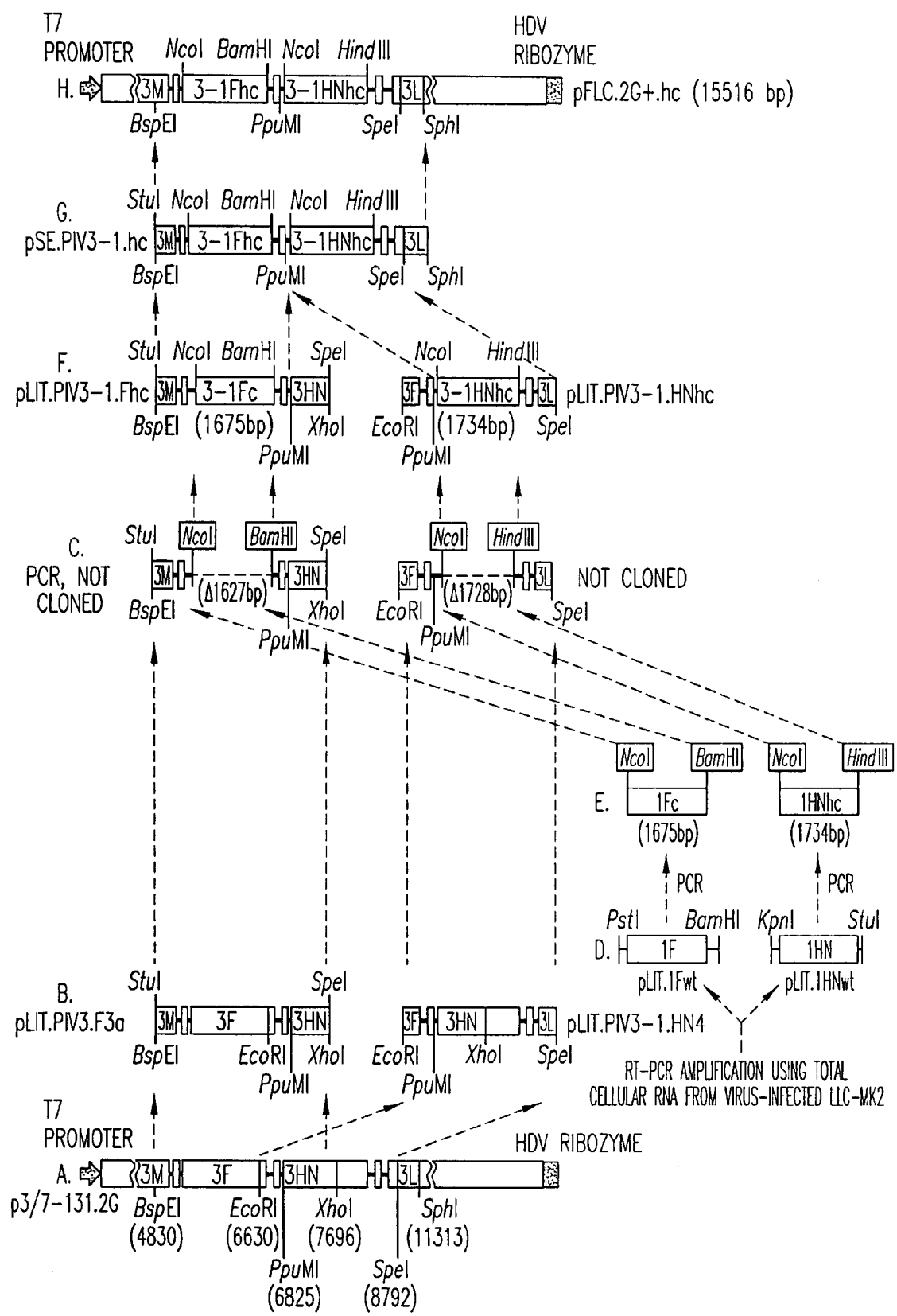

FIG. 14 illustrates construction of cDNA encoding the chimeric PIV3-PIV1 antigenome in which the PIV3 HN and F ORFs were replaced by those of PIV1. First (starting from the bottom left) the PIV3 F and HN genes were subcloned (as BspE-I I-Xho I and EcoR I-Spe I fragments) from the full-length PIV3 cDNA clone p3/7(131)2G (Panel A) to generate pLit.PIV3.F3a and pLit.PIV3.HN4 (Panel B), respectively. PCR mutagenesis (Panel C) was performed to delete the complete coding regions of the PIV3 F and HN genes and to introduce new restriction sites (boxed). PIV1 F and HN cDNAs were prepared from infected-cell RNA by RT-PCR and cloned into pLITMUS28 (Panel D). These clones, pLit.1 Fwt and pLit.1 HNwt, were used as templates for modification of the PIV1 F and HN genes at their start and stop codons to introduce new restriction sites compatible with those introduced in the PIV3 deletions (Panel E). Chimeric F and HN genes were constructed by importing the PIV1 coding regions into the PIV3 deletions to generate pLit.PIV3-1.Fhc and pLit.PIV3-1.HNhc (Panel F). The chimeric F and HN were assembled together to generate pSE.PIV3-1.hc (Panel G). The F and HN chimeric segment was introduced into full-length PIV3 clone p3/7(131)2G by replacing its BspE I-Sph I fragment to generate pFLC.2G+.hc (Panel H). The small boxes between genes represent the gene end, intergenic, and gene start regions, and the lines represent the non-coding regions. Shaded portions are from PIV1, open boxes are from PIV3. The black arrows depict the T7 promoter, while black boxes depict the hepatitis delta virus (HDV) ribozyme.

FIG. 15A is a diagram of the chimeric HN and F genes of the chimeric rPIV3-1 (middle) in parallel with that of rPIV3/JS (top; alternatively referred to herein as rJS and JS wt rPIV3) and PIV1/Wash64 (bottom). The four junction regions containing the sequence transitions from PIV3 to PIV1 are boxed and numbered I to IV. Each small box between genes represents the gene end, intergenic, and gene start region, and the lines represent the non-coding regions. RT-PCR primers, specific to PIV3 M and L genes (primer pair A at top) or specific to PIV1 M and HN genes (primer pair B at bottom) used in FIG. 14B, are depicted as arrows.

FIG. 15B shows an evaluation of RT-PCR products generated using virion RNA (vRNA) as template and the PIV3- or PIV1-specific primer pairs described in FIG. 14A. The reverse transcription step was omitted in a duplicate of each template, as indicated, to confirm that the PCR product was derived from RNA. For rPIV3-1, the PIV3-specific primer pair A gave rise to the expected 4.6 kb product, whereas primer pair B, specific to PIV-1 sequences not present in rPIV3-1, did not yield product. Positive controls using rPIV3/JS (labeled as rPIV3) or PIV1/Wash64 (labeled as PIV1) vRNA are shown in parallel.

Figure 16:
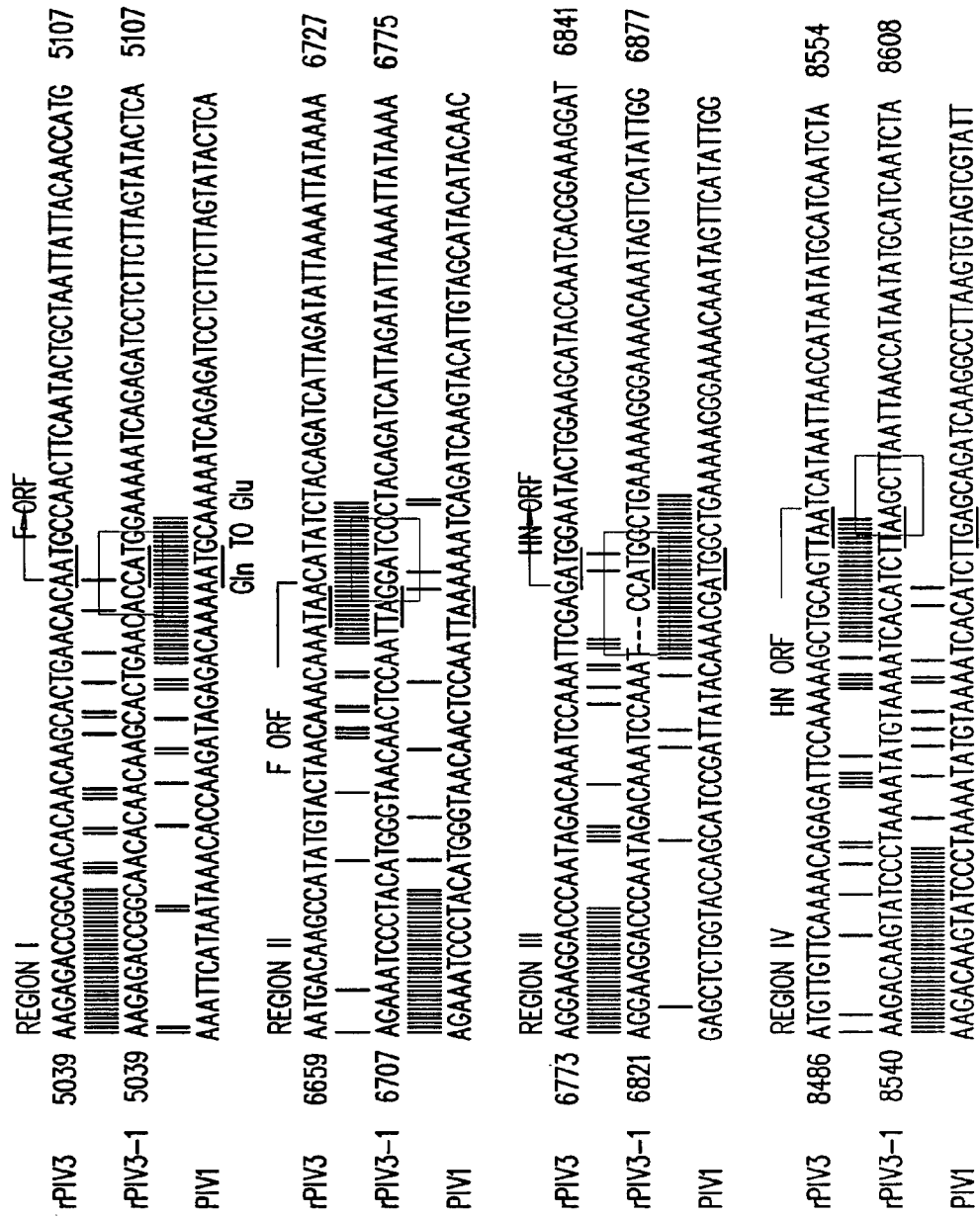

FIG. 16 represents sequences of PIV3-PIV1 junctions in the RT-PCR products of rPIV3-1 shown in FIG. 14B were determined. The sequence for each of the four junction regions (Regions I-IV) is presented and aligned with the corresponding regions of rPIV3/JS (top line) and PIV1/Wash64 (bottom line), which were sequenced in parallel from RT-PCR products. Vertical bars indicate sequence identity, and the boxed regions indicate introduced mutations and restriction sites. The Gln to Glu codon change in the chimeric F gene is indicated by shaded box. Start and stop codons are underlined.

Figure 17:
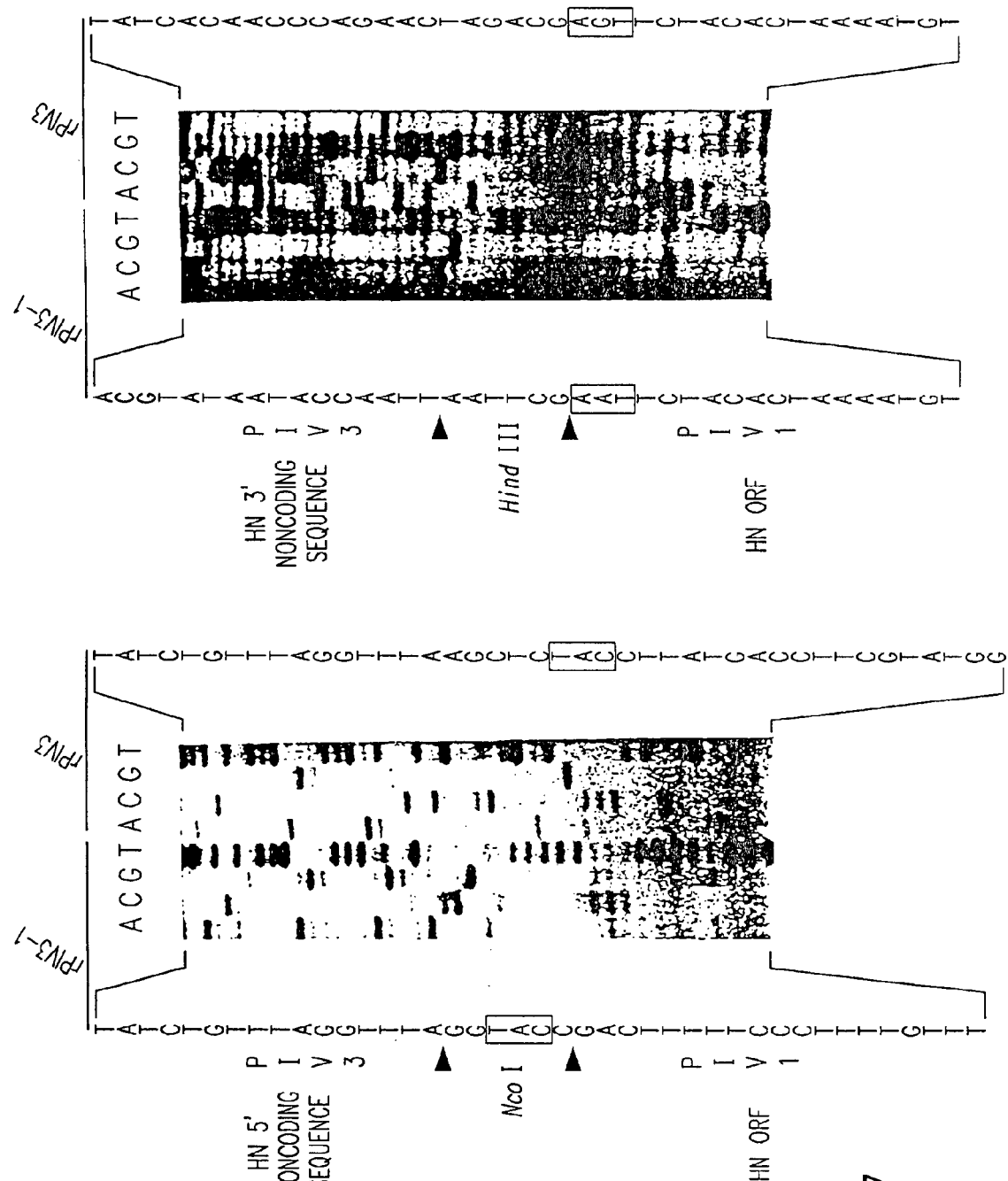

FIG. 17 shows sequencing gels for region III (left) and IV (right) of RT-PCR products of rPIV3-1 compared with rPIV3 (left) or PIV1 (right). Start and stop codons are marked by a box, restriction sites are marked by arrows.

Figure 18:
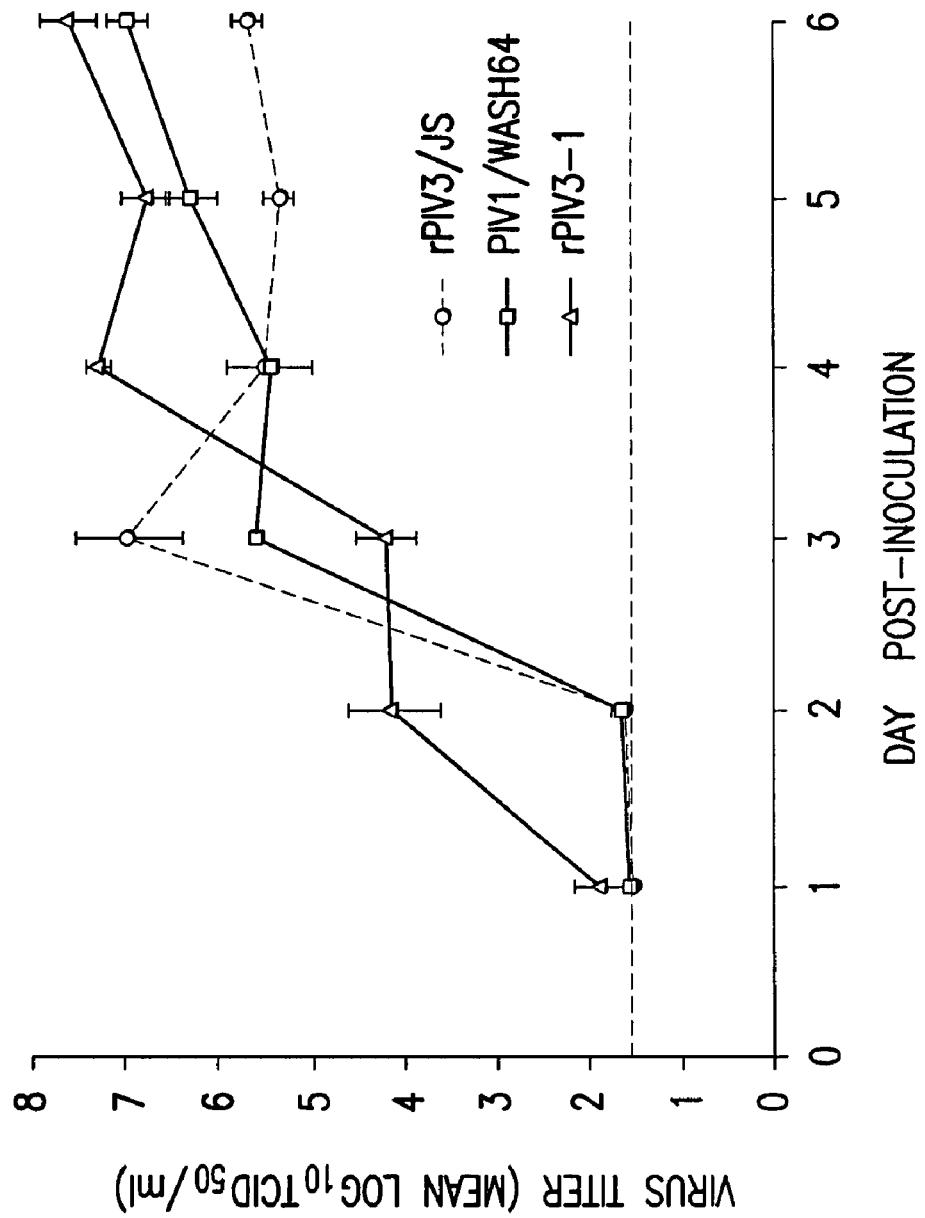

FIG. 18 depicts multicycle growth of parental and chimeric PIVs in tissue culture. LLC-MK2 cell monolayers were inoculated with virus at an MOI of 0.01, and virus-infected cells were incubated at 32° C. in the presence of trypsin. Tissue culture supernatants were harvested at 24 hour intervals, frozen, and analyzed in the same TCID50 assay using hemadsorption to identify virus-infected cultures. Each point represents the mean titer of three separate cultures, with S.E. Indicated. The dotted horizontal line indicates the lower limit of viral detection.

Figure 19:
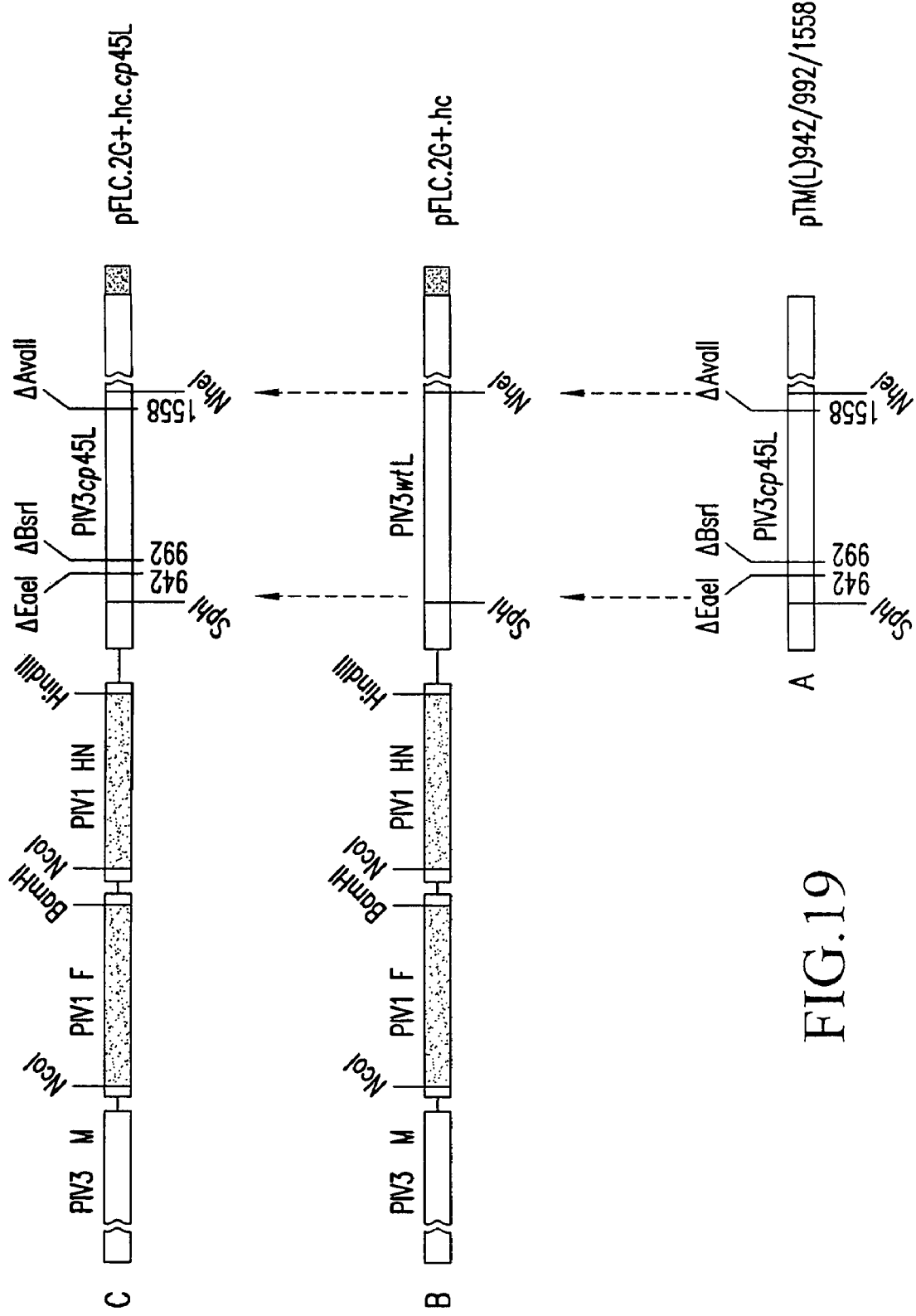

FIG. 19 illustrates introduction of the three L gene mutations of cp45 into pFLC.2G+.hc, the antigenomic cDNA clone of the chimeric virus rPIV3-1. pTM(L)942/992/1558 (A) is a plasmid clone of the L gene that carries the three mutations found in cp45. The mutation at amino acid position 942 in the PIV3 L protein is a tyr (wt) to his (cp45) substitution and a nearby Eae I site was ablated to mark this site. Similarly, the 992 mutation is a leu to phe change with a Bsr I site ablated and the 1558 mutation is a thr to Ile change with an Ava II site ablated. The 2.9 kb SphI-NheI fragment present in pTM(L)942/992/1558 was introduced into pFLC.2G+hc (B), the plasmid carrying the full length cDNA clone of rPIV3-1, to give pFLC+hc.cp45L (C). For the constructs in (B) and (C), the black boxes indicate the location of the hepatitis D virus ribozyme and the T7 teminator, the shaded regions are the PIV1 HN and F ORFs, and the open boxes represent sequences derived from PIV3. pFLC.2G+.hc.cp45L was used in the transfection to yield the attenuated chimeric recombinant virus designated rPIV3-1.cp45L.

Figure 20A:
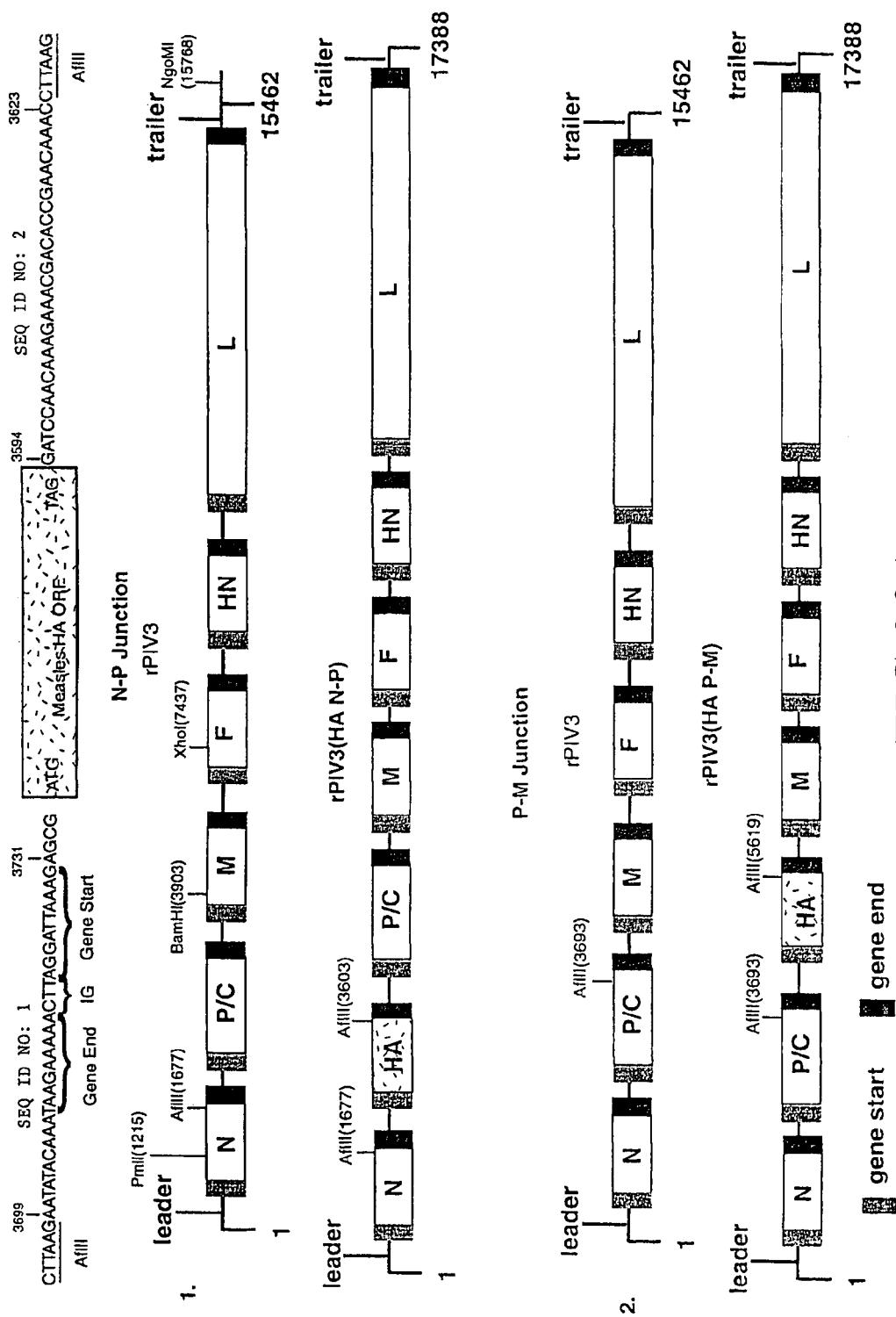

FIGS. 20A and 20B illustrate insertion of the HA gene of measles virus into the HPIV3 genome (Note: all of the figures presented herein and related descriptions refer to the positive-sense antigenome of HPIV3, 5' to 3').

FIG. 20A provides a diagram (top; not to scale) of the 1926 nt insert containing the complete open reading frame of the hemagglutinin (HA) gene of the Edmonston wildtype strain of measles virus engineered to express the measles virus HA from an extra transcriptional unit. The insert contains, in 5' to 3' order: an AflII site; nts 3699-3731 from the HPIV3 antigenome which contains the P/M gene junction, including downstream noncoding sequence for the P gene, its gene-end signal, the intergenic region, and the M gene-start signal; three additional nts (GCG); the complete measles virus HA ORF; HPIV3 nt 3594-3623 from the downstream noncoding region of the P gene; and a second AflII site. FIG. 20A, Panel 1 illustrates the complete antigenome of the JS wildtype strain of HPIV3 (rPIV3) with the introduced AflII site in the 3'-noncoding region of the N gene before (top) and after (bottom) insertion of the measles HA ORF. FIG. 20A, Panel 2 illustrates the complete antigenome of the JS wildtype strain of HPIV3 (rPIV3) with the introduced AflII site in the 3'-noncoding region of the P gene before (top) and after (bottom) insertion of the measles HA ORF. SEQ ID NO: 1 and SEQ ID NO: 2 are shown in FIG. 20A.

FIG. 20B provides a diagram (top; not to scale) of the 2028 nt insert containing the compete ORF of the HA gene of measles virus. The insert contains, in 5' to 3' order: a StuI site; nts 8602 to 8620 from the HPIV3 antigenome, which consist of downstream noncoding sequence from the HN gene and its gene-end signal; the conserved HPIV3 intergenic trinucleotide; nts 6733 to 6805 from the HPIV3 antigenome, which contains the HN gene-start and upstream noncoding region; the measles virus HA ORF; HPIV3 nts 8525-8597, which are downstream noncoding sequences from the HN gene; and a second StuI site. The construction is designed to, upon insertion, regenerate the HPIV3 HN gene containing the StuI site, and place the measles virus ORF directly after it flanked by the transcription signals and noncoding region of the HPIV3 HN gene. The complete antigenome of HPIV3 JS wildtype (rPIV3) with the introduced StuI site at nt position 8600 in the 3'-noncoding region of the HN gene is illustrated in the next (middle) diagram. Below is the antigenome of HPIV3 expressing the measles HA protein inserted into the StuI site. The HA cDNA used for this insertion came from an existing plasmid, rather than from the Edmonston wild type measles virus, which was used for the insertions in the N/P and P/M regions. This cDNA had two amino acid differences from the HA protein inserted in FIG. 20A, and their location in the HA gene of measles virus is indicated by the asterisks in FIG. 20B. SEQ ID NO: 3 and SEQ ID NO: 4 are shown in FIG. 20B.

Figure 21:
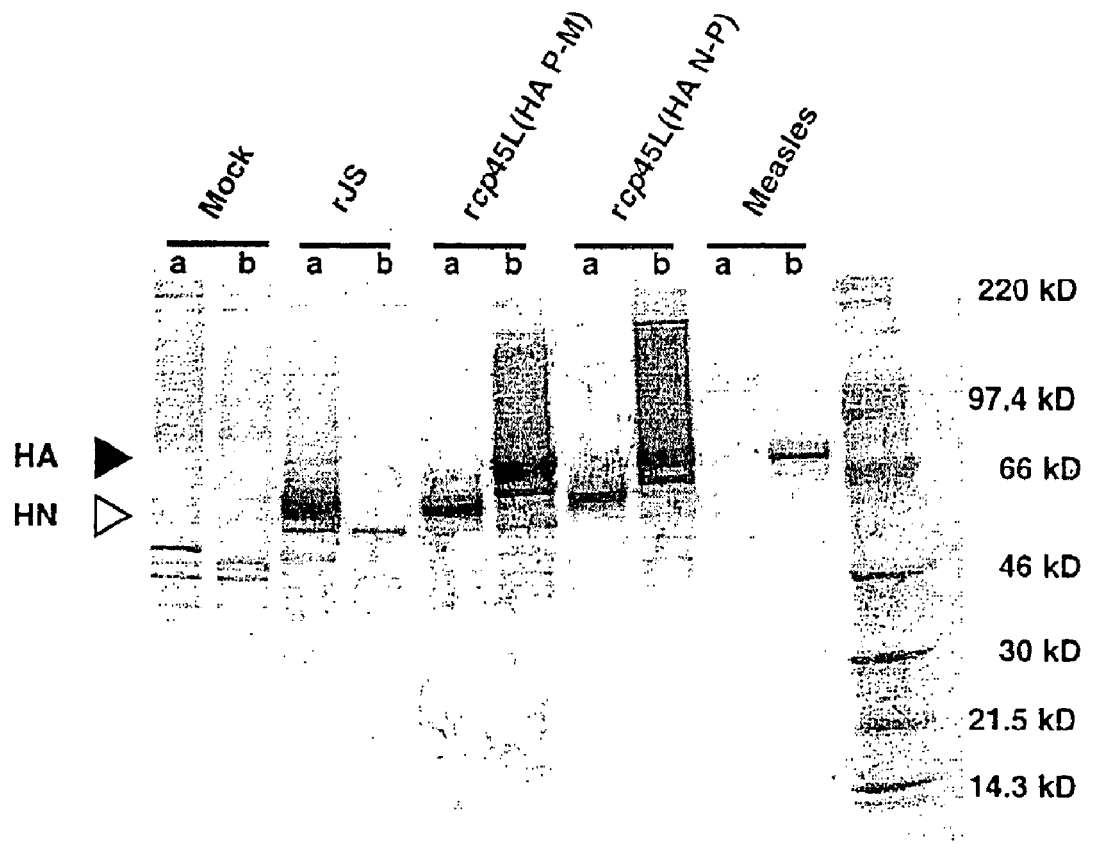

FIG. 21 illustrates expression of the HA protein of measles virus by rHPIV3-measles virus-HA chimeric viruses in LLC-MK2 cells. The figure presents a radioimmunoprecipitation assay (RIPA) demonstrating that the measles HA protein is expressed by the recombinant chimeric viruses rcp45L(HA P-M) and rcp45L(HA N-P), and by the Edmonston wild type strain of measles virus (Measles), but not by the rJS wild type HPIV3 (rJS). Lanes A-35S-labeled infected cell lysates were immunoprecipitated by a mixture of three monoclonal antibodies specific to the HPIV3 HN protein). The 64 kD band corresponding to the HN protein (open arrow) is present in each of the three HPIV3 infected cell lysates (lanes 3, 5, and 7), but not in the measles virus infected cell lysates (lane 9), confirming that the rcp45L(HA P-M) and rcp45L(HA N-P) chimeras are indeed HPIV3 and express similar levels of HN proteins. Lanes (b)-35S-labeled infected cell lysates were immunoprecipitated by a mixture of monoclonal antibodies which recognizes the HA glycoprotein of measles virus (79-XV-V17, 80-III-B2, 81-1-366) (Hummel et al., J. Virol. 69:1913-6, 1995; Sheshberadaran et al., Arch. Virol. 83:251-68, 1985, each incorporated herein by reference). The 76 kD band corresponding to the HA protein (closed arrow) is present in lysates from cells infected with the rcp45L(HA) chimeric viruses (lanes 6, 8) and the measles virus (lane 10), but not in the lysates from rJS infected cells (lane 4), a HPIV3 wild type virus which does not encode a measles virus HA gene.

Figure 22:
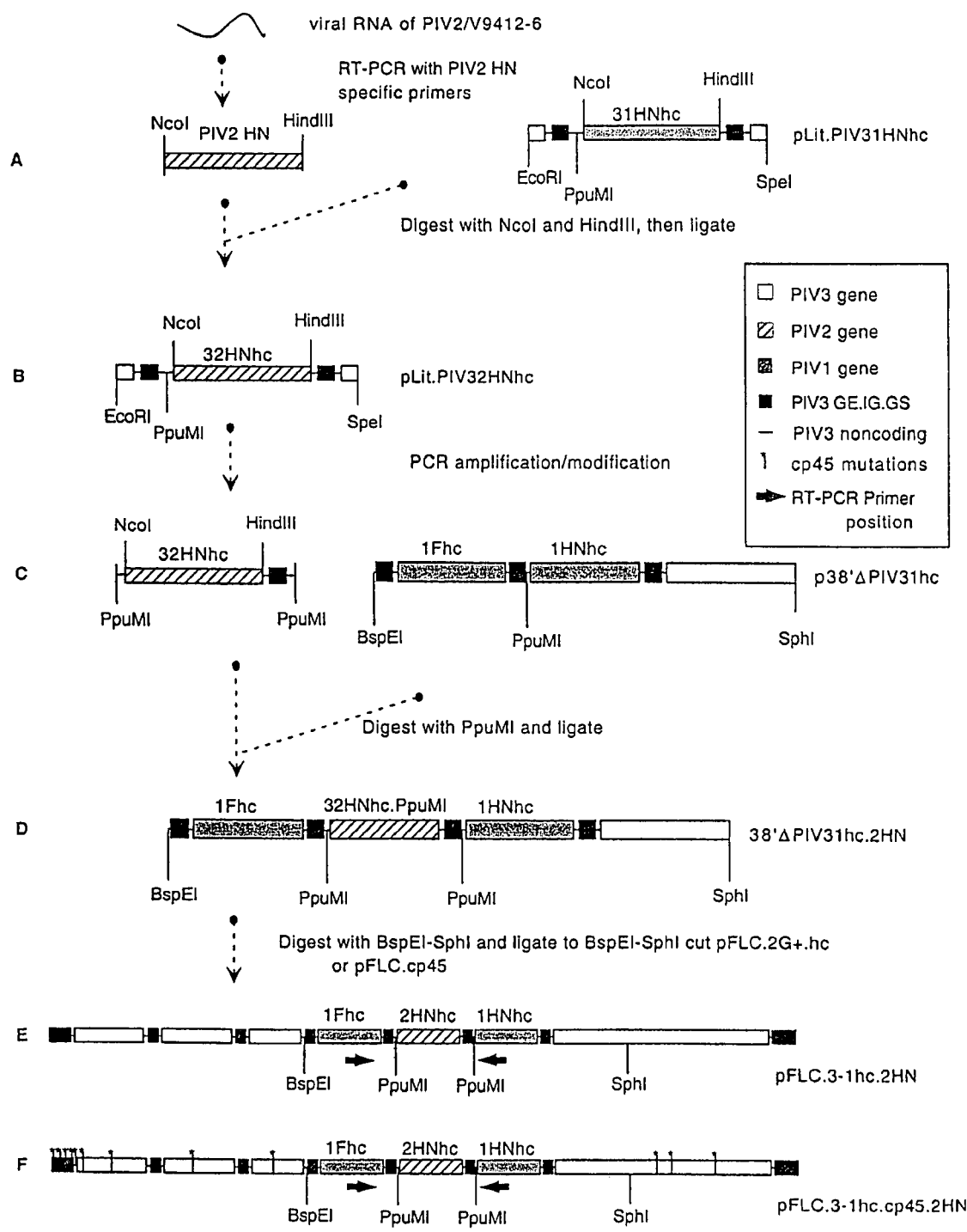
Figure 23A:
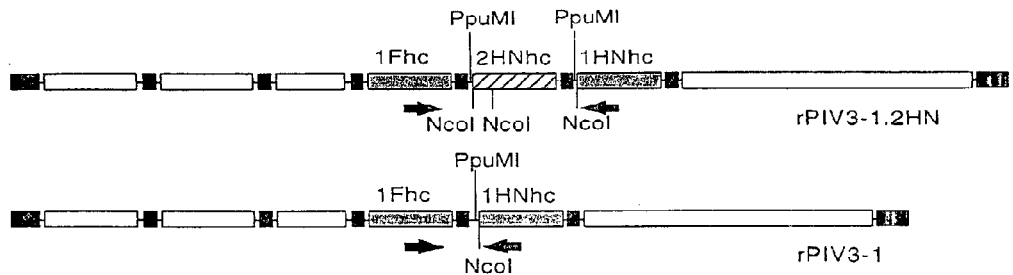
Figure 23B:
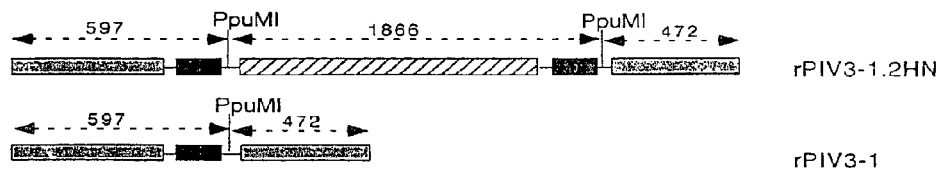
Figure 23C:
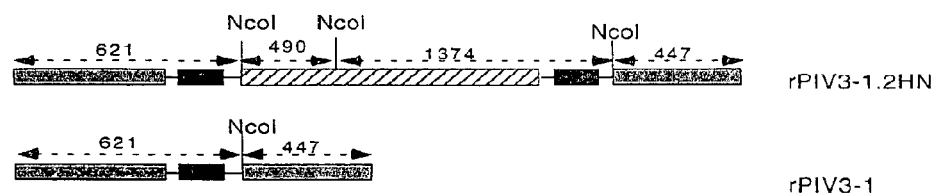
Figure 23D:
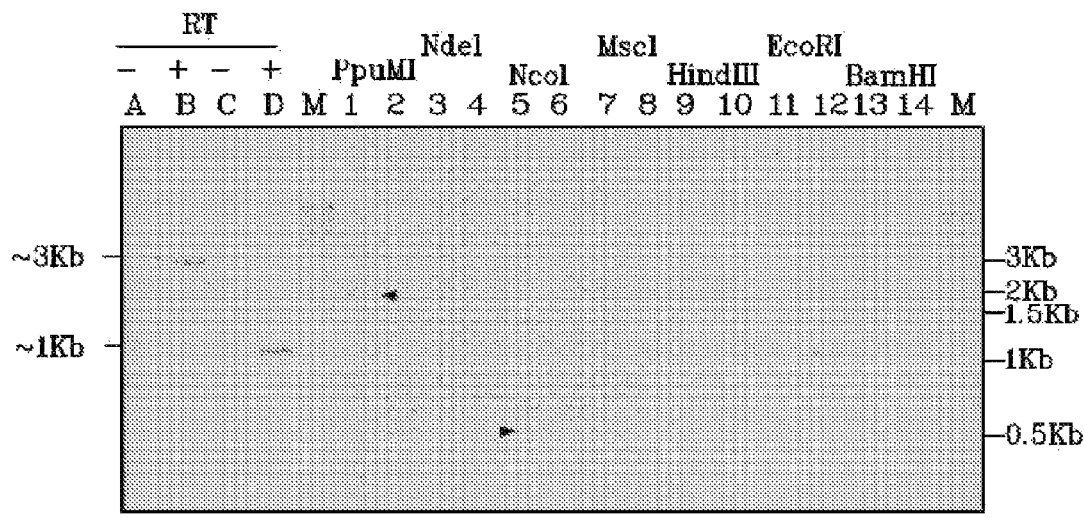

FIG. 22 illustrates insertion of the HPIV2 HN gene as an extra transcription/translation unit into the antigenomic cDNA encoding rPIV3-1 or rPIV3-1 cp45 chimeric virus (Note: rPIV3-1 is a rPIV3 in which the HN and F genes were replaced by those of HPIV1, and rPIV3-1 cp45 is a version which contains, in addition, 12 mutations from the cp45 attenuated virus). The HPIV2 HN gene was amplified from vRNA of HPIV2 using RT-PCR with HPIV2 HN gene specific primers (Panel A). The amplified cDNA, carrying a primer-introduced NcoI site at its 5'-end and a HindIII site at its 3'-end, was digested with NcoI-HindIII and ligated into pLit.PIV31HNhc, that had been digested with NcoI-HindIII, to generate pLit.PIV32HNhc (Panel B). The pLit.PIV32HNhc plasmid was used as a template to produce a modified PIV2 HN cassette (Panel C), which has a PpuMI site at its 5'-end and an introduced PpuMI site at its 3'-end. This cassette contained, from left to right: the PpuMI site at the 5'-end, a partial 5'-untranslated region (UTR) of PIV3 HN, the PIV2 HN ORF, a 3'-UTR of PIV3 HN, the gene-end, intergenic, gene-start sequence that exists at the PIV3 HN and L gene junction, a portion of the 5'-untranslated region of PIV3 L, and the introduced PpuMI site at the 3'-end. This cDNA cassette was digested with PpuMI and then ligated to p38'ΔPIV31hc, that had been digested with PpuMI, to generate p38'ΔPIV31hc.2HN (Panel D). The 8.5 Kb BspEI-SphI fragment was assembled into the BspEI-SphI window of pFLC.2G+.hc or pFLCcp45 to generate the final full-length antigenomic cDNA, pFLC.3-1hc.2HN (Panel E) or pFLC.3-1hc.cp45.2HN (Panel F), respectively. pFLC.2G+.hc and pFLCcp45 are full-length antigenomic clones encoding wild type rPIV3-1 and rPIV3 cp45, respectively, that have been described previously (Skiadopoulos et al., J. Virol. 73:1374-81, 1999a; Tao et al., J. Virol. 72:2955-2961, 1998, incorporated herein by reference).

FIG. 23 details and verifies construction of the rPIV3-1.2HN chimeric virus carrying the PIV2 HN ORF insert between the PIV1 F and HN genes. Panel A depicts the differences in the structures of rPIV3-1 and rPIV3-1.2HN, which contains the PIV2 HN ORF insert between the PIV1 F and HN ORFs of rPIV3-1. The arrows indicate the approximate locations of the RT-PCR primers used to amplify fragments analyzed in Panels B-D. Panels B and C depict the expected sizes of the restriction enzyme digestion fragments generated from the RT-PCR products amplified from rPIV3-1 and rPIV3-1.2HN using either the PpuMI or NcoI restriction endonucleases, with the fragment sizes in base pairs (bp) indicated, and the results presented in panel D. vRNA extracted from virus harvested from rPIV3-1.2HN or from rPIV3-1 infected LLC-MK2 cells was used as a template in the presence and absence of reverse transcriptase (RT) to amplify cDNA fragments by PCR using primers indicated in panel A. PCR fragments were absent in RT-PCR reactions lacking RT indicating that the template employed for amplification of the DNA fragments was RNA and not contaminating cDNA (Lanes A and C of panel D). When the RT step was included, rPIV3-1.2HN vRNA (Lane B) yielded a fragment that was approximately 2 kb larger than that of its rPIV3-1 parent (Lane D) indicating the presence of an insert of 2 kb. Furthermore, digestion of this 3 kb fragment with several different restriction endonucleases indicated that the RT-PCR fragment from rPIV3-1.2HN (odd numbered lanes) has patterns that are different from those of the rPIV3-1 parent (even numbered lanes) for each restriction endonuclease tested. For each digestion, the number of sites and the sizes of the fragments obtained were completely consistent with the predicted sequence of the RT-PCR products of rPIV3-1 and rPIV3-1.2HN. Representative examples are presented. First, the PpuMI digestion of the RT-PCR product from rPIV3-1.2HN (Lane 1) produced three bands of the expected sizes indicating the presence of two PpuMI sites and PpuMI digestion of the RT-PCR product from rPIV3-1 produced two bands of the expected sizes for rPIV3-1 (Lane 2) indicating the presence of just one PpuMI site. Second, the NcoI digestion of the RT-PCR product from rPIV3-1.2HN (Lane 5) produced 4 bands including the 0.5 kb fragment indicative of the HPIV2 HN gene and the NcoI digestion of the RT-PCR product from rPIV3-1 (Lane 6) produced the expected two fragments. M identifies the lane containing the 1 kb DNA ladder used as nucleotide (nt) size markers (Life Technology). Similar results confirmed the presence of the HPIV2 HN insert in rPIV3-1 cp45.2HN.

FIG. 24 demonstrates that rPIV3-1.2HN expresses the HPIV2 HN protein. LLC-MK2 monolayers were infected with rPIV3-1, rPIV3-1.2HN, or the PIV2/V94 wild type virus at a MOI of 5. Infected monolayers were incubated at 32° C. and labeled with 35S-met and 35S-cys mixture from 18-36 hours post-infection. Cells were harvested and lysed, and the proteins were immunoprecipitated with anti-HPIV2 HN mAb 150S1 (Durbin et al., Virology 261:319-330, 1999; Tsurudome et al., Virology 171:38-48, 1989, incorporated herein by reference) Immunoprecipitated samples were denatured, separated on a 4-12% SDS PAGE gel, and autoradiographed (Lanes: 1, rPIV3-1; 2, rPIV3-1.2HN; 3, PIV2/V9412-6). The mAb, specific to HPIV2 HN, precipitated a protein from both rPIV3-1.2HN and PIV2/V94 infected LLC-MK2 cells, but not from rPIV3-1-infected cells, with a size expected for the 86 kD Kd HN protein of HPIV2 (Rydbeck et al., J. Gen. Virol. 69:931-5, 1988, incorporated herein by reference).

FIG. 25 depicts the location and construction of gene unit (GU) insertions or HN gene 3'-noncoding region (NCR) extensions. The nucleotide sequences and unique restriction enzyme cloning sites of the GU (SEQ ID NO: 5) and NCR (SEQ ID NO: 6) insertion sites are shown in panels A and B, respectively. Cis-acting transcriptional signal sequences, i.e., gene-end (GE), intergenic (IG), and gene-start (GS) signal sequences, are indicated. In FIG. 6, Panel A, an oligonucleotide duplex specifying the HN GE, IG and GS signal sequences as well as the unique restriction enzyme recognition sequences are shown inserted into the introduced StuI restriction site (underlined nucleotides) (see FIG. 1B and Example I for the location of the introduced StuI site). A restriction fragment from an RSV antigenome plasmid was cloned into the HpaI site. As necessary, a short oligonucleotide duplex was inserted into the MluI site of the multiple cloning site, so that the total length of the insert would conform to the rule of six. In FIG. 6, Panel B, HN gene 3'-NCR insertions were cloned into the HpaI site of the indicated 32 nt multiple cloning site, which had been cloned into the StuI restriction site as described in FIG. 6, Panel A. Inserted sequences were made to conform to the rule of six by insertion of short oligonucleotide duplexes into the MluI site in the multiple cloning site.

FIG. 26 illustrates open reading frames (ORFs) in the 3079 bp RSV insert. The six possible reading frames in the 3079 bp RSV fragment are shown (three in each orientation; 3, 2, 1, −1, −2, −3). Short bars represent translation start codons. Long bars represent translation stop codons. The 3079 bp fragment was inserted into the HN 3' NCR(NCR ins) or between the HN and L genes as a gene unit (GU ins) in such an orientation that the reading frames encountered by the PIV3 translation machinery correspond to −3, −2 and −1 in the figure. These reading frames contain numerous stop codons across the entire length of the sequence, and should therefore not produce any functional proteins.

FIG. 27 demonstrates that rPIV3 insertion and extension mutants contain inserts of the appropriate size. RT-PCR was performed using a PIV3-specific primer pair flanking the insertion site, and RT-PCR products were separated by agarose gel electrophoresis. The expected size of the RT-PCR fragment for rPIV3 wt (also referred to as rJS) is 3497 bp and that for each of the other rPIV3s GU or NCR mutants is increased in length depending on the size of the insertion.

Panel A depicts GU insertion (ins) mutants: 1. rPIV3 wt; 2. r168 nt GU ins; 2. r678 nt GU ins; 3. r996 nt GU ins; 4. r1428 nt GU ins; 5. r1908 nt GU ins; 6. r3918 nt GU ins. M: HindIII restriction enzyme digestion products of lamda phage DNA. Sizes of relevant size markers are indicated. Panel B depicts NCR insertion mutants: 1. rPIV3 wt; 2. r258 nt NCR ins; 3. r972 nt NCR ins; 4. r1404 nt NCR ins; 5. r3126 nt NCR ins; 6. r3894 nt NCR ins. M: HindIII restriction enzyme digestion products of lambda phage DNA. Sizes of relevant size markers are indicated.

Figure 28A:
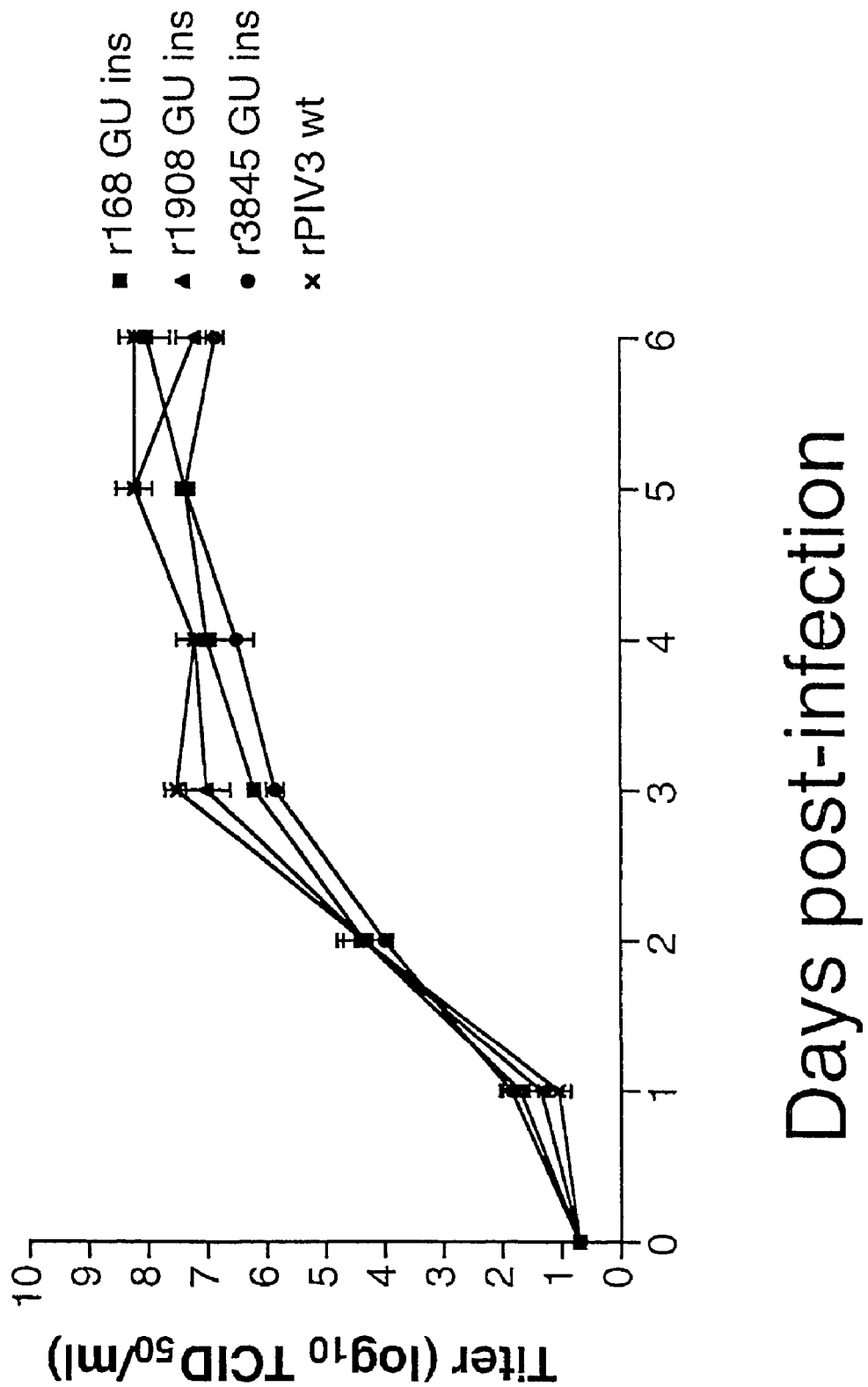
Figure 28B:
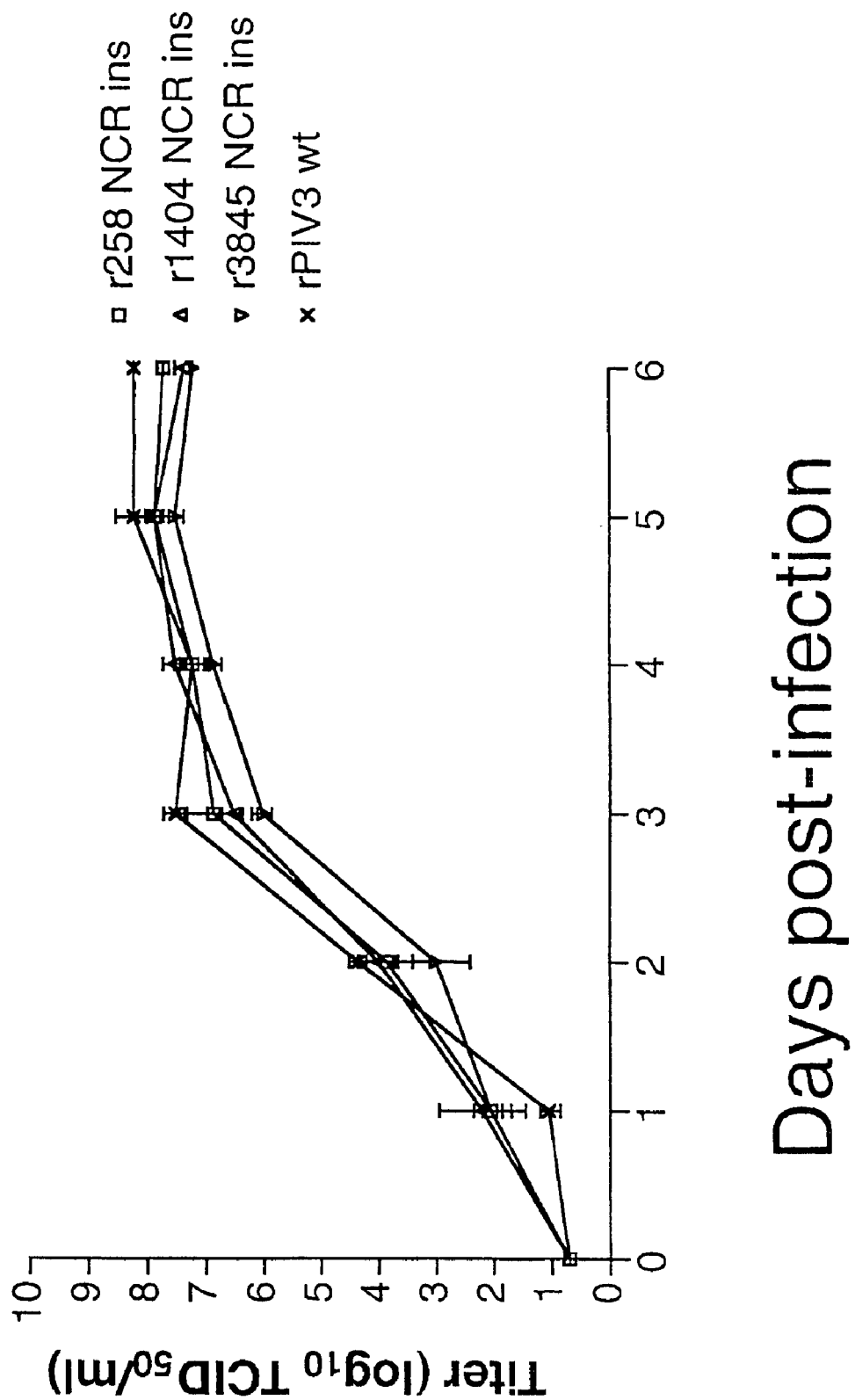
Figure 28C:
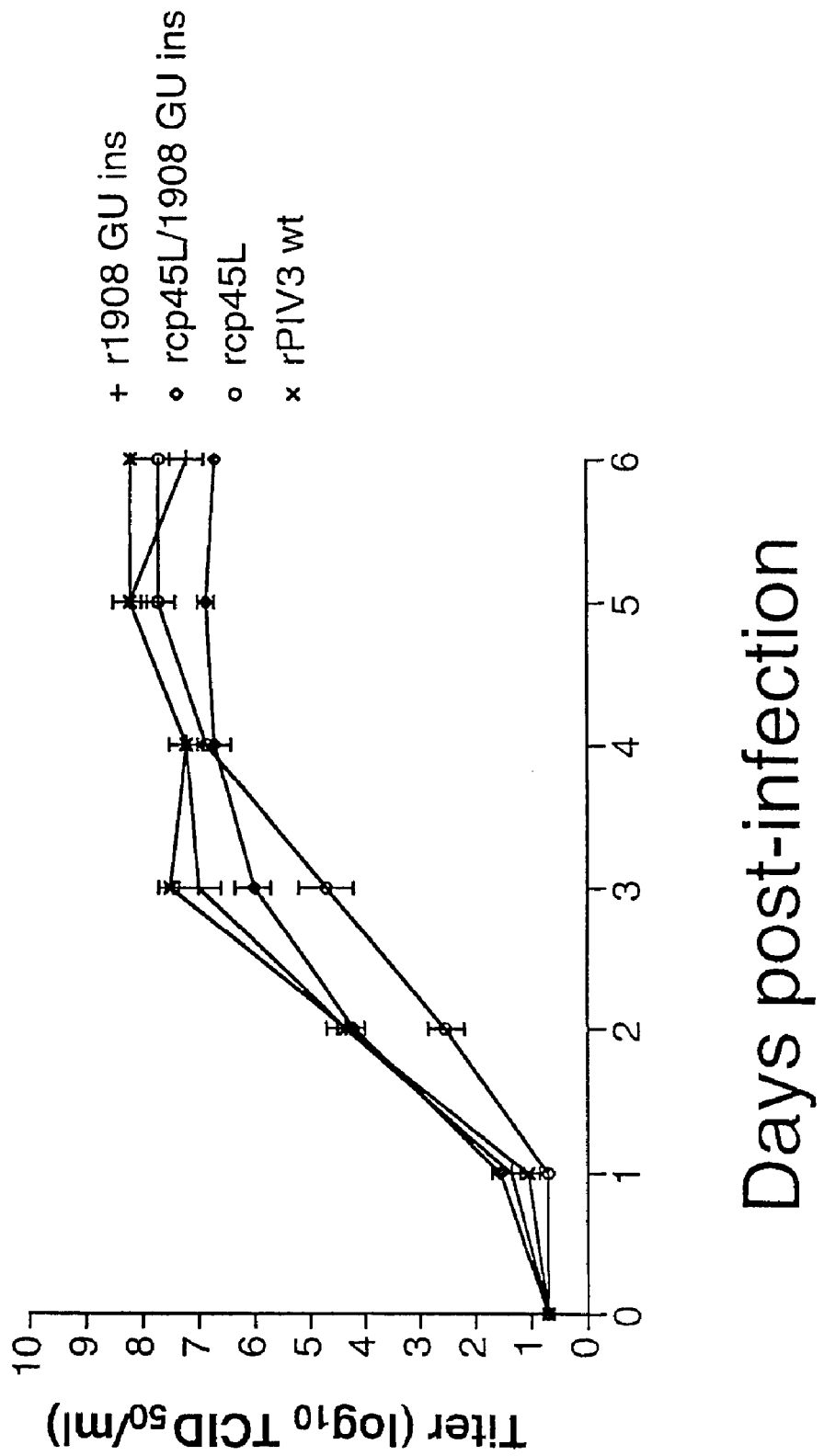

FIGS. 28A-28C present multi-step growth curves of GU and NCR insertion mutations compared with rHPIV3 wt and rcp45L. LLC-MK2 monolayers in 6-well plates were infected with each HPIV3 in triplicate at a multiplicity of infection (m.o.i.) of 0.01 and were washed 4 times after removal of the virus supernatant. At 0 hr and at 24 hrs intervals for 6 days post-infection, 0.5 ml virus medium from each well was harvested and 0.5 ml fresh medium was added to each well. Harvested samples were stored at −80° C. Virus present in the samples was quantified by titration on LLC-MK2 monolayers in 96-well plates incubated at 32° C. The titers of viruses are expressed as TCID50/ml. The average of three independent infections from one experiment is shown. The lower limit of detection is 0.7 log 10TCID50/ml. FIG. 28A-GU insertion mutants; FIG. 28B-NCR insertion mutants; FIG. 28C-cp45L/GU insertion mutant.

Figure 29:
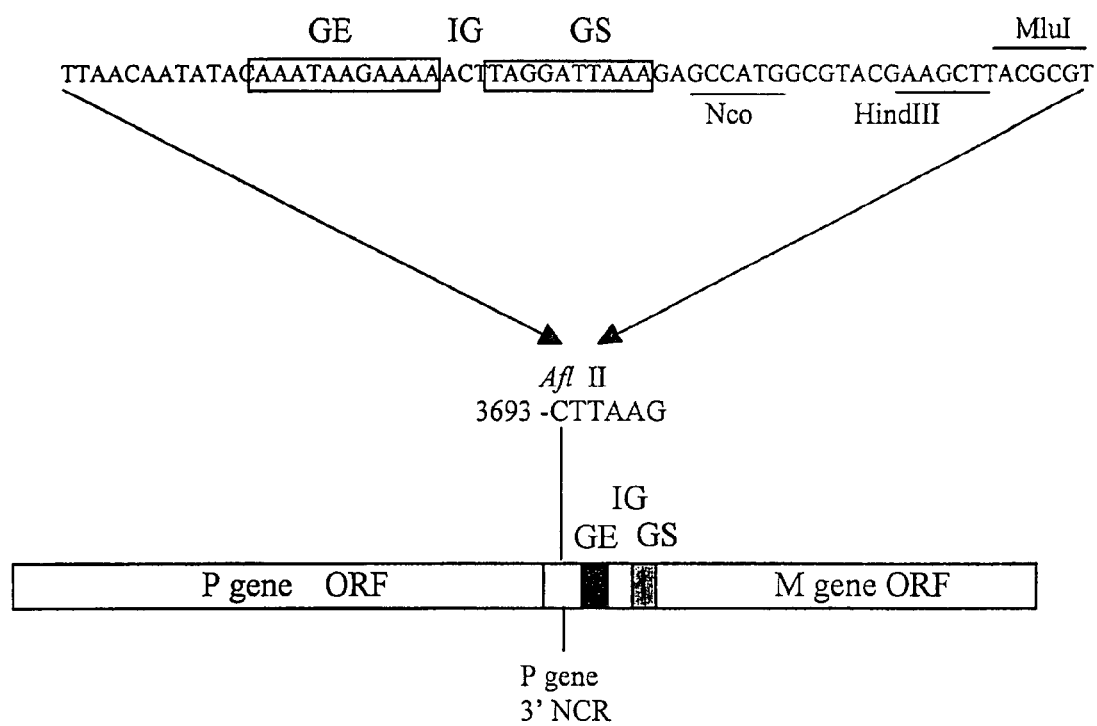

FIG. 29 illustrates the strategy for placing a supernumerary gene insert between the P and M genes of rHPIV3. The downstream (3') NCR of the rHPIV3 P gene was modified to contain an AflII restriction site at antigenomic sequence positions 3693-3698 (Durbin, J. Virol. 74:6821-31, 2000, incorporated herein by reference). This site was then used to insert an oligonucleotide duplex (shown at the top) (SEQ ID NO: 7) that contains HPIV3 cis-acting transcriptional signal sequences, i.e., gene-end (GE), intergenic (IG), and gene-start (GS) motifs. The duplex also contains a series of restriction enzyme recognition sequences available for insertion of foreign ORFs. In the case of the HPIV1 and HPIV2 HN ORFs, the cloning sites were NcoI and HindIII. Insertion of a foreign ORF into the multiple cloning sites places it under the control of a set of HPIV3 transcription signals, so that in the final recombinant virus the gene is transcribed into a separate mRNA by the HPIV3 polymerase. As necessary, a short oligonucleotide duplex was inserted into the MluI site of the multiple cloning site to adjust the final length of the genome to be an even multiple of six, which has been shown to be a requirement for efficient RNA replication (Calain et al., J. Virol. 67:4822-30, 1993; Durbin et al., Virology 234:74-83, 1997b). A similar strategy was used to place HPIV1 and HPIV2 gene inserts between the N and P genes of rHPIV3 using an introduced AflII restriction site at positions 1677-1682.

FIG. 30 is a diagram (not to scale) of the genomes of a series of chimeric rHPIV3s that contain one, two or three supernumerary gene inserts, each of which encodes a protective antigen of PIV1, PIV2, or measles virus. Schematic representation of rHPIV3s (not to scale) showing the relative position of the added insert(s) encoding the HN (hemagglutinin-neuraminidase) glycoprotein of HPIV1 or HPIV2 or the HA (hemagglutinin) glycoprotein of measles virus inserted into the rHPIV3 backbone (□). The rHPIV3 construct that is diagrammed at the bottom contains a 3918-nt insert (GU) that does not encode a protein (■) (Skiadopoulos et al., Virology 272:225-34, 2000, incorporated herein by reference). Each foreign insert is under the control of a set of HPIV3 gene start and gene end transcription signals and is expressed as a separate mRNA. a. LLC-MK2 monolayers on 6 well plates (Costar) were separately infected in triplicate at an m.o.i. of 0.01 with each of the indicated viruses. Supernatants were harvested on days 5, 6 and 7 and virus was quantified as described previously (Skiadopoulos et al., Virology 272:225-34, 2000). The mean peak titer obtained for each virus is shown as log 10 TCID50/ml. b. Mean of two experiments. Serially-diluted viruses were incubated at 32° C. and 39° C. on LLC-MK2 monolayer cultures for 7 days, and the presence of virus was determined by hemadsorbtion with guinea pig erythrocytes. The mean reduction in titer at 39° C. compared to that of 32° C. is shown.

FIG. 31 provides a diagram (not to scale) illustrating insertion of a supernumerary gene insert into an rHPIV3 backbone, rHPIV3-$N_B$, in which the HPIV3 N ORF has been replaced by its BPIV3 counterpart, conferring an attenuation phenotype due to host range restriction (Bailly et al., J. Virol. 74:3188-3195, 2000a, incorporated herein by reference). Schematic representations are shown of rHPIV3 (top) and biologically derived BPIV3 (bottom). The relative position of the N ORF sequence derived from the Kansas strain of BPIV3 and the measles virus hemagglutinin gene in the PIV3 backbone are shown. In each case, the foreign sequence is under the control of a set of HPIV3 transcription signals. A portion of the plasmid vector containing the NgoMIV site is shown. Designations are provided for the antigenomic cDNA clones (left) and their encoded recombinant viruses (right).

FIG. 32 illustrates insertion of RSV G or F as an additional, supernumerary gene in a promoter-proximal position into the genome of rB/HPIV3. rB/HPIV3 is a recombinant version of BPIV3 in which the BPIV3 F and HN genes have been replaced by their HPIV3 counterparts (FH and HNH respectively). A BlpI site was created in the B/HPIV3 backbone immediately upstream of the ATG start codon of the N ORF. The RSV G or F open reading frames (ORFs) were inserted into this BlpI site. The downstream end of either RSV insert was designed to contain a PIV3 gene end (GE) and gene start (GS) sequences (AAGTAAGAAAAA (SEQ ID NO. 8) and AGGATTAAAG (SEQ ID NO: 13), respectively, in positive sense) separated by the intergenic sequence CTT. Each insert also contained an NheI site that can serve as an insertion site for an additional supernumerary gene.

(SEQ ID NO. 9)
AGGATTAAAGAACTTTACCGAAAGGTAAGGGGAAAGAAATCCTAAGAGCT
TAGCGATG.

(SEQ ID NO. 10)
GCTTAGCGATG.

(SEQ ID NO. 11)
AAGCTAGCGCTTAGC.

(SEQ ID NO. 12)
GCTTAGCAAAAAGCTAGCACAATG.

FIG. 33 illustrates multicycle replication of rB/HPIV3-G1, rB/HPIV3-F1 and their recombinant and biological parent viruses in simian LLC-MK2 cells. Triplicate monolayer cultures were infected at an input MOI of 0.01 TCID50 per cell with rB/HPIV3-G1, rB/HPIV3-F1, or the following control viruses: rBPIV3 Ka, which is the recombinant version of BPIV3 strain Ka; rB/HPIV3, with is the version of rBPIV3 in which the BPIV3 F and HN glycoprotein genes were replaced with their HPIV3 counterparts; HPIV3 JS, which is biologically-derived HPIV3 strain JS; and BPIV3 Ka, which is the biologically-derived version of BPIV3 strain Ka. The virus titers are shown as mean log 10 TCID50/ml of triplicate samples. The lower limit of detection of this assay is 101.45 TCID50/ml.

Figure 34:
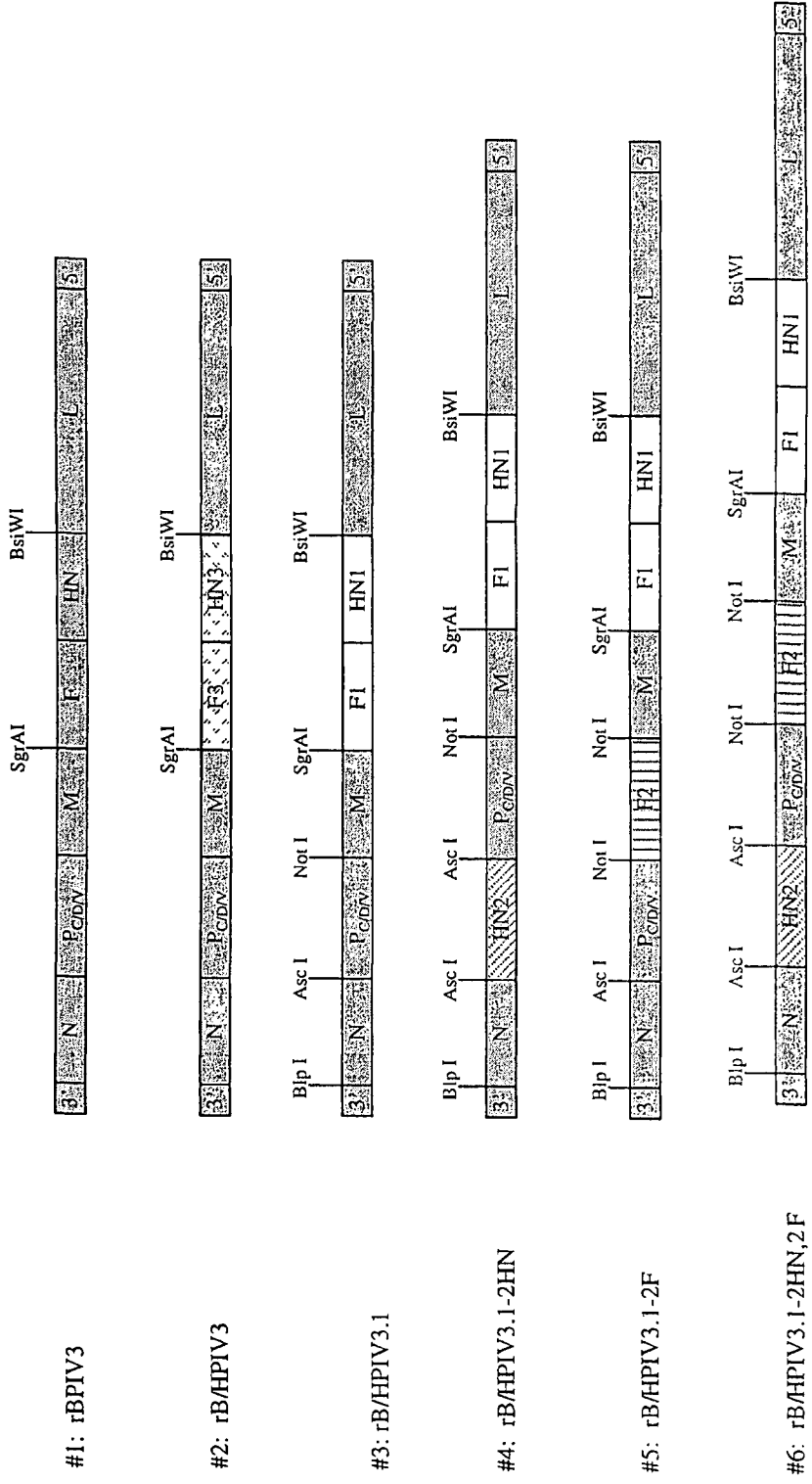

FIG. 34 is a diagram (not to scale) of the genomes of rBPIV3 (#1) and a series of chimeric rB/HPIV3s (#2-6) that contain substitutions of BPIV3 F and HN genes by those of HPIV3 (#2) or HPIV1 (#3-6), and one or two supernumerary gene inserts encoding the F and/or HN ORF of HPIV2 (#4-6). Schematic representation of the rB/HPIV3.1 chimeric viruses (not to scale) showing the relative position of the supernumerary gene encoding the F or HN glycoprotein of HPIV2 (F2 and HN2, respectively). Each foreign insert is under the control of a set of HPIV3 gene start and gene end transcription signals and is designed to be expressed as a separate mRNA.

Figure 35:
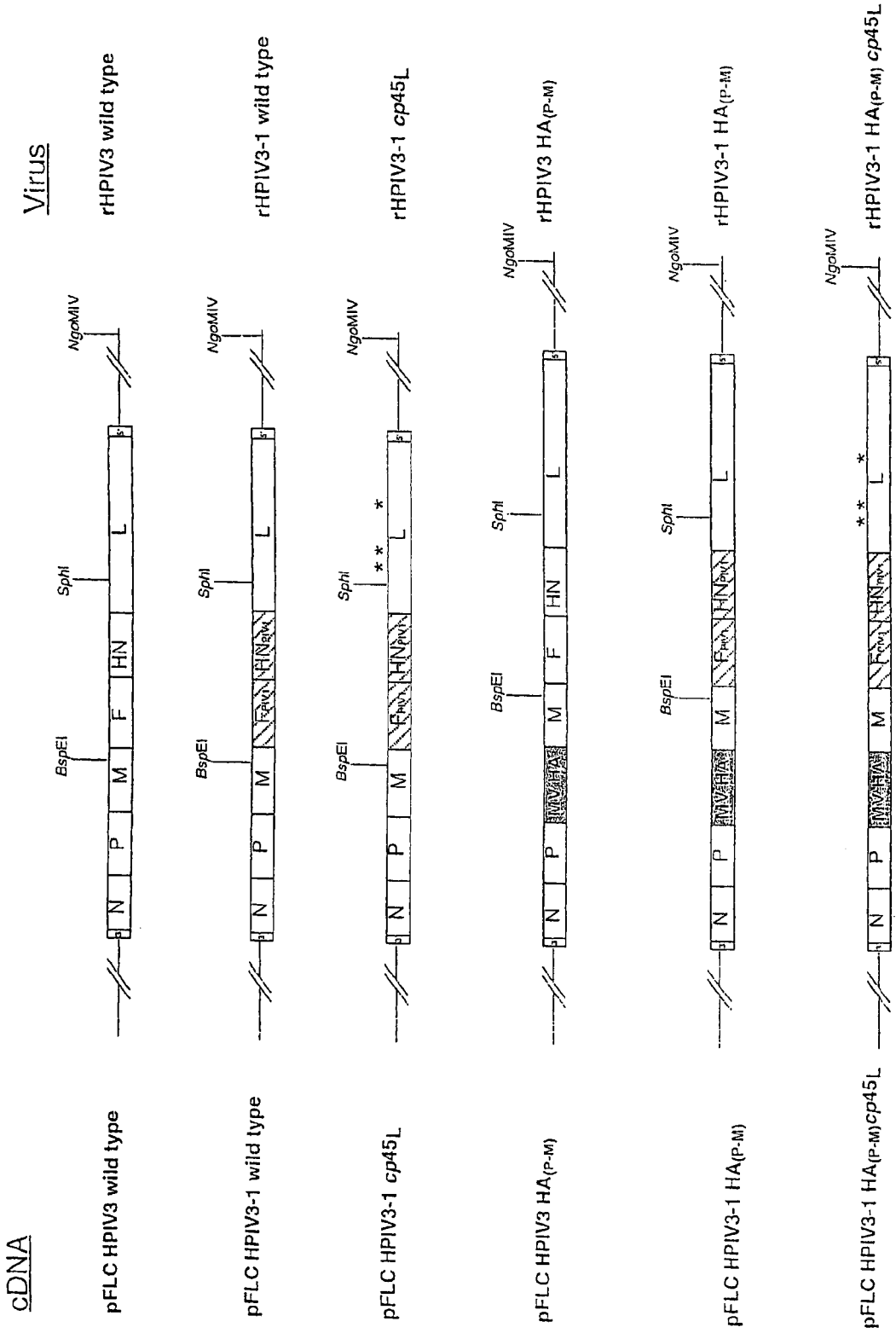

FIG. 35 provides a diagram (not to scale) illustrating the insertion of a the measles virus HA coding sequence into several different rPIV3 backbones. Three backbones are illustrated: wild type rHPIV3 (top construct); wild type rHPIV3-1 (second construct from top) (Tao et al. J. Virol. 72:2955-2961, 1998, incorporated herein by reference) in which the HPIV3 F and HN glycoprotein genes have been replaced by those of HPIV1; and rHPIV3-1cp45L (third construct), a derivative of wild type rHPIV3-1 that contains three attenuating amino acid point mutations in the L gene derived from the cp45 vaccine strain (Skiadopoulos et al., J. Virol. 72:1762-8, 1998, incorporated herein by reference). The relative position of the HPIV1 F and HN ORF sequences (□) and the measles virus HA gene (▨) in the rPIV3 backbone (■) are shown. In each case, each foreign ORF is under the control of a set of HPIV3 transcription signals. The relative locations of the three cp45 L amino acid point mutations in the L gene are indicated (*). A portion of the plasmid vector is containing the unique NgoMIV site is shown.

Figure 36:
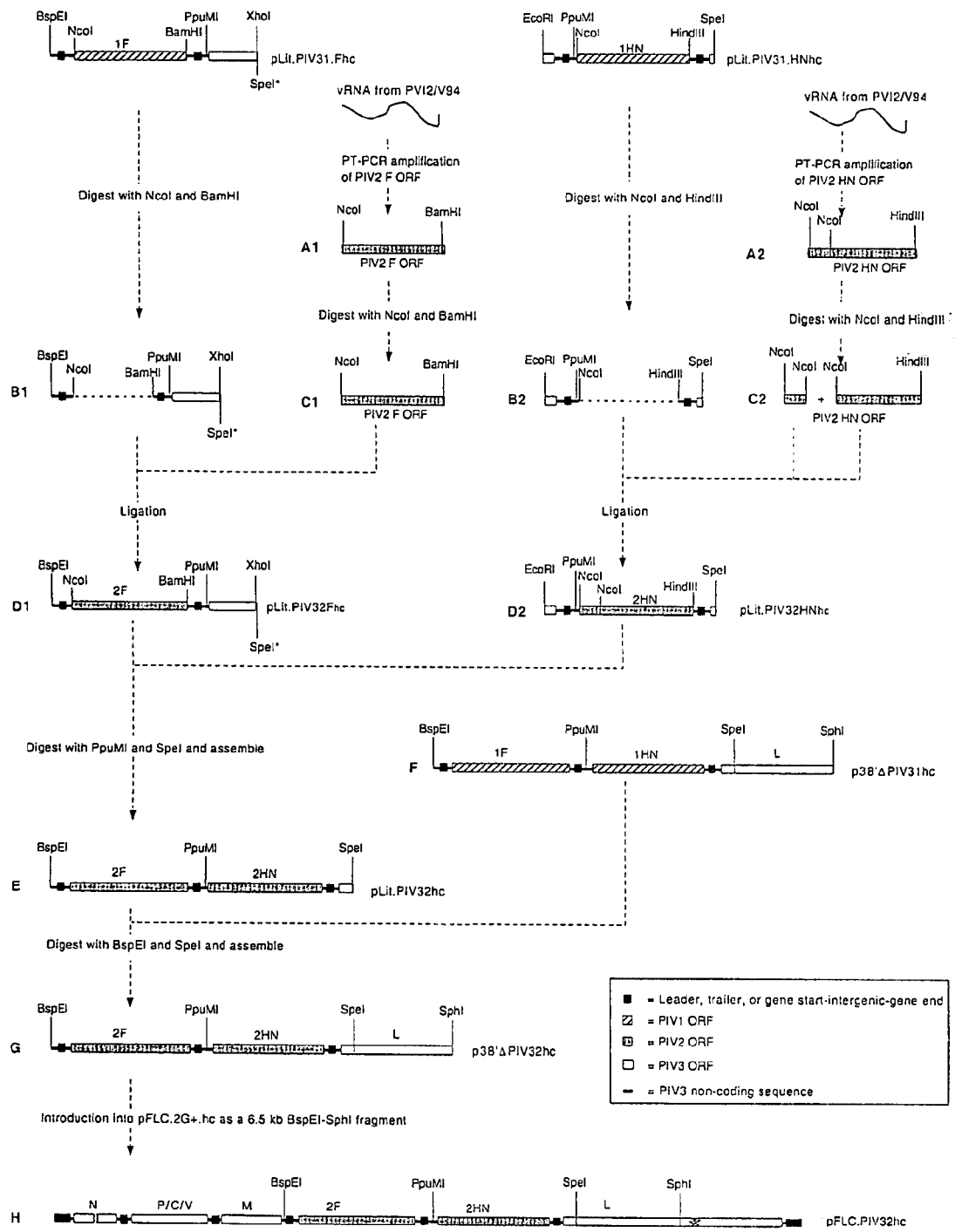

FIG. 36 illustrates construction of the PIV3-PIV2 chimeric antigenomic cDNA pFLC.PIV32hc encoding the full-length PIV2 HN and F proteins. The cDNA fragment containing the full-length PIV2 F ORF flanked by the indicated restriction sites (A1) was amplified from PIV2/V94 vRNA using RT-PCR and a PIV2 F specific primer pair (1, 2 in Table 22). This fragment was digested with NcoI plus BamHI (C1) and ligated to the NcoI-BamHI windown of pLit.PIV31.fhc (B1) to generate pLit.PIV32Fhc (D1). In parallel, the cDNA fragment containing the full-length PIV2 HJN ORF flanked by the indicated restriction sites (A2) was amplified from PIV2/V94 vRNA using RT-PCR and a PIV2 HN specific primer pair (3, 4 in Table 22). This fragment was digested with NcoI plus HindIII (C2) and ligated to the NcoI-HindIII window of pLit.PIV31.HNhc (B2) to generate pLit.PIV32HNhc (D2). pLit.PIV32Fhc and pLit.PIV32HNhc were digested with PpuMI and SpeI and assembled together to generate pLit.PIV32hc (E). pLit.PIV32hc was further digested with BspEI and SpeI and introduced into the BspEI-SpeI window of p38'ΔPIV31hc (F) to generate p38'ΔPIC32hc (G). The chimeric PIV3-PIV2 construct was introduced into the BspEI-SphI window of pFLC.2G+hc to generate pFLC.PIC32hc (H).

Figure 37:
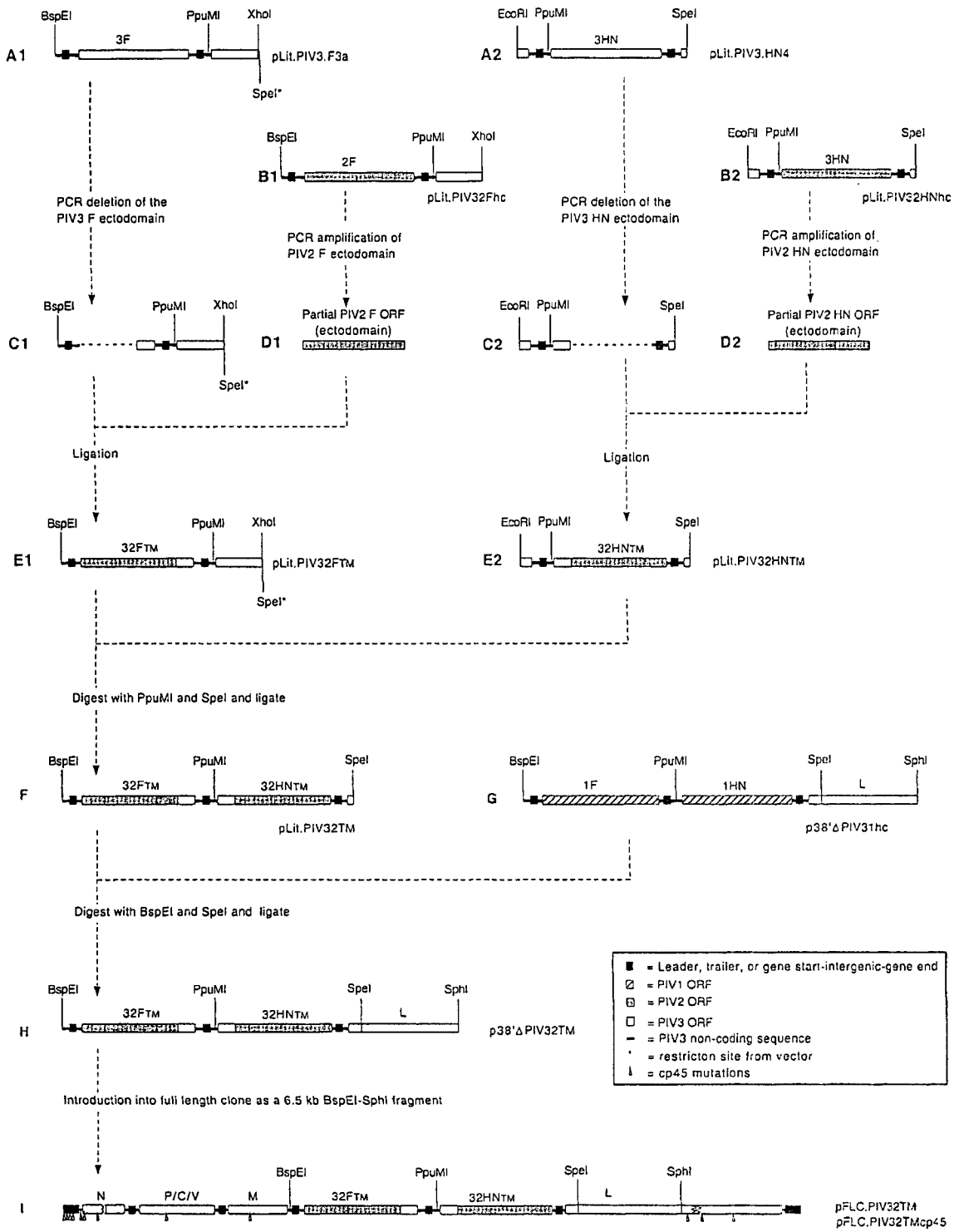

FIG. 37 depicts construction of full-length PIV3-PIV2 chimeric antigenomic cDNA pFLC.PIV32TM and pFLC.PIV32TMcp45, which encode F and HN proteins containing PIV2-derived ectodomains and PIV3-derived transmembrane and cytoplasmic domains. The region of the PIV3 F ORF, in pLit.PIV3.F3a (A1), encoding the ectodomain was deleted (C1) by PCR using a PIV3 F specific primer pair (9, 10 in Table 22. The region of the PIV2 F ORF encoding the ectodomain was amplified from pLit.PIV32Fhc (B1) using PCR and PIV2 F specific primer pair (5, 6 in Table 22). The two resulting fragments (C1 and D1) were ligated to generate pLit.PIV3FTM (E1). In parallel, the region of the PIV3 HN ORF, in pLit.PIV3.HN4 (A2), encoding the ectodomain was deleted (C2) by PCR using a PIV3 HN specific primer pair (11, 12 in Table 22). The region of the PIV2 HN ORF encoding the ectodomain was amplified from pLit.PIV32HNhc (B2) by PCR and a PIV2 HN specific primer pair (8, 9 in Table 22). Those two DNA fragments (C2 and D2) were ligated together to generate pLit.PIV32HNTM (E2). pLit.PIV32FTM and pLit.PIV32HNTM were digested with PpuMI and SpeI and assembled to generate pLit.PIV32TM (F). The BspEI-SpeI fragment from pLit.PIV32TM was ligated to the BspEI-SpeI window of p38'_PIV31hc (G) to generate p38'_PIV32TM (H). The insert containing chimeric PIV3-PIV2 F and HN was introduced as a 6.5 kb BspEI-SphI fragment into the BspEI-SphI window of pFLC.2G+.hc and pFLCcp45 to generate pFLC.PIV32TM and pFLC.PIV32TMcp45 (I), respectively.

Figure 38:
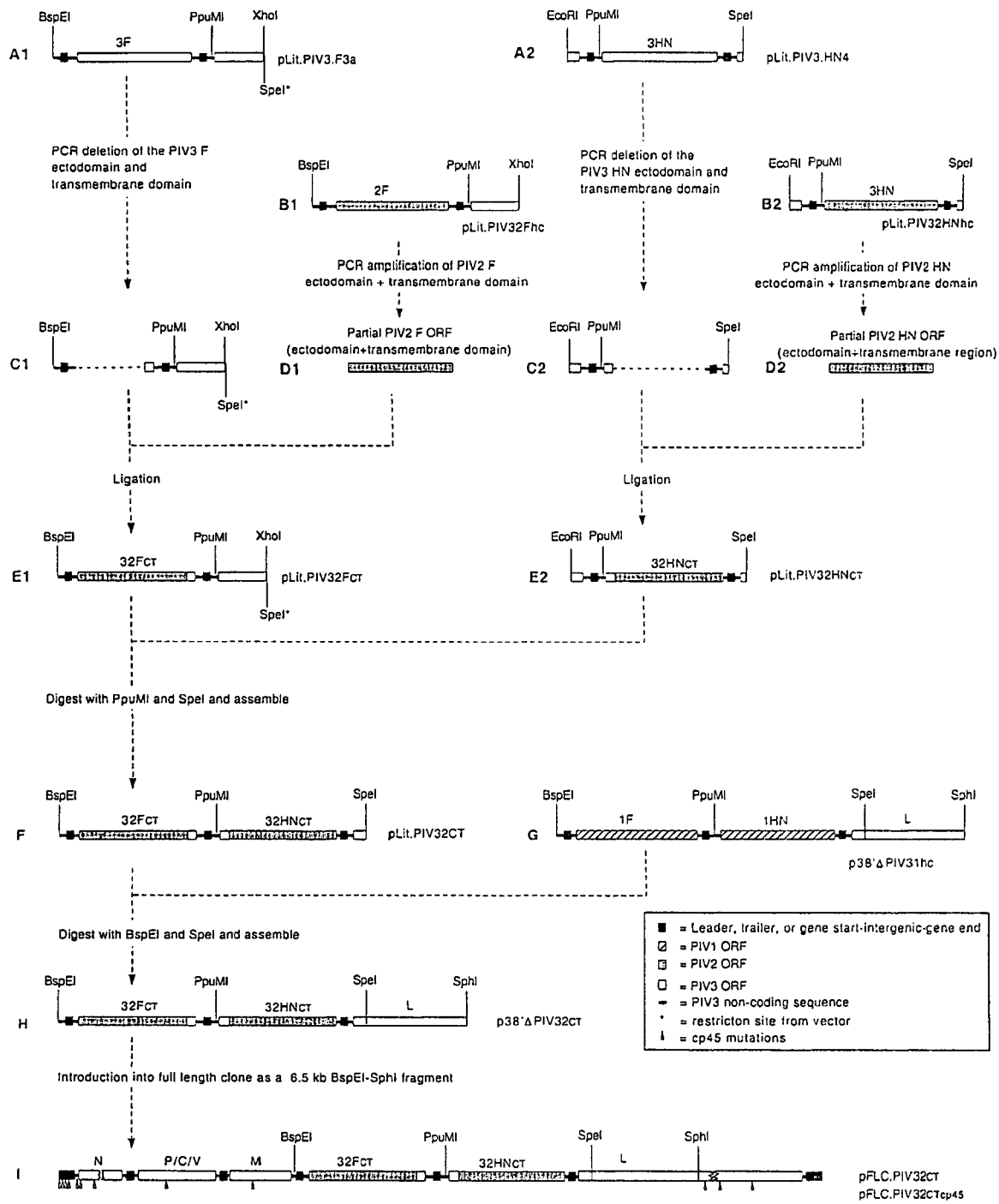

FIG. 38 shows construction of full-length PIV3-PIV2 chimeric antigenomic cDNA pFLC.PIV32CT and pFLC.PIV32Ctcp45 which encode F and HN proteins containing a PIV2-derived ectodomain, a PIV2-derived transmembrane domain, and a PIV3-derived cytoplasmic domain. The region of the PIV3 F ORF in pLit.PIV3.F3a (A1) encoding the ectodomain and the transmembrane domain was deleted (C1) by PCR using a PIV3 F specific primer pair (17, 18 in Table 22). The region of the PIV2 F ORF encoding the ectodomain plus the transmembrane domain was amplified from pLit.PIV32Fhc (B1) using PCR and a PIV2 F specific primer pair (13, 14 in Table 22). The two resulting fragments (C1 and D1) were ligated to generate pLit.PIV32FCT (E1). In parallel, the region of the PIV3 HN ORF in pLit.PIV3.HN4 (A2), encoding the ectodomain and transmembrane domain was deleted (C2) by PCR using a PIV3 HN specific primer pair (19, 20 in Table 22). The region of the PIV2 HN ORF encoding the ectodomain plus the transmembrane domain was amplified from pLit.PIV32HNhc (B2) by PCR using a PIV2 HN specific primer pair (15, 16 in Table 22). Those two DNA fragments (C2 and D2) were ligated to generate pLit.PIV32HNCT (E2). pLit.PIV32FCT and pLit.PIV32HNCT were digested with PpuMI and SpeI and assembled to generate pLit.PIV32CT (F). The BspEI-SpeI fragment from pLit.PIV32CT was ligated to the BspEI-SpeI window of p38'_PIV31hc (G) to generate p38'_PIV32CT (H). The insert containing chimeric PIV3-PIV2 F and HN was introduced as a 6.5 kb BspEI-SphI fragment into the BspEI-SphI window of pFLC.2G+.hc and pFLC.cp45 to generate pFLC.PIV32CT and pFLC.PIV32CTcp45 (I), respectively.

FIG. 39 details genetic structures of the PIV3-PIV2 chimeric viruses and the gene junction sequences for rPIV3-2CT and rPIV3-2TM. Panel A illustrates the genetic structures of rPIV3-2 chimeric viruses (middle three diagrams) are compared with that of rPIV3 (top diagram) and rPIV3-1 (bottom diagram) viruses. The cp45 derivatives are shown marked with arrows depicting the relative positions of cp45 mutations. For the cp45 derivatives, only the F and HN genes are different while the remaining genes remained identical, all from PIV3. From top to bottom, the three chimeric PIV3-PIV2 viruses carry decreasing amount of PIV3 glycoprotein genes. Note that rPIV3-2, carrying the complete PIV2 HN and F ORF, was not recoverable. Panel B provides the nucleotide sequences (SEQ ID NOS: 181, 14-15, 18-20) of the junctions of the chimeric F and HN glycoprotein genes for rPIV3-2TM are given along with the protein translation (SEQ ID NOS: 16-17, 21-22). The shaded portions represent sequences from PIV2. The amino acids are numbered with respect to their positions in the corresponding wild type glycoproteins. Three extra nucleotides were inserted in PIV3-PIV2 HN TM as indicated to make the construct conform to rule of six.

Panel C shows the nucleotide sequences (SEQ ID NOS: 181, 23-24, 18, 26-27) of the junctions of the chimeric F and HN glycoprotein genes for rPIV3-2CT, given along with the protein translation (SEQ ID NOS: 16, 25, and 28). The shaded portions represent sequences from PIV2. The amino acids are numbered with respect to their positions in the corresponding wild type glycoproteins. GE=gene end; I=intergenic; GS=gene start; ORF=open reading frame; TM=transmembrane domain; CT=clytoplasmic domain; *=stop codon.

Figure 40A:
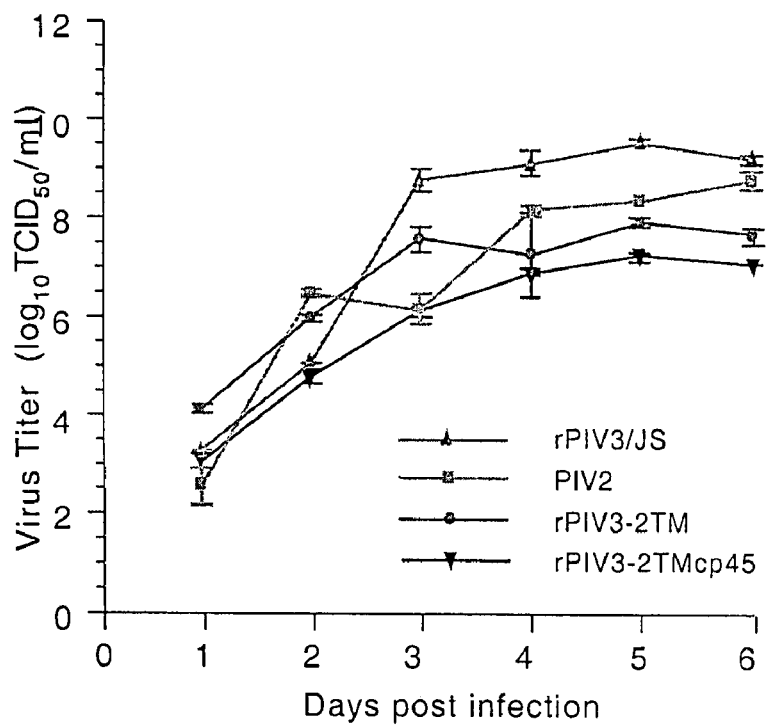
Figure 40B:
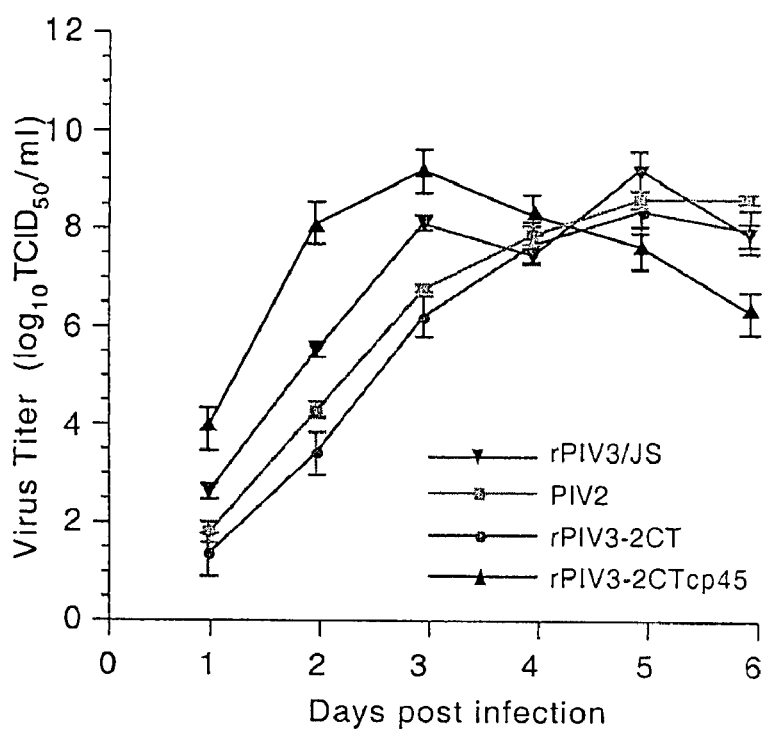
Figure 44A:
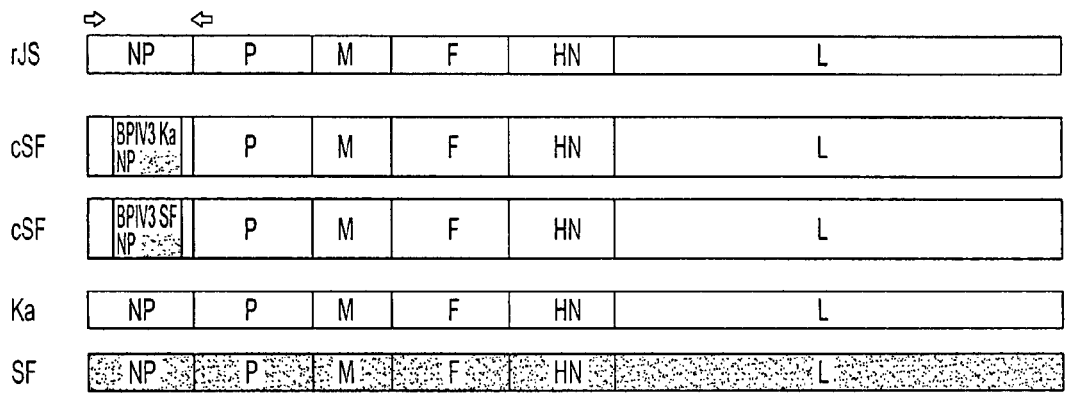
Figure 44B:
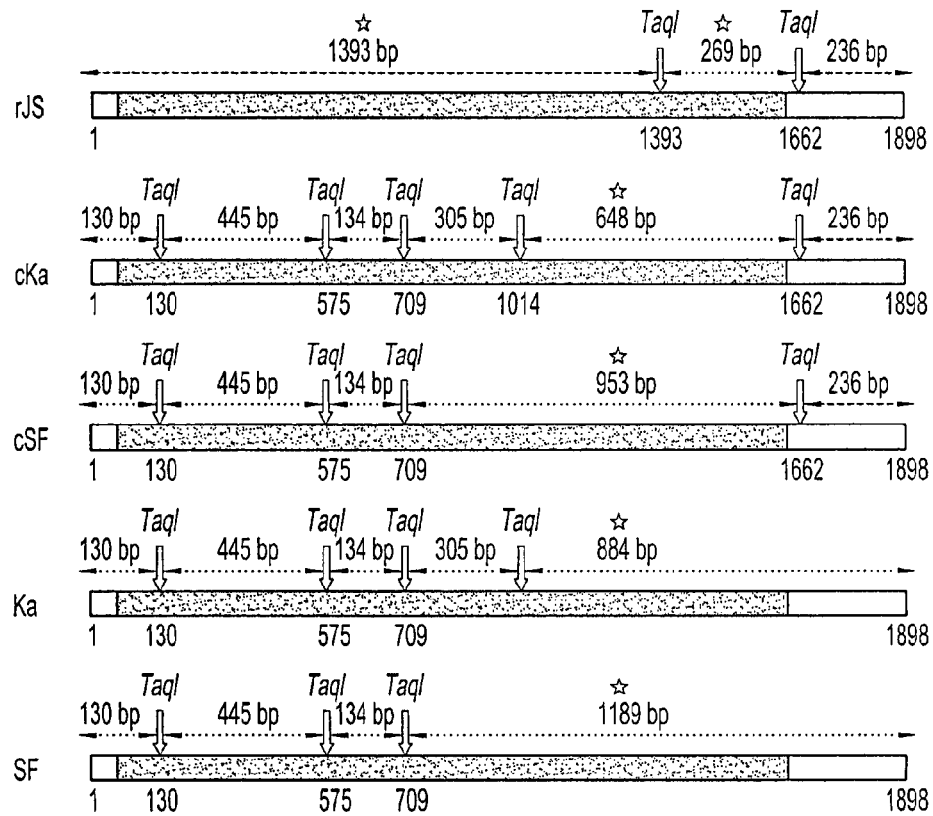
Figure 44C:
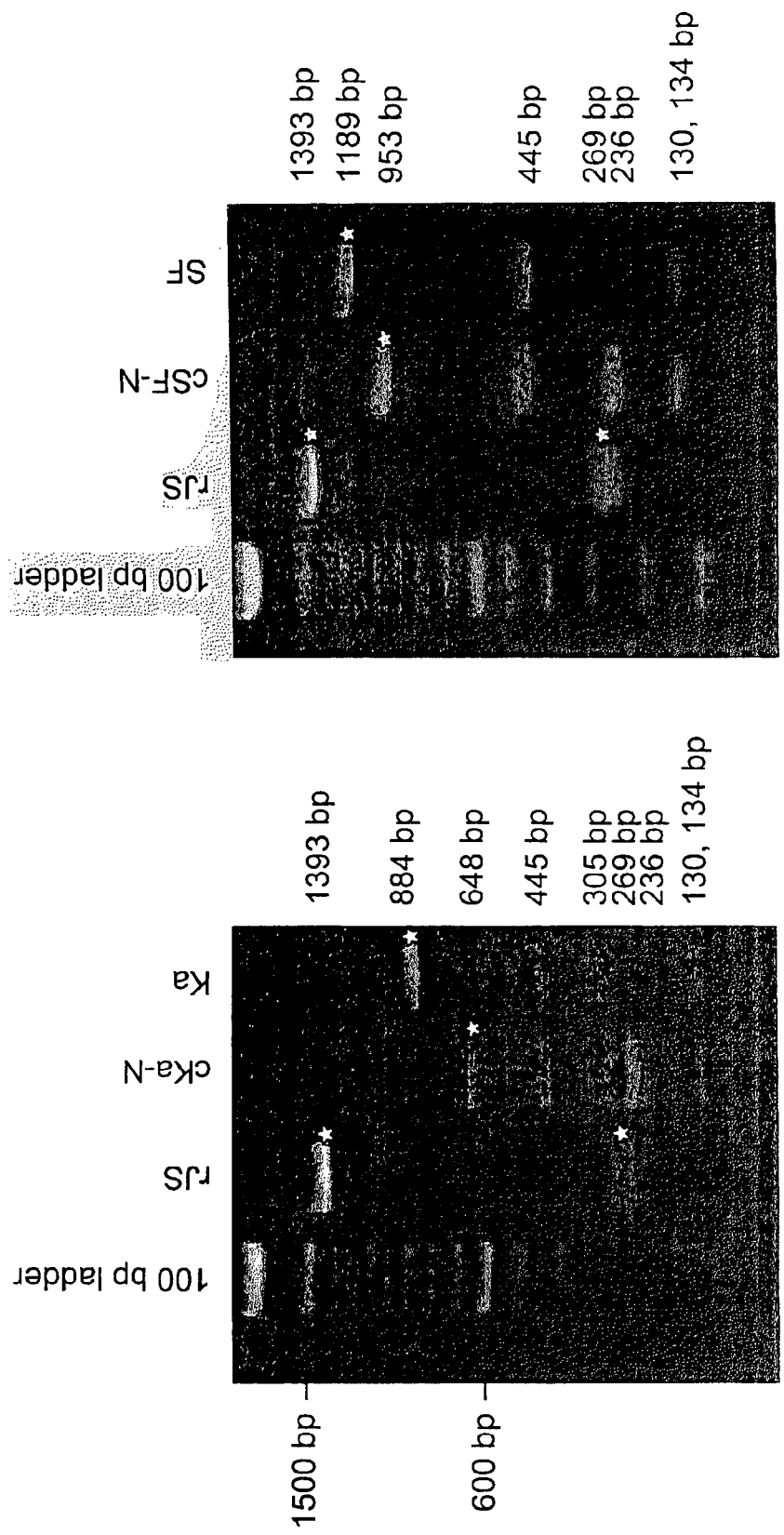

FIG. 40 documents multicycle replication of rPIV3-2 chimeric viruses compared with that of rPIV3/JS and PIV2/V94 wild type parent viruses. Panel A—the rPIV3-2TM and rPIV3-2TMcp45 viruses, along with the rPIV3/JS and PIV2/V94 wt parent viruses, were used to infect LLC-MK2 cells in 6 well plates, each in triplicate, at an MOI of 0.01. All cultures were incubated at 32° C. After a 1 hour adsorption period, the inocula were removed, and the cells were washed three times with serum-free OptiMEM. The cultures were overlayed with 2 ml per well of the same medium. For rPIV3-2TM and rPIV3-2TMcp45 infected plates, 0.5 mg/ml of p-trypsin was added to each well. Aliquots of 0.5 ml were taken from each well at 24 hour intervals for 6 days, flash frozen on dry ice, and stored at −80° C. Each aliquot was replaced with 0.5 ml of fresh medium with or without p-trypsin as indicated above. The virus present in the aliquots was titered on LLC-MK2 plates with liquid overlay at 32° C. for 7 days, and the endpoints were identified with hemadsorption. Panel B—The rPIV3-2CT and rPIV3-2CTcp45, along with the rPIV3/JS and PIV2/V94 wt parent viruses, were used to infect LLC-MK2 in 6 well plates, each in triplicate, as described in Panel A. Aliquots were taken and processed in the same manner as described in Panel A. Virus titers are expressed as log 10TCID50/ml±standard errors for both experiments presented in Panel A and B.

FIG. 41 illustrates cloning of the N coding region of bovine PIV strains Ka or SF into HPIV3. In FIG. 41A-41C (SEQ ID NOS: 29-34), the BPIV3 N open reading frame (ORF) replaces its corresponding HPIV3 sequence in the full-length rJS antigenomic cDNA (Durbin et al., 1997a, supra). BPIV3 Ka and SF N genes were first amplified by RT-PCR using standard molecular biological techniques from virion RNA and subcloned as 1.9 kb fragments into pBluescript to give pBS-KaN or pBS-SFN, respectively. The HPIV3 rJS N gene was subcloned as a 1.9 kb MluI/EcoRI fragment into pUC 119 from a plasmid containing the 5' half of the rJS HPIV3 antigenome (Durbin et al., 1997a, supra; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference) to give pUC 119JSN. Each N gene was modified by site-directed mutagenesis to place an NcoI and AflII site at the translational start and stop sites, respectively. The Ka and SF N genes are identical in the translational start and stop site regions and, therefore, identical mutagenesis reactions were performed on both BPIV3 N genes as depicted in 4IA. FIG. 4IB-Following AflII/NcoI digestion, a 1.5 kb fragment from pBS-KaN or pBS-SFN representing the BPIV3 N coding region was introduced into the NcoI/AflII window of the HPIV3 N subclone pUC119JSN-NcoI/AflII as a replacement for its HPIV3 counterpart. FIG. 41C—Each chimeric subclone was then subjected to site-directed mutagenesis to restore the sequence present in HPIV3 rJS before the translation start codon or after the stop codon and BPIV3 coding sequence immediately after the start codon and before the stop codon. This yielded pUC119B/HKaN and pUC119B/HSFN, which were used to import the BPIV3 N gene into the HPIV3 cDNA clone as shown in FIG. 42.

FIG. 42 illustrates insertion of the HPIV3/BPIV3 (strain Ka or SF) chimeric N gene into the HPIV3 antigenomic cDNA. In FIG. 42A, the BPIV3 N ORF of Ka or SF flanked by HPIV3 sequence was subcloned as an MluI/EcoRI fragment from pUC119B/HKaN or pUC119B/HSFN and inserted into pLeft+2G (Durbin et al., 1997a, supra). The pLeft+2G plasmid contains the 5' half of the HPIV3 rJS antigenome from nt 1-7437 (genome sense) behind a T7 promoter. The location of two G residues that were inserted between T7 promoter and HPIV3 sequence to improve transcription is indicated by an asterisk. FIG. 42B-A*n* XhoI/NgoMI fragment of pRight (Durbin et al., 1997a, supra; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference) containing the 3' end of the HPIV3 antigenome flanked by the hepatitis delta virus ribozyme and T7 terminator was cloned into the XhoI/NgoMI window of the modified pLeft plasmid resulting in plasmids pB/HPIV3KaN and pB/HPIV3SFN. Each of these chimeric constructs contains the complete positive sense sequence of the HPIV3 antigenomic RNA except for the N coding region which has been replaced by its BPIV3 Ka or SF counterpart.

FIG. 43 provides nucleotide sequences of HPIV3, BPIV3 and chimeric viruses of the invention around N translation start (A) and stop (B) codons. The position of the individual ORFs is described in the respective Genbank reports (#AF178654 for BPIV3 Ka, #AF178655 for BPIV3 SF and #Z11515) and included herein by reference. The sequences (SEQ ID NOS: 35-40) (positive-sense) flanking the translational start (A) and stop (B) codons (each underlined) in the N gene are shown for the parental recombinant HPIV3 JS (rJS), the parental biologically-derived BPIV3 Ka and SF viruses (Ka and SF), and the chimeric cKa and cSF viruses. Host-specific residues in the cKa and cSF virus sequences and their counterparts in rJS (before the start codon and after the stop codon) and SF or Ka (start codon through stop codon, inclusive) are in boldface type. Plaque-purified chimeric virus was amplified by RT-PCR from virion RNA and sequenced using the Taq Dye Deoxy Terminator Cycle kit (ABI, Foster City, Calif.). This confirmed that the predicted sequences were present in each chimeric virus.

FIG. 44 details the structure of the BPIV3/HPIV3 chimeric viruses of the invention, and their confirmation by TaqI digestion of RT-PCR products generated from virus RNA. In FIG. 44A the genomes of the chimeric cKa and cSF viruses are shown schematically (not to scale) relative to that of HPIV3 and BPIV3 parent viruses. Ka- and SF-specific regions are indicated by light and dark shading respectively. Arrows above the rJS genome indicate the locations of primers used for RT-PCR amplification of chimeric and parent viruses for the purposes of diagnostic TaqI digestion. These primers were directed to regions conserved between HPIV3 and BPIV3 so that they could be used for the amplification of HPIV3, BPIV3 and chimeric BPIV3/HPIV3 viruses. In FIG. 44B the expected sizes of TaqI digestion products for each virus are shown for a 1898-bp PCR product amplified from RNA with the primer pair illustrated in FIG. 44A. This PCR product is illustrated at the top in FIG. 44B, and the N ORF is indicated as a filled rectangle. TaqI fragments unique to each virus and which therefore serve in virus identification are indicated with an asterisk. FIG. 44C provides TaqI profiles of PCR products containing the PIV3 N coding region of chimeric cKa (left) or cSF (right) flanked by those of the HPIV3 and BPIV3 parent viruses. Unique TaqI fragments diagnostic of virus identity and corresponding to those identified in (44B) are indicated with an asterisk. Calculated lengths (bp) of DNA gel bands are indicated.

Figure 45A:
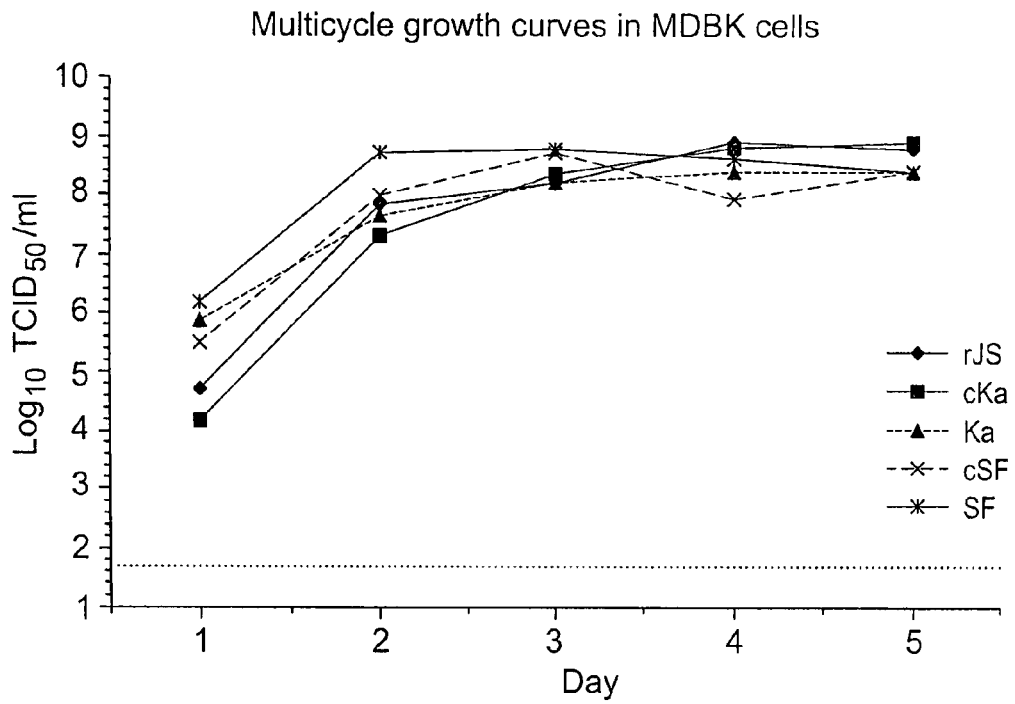
Figure 45B:
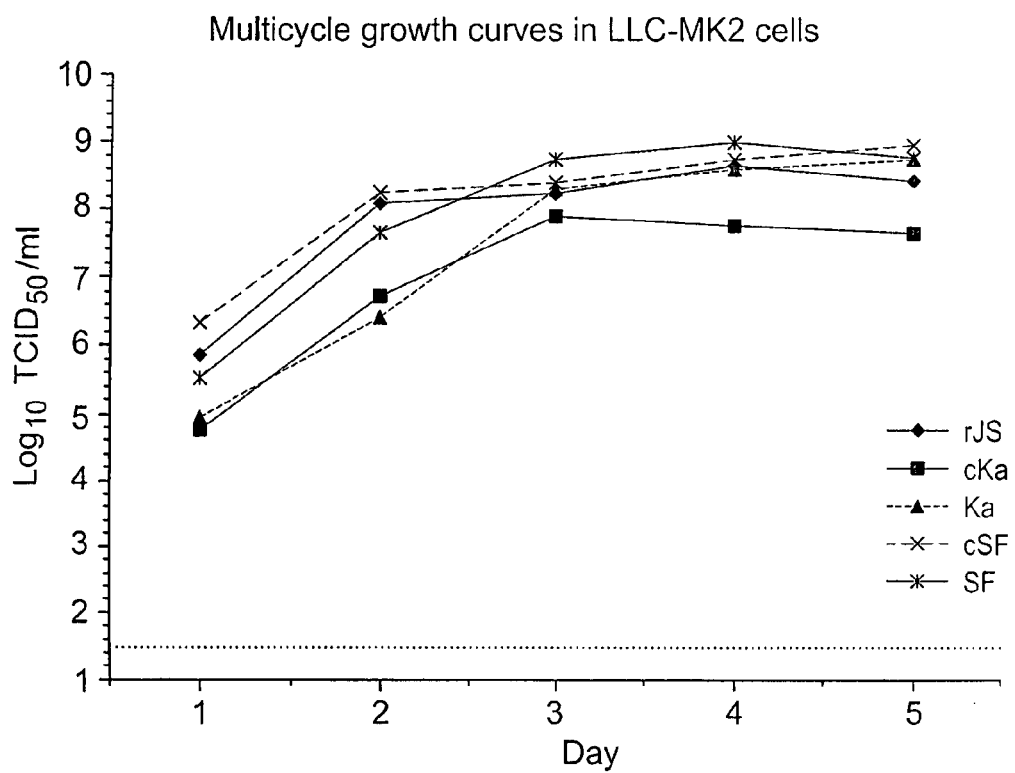

FIG. 45 provides multicycle growth curves of parental and chimeric viruses in MDBK (A) or LLC-MK2 (B) cells. Monolayers of bovine MDBK (A) or simian LLC-MK2 (B) cells in wells (9.6 cm2 each) of a 6 well plate were infected individually at a multiplicity of infection of 0.01 with the indicated parental or chimeric virus. Three replicate infections were performed for each virus. Samples were taken at the indicated time points, stored at −70° C., and titered by TCID50 assay in parallel. Growth curves are constructed using the average of 3 replicate samples at each time point. The lower limit of virus detectability was 101.5TCID50/ml, which is indicated by a dotted line.

FIGS. 46A-46G set forth the complete positive sense nucleotide sequence (SEQ ID NO: 41) of the bovine PIV3 Ka strain.

FIGS. 47A-47G set forth the complete positive sense nucleotide sequence (SEQ ID NO: 42) of the bovine PIV3 SF strain.

Figure 48A:
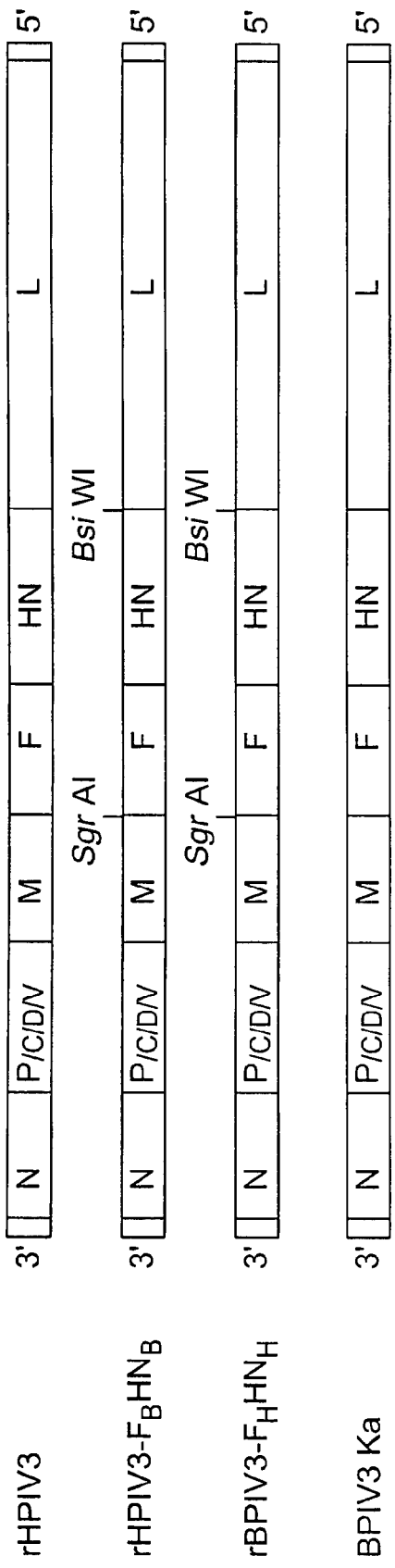

FIG. 48A provides a schematic depiction of the genomes of chimeric rHPIV3-FBHNB and rBPIV3-FHHNH viruses, and of their parent viruses, rHPIV3 JS and BPIV3 Ka (not to scale). The F and HN genes were exchanged in a single restriction fragment between rHPIV3 and rBPIV3 using SgrAI and BsiWI sites that had been introduced in front of the M and HN gene end sequences, respectively.

Figure 48B:
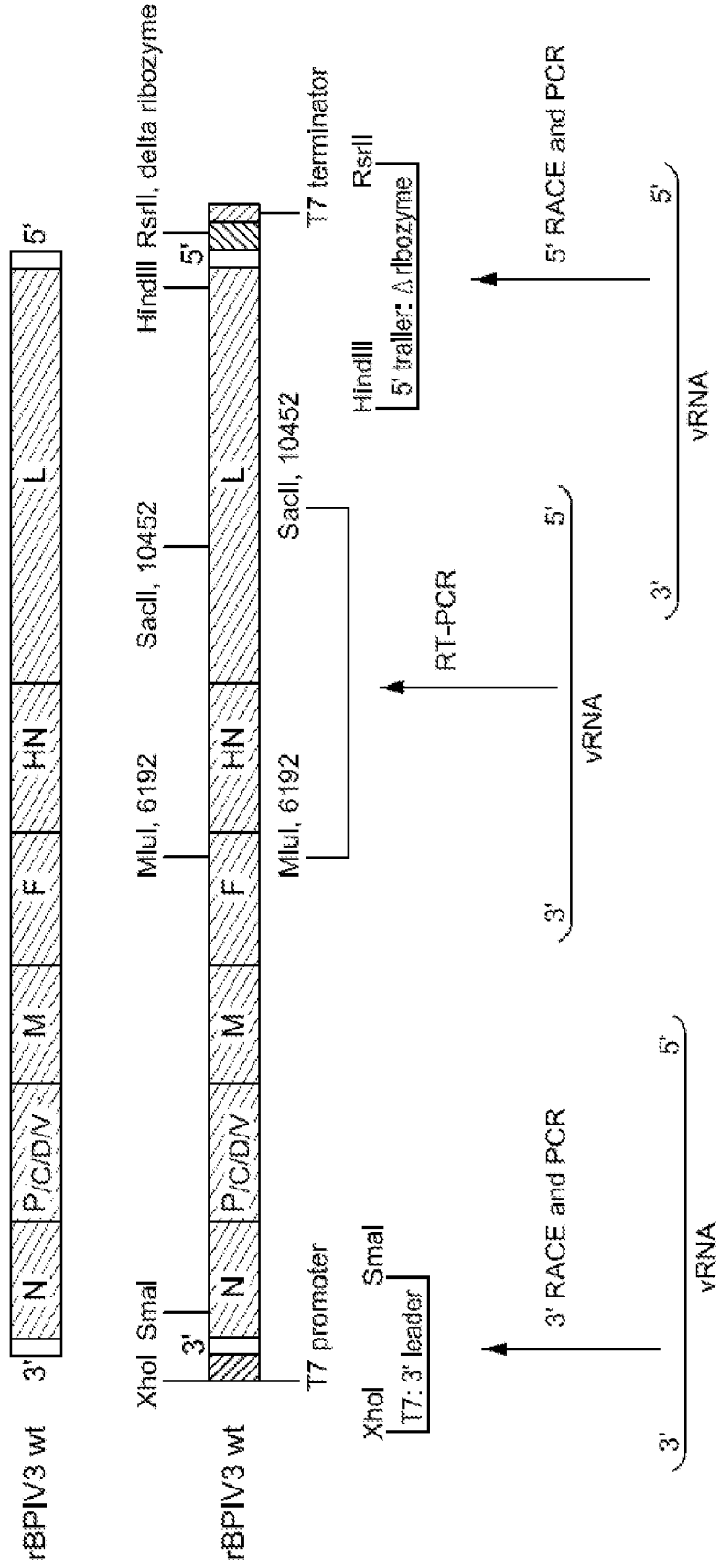

FIG. 48B depicts assembly of an antigenomic cDNA for BPIV3 Ka. A full length cDNA was constructed to encode the complete antigenomic sequence of BPIV3 Ka (GenBank accession #AF178654). The cDNA was assembled from subclones derived from reverse transcription (RT) of viral (v)RNA and polymerase chain reaction (PCR) amplification. Multiple subclones of the antigenome were sequenced, and only clones matching the consensus sequence of BPIV3 Ka were used for assembly of the full length clone, with the exception of nt 21 and nt 23, which differ from the published sequence but occur with similar frequency in the virus population.

Figure 48C:
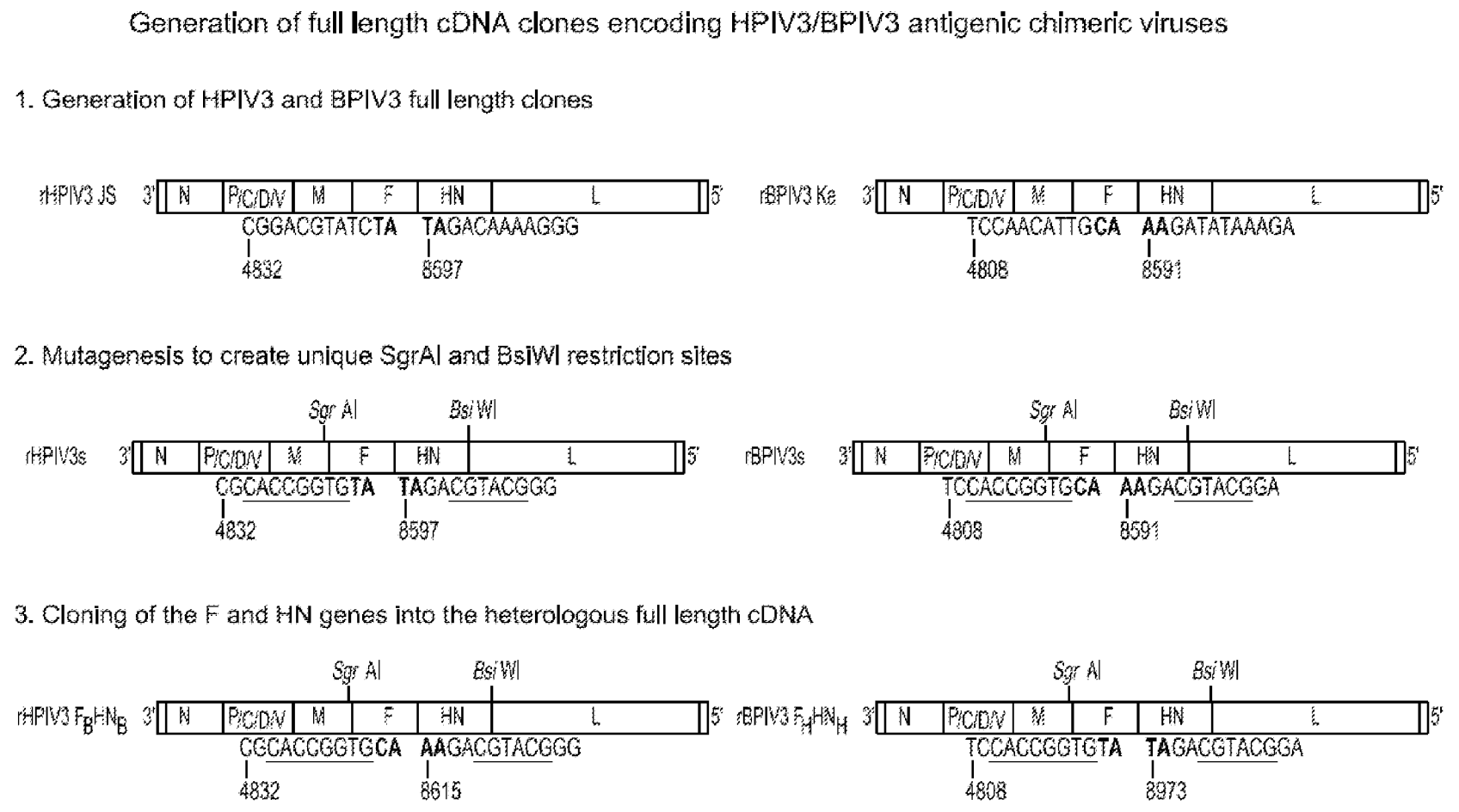

FIG. 48C illustrates features of parental and chimeric bovine-human PIV genomes. The genomes of the chimeric rHPIV3 FBHNB and rBPIV3 FHHNH viruses and those of their parent viruses rHPIV3 JS and BPIV3 Ka are shown schematically (not to scale). Two unique restriction enzyme recognition sites, SgrAI and BsiWI, were introduced near the M and HN gene ends, respectively. The recombinant HPIV3 and BPIV3 viruses bearing these introduced restriction sites were designeated rHPIV3s and rBPIV3s as indicated in FIG. 48C. 2. Glycoprotein genes were exchanged between rHPIV3 JS and rBPIV3 Ka. The nucleotide sequence (SEQ ID NOS: 43-54) that was mutagenized is shown below each cDNA construct, with the position of the first nucleotide of each sequence indicated. The introduced SgrAI and BsiWI restriction sites are underlined and nucleotides that differ between HPIV3 and BPIV3 and thus identify the origin of the gene inserts are depicted in bold print.

Figure 49:
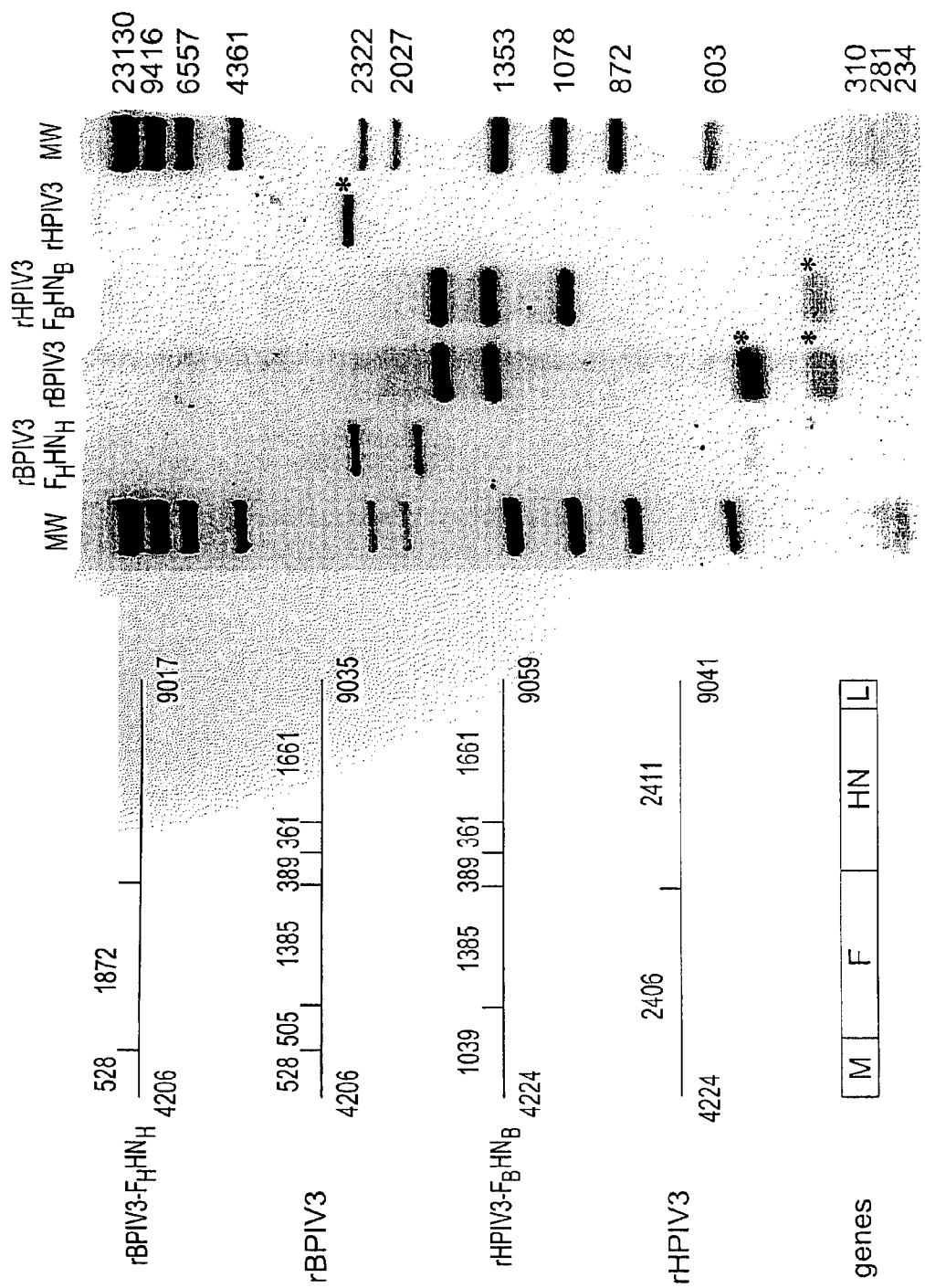

FIG. 49 provides a confirmation of the identity of recombinant viruses by RT-PCR of viral RNA and Eco RI digestion. RT-PCR products of viral RNA were prepared with a primer pair that recognized conserved regions on either side of the F and HN genes in both BPIV3 and HPIV3. Digestion with Eco RI resulted in a unique pattern of restriction fragments for each of the four viruses. In the schematic diagram on the left, horizontal lines symbolize the amplified viral sequences and vertical bars show the positions of Eco RI sites. The expected size of each restriction fragment is indicated above the line. The numbers below each line correspond to the sequence position in the antigenomic RNA of BPIV3 Ka, HPIV3 JS (GenBank accession #AF178654 and Z11575), or of the indicated chimeric derivative. On the right, a 1% agarose gel of the Eco RI digestion of PCR products is shown, confirming the identity of parental and chimeric viruses. The asterisks indicate gel bands that contain two restriction fragments that comigrate due to close similarity in size.

Figure 50:
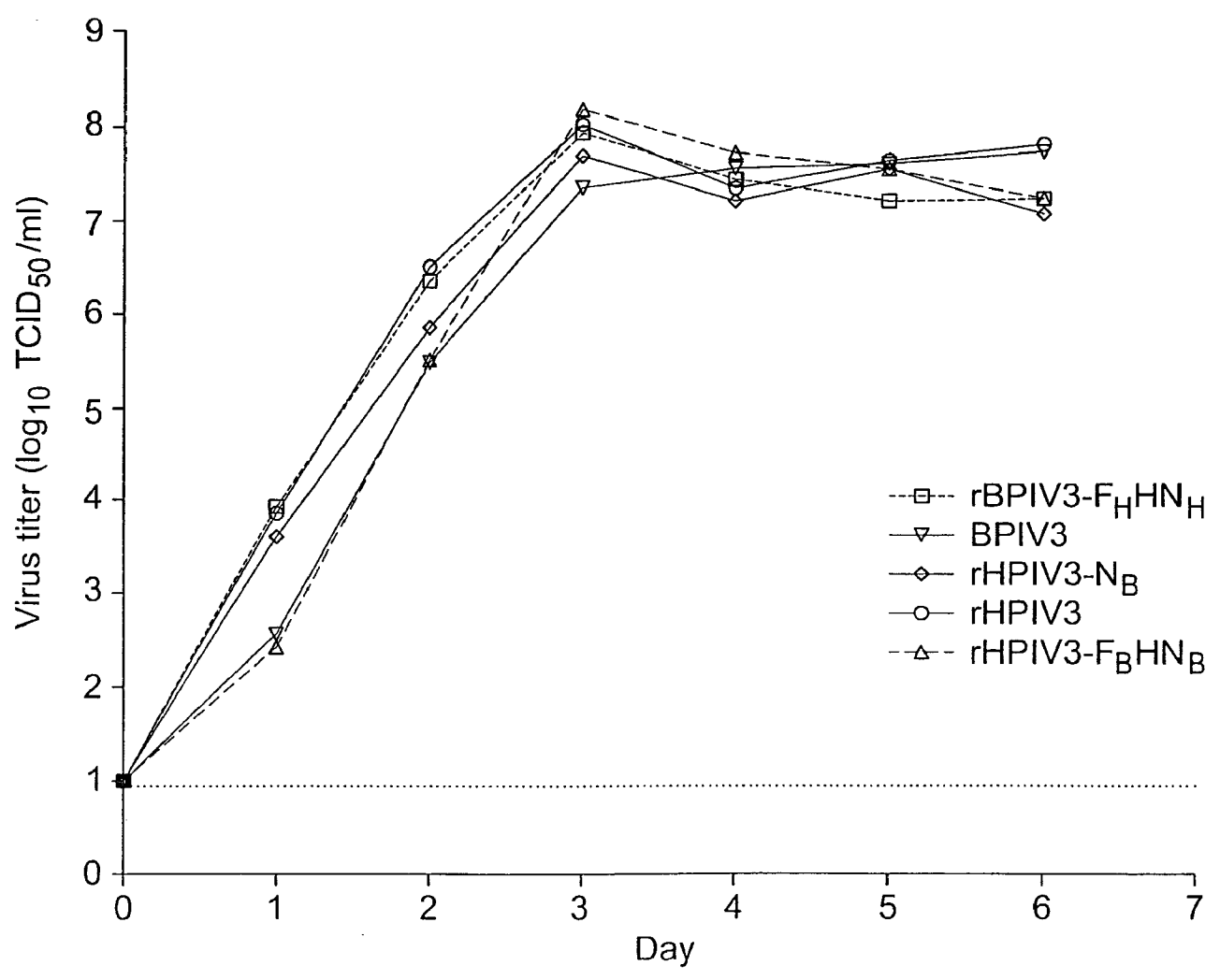

FIG. 50 depicts multicycle replication of chimeric and parental viruses in simian LLC-MK2 cells. Multicycle replication (the input inoculum had an MOI of 0.01) of the three chimeric viruses rHPIV3-FBHNB, rBPIV3-FHHNH and rHPIV3-NB (also referred to as cKa) is compared with the replication of their parental viruses BPIV3 Ka and rHPIV3. The virus titers are shown as mean log 10 TCID50/ml±standard error of triplicate samples. The lower limit of detection of this assay is 10 TCID50, as indicated by the dotted horizontal line.

Figures 51A, 51B:
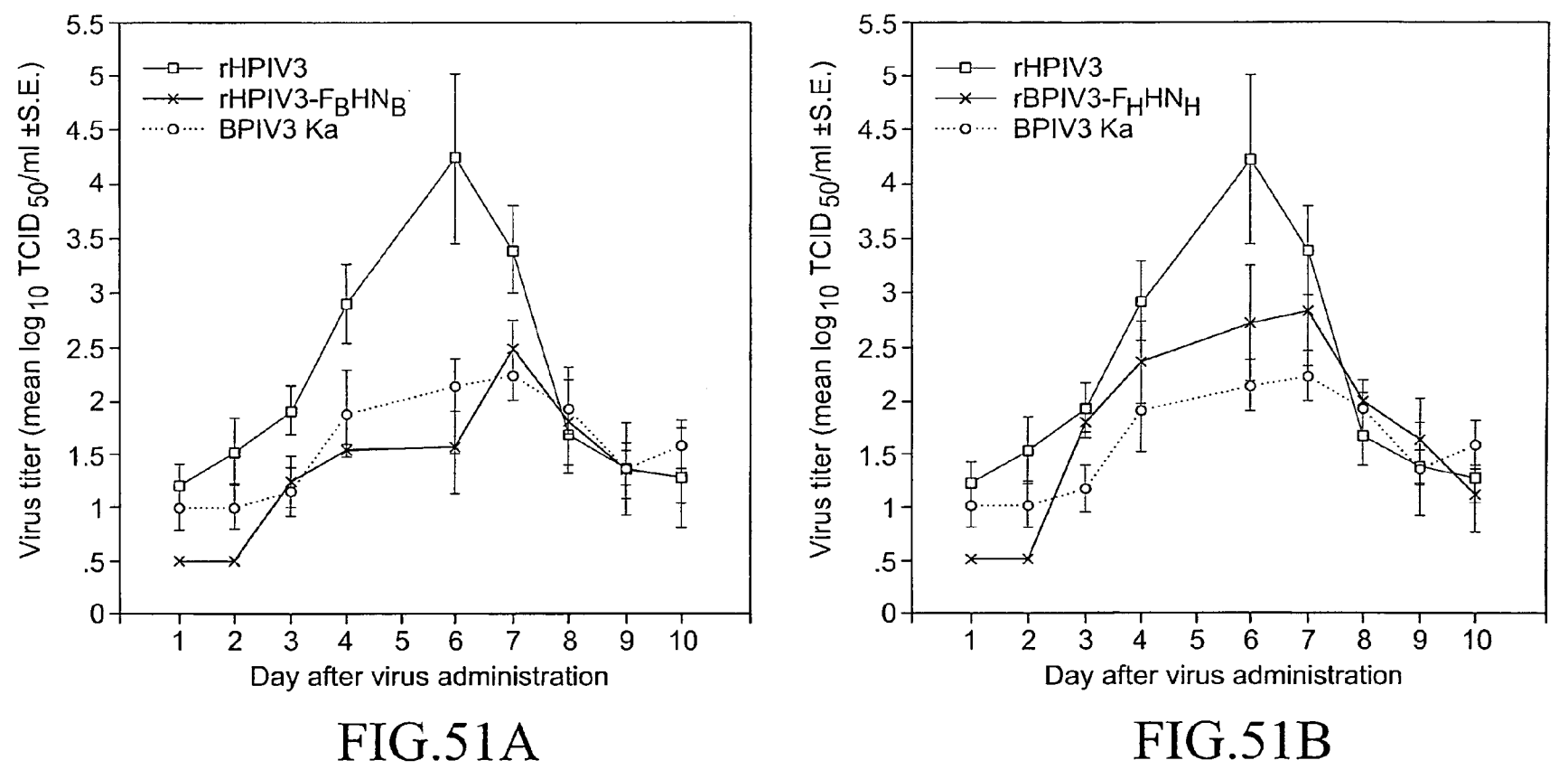

FIG. 51 documents mean titers of chimeric and parental viruses in nasopharyngeal swabs of infected rhesus monkeys over the course of infection. Virus titers are shown as mean TCID50/ml in LLC-MK2 cells±standard error for groups of 4 or 6 monkeys infected with the same virus. This illustrates the same experiment as shown in Table 3. In panel A, mean titers of rHPIV3-FBHNB are compared to rHPIV3 and BPIV3 Ka titers. In panel B, mean rBPIV3-FHHNH titers are compared to those of BPIV3 Ka and rHPIV3, which, for the last two viruses, are the same values in panel A but are presented separately to facilitate comparison. Day 5 titers were excluded from the figures because they were much lower than day 4 and day 6 titers, most likely due to technical problems during the sample collection.

DESCRIPTION OF THE SPECIFIC EMBODIMENTS

The present invention provides compositions and methods for producing and modifying infectious PIV from isolated polynucleotide molecules, preferably cDNA. Infectious PIV particles are produced by a recombinant coexpression system that permits introduction of defined changes into infectious PIV. These modifications are useful in a wide variety of applications, including the development of live attenuated vaccine strains bearing predetermined, defined attenuating mutations.

To produce infectious PIV from cDNA-expressed genome or antigenome, the genome or antigenome is coexpressed with those PIV proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Infectious PIV of the invention are produced by intracellular or cell-free coexpression of one or more isolated polynucleotide molecules that encode a PIV genome or antigenome RNA, together with one or more polynucleotides encoding viral proteins necessary to generate a transcribing, replicating nucleocapsid. Among the viral proteins useful for coexpression to yield infectious PIV are the major nucleocapsid protein (N) protein, nucleocapsid phosphoprotein (P), large (L) polymerase protein, fusion protein (F), hemagglutinin-neuraminidase glycoprotein (HN), and matrix (M) protein. Also useful in this context are products of the C, D and V ORFs of PIV.

cDNAs encoding a PIV genome or antigenome are constructed for intracellular or in vitro coexpression with the necessary viral proteins to form infectious PIV. By "PIV antigenome" is meant an isolated positive-sense polynucleotide molecule which serves as a template for synthesis of progeny PIV genome. Preferably a cDNA is constructed which is a positive-sense version of the PIV genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant PIV (rPIV) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant PIV" is meant a PIV or PIV-like viral or subviral particle obtained directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from a cDNA-expressed PIV genome or antigenome, the genome or antigenome is coexpressed with those PIV N, P and L proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Synthesis of PIV antigenome or genome together with the above-mentioned viral proteins can also be achieved in vitro (cell-free), e.g., using a combined transcription-translation reaction, followed by transfection into cells. Alternatively, antigenome or genome RNA can be synthesized in vitro and transfected into cells expressing PIV proteins.

In certain embodiments of the invention, complementing sequences encoding proteins necessary to generate a transcribing, replicating PIV nucleocapsid are provided by one or more helper viruses. Such helper viruses can be wild type or mutant. Preferably, the helper virus can be distinguished phenotypically from the virus encoded by the PIV cDNA. For example, it is desirable to provide monoclonal antibodies which react immunologically with the helper virus but not the virus encoded by the PIV cDNA. Such antibodies can be neutralizing antibodies. In some embodiments, the antibodies can be used in affinity chromatography to separate the helper virus from the recombinant virus. To aid the procurement of such antibodies, mutations can be introduced into the PIV cDNA to provide antigenic diversity from the helper virus, such as in the HN or F glycoprotein genes.

In alternate embodiments of the invention, the N, P, L and other desired PIV proteins are encoded by one or more non-viral expression vectors, which can be the same or separate from that which encodes the genome or antigenome. Additional proteins may be included as desired, each encoded by its own vector or by a vector encoding one or more of the N, P, L and other desired PIV proteins, or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., Virology, 210: 202-205 (1995), incorporated herein by reference in its entirety). The viral proteins, and/or T7 RNA polymerase, can also be provided by transformed mammalian cells or by transfection of preformed mRNA or protein.

A PIV antigenome may be constructed for use in the present invention by, e.g., assembling cloned cDNA segments, representing in aggregate the complete antigenome, by polymerase chain reaction or the like (PCR; described in, e.g., U.S. Pat. Nos. 4,683,195 and 4,683,202, and PCR Protocols: A Guide to Methods and Applications, Innis et al., eds., Academic Press, San Diego (1990), each incorporated herein by reference in its entirety) of reverse-transcribed copies of PIV mRNA or genome RNA. For example, a first construct is generated which comprises cDNAs containing the left hand end of the antigenome, spanning from an appropriate promoter (e.g., T7 RNA polymerase promoter) and assembled in an appropriate expression vector, such as a plasmid, cosmid, phage, or DNA virus vector. The vector may be modified by mutagenesis and/or insertion of synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and tandem T7 transcriptional terminators. The ribozyme can be hammerhead type (e.g., Grosfeld et al., (1995), supra), which would yield a 3' end containing a single nonviral nucleotide, or can be any of the other suitable ribozymes such as that of hepatitis delta virus (Perrotta et al., Nature 350:434-436 (1991), incorporated herein by reference in its entirety) which would yield a 3' end free of non-PIV nucleotides. The left- and right-hand ends are then joined via a common restriction site.

A variety of nucleotide insertions, deletions and rearrangements can be made in the PIV genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Alternative means to construct cDNA encoding the genome or antigenome include reverse transcription-PCR using improved PCR conditions (e.g., as described in Cheng et al., Proc. Natl. Acad. Sci. USA 91:5695-5699 (1994)), incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the larger size genome or antigenome.

Isolated polynucleotides (e.g., cDNA) encoding the genome or antigenome may be inserted into appropriate host cells by transfection, electroporation, mechanical insertion, transduction or the like, into cells which are capable of supporting a productive PIV infection, e.g., HEp-2, FRhL-DBS2, LLC-MK2, MRC-5, and Vero cells. Transfection of isolated polynucleotide sequences may be introduced into cultured cells by, for example, calcium phosphate-mediated transfection (Wigler et al., Cell 14: 725 (1978); Corsaro and Pearson, Somatic Cell Genetics 7: 603 (1981); Graham and Van der Eb, Virology 52:456 (1973)), electroporation (Neumann et al., EMBO J. 1: 841-845 (1982)), DEAE-dextran mediated transfection (Ausubel et al., (ed.) Current Protocols in Molecular Biology, John Wiley and Sons, Inc., NY (1987), cationic lipid-mediated transfection (Hawley-Nelson et al., Focus 15: 73-79 (1993)) or a commercially available transfection regent, e.g., LipofectACE® (Life Technologies, Gaithersburg, Md.) or the like (each of the foregoing references are incorporated herein by reference in its entirety).

As noted above, in some embodiments of the invention the N, P, L and other desired PIV proteins are encoded by one or more helper viruses which is phenotypically distinguishable from that which encodes the genome or antigenome. The N, P, L and other desired PIV proteins can also be encoded by one or more expression vectors which can be the same or separate from that which encodes the genome or antigenome, and various combinations thereof. Additional proteins may be included as desired, encoded by its own vector or by a vector encoding one or more of the N, P, L and other desired PIV proteins, or the complete genome or antigenome.

The compositions and methods of the invention permit analysis and manipulation of PIV molecular biology and pathogenic mechanisms using, e.g., defined mutations to alter the function or expression of selected PIV proteins. Using these methods and compositions, one can readily distinguish mutations responsible for desired phenotypic changes from silent incidental mutations, and select phenotype-specific mutations for incorporation into a recombinant PIV genome or antigenome for vaccine production.

Modifications of PIV provided within the invention are directed toward the production of improved vaccine viruses, e.g., to enhance viral attenuation and vaccine immunogenicity, to ablate epitopes associated with undesirable immunopathology, to accommodate antigenic drift, etc. To achieve these and other objectives, the compositions and methods of the invention allow for a wide variety of modifications to be introduced into a PIV genome or antigenome for incorporation into infectious, recombinant PIV. For example, foreign genes or gene segments encoding protective antigens or epitopes may be added within a PIV clone to generate PIV virus strains capable of inducing immunity to both PIV and another virus or agent from which the protective antigen was derived. Alternatively, foreign genes may be inserted, in whole or in part, encoding modulators of the immune system, such as cytokines, to enhance immunogenicity of a vaccine virus.

Other mutations which may be included within PIV clones of the invention include, for example, substitution of heterologous genes or gene segments (e.g., a gene segment encoding a cytoplasmic tail of a glycoprotein gene) with a counterpart gene or gene segment in a PIV clone. Alternatively, the relative order of genes within a PIV clone can be changed, the PIV genome promoter can be replaced with its antigenome counterpart, or selected gene(s) rendered non-functional (e.g., by functional ablation involving introduction of a stop codon to prevent expression of the gene). Other modifications in a PIV clone can be made to facilitate manipulations, such as the insertion of unique restriction sites in various non-coding or coding regions or elsewhere. In addition, nontranslated gene sequences can be removed to increase capacity for inserting foreign sequences.

Thus, by providing infectious clones of PIV the invention permits a wide range of alterations to be recombinantly produced within the PIV genome (or antigenome), yielding defined mutations which specify desired phenotypic changes. By "infectious clone" is meant cDNA or its product, synthetic or otherwise, RNA capable of being directly incorporated into infectious virions which can be transcribed into genomic or antigenomic RNA capable of serving as a template to produce the genome of infectious viral or subviral particles. As noted above, defined mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA subjects provide for better ease of manipulation than large cDNA subjects, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gen® kit of Bio-Rad Laboratories (Richmond, Calif.), or a method using the double-stranded plasmid directly as a template such as the Chameleon® mutagenesis kit of Strategene (La Jolla, Calif.), or by the polymerase chain reaction employing either an oligonucleotide primer or a template which contains the mutation(s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding an PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15-35 nucleotides in the case of genome segments encoding small functional domains of proteins, e.g., epitopic sites, to about 50, 75, 100, 200-500, and 500-1,500 or more nucleotides.

The ability to introduce defined mutations into infectious PIV has many applications, including the manipulation of PIV pathogenic and immunogenic mechanisms. For example, the functions of PIV proteins, including the N, P, M, F, HN, and L proteins and C, D and V ORF products, can be manipulated by introducing mutations which ablate or reduce the level of protein expression, or which yield mutant protein. In one such exemplary modification, a sequence at the cleavage site of the F protein can be modified and the effects of this modification on growth in tissue culture and infection and pathogenesis of the resultant PIV can be routinely determined in experimental animals.

Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock, et al., J. Virol. 67: 2772-8 (1993), incorporated herein by reference in its entirety), whose rescue-dependent status is useful in characterizing those mutants that may be too inhibitory to be recovered in replication-independent infectious virus.

The present invention further provides tools and methods to readily distinguish between silent incidental mutations and mutations responsible for phenotype differences, for example by introducing suspect mutations, separately and in various combinations, into the genome or antigenome of infectious wild-type (i.e., for one or more phenotypic character such as temperature sensitivity, replication in a selected host, etc.) PIV. This process permits identification of mutations responsible for desired vaccine phenotypes such as attenuation, temperature sensitivity, cold-adaptation, small plaque size, host range restriction, etc. Mutations identified by these methods can then be introduced in various combinations to modify a vaccine virus to an appropriate level of attenuation, etc., as desired. Moreover, the present invention provides the ability to combine mutations from different strains of virus into a single vaccine strain.

As noted above, mutations incorporated within recombinantly altered PIV clones may be selected based on their ability to alter expression and/or function of a selected PIV protein, yielding a desired phenotypic change, or for a variety of other purposes. Desired phenotypic changes include, e.g., changes in viral growth in culture, temperature sensitivity, plaque size, attenuation, and immunogenicity. For example, a polynucleotide sequence encoding the genome or antigenome can be modified by a nucleotide insertion, rearrangement, deletion or substitution to specify attenuation, temperature-sensitivity, cold-adaptation, small plaque size, host range restriction, alteration in gene expression, or a change in an immunogenic epitope.

In one aspect of the invention, mutations occurring in biologically derived, attenuated PIV are identified and introduced individually or in combination into a full-length PIV clone, and the phenotypes of rescued recombinant viruses containing the introduced mutations are determined. In exemplary embodiments, amino acid changes displayed by biologically derived mutant viruses over a wild-type PIV, for example changes exhibited by PIV mutants having ts, ca or att phenotypes, are incorporated within recombinant PIV clones. These changes from biologically derived mutant PIV specify desired characteristics in the resultant clones, e.g., an attenuation phenotype specified by a mutation adopted from the HPIV3 mutant JS cp45. These changes are preferably introduced into recombinant virus using two or three nucleotide changes compared to a corresponding wild type or biologically derived mutant sequence, which has the effect of stabilizing the mutation against genetic reversion.

The present invention also provides recombinant PIV having multiple, phenotype-specifying mutations introduced in selected combinations into the genome or antigenome of an infectious clone. This process, coupled with evaluation of phenotype, provides mutant recombinant PIV having such desired characteristics as attenuation, temperature sensitivity, cold-adaptation, small plaque size, host range restriction, etc. Thus, exemplary PIV clones are disclosed herein which incorporate one or more, and preferably at least two attenuating mutations, e.g., ts, ca or att mutations adopted from a biologically derived PIV mutant, such as JS cp45. Target genes for adopting biologically derived mutations in a recombinant PIV in this context include the nucleocapsid protein N, phosphoprotein P, large polymerase subunit L, matrix protein M, hemagglutinin-neuraminidase protein HN, fusion protein F and the C, D and V ORF products. Also targeted are extragenic sequences, eg., sequences in the 3' leader or trailer regions of a PIV genome, and in cis-acting elements such as gene start and gene end sequences, eg., the N gene start signal. Exemplary mutations incorporated in recombinant PIV herein include one or more nucleotide substitutions specifying amino acid change(s) in the polymerase L gene, e.g., at Tyr942, Leu992, and/or Thr1558. For example, PIV recombinants are disclosed wherein Tyr942 is replaced by His, Leu992 is replaced by Phe, and/or Thr1558 is replaced by Ile. These mutations have been successfully incorporated in various exemplary PIV recombinants herein, including r942, r992, r1558, r942/992, r992/1558, r942/1558, or r942/992/1558 recombinants described in the Examples below. Other exemplary mutations adopted from a biologically derived PIV mutant include one or more mutations in the N protein, including specific mutations at a position corresponding to residues Val96 or Ser389 of JS cp45. In more detailed aspects, these mutations are represented as Val96 to Ala or Ser389 to Ala. Also disclosed in the Examples below are recombinant PIV which encode an amino acid substitution in the C protein, eg., a mutation at a position corresponding to Ile96 of JS cp45, preferably represented by a substitution of Ile96 to Thr. Further exemplary mutations adopted from biologically derived PIV mutants include one or more mutations in the F protein, including mutations adopted from JS cp45 at a position corresponding to residues Ile420 or Ala450 of JS cp45, preferably represented by acid substitutions Ile420 to Val or Ala450 to Thr. Other PIV recombinants within the invention adopt one or more amino acid substitutions in the HN protein, as exemplified hereinbelow by a recombinant PIV adopting a mutation at a position corresponding to residue Val384 of JS cp45, preferably represented by the substitution Val384 to Ala. Yet additional examples within this aspect of the invention include recombinant PIV which incorporate one or more mutations in an extragenic sequence, eg., a 3' leader sequence of recombinant PIV genome or antigenome. Exemplary mutations in this context include mutations in the 3' leader occurs at one or more positions corresponding to nucleotide 23, 24, and/or 28 of JS cp45, for example a T to C change at nucleotide 23, a C to T change at nucleotide 24, or a G to T change at nucleotide 28. Yet additional extragenic mutations include one or more mutations in a N gene start sequence, as exemplified hereinbelow by a mutation in the N gene start sequence at a position corresponding to nucleotide 62 of JS cp45, preferably represented by a A to T change. The above exemplary mutations adopted from biologically derived mutant PIV are evaluated and combined into recombinant PIV in the Examples below to result, individually and/or in combination, in novel, attenuated candidate vaccine strains, as exemplified by the recombinants designated herein as rcp45, rcp45 3'NCMFHN, rcp45 3'NL, rcp45 3'N, and rcp45 F. Other PIV recombinants within the invention will incorporate a plurality and up to a full complement of the mutations present in one or more of these exemplary recombinants, as well as mutations identified in other biologically derived mutant PIV strains identified and adopted in a recombinant PIV according to the teachings herein.

Mutations identified according to the methods disclosed herein are compiled into a "menu" and introduced in various combinations to calibrate a vaccine virus to a selected level of attenuation, immunogenicity and stability. In preferred embodiments, the invention provides for supplementation of one or more mutations adopted from biologically derived PIV, e.g., ts, ca or att mutations, with additional types of mutations involving the same or different genes. Target genes for mutation in this context also include the nucleocapsid protein N, phosphoprotein P, large polymerase subunit L, matrix protein M, hemagglutinin-neuraminidase protein HN, fusion protein F and the C, D and V ORF products. In one aspect, recombinant PIVs are provided wherein at least one attenuating mutation occurs in the PIV polymerase gene L and involves a nucleotide substitution specifying a ts or att phenotype adopted from a biologically derived mutant PIV strain, for example JS cp45. Exemplary HPIV3 recombinants disclosed herein include the r942, r992, r1558, r942/992, r992/1558, r942/1558, or r942/992/1558 recombinants described in the Examples below. These exemplary PIV clones incorporate one or more nucleotide substitutions resulting in an amino acid change in the polymerase gene, e.g., at Tyr942, Leu992, and/or Thr1558. For example, PIV recombinants are disclosed wherein Tyr942 is replaced by His, Leu992 is replaced by Phe, and/or Thr1558 is replaced by Ile. Preferably, two or three mutations are incorporated in a codon specifying an attenuating mutation adding increased stability against phenotypic reversion.

In additional aspects, a variety of other genetic alterations can be produced in a recombinant PIV genome or antigenome for incorporation into infectious recombinant PIV, alone or together with one or more attenuating mutations adopted from a biologically derived mutant PIV. Heterologous genes (e.g. from different PIV strains or non-PIV sources such as another virus, e.g., RSV or measles virus) may be inserted or substituted, in whole or in part, the order of genes changed, gene overlap removed, the PIV genome promoter replaced with its antigenome counterpart, and even entire, non-essential genes deleted. In one aspect, a selected PIV gene, for example the C, D, or V ORF, is functionally deleted to yield a recombinant PIV having novel phenotypic characteristics, for example enhanced growth in vitro and/or attenuation in vivo. An infectious PIV clone of the invention can also be engineered to enhance its immunogenicity and induce a level of protection greater than that provided by natural infection, or to ablate epitopes associated with undesirable immunopathologic reactions. Enhanced immunogenicity of the vaccines produced by the present invention addresses one of the greatest obstacles to controlling PIV, namely the incomplete nature of immunity induced by natural infection. In this context, additional gene(s) or gene segment(s) may be inserted into or proximate to the PIV genome or antigenome which may be placed under the control of a common or independent set of transcription signals. Genes of interest include those encoding cytokines (e.g., IL-2 through IL-15, especially IL-2, IL-6 and IL-12, etc.) and proteins rich in T helper cell epitopes. The additional protein can be expressed either as a separate protein or as a chimera engineered from a second copy of one of the PIV proteins, such as HN. This provides the ability to modify and improve the immune response against PIV both quantitatively and qualitatively.

Other mutations useful within the invention involve replacement of the 3' end of genome with its counterpart from antigenome, which is associated with changes in RNA replication and transcription. In addition, intergenic regions can be shortened or lengthened or changed in sequence content. In yet additional aspects, PIV useful in a vaccine formulation can be conveniently modified to accommodate antigenic drift in circulating virus. Typically the modification will be in the HN and/or F proteins. For example, a selected antigenic form of an entire HN or F gene, or the segment(s) encoding particular immunogenic regions thereof, is incorporated into a PIV genome or antigenome cDNA by replacement of a counterpart region in the infectious clone, or by adding one or more copies of the gene such that several antigenic forms are represented in the resultant clone. Progeny virus produced from the modified PIV cDNA are then used in vaccination protocols against emerging strains.

Other mutations for use in infectious PIV of the invention include mutations in cis-acting signals identified during mutational analysis of PIV minigenomes. For example, insertional and deletional analysis of leader and trailer and flanking sequences identify viral promoters and transcription signals and provide a series of mutations associated with varying degrees of reduction of RNA replication or transcription. Saturation mutagenesis (whereby each position in turn is modified to each of the nucleotide alternatives) of these cis-acting signals also identifies mutations which reduce or increase RNA replication or transcription. Any of these mutations can be inserted into the complete antigenome or genome as described herein.

Additional modifications in PIV clones can be made to facilitate manipulations, such as the insertion of unique restriction sites in various intergenic regions or elsewhere. Nontranslated gene sequences can also be removed to increase capacity for inserting foreign sequences.

Certain substitutions, insertions, deletions or rearrangements of genes or gene segments within recombinant PIV of the invention (e.g., substitutions of a gene segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or gene segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, gene segments, proteins or protein regions, are typically from heterologous sources (e.g., from different PIV genes, or representing the same (i.e., homologous or allelic) gene or gene segment in different PIV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding gene segments embrace an assemblage of species having a range of size and sequence variations defined by a common biological activity among the domain or gene segment variants. For example, two selected protein domains encoded by counterpart gene segments within the invention share substantially the same qualitative activity, such as providing a membrane spanning function, a specific binding activity, an immunological recognition site, etc. More typically, a specific biological activity shared between counterparts, e.g., between selected protein segments or proteins, will be substantially similar quantitatively, i.e., they will not vary in respective quantitative activity levels by more than 30%, preferably by no more than 20%, more preferably by no more than 5-10%.

Counterpart genes and gene segments, as well as other polynucleotides disclosed herein for producing recombinant PIV within the invention, preferably share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or 1) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant PIV of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (Immunology—A Synthesis (2nd ed., E. S. Golub & D. R. Gren, eds., Sinauer Associates, Sunderland, MA, 1991), incorporated herein by reference). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). Moreover, amino acids may be modified by glycosylation, phosphorylation and the like.

The infectious PIV produced from cDNA-expressed genome or antigenome can be any of the PIV or PIV-like strains, e.g., human, bovine, murine, etc. To engender a protective immune response, the PIV strain may be one which is endogenous to the subject being immunized, such as human PIV being used to immunize humans. The genome or antigenome can be modified, however, to express heterologous PIV genes or gene segments, or genes or gene segments from other heterologous sources, e.g., RSV or measles virus. Thus, infectious PIV intended for administration to humans may be human PIV that has been modified to contain genes or gene segments from a bovine or murine PIV type such as for the purpose of attenuation. BPIV3 possesses host range mutations that restrict its replication in rhesus monkeys and humans (Karron et al., supra, 1995a; van Wyke Coelingh et al., 1988), each incorporated herein by reference in its entirety). Gene(s), mutations and cis-acting regulatory sequences of BPIV3 that specify desired phenotypes, e.g., host range restriction, will be identified by their substitution for corresponding sequences in rPIV of the invention, and incorporated within further modified rPIV to develop yet additional useful vaccine agents. Similarly, mutations of JS cp45 which are known to impart non-ts host-range attenuating mutations for the rhesus monkey (Hall et al., supra, (1992)) will likewise be identified and incorporated into modified rPIV vaccine agents of the invention. Alternatively, a bovine PIV may be modified to contain genes that encode, e.g., proteins or immunogenic epitopes that elicit protection against human PIV infection. For example, human PIV glycoprotein genes can be substituted for counterpart bovine glycoprotein genes, such that the bovine PIV elicits a protective immune response in humans against human PIV strains.

In exemplary embodiments, individual genes, gene segments, or single or multiple nucleotides of one PIV are substituted by counterpart sequence(s) from a heterologous PIV or other source. For example, heterologous gene segments, such as one encoding a cytoplasmic tail, transmembrane domain or ectodomain, an epitopic site or region, a binding site or region, an active site or region containing an active site, etc., of a selected protein from one PIV is substituted for a counterpart gene segment in another PIV to yield novel recombinants, for example recombinants expressing a chimeric protein having a cytoplasmic tail and/or transmembrane domain of one PIV fused to an ectodomain of another PIV. Preferred genome segments in this regard range from about 15-35 nucleotides in the case of gene segments encoding small functional domains of proteins, e.g., epitopic sites, to about 50, 75, 100, 200-500, or 500-1,500 or more nucleotides for gene segments encoding larger domains or protein regions.

In one aspect of the invention, selected domains of HN and/or F proteins of one PIV strain are substituted into a heterologous PIV clone to produce a recombinant virus capable of stimulating a cross-protective immune response against both PIV strains in an immunized host. In other aspects, modified PIV clones are provided which comprise a chimera of a human PIV genomic or antigenomic sequence and at least one non-human PIV sequence, for example a polynucleotide containing sequences from both human and bovine PIV. The replacement of a human PIV coding sequence or non-coding sequence (e.g., a promoter, gene-end, gene-start, intergenic or other cis-acting element) with a counterpart bovine or murine PIV sequence yields recombinants having a variety of possible attenuating effects. For example, a host range effect will often arise from a heterologous PIV gene not functioning efficiently in a human cell, from incompatibility of the heterologous sequence or protein with a biologically interactive human PIV sequence or protein (e.g., a sequence or protein that ordinarily cooperates with the substituted sequence or protein for viral transcription, translation, assembly, etc.), among other useful attenuating effects. In yet another aspect of the invention, insertion of foreign genes or gene segments, and in some cases of noncoding nucleotide sequences, into the PIV genome results in a desired increase in genome length causing yet additional, desired phenotypic effects. Increased genome length is expected to result in attenuation of the resultant PIV clone, dependent in part upon the length of the insert. In addition, the expression of certain proteins from a gene inserted into recombinant PIV will result in attenuation of the virus due to the action of the protein. This has been described for IL-2 expressed in vaccinia virus (see, e.g., Flexner et al., Nature 33:-259-62 (1987)) and also would be expected for gamma interferon.

Deletions, insertions, substitutions and other mutations involving changes of whole viral genes or gene segments in recombinant PIV of the invention yield highly stable vaccine candidates, which are particularly important in the case of immunosuppressed individuals. Many of these mutations will result in attenuation of resultant vaccine strains, whereas others will specify different types of desired phenotypic changes. For example, certain viral genes are known which encode proteins that specifically interfere with host immunity (see, e.g., Kato et al., EMBO. J. 16:578-87 (1997), incorporated herein by reference). Ablation of such genes in vaccine viruses is expected to reduce virulence and pathogenesis and/or improve immunogenicity.

In preferred aspects of the invention, the modified PIV clones represent a chimera of two or more human PIV genomes, for example a clone containing polynucleotide sequences from HPIV3 joined to sequences from one or more heterologous human PIV, such as HPIV1 and HPIV2. Thus, individual genes or gene segments of human PIV3 may be replaced or supplemented with counterpart genes or gene segments from HPIV1 or HPIV2, or visa versa. In one example described hereinbelow, the invention provides a PIV clone, rPIV3-1, into which both the HN and F glycoprotein genes of HPIV1 are substituted for their counterpart genes in an HPIV3 background, yielding a chimeric virus having immunological characteristics representative of both parental strains.

In additional aspects of the invention, chimeric PIV or PIV clones having other alterations of genes or gene segments, as described above, are further modified by introducing one or more attenuating mutations adopted from a biologically derived mutant PIV, e.g., HPIV3 JS cp45 to achieve an attenuated, or further attenuated, chimeric mutant derivative. For example, one or more human PIV coding or non-coding polynucleotides may be substituted with a counterpart sequence from a heterologous human PIV, bovine PIV or murine PIV as described above, and this alteration may be combined with one or more mutations specifying, e.g., a ts, ca or att phenotype adopted from a biologically derived attenuated PIV mutant, to yield an attenuated or further attenuated (i.e., compared to either the chimeric clone or biologically derived parent virus) vaccine virus. Alternatively, functional deletion of a non-essential gene or gene segment, such as the C, D or V ORF, may be combined in a recombinant PIV with one or more mutations specifying a ts, ca or att phenotype from biologically derived PIV mutants to yield an attenuated vaccine strain. These combinatorial modifications yield recombinant PIV having desired phenotypic characteristics, e.g., increased yield of virus, enhanced attenuation, and/or genetic resistance to reversion from an attenuated phenotype, due to the combined effects of the different selected mutations.

In one combinatorial mutation design, a modified PIV is provided which comprises a chimera of a human PIV genomic or antigenomic sequence and at least one non-human PIV sequence, for example a polynucleotide containing sequences from both human and bovine PIV, and which also incorporates one or more mutations adopted from biologically derived PIV, e.g., one or more naturally occurring ts, ca or att mutations. Alternatively, the modified PIV can be a chimera of two or more human PIV genomes, for example a polynucleotide containing sequences from HPIV3 joined to sequences from one or more heterologous human PIVs, such as HPIV1 and HPIV2, which further incorporates one or more ts, ca att or other selected mutations from biologically derived PIV (e.g., a nucleotide substitution specifying a ts, ca or att phenotype adopted from a biologically derived mutant PIV strain such as JS cp45). In more detailed aspects, individual genes or gene segments of human PIV3 are replaced or supplemented with counterpart genes or gene segments from HPIV1 or HPIV2, or visa versa, in a clone that is attenuated or further attenuated by, e.g., a nucleotide change encoding an amino acid substitution conferring a ts mutation in the large polymerase L gene. For example, the invention provides PIV clones having the HN and/or F glycoprotein genes of HPIV1 substituted for their counterpart genes in an HPIV3 background, wherein the phenotype of the resultant chimeric clone is further modified by ts, ca or att mutation(s) encoded within one or more of the N, P, L, M, HN, F, C, D and V genes. Various combinations from a menu of possible mutations disclosed herein can be made to calibrate a vaccine virus to a selected level of attenuation, immunogenicity and stability, e.g., to achieve a satisfactorily attenuated and immunogenic, chimeric virus having immunological characteristics representative of multiple PIV strains. In one aspect, recombinant PIVs are provided wherein at least one attenuating mutation occurs in the PIV polymerase gene L (as exemplified by the recombinants r942, r992, r1558, r942/992, r942/1558, r992/1558, or r942/992/1558 described in the Examples below) incorporated in a chimeric PIV background. For example, useful chimeric PIV recombinants within this aspect of the invention will have one or more genes or gene segments of the HN and/or F glycoprotein genes from, e.g., HPIV1 substituted for their counterpart gene(s) in a heterologous background, e.g., in an HPIV3 clone, and will further incorporate one or more attenuating mutations, eg., nucleotide substitutions resulting in an amino acid change in the polymerase gene (such as change from Tyr to His at position 942, a change from Leu to Phe at position 992, and/or a change from Thr to Ile at position 1558) from a biologically derived PIV mutant. One such chimeric, attenuated recombinant exemplified hereinbelow is rPIV3-1.cp45L, a derivative of rPIV3-1 which incorporates all three L gene mutations specified above from JS cp45.

Yet additional mutations which can be incorporated in a chimeric PIV background for developing vaccine strains will be selected from biologically derived mutations in other genes, or will be created de novo in a recombinant genome by standard site directed mutagenesis or other purely recombinant mutagenic methods. Target genes for adopting biologically derived mutations or creating novel mutations in a recombinant PIV in this context include the nucleocapsid protein N, phosphoprotein P, large polymerase subunit L, matrix protein M, hemagglutinin-neuraminidase protein HN, fusion protein F and the C, D and V ORF products. Also targeted are extragenic sequences, eg., sequences in the 3' leader or trailer regions of a PIV genome. Exemplary mutations identified and incorporated in non-chimeric, recombinant PIV, described above will thus be readily incorporated within a chimeric PIV background, eg., as exemplified by rPIV3-1. These exemplary mutations include one or more mutations in the N protein, including specific mutations at a position corresponding to residues Val96 or Ser389 of JS cp45. In more detailed aspects, these mutations are represented as Val96 to Ala or Ser389 to Ala. Also desired for incorporation in chimeric PIV recombinants are mutations in the C protein, eg., a mutation at a position corresponding to Ile96 of JS cp45, preferably represented by a substitution of Ile96 to Thr, as described above. Further exemplary mutations for incorporation in a chimeric PIV background include one or more mutations in the F protein, for example adopted from JS cp45 at a position corresponding to residues Ile420 or Ala450, eg., substitutions Ile420 to Val or Ala450 to Thr. Yet additional chimeric PIV recombinants within the invention will adopt one or more amino acid substitutions in the HN protein, for example a mutation at a position corresponding to residue Val384 of JS cp45, such as Val384 to Ala. Yet additional chimeric recombinants will incorporate one or more mutations in an extragenic sequence, eg., a 3' leader sequence of the recombinant genome or antigenome. Exemplary mutations in this context include mutations in the 3' leader occurs at one or more positions corresponding to nucleotide 23, 24, 28, and/or 45 of JS cp45, for example a T to C change at nucleotide 23, a C to T change at nucleotide 24, a G to T change at nucleotide 28, or a T to A change at nucleotide 45. Yet additional extragenic mutations for incorporation within a chimeric PIV background include one or more mutations in a N gene start sequence, as exemplified herein by a mutation in the N gene start sequence at a position corresponding to nucleotide 62 of JS cp45, such as a A to T change. These exemplary mutations evaluated and combined into recombinant PIV in the Examples below will be readily incorporated within a chimeric PIV recombinant using the methods and tools provided herein, and will specify, individually and/or in combination, desired phenotypic changes to yield yet additional attenuated chimeric vaccine strains within the invention.

In additional combinatorial mutation designs, modified PIVs are provided which incorporate one or more of the foregoing ts, ca or att mutations adopted from biologically derived PIV or generated recombinantly in a PIV clone of the invention, in combination with another, distinct mutation disclosed herein (e.g., a deletion, addition, or rearrangement of a PIV N, P, L, M, HN, F, C, D or V gene or gene segment, or a gene or gene segment from another source such as RSV or measles virus). Also in this case, various combinations from a menu of mutations disclosed herein can be made to calibrate the vaccine virus to a selected level of attenuation, immunogenicity and stability. Thus, recombinant PIVs are provided which exhibit at least one attenuating mutation from a biologically derived PIV mutant, e.g., a mutation in the PIV polymerase gene L as found in JS cp45, or a recombinantly generated mutation, and which further incorporates one or more additional changes selected from, e.g., substitution or introduction of a heterologous gene or gene segment from a non-PIV source (e.g., an immunogenic RSV or measles gene or epitope, or a gene encoding a cytokine), a change in the order of viral genes to alter expression levels, removal of gene overlap, substitution of a PIV genome promoter with its antigenome counterpart, shortening, lengthening or removal of intergenic regions, e.g., to increase capacity for inserting foreign sequences, mutations in cis-acting signals to reduce or increase RNA replication or transcription, insertion of unique restriction sites, or deletion of even entire, non-essential genes, among other changes.

The instant invention also provides methods and compositions for the production and use of novel, chimeric parainfluenza viruses (PIVs) and associated vaccines. The chimeric viruses of the invention are infectious and immunogenic in humans and other mammals and are useful for generating immune responses against one or more PIVs, for example against one or more human PIVs (HPIVs). Alternatively, chimeric PIVs are provided that elicit an immune response against a selected PIV and one or more additional pathogens, for example against both a HPIV and measles virus. The immune response elicited can involve either or both humoral and/or cell mediated responses. Preferably, chimeric PIVs of the invention are attenuated to yield a desired balance of attenuation and immunogenicity for vaccine use.

The invention thus provides novel methods for designing and producing attenuated, chimeric PIVs that are useful as vaccine agents for preventing and/or treating infection and related disease symptoms attributable to PIV and other pathogens. In accordance with the methods of the invention, chimeric parainfluenza viruses or subviral particles are constructed using a PIV "vector" genome or antigenome that is recombinantly modified to incorporate one or more antigenic determinants of a heterologous pathogen. The vector genome or antigenome is comprised of a partial or complete PIV genome or antigenome, which may itself incorporate nucleotide modifications such as attenuating mutations. The vector genome or antigenome is modified to form a chimeric structure through incorporation of a heterologous gene or genome segment. More specifically, chimeric PIVs of the invention are constructed through a cDNA-based virus recovery system that yields recombinant viruses that incorporate a partial or complete vector or "background" PIV genome or antigenome combined with one or more "donor" nucleotide sequences encoding the heterologous antigenic determinant(s). Preferably the PIV vector comprises a HPIV genome or antigenome, although non-human PIVs, for example a bovine PIV (BPIV), can be employed as a vector to incorporate antigenic determinants of human PIVs and other human pathogens. In exemplary embodiments described herein, a human PIV3 (HPIV3) vector genome or antigenome is modified to incorporate one or more genes or genome segments that encode antigenic determinant(s) of one or more heterologous PIVs (e.g., HPIV1 and/or HPIV2), and/or a non-PIV pathogen (e.g., measles virus). Thus constructed, chimeric PIVs of the invention may elicit an immune response against a specific PIV, e.g., HPIV1, HPIV2, and/or HPIV3, or against a non-PIV pathogen. Alternatively, compositions and methods are provided for eliciting a polyspecific immune response against multiple PIVs, e.g., HPIV1 and HPIV3, or against one or more HPIVs and a non-PIV pathogen such as measles virus.

Exemplary chimeric PIV of the invention incorporate a chimeric PIV genome or antigenome as described above, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components. Additional PIV proteins may be included in various combinations to provide a range of infectious subviral particles, up to a complete viral particle or a viral particle containing supernumerary proteins, antigenic determinants or other additional components.

In preferred aspects of the invention, chimeric PIV incorporate a partial or complete human PIV vector genome or antigenome combined with one or more heterologous gene(s) or genome segment(s) from a second human PIV or a non-PIV pathogen such as measles virus. The PIV "vector" genome or antigenome typically acts as a recipient or carrier to which are added or incorporated one or more "donor" genes or genome segments of a heterologous pathogen. Typically, polynucleotides encoding one or more antigenic determinants of the heterologous pathogen are added to or substituted within the vector genome or antigenome to yield a chimeric PIV that thus acquires the ability to elicit an immune response in a selected host against the heterologous pathogen. In addition, the chimeric virus may exhibit other novel phenotypic characteristics compared to one or both of the vector PIV and heterologous pathogens.

The partial or complete vector genome or antigenome generally acts as a backbone into which heterologous genes or genome segments of a different pathogen are incorporated. Often, the heterologous pathogen is a different PIV from which one or more gene(s) or genome segment(s) is/are of are combined with, or substituted within, the vector genome or antigenome. In addition to providing novel immunogenic characteristics, the addition or substitution of heterologous genes or genome segments within the vector PIV strain may confer an increase or decrease in attenuation, growth changes, or other desired phenotypic changes as compared with the corresponding phenotype(s) of the unmodified vector and donor viruses. Heterologous genes and genome segments from other PIVs that may be selected as inserts or additions within chimeric PIV of the invention include genes or genome segments encoding the PIV N, P, C, D, V, M, F, HN and/or L protein(s) or one or more antigenic determinant(s) thereof.

Heterologous genes or genome segments of one PIV may be added as a supernumerary genomic element to a partial or complete genome or antigenome of a different PIV. Alternatively, one or more heterologous gene(s) or genome segment(s) of one PIV may be substituted at a position corresponding to a wild-type gene order position of a counterpart gene(s) or genome segment(s) that is deleted within the PIV vector genome or antigenome. In yet additional embodiments, the heterologous gene or genome segment is added or substituted at a position that is more promoter-proximal or promotor-distal compared to a wild-type gene order position of the counterpart gene or genome segment within the vector genome or antigenome to enhance or reduce, respectively, expression of the heterologous gene or genome segment.

The introduction of heterologous immunogenic proteins, protein domains and immunogenic epitopes to produce chimeric PIV is particularly useful to generate novel immune responses in an immunized host. Addition or substitution of an immunogenic gene or genome segment from one, donor pathogen within a recipient PIV vector genome or antigenome can generate an immune response directed against the donor pathogen, the PIV vector, or against both the donor pathogen and vector.

To achieve this purpose, chimeric PIV may be constructed that express a chimeric protein, for example an immunogenic glycoprotein having a cytoplasmic tail and/or transmembrane domain specific to a vector fused to a heterologous ectodomain of a different PIV or non-PIV pathogen to provide a fusion protein that elicits an immune response against the heterologous pathogen. For example, a heterologous genome segment encoding a glycoprotein ectodomain from a human PIV1 HN or F glycoprotein may be joined with a genome segment encoding the corresponding HPIV3 HN or F glycoprotein cytoplasmic and transmembrane domains to form a HPIV3-1 chimeric glycoprotein that elicits an immune response against HPIV1.

Briefly, PIV of the invention expressing a chimeric glycoprotein comprise a major nucleocapsid (N) protein, a nucleocapsid phosphoprotein (P), a large polymerase protein (L), and a HPIV vector genome or antigenome that is modified to encode a chimeric glycoprotein. The chimeric glycoprotein incorporates one or more heterologous antigenic domains, fragments, or epitopes of a second, antigenically distinct HPIV. Preferably, this is achieved by substitution within the HPIV vector genome or antigenome of one or more heterologous genome segments of the second HPIV that encode one or more antigenic domains, fragments, or epitopes, whereby the genome or antigenome encodes the chimeric glycoprotein that is antigenically distinct from the parent, vector virus.

In more detailed aspects, the heterologous genome segment or segments preferably encode a glycoprotein ectodomain or immunogenic portion or epitope thereof, and optionally include other portions of the heterologous or "donor" glycoprotein, for example both an ectodomain and transmembrane region that are substituted for counterpart glycoprotein ecto- and transmembrane domains in the vector genome or antigenome. Preferred chimeric glycoproteins in this context may be selected from HPIV HN and/or F glycoproteins, and the vector genome or antigenome may be modified to encode multiple chimeric glycoproteins. In preferred embodiments, the HPIV vector genome or antigenome is a partial HPIV3 genome or antigenome and the second, antigenically distinct HPIV is either HPIV1 or HPIV2. In one exemplary embodiment described below, both glycoprotein ectodomain(s) of HPIV2 HN and F glycoproteins are substituted for corresponding HN and F glycoprotein ectodomains in the HPIV3 vector genome or antigenome. In another exemplary embodiment, PIV2 ectodomain and transmembrane regions of one or both HN and/or F glycoproteins are fused to one or more corresponding PIV3 cytoplasmic tail region(s) to form the chimeric glycoprotein. Further details concerning these aspects of the invention are provided in United States patent application entitled CONSTRUCTION AND USE OF RECOMBINANT PARAINFLUENZA VIRUSES EXPRESSING A CHIMERIC GLYCOPROTEIN, filed on Dec. 10, 1999 by Tao et al. and identified by Attorney Docket No. 17634-000340, incorporated herein by reference.

To construct chimeric PIVs of the invention carrying a heterologous antigenic determinant of a non-PIV pathogen, a heterologous gene or genome segment of the donor pathogen may be added or substituted at any operable position in the vector genome or antigenome. In one embodiment, heterologous genes or genome segments from a non-PIV pathogen can be added (i.e., without substitution) within a PIV vector genome or antigenome to create novel immunogenic properties within the resultant clone. In these cases, the heterologous gene or genome segment may be added as a supernumerary gene or genome segment, optionally for the additional purpose of attenuating the resultant chimeric virus, in combination with a complete PIV vector genome or antigenome. Alternatively, the heterologous gene or genome segment may be added in conjunction with deletion of a selected gene or genome segment in the vector genome or antigenome.

In preferred embodiments of the invention, the heterologous gene or genome segment is added at an intergenic position within the partial or complete PIV vector genome or antigenome. Alternatively, the gene or genome segment can be inserted within other noncoding regions of the genome, for example, within 5' or 3' noncoding regions or in other positions where noncoding nucleotides occur within the vector genome or antigenome. In one aspect, the heterologous gene or genome segment is inserted at a non-coding site overlapping a cis-acting regulatory sequence within the vector genome or antigenome, e.g., within a sequence required for efficient replication, transcription, and/or translation. These regions of the vector genome or antigenome represent target sites for disruption or modification of regulatory functions associated with introduction of the heterologous gene or genome segment.

As used herein, the term "gene" generally refers to a portion of a subject genome, e.g., a PIV genome, encoding an mRNA and typically begins at the upstream end with a gene-start (GS) signal and ends at the downstream end with the gene-end (GE) signal. The term gene is also interchangeable with the term "translational open reading frame", or ORF, particularly in the case where a protein, such as the PIV C protein, is expressed from an additional ORF rather than from a unique mRNA. In the exemplary case of HPIV3, the genome is a single strand of negative-sense RNA 15462 nucleotides (nt) in length (Galinski et al., Virology 165: 499-510, (1988); Stokes et al., Virus Res. 25:91-103 (1992)). At least eight proteins are encoded by the HPIV3 genome: the nucleocapsid protein N, the phosphoprotein P, the C and D proteins of unknown functions, the matrix protein M, the fusion glycoprotein F, the hemagglutinin-neuraminidase glycoprotein HN, and the large polymerase protein L (Collins et al., 3rd ed. In "Fields Virology," B. N. Fields, D. M. Knipe, P. M. Howley, R. M. Chanock, J. L. Melnick, T. P. Monath, B. Roizman, and S. E. Straus, Eds., Vol. 1, pp. 1205-1243.

Lippincott-Raven Publishers, Philadelphia, 1996). The viral genome of all PIVs also contains extragenic leader and trailer regions, possessing all or part of the promoters required for viral replication and transcription, as well as non-coding and intergenic regions. Thus, the PIV genetic map is represented as 3' leader-N-P/C/D/V-M-F-HN-L-5' trailer. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination. Exemplary genome sequences have been described for the human PIV3 strains JS (GenBank accession number Z11575, incorporated herein by reference) and Washington (Galinski M. S. In Kingsbury, D. W. (Ed.), the Parayxoviruses, pp. 537-568, Plenum Press, New York, 1991, incorporated herein by reference), and for the bovine PIV3 strain 910N (GenBank accession number D80487, incorporated herein by reference).

To construct chimeric PIVs of the invention, one or more PIV gene(s) or genome segment(s) may be deleted, inserted or substituted in whole or in part. This means that partial or complete deletions, insertions and substitutions may include open reading frames and/or cis-acting regulatory sequences of any one or more of the PIV genes or genome segments. By "genome segment" is meant any length of continuous nucleotides from the PIV genome, which might be part of an ORF, a gene, or an extragenic region, or a combination thereof. When a subject genome segment encodes an antigenic determinant, the genome segment encodes at least one immunogenic epitope capable of eliciting a humoral or cell mediated immune response in a mammalian host. The genome segment may also encode an immunogenic fragment or protein domain. In other aspects, the donor genome segment may encode multiple immunogenic domains or epitopes, including recombinantly synthesized sequences that comprise multiple, repeating or different, immunogenic domains or epitopes.

Alternative chimeric PIV of the invention will contain protective antigenic determinants of HPIV1, HPIV2 and/or HPIV3. This is preferably achieved by expression of one or more HN and/or F genes or genome segments by the vector PIV, or as extra or substitute genes from the heterologous donor pathogen. In certain embodiments, a HPIV3-1 or HPIV3-2 chimeric virus may be constructed for use as a vaccine or vector strain, in which the HPIV1 or HPIV2 HN and/or F genes replace their PIV3 counterpart(s) (Skiadopoulos et al., Vaccine In press, 1999; Tao et al., Vaccine 17:1100-

1108, 1999; U.S. patent application Ser. No. 09/083,793, filed May 22, 1998, each incorporated herein by reference). In this context, a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., J Virol 72:1762-8, 1998; Tao et al., J Virol 72:2955-2961, 1998; Tao et al., Vaccine 17:1100-1108, 1999, incorporated herein by reference). rPIV3-1.cp45L is attenuated in hamsters and induced a high level of resistance to challenge with PIV1. A recombinant chimeric virus, designated rPIV3-1.cp45, has also been produced that contains 12 of the 15 cp45 mutations, i.e., excluding the mutations in HN and F, and is highly attenuated in the upper and lower respiratory tract of hamsters (Skiadopoulos et al., Vaccine 18:503-510, 1999, incorporated herein by reference).

In preferred embodiments of the invention, the chimeric PIV bear one or more major antigenic determinants of a human PIV, or against multiple human PIVs, including HPIV1, HPIV2 or HPIV3. These preferred vaccine candidates elicit an effective immune response in humans against one or more selected HPIVs. As noted above, the antigenic determinant(s) that elicit(s) an immune response against HPIV may be encoded by the vector genome or antigenome, or may be inserted within or joined to the PIV vector genome or antigenome as a heterologous gene or gene segment. The major protective antigens of human PIVs are their HN and F glycoproteins. However, all PIV genes are candidates for encoding antigenic determinants of interest, including internal protein genes which may encode such determinants as, for example, CTL epitopes.

Preferred chimeric PIV vaccine viruses of the invention bear one or more major antigenic determinants from each of a plurality of HPIVs or from a HPIV and a non-PIV pathogen. Chimeric PIV thus constructed include a partial or complete HPIV genome or antigenome, for example of HPIV3, and one or more heterologous gene(s) or genome segment(s) encoding antigenic determinant(s) of a heterologous PIV, for example HPIV1 or HPIV2. In alternative embodiments, one or more genes or genome segments encoding one or more antigenic determinants of HPIV1 or HPIV2 may be added to or substituted within a partial or complete HPIV3 genome or antigenome. In various exemplary embodiments described below, both HPIV1 genes encoding the HN and F glycoproteins are substituted for counterpart HPIV3 HN and F genes in a chimeric PIV vaccine candidate. These and other constructs yield chimeric PIVs that elicit either a mono- or poly-specific immune response in humans to one or more HPIVs.

In exemplary aspects of the invention, heterologous genes or genome segments encoding antigenic determinants from both HPIV1 and HPIV2 are added to or incorporated within a partial or complete HPIV3 vector genome or antigenome. For instance, one or more HPIV1 genes or genome segments encoding HN and/or F glycoproteins, or antigenic determinant(s) thereof, and one or more HPIV2 genes or genome segments encoding HN and/or F glycoproteins or antigenic determinants can be added to or incorporated within a partial or complete HPIV3 vector genome or antigenome. In one example described below, both HPIV1 genes encoding HN and F glycoproteins are substituted for counterpart HPIV3 HN and F genes to form a chimeric HPIV3-1 vector genome or antigenome. This vector construct can be further modified by addition or incorporation of one or more genes or gene segments encoding antigenic determinant(s) of HPIV2. Thus, specific constructs exemplifying the invention are provided which yield chimeric PIVs having antigenic determinants of both HPIV1 and HPIV2, as exemplified by the vaccine candidates rPIV3-1.2HN and rPIV3-1 cp45.2HN described herein below.

In other preferred aspects of the invention, chimeric PIV incorporate a HPIV vector genome or antigenome modified to express one or more major antigenic determinants of non-PIV pathogen, for example measles virus. The methods of the invention are generally adaptable for incorporation of antigenic determinants from a wide range of additional pathogens within chimeric PIV vaccine candidates. In this regard the invention also provides for development of vaccine candidates against subgroup A and subgroup B respiratory syncytial viruses (RSV), mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses, among other pathogens. In this regard, pathogens that may be targeted for vaccine development according to the methods of the invention include viral and bacterial pathogens, as well as protozoans and multicellular pathogens. Useful antigenic determinants from many important human pathogens in this context are known or readily identified for incorporation within chimeric PIV of the invention. Thus, major antigens have been identified for the foregoing exemplary pathogens, including the measles virus HA and F proteins; the F, G, SH and M2 proteins of RSV, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, flavivirus E and NS1 proteins, and alphavirus E. These major antigens, as well as other antigens known in the art for the enumerated pathogens and others, are well characterized to the extent that many of their antigenic determinants, including the full length proteins and their constituent antigenic domains, fragments and epitopes, are identified, mapped and characterized for their respective immunogenic activities.

Among the numerous, exemplary mapping studies that identify and characterize major antigens of diverse pathogens for use within the invention are epitope mapping studies directed to the hemagglutinin-neuraminidase (HN) gene of HPIV3. van Wyke Coelingh et al., J. Virol. 61 (5):1473-1477, 1987, incorporated herein by reference. This report provides detailed antigenic structural analyses for 16 antigenic variants of HPIV3 variants selected by using monoclonal antibodies (MAbs) to the HN protein which inhibit neuraminidase, hemagglutination, or both activities. Each variant possessed a single-point mutation in the HN gene, coding for a single amino acid substitution in the HN protein. Operational and topographic maps of the HN protein correlated well with the relative positions of the substitutions. Computer-assisted analysis of the HN protein predicted a secondary structure composed primarily of hydrophobic β sheets interconnected by random hydrophilic coil structures. The HN epitopes were located in predicted coil regions. Epitopes recognized by MAbs which inhibit neuraminidase activity of the virus were located in a region which appears to be structurally conserved among several paramyxovirus HN proteins and which may represent the sialic acid-binding site of the HN molecule.

This exemplary work, employing conventional antigenic mapping methods, identified single amino acids which are important for the integrity of HN epitopes. Most of these epitopes are located in the C-terminal half of the molecule, as expected for a protein anchored at its N terminus (Elango et al., J. Virol. 57:481-489, 1986). Previously published operational and topographic maps of the PIV3 HN indicated that the MAbs employed recognized six distinct groups of epitopes (I to VI) organized into two topographically separate sites (A and B), which are partially bridged by a third site (C). These groups of epitopes represent useful candidates for antigenic determinants that may be incorporated, alone or in various combinations, within chimeric PIVs of the invention. (See, also, Coelingh et al., Virology 143:569-582, 1985; Coelingh et al., Virology 162:137-143, 1988; Ray et al., Virology 148:232-236, 1986; Rydbeck et al., J. Gen. Virol. 67:1531-1542, 1986, each incorporated herein by reference).

Additional studies by van Wyke Coelingh et al., J. Virol. 63(1):375-382, 1989, provide further information relating to selection of PIV antigenic determinants for use within the invention. In this study, twenty-six monoclonal antibodies (MAbs) (14 neutralizing and 12 nonneutralizing) were used to examine the antigenic structure, biological properties, and natural variation of the fusion (F) glycoprotein of HPIV3. Analysis of laboratory-selected antigenic variants and of PIV3 clinical isolates indicated that the panel of MAbs recognizes at least 20 epitopes, 14 of which participate in neutralization. Competitive binding assays confirmed that the 14 neutralization epitopes are organized into three nonoverlapping principal antigenic regions (A, B, and C) and one bridge site (AB), and that the 6 nonneutralization epitopes form four sites (D, E, F, and G). Most of the neutralizing MAbs were involved in nonreciprocal competitive binding reactions, suggesting that they induce conformational changes in other neutralization epitopes.

Other antigenic determinants for use within the invention have been identified and characterized for respiratory syncytial virus (RSV). For example, Beeler et al., J. Virol. 63(7): 2941-2950, 1989, incorporated herein by reference, employed eighteen neutralizing monoclonal antibodies (MAbs) specific for the fusion glycoprotein of the A2 strain of RSV to construct a detailed topological and operational map of epitopes involved in RSV neutralization and fusion. Competitive binding assays identified three nonoverlapping antigenic regions (A, B, and C) and one bridge site (AB). Thirteen MAb-resistant mutants (MARMs) were selected, and the neutralization patterns of the MAbs with either MARMs or RSV clinical strains identified a minimum of 16 epitopes. MARMs selected with antibodies to six of the site A and AB epitopes displayed a small-plaque phenotype, which is consistent with an alteration in a biologically active region of the F molecule. Analysis of MARMs also indicated that these neutralization epitopes occupy topographically distinct but conformationally interdependent regions with unique biological and immunological properties. Antigenic variation in F epitopes was then examined by using 23 clinical isolates (18 subgroup A and 5 subgroup B) in cross-neutralization assays with the 18 anti-F MAbs. This analysis identified constant, variable, and hypervariable regions on the molecule and indicated that antigenic variation in the neutralization epitopes of the RSV F glycoprotein is the result of a noncumulative genetic heterogeneity. Of the 16 epitopes, 8 were conserved on all or all but 1 of 23 subgroup A or subgroup B clinical isolates. These antigenic determinants, including the full length proteins and their constituent antigenic domains, fragments and epitopes, all represent useful candidates for integration within chimeric PIV of the invention to elicit novel immune responses as described above. (See also, Anderson et al., J. Infect. Dis. 151:626-633, 1985; Coelingh et al., J. Virol. 63:375-382, 1989; Fenner et al., Scand. J. Immunol. 24:335-340, 1986; Fernie et al., Proc. Soc. Exp. Biol. Med. 171:266-271, 1982; Sato et al., J. Gen. Virol. 66:1397-1409, 1985; Walsh et al., J. Gen. Virol. 67:505-513, 1986, and Olmsted et al., J. Virol. 63(1):411-420, 1989, each incorporated herein by reference).

To express antigenic determinants of heterologous PIVs and non-PIV pathogens, the invention provides numerous human and non-human PIV vectors, including bovine PIV (BPIV) vectors. These vectors are readily modified according the recombinant methods described herein to carry heterologous antigenic determinants and elicit one or more specific humoral or cell mediated immune responses against the heterologous pathogen and vector PIV. In exemplary embodiments, one or more heterologous genes or genome segments from a donor pathogen is combined with a HPIV3 vector genome or antigenome. In other exemplary embodiments, the heterologous gene or genome segment is incorporated within a chimeric HPIV vector genome or antigenome, for example a chimeric HPIV3-1 vector genome or antigenome having one or both HPIV1 genes encoding the HN and F glycoproteins substituted for their counterpart HPIV3 HN and/or F gene(s). In more detailed embodiments, a transcription unit comprising an open reading frame (ORF) of the measles virus HA gene is added to a HPIV3 vector genome or antigenome at various positions, yielding exemplary chimeric PIV/measles vaccine candidates rPIV3(HA HN-L), rPIV3(HA N-P), rcp45L(HA N-P), rPIV3(HA P-M), or rcp45L(HA P-M). Alternatively, chimeric PIV for vaccine use may incorporate one or more antigenic determinants of HPIV2, for example an HPIV2 HN gene, within a chimeric HPIV3-1 vector genome or antigemome.

In other detailed embodiments of the invention, chimeric PIVs are engineered that incorporate heterologous nucleotide sequences encoding protective antigens from respiratory syncytial virus (RSV) to produce infectious, attenuated vaccine candidates. The cloning of RSV cDNA and other disclosure is provided in U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 (corresponding to International Publication No. WO 98/02530); U.S. patent application Ser. No. 09/291,894, filed on Apr. 13, 1999; U.S. Provisional Patent Application Ser. No. 60/129,006, filed on Apr. 13, 1999; Collins, et al., Proc Nat. Acad. Sci. USA 92:11563-11567, 1995; Bukreyev, et al., J Virol 70:6634-41, 1996, Juhasz et al., J. Virol. 71(8):5814-5819, 1997; Durbin et al., Virology 235: 323-332, 1997; He et al. Virology 237:249-260, 1997; Baron et al. J. Virol. 71:1265-1271, 1997; Whitehead et al., Virology 247(2):232-9, 1998a; Whitehead et al., J. Virol. 72(5):4467-4471, 1998b; Jin et al. Virology 251:206-214, 1998; and Whitehead et al., J. Virol. 73:(4)3438-3442, 1999, and Bukreyev, et al., Proc Nat Acad Sci USA 96:2367-72, 1999, each incorporated herein by reference in its entirety for all purposes). Other reports and discussion incorporated or set forth herein identify and characterize RSV antigenic determinants that are useful within the invention.

PIV chimeras incorporating one or more RSV antigenic determinants, preferably comprise a human PIV (e.g., HPIV1, HPIV2, HPIV3) vector genome or antigenome with a heterologous gene or genome segment encoding an antigenic RSV glycoprotein, protein domain (e.g., a glycoprotein ectodomain) or one or more immunogenic epitopes. In one embodiment, one or more genes or genome segments from RSV F and/or G genes is/are combined with the vector genome or antigenome to form the chimeric PIV vaccine candidate. Certain of these constructs will express chimeric proteins, for example fusion proteins having a cytoplasmic tail and/or transmembrane domain of PIV fused to an ectodomain of RSV to yield a novel attenuated virus that elicits a multivalent immune response against both PIV and RSV The present invention provides recombinant parainfluenza virus (PIV) cloned as a chimera of human and bovine PIV genomic or antigenomic sequences to yield a human-bovine chimeric PIV. The chimeric construction of human-bovine PIV yields a viral particle or subviral particle that is infectious in mammals, particularly humans, and useful for generating immunogenic compositions for clinical or veterinary use. Also provided within the invention are novel methods and compositions for designing and producing attenuated, human-bovine chimeric PIV, as well as methods and compositions for the prophylaxis and treatment of PIV infection.

Chimeric human-bovine PIV of the invention are recombinantly engineered to incorporate nucleotide sequences from both human and bovine PIV strains to produce an infectious, chimeric virus or subviral particle. In this manner, candidate vaccine viruses are recombinantly engineered to elicit an immune response against PIV in a mammalian host susceptible to PIV infection, including humans and non-human primates. Human-bovine chimeric PIV according to the invention may elicit an immune response to a specific PIV, e.g., HPIV3, or a polyspecific response against multiple PIVs, e.g., HPIV1 and HPIV3.

Exemplary human-bovine chimeric PIV of the invention incorporate a chimeric PIV genome or antigenome comprising both human and bovine polynucleotide sequences, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components.

Chimeric human-bovine PIV of the invention include a partial or complete "background" PIV genome or antigenome derived from or patterned after a human or bovine PIV strain or serotype virus combined with one or more heterologous gene(s) or genome segment(s) of a different PIV strain or serotype virus to form the human-bovine chimeric PIV genome or antigenome. In certain aspects of the invention, chimeric PIV incorporate a partial or complete human PIV (HPIV) background genome or antigenome combined with one or more heterologous gene(s) or genome segment(s) from a bovine PIV. In alternate aspects of the invention, chimeric PIV incorporate a partial or complete bovine PIV (BPIV) background genome or antigenome combined with one or more heterologous gene(s) or genome segment(s) from a human PIV.

The partial or complete background genome or antigenome typically acts as a recipient backbone or vector into which are imported heterologous genes or genome segments of the counterpart, human or bovine PIV. Heterologous genes or genome segments from the counterpart, human or bovine PIV represent "donor" genes or polynucleotides that are combined with, or substituted within, the background genome or antigenome to yield a human-bovine chimeric PIV that exhibits novel phenotypic characteristics compared to one or both of the contributing PIVs. For example, addition or substitution of heterologous genes or genome segments within a selected recipient PIV strain may result in an increase or decrease in attenuation, growth changes, altered immunogenicity, or other desired phenotypic changes as compared with a corresponding phenotype(s) of the unmodified recipient and/or donor. Genes and genome segments that may be selected for use as heterologous inserts or additions within human-bovine chimeric PIV of the invention include genes or genome segments encoding a PIV N, P, C, D, V, M, SH, where applicable, F, HN and/or L protein(s) or portion(s) thereof. Regulatory regions, such as the extragenic leader or trailer or intergenic regions, are also useful as heterologous inserts or additions.

The heterologous gene(s) or genome segment(s) may be added or substituted at a position corresponding to a wild-type gene order position of the counterpart gene(s) or genome segment(s) within the partial or complete PIV background genome or antigenome, which counterpart gene or genome segment is thereby replaced or displaced (e.g., to a more promotor-distal position). In yet additional embodiments, the heterologous gene or genome segment is added or substituted at a position that is more promoter-proximal or promotor-distal compared to a wild-type gene order position of the counterpart gene or genome segment within the background genome or antigenome, which enhances or reduces, respectively, expression of the heterologous gene or genome segment.

The introduction of heterologous immunogenic proteins, domains and epitopes to produce human-bovine chimeric PIV is particularly useful to generate novel immune responses in an immunized host. Addition or substitution of an immunogenic gene or genome segment from one, donor PIV within a recipient genome or antigenome of a different PIV can generate an immune response directed against the donor subgroup or strain, the recipient subgroup or strain, or against both the donor and recipient subgroup or strain. To achieve this purpose, human-bovine chimeric PIV may also be constructed that express a chimeric protein, e.g., an immunogenic glycoprotein having a cytoplasmic tail and/or transmembrane domain specific to one PIV fused to an ectodomain of a different PIV to provide, e.g., a human-bovine fusion protein, or a fusion protein incorporating domains from two different human PIVs. In a preferred embodiment, a human-bovine chimeric PIV genome or antigenome encodes a chimeric glycoprotein in the recombinant virus or subviral particle having both human and bovine glycoprotein domains or immunogenic epitopes. For example, a heterologous genome segment encoding a glycoprotein ectodomain from a human PIV HN or F glycoprotein may be joined with a polynucleotide sequence (i.e., a genome segment) encoding the corresponding bovine HN or F glycoprotein cytoplasmic and transmembrane domains to form the human-bovine chimeric PIV genome or antigenome.

In other embodiments, human-bovine chimeric PIV useful in a vaccine formulation can be conveniently modified to accommodate antigenic drift in circulating virus. Typically the modification will be in the HN and/or F proteins. This might involve the introduction of one or more point mutations; it might also involve an entire HN or F gene, or a genome segment encoding a particular immunogenic region thereof, from one PIV strain or group is incorporated into a chimeric PIV genome or antigenome cDNA by replacement of a corresponding region in a recipient clone of a different PIV strain or group, or by adding one or more copies of the gene, such that multiple antigenic forms are represented. Progeny virus produced from the modified PIV clone can then be used in vaccination protocols against emerging PIV strains.

Replacement of a human PIV coding sequence or non-coding sequence (e.g., a promoter, gene-end, gene-start, intergenic or other cis-acting element) with a heterologous counterpart yields chimeric PIV having a variety of possible attenuating and other phenotypic effects. In particular, host range and other desired effects arise from substituting a bovine or murine PIV (MPIV) protein, protein domain, gene or genome segment imported within a human PIV background, wherein the bovine or murine gene does not function efficiently in a human cell, e.g., from incompatibility of the heterologous sequence or protein with a biologically interactive human PIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into human PIV based on known aspects of bovine and human PIV structure and function.

HPIV3 is a member of the Respirovirus genus of the Paramyxoviridae family in the order Mononegavirales (Collins et al., 1996, supra). HPIV3 is the best characterized of the HPIVs and represents the prototype HPIV. Its genome is a single strand of negative-sense RNA 15462 nucleotides (nt) in length (Galinski et al., Virology 165:499-510, 1988; and Stokes et al., Virus Res. 25:91-103, 1992; each incorporated herein by reference). At least eight proteins are encoded by the PIV3 genome: the nucleocapsid protein N, the phosphoprotein P, the C and D proteins of unknown functions, the matrix protein M, the fusion glycoprotein F, the hemagglutinin-neuraminidase glycoprotein HN, and the large polymerase protein L (Collins et al., 1996, supra). A protein containing the V ORF in the P gene might also be produced (Durbin et al., Virology 261:319-333, 1999)

The M, HN, and F proteins are envelope-associated, and the latter two are surface glycoproteins which, as is the case with each PIV, are the major neutralization and protective antigens (Collins et al., 1996, supra). The significant sequence divergence between comparable PIV HN or F proteins among the PIVs is thought to be the basis for the type specificity of the protective immunity (Collins et al., 1996, supra; Cook et al., Amer. Jour. Hyg. 77:150-159, 1963; Ray et al., J. Infect. Dis. 162:746-749, 1990; each incorporated herein by reference).

The HPIV3 genes are each transcribed as a single mRNA that encodes a single protein, with the exception of the P mRNA which contains four ORFs, namely P, C, D and V (Galinski et al., Virology 186:543-550, 1992; and Spriggs et al., J. Gen. Virol. 67:2705-2719, 1986; each incorporated herein by reference). The P and C proteins are translated from separate, overlapping ORFs in the mRNA. Whereas all paramyxoviruses encode a P protein, only members of the genus Respirovirus and Morbillivirus encode a C protein. Individual viruses vary in the number of proteins expressed from the C ORF and in its importance in replication of the virus in vitro and in vivo. Sendai virus (SeV) expresses four independently initiated proteins from the C ORF: C', C, Y1, and Y2, whose translational start sites appear in that order in the mRNA (Curran, et al., Enzyme 44:244-249, 1990; Lamb et al., in The Paramyxoviruses, D. Kingsbury, ed., pp. 181-214, Plenum Press, New York, 1991; incorporated herein by reference), whereas HPIV3 and measles virus (MeV) express only a single C protein (Bellini et al., J. Virol. 53:908-919, 1985; Sanchez et al., Virology 147:177-86, 1985; and Spriggs et al., 1986, supra; each incorporated herein by reference).

The PIV3 D protein is a fusion protein of the P and D ORFs, and is expressed from the P gene by the process of co-transcriptional RNA editing in which two nontemplated G residues are added to the P mRNA at the RNA editing site (Galinski et al., 1992, supra; and Pelet et al., EMBO J. 10:443-448, 1991; each incorporated herein by reference). BPIV3, the only other paramyxovirus which expresses a D protein, uses RNA editing to express this protein as well as a second protein, the V protein.

Nearly all members of the genera Respirovirus, Rubulavirus, and Morbillivirus express a V protein. The one member which clearly does not is HPIV1, which lacks an intact V ORF (Matsuoka et al., J. Virol. 65:3406-3410, 1991, incorporated herein by reference). The V ORF is characterized by the presence of a cysteine-rich domain that is highly conserved (Cattaneo et al., Cell 56:759-764, 1989; Park et al., J. Virol. 66:7033-7039, 1992; Thomas et al., Cell 54:891-902, 1988; and Vidal et al., J. Virol. 64:239-246, 1990; each incorporated herein by reference). The V ORF is maintained in each of the HPIV3 viruses sequenced to date suggesting that this ORF is expressed and retains function for this virus (Galinski et al., Virology 155:46-60, 1986; Spriggs et al., 1986, supra; and Stokes et al., 1992, supra; incorporated herein by reference).

The BPIV3 V protein is expressed when one nontemplated G residue is added at the RNA editing site (Pelet et al., 1991, supra; incorporated herein by reference). However, in the case of HPIV3, two translation stop codons lie between the editing site and the V ORF, and it is not clear whether HPIV3 represents another example in which this ORF is not expressed, or whether it is expressed by some other mechanism. One possibility is that HPIV3 editing also occurs at a second, downstream site in the P gene, although this did not appear to occur in cell culture (Galinski et al., 1992, supra). Alternatively, it might be that ribosomes gain access to the V ORF by ribosomal frameshifting. This would be comparable to the situation with the P locus of MV. MV expresses C, P, and V proteins, but also expresses a novel R protein which is synthesized by frameshifting from the P ORF to the V ORF (Liston et al., J. Virol. 69:6742-6750, 1995, incorporated herein by reference). Genetic evidence suggests that the V ORF of HPIV3 is functional (Durbin et al., 1999, supra).

Although the means by which HPIV3 expresses its V protein is unclear, the extreme conservation of the its V ORF in different strains suggests that it is indeed expressed. The function of the V protein is not well defined, but V-minus MV and SeV recombinants have been recovered that replicate efficiently in vitro but exhibit reduced replication in vivo (Delenda, et al., Virology 228:55-62, 1997; Delenda et al., Virology 242:327-337, 1998; Kato et al., 1997a, supra; Kato et al., J. Virol. 71:7266-7272, 1997b; and Valsamakis et al., J. Virol. 72:7754-7761, 1998; each incorporated herein by reference).

The viral genome of PIV also contains extragenic leader and trailer regions, possessing all or part of the promoters required for viral replication and transcription, as well as non-coding and intergenic regions. Thus, the PIV genetic map is represented as 3' leader-N-P/C/D/V-M-F-HN-L-5' trailer. Some viruses, such as simian virus 5 and mumps virus, have a gene located between F and HN that encodes a small hydrophobic (SH) protein of unknown function. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination. Exemplary sequences have been described for the human PIV3 strains JS (GenBank accession number Z11575, incorporated herein by reference) and Washington (Galinski M. S., in The Paramyxoviruses, Kingsbury, D. W., ed., pp. 537-568, Plenum Press, New York, 1991, incorporated herein by reference), and for the bovine PIV3 strain 910N (GenBank accession number D80487, incorporated herein by reference).

As used herein, "PIV gene" generally refers to a portion of the PIV genome encoding an mRNA and typically begins at the upstream end with a gene-start (GS) signal and ends at the downstream end with the gene-end (GE) signal. The term PIV gene also includes what is described as "translational open reading frame", or ORF, particularly in the case where a protein, such as C, is expressed from an additional ORF rather than from a unique mRNA. To construct human-bovine chimeric PIV of the invention, one or more PIV gene(s) or genome segment(s) may be deleted, inserted or substituted in whole or in part. This means that partial or complete deletions, insertions and substitutions may include open reading frames and/or cis-acting regulatory sequences of any one or more of the PIV genes or genome segments. By "genome segment" is meant any length of continuous nucleotides from the PIV genome, which might be part of an ORF, a gene, or an extragenic region, or a combination thereof.

The instant invention involves a method for developing live attenuated PIV vaccine candidates based on chimeras between HPIVs and BPIV3. Chimeras are constructed through a cDNA-based virus recovery system. Recombinant viruses made from cDNA replicate independently and are propagated in the same manner as if they were biologically-derived viruses. Preferred human-bovine chimeric PIV vaccine candidates of the invention bear one or more of the major antigenic determinants of one or more human PIV(s), e.g., HPIV1, HPIV2, and/or HPIV3, in a background which is attenuated by the substitution or addition of one or more BPIV genes or genome segments. The major protective antigens of PIVs are their HN and F glycoproteins, although other proteins can also contribute to a protective immune response.

Thus, the invention provides a new basis for attenuating a wild type or mutant parental virus for use as a vaccine against PIV, one which is based on host range effects due to the introduction of one or more gene(s) or genome segment(s) between HPIV and BPIV. There are numerous nucleotide and amino acid sequence differences between BPIV and HPIV, which are reflected in host range differences. For example, between HPIV3 and BPIV3 the percent amino acid identity for each of the following proteins is: N (86%), P (65%), M (93%), F (83%), HN (77%), and L (91%). The host range difference is exemplified by the highly permissive growth of HPIV3 in rhesus monkeys, compared to the restricted replication of two different strains of BPIV3 in the same animal (van Wyke Coelingh et al., 1988, supra). Although the basis of the host range differences between HPIV3 and BPIV3 remains to be determined, it is likely that they will involve more than one gene and multiple amino acid differences. The involvement of multiple genes and possibly cis-acting regulatory sequences, each involving multiple amino acid or nucleotide differences, gives a very broad basis for attenuation, one which cannot readily be altered by reversion. This is in contrast to the situation with other live attenuated HPIV3 viruses which are attenuated by one or several point mutations. In this case, reversion of any individual mutation may yield a significant reacquisition of virulence or, in a case where only a single residue specified attenuation, complete reacquisition of virulence.

In exemplary embodiments of the invention described hereinbelow, the background genome or antigenome is an HPIV3 genome or antigenome, and the heterologous gene or genome segment is a N ORF derived from, alternatively, a Ka or SF strain of BPIV3 (which are 99% related in amino acid sequence). The N ORF of the HPIV3 background antigenome is substituted by the counterpart BPIV3 N ORF yielding a novel recombinant human-bovine chimeric PIV cDNA clone. Replacement of the HPIV3 N ORF of HPIV3 with that of BPIV3 Ka or SF results in a protein with approximately 70 amino acid differences (depending on the strain involved) from that of HPIV3 N. N is one of the more conserved proteins, and substitution of other proteins such as P, singly or in combination, would result in many more amino acid differences. The involvement of multiple genes and genome segments each conferring multiple amino acid or nucleotide differences provides a broad basis for attenuation which is highly stable to reversion.

This mode of attenuation contrasts sharply to current HPIV vaccine candidates that are attenuated by one or more point mutations, where reversion of an individual mutation may yield a significant or complete reacquisition of virulence. In addition, several known attenuating point mutations in HPIV typically yield a temperature sensitive phenotype. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media, whereas overattenuation in the lower respiratory tract can reduce immunogenicity. Thus, attenuation achieved solely by temperature sensitive mutations may not be ideal. In contrast, host range mutations present in human-bovine chimeric PIV of the invention will not in most cases confer temperature sensitivity. Therefore, the novel method of PIV attenuation provided by the invention will be more stable genetically and phenotypically and less likely to be associated with residual virulence in the upper respiratory tract compared to other known PIV vaccine candidates.

Surprisingly, both the Ka and SF HPIV3/BPIV3 chimeric recombinants involving the N ORF replacement were viable. Since the N protein of Ka or SF strain BPIV3 differs in 70 of 515 amino acid residues, respectively, from that of the JS strain of HPIV3. It was therefore unexpected that a bovine N protein with this level of amino acid sequence divergence could efficiently interact with the HPIV3 RNA, or with other HPIV3 proteins that constitute the functional replicase/transcriptase. Equally surprising was the finding that the Ka and SF chimeric viruses replicated as efficiently in cell culture as either HPIV3 or BPIV3 parent indicating that the chimeric recombinants did not exhibit gene incompatibilities that restricted replication in vitro. This property of efficient replication in vitro is important since it permits efficient manufacture of this biological.

Also surprising is the observation, based on the studies hereinbelow, that the Ka and the SF HPIV3/BPIV3 chimeric recombinants (termed cKa and cSF), bearing only one bovine gene, are nearly equivalent to their BPIV3 parents in the degree of host range restriction in the respiratory tract of the rhesus monkey. In particular, the cKa and cSF viruses exhibited approximately a 60-fold or 30-fold reduction, respectively, in replication in the upper respiratory tract of rhesus monkeys compared to replication of HPIV3. Based on this finding, it is possible that other BPIV3 genes will also confer desired levels of host range restriction within human-bovine chimeric PIV of the invention. Thus, according to the methods herein, a list of attenuating determinants will be readily identified in heterologous genes and genome segments of both HPIV and BPIV that will confer, in appropriate combination, an optimal level of host range restriction and immunogenicity on human-bovine chimeric PIV selected for vaccine use. In preferred vaccine recombinants, attenuation marked by replication in the lower and/or upper respiratory tract in an accepted animal model for PIV replication in humans, e.g., hamsters or rhesus monkeys, may be reduced by at least about two-fold, more often about 5-fold, 10-fold, or 20-fold, and preferably 50-100-fold and up to 1,000-fold or greater overall (e.g., as measured between 3-8 days following infection) compared to growth of the corresponding wild-type or mutant parental PIV strain.

Confirming the unexpected nature and advantages provided by the human-bovine chimeric PIV of the invention, both the cKa and cSF induced a high level of protection against HPIV3 challenge in the respiratory tract of rhesus monkeys, despite the exceptional degree of restriction of replication exhibited by these viruses in this model for human PIV infection and protection. In particular, previous infection with either chimeric virus induced a high level of resistance to replication of the rJS challenge virus in both the upper and lower respiratory tract. Infection of monkeys with cKa elicited a high degree of protection as indicated by an approximate 300-fold reduction of replication of wild type HPIV3 (rJS) in the upper respiratory tract, and an approximate 1000-fold reduction in the lower tract compared to uninoculated control monkeys. Monkeys infected with cSF manifested a 2000-fold reduction of replication of rJS in the upper respiratory tract, and a 1000-fold reduction in the lower tract compared to uninoculated control monkeys. The levels of protection elicited by cKa or cSF were comparable to those seen in monkeys previously infected with either the bovine or the human PIV parent. Thus, infection with human-bovine chimeric PIV of the invention provides a high level of protection in the upper and lower respiratory tract of monkeys, and both chimeric viruses represent promising vaccine candidates. In other preferred vaccine recombinants, the immunogenic activity of human-bovine chimeric PIV will be balanced against the level of attenuation to achieve useful vaccine candidates, and will typically be marked by a reduction of replication of challenge virus, e.g., rJS in the lower and/or upper respiratory tract by about 50-100-fold, 100-500-fold, preferably about 500-2,000-fold and up to 3,000-fold or greater overall (e.g., as measured between 3-8 days post-challenge). Thus, the recombinant vaccine viruses of the invention maintain immunogenicity while exhibiting concomitant reductions in replication and growth. This surprising assemblage of phenotypic traits is highly desired for vaccine development.

The observation that the N gene from two independent strains of BPIV3 confers an attenuation phenotype on HPIV3 for the rhesus monkey indicates that this is likely a property shared by N genes of other BPIV strains. Accordingly, within the methods of the invention any BPIV gene or genome segment, singly or in combination with one or more other BPIV gene(s) or genome segment(s), can be combined with HPIV sequences to produce an attenuated HPIV3/BPIV3 chimeric recombinant virus suitable for use as a vaccine virus. In preferred embodiments, all HPIVs, including HPIV1, HPIV2, HPIV3 and variant strains thereof, are useful recipients for attenuating BPIV gene(s) and/or genome segment(s). In general, the HPIV genes selected for inclusion in a HPIV3/BPIV3 chimeric virus will include one or more of the protective antigens, such as the HN or F glycoproteins.

Alternative human-bovine chimeric PIV of the invention will contain protective antigenic determinants of HPIVI or HPIV2. This may be achieved, for example, by expression of an HN and/or F gene of HPIV1 or HPIV2 as an extra gene(s) in an attenuated HPIV3/BPIV3 chimeric recombinant. Alternatively, it is possible to use a HPIV3/HPIV1 or a HPIV3/HPIV2 antigenic chimeric virus, in which the HPIV1 or HPIV2 HN and/or F genes replace their PIV3 counterpart(s) (Skiadopoulos et al., 1999a, supra; Tao et al., 1999, supra; and U.S. patent application Ser. No. 09/083,793, filed May 22, 1998; each incorporated herein by reference), as a recipient or background virus for one or more heterologous, attenuating bovine gene(s) or genome segment(s), for example a Ka or SF N gene or genome segment. Such antigenic chimeric viruses will be attenuated by the bovine N gene, but will induce immunity to the HPIVI or HPIV2 virus. In this context, a chimeric PIVI vaccine candidate has been generated using the PIV3 cDNA rescue system by replacing the PIV3 HN and F open reading frames (ORFs) with those of PIVI in a PIV3 full-length cDNA that contains the three attenuating mutations in L. The recombinant chimeric virus derived from this cDNA is designated rPIV3-1.cp45L (Skiadopoulos et al., 1998, supra; Tao et al., 1998, supra; Tao et al., 1999, supra). rPIV3-1.cp45L was attenuated in hamsters and induced a high level of resistance to challenge with PIV1. A recombinant chimeric virus, designated rPIV3-1 cp45, has also been produced that contains 12 of the 15 cp45 mutations, i.e., excluding the mutations in HN and F, and is highly attenuated in the upper and lower respiratory tract of hamsters (Skiadopoulos et al., 1999a, supra).

Still other HPIV/BPIV chimeric recombinants will incorporate two or more BPIV genes or genome segments, in any combination, up to and including all of the BPIV genome other than selected genes or antigenic determinants selected from HN or F gene(s) and genome segment(s), which could come from a human HPIV1, HPIV2, or HPIV3 virus. Yet additional embodiments of the invention are directed to human-bovine chimeric PIV incorporating attenuating genes from other animal PIVs, such as murine PIV1, the canine SV5 PIV2 virus, or another avian or mammalian PIV in combination with a HPIV backbone, alternatively including a chimeric HPIV backbone, from HPIV1, HPIV2, and/or HPIV3.

In other detailed aspects of the invention, human-bovine chimeric PIV are employed as vectors for protective antigens of heterologous pathogens, including other PIVs and non-PIV viruses and non-viral pathogens. Within these aspects, the bovine-human chimeric genome or antigenome comprises a partial or complete PIV "vector genome or antigenome" combined with one or more heterologous genes or genome segments encoding one or more antigenic determinants of one or more heterologous pathogens (see, e.g., U.S. Provisional Patent Application Ser. No. 60/170,195, filed Dec. 10, 1999 by Murphy et al., incorporated herein by reference). The heterologous pathogen in this context may be a heterologous PIV and the heterologous gene(s) or genome segment(s) can be selected to encodes one or more PIV N, P, C, D, V, M, F, SH (where applicable), HN and/or L protein(s), as well as protein domains, fragments, and immunogenic regions or epitopes. PIV vector vaccines thus constructed may elicit a polyspecific immune response and may be administered simultaneously or in a coordinate administration protocol with other vaccine agents.

In exemplary embodiments of the invention, human-bovine chimeric PIV may comprise a vector genome or antigenome that is a partial or complete HPIV genome or antigenome, which is combined with or is modified to incorporate one or more heterologous genes or genome segments encoding antigenic determinant(s) of one or more heterologous PIV(s), including heterologous HPIVs selected from HPIV1, HPIV2, or HPIV3. In more detailed aspects, the vector genome or antigenome is a partial or complete HPIV3 genome or antigenome and the heterologous gene(s) or genome segment(s) encoding the antigenic determinant(s) is/are of one or more heterologous HPIV(s). Typically, the chimeric genome or antigenome incorporates one or more gene(s) or genome segment(s) of a BPIV that specifies attenuation.

In exemplary aspects of the invention, the bovine-human chimeric PIV incorporates one or more HPIV1 or HPIV2 genes or genome segments that encode(s) one or more HN and/or F glycoproteins or antigenic domains, fragments or epitopes thereof within a partial or complete HPIV3 vector genome or antigenome. In more detailed aspects, both HPIV1 genes encoding HN and F glycoproteins are substituted for counterpart HPIV3 HN and F genes to form a chimeric HPIV3-1 vector genome or antigenome. Such recombinant constructs can be used to produce vaccine virus directly, or can be further modified by addition or incorporation of one or more genes or gene segments encoding one or more antigenic determinants. Such constructs for the production of vaccine viruses typically incorporate one or more heterologous gene(s) or genome segment(s) of a BPIV that specifies attenuation, for example an open reading frame (ORF) encoding an attenuating BPIV protein, such as N. Certain human-bovine chimeric PIV of the invention may be employed as vectors for generating specific vaccines to HPIV2, for example wherein a transcription unit comprising an open reading frame (ORF) of an HPIV2 HN gene is added to or incorporated within a chimeric HPIV3-1 vector genome or antigenome and the chimeric construct is attenuated by incorporation of a BPIV gene or genome segment.

Within related aspects of the invention, the vector genome or antigenome is a partial or complete BPIV genome or antigenome, and the heterologous genes or genome segments encoding the antigenic determinant(s) is/are of one or more HPIV(s). Typically, the determinant(s) is/are selected from HPIV1, HPIV2 or HPIV3 HN and F glycoproteins, but antigenic domains, fragments and epitopes of these and other antigenic proteins are also useful. In certain embodiments, one or more genes or genome segments encoding one or more antigenic determinant(s) of HPIV2 is/are added to or substituted within the partial or complete BPIV vector genome or antigenome. Alternatively, a plurality of heterologous genes or genome segments encoding antigenic determinants of multiple HPIVs may be added to or incorporated within the partial or complete BPIV vector genome or antigenome.

In yet additional aspects of the invention, human-bovine chimeric PIV are provided as vectors for a range of non-PIV pathogens (see, e.g., U.S. Provisional Patent Application Ser. No. 60/170,195, filed Dec. 10, 1999 by Murphy et al., incorporated herein by reference). The vector genome or antigenome for use within these aspects of the invention may comprise a partial or complete BPIV or HPIV genome or antigenome, and the heterologous pathogen may be selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses.

For example, a HPIV or BPIV vector genome or antigenome for constructing bovine-human chimeric PIV of the invention may incorporate heterologous antigenic determinant(s) selected from the measles virus HA and F proteins, or antigenic domains, fragments and epitopes thereof. In exemplary embodiments, a transcription unit comprising an open reading frame (ORF) of a measles virus HA gene is added to or incorporated within a BPIV or HPIV3 vector genome or antigenome.

Alternatively bovine-human chimeric PIV of the invention may used as vectors to incorporate heterologous antigenic determinant(s) from respiratory syncytial virus (RSV), for example by incorporating one or more genes or genome segments that encode(s) RSV F and/or G glycoprotein or immunogenic domain(s) or epitope(s) thereof. In this context, the cloning of RSV cDNA and other disclosure is provided in U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 (corresponding to International Publication No. WO 98/02530); U.S. patent application Ser. No. 09/291,894, filed on Apr. 13, 1999; U.S. Provisional Patent Application Ser. No. 60/129,006, filed on Apr. 13, 1999; Collins, et al., 1995, supra; Bukreyev, et al., J. Virol. 70:6634-6641, 1996; Juhasz et al., 1997, supra; Durbin et al., 1997a, supra; He et al., 1997, supra; Baron et al., 1997, supra; Whitehead et al., 1998a, supra; Whitehead et al., 1998b, supra; Jin et al., 1998, supra; and Whitehead et al., 1999, supra; and Bukreyev et al., Proc. Natl. Acad. Sci. USA 96:2367-2372, 1999, each incorporated herein by reference in its entirety for all purposes).

According to this aspect of the invention, human-bovine chimeric PIV are provided which incorporate at least one antigenic determinant from a heterologous PIV or non-PIV pathogen. For example, one or more individual gene(s) or genome segment(s) of HPIV3 may be replaced with counterpart gene(s) or genome segment(s) from human RSV, or an RSV gene or genome segment can be inserted or added as an supernumerary gene. Alternatively, a selected, heterologous genome segment, e.g. encoding a cytoplasmic tail, transmembrane domain or ectodomain of an RSV glycoprotein, is substituted for a counterpart genome segment in, e.g., the same gene in HPIV3 or within a different gene in HPIV3, or added within a non-coding sequence of the HPIV3 genome or antigenome to yield a chimeric PIV-RSV glycoprotein. In one embodiment, a genome segment from an F gene of human RSV is substituted for a counterpart HPIV3 genome segment to yield constructs encoding chimeric proteins, e.g. fusion proteins having a cytoplasmic tail and/or transmembrane domain of PIV fused to an ectodomain of RSV to yield a novel attenuated virus, and/or a multivalent vaccine immunogenic against both PIV and RSV.

As noted above, it is often desirable to adjust the attenuation phenotype of chimeric PIV for vaccine use by introducing additional mutations that increase or decrease attenuation or otherwise alter the phenotype of the chimeric virus. Detailed descriptions of the materials and methods for producing recombinant PIV from cDNA, and for making and testing various mutations and nucleotide modifications set forth herein as supplemental aspects of the present invention are provided in, e.g., Durbin et al., Virology 235:323-332, 1997; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference. In particular, these documents describe methods and procedures for mutagenizing, isolating and characterizing PIV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human PIV in accepted model systems, including murine and non-human primate model systems. In addition, these documents describe general methods for developing and testing immunogenic compositions, including monovalent and bivalent vaccines, for prophylaxis and treatment of PIV infection. Methods for producing infectious recombinant PIV by construction and expression of cDNA encoding a PIV genome or antigenome coexpressed with essential PIV proteins are also described in the above-incorporated documents, which include description of the following exemplary plasmids that may be employed to produce infectious PIV clones: p3/7 (131) (ATCC 97990); p3/7(131)2G (ATCC 97889); and p218 (131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

Also disclosed in the above-incorporated references are methods for constructing and evaluating infectious recombinant PIV that are modified to incorporate phenotype-specific mutations identified in biologically-derived PIV mutants, e.g., cold passaged (cp), cold adapted (ca), host range restricted (hr), small plaque (sp), and/or temperature sensitive (ts) mutants, for example the JS HPIV3 cp 45 mutant strain. Mutations identified in these mutants can be readily incorporated into chimeric PIV of the instant invention. In exemplary embodiments, one or more attenuating mutations occur in the polymerase L protein, e.g., at a position corresponding to Tyr942, Leu992, or Thr1558 of JS cp45. Preferably, these mutations are incorporated in chimeric PIV of the invention by an identical, or conservative, amino acid substitution as identified in the biological mutant. In more detailed aspects, chimeric PIV for vaccine use incorporate one or more mutation wherein Tyr942 is replaced by His, Leu992 is replaced by Phe, and/or Thr1558 is replaced by Ile. Substitutions that are conservative to these replacement amino acids are also useful to achieve desired attenuation in chimeric vaccine candidates.

Other exemplary mutations that can be adopted in chimeric PIVs from biologically derived PIV mutants include one or more mutations in the N protein, including specific mutations at a position corresponding to residues Val96 or Ser389 of JS cp45. In more detailed aspects, these mutations are represented as Val96 to Ala or Ser389 to Ala or substitutions that are conservative thereto. Also useful within chimeric PIV of the invention are amino acid substitution in the C protein, e.g., a mutation at a position corresponding to Ile96 of JS cp45, preferably represented by an identical or conservative substitution of Ile96 to Thr. Further exemplary mutations that can be adopted from biologically derived PIV mutants include mutation in the M gene such as Pro199 in JS cp45, one or more mutations in the F protein, including mutations adopted from JS cp45 at a position corresponding to residues Ile420 or Ala450 of JS cp45, preferably represented by acid substitutions Ile420 to Val or Ala450 to Thr or substitutions conservative thereto. Alternatively or in addition, chimeric PIV of the invention can adopt one or more amino acid substitutions in the HN protein, as exemplified by a mutation at a position corresponding to residue Val384 of JS cp45, preferably represented by the substitution Val384 to Ala.

Yet additional embodiments of the invention include chimeric PIV which incorporate one or more mutations in non-coding portions of the PIV genome or antigenome, for example in a 3' leader sequence, that specify desired phenotypic changes such as attenuation. Exemplary mutations in this context may be engineered at a position in the 3' leader of the chimeric virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45. In more detailed aspects, chimeric PIV incorporate a T to C change at nucleotide 23, a C to T change at nucleotide 24, a G to T change at nucleotide 28, and/or a T to A change at nucleotide 45. Additional mutations in extragenic sequences are exemplified by a A to T change in the N gene start sequence at a position corresponding to nucleotide 62 of JS.

These foregoing exemplary mutations which can be engineered in a chimeric PIV of the invention have been successfully engineered and recovered in recombinant PIV□as represented by the recombinant PIV clones designated rcp45, rcp45 L, rcp45 F, rcp45 M, rcp45 HN, rcp45 C, rcp45 F, rcp45 3'N, rcp3'NL, and rcp45 3'NCMFHN (Durbin et al., Virology 235:323-332, 1997; Skiadopolos et al., J. Virol. 72:1762-1768 (1998); Skiadopolos et al., J. Virol. 73:1374-1381, 1999; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45. It has since been shown that all of the cp45 mutations outside of the heterologous (HPIV1) HN and F genes can be incorporated in a HPIV3-1 recombinant to yield an attenuated, chimeric vaccine candidate.

From JS cp45 and other biologically derived PIV mutants, a large "menu" of attenuating mutations is provided, each of which can be combined with any other mutation(s) for adjusting the level of attenuation, immunogenicity and genetic stability in a recombinant PIV bearing C, D, and/or V deletion or knock out mutation(s). In this context, many recombinant PIVs of the invention will include one or more, and preferably two or more, mutations from biologically derived PIV mutants, e.g., any one or combination of mutations identified in JS cp45. Preferred PIV recombinants within the invention will incorporate a plurality and up to a full complement of the mutations present in JS cp45 or other biologically derived mutant PIV strains. Preferably, these mutations are stabilized against reversion in chimeric PIV by multiple nucleotide substitutions in a codon specifying each mutation.

Yet additional mutations that may be incorporated in chimeric PIV of the invention are mutations, e.g., attenuating mutations, identified in heterologous PIV or more distantly related nonsegmented negative stranded RNA viruses. In particular, attenuating and other desired mutations identified in one negative stranded RNA virus may be "transferred", e.g., introduced by mutagenesis in a corresponding position within the genome or antigenome of a chimeric PIV. Briefly, desired mutations in one heterologous negative stranded RNA virus are transferred to the chimeric PIV recipient (either in the vector genome or antigenome or in the heterologous donor gene or genome segment). This involves mapping the mutation in the heterologous mutant virus identifying by routine sequence alignment the corresponding site in the recipient PIV, and mutating the native sequence in the PIV recipient to the mutant genotype (either by an identical or conservative mutation), as described in U.S. Provisional Patent Application Ser. No. 60/129,006, filed on Apr. 13, 1999, incorporated herein by reference. As this disclosure teaches, it is preferable to modify the recipient chimeric PIV genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution can be engineered at the corresponding residue(s) in the recombinant virus. Preferably the substitution will specify an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue).

Negative stranded RNA viruses from which exemplary mutations are identified and transferred into a recombinant PIV of the invention include other PIVs (e.g., HPIV1, HPIV2, HPIV3, HPIV4A, HPIV4B and BPIV3, MPIV), RSV, Sendai virus (SeV), Newcastle disease virus (NDV), simian virus 5 (SV5), measles virus (MeV), rinderpest virus, canine distemper virus (CDV), rabies virus (RaV) and vesicular stomatitis virus (VSV), among others.

A variety of exemplary mutations are disclosed, including but not limited to an amino acid substitution of phenylalanine at position 521 of the RSV L protein corresponding to and therefore transferable to a substitution of phenylalanine (or a conservatively related amino acid) at position 456 of the HPIV3 L protein. In the case of mutations marked by deletions or insertions, these can be introduced as corresponding deletions or insertions into the recombinant virus, either within the background genome or antigenome or within the heterologous gene or genome segment incorporated therein. However the particular size and amino acid sequence of the deleted or inserted protein fragment can vary.

Yet additional human-bovine PIV vaccine candidates within the invention can be achieved by modifying the chimeric PIV genome or antigenome to encode an analogous mutation to an attenuating mutation identified in Sendai virus (SeV). In one example, the attenuating mutation comprises an amino acid substitution of phenylalanine at position 170 of the C protein of SeV. The PIV genome or antigenome is modified to encode an alteration of a conserved residue that corresponds conservatively to the alteration marking the attenuating mutation in the heterologous, SeV mutant. In one embodiment, the mutation is incorporated within a recombinant HPIV3 protein and comprises an amino acid substitution of phenylalanine at position 164 of the C protein of HPIV3.

Various target proteins are amenable to introduction of attenuating mutations from one negative stranded RNA virus at a corresponding site within chimeric human-bovine PIV of the invention. Throughout the order Mononegavirales, five target proteins are strictly conserved and show moderate to high degrees of sequence identity for specific regions or domains. In particular, all known members of the order share a homologous constellation of five proteins: a nucleocapsid protein (N), a nucleocapsid phosphoprotein (P), a nonglycosylated matrix (M) protein, at least one surface glycoprotein (HN, F, H, or G) and a large polymerase (L) protein. These proteins all represent useful targets for incorporating attenuating mutations by altering one or more conserved residues in a protein of the recombinant virus at a site corresponding to the site of an attenuating mutation identified in the heterologous, mutant virus.

In this context, the methods for transferring heterologous mutations into chimeric human-bovine PIV of the invention are based on identification of an attenuating mutation in a first negative stranded RNA virus. The mutation, identified in terms of mutant versus wild-type sequence at the subject amino acid position(s) marking the site of the mutation, provides an index for sequence comparison against a homologous protein in the chimeric virus (either in the background genome or antigenome or in the heterologous gene or gene segment added or substituted therein) that is the target for recombinant attenuation. The attenuating mutation may be previously known or may be identified by mutagenic and reverse genetics techniques applied to generate and characterize biologically-derived mutant virus. Alternatively, attenuating mutations of interest may be generated and characterized de novo, e.g., by site directed mutagenesis and conventional screening methods.

Each attenuating mutation identified in a negative stranded RNA virus provides an index for sequence comparison against a homologous protein in one or more heterologous negative stranded virus(es). In this context, existing sequence alignments may be analyzed, or conventional sequence alignment methods may be employed to yield sequence comparisons for analysis, to identify corresponding protein regions and amino acid positions between the protein bearing the attenuating mutation and a homologous protein of a different virus that is the target recombinant virus for attenuation. Where one or more residues marking the attenuating mutation have been altered from a "wild-type" identity that is conserved at the corresponding amino acid position(s) in the target human-bovine chimeric virus protein, the genome or antigenome of the target virus is recombinantly modified to encode an amino acid deletion, substitution, or insertion to alter the conserved residue(s) in the target virus protein and thereby confer an analogous, attenuated phenotype on the recombinant virus.

Within this rational design method for constructing attenuated recombinant negative stranded viruses, the wild-type identity of residue(s) at amino acid positions marking an attenuating mutation in one negative stranded RNA virus may be conserved strictly, or by conservative substitution, at the corresponding amino acid position(s) in the target, human-bovine chimeric virus protein. Thus, the corresponding residue(s) in the target virus protein may be identical, or may be conservatively related in terms of amino acid side-group structure and function, to the wild-type residue(s) found to be altered by the attenuating mutation in the heterologous, mutant virus. In either case, analogous attenuation in the recombinant virus may be achieved according to the methods of the invention by modifying the recombinant genome or antigenome of the target virus to encode the amino acid deletion, substitution, or insertion to alter the conserved residue(s).

In this context, it is preferable to modify the genome or antigenome to encode an alteration of the conserved residue(s) that corresponds conservatively to the alteration marking the attenuating mutation in the heterologous, mutant virus. For example, if an amino acid substitution marks a site of mutation in the mutant virus compared to the corresponding wild-type sequence, then a substitution should be engineered at the corresponding residue(s) in the recombinant virus. Preferably the substitution will be identical or conservative to the substitute residue present in the mutant viral protein. However, it is also possible to alter the native amino acid residue at the site of mutation non-conservatively with respect to the substitute residue in the mutant protein (e.g., by using any other amino acid to disrupt or impair the identity and function of the wild-type residue). In the case of mutations marked by deletions or insertions, these can transferred as corresponding deletions or insertions into the recombinant virus, however the particular size and amino acid sequence of the deleted or inserted protein fragment can vary.

Within alternative aspects of the invention, mutations thus transferred from heterologous mutant negative stranded viruses may confer a variety of phenotypes within human-bovine chimeric PIV of the invention, in addition to or associated with the desired, an attenuated phenotype. Thus, exemplary mutations incorporated within recombinant proteins of the virus may confer temperature sensitive (ts), cold-adapted (ca), small plaque (sp), or host range restricted (hr) phenotypes, or a change in growth or immunogenicity, in addition to or associated with the attenuated phenotype.

Attenuating mutations in biologically derived PIV and other nonsegmented negative stranded RNA viruses for incorporation within chimeric PIV of the invention may occur naturally or may be introduced into wild-type PIV strains by well known mutagenesis procedures. For example, incompletely attenuated parental PIV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as described in the above incorporated references.

By "biologically derived PIV" is meant any PIV not produced by recombinant means. Thus, biologically derived PIV include all naturally occurring PIV, including, e.g., naturally occurring PIV having a wild-type genomic sequence and PIV having allelic or mutant genomic variations from a reference wild-type PIV sequence, e.g., PIV having a mutation specifying an attenuated phenotype. Likewise, biologically derived PIV include PIV mutants derived from a parental PIV by, inter alia, artificial mutagenesis and selection procedures.

As noted above, production of a sufficiently attenuated biologically derived PIV mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cp mutant or other partially attenuated PIV strain is adapted to efficient growth at a lower temperature by passage in culture. This selection of mutant PIV during cold-passage substantially reduces any residual virulence in the derivative strains as compared to the partially attenuated parent.

Alternatively, specific mutations can be introduced into biologically derived PIV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into PIV include replication of the virus in the presence of a mutagen such as 5-fluorouridine according to generally known procedures. Other chemical mutagens can also be used. Attenuation can result from a ts mutation in almost any PIV gene, although a particularly amenable target for this purpose has been found to be the polymerase (L) gene.

The level of temperature sensitivity of replication in exemplary attenuated PIV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of PIV correlate with the mutant's shutoff temperature.

The JS cp45 HPIV3 mutant has been found to be relatively stable genetically, highly immunogenic, and satisfactorily attenuated. Nucleotide sequence analysis of this biologically derived virus, and of recombinant viruses incorporating various individual and combined mutations found therein, indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious PIV clones. This process coupled with evaluation of phenotype characteristics of parental and derivative viruses identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to adjust chimeric PIV of the invention to an appropriate level of attenuation, immunogenicity, genetic resistance to reversion from an attenuated phenotype, etc., as desired. In accordance with the foregoing description, the ability to produce infectious PIV from cDNA permits introduction of specific engineered changes within chimeric PIV. In particular, infectious, recombinant PIVs are employed for identification of specific mutation(s) in biologically derived, attenuated PIV strains, for example mutations which specify ts, ca, att and other phenotypes. Desired mutations are thus identified and introduced into chimeric PIV vaccine strains. The capability of producing virus from cDNA allows for routine incorporation of these mutations, individually or in various selected combinations, into a full-length cDNA clone, whereafter the phenotypes of rescued recombinant viruses containing the introduced mutations to be readily determined.

By identifying and incorporating specific mutations associated with desired phenotypes, e.g., a cp or ts phenotype, into infectious chimeric PIV clones, the invention provides for other, site-specific modifications at, or within close proximity to, the identified mutation. Whereas most attenuating mutations produced in biologically derived PIVs are single nucleotide changes, other "site specific" mutations can also be incorporated by recombinant techniques into a chimeric PIV. As used herein, site-specific mutations include insertions, substitutions, deletions or rearrangements of from 1 to 3, up to about 5-15 or more altered nucleotides (e.g., altered from a wild-type PIV sequence, from a sequence of a selected mutant PIV strain, or from a parent recombinant PIV clone subjected to mutagenesis). Such site-specific mutations may be incorporated at, or within the region of, a selected, biologically derived point mutation. Alternatively, the mutations can be introduced in various other contexts within a PIV clone, for example at or near a cis-acting regulatory sequence or nucleotide sequence encoding a protein active site, binding site, immunogenic epitope, etc. Site-specific PIV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant PIV designed to incorporate additional, stabilizing nucleotide mutations in a codon specifying an attenuating point mutation. Where possible, two or more nucleotide substitutions are introduced at codons that specify attenuating amino acid changes in a parent mutant or recombinant PIV clone, yielding a PIV with greater genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to the chimeric PIV disclosed herein include deletions, insertions, substitutions or rearrangements of one or more gene(s) or genome segment(s). Particularly useful are deletions involving one or more gene(s) or genome segment(s), which deletions have been shown to yield additional desired phenotypic effects for adjusting the characteristics of human-bovine chimeric PIV within the invention. Thus, U.S. patent application Ser. No. 09/350,821, filed by Durbin et al. on Jul. 9, 1999) describes methods and compositions whereby expression of one or more HPIV genes, exemplified by the C, D, and/or V ORFs, is reduced or ablated by modifying the PIV genome or antigenome to incorporate a mutation that alters the coding assignment of an initiation codon or mutation(s) that introduce one or one or more stop codon(s). Alternatively, one or more of the C, D, and/or V ORFs can be deleted in whole or in part to render the corresponding protein(s) partially or entirely nonfunctional or to disrupt protein expression altogether. Recombinant PIV having such mutations in C, D, and/or V, or other non-essential gene(s), possess highly desirable phenotypic characteristics for vaccine development. For example, these modifications may specify one or more desired phenotypic changes including (i) altered growth properties in cell culture, (ii) attenuation in the upper and/or lower respiratory tract of mammals, (iii) a change in viral plaque size, (iv) a change in cytopathic effect, and (v) a change in immunogenicity. One such exemplary "knock out" mutant lacking C ORF expression, designated rC-KO, was able to induce a protective immune response against wild type HPIV3 challenge in a non-human primate model despite its beneficial attenuation phenotype.

Thus, in more detailed aspects of the instant invention, chimeric PIV incorporate deletion or knock out mutations in a C, D, and/or V ORF(s) or other non-essential gene which alters or ablates expression of the selected gene(s) or genome segment(s). This can be achieved, e.g., by introducing a frame shift mutation or termination codon within a selected coding sequence, altering translational start sites, changing the position of a gene or introducing an upstream start codon to alter its rate of expression, changing GS and/or GE transcription signals to alter phenotype, or modifying an RNA editing site (e.g., growth, temperature restrictions on transcription, etc.). In more detailed aspects of the invention, chimeric PIVs are provided in which expression of one or more gene(s), e.g., a C, D, and/or V ORF(s), is ablated at the translational or transcriptional level without deletion of the gene or of a segment thereof, by, e.g., introducing multiple translational termination codons into a translational open reading frame (ORF), altering an initiation codon, or modifying an editing site. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described, to effectively preclude correcting mutations that may restore synthesis of a target protein. Several other gene knock-outs for the C, D, and/or V ORF(s) deletion and knock out mutants can be made using alternate designs and methods that are well known in the art (as described, for example, in (Kretschmer et al., Virology 216:309-316, 1996; Radecke et al., Virology 217:418-421, 1996; and Kato et al., EMBO J. 16:578-587, 1987; and Schneider et al., Virology 277:314-322, 1996, each incorporated herein by reference).

Nucleotide modifications that may be introduced into chimeric PIV constructs of the invention may alter small numbers of bases (e.g., from 15-30 bases, up to 35-50 bases or more), large blocks of nucleotides (e.g., 50-100, 100-300, 300-500, 500-1,000 bases), or nearly complete or complete genes (e.g., 1,000-1,500 nucleotides, 1,500-2,500 nucleotides, 2,500-5,000, nucleotides, 5,00-6,5000 nucleotides or more) in the vector genome or antigenome or heterologous, donor gene or genome segment, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In related aspects, the invention provides for supplementation of mutations adopted into a chimeric PIV clone from biologically derived PIV, e.g., cp and ts mutations, with additional types of mutations involving the same or different genes in a further modified PIV clone. Each of the PIV genes can be selectively altered in terms of expression levels, or can be added, deleted, substituted or rearranged, in whole or in part, alone or in combination with other desired modifications, to yield a chimeric PIV exhibiting novel vaccine characteristics. Thus, in addition to or in combination with attenuating mutations adopted from biologically derived PIV mutants, the present invention also provides a range of additional methods for attenuating or otherwise modifying the phenotype of a chimeric PIV based on recombinant engineering of infectious PIV clones. A variety of alterations can be produced in an isolated polynucleotide sequence encoding a targeted gene or genome segment, including a donor or recipient gene or genome segment in a chimeric PIV genome or antigenome for incorporation into infectious clones. More specifically, to achieve desired structural and phenotypic changes in recombinant PIV, the invention allows for introduction of modifications which delete, substitute, introduce, or rearrange a selected nucleotide or nucleotide sequence from a parent genome or antigenome, as well as mutations which delete, substitute, introduce or rearrange whole gene(s) or genome segment(s), within a chimeric PIV clone.

Thus provided are modifications in chimeric PIV of the invention which simply alter or ablate expression of a selected gene, e.g., by introducing a termination codon within a selected PIV coding sequence or altering its translational start site or RNA editing site, changing the position of a PIV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s). In this context, any PIV gene or genome segment which is not essential for growth can be ablated or otherwise modified in a recombinant PIV to yield desired effects on virulence, pathogenesis, immunogenicity and other phenotypic characters. As for coding sequences, noncoding, leader, trailer and intergenic regions can be similarly deleted, substituted or modified and their phenotypic effects readily analyzed, e.g., by the use of minireplicons and recombinant PIV.

In addition, a variety of other genetic alterations can be produced in a PIV genome or antigenome for incorporation into a chimeric PIV, alone or together with one or more attenuating mutations adopted from a biologically derived mutant PIV, e.g., to adjust growth, attenuation, immunogenicity, genetic stability or provide other advantageous structural and/or phenotypic effects. These additional types of mutations are also disclosed in the foregoing incorporated references and can be readily engineered into chimeric PIV of the invention. For example, restriction site markers are routinely introduced within chimeric PIVs to facilitate cDNA construction and manipulation.

In addition to these changes, the order of genes in a chimeric PIV construct can be changed, a PIV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Other mutations for incorporation into chimeric PIV constructs of the invention include mutations directed toward cis-acting signals, which can be readily identified, e.g., by mutational analysis of PIV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which affect RNA replication or transcription. Any of these mutations can be inserted into a chimeric PIV antigenome or genome as described herein. Evaluation and manipulation of trans-acting proteins and cis-acting RNA sequences using the complete antigenome cDNA is assisted by the use of PIV minigenomes as described in the above-incorporated references.

Additional mutations within chimeric PIVs of the invention may also include replacement of the 3' end of genome with its counterpart from antigenome, which is associated with changes in RNA replication and transcription. In one exemplary embodiment, the level of expression of specific PIV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Haas et al., Current Biol. 6:315-324, 1996, incorporated herein by reference). Optimization by recombinant methods of the codon usage of the mRNAs encoding the HN and F proteins of PIV will provide improved expression for these genes.

In another exemplary embodiment, a sequence surrounding a translational start site (preferably including a nucleotide in the −3 position) of a selected PIV gene is modified, alone or in combination with introduction of an upstream start codon, to modulate PIV gene expression by specifying up- or down-regulation of translation (Kozak et al., J. Mol. Biol. 196:947-950, 1987). Alternatively, or in combination with other PIV recombinant modifications disclosed herein, gene expression of a chimeric PIV can be modulated by altering a transcriptional GS or GE signal of any selected gene(s) of the virus. In alternative embodiments, levels of gene expression in a chimeric PIV vaccine candidate are modified at the level of transcription. In one aspect, the position of a selected gene in the PIV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. These and other transpositioning changes yield novel chimeric PIV vector virus having attenuated phenotypes, for example due to decreased expression of selected viral proteins involved in RNA replication, or having other desirable properties such as increased antigen expression.

In other embodiments, chimeric PIVs useful in vaccine formulations can be conveniently modified to accommodate antigenic drift in circulating virus. Typically the modification will be in the HN and/or F proteins. An entire HN or F gene, or a genome segment encoding a particular immunogenic region thereof, from one PIV strain or group is incorporated into a chimeric PIV genome or antigenome cDNA by replacement of a corresponding region in a recipient clone of a different PIV strain or group, or by adding one or more copies of the gene, such that multiple antigenic forms are represented. Progeny virus produced from the modified PIV clone can then be used in vaccination protocols against emerging PIV strains.

Replacement of a human PIV coding sequence or non-coding sequence (e.g., a promoter, gene-end, gene-start, intergenic or other cis-acting element) with a heterologous counterpart yields chimeric PIV having a variety of possible attenuating and other phenotypic effects. In particular, host range and other desired effects arise from substituting a bovine PIV (BPIV) or murine PIV (MPIV) protein, protein domain, gene or genome segment imported within a human PIV background, wherein the bovine or murine gene does not function efficiently in a human cell, e.g., from incompatibility of the heterologous sequence or protein with a biologically interactive human PIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into human PIV based on known aspects of bovine and human PIV structure and function.

In more detailed aspects, the invention provides methods for attenuating chimeric PIV vaccine candidates based on the further construction of chimeras between HPIV and a non-human PIV, for example HPIV3 and BPIV3 (e.g., as disclosed in U.S. Provisional Application Ser. No. 60/143,134 filed on Jul. 9, 1999, incorporated herein by reference). This method of attenuation is based on host range effects due to the introduction of one or more gene(s) or genome segment(s) of the non-human PIV into a human PIV vector-based chimeric virus. For example, there are numerous nucleotide and amino acid sequence differences between BPIV and HPIVs, which are reflected in host range differences. Between HPIV3 and BPIV3 the percent amino acid identity for each of the following proteins is: N (86%), P (65%), M (93%), F (83%), HN (77%), and L (91%). The host range difference is exemplified by the highly permissive growth of HPIV3 in rhesus monkeys, compared to the restricted replication of two different strains of BPIV3 in the same animal (van Wyke Coelingh et al., J. Infect. Dis. 157:655-662, 1988, incorporated herein by reference). Although the basis of the host range differences between HPIV3 and BPIV3 remains to be determined, it is likely that they will involve more than one gene and multiple amino acid differences. The involvement of multiple genes and possibly cis-acting regulatory sequences, each involving multiple amino acid or nucleotide differences, gives a very broad basis for attenuation, one which cannot readily be altered by reversion. This is in contrast to the situation with other live attenuated HPIV3 viruses which are attenuated by one or several point mutations. In this case, reversion of any individual mutation may yield a significant reacquisition of virulence or, in a case where only a single residue specified attenuation, complete reacquisition of virulence.

In exemplary embodiments of the invention, the vector genome or antigenome is an HPIV3 genome or antigenome, and the heterologous gene or genome segment is a N ORF derived from, alternatively, a Ka or SF strain of BPIV3 (which are 99% related in amino acid sequence). The N ORF of the HPIV3 background antigenome is substituted by the counterpart BPIV3 N ORF-yielding a novel recombinant chimeric PIV clone. Replacement of the HPIV3 N ORF of HPIV3 with that of BPIV3 Ka or SF results in a protein with approximately 70 amino acid differences (depending on the strain involved) from that of HPIV3 N. N is one of the more conserved proteins, and substitution of other proteins such as P, singly or in combination, would result in many more amino acid differences. The involvement of multiple genes and genome segments each conferring multiple amino acid or nucleotide differences provides a broad basis for attenuation which is highly stable to reversion.

This mode of attenuation contrasts sharply to HPIV vaccine candidates that are attenuated by one or more point mutations, where reversion of an individual mutation may yield a significant or complete reacquisition of virulence. In addition, several known attenuating point mutations in HPIV typically yield a temperature sensitive phenotype. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media. Thus, attenuation achieved solely by temperature sensitive mutations may not be ideal. In contrast, host range mutations present in chimeric PIV of the invention will not in most cases confer temperature sensitivity. Therefore, the novel method of PIV attenuation provided by these kinds of modifications will be more stable genetically and phenotypically and less likely to be associated with residual virulence in the upper respiratory tract compared to other known PIV vaccine candidates.

The above-incorporated reference discloses that both Ka and SF HPIV3/BPIV3 chimeric recombinants are viable and replicate as efficiently in cell culture as either HPIV3 or BPIV3 parent☐indicating that the chimeric recombinants did not exhibit gene incompatibilities that restricted replication in vitro. This property of efficient replication in vitro is important since it permits efficient manufacture of this biological. Also, the Ka and the SF HPIV3/BPIV3 chimeric recombinants (termed cKa and cSF), bearing only one bovine gene, are nearly equivalent to their BPIV3 parents in the degree of host range restriction in the respiratory tract of the rhesus monkey. In particular, the cKa and cSF viruses exhibit approximately a 60-fold or 30-fold reduction, respectively, in replication in the upper respiratory tract of rhesus monkeys compared to replication of HPIV3. Based on this finding, it is expected that other BPIV3 genes will also confer desired levels of host range restriction within chimeric PIV of the invention. Thus, according to the methods herein, a list of attenuating determinants will be readily identified in heterologous genes and genome segments of BPIV and other non-human PIVs that will confer, in appropriate combination, a desired level of host range restriction and immunogenicity on chimeric PIV selected for vaccine use.

In preferred chimeric vaccine candidates of the invention, attenuation marked by replication in the lower and/or upper respiratory tract in an accepted animal model for PIV replication in humans, e.g., hamsters or rhesus monkeys, may be reduced by at least about two-fold, more often about 5-fold, 10-fold, or 20-fold, and preferably 50-100-fold and up to 1,000-fold or greater overall (e.g., as measured between 3-8 days following infection) compared to growth of the corresponding wild-type or mutant parental PIV strain.

Infectious chimeric PIV vector clones of the invention can also be engineered according to the methods and compositions disclosed herein to enhance immunogenicity and induce a level of protection greater than that provided by infection with a wild-type, parental (i.e., vector or heterologous donor) PIV or non-PIV pathogen. For example one or more supplemental immunogenic epitope(s), protein domains, or proteins from a heterologous PIV strain or type, or from a non-PIV pathogen such as measles or RSV, can be added to a chimeric PIV by appropriate nucleotide changes in the chimeric genome or antigenome. Alternatively, chimeric PIVs of the invention can be engineered to add or ablate (e.g., by amino acid insertion, substitution or deletion) immunogenic proteins, protein domains, or forms of specific proteins associated with desirable or undesirable immunological reactions.

Within the methods of the invention, additional genes or genome segments may be inserted into or proximate to the chimeric PIV vector genome or antigenome. These genes may be under common control with recipient genes, or may be under the control of an independent set of transcription signals. In addition to genes and genome segments encoding antigenic determinants, genes of interest in this context include genes encoding cytokines, for example, an interleukin (e.g., interleukin 2 (IL-2), interleukin 4 (IL-4), interleukin 5 (IL-5), interleukin 6 (IL6), interleukin 18 (IL-18)), tumor necrosis factor alpha (TNF☐), interferon gamma (IFN☐), or granulocyte-macrophage colony stimulating factor (GM-CSF), as well as IL-2 through IL-18, especially IL-2, IL-6 and IL-12, and IL-18, gamma-interferon (see, e.g., U.S. Provisional Application Ser. No. 60/143,425 filed Jul. 13, 1999, incorporated herein by reference). Coexpression of these additional proteins provides the ability to modify and improve immune responses against chimeric PIV of the invention both quantitatively and qualitatively.

Deletions, insertions, substitutions and other mutations involving changes of whole viral genes or genome segments within chimeric PIV of the invention yield highly stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., EMBO. J. 16:578-87, 1997, incorporated herein by reference). Ablation of such genes in vaccine viruses is expected to reduce virulence and pathogenesis and/or improve immunogenicity.

In another aspect of the invention, compositions (e.g., isolated polynucleotides and vectors incorporating human-bovine chimeric PIV-encoding cDNA) are provided for producing an isolated infectious PIV. Using these compositions and methods, infectious PIV are generated from a PIV genome or antigenome, a nucleocapsid (N) protein, a nucleocapsid phosphoprotein (P), and a large (L) polymerase protein. In related aspects of the invention, compositions and methods are provided for introducing the aforementioned structural and phenotypic changes into a recombinant PIV to yield infectious, attenuated vaccine viruses.

Introduction of the foregoing defined mutations into an infectious, chimeric PIV clone can be achieved by a variety of well known methods. For example, the Muta-gene® kit or Chameleon® kit may be used as described above.

The invention also provides methods for producing infectious chimeric PIV from one or more isolated polynucleotides, e.g., one or more cDNAs. According to the present invention cDNA encoding a PIV genome or antigenome is constructed for intracellular or in vitro coexpression with the necessary viral proteins to form infectious PIV. By "PIV antigenome" is meant an isolated positive-sense polynucleotide molecule which serves as the template for the synthesis of progeny PIV genome. Preferably a cDNA is constructed which is a positive-sense version of the PIV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, and L proteins.

For purposes of the present invention the genome or antigenome of the recombinant PIV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant PIV is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15-35 nucleotides in the case of genome segments encoding small functional domains of proteins, e.g., epitopic sites, to about 50, 75, 100, 200-500, and 500-1,500 or more nucleotides.

The ability to introduce defined mutations into infectious PIV has many applications, including the manipulation of PIV pathogenic and immunogenic mechanisms. For example, the functions of PIV proteins, including the N, P, M, F, HN, and L proteins and C, D and V ORF products, can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock, et al., J. Virol. 67: 2772-8 (1993), incorporated herein by reference in its entirety), whose rescue-dependent status is useful in characterizing those mutants that may be too inhibitory to be recovered in replication-independent infectious virus.

Certain substitutions, insertions, deletions or rearrangements of genes or genome segments within recombinant PIV of the invention (e.g., substitutions of a genome segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or genome segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. The recombinant PIV of the invention are not only viable and more appropriately attenuated than previous vaccine candidates, but are more stable genetically in vivo—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like.

Recombinant PIV of the invention can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant PIV) is tested, e.g., for temperature sensitivity of virus replication, i.e. ts phenotype, and for the small plaque or other desired phenotype. Modified viruses are further tested in animal models of PIV infection. A variety of animal models have been described and are summarized in various references incorporated herein. PIV model systems, including rodents and non-human primates, for evaluating attenuation and immunogenic activity of PIV vaccine candidates are widely accepted in the art, and the data obtained therefrom correlate well with PIV infection, attenuation and immunogenicity in humans.

In accordance with the foregoing description, the invention also provides isolated, infectious recombinant PIV compositions for vaccine use. The attenuated virus which is a component of a vaccine is in an isolated and typically purified form. By isolated is meant to refer to PIV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated PIV of the invention may be produced by an infected cell culture, separated from the cell culture and added to a stabilizer.

For vaccine use, recombinant PIV produced according to the present invention can be used directly in vaccine formulations, or lyophilized, as desired, using lyophilization protocols well known to the artisan. Lyophilized virus will typically be maintained at about 4□C. When ready for use the lyophilized virus is reconstituted in a stabilizing solution, e.g., saline or comprising SPG, Mg++ and HEPES, with or without adjuvant, as further described below.

PIV vaccines of the invention contain as an active ingredient an immunogenically effective amount of PIV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPLTM (3-o-deacylated monophosphoryl lipid A; RIBI ImmunoChem Research, Inc., Hamilton, Mont.) and IL-12 (Genetics Institute, Cambridge Mass.), among many other suitable adjuvants well known in the art.

Upon immunization with a PIV composition as described herein, via aerosol, droplet, oral, topical or other route, the immune system of the host responds to the vaccine by producing antibodies specific for PIV proteins, e.g., F and HN glycoproteins. As a result of the vaccination with an immunogenically effective amount of PIV produced as described herein, the host becomes at least partially or completely immune to PIV infection, or resistant to developing moderate or severe PIV infection, particularly of the lower respiratory tract.

The host to which the vaccines are administered can be any mammal which is susceptible to infection by PIV or a closely related virus and which host is capable of generating a protective immune response to the antigens of the vaccinizing strain. Accordingly, the invention provides methods for creating vaccines for a variety of human and veterinary uses.

The vaccine compositions containing the PIV of the invention are administered to a host susceptible to or otherwise at risk for PIV infection to enhance the host's own immune response capabilities. Such an amount is defined to be a "immunogenically effective dose." In this use, the precise amount of PIV to be administered within an effective dose will depend on the host's state of health and weight, the mode of administration, the nature of the formulation, etc., but will generally range from about 103 to about 107 plaque forming units (PFU) or more of virus per host, more commonly from about 104 to 106 PFU virus per host. In any event, the vaccine formulations should provide a quantity of modified PIV of the invention sufficient to effectively protect the host patient against serious or life-threatening PIV infection.

The PIV produced in accordance with the present invention can be combined with viruses of other PIV serotypes or strains to achieve protection against multiple PIV serotypes or strains. Alternatively, protection against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may protect against different strains of the same or different serotype.

In some instances it may be desirable to combine the PIV vaccines of the invention with vaccines which induce protective responses to other agents, particularly other childhood viruses. In another aspect of the invention the PIV can be employed as a vector for protective antigens of other pathogens, such as respiratory syncytial virus (RSV) or measles virus, by incorporating the sequences encoding those protective antigens into the PIV genome or antigenome which is used to produce infectious PIV, as described herein. The cloning of RSV cDNA and other disclosure relevant to the invention is described in copending U.S. patent application Ser. Nos. 08/534,768, 60/021,773, 08/720,132, 60/046,141, 60/047,634, and 08/892,403, and PCT patent application PCT/US97/12269, each incorporated herein by reference.

In all subjects, the precise amount of recombinant PIV vaccine administered, and the timing and repetition of administration, will be determined based on the patient's state of health and weight, the mode of administration, the nature of the formulation, etc. Dosages will generally range from about 103 to about 107 plaque forming units (PFU) or more of virus per patient, more commonly from about 104 to 106 PFU virus per patient. In any event, the vaccine formulations should provide a quantity of attenuated PIV sufficient to effectively stimulate or induce an anti-PIV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated PIV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) PIV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered PIV strain expressing a cytokine or an additional protein rich in T cell epitopes may be particularly advantageous for adults rather than for infants.

PIV vaccines produced in accordance with the present invention can be combined with viruses expressing antigens of another subgroup or strain of PIV to achieve protection against multiple PIV subgroups or strains. Alternatively, the vaccine virus may incorporate protective epitopes of multiple PIV strains or subgroups engineered into one PIV clone, as described herein.

The PIV vaccines of the invention elicit production of an immune response that is protective against serious lower respiratory tract disease, such as pneumonia and bronchiolitis when the individual is subsequently infected with wild-type PIV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

Preferred PIV vaccine candidates of the invention exhibit a very substantial diminution of virulence when compared to wild-type virus that is circulating naturally in humans. The virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of PIV vaccine candidates may be determined by, for example, quantifying the amount of virus present in the respiratory tract of an immunized host and comparing the amount to that produced by wild-type PIV or other attenuated PIV which have been evaluated as candidate vaccine strains. For example, the attenuated virus of the invention will have a greater degree of restriction of replication in the upper respiratory tract of a highly susceptible host, such as a chimpanzee, or rhesus monkey, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of PIV in the nasopharynx of an infected host are well known in the literature.

Levels of induced immunity provided by the vaccines of the invention can also be monitored by measuring amounts of neutralizing secretory and serum antibodies. Based on these measurements, vaccine dosages can be adjusted or vaccinations repeated as necessary to maintain desired levels of protection. Further, different vaccine viruses may be advantageous for different recipient groups. For example, an engineered PIV strain expressing an additional protein rich in T cell epitopes may be particularly advantageous for adults rather than for infants.

In yet another aspect of the invention the PIV is employed as a vector for transient gene therapy of the respiratory tract. According to this embodiment the recombinant PIV genome or antigenome incorporates a sequence which is capable of encoding a gene product of interest. The gene product of interest is under control of the same or a different promoter from that which controls PIV expression. The infectious PIV produced by coexpressing the recombinant PIV genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant PIV is administered in an amount sufficient to result in the expression of therapeutic or prophylactic levels of the desired gene product. Representative gene products which may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

Example I

Construction of Plasmid p218(131) Encoding Negative Sense PIV Genomic RNA

A full cDNA clone designated p218(131) (FIG. 1; SEQ ID NO: 71) (deposited under the terms of the Budapest Treaty with the American Type Culture Collection (ATCC) of 12301 Parklawn Drive, Rockville, Md. 20852, U.S.A., and granted the designation 97991) was constructed to encode the complete 15462 nt genomic sequence of HPIV3 JS strain (SEQ ID NO: 180). A hepatitis delta ribozyme was placed abutting the 3' end of the genomic sequence such that self-cleavage would yield the 3' end of HPIV3 (Perrotta and Been, *Nature* 350: 434-436, (1991), incorporated herein by reference in its entirety). A T7 transcription terminator was placed following the delta ribozyme. The T7 promoter was placed adjacent to the 5' end of the genomic sequence such that the 5' terminal nucleotide of the HPIV3 genome was the first nucleotide synthesized. In this configuration, the cDNA encodes a complete negative-sense copy of PIV3 genomic RNA containing the correct genomic termini without any additional heterologous nucleotides.

The HPIV3 cDNA was assembled from 14 overlapping subclones (termed A*-L, which letters in parentheses designate individual plasmids and do not refer to specific viral genes) constructed by reverse transcription (RT) and polymerase chain reaction (PCR) of RNA isolated from virions purified by sucrose gradient centrifugation (Stokes et al., supra, 1992; Stokes et al., supra, 1993, each incorporated herein by reference in its entirety). The subclones spanned the following nucleotides of genomic RNA (numbered with the 3' end designated as position 1): 1-2058 (A*), 1874-3111 (A'), 3086-5140 (C), 4348-5276 (C'), 5072-6695 (D*), 5904-8532 (E), 7806-9898 (F), 9632-10740 (F'), 9760-10955 (G), 10862-11925 (H), 11835-12868 (I), 12426-13677 (J), 13630-

14496 (K), and 14467-15462 (L). Each fragment was cloned into pBluescript KSII (Strategene, La Jolla, Calif.) using conventional cloning techniques and was sequenced completely.

Plasmid p(L) was then subjected to site-directed mutagenesis to introduce the T7 promoter via a single-stranded DNA intermediate according to the MUTA-GENE procedure (Bio-Rad, Hercules, Calif.). The T7 promoter was positioned so that transcription initiates at the precise 5' end of the HPIV3 genome using the negative-sense mutagenic primer: 5'-AATACGACTCACTATA*ACCAAACAAGAGAAG-3 (SEQ ID NO: 55; T7 sequences are italicized, HPIV3-specific sequences are underlined, and the 5'-end HPIV3 nucleotide, genome position 15462, is indicated by an asterisk). This modified p(L) was designated p(L*). Plasmid p(E) was modified to yield p(E*) by the same method using the negative-sense mutagenic oligonucleotide 5'-CCAAG TACTATGAGATGCTTGATT-3' (SEQ ID NO: 56) to insert three nucleotide substitutions (underlined) into the HN gene at HPIV3 position 7903, 7913, 7915 (FIG. 1). These substitutions removed an Hga I site, inserted a Sca I site, and modified amino acid 370 of the encoded HN protein such that the epitope recognized by monoclonal antibodies (mAb) 423/6 and 170/7 was ablated (van Wyke Coelingh et al., *J. Virol.* 61:1473-1477, (1987), incorporated herein by reference). The p(E*) to p(K) subclones were assembled in a step-wise fashion into the p(L*) plasmid to give p(E*FF'GHIJKL*) (FIG. 1A). This plasmid includes HPIV3 nucleotides 5904-15462 with the T7 promoter adjacent to nucleotide 15462 at the 5' end of the genome. Subclones p(A*) to p(E) were assembled into a second, overlapping subclone, p(A*A'CC'D*E) which contained HPIV3 nucleotides 1-8532.

Both subclones p(E*FF'GHIJKL*) and p(A*A'CC'D*E) were sequenced completely. In addition to the introduced point mutations described above, the cDNA differed from the authentic JS HPIV3 sequence (Stokes et al., supra, 1992) by a single nucleotide substitution at position 1615 which was within the N gene and caused a substitution at amino acid 506 in the encoded protein. Three other nucleotide substitutions were found at positions 10355, 11333, and 15248 in the L gene which did not change the encoded protein (FIG. 2). These three noncoding changes were retained as additional sequence markers to identify recombinant virus (designated rPIV) derived from cDNA, and the mutation in the N gene was corrected as described later.

Subclone p(A*A'CC'D*E) was then modified to insert the hepatitis delta virus ribozyme and T7 terminator adjacent to HPIV3 position 1. An HPIV3 minigenome in which the 3' end of the HPIV3 genome (GGT↓GGG) (underlined) was generated through self-cleavage of a flanking hepatitis delta virus antigenomic ribozyme (shown in part in bold-type) was previously constructed (Dimock and Collins, *J. Virol.* 67: 2772-2778, (1993); Perrotta and Been, supra, (1991), each incorporated herein by reference in its entirety). The ribozyme in turn was followed by a T7 transcription terminator. This minigenome cDNA was used as a template in a PCR reaction which modified the sequence adjacent to the ribozyme cleavage site to be a Sma I site (CCC↓GGG) and placed an ApaI site (GGGCC↓C) on the downstream side of the T7 terminator. The PCR product was cloned into pKSII which had been digested with BssHII and made blunt-ended by filling in, yielding p218.

p218 was designed such that any sequence could be introduced into the opened Sma I site by blunt-end ligation and its RNA transcript would be cleaved at the delta ribozyme cut site (NNN↓GGG). The p(A*A'CC'D*E) subclone was digested with Hga I and Sal I (8533), which released the HPIV3 cDNA, and was filled in with dNTPs and T4 DNA polymerase to give blunt termini. The Hga I site is 10 nucleotides upstream of HPIV3 position 1 and, when digested and filled in, leaves a blunt terminus beginning with HPIV3 position 1. The modified Hga I-Sal I fragment was gel purified and cloned into the Sma I site of p218. The mutation in the N gene (T at nt 1615) was corrected to the JS wt sequence (A at nt 1615) (see GenBank accession #Z11575, incorporated herein by reference) using Kunkel mutagenesis (Kunkel et al., *Methods Enzymol.* 154: 367-382, (1987), incorporated herein by reference in its entirety). This plasmid was designated p218 (A*A'CC'D*E) (FIG. 1).

The Xho I-Ngo MI fragment of p(E*FF'GHIJKL*), which contained the T7 promoter and the HPIV3 cDNA from nucleotides 7438-15462, was cloned into the Xho I-Ngo MI window of p218(A*A'CC'D*E) (FIG. 1). This joined the two fragments of HPIV3 cDNA at HPIV3 nucleotide 7438, yielding a plasmid containing a full-length HPIV3 cDNA encoding a negative-sense genomic RNA with the above-mentioned three desired mutations in the HN gene and three incidental mutations in the L gene. The final construct, designated p218 (131) (FIG. 1; SEQ ID NO: 71), was then sequenced in its entirety by automated sequencing at the NCI Frederick Cancer Research and Development Center (Frederick, Md.) using the Taq DYE Deoxy Terminator cycle sequencing kit (ABI, Foster City, Calif.). This identified an additional change in the HN gene, namely a change of C to T in the HN gene at position 7593 which changed HN amino acid 263 from threonine to isoleucine that is also indicated in FIG. 2.

Example II

Transcription and RNA Replication System for HPIV3

The present example describes compositions and methods for producing a reconstituted transcription and RNA replication system for human parainfluenza virus type 3 (HPIV3). This exemplary system was developed using components expressed intracellularly from transfected plasmids driven by a T7 RNA polymerase supplied by a vaccinia virus recombinant. The system is based on a negative-sense analog of HPIV3 genomic RNA in which the viral genes were deleted and replaced with a polynucleotide encoding bacterial chloramphenicol acetyl transferase (CAT). The N, P and L proteins are expressed from cotransfected plasmids so as to direct efficient transcription and RNA replication. Transcription according to this example yields subgenomic polyadenylated mRNA, which can be readily isolated, e.g., by oligo (dT) chromatography. RNA replication according to this example yields mini-antigenome and progeny minigenome, which are shown to be encapsidated based on resistance to digestion with micrococcal nuclease.

A) Viruses and Cells

A vaccinia virus recombinant, vTF7-3, that expresses bacteriophage T7 RNA polymerase, was provided as described by Fuerst et al. (*Proc. Natl. Acad. Sci. U.S.A.* 83: 8122-8126, 1986, incorporated herein by reference in its entirety). HEp-2 monolayer cultures were maintained at 37° C. in 5% $CO_2$ with OptiMEM 1 (Life Technologies, Gaithersburg, Md.) supplemented with 2% fetal bovine serum (FBS), 50 μg/ml gentamicin sulfate and 2 mM glutamine.

B) cDNAs cDNAs corresponding to ORFs of the N, P, and L genes of the JS strain of HPIV3 (GenBank #Z11575; Stokes et al., 1992) were individually cloned into the Nco I-Sal I window of plasmid pTM-1, in which transcription is mediated by T7 RNA polymerase and translation by an internal ribosome entry site preceding the foreign ORF (Elroy-Stein et al., *Proc. Natl. Acad. Sci. U.S.A.* 86: 6126-6130 (1989), incorporated herein by reference in its entirety). Each gene was first modified by polymerase chain reaction (PCR) to place an Nco I or Nco I-compatible site at the translational start site and a Sal I site on the downstream end.

The plasmid p(131), which is similar to p218(131) except that it lacks the hepatitis delta virus ribozyme, was used as a template for each PCR. The primers used to amplify the N ORF were CCCTATAATTTCAACATGTTGAGC-CTATTTG (SEQ ID NO: 57; forward primer relative to positive-sense) and GATTAAAATGTTGGTCGACTTAGT-TGCTTCC (SEQ ID NO: 58; italics represent restriction enzyme sites, and the translational start site is in bold). The PCR product, a 1578 bp fragment flanked by an Afl III and Sal I site, was cloned into the Nco I-Sal I window of pTM-1 to yield pTM(N).

The primers used to amplify the PIV3 phosphoprotein (P)ORF were 5'-CCATAGAGAGTCCATGGAAAGCGAT-GCTAAAAACTATC-3' (SEQ ID NO:59; forward primer) and 5'-CGGTGTCGTTTCTTTGTCGACTCATTG-GCAATTGTTG-3' (SEQ ID NO:60; reverse primer). A full-length cDNA of JS strain of genomic RNA (p131) was used as template for the PCR. The resultant PCR product was an 1851 bp fragment flanked by an Nco I and Sal I restriction site (in italics). The PCR product was then cloned into the Nco I-Sal I window of pTM-1 to yield pTM(P).

A second PCR was performed to amplify the PIV3 phosphoprotein P ORF without the C ORF. p131 was again used as template cDNA. A different forward primer and the same reverse primer were used to amplify the PIV3 P ORF without C; 5'-CCATAGAGAGTCCATGGAAAGCGACGCTAAA-AACTATC-3' (SEQ ID NO: 61; forward primer) and 5'-CG-GTGTCGTTTCTTTGTCGACTCATTGGCAATTGTTG-3' (SEQ ID NO:60; reverse primer). The resultant PCR product was an 1851 bp fragment flanked by an Nco I and Sal I restriction site (designated by italics). The underlined nucleotide in the forward primer represents a nucleotide substitution which is silent in the P ORF but changes the start codon of the C ORF to threonine. The next start codon for the C ORF is more than 400 nucleotides downstream. Thus, only the P protein would be produced. The PCR product was then cloned into the Nco I-Sal I window of pTM-1 to yield a second plasmid, pTM(P no C).

The L ORF of HPIV3 was cloned into pTM-1 in three parts: the ends were derived from PCR products and the main body was a restriction fragment from p218(131). The upstream end of the L ORF was amplified using the primers GCAAAGCGTGCCCGGGCCATGGACACTGAATCTA-ACAATGC (SEQ ID NO: 62) and GAAATTCCTTAATC-GATTCTCTAGATTC (SEQ ID NO: 63). This yielded the 1,020-bp PCR product L1 in which positions 8625-9645 of the full-length genome were flanked by Sma I and Nco I sites on the upstream end and a Cla I site on the downstream end (all three sites are italicized). The downstream end of the L ORF was amplified using the primers CCCATCAACTG-TAACATACGTAAGAAAGAC (SEQ ID NO: 64) and GGT-TAGGATATGTCGACATTGTATTTATG (SEQ ID NO: 65). This yielded the 1,733-bp PCR product L2 in which positions 13,645-15,378 of the full-length genome were flanked by a SnaB I and Sal I site (italicized). Plasmid p(131) was digested with Cla I and Pst I to yield the 4,487-bp fragment L middle containing positions 9,630-14,120 of the full-length genome. L1 and L middle were joined at the common Cla I site and cloned into the Sma I-Pst I window of pBluescript to yield p(L1+L middle). The L2 fragment was then cloned into the Pst I-Sal I window of p(L1+L middle) to yield the complete L ORF flanked by Nco I and Sal I. This was then cloned into the Nco I-Sal I window of pTM-1 to yield pTM(L). The sequences of PCR-generated regions of pTM(N) (SEQ ID NO: 66), pTM(P) (SEQ ID NO: 67), and pTM(L) (SEQ ID NO: 68) were confirmed by the dideoxynucleotide sequencing method.

To increase the efficiency of T7 transcription, certain modifications were made to a cDNA construct encoding a negative-sense PIV minigenome, called PIV3-CAT(−) (Dimock and Collins, *J. Virol.* 67: 2772-2778 (1993), incorporated herein by reference in its entirety). PIV3-CAT(−) includes the 3'-terminal 111 nucleotides and 5'-terminal 115 nucleotides of the HPIV3 genome fused to a negative-sense copy of the CAT ORF. This cDNA was designed to yield, upon linearization with HgaI and transcription with T7 RNA polymerase, a minigenome containing the exact correct ends of the HPIV3 genome. Two successive rounds of PCR, using mutagenic oligonucleotides which added successive extensions to the cDNA end, were used to replace the HgaI site with the hepatitis delta ribozyme (Perotta and Been, *Nature* 350: 434-436 (1991), incorporated herein by reference in its entirety), such that self-cleavage generates the correct 3' HPIV3 genomic end. A T7 transcriptional termination signal was inserted immediately after the ribozyme (FIG. 3) to yield PIV3-CAT-delta.

PIV3-CAT-delta cDNA was modified by PCR mutagenesis to insert one, two or three G residues between the T7 promoter and the 5' end of the minigenome, using restriction sites flanking the trailer and T7 promoter. This modification yielded increased efficiency of T7 transcription. In preliminary experiments, the minigenome containing two G residues, called PIV3-CAT-GG, was the most active in the expression of CAT in the reconstituted transcription and replication system described below, and was used for all subsequent derivatives.

Figure 3:
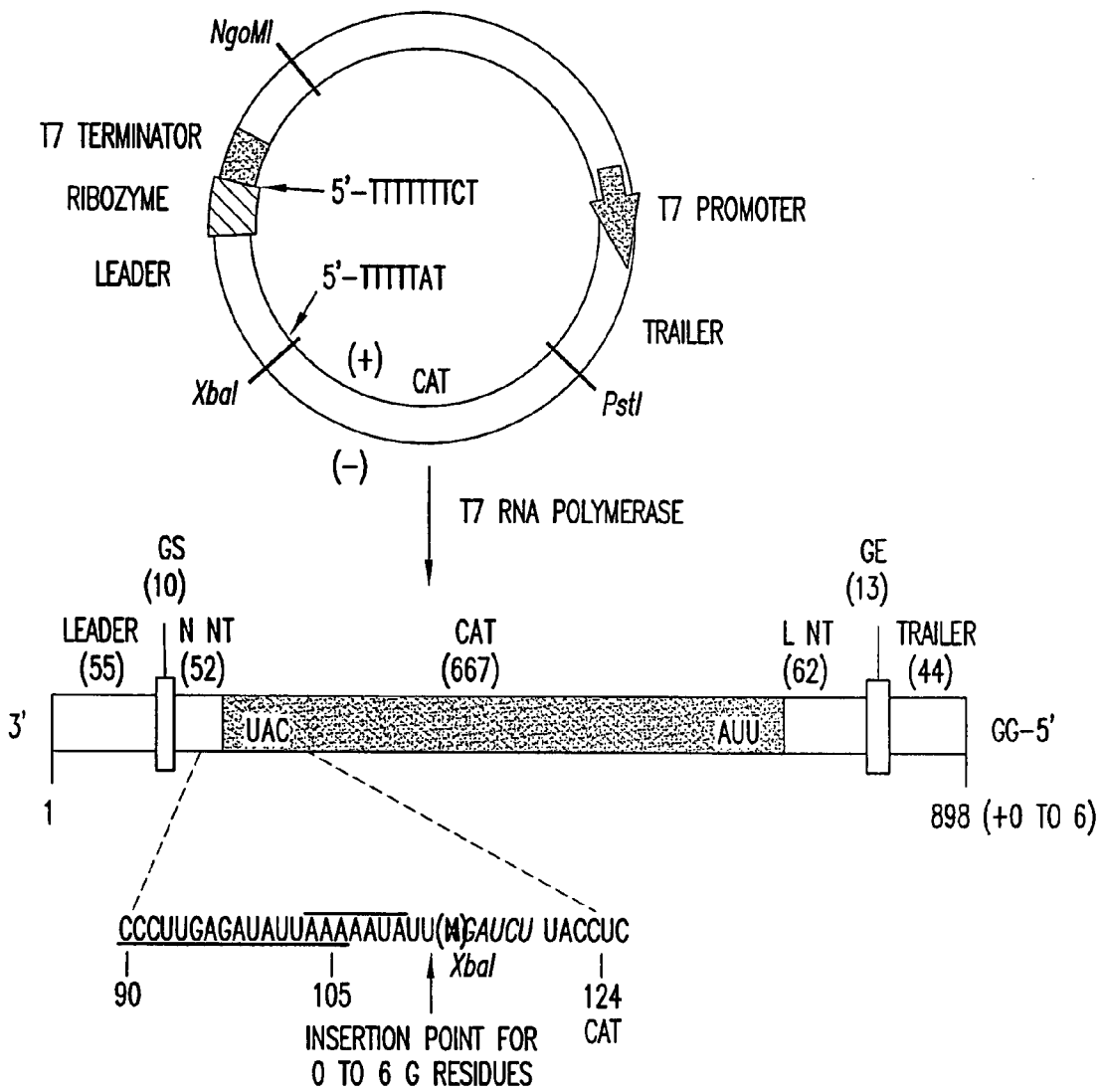

The PIV3-CAT-GG cDNA was further modified by overlapping PCR mutagenesis to introduce modifications simultaneously at two sites, as follows. First, the sequence $T_7CT$, which contains tandem transcriptional termination motifs for the vaccinia virus early-stage RNA polymerase ($T_5NT$) (Yuen and Moss, *Proc. Natl. Acad. Sci. U.S.A.* 84: 6417-6421 (1987), incorporated herein by reference in its entirety), was inserted into the positive-sense strand cDNA strand between the delta ribozyme and T7 transcriptional terminator (FIG. 1). This motif, and a second motif described herein below, were added to prevent promiscuous transcription of the CAT gene by the vaccinia virus early RNA polymerase. Second, the minigenome cDNA insert was modified at the junction between the N nontranslated region and CAT gene to contain (i) the insertion of a second vaccinia virus termination motif ($T_5AT$) into the positive-sense cDNA strand at positions 103 to 109 relative to the encoded minigenome, and (ii) the insertion of 0 to 6 G residues (negative-sense) at minigenome position 112 (FIG. 3). The overlapping PCR mutagenesis involved three sets of reactions (PCR 1, 2 and 3) performed as follows. PCR 1 was a set of seven parallel reactions [PCR1 (0) to (+6)] which used the PIV3-CAT-GG cDNA as a template and the following two mutagenic oligonucleotides as primers: the forward primer was: $^{-111}$GGGGTTATGCTACTG-CAGGCTTTTTTTCTCCCTTAGCCATCCG$^{-62}$ (SEQ ID NO: 69) and the reverse primer was: $^{124}$CTC CATTCTAGA(N)TTATAAAAATTATAGAGTTCCC$^{90}$ (SEQ ID NO: 70). The bold sequence in the first oligonucleotide is the upstream tandem vaccinia terminator, and the bold sequence in the second oligonucleotide is the second terminator. This reaction amplified the ribozyme and adjacent leader region and inserted the mutations described above. PCR 2 was a single reaction that used the PIV3-CAT-GG cDNA as a template, and a forward primer that hybridized in plasmid sequence upstream of a unique NgoMI site (FIG. 3), and a reverse primer complementary to the forward primer of reaction one. Thus, the products of PCR 1 and 2 overlapped at this latter sequence. The products of PCR 1 (0) to (+6) and PCR 2 were gel purified. The products of PCR1 (0) to (+6) were each mixed separately with an aliquot of PCR 2 product and amplified in a third reaction (PCR3 (0) to (+6)) which also contained the forward primer of PCR 2 and the reverse primer of PCR 1. The products of PCR3 (0) to (+6) were digested with NgoMI, which cuts in plasmid-specific sequence, and XbaI, which cuts at the upstream end of the CAT gene (FIG. 3), and cloned into the NgoMI-XbaI window of PIV3-CAT-GG. This resulted in a panel of cDNAs encoding minigenomes which were named according to the number of inserted G residues: PIV3-CAT 0 to PIV3-CAT +6. The structures of all DNA regions derived from PCR were confirmed by dideoxynucleotide sequencing.

C) Transfection

HEp-2 cells were grown to 90% confluence in 6 well plates. Each well of a six-well plate (1.5×106 cells) was transfected with 0.4 µg pTM(P), 0.4 µg pTM(N), 0.05 µg pTM(L), and 0.4 µg minigenome plasmid. The plasmids were added to 0.1 ml of OptiMEM (Life Technologies) and mixed with 0.1 ml of OptiMEM containing 12 µl of LipofectACE (Life Technologies). After an incubation period of approximately 15 minutes at room temperature, 0.8 ml of OptiMEM 1 containing 2% calf serum and 1.5×107 pfu of vTF7-3 was added to each well. The plates were incubated at 37° C. for 12 hours after which the media was replaced with fresh OptiMEM 1 containing 2% fetal bovine serum. The cells were then incubated at 37° C. for a total of 48 hours and harvested for RNA analysis and CAT assay. Each minigenome was represented in triplicate (3 wells) which was scraped into the medium and pooled.

D) CAT Assay

An aliquot representing 3.33% (1.5×105 cells) of each pooled sample of harvested cells described above was removed for CAT assay. The aliquot was centrifuged at 1,000 rpm for 5 minutes and the supernatant discarded. The cell suspension was washed with 1 ml of 40 mM Tris, pH 7.5, 1 mM EDTA, 150 mM NaCl and resuspended in 50 µl 0.25 M Tris, pH 7.5. Lysate was prepared by three cycles of freezing and thawing and clarified by centrifuging at 8,000 rpm for 5 minutes. 1 µl of lysate was assayed for the ability to acetylate D-threo-[dichloroacetyl 1-14C]chloramphenicol (Amersham) using a conventional assay (Gorman et al., Mol. Cell. Biol. 2: 1044-1051 (1982), incorporated herein by reference in its entirety). Acetylation was visualized by thin-layer chromatography and quantified by phosphoimager analysis (Molecular Dynamics, Sunnyvale, Calif.).

E) RNA Analysis

The remaining cell harvest of each pooled sample was divided into three equal parts for isolation of encapsidated RNA, total RNA, and mRNA. The three aliquots were centrifuged at 1,000 rpm for five minutes and the supernatants discarded. Two aliquots of cell suspension were resuspended in 50 µl of RSB (10 mM NaCl, 10 mM Tris, pH 7.5, 1.5 mM MgCl2) containing 1% Triton X-100, 0.5% DOC. 50 µl of 10 mM Tris 7.5, 1 mM CaCl2, and 20 µg (1 mg/ml stock) of micrococcal nuclease was then added to one aliquot, and the other received the same mixture without micrococcal nuclease (Baker & Moyer, J. Virol. 62: 834-838 (1988), incorporated herein by reference in its entirety). The purpose of the micrococcal nuclease was to destroy nonencapsidated RNA, and the conditions used had been optimized in preliminary experiments. The mixtures were incubated at 30° C. for 30 min and the RNA was isolated with Trizol (Life Technologies) according to the procedure of the supplier. The third aliquot of cell suspension was processed for RNA purification with Trizol and the purified RNA was separated by oligo(dT) cellulose chromatography into polyadenylated and nonpolyadenylated fractions (Grosfeld et al., J. Virol. 69: 5677-5686 (1995), incorporated herein by reference in its entirety). RNA samples were run on 1.5% agarose gels containing 0.44 M formaldehyde, transferred to nitrocellulose (Chomczynski, Anal. Biochem. 201: 134-139 (1992), incorporated herein by reference in its entirety), hybridized with strand specific riboprobes, and quantified by phosphoimager analysis.

Example III

Construction and Expression of Modified PIV3 Minigenomes

In the present example, a panel of cDNAs was constructed to encode PIV3 minigenomes which differed in length by single nucleotide increments. Transcription and RNA replication in this reconstituted system were the most efficient for the minigenome whose length was an even multiple of six. In this context, members of the Paramyxovirus and Morbillivirus genera typically abide by a "rule of six," i.e., genomes (or minigenomes) replicate efficiently only when their nucleotide length is a multiple of six (thought to be a requirement for precise spacing of nucleotide residues relative to encapsidating NP protein). However, the present findings illustrate that minigenomes whose lengths were one nucleotide greater than or less than an even multiple of six were surprisingly active, especially in RNA replication.

Figure 4:
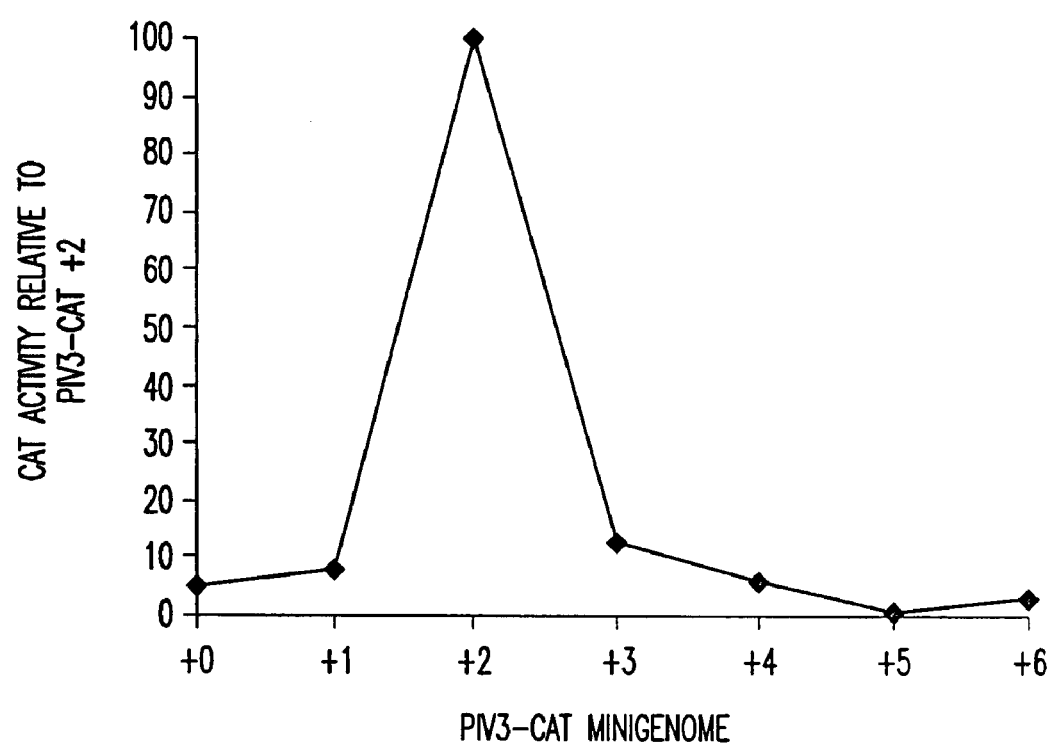

A panel of seven cDNAs was constructed to encode seven PIV3-CAT minigenomes, called PIV3-CAT 0 to +6, that differ in length by single-nucleotide increments (FIG. 3). Each minigenome is a short negative-sense analog of HPIV3 genomic RNA in which the viral genes had been deleted and replaced with a negative-sense copy of the CAT ORF. The CAT ORF is flanked by nontranslated segments of the N and L genes, the N GS and L GE transcription motifs, and the 3' leader and 5' trailer extragenic termini of genomic RNA. The 5' end of each PIV3-CAT minigenome is defined by the adjacent promoter for T7 RNA polymerase. This promoter was constructed to contribute an extension of two nonviral G residues to the 5' end of the encoded minigenome, as described above. The presence of additional G residues adjacent to the nontranscribed core of the T7 promoter improves its transcriptional efficiency, and preliminary work showed that presence of two G residues provided the highest levels of activity in the reconstituted system described below. These two G residues are not included in minigenome length calculations. The 3' minigenome end is created by self-cleavage by an abutting hepatitis delta virus ribozyme, which would generate the correct 3'-terminal nucleotide. The seven PIV3-CAT minigenomes differ by single-nucleotide increases in length due to the insertion of 0 to 6 G residues at the junction between the N nontranslated region and the CAT gene (FIG. 3), and range in length from 898 to 904 nucleotides. The PIV3-CAT +2 minigenome is the only one which is an even multiple of six (it should be noted that each minigenome contained two additional nonviral G residues at the 5' end contributed by the T7 promoter, but it is assumed that these would be lost during intracellular HPIV3-mediated RNA replication).

Each PIV3-CAT cDNA was transfected into HEp-2 cells that had been infected with vTF7-3, a vaccinia virus recombinant that expresses T7 RNA polymerase. Plasmids encoding the N, P and L proteins under the control of the T7 promoter were transfected in parallel. The P cDNA had been modified by site-directed mutagenesis to eliminate the translational start site of the C ORF, as described above. Cells were harvested at 48 h post-infection. An aliquot of the cell suspension was processed for CAT enzyme assay (FIG. 4). The remaining cells were divided into three equal aliquots and processed for RNA analysis as described below.

The minigenome cDNA was further modified to contain two tandem vaccinia virus early-gene transcription termination motifs ($T_7NT$) in the positive-sense plasmid strand upstream of the PIV3-CAT insert, and a third one ($T_5AT$) in the same strand immediately upstream of the CAT ORF (FIG. 3). These were designed to minimize promiscuous transcription of the CAT ORF by vaccinia virus polymerase (Grosfeld et al. (1995), supra). CAT expression was reproducibly detected when each of PIV3-CAT minigenomes was complemented by the N, P and L plasmids (FIG. 4), and detection of CAT was dependent on all three PIV3 proteins. However, expression was much higher for PIV3-CAT +2, which has a nucleotide length that is an even multiple of six. Preferred ratios and amounts of the minigenome and support plasmids were determined based on CAT enzyme expression.

Example IV

Synthesis of Positive-Sense RNAs by PIV Minigenomes

Transcription and replication of PIV minigenomes was confirmed by detection of RNA products of both processes. As described in the foregoing Example, three equal aliquots of cell suspension were taken for RNA analysis. One aliquot was used for oligo(dT) analysis, as described below. The other two aliquots were lysed with detergent and incubated with micrococcal nuclease or mock-treated. RNA was then isolated, separated by electrophoresis on formaldehyde agarose gels, transferred to nitrocellulose, and analyzed by hybridization with negative-sense CAT riboprobe. RNA from micrococcal-treated and mock-treated lysates are shown in FIG. 5A upper and lower panels, respectively.

Analysis of RNA from mock-treated lysates showed that complementation of each minigenome with the N, P and L plasmids resulted in the synthesis of a band of RNA which was very similar in size to a marker consisting of RNA expressed by the 931-nucleotide RSV-CAT C2 minigenome (Grosfeld et al. (1995), supra). Phosphorimagery analysis is shown in FIG. 5B. Little or no RNA was detected when the N or L plasmids were omitted, confirming that these RNAs are products of the reconstituted PIV3 polymerase.

Each PIV3-CAT minigenome is expected to encode two positive-sense RNAs, namely the mini-antigenome and the subgenomic CAT mRNA. Each mini-antigenome is expected to be the exact complement of its minigenome, which was 898 to 904 nucleotides in length. The predicted subgenomic mRNA is defined by the GS and GE signals, and is expected to be 804 nucleotides in length and contain a polyA tail of 100 to 200 nucleotides.

Detection of a single gel band of positive-sense RNA in FIG. 5A (lower panel) suggested that the antigenome and mRNA were not resolved by gel electrophoresis. Accordingly, treatment with micrococcal nuclease was used to identify antigenome RNA, since the antigenome (and genome) but not mRNA would be encapsidated and resistant to digestion. The use of micrococcal nuclease for this purpose is well established (Baker & Moyer (1988), supra), and the conditions selected were verified with RSV minireplicons and shown to completely degrade mRNA contained in the HEp-2 cell lysates. Residual RNA was purified and analyzed by Northern blot analysis with negative-sense riboprobe (FIG. 5A, upper panel) and quantitated by phosphorimagery (FIG. 5B; note that in this analysis the micrococcal-treated and untreated RNA amounts were normalized separately). These investigations revealed the presence of a population of protected RNA corresponding to the positive-sense encapsidated mini-antigenome. Among several experiments, this protected RNA accounted for approximately 3 to 15% of the positive-sense RNA.

For both the total and the micrococcal-resistant RNA, accumulation was greatest in the case of the +2 minigenome, which is 900 nucleotides in length and thus a multiple of six. However, substantial amounts of RNA also accumulated in the case of the minigenomes which did not exhibit a length corresponding to a multiple of six nucleotides, in particular minigenomes +1 and +3 which were one nucleotide longer or shorter than the +2 minigenome. In fact, the amount of encapsidated antigenome produced by the +1 and +3 mingenomes was 85% and 72% that of the +2 minigenome (FIG. 5B). Even the least efficient minigenome, the +5 minigenome, was 20% as active as the +2 minigenome as determined by measurement of accumulated encapsidated RNA. In the case of measurements to detect total positive-sense RNA, the +1 and +3 minigenomes produced 52% and 45% as much total RNA as the +2 minigenome.

To confirm the presence of subgenomic mRNA, the final aliquot of harvested cell suspension was processed for RNA purification. The RNA was then subjected to oligo(dT) chromatography. RNAs which failed to bind, and those which bound and were eluted in low salt buffer, were analyzed by Northern blot hybridization (FIG. 6A) and phosphorimagery (FIG. 6B; note that in this case the bound and unbound are normalized together relative to the bound RNA of the +2 minigenome). These assays showed that approximately 64% of positive-sense RNA was polyadenylated, as expected for subgenomic mRNA. The accumulation of mRNA was greatest for the +2 minigenome. However, substantial amounts of mRNA also were observed for the other minigenomes. The amount of mRNA synthesized by the +1 and +3 minigenomes was 30% and 20% respectively compared to that synthesized by the +2 minigenome, and was approximately 13% for the least active minigenomes.

Example V

Synthesis of Negative Sense RNA by PIV Minigenomes

The various PIV3-CAT minigenomes described in the foregoing examples directed synthesis of mRNA and positive-sense encapsidated mini-antigenome, the latter representing the first step in RNA replication. The second step in RNA replication involves synthesis of encapsidated progeny minigenome from the mini-antigenome product. To evaluate this latter process, the samples of RNA from mock-treated and nuclease-treated lysates described in the preceding Example were analyzed by Northern blot hybridization with positive-sense CAT riboprobe (FIG. 7A) and quantitated by phosphorimagery (FIG. 7B).

Analysis of RNA from mock-treated lysates (FIG. 7A, lower panel) showed that considerable amounts of minigenome accumulated intracellularly in all samples, including negative controls in which the N or L support plasmid was omitted. The analyses described in FIGS. 5A-B and 6A-B showed that the synthesis of positive-sense RNA was insignificant under these conditions. Therefore, the minigenome observed in the absence of N or L could not be the product of RNA replication mediated by the reconstituted HPIV3 polymerase, and instead must be the product of T7 transcription of transfected plasmid.

Minigenome produced by the reconstituted HPIV3 polymerase is expected to be encapsidated, whereas much of the minigenome produced by T7 RNA polymerase is expected to be unencapsidated. Therefore, RNA from the same micrococcal nuclease-treated samples described for FIGS. 5A-B were used to prepare a second blot, which was hybridized with positive-sense CAT riboprobe (FIG. 7A, upper panel). This showed that all minigenome RNA accumulated in the absence of the N protein was degraded (FIG. 7A, upper panel, lane 1), as expected. Essentially all of the minigenome which accumulated in the absence of L was also sensitive to degradation (FIG. 7A, upper panel, lane 2). Plasmid-derived minigenome synthesized in the absence of L, and in the presence of N and P alone, did not appear to occur efficiently.

When the complete set of three support plasmids was present, significant amounts of micrococcal nuclease-resistant minigenome RNA accumulated for each of the minigenomes (FIG. 7A, upper panel). As was the case with the positive-sense RNAs, the greatest amount of progeny minigenome was observed with the +2 minigenome. The +1 and +3 minigenomes were next in abundance, with levels of genomic RNA that were 67% and 42% of that of the +2 minigenome.

The foregoing examples demonstrate that the HPIV3 N, P and L proteins were necessary and sufficient for efficient transcription and RNA replication. The very robust nature of transcription and RNA replication mediated by the reconstituted PIV3 polymerase confirmed the functionality of the encoded proteins. It is further expected that inclusion of additional viral proteins within the expression system will augment or modify these processes. Coexpression of PIV C, D and potentially V, within the compositions and methods of the invention will be useful, e.g., to augment and/or modify RNA replication. For this purpose, plasmids will be constructed and assayed according to the foregoing methods to achieve coexpression of one or more of these elements to determine their effects on PIV transcription and RNA replication, as well as on PIV phenotype in suitable infection models.

Example VI

Construction of Infectious, Recombinant PIV from cDNA

The following examples describe production of infectious, recombinant PIV (rPIV) by intracellular co-expression of four plasmid-borne cDNAs. These cDNAs separately encode a complete HPIV3 genome and the HPIV3 nucleocapsid protein N, the phosphoprotein P, and the polymerase protein L.

A) Viruses and Cells

Modified vaccinia strain Ankara (MVA), the vaccinia virus recombinant that expresses bacteriophage T7 RNA polymerase, was provided according to Wyatt et al., *Virol.* 210: 202-205, 1995, incorporated herein by reference in its entirety. HEp-2 monolayer cultures were maintained at 37° C. in 5% $CO_2$ with OptiMEM 1 (Life Technologies) supplemented with 2% FBS, 50 μg/ml gentamicin sulfate and 2 mM glutamine. The JS wt strain of HPIV3 and its attenuated ts derivative, JS cp45, were propagated in LLC-MK2 cells as described by Hall et al., *Virus Res.* 22: 173-184, (1992), incorporated herein by reference in its entirety.

B) cDNAs

The full cDNA clone designated p218(131) (FIG. 1, SEQ ID NO: 71) encoding a complete genomic sequence of HPIV3 was constructed as described above. A second cDNA clone designated p3/7(131) (SEQ ID NO: 72) (deposited under the terms of the Budapest Treaty with the ATCC, and granted the designation 97990) was constructed to encode a complete antigenomic sequence of HPIV3. p3/7(131) differs from p218(131) in that the positions of the T7 promoter and the ribozyme/T7 terminator relative to the HPIV3 cDNA insert have been interchanged. Thus, the first nucleotide synthesized in p3/7(131) is the 5' end of the antigenome, namely the positive-sense complement of genome position 1, and the 3' antigenome end defined by ribozyme cleavage is the complement of genome position 15462. A third clone designated p3/7(131)2G (SEQ ID NO: 73) (deposited under the terms of the Budapest Treaty with the ATCC, and granted the designation 97989) was also constructed identical to p3/7(131), except that two G residues were inserted between the 5' end of the antigenome and the T7 promoter.

For construction of p/37(131)2G and p3/7(131), the two plasmids p(A*A'CC'D*E) and p(E*FF'GHIJKL*) were modified and joined to encode the complete positive-sense antigenome of HPIV3. First, the T7 terminator and delta ribozyme abutting the 3' end of HPIV3 in p(A*A'CC'D*E) were replaced by a T7 promoter using PCR (see FIG. 8). The positive-sense primer 5'-GGCCCGTCGACGCGTAATACGACTCACTATAGGACCAAACAAGAG-3' (SEQ ID NO: 74) placed the T7 promoter (bold) adjacent to the 3' leader of HPIV3 (HPIV3 sequence underlined) with 2 G residues inserted between these two elements to improve transcription. A unique Mlu I site (italicized) was placed upstream of the T7 promoter for cloning purposes (FIG. 8). The negative-sense primer 5'-$^{1224}$CGGCATCACGTGCTAC$^{1209}$-3' (SEQ ID NO: 75) spanned nt 1209-1224 of the HPIV3 N gene and included a unique Pml I site (italicized) present in the natural HPIV3 sequence. Both the PCR product and the parent template p218(A*A'CC'D*E) were digested with Mlu I and Pml I and the PCR product was then cloned into the Mlu I-Pml I window. A second PCR reaction was done using the same negative-sense primer and a positive-sense primer without 2G residues inserted between the T7 promoter and 3' end of HPIV3. These plasmids were designated p(Left +2G) and p(Left+). The construction of p(Left+2G) is illustrated in FIG. 8, the construction of p(Left+) followed the same strategy.

Plasmid p(E*FF'GHIJKL*) was modified by PCR to place the delta ribozyme and T7 terminator adjacent to the 5' end of HPIV3 (FIG. 9). The positive-sense primer: 5'-GGATTTGCGCGC$^{14813}$AATTTAAATCATCTGG$^{14828}$-3' (SEQ ID NO: 76) introduced a BssH II site (italicized) just upstream of a unique Swa I site (italicized, underlined) in the L gene of HPIV3 (HPIV3 specific sequence is underlined). The negative-sense primer: 5'-CCCAGGTCGGACCGCGAGGAGGTGGAGATGCCATGCCAGCCC$^{15462}$ACCAAAACAAGAGAAGAACTCTGTTTGG$^{15435}$-3' (SEQ ID NO: 77) placed a portion of the delta ribozyme (bold) which included a naturally-occurring unique Rsr II site (italicized) adjacent to the 5' end of the HPIV3 genome (negative-sense underlined). This PCR product was digested with BssH II and Rsr II and cloned into the BssH II-Rsr II window of plasmid p3/7 (FIG. 9). Plasmid p3/7 is identical to p218 except that the delta ribozyme and T7 terminator are in the reverse orientation. The p3/7 plasmid containing the above-mentioned insertion was designated pPIV3-3/7 and contained the complete delta ribozyme and T7 terminator adjacent to 5' terminal 651 nucleotides of HPIV3. The SwaI and NgoMI fragment of plasmid pPIV3-3/7 was then isolated and cloned into the SwaI-NgoM I window of p(E*FF'GHIJKL*). The resulting plasmid, designated p(Right+) placed the complete delta ribozyme and T7 terminator adjacent to the 5' end of HPIV3 (see FIG. 9). The Xho I-NgoM I fragment of p(Right+) was cloned into the Xho I-NgoM I window of p(Left+) and p(Left+2G) resulting in plasmids p3/7(131) (SEQ ID NO: 72) and p3/7(131 2G) (SEQ ID NO: 73), respectively (FIG. 10). These each encode the complete positive-sense analog of HPIV3 antigenomic RNA, with the latter cDNA containing two G residues adjacent to the T7 promoter for improved transcriptional efficiency.

C) Transfection

HEp-2 cells were grown to 90% confluence in six well plates. Each well of a six-well plate ($1.5\times10^6$ cells) was transfected with the three previously-described support plasmids, 0.4 μg pTM(P), 0.4 μg pTM(N), 0.05 μg pTM(L), together with 5 μg of full-length genomic or antigenomic HPIV3 cDNA. The plasmids were added to 0.2 ml of OptiMEM 1 (Life Technologies) containing 12 μl of LipofectACE (Life Technologies). After an incubation period of approximately 15 minutes at room temperature, 0.8 ml of OptiMEM 1 containing 2% fetal bovine serum and $1.5\times10^7$ pfu of MVA-T7 was added to each well. The cultures were incubated at 32° C. for 12 hours, after which the media was replaced with fresh OptiMEM 1 containing 2% fetal bovine serum. The cultures were incubated at 32° C. for three additional days then harvested and passaged (referred to as passage 1) onto fresh HEp-2 monolayers. These passage 1 cultures were incubated at 32° C. for five days, and virus present in the culture was harvested, passaged once in LLC-MK2 cultures, and characterized by hemagglutination-inhibition (HAI) as described (van Wyke Coelingh et al., *Virol.* 143: 569-582, (1985) (incorporated herein by reference in its entirety) to determine if it possessed the monoclonal antibody resistant mutation (MARM) that marked virus recovered from cDNA.

D) Sequencing of Recombinant Virus

The presence of nucleotide sequence markers in the HN and L genes of recombinant PIV was determined by RT-PCR of RNA isolated from recovered virions. 1 ml of rPIV ($1\times10^5$ pfu/ml, passage level 2) was precipitated with 200 μl 25% polyethylene glycol by incubation on ice for one hour and centrifuging at 12,000 g for 15 minutes. The RNA was purified with TRIzol reagent (Life Technologies) following the manufacturer's recommended procedure. RT-PCR was performed with the Superscript kit (Life Technologies) following the manufacturer's recommended protocol. Control reactions were identical except that reverse transcriptase was omitted from the reaction to confirm that the PCR products were derived solely from virus RNA and not from possible contaminating cDNA plasmids. Four primer pairs were used to generate PCR products from nt 7334-8715, 9364-10854, 10939-15392, and 13623-15392. The resultant PCR products were then sequenced using cycle dideoxynucleotide sequence analysis (New England Biolabs, Beverly, Mass.).

Example VII

Recovery of Recombinant Virus from cDNA Encoding Negative-Sense Genomic RNA

Plasmid p218(131) and the three support plasmids pTM (N), pTM(P), and pTM(L) were transfected into HEp-2 cells with MVA expressing T7 RNA polymerase. A control group consisting of pTM(N), pTM(P), pTM(L), and MVA was cotransfected into HEp-2 cells without p218(131). On day four, the transfection was harvested, passaged onto fresh HEp-2 cell monolayers for five days, and passaged again for 5 days in LLC-MK2 cultures (passage 2). Virus present in the passage 2 harvest was further characterized by HAI. Cultures from the transfection group which received the three support plasmids without the full-length genomic clone p218(131) did not yield HPIV3. The rPIV recovered virus was confirmed to be HPIV3 since it reacted in the HAI assay with the mAbs 77/5, 101/1, and 454/11 which are specific for HPIV3 (Table 1). It was presumptively identified as being cDNA-derived because it failed to react with mAbs 170/7 and 423/6, consistent with the MARM mutation which had been introduced into the cDNA.

TABLE 1 rJS-NS Contains the MARM Mutation Introduced into the p218(131) Full-Length Negative Sense cDNA

| | Hemagglutination-inhibiting | | Antibody Titer (Reciprocal) of Indicated mAb | | |
|---|---|---|---|---|---|
| Virus | 77/5[1] | 101/1[1] | 454/11[1] | 170/1[2] | 423/6[2] |
| JS wt[3] | 800 | 6400 | 6400 | 25,600 | 25,600 |
| rJS-NS[4] | 3200 | 25,600 | 6400 | ≦25 | ≦25 |

[1]mAb 77/5 recognizes antibody epitope IIB, mAbs 101/1 and 454/11 recognize antibody epitope IIIA of HN glycoprotein, all of which were not altered in p218(131).
[2]Mabs 170/7 and 423/6 which both recognize antibody epitope I of JSwt, fail to recognize rJS due to the MARM mutation at this site.
[3]Biologically derived wild type HPIV3 JS.
[4]Recombinant JS virus derived from negative-sense genomic cDNA.

To confirm that rPIV was indeed recovered from cDNA, it was analyzed in parallel with wild-type JS strain HPIV3 by RT-PCR using four primer pairs flanking the seven inserted marker mutations. Each PCR product obtained was dependent upon the inclusion of RT, indicating that each was derived from RNA and not from contaminating cDNA. Cycle-sequencing of the four PCR products confirmed that the sequence of the rPIV contained each of the seven markers, sequencing data showing three of the markers is illustrated in FIG. 11. The sequence differences between rPIV and JS wt in the HN gene, including nt 7903, 7913, and 7915 are readily apparent. Similar sequence analyses were carried out for the other four markers at nt positions 7593, 10355, 11333, and 15248, and the rPIV possessed each mutation.

These results demonstrate successful recovery of infectious rPIV from cDNA encoding a negative-sense genomic RNA. This differs from most published reports for recovery of nonsegmented negative strand RNA viruses, in which the cDNA used for virus recovery had been designed to encode positive-sense antigenomic RNA (Baron and Barrett, supra, 1997; Collins et al., supra, 1995; Conzelmann, supra, 1996; Garcin et al., supra, 1995; Lawson et al., supra, 1995; Radecke et al., supra, 1995; Whelan et al., supra, 1995). The recovery of infectious virus from a cDNA encoding genomic RNA had previously been reported only in the case of Sendai virus, and the efficiency of recovery was much lower than for cDNA encoding antigenomic RNA (Kato et al., 1996). In most other studies, the recovery of virus was achieved with antigenomic cDNA but not with genomic cDNA (Lawson et al., 1995; Whelan et al., 1995). A number of potential problems have been noted which may explain these refractory results, including possible annealment of cDNA-encoded genomic RNA with mRNA produced by the support plasmids; resulting in inactive hybrids (Conzelmann, supra, 1996; Lawson et al., supra, 1995). It has also been noted that T7 RNA polymerase appears to terminate preferentially at the gene junctions of genomic RNA, perhaps because the oligo U tract of the GE signal resembles the natural signal for transcription termination by T7 RNA polymerase (Whelan et al., supra, 1995).

Example VIII

Recovery of Recombinant Virus from cDNA Encoding Positive-Sense Antigenomic RNA

As described in more detail above, p3/7(131) and p3/7(131)2G were constructed to encode a positive-sense, antigenome that give rise to recombinant PIV. Plasmid p3/7(131)2G is identical to p3/7(131) but for the addition of two G residues between the T7 promoter and the first nucleotide of the antigenome. The addition of two G residues between the T7 promoter and the first HPIV3 nucleotide p3/7(131)2G is based on the preceding examples demonstrating that the presence of the two added G residues (as opposed to 0, 1 or 3 added G residues) yielded substantially increased levels of minireplicon replication.

The two antigenome cDNAs [p3/7(131) and p3/7(131)2G] were transfected separately into cells together with the N, P and L support plasmids, and were infected simultaneously with the MVA-T7 recombinant virus using the same procedure described above for p218(131). Infectious virus from each antigenomic cDNA was recovered and was presumptively identified as being cDNA-derived by its inability to react with mAbs 423/6 and 170/7.

The efficiency of virus recovery was evaluated for each of the antigenome cDNAs versus the genome cDNA p218(131). Twelve transfection reactions using the negative-sense genome cDNA p218(131) (SEQ ID NO: 71) were conducted in parallel with twelve transfections using the positive-sense antigenome cDNA p3/7(131)2G (SEQ ID NO: 73) to compare efficiency of virus recovery from the two cDNAs. One ml of the transfection harvest from each well was titered on LLC-MK2 cells and the remaining 2 mls were passaged (passage 1) onto fresh LLC-MK2 cells. At day five, passage 1 was harvested and titered as described above. Recombinant virus was recovered from 12/12 wells transfected with p3/7(131)2G but from only 4/12 wells transfected with p218(131). The mean titer of virus present in culture of the passaged virus from the positive-sense antigenome was $10^{5.0}$, nearly ten-fold higher than that from the negative-sense genome, which was $10^{4.1}$. However, with one additional amplification the titers became equivalent.

TABLE 2

Comparison of the Efficiency of Recovery of Recombinant Virus from cDNAs Encoding Genomic or Antigenomic RNA, the latter with or without 2G residues adds to the T7 promoter.

| Experiment# | Transfected cDNA | Sense of Encoded RNA | Rescue Efficiency[1] | Mean Titer ($log_{10}$ pfu/ml) of Recovered Virus[2] |
|---|---|---|---|---|
| #1 | p3/7(131)2G[3] | Antigenomic | 12/12 (100%) | 5.0 ± 0.27 |
| | p218(131) | Genomic | 4/12 (33%) | 4.1 ± 0.27 |
| #2 | p3/7(131)2G[3] | Antigenomic | 6/6 (100%) | 6.6 ± 0.18 |
| | p3/7(131) | Antigenomic | 12/12 (100%) | 5.3 ± 0.12 |
| | p218(131) | Genomic | 5/5 (100%) | 4.9 ± 0.19 |

[1]Number of transfection cultures yielding rJS/number tested.
[2]The mean Titer ± standard error was determined following one passage of transfection harvest for five days in LLC-MK2 cells.
[3]Contains 2 G residues between the T7 promoter and the 5' end of the antigenome.

The efficiency of recovery of recombinant virus from the three full-length plasmids encoding the genomic or antigenomic HPIV3 RNAs was next studied, (i) to determine whether genomic or antigenomic cDNA is more efficient at generating recombinant virus and (ii) to determine the effect of two extra 5' terminal G residues on the yield of recombinant viruses (Table 2.) Unfortunately, it was not possible to directly titer the transfection harvest by plaque titration because residual MVA-T7 interfered with plaque formation of rJS on LLC-MK2 monolayer cultures. Therefore, we first compared the efficiency of recovery of rJS from multiple independent transfections and, as seen in other experiments, found that rJS was more frequently recovered from cultures transfected with p3/7(131)2G than from cultures transfected with p218(131). Since each transfection harvest, including those with p218(131) yielded rJS in other experiments, it was not possible to use this method of analysis to compare the relative efficiency of generating recombinant virus. We therefore estimated the relative quantity of virus present in the transfection harvest by quantitating the amount of virus following one passage of the transfection harvest (Table 2). Since each plasmid was designed to yield an identical virus (rJS), differences in titers of the passaged virus were considered a reflection of differences in the titer of virus present in transfection harvest. In the above experiments, the construct with two 5' terminal G residues was the most efficient in generating rJS. This indicated that the two added residues indeed increased efficiency of recovery, but the mechanism for this small increment in efficiency was not defined. These findings indicate a small, but measurable, advantage of using p3/7(131)2G as substrate for future experiments designed to introduce mutations into the HPIV3 cDNA. The small advantage in recovery of recombinant virus from p3/7(131)2G might be especially needed to recover viruses that have attenuating mutations that restrict replication in vitro. Although VSV has been recovered from antigenomic cDNA which included three G residues at the 5'-terminal end, the efficiency of recovery of virus from this construct was not compared with recovery from the same construct lacking the extra residues (Whelan et al., *Proc. Natl. Acad. Sci. USA* 92:8388-8392 (1995), incorporated herein by reference). In contrast to the experience with Sendai virus and measles virus, it is clear that extra-viral G residues at the 5'-terminal end of the antigenome are not deleterious to recovery of recombinant virus, and, in fact, appear to be advantageous [Garcin et al., supra, 1995; Radecke et al., supra, 1995; Kato et al., 1996). The genomic and antigenomic plasmids without two 5'-terminal guanine residues appeared equally efficient in generating recombinant virus. This is in contrast to previous reports which have found genomic cDNA to be less efficient than antigenomic cDNA in generating recombinant virus (Whelan, 1995; Kato et al., 1996).

The efficiency of recovery of virus from p3/7(131) (SEQ ID NO: 72) was compared to that of p3/7(131)2G (SEQ ID NO: 73 and p218(131) (SEQ ID NO: 71) in a similar experiment as above. Recovery from p3/7(131) was comparable to that of p217(131). Recovery was more consistent and efficient with both antigenome cDNAs containing the extra Gs (Table 2).

Example IX

Efficiency of Plaque Formation of rPIV at Permissive and Restrictive Temperatures The level of temperature sensitivity of replication in vitro of control viruses and rPIV derived from both p218(131) and p3/7(131)2G was determined at 32° C., 37° C., 39° C., and 40° C. in LLC-MK2 monolayer cultures as previously described (Hall et al., *Virus Res.* 22: 173-184, (1992), incorporated herein by reference in its entirety), with the following modifications. Viruses were inoculated onto LLC-MK2 monolayers on 24-well plates in serial 10-fold dilutions allowed to adsorb for one hour at room temperature. The cultures were then overlaid with 1 ml of L-15 supplemented with 2 mM glutamine and 0.8% methylcellulose and the plates were then incubated for 5 days at the indicated temperature. The methylcellulose overlay was removed and the monolayer fixed with 80% methanol at 4° C. for 1 h. The viral plaques present in the monolayer were scored using a mixture of two HPIV3-specific anti-HN murine mAbs 101/1 and 66/4 as ascites fluid used at a dilution of 1:500, using an immunoperoxidase method of staining specific for murine antibodies as previously described (Murphy et al., Vaccine 8: 497-502 (1990), incorporated herein by reference in its entirety).

Recombinant virus derived from either positive or negative-sense cDNA were characterized by plaque assay at 32° C., 37° C., 39° C., and 40° C. to determine if they were phenotypically similar to JS wt virus. Both positive and negative-sense rPIV were comparable to the JS wt virus in their level of replication at elevated temperatures of 39° C. and 40° C. (Table 3). This is in contrast to the ts mutant JS cp45 which exhibits a 30-fold reduction in titer at 37° C. and fails to produce plaques at 39° C. or 40° C.

TABLE 3

The rJS Resembles its Biologically Derived Parent JS Wild-Type Virus in the Level of Replication at Restrictive Temperature (39° C.-40° C.)

| Virus | Virus Titer (log 10 pfu/ml) | | | |
|---|---|---|---|---|
| | 32° C. | 37° C. | 39° C. | 40° C. |
| rJS-PS[1] | 6.1 | 6.1 | 6.1 | 6.6 |
| rJS-NS[2] | 6.9 | 7.1 | 7.1 | 7.0 |
| JScp45[3] | 6.3 | 4.3 | <0.7 | <0.7 |
| JS wt | 6.5 | 6.8 | 6.6 | 6.7 |

[1]Recombinant virus derived from the antigenomic-sense clone p3/7(131)2G
[2]Recombinant virus derived from the genomic-sense clone p218(131)
[3]JScp45 is a temperature sensitive mutant derived from JS wt.

The sequence of JS cp45 has been fully determined (Stokes et al., supra, 1993) and mutations have been identified in the leader, N, P, M, F, HN, and L genes. However, it is unknown which mutation(s) are responsible for the ca, att, or ts phenotypes. Because exemplary rPIV of the invention demonstrate the ts+ phenotype like the JS wt parent, cp45 mutations among other mutations known or yet to be discovered for PIV can be introduced, alone or in combination, into the full-length cDNA to pinpoint the effects of individual mutations or combinations thereof, e.g., by evaluating replication of the recombinant virus incorporating the mutation(s) of interest at elevated temperatures. The mutation(s) thus identified can be incorporated into effective, attenuated vaccine agents as described in the Examples below. These and other mutations incorporated into recombinant PIV can be further optimized by, e.g., mutagenesis to create two or more nucleotide substitutions per codon to render a recombinant virus that is more genetically stable than a biologically derived mutant strain.

Example X

Replication of rPIV in Hamsters

Thirty-six 16-week-old golden Syrian hamsters were divided into four groups of nine and inoculated intranasally with 0.1 ml containing $10^{5.5}$ pfu of either rPIV recovered from negative-sense cDNA, rPIV recovered from positive-sense cDNA, JS cp45, or JS wt virus. On day 4, the hamsters were sacrificed and the lungs and nasal turbinates harvested. The lungs were homogenized in a 20% w/v L-15 suspension containing 2.5 µg/ml amphotericin B (Quality Biologicals, Gaithersburg, Md.), 2001 g/ml pipericillin (Lederle Laboratories, Pearl River, N.Y.), and 50 µg/ml gentamicin (Quality Biologicals). The nasal turbinates similarly were homogenized in a 10% w/v L-15 suspension. After homogenization, the samples were aliquoted and rapidly frozen in a dry ice-ethanol bath. Virus present in the samples were titered at a later date in 96 well plates of LLC-MK2 cells at 32° C. scoring CPE at five and seven days after inoculation. The mean $\log_{10} TCID_{50}$/gm was calculated for each group of nine hamsters.

Table 4 illustrates that rPIV recovered from negative-sense cDNA, rPIV recovered from positive-sense cDNA replicate to substantially the same level as the JS wt in the upper and lower respiratory tract of hamsters. This is in contrast to the JS cp45 virus, which is attenuated at each site.

TABLE 4

The rJS Resembles its Biologically Derived Parent JS wt Virus in the Level of Replication in the Upper and Lower Respiratory Tract of Hamsters.

| | Mean Virus Titer ($\log_{10} TCID_{50}$/g)[5] | |
|---|---|---|
| Virus | Nasal Turbinates | Lungs |
| rJS-PS[1] | 6.6 ± 0.2 | 4.1 ± 0.3 |
| rJS-NS[2] | 6.4 ± 0.1 | 4.2 ± 0.2 |
| JScp45[3] | 4.2 ± 0.2 | ≦1.4 ± 0.0 |
| JS wt[4] | 6.3 ± 0.2 | 4.6 ± 0.3 |

[1]Recombinant virus recovered using p3/7(131)2G encoding the positive-sense HPIV3 antigenome.
[2]Recombinant virus recovered using p218(131) encoding the negative-sense HPIV3 genome.
[3]Biologically derived ts mutant.
[4]Biologically derived parent virus.
[5]Mean titers ± standard errors for nine hamsters per group.

Thus, exemplary rPIVs of the invention can retain the replicative capacity in hamsters exhibited by the biologically derived JS wt parent strain, whereby mutations such as those present in the JS cp45 candidate vaccine that restrict replication in hamsters and other hosts, including non-human primates and humans, can be identified and incorporated within modified rPIV strains of the invention, as described in FURTHER Examples herein.

Example XI

Identification of Amino Acid Substitutions in HPIV3 Specifying Attenuated Phenotypes, and Incorporation of Attenuating Mutations into Infections, Attenuated PIV Clones The ability to generate infectious PIV from cDNA facilitates development of live-attenuated parainfluenza virus vaccines. More specifically, by using the methods and tools disclosed herein the genetic basis of attenuation of PIV candidate vaccines can be readily determined, and infectious PIV vaccines produced from cDNA can be designed to achieve a finely calibrated level of attenuation and immunogenicity.

In addition, the tools and methods of the invention provide for vaccine development for all three human parainfluenza viruses, HPIV1, HPIV2 and HPIV3 that are most important in human disease. For example, to produce and select effective HPIV3 vaccine agents within the invention, mutations associated with desired phenotypes of biologically deriving HPIV3 candidate vaccines or the attenuated BPIV3 virus, e.g. attenuating mutations, can be identified and incorporated into rPIV. Applying these methods, attenuating mutations from a large menu of candidate mutations are selected and combined to generate rPIV having a desired balance between attenuation and immunogenicity, and which retain the attenuation phenotype following replication in humans.

In the present example, the genetic bases of temperature-sensitive (ts) and in vivo attenuation (att) phenotypes of the PIV3 JS cp45 live-attenuated virus are described. Seven exemplary recombinant PIV3 viruses (three single-, three double-, and one triple-lesioned virus) were recovered from full-length antigenomic cDNA and analyzed for their ts and att phenotypes. These recombinants bore one or more amino acid substitution mutations present in the L gene of JS cp45 (alternatively referred to herein as cp45), adopted within a cDNA clone of the JS wt parent. These three exemplary, biologically derived mutations are all present in a representative strain of JS cp45 grown in Vero cells, designated JS cp45 Vero, deposited on Aug. 21, 1997 under the terms of the Budapest Treaty with the American Type Culture Collection (ATCC) of 12301 Parklawn Drive, Rockville, Md. 20852, U.S.A., and granted the accession number ATCC VR 2588.

Analyses of exemplary PIV recombinants, presented below, demonstrate that each of the three exemplary mutations in L (Tyr$_{942}$ to His, Leu$_{992}$ to Phe, and Thr$_{1558}$ to Ile) contribute to the ts and att phenotypes of cp45 and are useful for generating of recombinant vaccine virus.

Viruses and Cells.

The PIV3 JS wt and cp45 viruses were grown in LLC-MK2 cells as described previously (Hall et al., Virus Res. 22:173-184 (1992), incorporated herein by reference). The vTF7-3 recombinant vaccinia virus is described in Fuerst et al., Virology 225: 419-422 (1996) and the modified vaccinia virus Ankara (MVA) which expresses the T7 polymerase is described in Wyatt et al., Virology 210:202-205 (1995) (each incorporated herein by reference). HEp-2 (ATCC CCL 23) and LLC-MK2 (ATCC CCL 7.1) cells were maintained in OptiMEM (Life Technologies) supplemented with 2% FBS and gentamicin sulfate (50 ug/mL).

Construction of Point Mutations in the L Gene of PIV3.

pUC19 was modified to accept a fragment of the JS wt PIV3 L gene in order to introduce point mutations into the L gene by site-directed mutagenesis. First, a unique Nhe I restriction site was introduced into pUC19 by ligating a pair of complementary oligonucleotides (5' GATCGAT-GCTAGCCC 3' (SEQ ID NO: 78) and 5' GATCGGGCTAG-CATC 3' (SEQ ID NO: 79)) containing an Nhe I restriction site into the Hind III site of pUC19 to create pUC19 (N). The Sph I (PIV3 nt 11317) to Nhe I (PIV3 nt 14087) fragment of pTM(L), which includes the positions where the three coding changes in cp45 occur and which can be directly introduced into the full-length PIV3 cDNA (see below), was cloned into the Sph I and Nhe I site of pUC19 (N) to create pUCL(N-S). Point mutations were introduced into pUCL(N-S) using mutagenic oligonucleotides with the Transformer mutagenesis kit (Clontech, Palo Alto, Calif.) for the purpose of (i) creating exemplary amino acid substitutions at L protein positions 942, 992, and 1558, individually and in combination, and (ii) ablating one specific naturally-occurring restriction enzyme site proximal to each codon substitution as a marker [See Table 5].

TABLE 5

Nucleotide substitutions introduced into rPIV3 that encode cp45L protein gene amino acid substitutions and, as markers, ablate naturally-occurring restriction enzyme sites.

| rPIV3 designation | Amino Acid Substitution (wt to cp45) | Sequence of wt$^a$ | Sequence of Mutant | Restriction Enzyme site Ablated |
|---|---|---|---|---|
| r942 | Tyr-942 to His | 11468-TTACATGGCCAT (SEQ ID NO: 80) | 11468-TCACATGGCGAT (SEQ. ID NO: 81) | Eae I |
| r992 | Leu-992 to Phe | 11618-TTTTGA*TT*GGGC (SEQ ID NO: 82) | 11618-TTTTGA*TT*GGGC (SEQ. ID NO: 83) | Bsr I |
| r1558 | Thr-1558 to Ile | 13307-T*GG*TCCTAATACTG (SEQ. ID NO: 84) | 13307-TGGGCCTAATATCG (SEQ. ID NO: 85) | Ava II |

$^a$The nucleotide sequence around each of the three mutated regions is shown. The first nucleotide in each provided sequence is numbered according to its position in the complete antigenomic RNA. The codon involved in each amino acid substitution is in bold. Naturally-occurring restriction enzyme sites present in the wt sequence, and which were ablated to mark the mutation, are in italics. The nucleotides that were mutated to produce an aa substitution or remove a restriction enzyme site are underlined Mutations introduced in pUCL(N-S) derivatives were verified by dideoxynucleotide sequencing of plasmid DNA. The Sph I to BamHI (nt 13733) fragment of pUCL(N-S) containing the cp45 individual L gene mutations was subcloned into the Sph I to BamHI sites of pTM(L) to give pTM(L)-942, -992, -942/992, and -1558; the other double and triple mutations were assembled using the Pin AI and Nhe I sites (FIG. 12). The mutant pTM(L) plasmids were each tested at permissive temperature (32° C.) for the ability to direct the expression of the chloramphenicol acetyl transferase marker gene in a minireplicon system comprising a plasmid-encoded minigenome RNA and the N, P and L proteins (Durbin et al., Virology 234:74-78 (1997), incorporated herein by reference). The various mutant L plasmids supported marker gene expression to 75-106% the level of wt L, indicating that each engineered cDNA was free of significant spurious mutation (not shown). The Sph I to Nhe I fragments of each of the mutant pTM(L) plasmids were then subcloned into the Sph I to Nhe I window of the full-length PIV3 JS antigenomic cDNA p3/7(131)2G to create seven full-length PIV3 cDNA clones representing every possible combination of the three substitutions.

Recovery of Recombinant PIV3 (rPIV3) Bearing One, Two or Three cp45 L Protein Substitutions.

Each full-length antigenomic cDNA bearing one or more cp45 L gene mutations, together with the three support plasmids pTM(N), pTM(P) and pTM(L), was transfected into HEp-2 cells on 6-well plates (Costar, Cambridge, Mass.) using LipofectACE (Life Technologies) and MVA-T7 as described above. After incubation at 32° C. for 4 days, the transfection harvest was passaged onto HEp-2 cells on 6-well plates which were incubated at 32° C. for 4 days. Each passage 1 supernatant was harvested and passed onto a T-25 flask of LLC-MK2 cells, which was incubated at 32° C. for 5-6 days. The passage 2 supernatant was harvested and the presence of recombinant virus was initially confirmed by immunoperoxidase staining of virus plaques (Murphy et al., Vaccine 8:497-502 (1990), incorporated herein by reference) with anti-HN monoclonal antibody (Mab) 77/5, which binds to both biologically derived and recombinant JS PIV3, and Mab 423/6, which does not bind to cDNA-derived virus because its epitope was ablated to serve as a marker. Virus present in passage 1 was subjected to two or three rounds of plaque purification on LLC-MK2 cells as described previously. Each biologically cloned recombinant virus was amplified twice in LLC-MK2 cells at 32° C. to produce virus for further characterization. Virus was concentrated from clarified medium by polyethylene glycol precipitation, and viral RNA (vRNA) was extracted with Trizol Reagent (Life Technologies). Reverse transcription (RT) was performed on vRNA using the Superscript II kit with random hexamer primers (Life Technologies). The Advantage cDNA PCR kit (Clontech, Palo Alto, Calif.) and sense (5' nt 11190-GCATTATCTAGATGTGTCTTCTGGTCAGAG 3' nt-11219) (SEQ ID NO: 182) and antisense (5' nt 14140-CCTGAATTATAATAATTAACTGCAGGTCCT 3' nt-14111) (SEQ ID NO: 86) primers specific for the PIV3 L gene were used to amplify the region spanning the Sph I to Nhe I fragment. The PCR fragments were analyzed by digestion with each of the restriction enzymes whose recognition sites had been ablated during insertion of the three cp45 mutations in L (see Table 5). Efficiency of Plaque Formation (EOP) at Permissive and Restrictive Temperatures of rPIV3 Bearing One, Two or Three cp45 L Protein Amino Acid Substitutions.

The level of temperature sensitivity of plaque formation in vitro of control and recombinant viruses was determined at 32° C., 37° C., 38° C., 39° C., 40° C., and 41° C. in LLC-MK2 monolayer cultures and plaques were enumerated by hemadsorption with guinea pig red blood cells following removal of the methylcellulose overlay. Alternatively, viral plaques present in the monolayer were identified by immunoperoxidase staining with a mixture of two PIV3-specific anti-HN murine mAbs 101/1 and 454/11 diluted 1:500, (Murphy et al., supra, (1990)).

Hamster Studies.

4 to 16 week-old golden Syrian hamsters in groups of six were inoculated intranasally with 0.1 ml OptiMEM1 per animal containing $10^{5.5}$ pfu of rPIV3 JS wt, PIV3 cp45 virus, or one of the rPIV3 containing one or more cp45 L protein substitution(s). On day 4 post-infection, the hamsters were sacrificed, the lungs and nasal turbinates were harvested, and the virus was quantified as described above. The mean $\log_{10}$ $TCID_{50}/g$ was calculated for each group of six hamsters.

Results

Introduction of the PIV3 cp45 L Protein Amino Acid Substitutions into wt JS rPIV3.

As noted above, the three amino acid substitutions present in the L protein of cp45 (Table 5) were introduced individually or in selected combinations into the antigenomic cDNA that encodes its wt parent, PIV3 JS strain. Each introduced mutation was engineered to be marked with a silent mutation that ablated a proximal, naturally-occurring restriction enzyme site to facilitate monitoring the mutation in recovered rPIV3 (Table 5, FIG. 12). The coding change at amino acid 1558 was designed to contain two nucleotide changes in r1558, compared to the one nt substitution in cp45, to reduce the chance of reversion at this site during in vitro or in vivo replication.

Seven rPIV3s bearing one, two or all three of the amino acid substitutions from cp45 were recovered in tissue culture by transfection of each antigenomic cDNA together with the pTM(N), pTM(P) and pTM(L) support plasmids and coinfection with the vaccinia virus MVA/T7 pol recombinant (Wyatt et al., supra, (1995)). Each rPIV3 possessed the Mab resistance marker that had been deliberately introduced into the HN gene by engineering the antigenomic cDNA. The rPIV3s were biologically cloned by two or three cycles of plaque to plaque passage to ensure that each virus preparation was genetically homogeneous. This precaution was taken because vaccinia virus can mediate recombination between the antigenomic cDNA and the support plasmids.

To confirm that each of the seven rPIV3 contained the engineered mutation(s) in the L gene, RNA was purified from precipitated virions and was copied into cDNA and amplified by RT-PCR. Control reactions showed that the RT step was required for generation of RT-PCR products, indicating that an RNA template rather than contaminating cDNA was required for the generation of the RT-PCR product. The RT-PCR products were subjected to digestion with the three restriction enzymes whose recognition sequences had been ablated as markers for the inserted coding changes. As expected, the RT-PCR product of JS wt rPIV3 was cleaved the appropriate number of times by each of the three enzymes, whereas r942/992/1558 lacked each of the three sites ablated during creation of the individual cp45 coding changes. Each of the other rPIV3s lacked the appropriate restriction site(s), indicating the presence of the introduced mutations.

Efficiency of Plaque Formation at 32° C., 37° C., 38° C., 39° C., 40° C., and 41° C. of rPIV3 Bearing cp45 L Mutations.

The seven rPIV3s bearing the various combinations of cp45 L protein amino acid substitutions were assayed for their ability to form plaques on LLC-MK2 monolayers at 32° C., 37° C., 38° C., 39° C., 40° C. and 41° C. As shown in Table 6, each rPIV3 bearing a cp45 aa substitution was ts, whereas the JS wt rPIV3 parent was not restricted in plaque formation at any temperature tested. The shut-off temperature of plaque formation of r942, r992 and r1558 was 40° C. r942 manifested a 700-fold reduction of plaque formation at 40° C., indicating that its replication was marginally reduced at this restrictive temperature. However, the plaque size of r942 also was greatly reduced at 40° C., which also indicates that its replication was restricted at this temperature compared to the JS wt. r942 was completely restricted in replication at 41° C. (data not shown). r992 and r1558 were greatly reduced (over a 1,000,000-fold reduction) in plaque formation at 40° C. These results indicate that each of the three cp45 L gene mutations individually specifies the ts phenotype, although that of the r942 mutation is somewhat less restrictive. The double mutant virus r942/1558 and the triple mutant r942/992/1558 had a shut-off temperature of 39° C., while that of r942/992 and cp45 was 38° C. The double mutant, r992/1558, was less ts than the r992 single mutant. r992/1558, like r942, was completely restricted in plaque formation at 41° C. The level of temperature sensitivity exhibited by double or triple results from a rPIVs delicate interplay of the three mutations that cannot be predicted from level of temperature-sensitivity exhibited by the single mutants. Also, since r942/992/1558 was slightly less ts than cp45, other mutations outside of the L gene also likely contribute to the ts phenotype of cp45, therefore representing additional mutations of interest within the invention.

TABLE 6

The efficiency of plaque formation (EOP) at 32° C., 37° C., 38° C., 39° C. and 40° C. of rPIV3 bearing one, two or three cp45 L protein amino acid substitutions.

| Virus[a] | Virus titer (log$_{10}$ pfu/ml) | | | | |
|---|---|---|---|---|---|
| | 32° C. | 37° C. | 38° C. | 39° C. | 40° C. |
| r942 | 6.8 | 6.8[b] | 6.6[b] | 6.5[b] | <u>4.3</u>[b] |
| r992 | 6.9 | 6.8[b] | 6.7[b] | 6.1[b] | <u><0.7</u> |
| r1558 | 6.6[b] | 6.6[b] | 6.4[b] | 5.0[b] | <u><0.7</u> |
| r942/992 | 6.7 | 6.5[b] | <u>4.5</u>[b] | 3.0[b] | <0.7 |
| r942/1558 | 5.2 | 5.0[b] | <u>4.0</u>[b] | 1.0[b] | <0.7 |
| r992/1558 | 6.7 | 6.7[b] | 6.5[b] | 5.9[a] | 5.1[b] |
| r942/992/1558 | 6.6 | 6.2[b] | 6.2[b] | <u>2.7</u>[b] | <0.7 |
| cp45[b] | 6.6 | 4.8 | <u>4.5</u>[b] | <0.7 | <0.7 |
| rPIV3 JS | 8.3 | 8.4 | 8.5 | 8.5 | 8.3 |

[a]The cp45 virus is a biologically derived virus, and each of the other viruses tested is a recombinant.
[b]Plaques were of pinpoint size.
c. Underlined numbers represent the shut-off temperature of plaque formation, which is defined as the lowest restrictive temperature at which a 100-fold reduction in titer is observed compared to the titer at 32° C.

Growth in hamsters. Groups of six Golden Syrian hamsters were inoculated intranasally with JS wt rPIV3, biologically-derived cp45, or with rPIV3 containing one or more cp45 L protein amino acid substitutions, and virus replication in the lungs and nasal turbinates was determined. In this experiment [Table 7], each of the rPIV3s bearing a single amino acid substitution was restricted in replication in the upper and lower respiratory tract [Table 7]. However, r942, the least ts virus, was only marginally suppressed in replication in the upper and lower respiratory tract in a second experiment. These data demonstrate that two of the three amino acid substitutions contribute to the att phenotype when present as single-lesioned recombinant viruses. However, the 942 mutation indeed contributes to attenuation (e.g., the r942/992 is more attenuated than r992 alone). Thus, each of the amino acid substitutions in L contribute to the att phenotype either acting alone or in concert with another L amino acid mutation. Each of the double mutants was attenuated indicating that loss of any of the three L gene substitutions following replication in vivo still leaves an attenuated virus. This is a partial explanation for the previously observed high level of stability of the ts phenotype of the cp45 following replication in vivo. The triple mutant r942/992/1558 was as restricted as cp45 for replication in the upper and lower respiratory tract indicating that the three amino acid substitutions in the L protein are the major contributors to the att phenotype of cp45.

TABLE 7

The level of replication in the upper and lower respiratory tract of hamsters of rPIV3 bearing one, two or three cp45 L protein amino acid substitutions, compared to JS wt rPIV3 and cp45[a].

| Virus | Mean virus titer (log$_{10}$ TCID$_{50}$/g ± S.E[b]) | |
|---|---|---|
| | Nasal turbinates | Lungs |
| rPIV3 wt | 7.4 ± .16 | 5.1 ± .49 |
| r942 | 6.6 ± .17 | 3.0 ± .78 |
| r992 | 4.4 ± .16 | 3.1 ± .11 |
| r1558 | 3.8 ± .40 | 4.3 ± .34 |

TABLE 7-continued

The level of replication in the upper and lower respiratory tract of hamsters of rPIV3 bearing one, two or three cp45 L protein amino acid substitutions, compared to JS wt rPIV3 and cp45[a].

| Virus | Mean virus titer (log$_{10}$ TCID$_{50}$/g ± S.E[b]) | |
|---|---|---|
| | Nasal turbinates | Lungs |
| r942/992 | <1.5 ± 0 | <1.5 ± 0 |
| r942/1558 | 2.9 ± .23 | 1.8 ± .17 |
| r992/1558 | 5.7 ± .16 | 3.2 ± .57 |
| r942/992/1558 | 3.9 ± .15 | <1.5 ± 0 |
| cp45 | 4.1 ± .27 | 1.6 ± .08 |

[a]Groups of six hamsters each were intranasally administered 10$^{5.5}$ pfu of virus per animal in an 0.1 ml inoculum, and lungs and nasal turbinates were harvested four days later.
[b]Standard Error
c. cp45 is a biologically derived virus and the others are recombinant.

To summarize the above results, substitutions at L protein amino acid positions 992 and 1558 each specified a 1,000,000-fold reduction in plaque formation in cell culture at 40° C., while the substitution at position 942 specified a 700-fold reduction. Thus, each of the three mutations individually contributes to the ts phenotype. The triple recombinant which possesses all three L mutations is slightly less ts than cp45, suggesting that there are mutations outside of the L gene in cp45 that also might contribute to its ts phenotype. Two of the three individual mutations in L each contributed to restricted replication in the upper or lower respiratory tract of hamsters, which accounts for the observed stability of ts and att phenotypes of cp45 during replication in vivo. Importantly, the level of temperature sensitivity of recombinant vaccine strains in vitro was closely predictive of attenuation in vivo. The recombinant virus possessing all three mutations was as restricted in replication as the cp45 mutant in both the upper and lower respiratory tract of hamsters, indicating that the L gene of the cp45 virus is a major attenuating component of this candidate vaccine strain. While each mutation on its own specifies the ts phenotype, when placed together they are not simply additive but instead somehow influence each other. The effect of the three mutations together in the triple mutant seemed to ameliorate rather than enhance the level of temperature-sensitivity observed in the two double mutants which were evaluated. Interestingly, this should provide an unanticipated selective pressure to maintain at least some of the cp45 L mutations, since the loss by reversion of either the 992 or 1558 substitution would increase rather than decrease the level of temperature sensitivity. Considered together, these findings indicate that the high level of the stability of the ts and att phenotypes of cp45 virus results from the contribution of multiple ts mutations in L to the att phenotype. The identification of these three mutations as the major attenuating mutations of cp45 provides the basis for monitoring virus during all stages of manufacture and following replication in humans.

It is of further interest that the tyrosine to histidine mutation at position 942, arguably the most conservative substitution of the three mutations, was the least temperature sensitive. The L polymerase of PIV3 is a large polypeptide, 2233 aa in length, and is thought to be a multifunctional protein that encodes multiple domains including those required for complex formation with the P protein, RNA binding, RNA polyadenylation, RNA transcription and RNA replication (Collins et al., supra, (1996)). The amino acid substitutions in L at positions 942 and 992 are located near regions that are well-conserved among other members of the Paramyxovirus family (Blumberg et al., *Virology* 164:487-497 (1982); Galinski et al., *Virology* 165:499-510 (1988)). The mutation at position 1558 is in a region of the polymerase which appears to share less sequence identity with other L polymerases. Although the mechanism by which the ts phenotype is conferred by the triple amino acid substitution in L is not known, it is likely that multiple L protein domains and activities are affected, or that a common mechanism involving various activities of L is affected.

EXAMPLE XII

Direct Identification, and Reconstitution into Recombinant Vaccine Viruses, of Mutations in a Biologically Derived, Live-Attenuated HPIV Type 3 Virus (cp45) Which Specify the Temperature-Sensitive, Cold-Adaptation and Attenuation Phenotypes The above Examples demonstrate that each of the three amino acid substitutions in the L polymerase protein of cp45 confer the temperature-sensitive (ts) and attenuation (att) phenotypes, but not the cold-adaptation (ca) phenotype (see also, Skiadopoulos et al., *J. Virol* 72(3):1762-8, 1998). cp45 contains twelve additional mutations in other proteins (N, C, M, F and HN) or potential cis-acting sequences (the leader region and the transcription gene start {GS} signal of the N gene), and their contribution to these phenotypes has been heretofore undefined. The present Example further characterizes the genetic basis for the ts, ca, and att phenotypes of cp45 to provide yet additional information regarding basis for the observed high level of stability of these phenotypes following replication of cp45 in humans or non-human primates. In one aspect of this study, a recombinant cp45 (rcp45) virus containing all fifteen cp45-specific mutations was constructed, using a reverse genetics system, and was found to be essentially indistinguishable from the biologically-derived virus on the basis of plaque size, level of temperature-sensitivity, cold-adaptation, and level of replication in the upper and lower respiratory tract of hamsters. In addition, recombinant viruses containing: (1) the cp45-specific changes in the C, M, F or HN proteins, (2) the combined leader and N gene mutations, or (3) several combinations of the cp45 mutations were constructed. Analysis of these recombinant viruses showed that multiple cp45 mutations distributed throughout the genome contribute to the ts, ca, and att phenotypes. The mutations in C and F were not ts at 40° C. but nonetheless conferred the att phenotype, and they, therefore, are non-ts att mutations. The HN mutation did not confer the ca, ts or att phenotypes. Viruses possessing the 3' leader and N mutations were ts, but exhibited only marginal attenuation in the lower respiratory tract of hamsters. Recombinants possessing several combinations of mutations exhibited a greater level of temperature sensitivity than cp45, but the increased level of temperature-sensitivity was not reflected in an increase in attenuation in vivo. These latter findings indicate that the multiple mutations identified in cp45 are interacting to affect replication in vitro. The presence of multiple ts and non-ts attenuating mutations in cp45 likely contributes to its high level of attenuation and phenotypic stability. Knowledge of the phenotypes associated with the various mutations of cp45 provided herein allows for accurate monitoring of biologically derived PIV viruses and ready manipulation of recombinant virus to achieve a large assemblage of useful vaccine recombinants within the invention.

Viruses and Cells.

The rPIV3s, PIV3 JS wt and cp45 viruses described in the present Example were grown in simian LLC-MK2 cells (ATCC CCL 7.1) as described above (see also, Durbin et al., *Virology* 235:323-332, 1997a; Hall et al., *Virus Res.* 22(3): 173-184, 1992; Skiadopoulos et al., *J. Virol* 72(3):1762-8, 1998). The modified vaccinia virus Ankara was provided as described above. HEp-2 (ATCC CCL 23) and LLC-MK2 cells were maintained in OptiMEM I (Life Technologies, Gaithersburg, Md.) supplemented with 2% FBS and gentamicin sulfate (50 ug/mL), or in EMEM supplemented with 10% FBS, gentamicin sulfate (50 ug/mL), and 2 mM glutamine. L-132 cells (ATCC CCL 5) were grown in Earl's MEM (Life Technologies) supplemented with 10% FBS, 2 mM glutamine, 20 mM Hepes, 1 mM non-essential amino acids, and 100 units streptomycin-neomycin/ml.

Construction of Point Mutations in PIV3.

Subgenomic fragments of p3/7(131)2G, the antigenomic cDNA clone of PIV3 JS wt used above to recover infectious virus (see also, Durbin et al., *Virology* 235:323-332, 1997a; Skiadopoulos et al., *J. Virol.* 72(3):1762-8, 1998), were cloned into pUC19 vectors modified to accept these fragments, using standard molecular cloning techniques. Point mutations corresponding to mutations identified in cp45, as well as mutations creating or ablating silent restriction enzyme recognition sequences (Table 8) were introduced using the Transformer Mutagenesis Kit (Clontech, Palo Alto, Calif.) as described previously.

TABLE 8

PIV3 cp45 mutations introduced into rPIV3

| seq id no | region affected | nt position[a] | sequence changes[b] | restriction marker[c] | amino acid substitution[d] |
|---|---|---|---|---|---|
| 1 | 87 88 | 3' leader | 20 | TTGTCTGGGAAT TTGCCTGGGAAT | none | non-coding |
| 2 | 87 89 | 3' leader | 20 | TTGTCTGGGAAT TTGTTTGGGAAT | none | non-coding |
| 3 | 87 90 | 3' leader | 20 | TTGTCTGGGAAT TTGTCTGGTAAT | none | non-coding |
| 4[e] | 91 92 | 3' leader | 40 | AAC*TTT*AAATTA AACTTAAAATTA | -Dra I | non-coding |
| 5[e] | 93 94 | N gene start | 60 | TTAAAGACATTG TTTAAGACATTG | none | non-coding |

TABLE 8-continued

PIV3 cp45 mutations introduced into rPIV3

| seq id no | region affected[a] | nt position[a] | sequence changes[b] | restriction marker[c] | amino acid substitution[d] |
|---|---|---|---|---|---|
| 6[e] 95 96 | N | 390 | GCAGATGTCAAG GCAGATGCCAAG | none | Val-96 to Ala |
| 7[e] 97 98 | N | 1271 | CGAATCTAAAGA CGAAGCTAAAGA | none | Ser-389 to Ala |
| 8 99 100 | C | 2076 | GAA*ATA*TTGATC GAAACATTGATC | −Ssp I | Ile-96 to Thr |
| 9 101 102 | M | 4341 | TCTCTACCCAAC TC*GTTA*ACCCAAC | +Hpa I | Pro-199 to Thr |
| 10[f] 103 104 | F | 6323 | AG*TACA*ATAGGT AG*TAC*TGTGGGT | +Sca I | Ile-420 to Val |
| 11 105 106 | F | 6419 | GCACTTGATCCA ACACT*GG*ATCCA | +Bam HI | Ala-450 to Thr |
| 12 107 108 | HN | 7944 | CCATCATTGTTGTTGACAA CCATCATTGT*G*GCTGACAA | +Bst XI | Val-384 to Ala |
| 13 109 110 | L | 11468 | TTACA*TGG*CCA TCACATGGCGA | −Eae I | Tyr-942 to His |
| 14 111 112 | L | 11618 | TTTGGA*CTGGGC* TTTTGA*T*TGGGC | −Bsr I | Leu-992 to Phe |
| 15[f] 113 114 | L | 13308 | *GG*TCCTAATACT *GGG*CCTAATATC | −Ava II | Thr-1558 to Ile |

[a]Position of the first nucleotide in the PIV3 sequence shown.
[b]Wild type sequence is shown above the mutant sequence.
Nucleotide changes are underlined.
Codon substitutions are in bold font.
[c]Each relevant restriction endonuclease recognition sequence is in italics;
(+) indicates addition of new restriction endonuclease recognition sequence;
(−) indicates ablation of a naturally occurring restriction endonuclease recognition sequence.
[d]Mutations are indicated as the three letter amino acid assignment of wt, followed by the amino acid position, followed by the cp45 assignment.
[e]These mutations were identified by Joanne Tatem (unpublished observations), the others were from Stokes et al., Virus Res. 30(1):43-52, 1993.
[f]Two nucleotides were changed in the indicated codon in order to reduce the chance of reversion to wild type sequence.

After mutagenesis, restriction endonuclease fragments were sequenced completely and cloned back into the full-length clone, p3/7(131)2G. The 3' leader and N mutations were amplified by reverse transcription (RT)-PCR directly from PIV3 cp45 virion RNA and were cloned into pLeft+2G (see above), or a modified pUC19 vector for further manipulation. Combinations of mutations were constructed using standard molecular cloning techniques. The full-length plasmid clone containing the cp45 mutations, designated pFLCcp45, was completely sequenced to determine if extraneous mutations had been introduced during the cloning process, but none were found.

Recovery of Recombinant PIV3 (rPIV3).

Each full-length antigenomic cDNA bearing cp45 mutations, together with the three support plasmids pTM(N), pTM(P no C) and pTM(L), was transfected into HEp-2 cells on 6-well plates (Costar, Cambridge, Mass.) using LipofectACE (Life Technologies, Gaithersburg, Md.) and MVA-T7 as described above. After incubation at 32° C. for 4 days, the transfection harvest was passaged onto LLC-MK2 cells in T-25 flasks which were incubated at 32° C. for four to eight days. This harvested virus was called passage 1 and was subjected to three rounds of plaque purification on LLC-MK2 cells as described above. Each biologically-cloned recombinant virus was amplified twice in LLC-MK2 cells at 32° C. to produce virus for further characterization. Virus was concentrated from clarified medium by polyethylene glycol precipitation (see, Mbiguino and Menezes, J. Virol Methods 31:2-3, 1991, incorporated herein by reference in its entirety), and viral RNA (vRNA) was extracted with Trizol Reagent (Life Technologies). Reverse transcription was performed on vRNA using the Superscript II Preamplification System (Life Technologies) with random hexamer primers. The Advantage cDNA PCR kit (Clontech) and sense and antisense primers specific for various portions of the PIV3 genome were used to amplify fragments for restriction endonuclease analysis. The PCR fragments were analyzed by digestion with each of the restriction enzymes whose recognition sites had been created or ablated during construction of the mutations (Table 8).

Efficiency of Plaque Formation (EOP) of rPIV3 Bearing cp45 Mutations at Permissive and Restrictive Temperatures.

The level of temperature-sensitivity of plaque formation in vitro of control and recombinant viruses was determined at 32° C., 35° C., 36° C., 37° C., 38° C., 39° C., 40° C., and 41° C. in LLC-MK2 monolayer cultures as described above (see also, Hall et al., Virus Res. 22(3):173-184, 1992, incorporated herein by reference in its entirety). Plaques were enumerated by hemadsorption with guinea pig red blood cells following removal of the methylcellulose overlay, or alternatively, the viral plaques present in the monolayer were identified by immunoperoxidase staining with a mixture of two PIV3-specific anti-HN murine mAbs 101/1 and 454/11 diluted 1:250 (see, Murphy et al., Vaccine 8(5):497-502, 1990; van Wyke Coelingh et al., Virology 143(2):569-582, 1985).

Evaluation of rPIV3 Mutant Viruses for Cold-Adaptation Phenotype.

Growth of mutant and wt rPIV3 viruses was determined at 32° C. and 20° C. on confluent L-132 cell monolayers prepared in 24-well tissue culture plates. Duplicate wells of each of two plates were inoculated with 0.2 ml of each mutant or wt rPIV3 virus at a multiplicity of infection of 0.01. After one hour adsorption at room temperature, the inoculum was aspirated and the monolayers were washed with 1 ml of PBS per well. The inoculated cultures were overlaid with 0.5 ml of Earl's MEM supplemented with 10% FBS, 2 mM glutamine, 20 mM Hepes, 1 mM non-essential amino acids, and 100 units streptomycin-neomycin/ml. One plate was sealed in a waterproof pouch (Kapak) and then submerged in a 20° C. bath for 13 days. The duplicate plate was placed at 32° C. in a $CO_2$ incubator for 3 days. At the end of the incubation period, virus was harvested by freeze/thawing. The titer of virus recovered from each well was determined by plaque assay in LLC-MK2 cells at 32° C. using hemadsorption with guinea pig red blood cells to visualize plaques. Two wt and two cp45 reference stocks were used as controls.

Hamster Studies.

5 week-old Golden Syrian hamsters in groups of five were inoculated intranasally with 0.1 ml OptiMEM I per animal containing $10^{6.0}$ pfu of JS wt rPIV3, PIV3 cp45 virus, or one of the mutant rPIV3s. On day 4 post-infection, the hamsters were sacrificed, the lungs and nasal turbinates were harvested, and the virus was quantified as described above. The mean $log_{10}$ $TCID_{50}$/gram at 32° C. was calculated for each group of hamsters.

Results

Introduction of the PIV3 cp45 Mutations into JS wt rPIV3.

The fifteen mutations in the 3' leader, the N GS signal, and the N, C, M, F, HN and L proteins of cp45 (Table 8) were introduced into the complete PIV3 antigenomic cDNA by site directed mutagenesis or by direct PCR amplification of a segment of cp45 cDNA bearing the desired mutations. The following antigenomic cDNAs were made (see FIG. 13): (i) rcp45 3'N, containing the four point mutations of the leader region, the point mutation in the N GS signal, and the two amino acid changes in the N protein; (ii) rcp45 C, containing the single amino acid change in the C protein; (iii) rcp45 M, containing the single amino acid change in M, (iv) rcp45 F, containing the two amino acid changes in F; (v) rcp45 HN, containing the single amino acid change in HN; (vi) rcp45 L, containing the three amino acid changes in L, as described above; (vii) rcp45 3'NL, containing the mutations from i. and vi. above; (viii) rcp45 3'NCMFHN, containing all of the mutations except for the three in L; and (ix) rcp45, containing all fifteen cp45 mutations listed in Table 8. In most cases, each cp45 change was engineered to be accompanied by one or more nearby silent changes which introduced or removed a restriction enzyme recognition site (Table 8). These served as markers to confirm the presence of the mutation in the cDNA and in recovered virus. Also, two of the amino acid coding changes (mutation numbers 10 and 15 in Table 8) were made using two nucleotide changes rather than the single change found in cp45, reducing the possibility of same-site reversion to wt. The cp45 cDNA, which contains all fifteen of the cp45 changes in Table 8, was assembled from the same mutagenized cDNA subclones as were used to introduce cp45 changes into the other antigenomic cDNAs; it was sequenced in its entirety, and was confirmed to contain only the intended mutations. This indicated that all of the regions which had been subjected to mutagenesis or PCR and had been manipulated by cloning possessed the desired sequences and lacked other unwanted mutations. Each full-length plasmid bearing one or more of the cp45 mutations was transfected into HEp-2 cells along with support plasmids and MVA-T7 to produce recombinant PIV3 as described above. Analysis of RT-PCR fragments encompassing the mutations indicated in Table 8 were amplified from virion RNA of the various recombinant viruses indicated in FIG. 13 confirmed the presence of the introduced mutations, and other unintended mutations were not found.

Plaque Morphology.

Several of the recombinant viruses exhibited distinctive plaque morphologies when tested on LLC-MK2 cells. JS wt rPIV3 plaques averaged 1 mm in size, and were indistinguishable in size from the biologically derived JS wt PIV3. Plaques of the cp45 and rcp45 viruses were larger than wt, averaging two- to three-fold larger in diameter than wt, and were indistinguishable from each other. This demonstrated the comparability of the biologically-derived and recombinant cp45 virus for this phenotype.

Efficiency of Plaque Formation of rPIV3s Bearing the cp45 Mutations in LLC-MK2 Cells at Permissive and Restrictive Temperatures.

The rPIV3s were assayed for their ability to form plaques at permissive and restrictive temperatures ranging from 32° C. to 41° C. (Table 9). Analysis of the ts phenotypes of viruses bearing individual components of cp45 revealed that the rcp45 3'N and rcp45 M viruses had a shutoff temperature of 40° C., and the rcp45 C mutant had a shutoff of 41° C. The shutoff temperature of rcp45 F and rcp45 HN mutants was greater than 41° C. Consistent with the above results, the rcp45 L virus had a shutoff temperature of 39° C. A virus is considered to have a ts phenotype, for example, if its reduction of replication at 40° C. (ie. titer at 32° C. minus titer at 40° C.) is approximately ≧100-fold that of wt virus at 40° C. Applying this definition, the present results indicated that at least two regions of cp45 (3'N, and L) contribute to the ts phenotype.

TABLE 9

The efficiency of plaque formation (EOP) of recombinant and biologically-derived viruses at permissive and restrictive temperatures.

| Virus | Mean Virus Titer$^a$ ($log_{10}$ pfu/ml) | | | | | | | | ts phenotype$^c$ |
|---|---|---|---|---|---|---|---|---|---|
| | 32° C. | 35° C. | 36° C. | 37° C. | 38° C. | 39° C. | 40° C. | 41° C. | |
| rcp45 3'N | 7.1 | — | — | 7.0 | 6.4 | 5.4 | <u>4.2</u> | <3.7 | + |
| rcp45 C | 6.9 | — | — | 7.0 | 6.7 | 6.6 | 5.9 | <u>≦3.7</u> | − |

TABLE 9-continued

The efficiency of plaque formation (EOP) of recombinant and biologically-derived viruses at permissive and restrictive temperatures.

| Virus | Mean Virus Titer[a] (log₁₀ pfu/ml) | | | | | | | | ts phenotype[c] |
|---|---|---|---|---|---|---|---|---|---|
| | 32° C. | 35° C. | 36° C. | 37° C. | 38° C. | 39° C. | 40° C. | 41° C. | |
| rcp45 M | 7.7 | — | — | 7.4 | 7.0 | 6.5 | <u>5.3</u> | <3.7 | − |
| rcp45 F | 7.5 | — | — | 7.2 | 6.0 | 6.6 | 5.9 | 5.7 | − |
| rcp45 HN | 6.4 | — | — | 6.5 | 6.2 | 6.4 | 4.7 | 4.4 | − |
| rcp45 L | 7.3 | — | — | 7.2 | 6.7 | <u>4.0</u> | <0.7 | <0.7 | + |
| rcp45 3'NL | 7.3 | 5.7 | <u>≤0.7</u> | <0.7 | <0.7 | <0.7 | <0.7 | — | + |
| rcp45 3'NCMFHN | 7.2 | 5.6 | <u>≤0.7</u> | 2.0 | 2.4 | <0.7 | <0.7 | — | + |
| rcp45 | 8.5 | 7.5 | 7.1 | 6.4 | <u>6.0</u> | 2.0 | <0.7 | <0.7 | + |
| cp45[b] | 8.3 | 8.0 | 7.4 | 7.0 | <u>6.2</u> | 2.3 | <0.7 | <0.7 | + |
| rPIV3 wt | 7.3 | 7.3 | 7.0 | 7.4 | 7.6 | 7.7 | 6.8 | 6.0 | − |

[a]Plaques were enumerated by immunoperoxidase staining after incubation for 6 days at the indicated temperature. Values are the mean of two experiments, values in bold are from a single experiment. Underlined values represent the lowest non-permissive temperature at which a 100-fold reduction of plaquing efficiency occurs compared to titer at 32° C., and this is defined as the shutoff temperature of plaque formation.
[b]cp45 is biologically-derived and the other viruses are recombinants.
[c]A virus is defined as bearing the ts phenotype if its reduction of replication at 40° C. (ie. titer at 32° C. minus titer at 40° C.) is ≧100-fold that of wt virus at 40° C.

As shown in Table 9, rcp45, containing all of the cp45 mutations, had a shut-off temperature of 38° C., which was identical to that of the biologically-derived cp45. These results show that the ts phenotype of cp45 was successfully reproduced in rcp45. In addition, these results validate the sequence analysis of cp45 and the subsequent reconstruction of mutations into recombinant virus.

The rcp45 3'NCMFHN virus, which is identical to rcp45 except that it lacks the three L mutations, exhibited a shutoff temperature of 36° C. Since the L mutations are known to confer temperature-sensitivity individually and in combination, it is somewhat paradoxical that rcp45 3'NCMFHN was more, rather than less, ts than cp45. This implies that there is an interaction of mutations within cp45 whereby mutations compensate for each other to give a level of temperature-sensitivity which is less than the sum of the individual components.

Virus rcp45 3'NL was constructed to investigate whether the L mutations interact with the leader and/or N mutations, since all of these elements are believed to interact during RNA synthesis. This virus had a shutoff temperature 36° C., compared to 40° C. and 39° C. for rcp45 3'N and rcp45 L, respectively. These results suggest that there is an interaction between the 3'N and L mutations that results in augmentation of temperature-sensitivity. These results also provide another example in which a subset of cp45 mutations specifies a level of temperature sensitivity greater than that observed for rcp45 which contains the entire set of mutations.

ca Phenotype of rPIV3s Bearing cp45 Mutations.

The rPIV3s were analyzed to determine which genetic elements of cp45 specified the ca phenotype (Table 10). It was demonstrated above that rcp45 L is ts and att, but not ca. This indicates that the genetic elements specifying the greater part of the ca phenotype are located outside L, and this was confirmed in the present study. Each of the rPIVs possessing the 3' leader and N mutations were ca except rcp45 3'NCMFHN, which exhibited an intermediate phenotype. This shows that the ca phenotype is specified mostly within the 3'N region. The finding that the level of ca of viruses containing the 3'N segment is less than that of cp45 or rcp45 indicates that other regions of cp45 contribute to the ca phenotype, even though this is not apparent from analysis of the other regions individually. The rcp45 3'NL virus is more ca than the rcp45 3'N virus, suggesting that the L mutations may make a modest contribution. The biologically-derived cp45 and rcp45 viruses exhibit comparable levels of ca, indicating that this phenotype, like the plaque size and ts phenotypes, was successfully reproduced in the recombinant cp45 virus provided herein. Therefore, the ca phenotype, like the ts phenotype, is a composite phenotype reflecting individual contributions to the overall phenotype as well as contributions from interacting genetic elements.

TABLE 10

Growth of wt and mutant PIV3s at 20° C. compared to 32° C.[a] (cold adaptation phenotype).

| Virus | 20° C. | 32° C. | ca Phenotype |
|---|---|---|---|
| cp45[b] | 6.72 | 8.49 | + |
| rcp45 | 6.57 | 8.35 | + |
| rcp45 3'NL | 5.02 | 7.23 | + |
| rcp45 3'N | 4.39 | 8.53 | + |
| rcp45 3'NCMFHN | 3.53 | 8.08 | +/− |
| rcp45 L | 3.18 | 7.98 | − |
| rcp45 C | 2.52 | 8.32 | − |
| rcp45 F | 2.47 | 8.10 | − |
| rcp45 HN | 2.11 | 8.01 | − |
| rcp45 M | 1.76 | 8.21 | − |
| PIV3 WT | 2.57 | 8.43 | − |

[a]Virus titer is expressed in log₁₀ PFU/mL.
[b]cp45 is biologically-derived and the other viruses are recombinant.
The ca phenotype is defined as a greater than 10-fold increase in growth at 20° C. relative to wt.

Growth of the rcp45 Mutant Viruses in Hamsters.

Groups of five Golden Syrian hamsters were inoculated intranasally with $10^6$ TCID$_{50}$ of recombinant or biologically-derived virus, and the level of virus replication in the lungs and nasal turbinates was determined four days later (Table 11). The fourth day post-inoculation has been shown previously to be the peak of virus replication in hamsters for both the wt and cp45 viruses (see, Crookshanks and Belshe, J. Med Virol 13(3):243-9, 1984, incorporated herein by reference in its entirety). The rcp45 virus was reduced approximately 40-fold in replication in the nasal turbinates and 1000-fold in the lungs, and thus was as attenuated as the biologically-derived cp45 virus. These results indicate that the attenuation phenotype of cp45 was successfully reproduced in its recombinant version. Since each phenotype of cp45 was fully reproduced in rcp45, the additional five mutations in cp45 that were not included in this Example likely made little contribution to the properties of cp45.

TABLE 11

Level of replication in the upper and lower respiratory tract of hamsters[a] of wt and mutant PIV3s[b].

| Virus | Mean virus titer (log$_{10}$ TCID$_{50}$/g ± S.E[c]) in: | |
|---|---|---|
| | Nasal turbinates | Lungs |
| JS wt rPIV3 | 6.9 ± 0.2 | 5.4 ± 0.5 |
| rcp45 3'N | 6.5 ± 0.2 | 3.9 ± 1.1 |
| rcp45 C | 4.8 ± 0.3 | 3.1 ± 0.7 |
| rcp45 M[d] | 6.8 ± 0.2 | 6.7 ± 0.3 |
| rcp45 F | 4.6 ± 0.2 | 3.4 ± 0.6 |
| rcp45 HN | 6.3 ± 0.2 | 5.3 ± 1.0 |
| rcp45L | 4.2 ± 0.1 | 2.1 ± 0.3 |
| rcp45 3'NL | 4.7 ± 0.2 | 2.1 ± 0.3 |
| rcp45 3'NCMFHN | 5.8 ± 0.3 | 2.9 ± 0.9 |
| rcp45 | 5.3 ± 0.1 | 2.4 ± 0.2 |
| cp45 | 4.9 ± 0.4 | 1.9 ± 0.2 |

[a]Groups of five hamsters each were intranasally administered 10$^{6.0}$ TCID$_{50}$ of virus per animal in an 0.1 ml inoculum, and lungs and nasal turbinates were harvested four days later.
[b]cp45 is a biologically-derived virus, the other viruses are recombinant.
[c]TCID$_{50}$, 50% tissue infectious dose ± Standard Error.
[d]The virus pool used in this study was found to contain a mixed plaque phenotype. The attenuation phenotype of this mutant will be reassessed using additional virus preparations.

As demonstrated above, the mutations in the L gene of cp45 specify the majority of the attenuation phenotype of this virus. In the present Example, the contribution of the cp45 mutations outside of L as a group was examined. The rcp45 3'NCMFHN mutant was only slightly reduced in replication in the nasal turbinates, but was more than 100-fold reduced in replication in the lungs, which shows that additional attenuating mutations were present outside of the L protein. Importantly, if each of the three mutations in the L gene of rcp45 reverted to wild type sequence, the resulting virus, rcp45 3'NCMFHN, would still retain the attenuation phenotype. The rcp45 M and rcp45 HN mutant viruses were not defective for replication in the respiratory tract of hamsters, and the rcp45 3'N virus showed only a marginal decrease in replication in the lower respiratory tract. This suggests that the mutations present in the 3' leader, in the N gene start site and the N, M and HN proteins are not attenuating in and of themselves. However, these mutations could contribute to the overall attenuation of cp45 in the context of the other cp45 mutations. Also, individual mutations within the 3'N region may have effects which are not apparent when the set of mutations is analyzed together, which can be readily determined according to the present disclosure.

Replication of the rcp45 C and rcp45 F mutant viruses was approximately 100-fold reduced in both the nasal turbinates and the lungs, demonstrating that the mutations present in the C and F proteins of cp45 confer the attenuation phenotype in hamsters, although the level of attenuation is not as great as that conferred by the cp45 L mutations. As described above, the rcp45 F and rcp45 C mutant viruses did not possess the ts phenotype, and therefore, the mutations that occur in the C and F proteins are considered to be non-ts attenuating mutations.

EXAMPLE XIII

Recovery of Recombinant. Chimeric PIV3 in which the Hemagglutinin and Fusion Glycoproteins have been Substituted with Corresponding Glycoproteins from PIV1

Within the present example, a chimeric rPIV virus is generated and selected which incorporates one or more heterologous genes or large polynucleotide sequences from one PIV into a different rPIV background. Within this aspect of the invention, individual genes or gene segments of one PIV are substituted by counterpart sequence(s) from a heterologous PIV or other source. In one embodiment described in the present Example, tools and methods are provided for substituting, e.g., the HN and/or F protective antigens of HPIV1 or HPIV2 into a recombinant HPIV3 to yield a chimeric recombinant suitable for developing live-attenuated vaccines.

Viruses and Cells.

The PIV1 strain used in this study, PIV1/Washington/20993/1964 (PIV1/Wash64), was isolated in Washington D.C. in 1964 and was confirmed to be a virulent wild type virus in clinical studies in adult human volunteers (Murphy et al. Infect. Immun. 12:62-8 (1975), incorporated herein by reference). It was propagated in LLC-MK2 cells (ATCC CCL 7.1) in Opti-MEM I (Life Technologies) with 50 µg/ml gentamicin sulfate, 2 mM glutamine and 0.75 µg/ml trypsin (Catalog No. 3741, Worthington Biochemical Corp., Freehold, N.J.). The Greer strain of human PIV2 (Catalog No. V-322-001-020, NIAID Repository, Rockville, Md.) used in the hemagglutination-inhibition assay (HAI) was propagated in the same way. The JS strain of human PIV3 virus and its recombinant derivative from cDNA (rPIV3/JS) with wild type phenotype were propagated as described above. The modified vaccinia Ankara (MVA) recombinant that expresses the bacteriophage T7 RNA polymerase is described in Wyatt et al., Virology 210:202-205 (1995) (incorporated herein by reference).

HEp-2 cells were obtained from ATCC (ATCC CCL 23) and maintained in Opti-MEM I (Life Technologies) with 2% fetal bovine serum (FBS), 50 µg/ml gentamicin sulfate and 2 mM glutamine.

Construction of a cDNA Encoding a Complete Chimeric PIV3-PIV1 Antigenome.

A cDNA encoding a full-length PIV3 antigenomic RNA in which the PIV3 HN and F ORFs were replaced by their PIV1 counterparts was constructed as shown in FIG. 14. cDNA clones of the HN and F genes of PIV1/Wash64 were prepared from RNA extracted from LLC-MK2 cells which had been infected with PIV1/Wash64 wild type virus. cDNA was generated using the SuperScript Preamplification System using random hexamer primers (Life Technologies). PIV1 F and HN cDNAs were amplified with Vent DNA polymerase (New England Biolabs, Beverly, Mass.) using gene specific primer pairs based on consensus sequences present in GenBank. All primers described below are annotated so that PIV specific sequences are underlined, restriction sites are in italics, nt altered from wild type sequences are in lowercase, and start and stop codons are in bold. The positive sense PIV1 F primer, hybridizing to nt 69-97 upstream of the start codon, was 5'-GGGAAAGAAtCCAGAGACAAGAACGG-3' (SEQ ID NO: 115). The negative-sense PIV1 F primer, hybridizing to nt 36-61 downstream of the F stop codon, was 5'-GGTGAAGTTGTGGATccATTTGATTG-3' (SEQ ID NO: 116). It carries a BamH I site. The positive-sense primer for PIV1 HN was 5'-CAACCTGTAAGGtAcCAGCATCCG-3' (SEQ ID NO: 117). It hybridizes to nt 13-36 upstream the HN start codon and carries a Kpn I site. The negative-sense PIV1 HN primer was 5'-GATATGGTGTTaGGcCTTGATC-TGTTC-3' (SEQ ID NO: 118). It hybridizes to the last two nt of the stop codon and 25 nt further downstream and carries a Stu I site. The PIV1 F cDNA was cloned as a BamH I and blunt-end fragment into BamH I-EcoR V digested pLIT-MUS28 (New England Biolabs), while the PIV1 HN cDNA was cloned as a Kpn I-Stu I fragment into the same vector. The nt sequences of the resulting plasmids, designated as pLit.1 HNwt and pLit.1 Fwt (GenBanK Accession number:

AF016280, AF016279), were determined using the Circumvent Sequencing Kit (New England Biolabs). These two clones were modified (FIG. 14) using mutagenic PCR primers to delete their non-coding regions and to introduce new restriction sites flanking their start and stop codons for the purpose of constructing the PIV3-1 chimeric HN and F genes. The sequences of positive-sense and negative-sense PIV1 F mutagenic primers were 5'-CgccATGgAAAAATCA-GAGATCCTCTTCT-3' (SEQ ID NO: 119) and 5'-CtggatcCt AATTGGAGTTGTTACCCATGTA-3' (SEQ ID NO: 120), respectively, the introduced restriction sites are Nco I and BamH I. The sequences of positive-sense and negative sense PIV1 HN mutagenic primers were 5'-AACcATGG CTGAAAAAGGGAAAA-3' (SEQ ID NO: 121) and 5'-GG-TGAaGCTtAAGATGTGATTTTACATATTTA-3' (SEQ ID NO: 122), respectively, the introduced restriction sites are Nco I and Hind III.

The second step involved the modification of the PIV3 HN and F genes to serve as acceptors of the PIV1 coding regions generated above. The PIV3 F and HN genes were subcloned in several steps from the full-length clone of PIV3/JS, p3/7(131)2G to generate pLit.PIV3.HN.4 and pLit.PIV3.F.3a (FIG. 14). The PIV3 F or HN coding regions were deleted by PCR mutagenesis and replaced by restriction sites appropriate to accept the PIV1 HN and F cDNA described above. The sequences of the PIV3 F positive sense and negative sense mutagenic primers were 5'-AAATAggatccCTACAGAT-CATTAGATATTAAAAT-3' (SEQ ID NO: 123) and 5'-Cgc-CATgGTGTTCAGTGCTTGTTG-3' (SEQ ID NO: 124), respectively, the introduced restriction sites were BamH I and Nco I. The sequences of PIV3 HN positive sense and negative sense mutagenic primers were 5'-CCACAAgCt TAATTAACCATAATATGCATCA-3' (SEQ ID NO: 125) and 5'-TTCCATggATTTGGATTTGTCTATTGGGT-3' (SEQ ID NO: 126), respectively, the introduced restriction sites were Hind III and Nco I. The stop codon for the chimeric HN would be regenerated upon ligation with mutagenized PIV1 HN cassette. The PIV1 HN or F cDNAs described above were imported in as a Nco I-Hind III fragment for HN or as a Nco I-BamH I fragment for F, which generated pLit.PIV3-1.HNhc and pLit.PIV3-1.Fhc. These two cDNAs were then joined into pSE.PIV3-1.hc, which was subsequently sequenced in its entirety. Then the BspE I-Sph I fragment was inserted into p3/7(131)2G to generate pFLC.2G+.hc (FIG. 14). The nucleotide sequence of this BspE I-Sph I fragment, containing the chimeric F and HN genes, is in GenBank (Accession No. AF016281). Importantly, the cDNA engineering was designed so that the final rPIV3-1 antigenome conformed to the rule of six (Durbin et al. *Virology* 234:74-78 (1997), incorporated herein by reference). The plasmid pFLC.2G+.hc encoding the rPIV3-1 chimera was deposited on Sep. 17, 1997 under the terms of the Budapest Treaty with the American Type Culture Collection (ATCC) of 12301 Parklawn Drive, Rockville, Md. 20852, U.S.A.

Transfection. HEp-2 cell monolayers were grown to confluence in six-well plates (Costar Corp, Cambridge, Mass.) and transfections were performed as described above. Cell monolayers were infected with MVA-T7 at a multiplicity of infection (MOI) of 3 in 0.8 ml of serum-free Opti-MEM I containing 50 μg/ml gentamicin, and 2 mM glutamine and then transfected with the three support plasmids, 0.4 μg pTM(N), 0.4 μg pTM(P), 0.05 μg pTM(L), and 5 μg the PIV3-1 antigenome cDNA. The plasmids were mixed in 0.2 ml of Opti-MEM I containing 12 μl LipofectACE (Life Technologies) and added to each well. The PIV3/JS cDNA plasmid, p3/7(131)2G, which encodes wild type PIV3/JS antigenomic RNA, was transfected in parallel as a positive control. After incubation at 32° C. for 12 hours, the transfection medium was replaced with 1.5 ml of fresh Opti-MEM I supplemented with 50 μg/ml gentamicin, and cultures were incubated at 32° C. for two additional days. Trypsin was added to a final concentration of 0.75 μg/ml on day 3 post transfection. Cell culture supernatants were harvested on day 4 and passaged (referred to as passage 1) onto fresh LLC-MK2 cell monolayers. After overnight adsorption, the medium was replaced with fresh Opti-MEM I with 0.75 μg/ml trypsin. Passage 1 cultures were incubated at 32° C. for 4 days, and the amplified virus was harvested and further passaged on LLC-MK2 cells (referred to as passage 2) for another 4 days at 32° C. in the presence of 0.75 μg/ml trypsin. The recovered virus was characterized by reaction with rabbit PIV1 antiserum, guinea pig PIV2 antiserum, and two PIV3 HN monoclonal antibodies in a hemagglutination-inhibition (HAI) assay as described previously (van Wyke Coelingh et al., supra, (1985)) with the exception that chicken red blood cells (RBCS) were used for viruses possessing the PIV1 HN glycoproteins, whereas guinea pig RBCs were used for PIV3. The HAI was performed to determine if rPIV3 possessed the monoclonal antibody resistant mutation (MARM) that marked virus recovered from cDNA or if rPIV3-1 possesses the PIV1 HN.

Nucleotide sequence analysis. The chimeric cDNA construct pSE.PIV3-1.hc was sequenced with the Circumvent Sequencing kit (New England Biolabs) before the final assembly into full-length clone pFLC.2G+.hc. For analysis of RNA, the appropriate PIVs were amplified in T75 flasks of LLC-MK2 cells. Virus was harvested on day 5 post-infection and concentrated by polyethylene glycol precipitation (Mbiguino et al., *J. Virol. Methods* 31:161-70 (1991)). Viral RNA was extracted from the viral pellets and used in reverse transcription (RT) with the Superscript Preamplification System (Life Technologies). RT-PCR was performed using the Advantage cDNA synthesis kit (Clontech) and PIV1 or PIV3 specific primer pairs. RT-PCR products were gel purified by electrophoresis onto, and elusion from, strips of NA45 DEAE nitrocellulose membrane (Schleicher & Schnuell, Keene, N.H.), and were sequenced.

Replication of PIVs in LLC-MK2 cells. Plaque enumeration on LLC-MK2 monolayers was performed as previously described except that trypsin was added in the case of the PIV1 and rPIV3-1 viruses (Hall et al. *Virus Res.* 22:173-84 (1992)). Briefly, serially-diluted virus was inoculated onto LLC-MK2 monolayers in six-well plates; virus was adsorbed for 1 hour at 32° C.; the cultures were overlaid with L-15 medium (Life Technologies) containing 0.8% agarose with or without added trypsin and incubated at 32° C. for 6 days; and plaques were identified by hemadsorption (HAD) with guinea pig red blood cells following the removal of the agarose overlay.

Growth of the PIV viruses in tissue culture was evaluated by infecting confluent LLC-MK2 monolayers on twelve-well plates with virus at a MOI of 0.01. After adsorption at 32° C. for 1 hour, the inoculum was replaced with 1.5 ml/well Opti-MEM I supplemented with gentamicin (50 μg/ml) and trypsin (0.75 μg/ml), and further incubated at 32° C. for 6 days. At 24 hour intervals, 0.3 ml medium was removed from each well and 0.3 ml fresh medium with trypsin was added back. The titer of virus was determined at 32° C. by hemadsorption assay on LLC-MK2 cell monolayers using fluid overlay as previously described (Hall et al. *Virus Res.* 22:173-84 (1992)), and the titers were expressed as $\log_{10}$ $TCID_{50}$/ml.

Replication of PIVs in the respiratory tract of hamsters. Golden Syrian hamsters in groups of 12 were each inoculated intranasally with 0.1 ml of L-15 medium containing $10^5$ pfu of rPIV3/JS, rPIV3-1, or PIV1/Wash64. On days 4 and 5 post-inoculation, six hamsters from each group were sacrificed, and their lungs and nasal turbinates harvested, and homogenized, and virus present in the samples was titered on LLC-MK2 cell monolayers at 32° C. The titers were expressed as mean $\log_{10}$ TCID$_{50}$/g for each group of six hamsters.

Results

Construction of a cDNA Clone Encoding a Full-Length, Chimeric PIV3-1 Antigenomic RNA Yielded Recovery of the Chimeric Virus rPIV3-1.

As noted above, the final construct of the PIV3 and PIV1 chimeric cDNA, in which the ORFs of the JS wild type PIV3 HN and F glycoprotein genes were replaced by those of PIV1/Wash64 coding sequences (FIG. 14) encodes a PIV3-1 chimeric antigenomic RNA of 15,516 nt, which conforms to the rule of six (Durbin et al., Virology 234:74-78 (1997)). The pFLC.2G+.hc cDNA encoding the chimeric PIV3-1 antigenome was transfected onto HEp-2 cells together with the N, P and L support plasmids. The p3/7(131)2G cDNA encoding the JS wt PIV3 antigenome was transfected in parallel to generate a rPIV3 control parental virus. Virus was recovered from each transfection following the second amplification on LLC-MK2 cells, and studies were initiated to confirm that each recombinant virus was derived from cDNA.

Recombinant viruses rPIV3-1 and rPIV3 were first characterized for the presence of the PIV1 or PIV3 HN glycoprotein by HAI assay with serotype-specific anti-HN monoclonal or polyclonal antibodies. As shown in Table 12, rPIV3 reacted with only one of the two PIV3 mAbs as expected, whereas its biologically derived parent PIV3/JS reacted with both. This confirmed that rPIV3 contained the introduced MARM mutation that marks this virus as being derived from cDNA. The rPIV3-1 virus reacted with antibodies specific to the PIV1 HN glycoprotein, but not to ones specific to HN of PIV3 or PIV2, showing that the virus contained the PIV1 HN gene as expected.

TABLE 12 rPIV3-1 possesses the HN glycoprotein of PIV1
Hemagglutination-inhibition titer[a] (reciprocal)
of indicated monoclonal antibody
or polyclonal antiserum

| Virus | PIV1[b] antiserum | PIV2[b] antiserum | α-PIV3 mAb 423/6[c] | α-PIV3 mAb 77/5[c] |
|---|---|---|---|---|
| PIV1/Wash64 | 256 | 32[d] | ≦50 | ≦50 |
| rPIV3-1 | 64 | ≦2 | ≦50 | ≦50 |
| rPIV3/JS | 4 | ≦2 | ≦50 | 3,200 |
| PIV3/JS | 8 | ≦2 | 12,800 | 6,400 |
| PIV2/Greer | 8 | 512 | ≦50 | ≦50 |

[a]Chick red blood cells (RBC) were used in HAI assay for PIV1, PIV2, and rPIV3-1 and guinea pig RBCs were used for PIV3/JS and rPIV3/JS.
[b]PIV1 rabbit antiserum was purchased from Denka Seiken Co. Ltd., Japan (Catalog No. 410-701), and PIV2 guinea pig antiserum was obtained from NIAID repository, Rockville, MD (Catalog No. V-322-50-558).
[c]Biologically derived PIV3/JS contains epitopes recognized by both mAb 423/6 and 77/5, whereas rPIV3/JS was engineered to lack reactivity with mAb 423/6.
[d]The PIV2 antiserum had some reactivity with PIV1 virus, and therefore is not completely type specific.

Figure 15A:
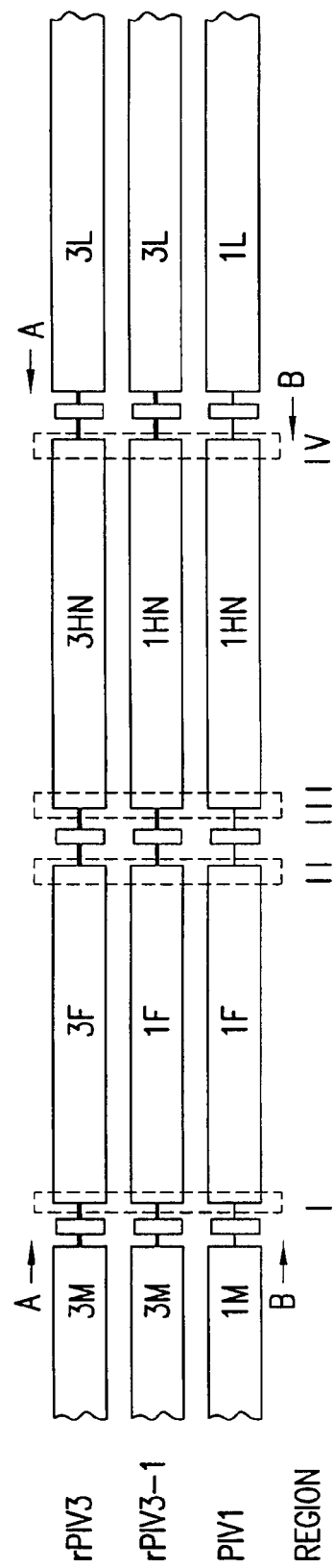
Figure 15B:
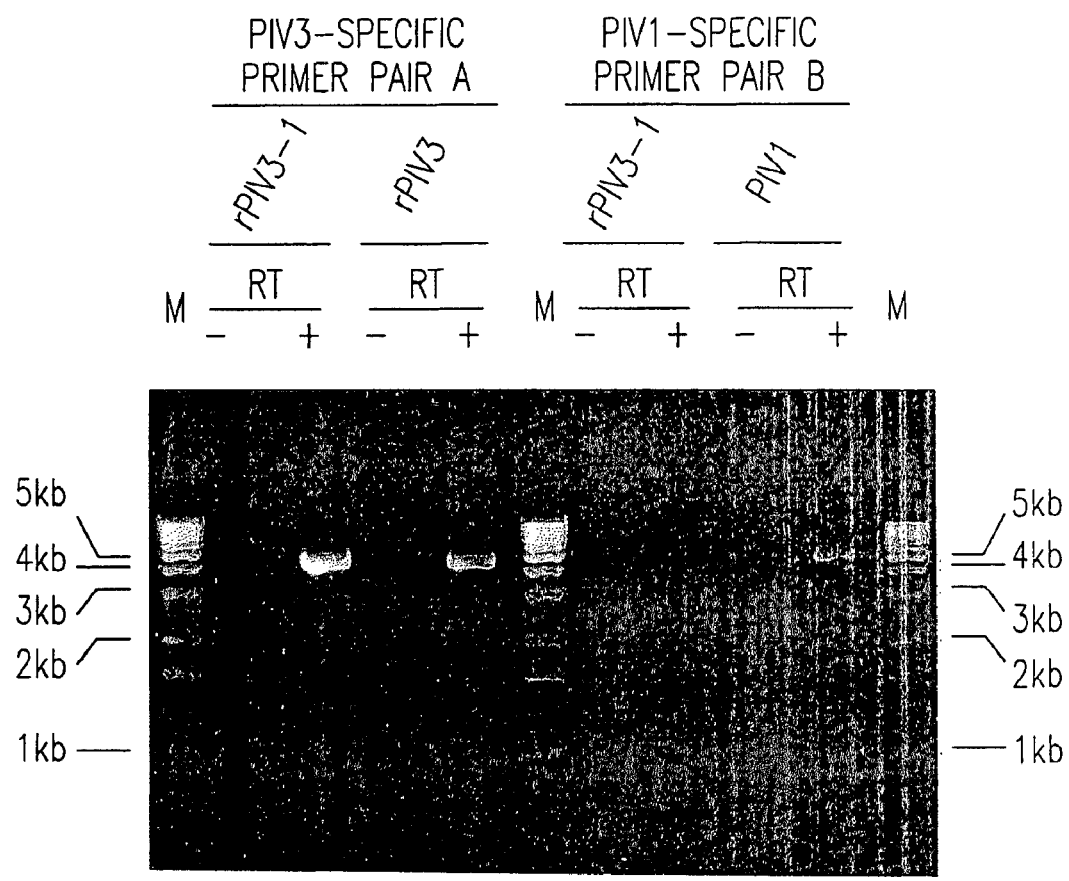

It was next confirmed that the rPIV3-1 virus contained the engineered, chimeric PIV3-1 HN and F genes. As designed, the genetic structure of rPIV3-1 was unique in four junction regions when compared with either of its parents, PIV1/Wash64 or rPIV3/JS (boxed in FIG. 15A). These regions are the transition points at which the sequence switches from the PIV3 non-coding region to the PIV1 coding region and then from the PIV1 coding region back to the PIV3 non-coding region. Using the primer pair A specific to PIV3 M and L genes, or primer pair B specific to the PIV1 M and the very 3'-end of HN gene, RT-PCR products were generated for virion-derived RNAs from rPIV3-1, rPIV3/JS, and PIV1/Wash64. Control reactions showed that the RT step was required for generation of RT-PCR products, indicating that an RNA template, rather than contaminating DNA, was required to produce the RT-PCR product. An early indication that rPIV3-1 was indeed a chimeric virus came from the finding that only the PIV3-specific primer pair A generated the expected 4.6 kb cDNA product that spans the F and HN genes (FIG. 15B). Thus, while rPIV3-1 virus contains only HPIV1-specific HN glycoprotein (See Table 12), the non-coding regions are specific to PIV3. Conversely, the PIV1 specific primer pair B amplified an appropriately sized product from PIV1 control but not from rPIV3-1. Restriction digestion analysis also demonstrated that rPIV3-1 RT-PCR product had unique restriction patterns different from that of rPIV3/JS and PIV1/Wash64 and appropriate for its predicted sequence.

The nt sequence of the 4.6 kb RT-PCR product of rPIV3-1 was determined in its four regions (FIG. 15 A) and compared with that of rPIV3/JS and PIV1/Wash64 (FIG. 16). The rPIV3-1 sequence was completely in agreement with the cDNA from which it was derived. Examination of the sequence alignment of the Region I-IV for the three RT-PCR products illustrates that rPIV3-1 contains the PIV1 F and HN glycoprotein ORFs with altered start and stop codons and flanked by the 5' and 3' non-coding regions of PIV3. Examples of sequencing ladders spanning the Region III and IV of rPIV3-1 (FIG. 17), compared in parallel with rPIV3/JS or PIV1/Wash64, were evaluated, and this analysis confirmed that rPIV3-1 is a recombinant chimeric virus whose structure is completely in agreement with the cDNA from which it was generated.

Trypsin-Dependence and Cytopathicity of rPIV3-1 In Vitro.

PIV1, like Sendai virus but contrary to PIV3, requires trypsin for cleavage of its F glycoprotein in order to undergo multicycle replication on continuous lines of tissue culture cells (Frank et al. J. Clin. Microbiol. 10:32-6 (1979)). In addition, PIV1 is a non-cytopathic virus whereas PIV3 readily produces extensive CPE (Collins et al. In Fields Virology, 3rd ed., 1:1205-43 (1996)). rPIV3-1, rPIV3 and PIV1/Wash64 were compared on the basis of these properties. rPIV3-1, like PIV1/Wash64, had a higher HA titer using chicken, rather than guinea pig (Table 13), RBCs. rPIV3-1, like its PIV1/Wash64 parent, required trypsin for efficient replication in cultures with fluid overlay as well as for efficient plaque formation. rPIV3-1 produced plaques at 32° C., 37° C. or 40° C. with similar efficiency. It is therefore evident that rPIV3-1 possesses the F glycoprotein of the PIV1 parent virus, and it is not temperature sensitive. On the other hand, rPIV3-1 produced CPE, as indicated by the cell rounding and detaching in the virus infected monolayers, almost to the same extent as its PIV3 parent suggesting that this biological property is a function of its PIV3 genes, which lie outside of the HN and F coding regions. Thus, rPIV3-1 possesses biological properties from both parents which is consistent with the findings above demonstrating that it is a chimeric virus. This exemplary recombinant, chimeric virus within the invention was deposited on May 21, 1998 under the terms of the Budapest Treaty with the American Type Culture Collection (ATCC) of 12301 Parklawn Drive, Rockville, Md. 20852, U.S.A.

TABLE 13

Comparison of the HA titer and the infectivity and cytopathicity of parental and chimeric PIVs[a]

| Virus | HA titer using indicated RBC | Infectious titer[b] ($Log_{10}TCID_{50}$/ml) using CPE or HAD as endpoint | PFU/ml[c] ($Log_{10}$) | | | | | |
|---|---|---|---|---|---|---|---|---|
| | | | Trypsin | | Trypsin | | Trypsin | |
| CPE | HAD Chicken | Guinea Pig | − | + | − | + | − | + |
| PIV1/Wash64 | 16 | 8 | ≤2.5 | ≤2.5 | 4.8[d] | 6.3 | ≤0.7[e] | 5.8 |
| rPIV3-1 | 64 | 16 | ≤2.5 | 5.8 | 5.5[d] | 7.8 | ≤0.7[e] | 7.1 |
| rPIV3/JS | 0 | 8 | 4.5 | 7.3 | 5.0[d] | 7.5 | 5.0 | 6.2 |

[a]Virus stocks were grown in LLC-MK2 cells which were infected at an MOI of 0.01 and incubated for 6 days in the presence (PIV1/Wash64, rPIV3-1) or absence (rPIV3/JS) of 0.75 μg/ml trypsin. The resulting virus stocks were assayed by the tests below in the presence or absence of trypsin as indicated.
[b]The $TCID_{50}$ assay was read at 6 days by direct visualization of CPE or by hemadsorption (HAD).
[c]Plaques were visualized by HAD after six days of incubation.
[d]The HAD of PIV3-infected monolayers was grossly apparent whereas that of PIV1 and rPIV3-1 was observable only under the microscope in which single cells with RBC adsorbed were observed.
[e]The lowest level of virus detectable was $10^{0.7}$/ml.

Comparison of the Level of Replication of rPIV3-1 and its Parental Viruses in LLC-MK2 Cells and Hamsters.

The multicycle replication of rPIV3, rPIV3-1, and PIV1 Wash/64 viruses was evaluated following inoculation of LLC-MK2 tissue culture cells at a MOI of 0.01 (FIG. 18). It can be seen that the kinetics and magnitude of replication of the three viruses are very similar. This indicates that the substitution of the HN and F genes of PIV1 for those of PIV3 did not attenuate the virus for replication in vitro. It was next determined whether rPIV3-1 was attenuated in vivo, specifically for replication in the upper and lower respiratory tracts of hamsters (TABLE 14). The observed level of replication of rPIV3-1 was similar to, if not slightly higher than, either parent in the upper and lower respiratory tract of hamsters.

TABLE 14

Level of replication of parental and chimeric PIVs in the upper and lower respiratory tract of hamsters[a]

| | Virus titer (mean $log_{10}$ $TCID_{50}$/gram ± S.E.) in indicated tissue | | | |
|---|---|---|---|---|
| | Nasal Turbinates | | Lungs | |
| Virus | Day 4 | Day 5 | Day 4 | Day 5 |
| PIV1/Wash64 | 5.2 ± .24 | 5.2 ± .12 | 5.0 ± .31 | 5.0 ± .38 |
| rPIV3-1 | 4.9 ± .23 | 6.2 ± .17 | 5.8 ± .15 | 6.0 ± .09 |
| rPIV3/JS | 4.5 ± .09 | 5.0 ± .18 | 5.1 ± .26 | 5.0 ± .32 |

[a]Hamsters were infected intranasally with $10^{5.0}$ $TCID_{50}$ per animal of the indicated virus, and lungs and nasal turbinates were removed on day 4 or 5 after infection. The titers are means of six animals per day and are expressed as mean $log_{10}TCID_{50}$/gram ± standard error.

In summary, the present Example demonstrates successful recovery of a rPIV3-1 chimeric virus in which the ORFs of the PIV1 HN and F glycoproteins were substituted for those of rPIV3. This chimeric virus replicated like its wild type PIV1 and PIV3 parental viruses in vitro and in vivo, demonstrating that the substitution of the glycoprotein ORFs did not result in attenuation of rPIV3-1. This successful recovery of a recombinant PIV3 which bears the HN and F glycoproteins of PIV1 is surprising because the two viruses, representing distinct serotypes, are not closely related. In particular, it is remarkable that the chimeric recombinant grows as well as the two parents. Notably, chimeric recombinant viruses possessing a substitution in the glycoprotein gene have also been recovered for vesicular stomatitis virus (VSV) (Lawson et al. *Proc. Natl. Acad. Sci. USA* 92:4477-81 (1995)). Specifically, the VSV G glycoprotein gene of Indiana serotype was replaced by that from New Jersey serotype which share only 50% amino acid sequence identity. In contrast to rPIV3-1, the chimeric recombinant $VSV_{I/NJ}$ replicates to only 10% the level of recombinant $VSV_I$ or biologically derived, VSV.

In the present Example, the HN and F glycoproteins have 43 and 47% sequence identity, respectively, between PIV1 and PIV3. The transfer of the two glycoproteins together would, of course, obviate glycoprotein-to-glycoprotein incompatibility (Tanabayashi, K. and Compans, R. W. *J. Virol.* 70:6112-18 (1996)). On the other hand, it is generally thought that the glycoproteins interact with the M protein (which is 63% identical between PIV1 and PIV3) through their cytoplasmic (CT) or transmembrane (TM) domains, and that this interaction is important in virion morphogenesis and structure. In this regard, the degree of sequence identity between the HN and F proteins of the two serotypes in the TM and CT domains is low indeed: 30% and 22%, respectively for the TM domain, and 9 and 11% respectively for the CT domain. In light of this low level of sequence relatedness, we have also pursued a parallel strategy of constructing chimeric glycoproteins in which the PIV1 ectodomain of each glycoprotein was fused to the PIV3 TM and CT domains. Regarding possible interaction with the M protein or other internal proteins, it might be that a conserved structure, such as a constellation of charged amino acids, is important rather than a conserved sequence. Alternatively, it might be that interaction of the TM and CT domains of the glycoproteins with internal proteins is not as critical as has been previously thought. It will be possible to examine these factors more closely using the methods and tools provided herein. For example, these factors will be further elucidated by work in progress employing the methods described above to construct a PIV3 virus bearing HN and F of PIV2.

It was expected that rPIV3-1 would require trypsin for efficient replication in tissue culture since this is a property conferred by the PIV1 F glycoprotein, and this was found to be the case. However, it was interesting to observe that rPIV3-1 caused CPE that more closely resembled that of PIV3 parent virus, indicating that a PIV3 gene(s) other than HN or F specifies this phenotype. These roles will also be further elucidated using the methods and tools provided herein to exchange additional gene(s) between the non-cytopathic PIV1 and the cytopathic PIV3.

EXAMPLE XIV

Recovery of Live-Attenuated Chimeric Recombinant PIV Encoding the Internal Proteins of PIV Type 3 and the Surface Glycoproteins of PIV Type 1

In the present Example, a derivative of rPIV3-1 carrying the three temperature-sensitive and attenuating amino acid coding changes found in the L gene of the live-attenuated cp45 PIV3 candidate vaccine virus, termed rPIV3-1.cp45L, is shown to exhibit a temperature sensitive phenotype with a shut-off temperature of 38° C., similar to that of the recombinant rPIV3 cp45L which possesses the same three mutations. rPIV3-1.cp45L is attenuated in the respiratory tract of hamsters to the same extent as rPIV3 cp45L. Infection of hamsters with rPIV3-1.cp45L generates a moderate level of hemagglutination-inhibiting antibodies against wt PIV1 and induces complete resistance to challenge with wild type PIV1. This demonstrates that attenuated chimeric PIV according to the invention are capable of inducing a highly effective immune response against PIV1. This disclosure also confirms the above described data demonstrating that the surface glycoproteins of parainfluenza viruses are sufficient to induce a high level of resistance to homologous virus challenge. Unexpectedly, infection with recombinant chimeric virus rPIV3-1.cp45L or rPIV3-1, each bearing the surface glycoprotein genes of PIV1 and the internal genes of PIV3, also induces a moderate level of resistance to replication of PIV3 challenge virus. This indicates that the internal genes of PIV3 can independently induce protective immunity against PIV3 in rodents. Thus, a reverse genetics system for PIV3 as disclosed herein successfully produces live attenuated PIV1 vaccine candidates that are attenuated and protective in accepted model subjects.

Viruses and Cells.

The wt PIV1 strain used in this study is PIV1/Washington/20993/1964 (PIV1/Wash64) (see, eg., Murphy et al., *Infect. Immun.* 12:62, 1975 (incorporated herein by reference in its entirety). Chimeric rPIV3-1, recovered from chimeric PIV3 cDNA in which the PIV3 F and HN ORFs were replaced with those of PIV1/Wash64, as described above and in Tao et al., *J. Virol.* 72:2955, 1998 (incorporated herein by reference in its entirety). These viruses were propagated in LLC-MK2 cells (ATCC CCL 7.1) in Opti-MEM I (Life Technologies, Gaithersburg, Md.) with 50 µg/ml gentamicin sulfate, and 0.75 µg/ml trypsin (Catalog No. 3741, Worthington Biochemical Corp., Freehold, N.J.). Trypsin is included because the F glycoprotein of PIV1, but not that of PIV3, is dependent on exogenous trypsin for cleavage when grown in cell culture under these conditions. The wt JS strain of human PIV3 virus and its recombinant derivative from cDNA (rPIV3/JS) were propagated as described above and in Durbin et al., *Virology* 235:323, 1997 (incorporated herein by reference in its entirety). The propagation of cp45, an attenuated derivative of wt PIV3/JS (see above; and Karron et al., *J. Infect. Dis.* 171:1107, 1995 (incorporated herein by reference in its entirely)), and rPIV3 cp45L, a recombinant PIV3 carrying the three ts mutations found in the L gene of cp45, were propagated as described above and in Skiadopoulos et al., *J Virol* 72:1762, 1998 (incorporated herein by reference in its entirety). The modified vaccinia Ankara (MVA) recombinant that expresses the bacteriophage T7 RNA polymerase is described in *Virology* 210: 202, 1995 (incorporated herein by reference in its entirety).

HEp-2 cells, which are used in transfection, were obtained from ATCC (ATCC CCL 23) and maintained in Opti-MEM I with 2% fetal bovine serum (FBS), 50 µg/ml gentamicin sulfate.

Introduction of L Mutations into rPIV3-1 Antigenomic cDNA.

The three L mutations of cp45 present in the pTM(L)942/992/1558 plasmid, described above (see also, Skiadopoulos et al., *J Virol* 72:1762, 1998, were introduced into chimeric cDNA pFLC.2G+.hc (described above; see also, Tao et al., *J Virol* 72:2955, 1998), as a 2.8 kb SphI-NheI fragment (nt 11313 to 14092 in PIV3 antigenomic cDNA) to generate the full-length pFLC.2G+.hc.cp45L bearing the PIV1 F and HN ORFs and the three cp45 L gene mutations (FIG. 19). The specific mutations present in pTM(L)942/992/1558 are indicated in the legend to FIG. 19.

Transfection. HEp-2 cell monolayers in six-well plates were grown to confluence and transfections were performed as described above (see also, Tao et al., *J Virol* 72:2955, 1998). Trypsin was added to a final concentration of 0.75 µg/ml on day 3 post transfection prior to harvesting on day 4. Cell culture supernatants were clarified and passaged (referred to as passage 1) onto fresh LLC-MK2 cell monolayers. After overnight adsorption, the medium was replaced with fresh Opti-MEM I with 0.75 µg/ml trypsin. Passage 1 cultures were incubated at 32° C. for 4 days, and the virus present in the supernatant was harvested and passaged again under the same conditions (referred to as passage 2). Virus present in the passage 2 harvest was tested for the presence of the PIV1 HN protein by hemagglutination-inhibition (HAI) assay as described above (see also Tao et al., *J Virol* 72:2955, 1998).

Replication of PIVs in LLC-MK2 at Various Temperatures.

Plaque enumeration on LLC-MK2 monolayers was performed as described above, with 0.75 µg/ml trypsin added to the agarose overlay in the case of PIV1 rPIV3-1, and rPIV3-1.cp45L (see also, Tao et al., *J Virol* 72:2955, 1998). After incubation at various temperatures for 6 days, the agarose overlay was removed and plaques were identified by hemadsorption (HAD) with guinea pig erythrocytes (RBCs).

Replication of PIVs in the Respiratory Tract of Hamsters.

Groups of five hamsters were inoculated intranasally with 0.1 ml of L15 medium containing $10^6$ plaque forming units (PFU) of rPIV3/JS, rPIV3 cp45L, cp45, PIV1/Wash64, rPIV3-1, or rPIV3-1.cp45L. Hamsters were sacrificed on day 4 post-infection, and their lungs and nasal turbinates were harvested and homogenized. Virus present in the tissue samples was titered on LLC-MK2 cell monolayers at 32° C. as described above and in Tao et al., *J Virol* 72:2955, 1998. The titers are expressed as reciprocal mean $\log_{10}$ TCID$_{50}$/gram of tissue for each group.

Immunization and Challenge Studies in Hamsters.

Groups of ten hamsters were immunized intranasally with $10^6$ PFU of virus per animal, as described above. Serum was collected for HAI assay prior to infection and on day 33. The level of HAI antibodies present in the sera of each group of 10 hamsters was determined using PIV1/Wash64 and PIV3/JS as antigens, and the HAI titers determined are presented as mean 1092 (see also, Tao et al., *J Virol* 72:2955, 1998).

Thirty-five days post-immunization, five hamsters from each group were challenged intranasally with $10^6$ PFU of either PIV1/Wash64 or rPIV3/JS. Nasal turbinates and lungs of these challenged hamsters were harvested four days post challenge. Virus titers in tissue samples were determined on LLC-MK2 monolayers as described above and in Tao et al., *J Virol* 72:2955, 1998, and the titers are presented as mean $\log_{10}$ TCID$_{50}$/gram of tissue.

Results

Recovery and Characterization of the Recombinant Chimeric Virus rPIV3-1.cp45L.

As noted above, the cDNA clone pFLC.2G+.hc, a full-length antigenomic cDNA of PIV3 in which the ORFs encoding the F and HN glycoproteins have been replaced by those of PIV1, was modified by introduction of three amino acid coding changes (designated 942, 992 and 1558, according to amino acid position in the L protein) identified in the L gene of cp45 and shown to be independent ts and attenuating mutations (FIG. 19; see also, Skiadopoulos et al., *J Virol* 72:1762, 1998). Each coding change was marked by the co-introduction of contiguous translationally silent nt substitutions that ablate a naturally-occurring restriction site (FIG. 19; Table 8). The final full-length plasmid construct, pFLC.2G+.hc.cp45L (FIG. 19), encodes a PIV3-1 chimeric antigenomic RNA of 15516 nt in length and conforms to the rule of six (see, Durbin et al., *Virology* 234:74, 1997, incorporated herein by reference in its entirety). The authenticity of pFLC.2G+.hc.cp45L was confirmed by digestion with appropriate restriction enzymes.

The pFLC.2G+.hc.cp45L cDNA was transfected into HEp-2 cells together with the PIV3 N, P and L support plasmids and infected with MVA-T7 as described above and in Tao et al., *J Virol* 72:2955, 1998). Virus recovered after two passages on LLC-MK2 cells, termed rPIV3-1.cp45L, was biologically cloned by plaque-to-plaque-to-plaque passage, and amplified virus was analyzed to confirm that it possessed the PIV1 glycoproteins and the three introduced mutations in L. First, the presence of the PIV1 HN protein in rPIV3-1.cp45L was confirmed by reactivity with PIV1 specific antibodies in HAI assay as described above and in Tao et al., *J Virol* 72:2955, 1998). The presence of the chimeric PIV3-1 HN and F genes as well as the introduced L gene mutations in rPIV3-1.cp45L genomic RNA was confirmed by restriction enzyme digestion or nucleotide sequence analysis of RT-PCR products generated from virion RNA as described above and in Tao et al., *J Virol* 72:2955, 1998. These data confirmed that rPIV3-1.cp45L is a recombinant chimeric virus bearing the three codon substitutions of the L gene of cp45.

rPIV3-1.cp45L is Temperature Sensitive.

The three L gene mutations of cp45 were shown above to confer the ts phenotype when introduced into wt PIV3 (see also, Skiadopoulos et al., *J Virol* 72:1762, 1998). To evaluate whether their presence in the chimeric virus would have the same effect, the efficiency of plaque formation of rPIV3-1.cp45L was determined at various temperatures. As shown in Table 15, the three L mutations indeed conferred the ts phenotype to the chimeric virus. The level of temperature sensitivity specified by the cp45 L mutations in the recombinant viruses rPIV3 cp45L and rPIV3-1.cp45L was equivalent (Table 15), indicating that the effect of the mutations is independent of the PIV3 or PIV1 HN and F glycoproteins. The level of temperature sensitivity of rPIV3 cp45L and rPIV3-1.cp45L was comparable to that of the biologically derived cp45 virus, despite the fact that the latter virus possesses mutations outside of L (see, Stokes et al., *Virus Res* 30:43, 1993, incorporated herein by reference in its entirety).

TABLE 15

The recombinant chimeric rPIV3-1.cp45L candidate vaccine virus is temperature sensitive

| Virus[a] | Virus titer[b] at indicated temperatures ($\log_{10}$PFU/ml) | | | | | |
|---|---|---|---|---|---|---|
| | 32° C. | 36° C. | 37° C. | 38° C. | 39° C. | 40° C. |
| rPIV3/JS | 7.4 | 7.2 | 7.2 | 7.2 | 7.2 | 7.2 |
| PIV1/Wash64[c] | 7.5 | 7.6 | 7.5 | 7.5 | 7.4 | 7.2 |
| rPIV3-1 | 7.5 | 7.5 | 7.5 | 7.2 | 6.0 | 6.1 |
| PIV3cp45[c] | 7.4 | 6.9 | 6.8 | 4.7[d] | <0.7 | <0.7 |
| rPIV3cp45L | 7.9 | 7.4 | 7.7 | 5.3 | 1.2 | <0.7 |
| rPIV3-1.cp45L | 8.1 | 8.0 | 8.2 | 6.1 | <0.7 | <0.7 |

[a]Virus nomenclature: rPIV3/JS, recombinant wt PIV3 strain JS; PIV1/Wash64, biologically-derived wt PIV1; rPIV3-1, recombinant chimeric PIV3 in which the F and HN ORFs have been replaced with those of PIV1/Wash64; PIV3cp45, biologically-derived cp45 candidate vaccine virus; rPIV3cp45L, recombinant PIV3 containing the three L gene mutations of cp45; rPIV3-1.cp45L, recombinant chimeric rPIV3-1 containing the three L gene mutations of cp45.
[b]Virus titers were determined using LLC-MK2 monolayers in 12-well plates. Titers are the average of two assays.
[c]Biologically-derived viruses. All others are recombinant viruses.
[d]The shut-off temperature, i.e. the lowest restrictive temperature at which a two $\log_{10}$ reduction in virus titer is observed, of each ts virus is indicated in bold.

Level of Replication of rPIV3-1.cp45L in Hamsters.

The three L gene mutations of cp45 were shown above to confer attenuation of virus replication in the upper and lower respiratory tract of hamsters when introduced into wt PIV3 (see also, Skiadopoulos et al., *J Virol* 72:1762, 1998). Their effect on the chimeric virus was evaluated by intranasal infection of hamsters, as shown in Table 16. These findings indicate that rPIV3-1.cp45L indeed was attenuated at both sites and, furthermore, that its level of attenuation was comparable to that of rPIV3 cp45L. Thus, the ability of the cp45 L mutations to confer attenuation, like temperature sensitivity, is independent of the antigenic specificity of the surface glycoproteins.

TABLE 16

The recombinant chimeric rPIV3-1.cp45L candidate vaccine virus is attenuated in the respiratory tract of hamsters[a]

| Virus | Virus titer in indicated tissue ($\log_{10}$TCID$_{50}$/g ± S.E)[b] | |
|---|---|---|
| | Nasal turbinates | Lungs |
| rPIV3-1.cp45L | 4.6 ± 0.3 | 1.9 ± 0.4 |
| rPIV3-1 | 6.0 ± 0.3 | 6.3 ± 0.4 |
| rPIV3cp45L | 3.0 ± 0.3 | <1.2 |
| rPIV3/JS | 5.7 ± 0.3 | 5.0 ± 0.3 |

[a]Groups of five hamsters were infected intranasally with indicated viruses at a dosage of $10^6$ PFU per hamster. On day 4 post infection, the tissue samples were harvested and assayed for virus.
[b]Virus titers are given as $\log_{10}$TCID$_{50}$ per gram of tissue.

Infection with rPIV3-1 or rPIV3-1.cp45L, Containing the Internal Proteins of PIV3 and the Glycoproteins of PIV1, Confers Resistance to PIV1 Challenge in Hamsters.

The chimeric rPIV3-1 virus and its attenuated rPIV3-1.cp45L derivative were evaluated for immunogenicity and protective efficacy in hamsters. As shown in Table 17, infection with either virus induced HAI antibodies against PIV1, but not PIV3, confirming that these chimeric viruses possess the PIV1 HN glycoprotein and are highly immunogenic. The level of HAI antibodies induced by rPIV3-1.cp45L was two-fold less than that by rPIV3-1, which indicates that its attenuation resulted in a modest decrease in immunogenicity. Similarly, rPIV3 and rPIV3 cp45L induced HAI antibodies against PIV3, but not PIV1, and the level induced by the attenuated virus was approximately two-fold lower. Despite the restricted replication in hamsters of the recombinant viruses bearing the cp45 L mutations, infection with either rPIV3 cp45L or rPIV3-1.cp45L induced complete resistance to replication of challenge virus bearing homologous glycoproteins.

TABLE 17

The recombinant chimeric rPIV3-1.cp45L candidate vaccine virus induces complete resistance to PIV1 and partial resistance to PIV3 upon challenge in hamsters[a]

| Virus used for immunization of PIV3 virus Lungs | Origin of glycoproteins | Post-immunization HAI titer (log$_2$Reciprocal ± S.E.) | | Virus Titer in Indicated Tissue[c] (log$_{10}$TCID$_{50}$/Gram ± S.E.) | | | |
|---|---|---|---|---|---|---|---|
| | | | | Replication of PIV1 challenge virus | | | Replication challenge |
| | | α-PIV1 | α-PIV3 | Nasal Turbinates | Lungs Turbinates | Nasal | |
| Control[b] | — | ≦1 | ≦1 | 5.0 ± 0.3 | 4.6 ± 0.5 | 5.5 ± 0.4 | 5.0 ± 0.7 |
| rPIV3-1.cp45L | PIV1 | 6.9 ± 0.5 | ≦1 | ≦1.2 | ≦1.2 | 1.9 ± 0.6 | 1.7 ± 0.5 |
| rPIV3-1 | PIV1 | 7.9 ± 0.4 | ≦1 | ≦1.2 | ≦1.2 | 2.9 ± 0.3 | 2.6 ± 0.4 |
| rPIV3cp45L | PIV3 | ≦1 | 9.3 ± 0.2 | 4.6 ± 0.2 | 2.8 ± 0.7 | ≦1.2 | ≦1.2 |
| rPIV3/JS | PIV3 | ≦1 | 10.3 ± 0.3 | 4.6 ± 0.4 | 2.4 ± 0.5 | ≦1.2 | ≦1.2 |
| PIV3cp45[d] | PIV3 | ≦1 | 8.9 ± 0.4 | 4.9 ± 0.2 | 2.5 ± 0.8 | ≦1.2 | ≦1.2 |

[a]Groups of 10 hamsters were immunized intranasally with 10$^6$ PFU of indicated viruses. Post-immunization sera were collected on days 33, two days prior to challenge (see[c]).
[b]Hamsters in control group were not inoculated.
[c]Five weeks after immunization, five hamsters from each group were challenged intranasally with 10$^6$ PFU of indicated virus. Tissue samples were harvested 4 days post challenge. Viruses present in tissue samples were titered on LLC-MK2 monolayers and the data are presented as log$_{10}$TCID$_{50}$/gram of tissue ± standard error.
[d]Biologically-derived virus.

Infection with rPIV3-1.cp45L also Confers Resistance to PIV3.

Information on the role of the non-HN or F glycoproteins of PIVs (i.e., the internal proteins) in resistance is limited. The disclosure and use of rPIV3-1 and rPIV3-1.cp45L herein provides an opportunity to examine the role that internal proteins play in resistance to challenge with PIV3, since the only genes shared by immunizing and challenge viruses are the internal protein genes. PIV3 challenge virus replication was significantly restricted in both the upper and lower respiratory tracts by prior infection of hamsters with rPIV3-1 or rPIV3-1.cp45L (Table 17). Thus, these data indicate that the internal proteins of PIV3, like the HN and F proteins, are capable of inducing partial resistance to replication of the challenge PIV3.

Among the findings demonstrated by the immunogenicity and efficacy studies above a particularly unexpected finding was that infection with wt or attenuated rPIV3 induced a 100-fold reduction in the replication of PIV1 challenge virus in the lungs. Thus, infection with one serotype of PIV provided significant protection against a heterologous serotype. This was unexpected in part because previous studies indicated that infection of animals with one type of human PIV did not induce significant heterologous protection against a PIV belonging to a different human serotype, conforming to a general belief that immunity to human PIV infections was largely type-specific (see, eg., Cook et al., Amer. Jour. Hyg. 77:150, 1963; Ray et al., J. Infect. Dis. 162:746, 1990, each incorporated herein by reference in its entirety).

The present Example demonstrates successful exploitation of novel methods and reagents developed for generating PIV3 vaccines to further provide rapid, rational development of live attenuated candidate vaccines for PIV1. A cDNA encoding infectious PIV3 was modified by substitution of the ORFs encoding the PIV1 HN and F protective antigens for their PIV3 counterparts. Subsequently, attenuating mutations, exemplified by three attenuating mutations present in the L gene of the cp45 PIV3, were incorporated within this modified chimeric PIV3-PIV1 cDNA. From this cDNA, a recombinant virus was recovered bearing the HN and F genes of PIV1, the internal proteins of PIV3, and the PIV3 cp45 L gene mutations. This recombinant, rPIV3-1.cp45L, was temperature sensitive, highly attenuated in hamsters, and highly efficacious against PIV1 challenge in hamsters. The level of temperature sensitivity, attenuation, and immunogenicity exhibited by rPIV3-1.cp45L was comparable to that of cp45 PIV3, indicating that the phenotypes specified by the set of cp45 L gene mutations are independent of the HN and F surface glycoproteins. These findings, which represent the first live attenuated PIV1 vaccine candidate generated by reverse genetics, provide a generally successful scheme for developing vaccines against PIV1.

Little information is known concerning the role that internal proteins of parainfluenza viruses play in resistance to reinfection with homologous virus. Infection with vaccinia recombinants expressing N, epitopes within N, or M reportedly induce resistance to replication of challenge virus, but the magnitude of the resistance reported is less than that induced by vaccinia recombinants bearing HN or F glycoproteins (see, eg., Kast et al., Proc. Natl. Acad. Sci. USA 88:2283, 1991; Sakaguchi et al., J. Gen. Virol. 74:479, 1993; Thomson et al., J. Immunol. 157:822, 1996, each incorporated herein by reference in its entirety). These studies suggested that the internal proteins were making only minor contributions to resistance to reinfection. Therefore, the present disclosure presents unexpected results by showing that prior infection of hamsters with rPIV3-1.cp45L or rPIV3-1 induced about 250- to 4000-fold reduction of replication of PIV3 in both the nasal turbinates and lungs. These two chimeric recombinant viruses differ from the PIV3 challenge virus in that they possess the HN and F glycoproteins of PIV1 rather than PIV3, but they share all other genes with the challenge virus. The HN and F glycoproteins of PIV1 share 47% and 43% sequence identity with those of PIV3, respectively. Although it is likely that the shared internal proteins are mediating the observed resistance, it is also possible that shared protein sequences between PIV1 and PIV3 F and HN glycoproteins are contributing to the observed immunity. For example, there are 5 stretches in HN and 2 stretches in F extending at least 9 amino acid residues in length that are shared between PIV1 and PIV3 and have the potential to act as protective CTL epitopes. It is reasonable to consider that the shared internal proteins are contributing to the restriction of replication of wt PIV3 challenge virus, since this level of cross-immunity has not been seen in previous studies (see, eg., Cook et al., Amer.

Jour. Hyg. 77:150, 1963; Ray et al., J. Infect. Dis. 162:746, 1990, incorporated herein by reference in its entirety).

The finding that the internal PIV3 proteins of the rPIV3-1 and rPIV3-1.cp45L chimeras conferred resistance to PIV3 challenge demonstrates that attenuated derivatives of PIV3 can be used as vectors for PIV1 and PIV2 protective antigens. Following the teachings of the invention, immunization with one PIV3-based live-attenuated vaccine virus can restrict the replication of other PIV3-based vaccine viruses administered subsequently, thereby decreasing the immunogenicity of the second virus. Since PIV3, like RSV, induces significant illness in early infancy, a combined RSV-PIV3 vaccine for use in the very young 2- to 4-week old infant is therefore an important aspect of the invention (see, eg., Collins et al., Fields Virology 3rd ed. Philadelphia: Lippincott-Raven Publishers, 1205(1), 1996; Reed et al., J. Infect. Dis. 175:807, 1997, each incorporated herein by reference in its entirety). According to this aspect of the invention, immunization with a PIV1-PIV2 vaccine will be preferably initiated at about 6 months of age, since most PIV1 and PIV2 disease occurs after the age of six months. In the possible circumstance that immunization with rPIV3 cp45 significantly inhibits replication of a chimeric recombinant PIV3-1 vaccine virus with which it shares internal protein genes, successful immunization with a recombinant PIV3-1 vaccine may be compromised. In this event, a trivalent PIV vaccine will be administered simultaneously rather than sequentially, thereby preventing the above noted inhibition.

The disclosure herein that infection with a vaccine or wt PIV3 would induce a 100-fold reduction of pulmonary virus replication of the heterologous wt PIV1 was clearly unexpected, in part because the human PIV viruses are serologically distinct by neutralization assay, and previous studies in hamsters found that prior infection with one type of PIV failed to induce resistance to challenge with a high dose of a different PIV type (see eg., Cook et al., Amer. Jour. Hyg. 77:150, 1963; Ray et al., J. Infect. Dis. 162:746, 1990; Cook et al., Amer. Jour. Hyg. 69:250, 1959). Furthermore, there is little epidemiological data documenting that prior infection with one PIV significantly modifies subsequent infection with a heterotypic PIV.

In summary, the present Example shows that rPIV3 was successfully converted into a vaccine for PIV1 by substituting the ORFs encoding the F and HN glycoproteins and introducing known attenuating mutations into the PIV3 internal genes. Thus, the extensive methods and reagents provided herein can be applied directly and predictably to attenuating the PIV3 backbone of the rPIV3-1 chimeric virus, as well as for generating live-attenuated PIV2 vaccine viruses.

The foregoing disclosure makes it possible to exploit the reagents and methods provided herein to develop a broad assemblage of PIV and related vaccines. In this context, recovery of live, immunogenic chimeras between PIV3 and PIV2 exemplifies powerful new tools for developing a range of recombinant PIV viruses for vaccine use. In conjunction with this work, identification and characterization of the genetic basis for attenuation of naturally occurring PIV mutants, e.g., cp45 and BPIV3 vaccine candidates, following the teachings of the present disclosure also enables development of a large host of recombinant vaccine viruses and subviral particles. In particular, desired mutations present in biologically derived mutant viruses will be readily identified and selected by their introduction, singly and in combination, into a wild type, partially attenuated, or chimeric PIV background, as shown in the Examples above. These findings will expand the menu of exemplary, attenuating mutations within the invention which can introduced into PIV clones to calibrate the level of attenuation and immunogenicity in vaccine recombinants. Biologically derived mutations can also be introduced within PIV clones having different types of mutations, e.g., mutations involving alterations, deletions, or substitutions of a gene or gene segment. Within this aspect of the invention, recombinant PIV are provided which have a selected gene deletion, addition, or substitution, such as rPIV having a deletion of the C, D or V ORF(s). Such alternatively mutated clones can be further modified according to the present disclosure by introducing one or more mutations specifying a ts, ca or att phenotype adopted from a biologically derived mutant PIV, as exemplified by the PIV recombinants r942, r992, r1558, r942/992, r992/1558, or r942/1558, and r942/992/1558. In additional aspects of the invention, biologically derived mutations will be combined with de novo attenuating mutations not found in nature, as exemplified by attenuating gene deletions, e.g., of the C, D and/or V ORFs. Other types of mutations disclosed herein conferring desired phenotypic characteristics will also be combined with biologically derived, attenuating mutations, similar to the range of combinatorial mutations disclosed for recombinant RSV vaccine strains in U.S. patent application Ser. No. 08/892,403, filed Jul. 15, 1997 (incorporated herein by reference). Comparable mutations can be readily introduced, e.g., into a chimeric virus, to achieve a desired levels of attenuation and immunogenicity in a chimeric vaccine strain. In this manner, a large menu of mutations are provided within the invention that are useful to engineer a wide assemblage of live attenuated rPIV vaccines having a desired balance of attenuation and immunogenicity, along with other desired phenotypic characteristics.

EXAMPLE XV

Construction of cDNAs Encoding a Chimeric HPIV3/Measles Virus-HA Antigenome and Recovery of Infectious Virus The full-length cDNA clones, p3/7(131)2G+, encoding the complete 15462 nucleotide antigenome of the JS PIV3 wt virus, and pFLCcp45L, which encodes the antigenome of the derivative of JS wt containing three cp45-specific temperature-sensitive mutations in the L ORF of PIV3, have been previously described (Durbin et al., Virology 235:323-332, 1997a; Skiadopoulos et al., J. Virol. 72:1762-8, 1998, each incorporated herein by reference). These clones were used as vectors for the insertion of the HA gene of measles virus to create both wildtype and attenuated HPIV3 chimeric constructs which express a heterologous antigenic determinant, exemplified by the HA protein, of measles virus. The size of each insert containing the HA gene of measles was a multiple of six such that the chimeric virus recovered from the cDNA would conform to the rule of six (Durbin et al., Virology 234:74-83, 1997b, incorporated herein by reference).

Construction of Full-Length Chimeric HPIV3 cDNAs Encoding the HA Protein of Measles Virus in the N/P or P/M Junctions.

The PmlI to BamHI fragment of p3/7(131)2G+ (nt 1215-3903 of the PIV3 antigenome) was subcloned into the plasmid pUC119 {pUC119(PmlI-BamHI)} which had been modified to include a PmlI site in the multiple cloning region. Two independent single-stranded mutagenesis reactions were performed on pUC119(PmlI-BamHI) using Kunkel's method (Kunkel et al., Methods Enzymol. 154:367-382, 1987, incorporated herein by reference); the first reaction introduced an AflII site in the 3' (downstream)-noncoding region of the N gene by mutating the CTAAAT sequence at nts 1677-1682 of the antigenome to CTTAAG (pAf/II N-P), and the second, separate, reaction introduced an Af/II site in the in the 3'-noncoding region of the P gene by mutating the TCAATC sequence at nts 3693-3698 of the antigenome to CTTAAG (pAf/II P-M).

The HA ORF of measles virus Edmonston strain was amplified from Edmonston wild type virus by reverse transcription polymerase chain reaction (RT-PCR). The nt sequence of the Edmonston wild type HA open reading frame (ORF) is in GenBank Accession # U03669, incorporated herein by reference (note that this sequence is the ORF only without the upstream 3 nts or the stop codon). Measles virus RNA was purified from clarified medium using TRIzol-LS (Life Technologies, Gaithersburg, Md.) following the manufacturer's recommended procedure. RT-PCR was performed with the Advantage RT-for-PCR and Advantage-HF PCR kits (Clontech, Palo Alto, Calif.) following the recommended protocols. Primers were used to generate a PCR fragment spanning the entire ORF of the measles virus HA gene flanked by PIV3 non-coding sequence and Af/II restriction sites. The forward primer 5'-TTAATCTTAAGAATATACAAATAA-GAAAAACTTAGGATTAAAGAGCGATGTCACCACAA-CGAGACCGGATAAATGCCTTCTAC-3' (SEQ ID NO. 127) encodes an Af/II site (italicized) upstream of PIV3 non-coding sequence derived from the N/P gene junction-nts 3699-3731 (underlined), containing GE, IG and GS sequences (FIG. 20A) and the beginning of the measles HA ORF (bolded) preceded by three non-HPIV3, non-measles virus nts designated in the primer. The reverse primer 5'-AT-TATTGCTTAAGGTTTGTTCGGTGTCGTTTCTTTGTT-GGATCCTATCTGCGATTGGTTCCATCTTC-3' (SEQ ID NO. 128) encodes an Af/II site (italicized) downstream (in the positive-sense complement) of PIV3 noncoding sequence derived from the P gene, nt 3594-3623 (underlined), and the end of the measles HA ORF (bolded). The resultant PCR fragment was then digested with Af/II and cloned into p(Af/II N-P) and p(Af/II P-M) to create pUC119(HA N-P) and pUC119(HA P-M) respectively. pUC119(HA N-P) and pUC119(HA P-M) were sequenced over the entire Af/II insert using dRhodamine Terminator Cycle Sequencing Ready Reaction (ABI prism, PE Applied Biosystems, Foster city, CA), and the sequence was confirmed to be correct.

The PmlI to BamHI fragments of pUC119(HA N-P) and pUC119(HA P-M) were separately cloned into the full-length antigenome cDNA plasmid p3/7(131)2G+as previously described (Durbin et al., Virology 235:323-332, 1997a, incorporated herein by reference) to create pFLC(HA N-P) and pFLC(HA P-M) (FIG. 20). The XhoI-NgoMI fragment (nt 7437-15929) of pFLCcp45L was then cloned into the XhoI-NgoMI window of both pFLC(HA N-P) and pFLC(HA P-M) to create pFLCcp45L(HA N-P) and pFLCcp45L(HA P-M). pFLCcp45L encodes the three amino acid changes in the L gene of PIV3 cp45 (aa position 942, 992, and 1558) which confer most of the temperature-sensitivity and attenuation of the cp45 vaccine candidate virus (Skiadopoulos et al., J. Virol. 72:1762-8, 1998, incorporated herein by reference), and the transfer of the XhoI-NgoMI fragment transferred those mutations.

Construction of Full-Length HPIV3 Chimeric cDNAs Encoding the HA Protein of Measles in the HN/L Junction A HPIV3 chimeric cDNA was constructed by PCR to include a heterologous polynucleotide sequence, exemplified by the measles virus HA gene, encoding a heterologous antigenic determinant of the measles virus, flanked by the transcription signals and the noncoding regions of the HPIV3 HN gene. This cDNA was designed to be combined with an rPIV3 vector as an extra gene following the HN gene. First, using Kunkel mutagenesis (Kunkel et al., Methods Enzymol. 154: 367-382, 1987, incorporated herein by reference), a StuI site was introduced in the 3'-noncoding region of the HN gene by mutating the AGACAA sequence at nts 8598-8603 of the antigenome to AGGCCT yielding plasmid p3/7(131)2G-Stu (FIG. 20B). A cDNA containing the measles HA ORF flanked by HPIV3 sequences (see FIG. 20B) was then constructed in three pieces by PCR. The first PCR synthesized the left-hand, upstream piece of the gene. The forward primer 5'-GACAAT-AGGCCTAAAAGGGAAATATAAAAAACTTAGGAGT-AAAGTTACGCAAT CC-3' (SEQ ID NO. 129) contains a StuI site (italicized) followed by HPIV3 sequence (underlined) which includes the downstream end of the HN gene (HPIV3 nts 8602-8620), an intergenic region, and the gene-start signal and sequence from the upstream end of the HN gene (HPIV3 nt 6733-6753). The reverse primer 5'-GTA-GAACGCGTTTATCCGGTCTCGTTGTGGTGACATCT-CGAATTTGGATTTGTCTATTGGGTCCTTCC-3' (SEQ ID NO. 130) contains an MluI site (italicized) downstream of the start of the measles HA ORF (bolded) followed by the complement to HPIV3 nts 6744-6805 (underlined), which are part of the upstream HN noncoding region. The MluI site present in the introduced measles virus ORF was created by changing nt 27 from T (in the wild type Edmonston HA gene) to C and nt 30 from C to G. Both of these changes are noncoding in the measles virus ORF. The PCR was performed using p3/7(131)2G-Stu as template. The resulting product, termed PCR fragment 1, is flanked by a StuI site at the 5'-end and an MluI site at the 3'-end and contains the first 36 nt of the measles HA ORF downstream of noncoding sequence from the HPIV3 HN gene. The second PCR reaction synthesized the right-hand end of the HN gene. The forward primer GTA-GAACGCGTTTATCCGGTCTCGTTGTGGTGACATCT-CGAATTTGGATTTGTCTATTGGGTCCTTCC-3' (SEQ ID NO. 130) contains the XmaI (italics) and the end of the measles HA ORF (bold), followed by HPIV3 nts 8525-8566 (underlined) representing part of the downstream nontranslated region of the HN gene. The reverse primer 5'-CCATG-TAATTGAATCCCCCAACACTAGC-3', (SEQ ID NO. 131) spans HPIV3 nts 11448-11475, located in the L gene. The template for the PCR was p3/7(131)2G-Stu. PCR fragment 2 which resulted from this reaction contains the last 35 nt of the measles HA ORF and approximately 2800 nt of the L ORF of PIV3 and is flanked by an XmaI site and an SphI site (which occurs naturally at HPIV3 position 11317). The third PCR reaction amplified the largest, central portion of the measles HA ORF from the template cDNA pTM-7, a plasmid which contains the HA ORF of the Edmonston strain of measles virus supplied by the ATCC. Sequence analysis of this plasmid showed that the measles virus HA ORF contained in PTM-7 contains 2 amino acid differences from pTM-7 of the Edmonston wild type HA sequence used for insertion into the N-P and M-P junction, and these were at amino acid positions 46 (F to S) and at position 481 (Y to N). The forward primer 5'-CGGATAAACGCGTFCTACAAAGATAACC-3' (SEQ ID NO. 132) (MluI site italicized) and reverse primer 5'-CG-GATAAACGCGTFCTACAAAGATAACC-3' (SEQ ID NO. 132) (XmaI site italicized) amplified PCR fragment 3 which contained nts 19-1838 of the measles HA ORF. To assemble the pieces, PCR fragment 1 was digested with StuI and MluI while PCR fragment 3 was digested with MluI and XmaI. These two digested fragments were then cloned by triple ligation into the StuI-XmaI window of pUC118 which had been modified to include a StuI site in its multiple cloning region. The resultant plasmid, pUC118(HA 1+3) was digested with StuI and XmaI while PCR fragment 2 was digested with XmaI and SphI. The two digested products were then cloned into the StuI-SphI window of p3/7(131)2G-Stu, resulting in the plasmid pFLC(HA HN-L). The StuI-SphI fragment, including the entire measles HA ORF, was then sequenced using dRhodamine Terminator Cycle Sequencing Ready Reaction (ABI prism, PE Applied Biosystems, Foster city, CA). The chimeric construct sequence was confirmed. In this way, the measles virus HA ORF flanked by HPIV3 transcription signals was inserted as an extra gene into the N/P, P/M, or HN/L junction of an antigenomic cDNA vector comprising a wild type HPIV3 or into the N/P or P/M junction of an antigenomic cDNA vector comprising an attenuated HPIV3.

Recovery of Chimeric rPIV3 Wild Type and rcp45L Expressing the HA Protein of Measles Virus The five full-length vector cDNAs bearing the measles HA ORF as a separate gene were transfected separately into HEp-2 cells on six-well plates (Costar, Cambridge, Mass.) together with the support plasmids {pTM(N), pTM(P no C), and pTM(L)}, and LipofectACE (Life Technologies), and the cells were simultaneously infected with MVA-T7, a replication-defective vaccinia virus recombinant encoding the bacteriophage T7 polymerase protein as previously described (Durbin et al., *Virology* 235:323-332, 1997; Durbin et al., *Virology* 234:74-83, 1997, each incorporated herein by reference). pTM(P no C) is a derivative of pTM(P) (Durbin et al., *Virology* 261:319-330, 1999) in which the C ORF expression has been silenced by mutation of the C start codon. After incubation at 32° C. for three days, the transfection harvest was passaged onto a fresh monolayer of Vero cells in a T25 flask and incubated for 5 days at 32° C. (referred to as passage 1). The presence of HPIV3 in the passage 1 harvest was determined by plaque titration on LLC-MK2 monolayer cultures with plaques visualized by immunoperoxidase staining with HPIV3 HN-specific and measles HA-specific monoclonal antibodies as previously described (Durbin et al., *Virology* 235:323-332, 1997, incorporated herein by reference).

The rPIV3(HA HN-L) virus present in the supernatant of the appropriate passage 1 harvest was biologically-cloned by plaque purification three times on LLC-MK2 cells as previously described (Hall et al., *Virus Res.* 22:173-184, 1992, incorporated herein by reference). rPIV3(HA N-P), rcp45L (HA N-P), rPIV3(HA P-M), and rcp45L(HA P-M) were biologically-cloned from their respective passage 1 harvests by terminal dilution using serial 2-fold dilutions on 96-well plates (12 wells per dilution) of Vero cell monolayers. The biologically-cloned recombinant viruses from the third round of plaque purification or from the second or third round of terminal dilution were then amplified twice in LLC-MK2 cells {rPIV3(HA HN-L} or Vero cells {rPIV3(HA N-P), rcp45L(HA N-P), rPIV3(HA P-M), rcp45L(HA P-M)} at 32° C. to produce virus for further characterization. As a first step in confirming and characterizing the recombinant chimeric PIV3s expressing the HA glycoprotein of measles virus, each passage 1 harvest was analyzed by RT-PCR using three different primer pairs; one pair for each location of the HA ORF insert. The first primer pair amplified a fragment of PIV3 spanning nucleotides 1596-1968 of the full-length HPIV3 genome, which includes the N/P insertion site. This fragment size increased to 2298 nucleotides with the measles HA ORF inserted between the N and P genes. The second primer pair amplified a fragment of PIV3 spanning nucleotides 3438-3866 of the full-length HPIV3 genome, which includes the P/M insertion site. With the measles HA ORF inserted between the P and M genes, this fragment size increased to 2352 nucleotides. The third primer pair amplified a fragment of PIV3 spanning nucleotides 8466-8649 of the full-length antigenome. With the measles HA ORF inserted between the HN and L genes, this fragment size increased to 2211 nucleotides, which includes the HN/L insertion site. All five recovered viruses contained an insert of the appropriate size at the appropriate location. The generation of each PCR product was dependent upon the inclusion of reverse transcriptase, indicating that each was derived from RNA and not from contaminating cDNA.

Monolayers of LLC-MK2 cells in T25 flasks were infected at a multiplicity of infection (MOI) of 5 with either rcp45L (HA N-P), rcp45L(HA P-M), rJS or were mock infected. Monolayers of Vero cells in T25 flasks were infected with the Edmonston wild type strain of measles virus at an MOI of 5. Vero cell monolayers were chosen for the measles Edmonston virus infection because measles virus does not grow well in LLC-MK2 cells. At 24 hours post-infection, the monolayer was washed with methionine-minus DMEM (Life Technologies). $^{35}$S methionine was added to DMEM-minus media at a concentration of 10 uCi/ml and 1 ml was added to each flask which was then incubated at 32° C. for 6 hours. The cells were harvested and washed 3 times in PBS. The cell pellets were resuspended in 1 ml RIPA buffer {1% (w/v) sodium deoxycholate, 1% (v/v) Triton X-100 (Sigma), 0.2% (w/v) SDS, 150 mM NaCl, 50 mM Tris-HCl, pH 7.4}, freeze-thawed and clarified by centrifugation at 6500×G for 5 minutes. The cell extract was transferred to a fresh eppendorf tube and a mixture of monoclonal antibodies which recognizes the HA glycoprotein of measles virus (79-XV-V17, 80-III-B2, 81-1-366) (Hummel et al., *J. Virol.* 69:1913-6, 1995; Sheshberadaran et al., *Arch. Virol.* 83:251-68, 1985, each incorporated herein by reference) or which recognizes the HN protein (101/1, 403/7, 166/11) of PIV3 (van Wyke Coelingh et al., *Virology* 160:465-72, 1987, incorporated herein by reference) was added to each sample and incubated with constant mixing for 2 hours at 4° C. Immune complexes were precipitated by adding 200 μl of a 10% suspension of protein A Sepharose beads (Sigma, St. Louis, Mo.) to each sample followed by constant mixing at 4° C. overnight. Each sample was suspended in 90 μl of 1× loading buffer and 10 μl of reducing agent was added. After heating at 70° C. for 10 minutes, 20 μl of each sample was loaded onto a 4-12% polyacrylamide gel (NuPAGE, Novex, San Diego, Calif.) per the manufacturer's recommendations. The gel was dried and autoradiographed (FIG. 21). rcp45L(HA P-M) and rcp45L (HA N-P) encoded a protein precipitated by the anti-measles HA monoclonal antibodies which was the same size as the authentic measles HA protein. rcp45L(HA P-M) and rcp45L (HA N-P) expressed the measles virus HA protein to a greater extent than did the Edmonston wild type strain of measles virus indicating that these constructs efficiently expressed the measles virus HA from the N/P and P/M junctions of the attenuated strain rcp45L. rcp45L(HA N-P) and rcp45L(HA P-M) were confirmed to be HPIV3-based by their reactivity with the PIV3 anti-HN monoclonal antibodies.

The Temperature Sensitivity of Replication of rPIV3 Parent and rPIV3(HA) Chimeric Viruses In Vitro The level of temperature sensitivity of replication of the chimeric rPIV3s bearing the measles virus HA insertion was evaluated to assess whether acquisition of the HA insert modified the level of replication in the chimeric virus compared to the parental, vector virus at various temperatures (Table 1). Serial 10-fold dilutions of rcp45L, rcp45L(N-P), rcp45L(HA P-M), rPIV3(HA HN-L), rPIV3(HA P-M), or rJS were carried out in L-15 supplemented with 5% FBS, 4 mM glutamine, and 50 μg/ml gentamicin on LLC-MK2 cell monolayers in 96 well plates and incubated at 32, 36, 37, 38, 39, or 40° C. for 6 days. Virus was detected by hemadsorption and reported as $\log_{10}$ TCID$_{50}$/ml. Interestingly, chimeric derivatives of both wild type vector viruses bearing the measles virus HA gene, rPIV3(HA HN-L) and rPIV3(HA P-M), were slightly restricted in replication at 40° C. (Table 18). The two attenuated rPIV3s bearing the measles virus HA gene, rcp45L(N-P) and rcp45L(HA P-M), possessed a level of temperature sensitivity similar to that of the rcp45L parental vector virus with rcp45L(HA P-M) being slightly more ts than its parent. Thus, the viruses bearing the inserts replicated in tissue culture similarly to the parental vector rPIV3 from which they were derived, with only a slight increase in temperature sensitivity. These results indicate that rPIV3 can readily serve as a vector to accommodate the HA insert at different sites without major alteration in replication in vitro, and that rPIV3(HA) chimeric viruses can readily accommodate the further addition of one or more attenuating mutations.

TABLE 18

Replication at permissive and elevated temperatures of recombinant HPIV3s expressing the HA protein of measles virus as an extra gene in the N-P, P-M, or HN-L junctions.

| | Virus titer ($\log_{10}TCID_{50}$/ml) at indicated temperature | | | | | |
|---|---|---|---|---|---|---|
| Virus | 32° C.[1] | 36° C. | 37° C. | 38° C. | 39° C. | 40° C. |
| rcp45L[2] | 8.2 | 8.2 | 7.2 | <u>5.2</u>[6] | 3.4 | 3.0 |
| rcp45L (HA P-M)[3] | 7.4 | 6.7 | <u>5.2</u> | 4.2 | 1.4 | 1.4 |
| rcp45L (HA N-P)[3] | 7.4 | 7.2 | 5.7 | <u>4.2</u> | 2.2 | ≤1.2 |
| rPIV3 (HA HN-L)[4] | 7.7 | 8.2 | 7.0 | 7.7 | 6.7 | <u>5.2</u> |
| rPIV3 (HA P-M)[4] | 7.7 | 7.4 | 6.7 | 6.2 | 6.2 | <u>4.7</u> |
| PIV3-rJS[5] | 8.7 | 9.0 | 9.0 | 8.4 | 8.2 | 9.0 |

[1]Permissive temperature.
[2]Recombinant ts derivative of the JS wild type strain of HPIV3, bearing 3 attenuating amino acid substitutions derived from cp45.
[3]Recombinant attenuated ts derivative of JS wild type HPIV3 expressing the HA protein of measles virus.
[4]Recombinant wild type HPIV3 expressing the HA protein of measles virus.
[5]Recombinant wild type HPIV3, strain JS.
[6]Underlined titer represents the lowest restrictive temperature at which a 100-fold or greater reduction in titer from that at 32° C. is seen and defines the shut-off temperature of the virus.

EXAMPLE XVI

Chimeric rPIV3s Bearing an Antigenic Determinant of Measles Virus Replicate Efficiently in Hamsters and Induce High Titers of Antibodies Against Both HPIV3 and Measles Determination of the Level of Replication and Immunogenicity of the rPIV3(HA) Viruses in Hamsters The levels of replication of chimeric rPIV3s bearing an antigenic determinant of the measles virus was compared with that of their parent rPIV3s to determine if the acquisition of the determinant, exemplified by an HA insert, significantly modified their ability to replicate and to induce an immune response in vivo. In two different experiments, groups of 6 or 7 4-6 week-old Golden Syrian hamsters were inoculated intranasally with 0.1 ml of EMEM (Life Technologies) containing $10^{6.0}$ PFU of rJS, rcp45L, rcp45L(HA P-M), rcp45L (HA N-P), rPIV3(HA HN-L), or rPIV3(HA P-M) (Tables 19 and 20). On day 4 post-inoculation the hamsters were sacrificed and the lungs and nasal turbinates were harvested. The nasal turbinates and lungs were homogenized in 10% or 20% w/v suspension of L-15 (Quality Biologicals, Gaithersburg, Md.) respectively, and the samples were rapidly frozen. Virus present in the samples was titered on 96 well plates of LLC-MK2 cell monolayers and incubated at 32° C. for 7 days. Virus was detected by hemadsorption, and the mean $\log_{10}$ $TCID_{50}$/g was calculated for each group of hamsters. Insertion of the HA gene into wild type rJS (Table 19) restricted its replication 4 to 20-fold in the upper respiratory tract and up to five-fold in the lower respiratory tract indicating only a slight effect of the acquisition of the HA gene on replication of wild type rJS virus in hamsters. The replication of each of the two rcp45(HA) antigenic chimeras was 10-fold less in the upper respiratory tract of hamsters (Table 20)—than that of rcp45L, the recombinant parent virus bearing the three attenuating ts mutations in the L protein, but was the same as the rcp45L parent in the lower respiratory tract. Thus, for each of the two rcp45(HA) antigenic chimeras there was a slight, but statistically significant, reduction in replication in the upper respiratory tract of hamsters indicating that the acquisition of the HA gene by rcp45L increased its attenuation for the upper, but not the lower, respiratory tract. Thus, the effect of the insertion of the HA gene on the replication of wild type or attenuated PIV3 was comparable in the upper respiratory tract.

TABLE 19

Replication of wildtype rPIV3(HA) chimeric viruses in the upper and lower respiratory tract of hamsters

| | | Virus Titer ($\log_{10}TCID_{50}$/gm ± S.E.[2]) [Tukey-Kramer Grouping][3] | |
|---|---|---|---|
| Virus[1] | # Animals | Nasal Turbinates | Lungs |
| rcp45L | 8 | 4.0 ± 0.1[A] | 1.5 ± 0.1[A] |
| rPIV3(HA N-P) | 8 | 5.1 ± 0.1[B] | 5.9 ± 0.1[B] |
| rPIV3(HA P-M) | 8 | 5.9 ± 0.1[C] | 6.7 ± 0.2[C] |
| rPIV3(HA HN-L) | 8 | 5.9 ± 0.2[C] | 5.8 ± 0.1[B] |
| rJS | 8 | 6.5 ± 0.1[D] | 6.6 ± 0.2[C] |

[1]Animals received $10^6 TCID^{50}$ of the indicated virus given intranasally in a 0.1 ml inoculum and the lungs and nasal turbinates were harvested 4 days later.
[2]Standard Error.
[3]Mean virus titers were assigned to statistically similar groups (A-D) by the Tukey-Kramer test. Therefore, means in each column with different letters are significantly different (α = 0.05) and those with the same letter are not significantly different.

TABLE 20

Replication of the rPIV3cp45L(HA) antigenic chimeric viruses in the upper and lower respiratory tract of hamsters

| | | Virus Titer ($\log_{10}TCID_{50}$/gm ± S.E.[2]) [Tukey-Kramer Grouping][3] | |
|---|---|---|---|
| Virus[1] | #Animals | Nasal Turbinates | Lungs |
| rcp45L | 6 | 4.7 ± 0.2[A] | 2.9 ± 0.1[A] |
| rcp45L(HA N-P) | 6 | 3.7 ± 0.2[B] | 2.9 ± 0.1[A] |
| rcp45L (HA P-M) | 7 | 3.7 ± 0.1[B] | 2.9 ± 0.2[A] |
| rJS | 7 | 6.5 ± 0.1[C] | 5.6 ± 0.2[B] |

[1]Animals received $10^6$ pfu of the indicated virus given intranasally in a 0.1 ml inoculum and the lungs and nasal turbinates were harvested 4 days later.
[2]Standard Error.
[3]Mean virus titers were assigned to statistically similar groups (A-D) by the Tukey-Kramer test. Therefore, means in each column with different letters are significantly different (α = 0.05) and those with the same letter are not significantly different.

The ability of the chimeric rHPIV3(HA) viruses to induce an immune response to HPIV3 and to measles virus was studied next. Groups of 6-24 Golden Syrian hamsters (age 4-6 weeks) were infected as described above with either $10^{6.0}$ PFU rJS, rPIV3(HA P-M), rcp45L, rcp45L(HA P-M), or rcp45L(HA N-P) (Table 4) on day 0, Serum was collected from each hamster on day ≦1 and on day 25 post-inoculation. The serum antibody response to HPIV3 was evaluated by hemagglutination-inhibition (HAI) assay as previously described (van Wyke Coelingh et al., *Virology* 143:569-582, 1985, incorporated herein by reference), and the serum antibody response to measles virus was evaluated by 60% plaque-reduction assay as previously described (Coates et al., *Am. J. Epidemiol.* 83:299-313, 1966, incorporated herein by reference). These results were compared with that from an additional control group of cotton rats that received $10^{5.0}$ of the live-attenuated measles virus (Moraten strain) administered intramuscularly on day 0. Cotton rats, rather than hamsters, were used in this group because measles virus is only weakly infectious for hamsters. As can be seen in Table 21, each of the PIV3(HA) chimeric viruses was able to elicit a robust serum neutralizing antibody response against measles virus. There was no significant difference between the amount of serum neutralizing antibody elicited by the attenuated derivative rcp45L(HA P-M) as compared to its counterpart in the wild type background, rPIV3(HA P-M). Furthermore, the level of measles virus-neutralizing serum antibodies induced by the rPIV3(HA) recombinants were on average 5-fold greater than that achieved by the intramuscular immunization with the live attenuated measles virus vaccine. In addition, the serum antibody response to HPIV3 produced by all the chimeric viruses was also robust and comparable to that produced by infection with wild type rJS.

Six hamsters from each group and from a control group similarly infected with RSV were challenged on day 25 with $10^{6.0}$ pfu of biologically-derived HPIV3 wildtype virus given intranasally in a 0.1 ml inoculum. The lungs and nasal turbinates were harvested on day 4 and processed as described above. Virus present in the samples was titered on 96 well plates of LLC-MK2 cell monolayers and incubated at 32° C. for 7 days. Virus was detected by hemadsorption and the mean $\log_{10}$ TCID$_{50}$/g was calculated for each group of hamsters. As shown in Table 5, those hamsters which had received the chimeric viruses, whether in the attenuated or wild type backbone, were highly protected against replication of challenge wild type HPIV3 in both the upper and the lower respiratory tract. Thus, despite the slight attenuating effect of the acquisition of the measles virus HA gene on replication of the rcp45(HA) chimeric viruses, infection with either rcp45L (HA P-M) or rcp45L(HA N-P) induced a high level of protection against HPIV3 as indicated by approximately a 1000-fold reduction of its replication in the upper and lower respiratory tract of hamsters. Since wild type measles virus does not replicate efficiently in hamsters, it cannot be used to challenge this host. However, it is expected that the attenuated chimeric rcp45L(HA) vaccine candidates will be highly efficacious against measles virus since high levels of neutralizing antibody, i.e., mean titer of greater than 1:5000, were induced. Comparable levels of measles virus antibodies are associated with strong resistance to measles virus disease in humans (Chen et al., *J. Infect. Dis.* 162:1036-42, 1990, incorporated herein by reference).

TABLE 21 rPIV3(HA) antigenic chimeric viruses elicit an excellent serum antibody response to both measles virus and PIV3

| Virus[1] | # Animals | Serum antibody titer to measles virus (60% plaque reduction neutralization titer, mean reciprocal $\log_2$ ± S.E.[2]) | | Serum antibody response to HPIV3 (HAI titer; mean reciprocal $\log_2$ ± S.E.) | |
|---|---|---|---|---|---|
| | | Day 0 | Day 25 | Day 0 | Day 25 |
| rcp45L[3] | 18 | ≦3.3 ± 0 | ≦3.3 ± 0 | ≦2.0 ± 0 | 10.7 ± 0.2 |
| rcp45L(HA P-M)[4] | 24 | ≦3.3 ± 0 | 12.8 ± 0.1 | ≦2.0 ± 0 | 9.2 ± 0.2 |
| rcp45L(HA N-P)[5] | 6 | ≦3.3 ± 0 | 13.4 ± 0.4 | ≦2.0 ± 0 | 10.8 ± 0.3 |
| rPIV3(HA P-M)[6] | 6 | ≦3.3 ± 0 | 13.3 ± 0.3 | ≦2.0 ± 0 | 10.3 ± 0.2 |
| Measles virus (Moraten)[7] | 4 | ≦3.3 ± 0 | 10.8 ± 0.2 | ≦2.0 ± 0 | ≦2.0 ± 0 |
| rJS[8] | 6 | ≦3.3 ± 0 | ≦3.3 ± 0 | ≦2.0 ± 0 | 10.7 ± 0.2 |

[1]Virus was administered at a dose of $10^{6.0}$ PFU in a 0.1 ml inoculum intranasally on day 0 to all animals with the exception of those in the measles virus group which received virus by intramuscular injection.
[2]Standard Error.
[3]Recombinant attenuated HPIV3 with three temperature sensitive (ts) mutations in the L protein, derived from cp45.
[4]Recombinant attenuated HPIV3 in the cp45L background with the HA ORF of measles virus in the P/M noncoding region of rPIV3.
[5]Recombinant attenuated HPIV3 in the cp45L background with the HA ORF of measles virus in the N/P noncoding region of rPIV3.
[6]Recombinant HPIV3 with the HA ORF of measles virus in the P/M noncoding region of wild type rPIV3.
[7]The live attenuated measles vaccine virus, Moraten strain, was administered at a dose of $10^5$ pfu in a 0.1 inoculum by IM injection to 4 cotton rats in a separate study. All other animals were hamsters.
[8]Recombinant wildtype HPIV3.

TABLE 21A

Attenuated and wildtype HPIV3-measles HA chimeric viruses are highly protective against replication of challenge wildtype PIV3 in the upper and lower respiratory tracts of hamsters.

| Animals Immunized with[1] | # Animals | Virus titer ($\log_{10}TCID_{50}/g$) [Tukey-Kramer Grouping[3]] | | Reduction in Titer ($\log_{10}$) | |
|---|---|---|---|---|---|
| | | Nasal Turbinates | Lungs | Nasal Turbinates | Lungs |
| RSV | 6 | 7.0 ± 0.3[A] | 5.7 ± 0.4[A] | NA[2] | NA |
| rcp45L(HA P-M) | 6 | 3.4 ± 0.3[B] | 2.9 ± 0.0[B] | 3.6 | 2.8 |
| rcp45L(HA N-P) | 6 | 2.6 ± 0.3[B] | 3.4 ± 0.2[B] | 4.4 | 2.3 |
| rPIV3(HA P-M) | 6 | 2.0 ± 0.3[B] | 3.2 ± 0.1[B] | 5.0 | 2.5 |
| rcp45L | 6 | 1.9 ± 0.2[B, C] | 3.6 ± 0.1[B] | 5.1 | 2.1 |
| rJS | 6 | <1.4 ± 0.0[C] | 2.9 ± 0.2[B] | >5.7 | 2.8 |

[1]All groups were challenged with $10^6$ pfu biologically-derived JS wildtype PIV3 in a 0.1 ml inoculum given intranasally.
[2]Not applicable.
[3]Mean virus titers were assigned to statistically similar groups (A-C) by the Tukey-Kramer test. Therefore, means in each column with different letters are significantly different ($\alpha = 0.05$) and means with the same letter are not significantly different.

EXAMPLE XVII

Construction of Antigenomic cDNAs Encoding a Chimeric HPIV3-1 Vector Bearing a HPIV2 HN Gene as an Extra Transcription/Translation Unit Inserted Between the F and HN Genes, and Recovery of Infectious Viruses rPIV3-1 is a recombinant chimeric HPIV3 in which the HN and F genes have been replaced by those of HPIV1 (see, e.g., Skiadopoulos et al., *Vaccine* 18:503-510, 1999; Tao et al., *Vaccine* 17:1100-1108, 1999; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999, each incorporated herein by reference). In the present example, the HN gene of HPIV2 was inserted into the rPIV3-1 chimeric virus that served as a vector to produce a chimeric derivative virus, bearing an introduced heterologous antigenic determinant from HPIV2, able to protect against both HPIV1 and HPIV2. The HPIV2 HN gene also was inserted into an attenuated derivative of rPIV3-1, designated rPIV3-1 cp45, which contains 12 of the 15 cp45 mutations, i.e., those mutations on genes other than HN and F, inserted into the rPIV3 backbone (Skiadopoulos et al., *Vaccine* 18:503-510, 1999). The source of the HPIV2 wild type virus was the wild type strain V9412-6 (designated PIV2/V94) (Tao et al., *Vaccine* 17:1100-1108, 1999), which was isolated in Vero cells from a nasal wash that was obtained in 1994 from a child with a natural HPIV2 infection. PIV2/V94 was plaque purified 3 times on Vero cells before being amplified twice on Vero cells using OptiMEM tissue culture medium without FBS. A cDNA clone of the HN gene of PIV2/V94 was generated from virion RNA by reverse transcription (RT) using random hexamers and Superscript Preamplification System (Life Technologies) followed by PCR using Advantage cDNA Synthesis kit (Clontech, Palo Alto, Calif.) and synthetic primers which introduced NcoI-HindIII sites flanking the HN cDNA (FIG. 22A). The sequences of these primers were: (with HPIV specific sequences in upper case, restriction sites underlined, nts which are non-HPIV or which are altered from wt in lower case, and start and stop codons in bold), upstream HPIV2 HN 5'-gggccATGGAAGATTACAG-CAAT-3' (SEQ ID NO. 133); downstream HPIV2 HN 5'-caat aagcTTAAAGCATTAGTTCCC-3' (SEQ ID NO. 134). The HN PCR fragment was digested with NcoI-HindIII and cloned into pLit.PIV31 HNhc to generate pLit.32HNhc (FIG. 22B). The HPIV2 HN heterologous gene insert in pLit.32HNhc was completely sequenced using the ThermoSequenase Kit and $^{33}$P-labeled terminators (Pharmacia Amersham, Piscataway, N.J.) and was confirmed to contain the authentic sequence of the PIV2/94 HN coding region.

The HPIV2 HN gene in pLit.32HNhc was further modified by PCR and Deep Vent thermostable DNA polymerase (New England Biolab, Beverly, Mass.) to introduce PpuMI sites for cloning into the unique PpuMI site in p38'ΔPIV31hc, FIG. 22C (Skiadopoulos et al., *Vaccine* 18:503-510, 1999). The sequences of these primers were (with HPIV specific sequences in upper case, relevant restriction sites underlined, non-HPIV nt or nt altered from wt in lower case): upstream HPIV2 HN 5'-gcgatgggcccGAGGAAGGACCCATA-GACA-3' (SEQ ID NO. 135); downstream HPIV2 HN 5'-ccc gggtcctgATTTCCCGAGCACGCTTTG-3' (SEQ ID NO. 136). The modified cDNA bearing the HPIV2 HN ORF consists of (from left to right) a partial 5'-untranslated region (5'-UTR) of HPIV3 HN including the PpuMI site at the 5'-end, the HPIV2 HN ORF, the 3'-UTR of HPIV3 HN, a complete set of HPIV3 transcription signals (i.e. gene stop, intergenic region and gene start sequences) whose sequences match those at the HPIV3 HN and L gene junction, a partial 5'-UTR of HPIV3 L, and an added PpuMI site at its 3'-end (FIG. 22C). This fragment was digested with PpuMI and inserted into p38'ΔPIV31hc digested with PpuMI to generate p38'ΔPIV31hc.2HN (FIG. 22D). The inserted PpuMI cassette was sequenced in full and found to be as designed. The insert from p38'ΔPIV31hc.2HN was isolated as a 8.5 kb BspEI-SphI fragment and introduced into the BspEI-SphI window of pFLC.2G+.hc or pFLCcp45 to generate pFLC.31 hc.2HN or pFLC.31 hc.cp45.2HN, respectively (FIGS. 22 E and 22F). pFLC.2G+.hc and pFLCcp45 are full-length antigenomic clones encoding wt rPIV3-1 and rPIV3 cp45, respectively, as described previously (Skiadopoulos et al., *J. Virol.* 73:1374-81, 1999; Tao et al., *J. Virol.* 72:2955-2961, 1998, each incorporated herein by reference).

Confluent HEp-2 cells were transfected with pFLC.31 hc.2HN or pFLC.3-1 hc.cp45.2HN plus the pTM(N), pTM(P no C), and pTM(L) support plasmids in the presence of MVA-T7 as previously described (Durbin et al., *Virology* 235:323-332, 1997, incorporated herein by reference). The recombinant chimeric viruses recovered from transfection were activated by addition of TPCK trypsin (Catalog No. 3741, Worthington Biochemical Corp., Freehold, N.J.) as were all passages and titrations of viruses bearing the HPIV1 HN and F glycoproteins as described previously (Tao et al., *J. Virol.* 72:2955-2961, 1998, incorporated herein by reference). Recovered chimeric recombinant viruses rPIV3-1.2HN and rPIV3-1 cp45.2HN were purified by plaque-to-plaque-to-plaque passage on LLC-MK2 monolayer in agarose overlay as previously described (Tao et al., *Vaccine* 17:1100-1108, 1999, incorporated herein by reference).

To determine if the rPIV3-1.2HN and rPIV3-1 cp45.2HN recombinants contain the heterologous HPIV2 HN gene, viral RNA from each recovered recombinant chimeric virus was amplified on LLC-MK2 cells and concentrated by polyethylene glycol (PEG) precipitation (Mbiguino et al., *J. Virol. Methods* 31:161-170, 1991, incorporated herein by reference). Virion RNA (vRNA) was extracted with Trizol (Life Technologies) and used as template to synthesize first strand cDNA using Superscript Preamplification system (Life Technologies, Gaithersburg, Md.) and random hexamer primers as described above. The synthesized cDNA was amplified by PCR with the Advantage cDNA Synthesis kit (Clontech, Palo Alto, Calif.) with primers specific for HPIV1 F and HPIV1 HN coding region (for HPIV1 F 5'-AGTGGCTAATTGCAT-TGCATCCACAT-3' (SEQ ID NO. 137) and for HPIV1 HN 5'-GCCGTCTGCATGGTGAATAGCAAT-3') (SEQ ID NO. 138). The relative locations of the PIV1 F and HN primers are indicated by arrows in FIGS. 22 and 23. Amplified DNA fragments were digested and analyzed on agarose gels (FIG. 23). Data for rPIV3-1 cp45.2HN is not shown, but was comparable and confirmed in structure. rPIV3-1.2HN and rPIV3-1 cp45.2HN each contained the insert of the expected size, and the digestion patterns with a number of restriction enzymes confirmed the identity and authenticity of the inserts. The presence of the cp45 mutations in rPIV3-1 cp45.2HN was also confirmed.

Figure 24:
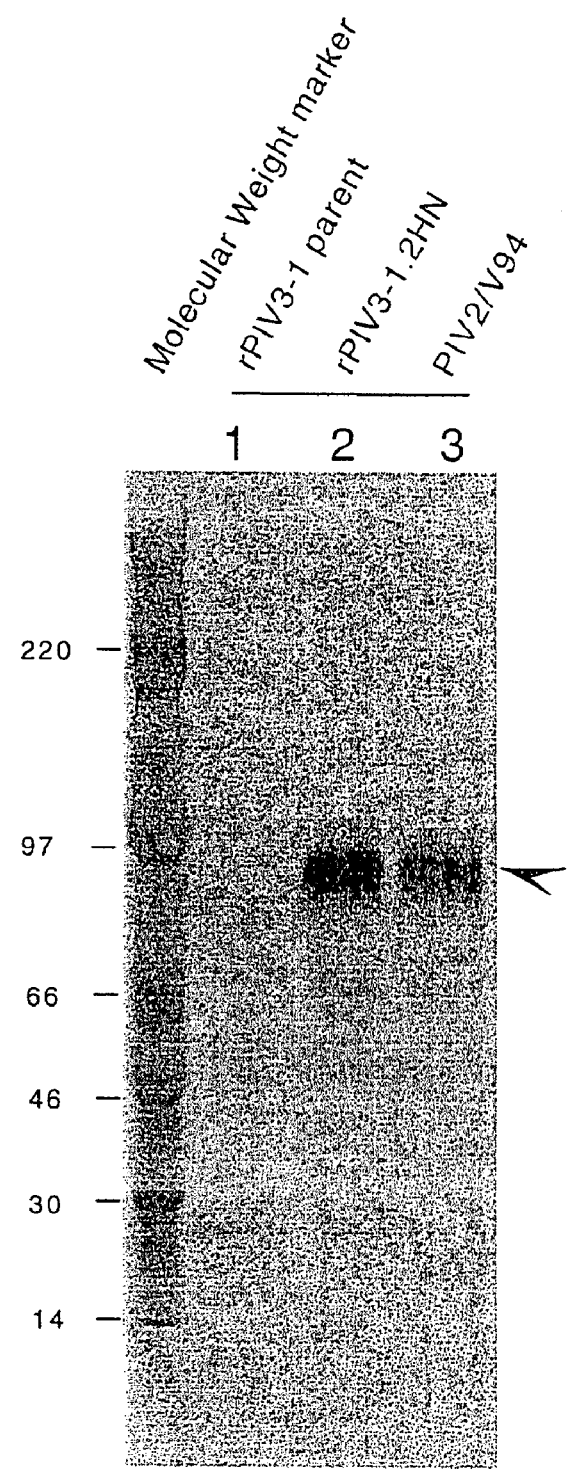

To confirm the expression of HPIV2 HN by the rPIV3-1.2HN chimeric virus, LLC-MK2 monolayers in T25 flasks were infected with PIV2/V94, rPIV3-1, or rPIV3-1.2HN at a MOI of 5 in 5 ml of serum-free OptiMEM containing 0.5 µg/ml TPCK trypsin. After incubation for 18 hours at 32° C., the flasks were washed three times with 5 ml of methionine and cysteine deficient DMEM (BioWhittacker, Walkersville, Md.). Cells were then fed with 1 ml of methionine and cysteine deficient DMEM supplemented with 120 µCi of ProMix 35S-methionine and 35S-cysteine mixture (Pharmacia Amersham, Piscataway, N.J.) and incubated for 18 hours at 32° C. Cells were scraped into medium, pelleted by brief centrifugation in a microfuge, and washed three times with cold PBS. Each cell pellet was resuspended in 1 ml RIPA buffer (1% sodium deoxycholate, 1% Triton X-100, 0.2% SDS, 150 mM NaCl, and 50 mM Tris-HCl, pH7.4) containing 250 units/ml of Benzonase (Sigma), freeze/thawed once, and clarified by centrifugation at 12,000×g for 5 min in a microfuge. Clarified supernatants were transferred to a clean microfuge tube, mixed with 50 µl of anti-HPIV2 HN monoclonal antibody (mAb) 150S1 (Tsurudome et al., *Virology* 171:38-48, 1989, incorporated herein by reference), and incubated with mixing at 4° C. for 3 hours. The monoclonal antibody was precipitated by the addition to each tube of 0.2 ml of 10% Protein A sepharose suspension (in RIPA buffer) and incubation with mixing at 40 for 18 hours. The beads were washed three times with RIPA buffer and pelleted by brief centrifugation in a microfuge. Each sample was suspended in 90 µl of 1× loading buffer, and 10 µl was resolved on a 4-12% SDS polyacrylamide gel (PAGE; NOVEX, San Diego, Calif.). The gel was dried and autoradiographed (FIG. 24). The mAb, specific to PIV2 HN, precipitated a protein from both rPIV3-1.2HN and PIV2/V94 infected LLC-MK2 cells, but not from rPIV3-1-infected cells, with a size expected for the 86 kD Kd HN protein of HPIV2 (Rydbeck et al., *J. Gen. Virol.* 69:931-5, 1988, incorporated herein by reference).

EXAMPLE XVIII

The rPIV3-1 Viruses Carrying an HPIV2 Antigenic Determinant Exhibit Temperature Sensitive Phenotypes Similar to those of their Parental Vector Viruses The level of temperature sensitivity of replication of rPIV3-1.2HN and rPIV3-1.cp45.2HN in LLC-MK2 cells was evaluated to determine if the acquisition of the HN ORF of HPIV2 by rPIV3-1 wild type or attenuated viruses employed as vectors altered the level of temperature sensitivity of replication in the resultant chimeric derivatives bearing the heterologous antigenic determinant of HPIV2 compared to the parental, vector viruses (Table 22). rPIV3-1.2HN and rPIV3-1 cp45.2HN, along with control viruses, were serially diluted 1:10 in 1×L15 supplemented with 0.5 µg/ml TPCK trypsin and used to infect LLC-MK2 monolayers in 96 well plates in quadruplicate. Infected plates were placed at various temperatures for 7 days before the virus titers were determined by hemadsorption using 0.2% guinea pig erythrocytes (in 1×PBS). The virus titers are presented as $\log_{10}$ TCID$_{50}$±standard error (S.E.). As shown in Table 22, rPIV3-1.2HN and rPIV3-1 cp45.2HN exhibited a level of temperature sensitivity similar to that of their parental, vector viruses, i.e. rPIV3-1 and rPIV3-1 cp45, respectively, each of which lacks the HPIV2 HN insert. This indicated that the introduction of one extra transcription/translation unit in rPIV3-1.2HN and rPIV3-1 cp45.2HN, does not significantly alter their level of temperature sensitivity of replication in vitro.

TABLE 22

The rPIV3-1 viruses carrying the PIV2 HN insertion have a temperature sensitive phenotype similar to that of their parental virus.

| Virus | Titer at 32° C.[a] ($\log_{10}$TCID$_{50}$) | Titer reduction ($\log_{10}$TCID$_{50}$) at various temperatures (° C.)[a] | | | | | |
|---|---|---|---|---|---|---|---|
| | | 35°[b] | 36° | 37° | 38° | 39° | 40° |
| PIV2/V9412 | 7.8 | 0.3 | (0.1)[c] | 0.0 | (0.4) | (0.4) | 0.0 |
| PIV1/Wash64 | 8.5 | 1.5 | 1.1 | 1.4 | 0.6 | 0.5 | 0.9 |
| rPIV3/JS | 7.9 | 0.3 | 0.1 | 0.1 | (0.3) | (0.4) | 0.4 |
| PIV3 cp45 | 7.8 | 0.5 | 0.3 | 1.3 | <u>3.4</u>[d] | 6.8 | 6.9 |
| rPIV3-1 | 8.0 | 0.8 | 0.5 | 0.6 | 0.9 | 1.1 | <u>2.6</u> |
| rPIV3-1.2HN | 8.3 | 0.5 | (0.3) | 0.3 | 0.6 | 1.5 | <u>2.6</u> |
| rPIV3-1 cp45 | 8.0 | 0.5 | 0.4 | <u>3.4</u> | 4.8 | 6.6 | 7.5 |
| rPIV3-1 cp45.2HN | 8.0 | 0.3 | 1.4 | <u>2.9</u> | 5.3 | 7.6 | 7.6 |

[a]Data presented are means of two experiments.
[b]Data at 35° C. were from single experiment.
[c]Numbers in parentheses represent titer increase.
[d]Underlined value indicates shut-off temperature at which the virus titer showed a reduction of 100-fold or more in comparison to the titer at 32° C.

EXAMPLE XIX

Replication and Immunogenicity of rHPIV3-1.2HN Chimeric Viruses in Animals

To determine the level of replication of the chimeric viruses in vivo, Golden Syrian hamsters in groups of six were inoculated intranasally with 0.1 ml of 1×L-15 medium containing $10^{5.3}$ TCID$_{50}$ (or $10^6$ pfu) of virus (Table 23). Four days after infection, hamsters were sacrificed and their lungs and nasal turbinates harvested. Virus titers, expressed as mean $\log_{10}$ TCID$_{50}$/gram of tissue (Table 23), were determined. rPIV3-1 expressing the PIV2 HN gene, termed rPIV2-1.2HN, is more restricted in replication than its rPIV3-1 parent as indicated by a 30-fold reduction in virus titer in both the upper and lower respiratory tracts of hamsters. Thus, the insertion of a transcription/translation unit expressing the PIV2 HN protein into rPIV3-1 attenuates the virus for hamsters. The attenuating effect of insertion of a transcription/translation unit containing PIV2 HN ORF into rPIV3-1 was slightly more than that observed for the insertion of a similar unit containing the measles HA ORF into the recombinant JS strain of wild type PIV3. The rPIV3-1 cp45.2HN virus was 1,000-fold more restricted in replication than the rPIV3-1 cp45 parent indicating that the attenuating effect of the PIV2 HN insertion and the cp45 mutations are additive. It should be possible to adjust the level of attenuation as needed by adding fewer cp45 mutations than the 12 that are present in rPIV3-1.cp45.2HN.

TABLE 23

The chimeric rPIV3-1 expressing the HN glycoprotein of PIV2 (rPIV3-1.2HN) is attenuated in the respiratory tract of hamsters

| Experiment No. | Virus | Virus titer in indicated tissue $\log_{10}$TCID$_{50}$/g ± S.E.)$^c$ | |
|---|---|---|---|
| | | NT | Lungs |
| 1$^a$ | rPIV3-1 | 6.9 ± 0.1[A]$^d$ | 6.0 ± 0.3[A] |
| | rPIV3-1.2HN | 5.4 ± 0.2[B] | 4.4 ± 0.4[C] |
| 2$^b$ | rPIV3-1 | 6.7 ± 0.1[A] | 6.6 ± 0.2[A] |
| | rPIV3-1.2HN | 5.1 ± 0.1[B, C] | 5.2 ± 0.2[B] |
| | rPIV3-1cp45 | 4.6 ± 0.3[C] | 1.8 ± 0.4[D] |
| | rPIV3-1cp45.2HN | 1.5 ± 0.1[D] | ≦1.2[D] |
| | rPIV3/JS | 6.5 ± 0.2[A] | 6.7 ± 0.1[A] |
| | rcp45 | 4.9 ± 0.2[B, C] | 1.2 ± 0.04[D] |

$^a$Groups of six animals were inoculated intranasally with $10^6$ pfu of indicated virus in 0.1 ml medium on day 0.
$^b$Groups of 6 hamsters were inoculated intranasally as in Experiment 1 with $10^{5.3}$ TCID$_{50}$ of indicated virus on day 0.
$^c$Lungs and nasal turbinates of the hamsters were harvested on day 4. Virus titers in tissue were determined and the titer expressed as $\log_{10}$TCID$_{50}$/gram ± standard error (S.E.).
NT = nasal turbinates.
$^d$Means in each column with a different letter are significantly different (a = 0.05) by Duncan's Multiple Range test whereas those with the same letter are not significantly different.

Since the single rPIV3-1.2HN virus expresses protective antigens of PIV1 (the F and HN glycoprotein) and PIV2 (the HN glycoprotein only), infection with this virus will induce resistance against challenge with either PIV1 or PIV2 wild type viruses. To verify this, Golden Syrian hamsters in groups of 12 were immunized intranasally with $10^{5.3}$ TCID$_{50}$ of virus as described above. Half of the hamsters were challenged with PIV2 on day 29, the remaining half with PIV1 on day 32. Hamster lung and nasal turbinate tissues were harvested 4 days after challenge, and titer of challenge virus were determined as described above (Table 24). Sera were obtained before and 28 days after immunization and tested for their neutralizing antibody titer against PIV1 and PIV2.

TABLE 24

The chimeric rPIV3-1 virus expressing the HN glycoprotein of PIV2 (rPIV3-1.2HN) protects hamsters against challenge with both PIV1 and PIV2

| | Serum neutralizing antibody titer against indicated virus (reciprocal mean $\log_2$ ± SE)$^b$ | | | | Titer of challenge virus in indicated tissues ($\log_{10}$TCID$_{50}$/g ± SE)$^c$ | | | |
|---|---|---|---|---|---|---|---|---|
| | PIV1 | | PIV2 | | PIV1 | | PIV2 | |
| Immunizing virus$^a$ | pre | post | pre | post | NT | Lung | NT | Lung |
| rPIV3/JS | ≦4.0 ± 0.0 | ≦4.0 ± 0.0 | 4.5 ± 0.1 | 4.6 ± 0.2 | 5.4 ± 0.2 | 5.1 ± 0.1 | 6.8 ± 0.2 | 6.0 ± 0.3 |
| PIV2 | ≦4.0 ± 0.0 | ≦4.0 ± 0.0 | 4.3 ± 0.2 | 9.6 ± 0.2 | 5.7 ± 0.2 | 5.7 ± 0.2 | ≦1.2 | ≦1.2 |
| rPIV3-1 | 4.2 ± 0.1 | 8.5 ± 0.3 | 4.0 ± 0.0 | 4.2 ± 0.1 | ≦1.2 | ≦1.2 | 6.3 ± 0.1 | 6.5 ± 0.2 |
| rPIV3-1.2HN | ≦4.0 ± 0.0 | 6.2 ± 0.2 | 4.1 ± 0.1 | 8.3 ± 0.2 | 2.3 ± 0.5 | ≦1.2 | ≦1.2 | ≦1.2 |
| rPIV3-1cp45 | ≦4.0 ± 0.0 | 6.2 ± 0.4 | ≦4.0 ± 0.0 | 4.0 ± 0.0 | 3.6 ± 0.3 | 2.7 ± 0.5 | 6.0 ± 0.1 | 5.7 ± 0.4 |
| rPIV3-1cp45.2HN | 4.0 ± 0.9 | 4.1 ± 0.1 | 4.0 ± 0.0 | 4.2 ± 0.1 | 5.1 ± 0.2 | 4.8 ± 0.2 | 6.8 ± 0.1 | 6.6 ± 0.2 |

$^a$Hamsters in groups of 12 were immunized with $10^{5.3}$ TCID$_{50}$ of indicated virus intranasally on day 0.
$^b$Serum was diluted 1:10 with OptiMEM and heat-inactivated by incubation at 56° for 30 min. The serum neutralizing antibody titer was determined on LLC-MK2, and the titers are expressed as reciprocal mean $\log_2$ ± standard error (SE).
$^c$Half of the hamsters from each immunized group were challenged with $10^6$ TCID$_{50}$ PIV2 on day 29, and the remaining half were challenged with $10^6$ TCID$_{50}$ PIV1 on day 32. Tissue samples were harvested 4 days after challenge, and challenge virus titers are expressed as $\log_{10}$TCID$_{50}$/gram of tissue ± SE.
NT = nasal turbinates.

As expected PIV3 provided no resistance against either PIV1 or PIV2 (Tao, *Vaccine* 17:1100-1108, 1999), while previous infection with PIV2 wild type virus and rPIV3-1 induced complete resistance to replication of PIV2 and PIV1 challenge viruses, respectively. In contrast to these viruses that provided protection against only one virus, rPIV3-1.2HN induced antibody to both PIV1 and PIV2 and included strong resistance to both PIV1 and PIV2 as indicated by the 1,000- to 10,000-fold reduction in replication of each virus in the upper and lower respiratory tract of rPIV3-1.2HN immunized hamsters. This indicated that a single recombinant chimeric PIV can induce resistance against two human viral pathogens. However, the derivative of rPIV3-1.2HN carrying the cp45 mutations failed to induce significant resistance to replication of wild type PIV1 or PIV2 challenge virus indicating that this particular recombinant chimeric virus is over-attenuated in hamsters. Introduction of one or several selected cp45 mutations, rather than the complete set of 12 mutations, into rPIV3-1.2HN can be done to adjust the level of attenuation of rPIV3-1.2HN to an appropriate level.

EXAMPLE XX

Construction of cDNAs Encoding rHPIV3 Viruses Containing Nucleotide Insertions As discussed above, insertion of the measles HA ORF between either the N/P or P/M gene junction of the attenuated vector virus, rPIV3 cp45L, as well as at the N/P, P/M, and HN/L junctions of wild type PIV3, further restricted its replication in the upper respiratory tract of hamsters, indicating that insertion of an additional gene at either location within the HPIV3 genome can augment attenuation of candidate vaccine viruses. In these exemplary aspects of the invention, the gene insert was relatively large (approximately 1900 nts). Further examples are provided herein that indicate the size of the insert specifies a selectable level of attenuation of the resulting recombinant virus. This was evaluated by introducing sequences of various lengths which were derived from a heterologous virus, exemplified by the RSV A2 strain, as single gene units (GUs) between the HPIV3 HN and L ORFs. The inserts were designed specifically to lack any significant ORF, whereby any effects observed would not be complicated by possible contribution of expressed protein. In order to distinguish between effects due to increased genome length versus expression of an additional mRNA, a second series of constructs was made in which inserts of similar sizes were introduced into the downstream noncoding region (NCR) of the HN gene. Thus, two series of rPIV3s were made containing insertions of increasing length: in the GU series, the insert was added as an extra gene encoding an extra mRNA, while in the NCR series the insert was made so that the gene number was unchanged.

Figure 26:
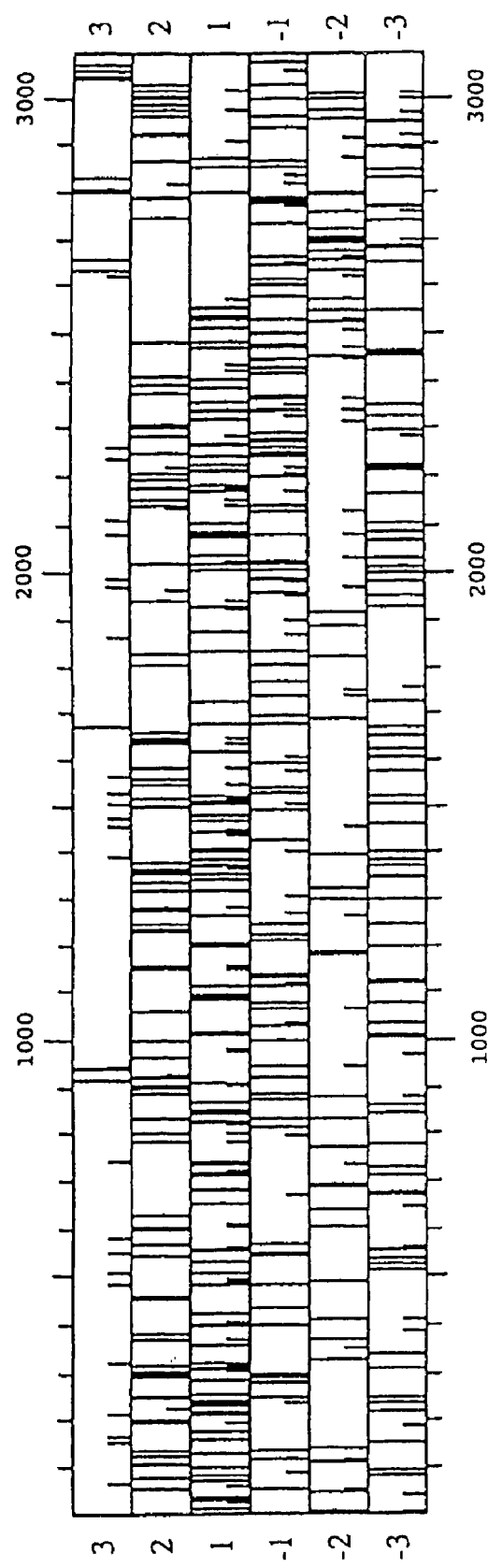

Construction of cDNAs Encoding rHPIV3 Viruses Containing GU and 3'-NCR Insertions Insertion mutations were constructed in a pUC based plasmid, pUC118-Stu, containing the XhoI to SphI fragment (HPIV3 nts 7437-11317) of the full length HPIV3 clone p3/7(131)2G-Stu. Two separate plasmids were constructed as acceptor plasmids for insertion of GUs and HN gene 3'-NCR extensions (FIG. 25). In each, a synthetic oligonucleotide duplex containing multiple cloning sites was inserted into the unique Stu I site. The inserted sequence for the GU insertion plasmid contained a HN gene-end (GE) signal sequence, the conserved intergenic (IG) trinucleotide sequence, and a L gene-start (GS) signal sequence, cis-acting sequences that direct termination of the HN gene transcription and initiation of transcription of the inserted sequence, respectively (FIG. 25). Additional unique restriction endonuclease sites were included in the multiple cloning region to facilitate subsequent screening and subcloning. The 3'-NCR extension acceptor plasmid was similarly designed and constructed, but it lacked the cis-acting GE, IG, and GS sequences at its 5'-end (FIG. 25B, Table 25). The RSV antigenomic plasmid d53RSV sites or subgenomic plasmid pUC118FM2 (Table 25) were digested with the appropriate restriction enzymes, and fragments of the desired sizes were isolated by electrophoresis on agarose gels and ligated individually into the unique HpaI site of the GU or the HN gene 3'-NCR extension acceptor plasmid (FIG. 25; Table 25). Clones were screened to identify ones in which the RSV restriction fragments were inserted in the reverse orientation, an orientation in which all reading frames contained multiple stop codons (FIG. 26). Short synthetic oligonucleotide duplexes ranging in size from 13 to 17 nucleotides also were inserted as necessary into the GU or 3'-NCR acceptor plasmids to modify the genome length to conform to the "rule of six" (Table 25). The specific RSV sequences and size of the short synthetic oligonucleotides added are summarized in Table 25. Plasmid clones were sequenced through all restriction enzyme sites used for subcloning, and XhoI-SphI fragments containing insertion mutations conforming to the rule of six, either as GUs or HN gene NCR extensions, were cloned into the full-length PIV3 cDNA plasmid p3/7(131)2G+. One insert, containing the 1908 GU insert, also was placed into an antigenomic cDNA bearing the three L mutations of cp45.

TABLE 25

Sources of nucleotides used to create the gene unit (GU) and HN gene 3' non coding region (NCR) extension insertions.

| Restriction fragment size (nts) | Restriction sites and nt position in the RSV antigenome | GU multiple cloning site (58 nt) + rule of 6 oligonucleotide[e] | GU insertion (total nts inserted) | NCR multiple cloning site (32 nt) + rule 6 oligonucleotide[e] | NCR insertion (total nts inserted) |
|---|---|---|---|---|---|
| 97[a]    | SspI-SspI; 7272-7369      | +58 + 13 | 168  | nd       | nd   |
| 212[b]   | HpaI-HpaI; 12243-12455    | nd       | nd   | +32 + 14 | 258  |
| 603[b]   | SspI-SspI; 309-912        | +58 + 17 | 678  | nd       | nd   |
| 925[b]   | HpaI-HpaI; 12455-13380    | +58 + 13 | 996  | +32 + 15 | 972  |
| 1356[b,c]| HincII-HincII; 5060-6417  | +58 + 14 | 1428 | +32 + 16 | 1404 |
| 1850[b,d]| HpaI-HpaI; 12455-13380    | +58 + 0  | 1908 | nd       | nd   |

TABLE 25-continued

Sources of nucleotides used to create the gene unit (GU) and HN gene 3' non coding region (NCR) extension insertions.

| Restriction fragment size (nts) | Restriction sites and nt position in the RSV antigenome | GU multiple cloning site (58 nt) + rule of 6 oligonucleotide[e] | GU insertion (total nts inserted) | NCR multiple cloning site (32 nt) + rule 6 oligonucleotide[e] | NCR insertion (total nts inserted) |
|---|---|---|---|---|---|
| 3079[b] | EcoRV-Ec/13611; 1403-4482 | nd | nd | +32 + 15 | 3126 |
| 3845[b] | ScaI-ScaI; 344-4189 | +58 + 15 | 3918 | +32 + 17 | 3894 |

[a]Source of RSV sequence is pUC118FM2, a plasmid containing a subgenomic cDNA fragment of RSV subgroup A as described previously (Juhasz, K. et al, J Virol., 71: 5814-5819, 1997.).
[b]Source of RSV sequence is D53sites, a plasmid containing the entire RSV subgroup A cDNA sequence with several introduced point mutations as described previously. The previously described D53sites plasmid was used to derive the rAsites virus descried inWhitehead, S. et al. J. Virol., 72: 4467-4471, 1998.
[c]The gel purified 1356 nt fragment contained a 1 nt deletion compared to the predicted 1357 nt restriction endonuclease cleavage product.
[d]The 1850 nt fragment is a product of two 3' to 3' adjoined 925 nt restriction fragments.
[e]The following oligonucleotides were inserted into the MluI restriction site to conform all the inserted foreign sequences to the rule of six: 13mer: CGCGGCAGGCCTG(SEQ ID NO. 139); 14mer: CGCGGCGAGGCCTG (SEQ ID NO. 140); 15mer: CGCGAGGCCTCCGCG (SEQ ID NO. 141); 16mer: CGCGCCGCGGAGGCCT (SEQ ID NO. 142); 17mer: CGCGCCCGCGGAGGCCT (SEQ ID NO. 143).
nd, not done.

Recovery of Recombinant PIV3s Bearing Insertion Mutations

Figure 27:
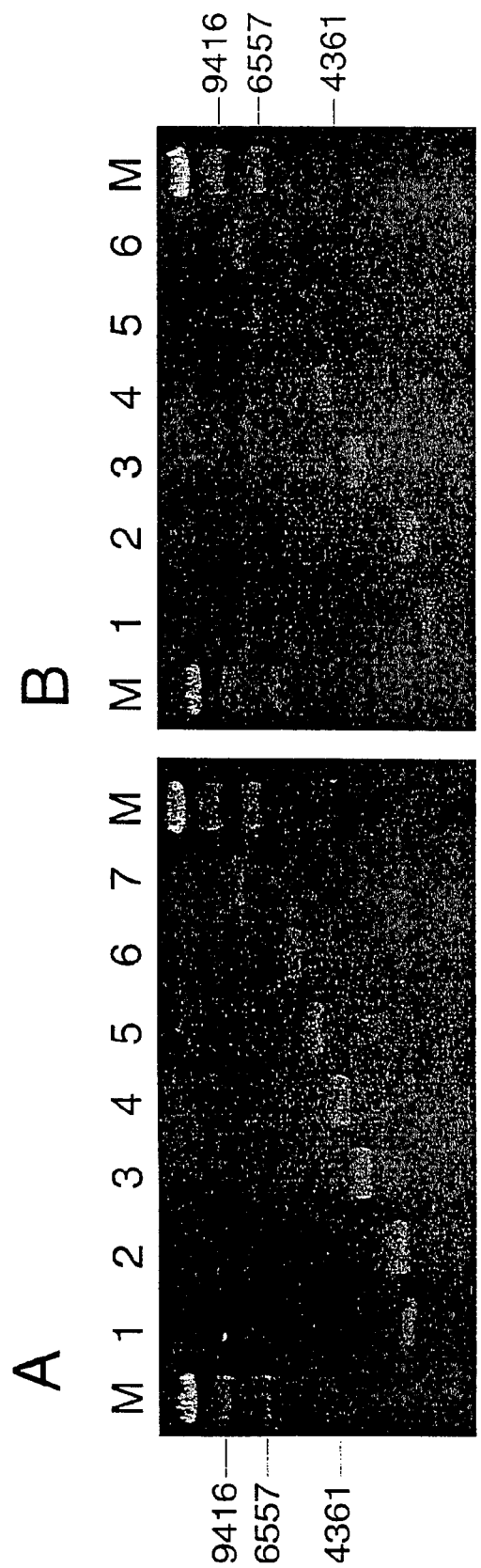

Full-length antigenomic cDNA derivatives bearing the insertion mutations and three support plasmids pTM(N), pTM(P no C) and pTM(L) (Durbin et al., Virology 235:323-332, 1997; Durbin et al., Virology 261:319-330, 1999, each incorporated herein by reference) were transfected into HEp-2 monolayers in 6-well plates (Costar, MA) using LipofectACE (Life Technologies, MD), and the monolayers were infected with MVA-T7 as described previously (Durbin et al., Virology 235:323-332, 1997; Skiadopoulos et al., J. Virol. 72:1762-8, 1998, each incorporated herein by reference). After incubation at 32° C. for 4 days, the transfection harvest was passaged onto LLC-MK2 cells in T-25 flasks which were incubated at 32° C. for four to eight days. The clarified medium supernatant was subjected to plaque purification on LLC-MK2 cells as described previously (Durbin et al., Virology 235:323-332, 1997; Hall et al., Virus Res. 22:173-184, 1992; Skiadopoulos et al., J. Virol. 72:1762-8, 1998, each incorporated herein by reference). Each biologically-cloned recombinant virus was amplified twice in LLC-MK2 cells at 32° C. to produce virus for further characterization. Virus was concentrated from clarified medium by polyethylene glycol precipitation (Mbiguino et al., J. Virol. Methods 31:161-170, 1991, incorporated herein by reference), and viral RNA (vRNA) was extracted with Trizol Reagent (Life Technologies). Reverse transcription was performed on vRNA using the Superscript II Preamplification System (Life Technologies) with random hexamer primers. The Advantage cDNA PCR kit (Clontech, CA) and sense (PIV3 nt 7108-7137) and antisense primers (PIV3 nt 10605-10576) were used to amplify fragments for restriction endonuclease digestion or sequence analysis. The PCR fragments were analyzed by agarose gel electrophoresis (FIG. 27) and sequencing. Each of the recovered rPIV3 insertion mutants contained insertions of the indicated sizes and they were next evaluated for their biological properties.

EXAMPLE XXI

Replication of rHPIV3 Viruses Containing GU or NCR Inserts in Animals and in Tissue Culture Multi-Step Growth Curves The growth properties of the rPIV3 GU and NCR insertion mutants were compared to rPIV3 wt and rcp45$_L$ in vitro. As shown in FIG. 28, the rate of replication and the peak virus titer of each of the rPIV3s containing either the GU or NCR insertions was indistinguishable from that of rPIV3 wt indicating that insertion of sequences of at least 3918 nts in length does not affect virus replication in vitro.

Replication in Hamsters of rPIVs Containing GU Insertions

Hamsters were inoculated intranasally with $10^{6.0}$ TCID$_{50}$ rPIV3 wt, rcp45$_L$ or with one of the indicated mutant rPIV3s bearing GU insertions (Table 26). Lungs and nasal turbinates were harvested on day four after infection and the level of replication of each virus was determined. Insertion of GUs ranging in size from 168 nt up to 1908 nt did not significantly reduce viral replication in the respiratory tract of hamsters. However, insertion of a 3918 nt gene unit between the HN and L ORF of wild type PIV3 resulted in a 5 and 25-fold reduction in viral replication in the nasal turbinates and lungs, respectively. This indicates that gene unit insertions of this size are attenuating for a wild type virus whereas shorter sizes, e.g., below approximately 2000 nt, have little effect on replication of wild type virus in the respiratory tract of hamsters. Thus, GU length can be altered to determine a desired level of attenuation in PIV vaccine viruses.

TABLE 26

Replication of rPIV3 GU insertion mutants in the respiratory tract of hamsters

| | Mean virus titer (log$_{10}$ TCID$_{50}$/g ± S.E.[b]) in: | |
|---|---|---|
| Virus[a] | Nasal Turbinates | Lungs |
| rPIV3 wt | 5.9 ± 0.2 | 6.0 ± 0.2 |
| r168 nt GU ins | 5.9 ± 0.1 | 6.4 ± 0.1 |
| r678 nt GU ins | 6.1 ± 0.1 | 6.2 ± 0.1 |
| r996 nt GU ins | 5.5 ± 0.2 | 5.4 ± 0.2 |
| r1428 nt GU ins | 5.9 ± 0.1 | 5.3 ± 0.6 |
| r1908 nt GU ins | 5.6 ± 0.1 | 5.7 ± 0.2 |
| r3918 nt GU ins | 5.2 ± 0.2 | 4.6 ± 0.3 |
| rcp45$_L$ | 3.1 ± 0.0 | 1.7 ± 0.2 |
| r1908 nt GU ins/cp45$_L$ | 1.8 ± 0.2 | 1.5 ± 0 |

[a]Hamsters, in groups of eight, were administered $10^{6.0}$ TCID$_{50}$ of virus intranasally in a 0.1 ml inoculum. Lungs and nasal turbinates were harvested four days later and virus titer was determined at 32° C.
[b]S.E.: Standard error.

As described above, the insertion of the HA gene of measles virus into the rJS wildtype and the attenuated cp45L virus further attenuated each virus for hamsters. Since the HA gene of measles virus is 1936 nt in length, we examined the effect of a similar size gene insertion (1908 nt) on replication of rcp45L. The 1908 gene insertion differs from the measles virus HA gene insertion in that it cannot synthesize a large polypeptide. When the 1908 nt GU insertion was combined with the cp45 L polymerase amino acid substitutions (r1908 nt GU ins/cp45$_L$ in Table 26), attenuation was augmented approximately 20-fold in the upper respiratory tract. Considered together, these findings indicate that GU insertions of approximately 3918 nts in length can attenuate a wild type PIV3 virus for hamsters and that GU insertions of about half this size can further attenuate an attenuated PIV3 vaccine candidate. Thus, GU insertions can have dual roles in the design of recombinant vaccines. The first role is to encode a protective antigen of a pathogen, and the second role is to confer an attenuation phenotype.

Replication in Hamsters of rPIVs Containing HN Gene 3'-NCR Insertions.

Hamsters were inoculated intranasally with rPIV3 control viruses or viruses bearing insertion mutations extending the length of the HN gene 3'-NCR (Table 27). Lungs and nasal turbinates were harvested four days after inoculation and the level of viral replication in each tissue was determined as described above. HN gene NCR insertions ranging in size from 258 nt up to 1404 nt did not significantly reduce viral replication in the respiratory tract of hamsters (Table 20). However, an insertion of 3126 nt effected a 16-fold reduction in viral titer in the upper and lower respiratory tracts of infected hamsters, and a 3894 nt HN gene NCR insertion resulted in a 12-fold reduction of viral replication in the upper and lower respiratory tracts, suggesting that increasing the genome length also confers an attenuating effect on viral replication.

TABLE 27

Replication of rPIV3 NCR insertion mutants in the respiratory tract of hamsters

| Virus[a] | Mean virus titer ($\log_{10}$ TCID$_{50}$/g ± S.E.[b]) in: | |
|---|---|---|
| | Nasal Turbinates | Lungs |
| rPIV3 wt | 6.2 ± 0.1 | 6.4 ± 0.1 |
| r258 nt NCR ins | 5.9 ± 0.1 | 6.5 ± 0.1 |
| r972 nt NCR ins | 5.9 ± 0.1 | 6.6 ± 0.1 |
| r1404 nt NCR ins | 5.9 ± 0.2 | 6.6 ± 0.1 |
| r3126 nt NCR ins | 5.0 ± 0.1 | 5.2 ± 0.1 |
| r3894 nt NCR ins | 5.1 ± 0.1 | 5.3 ± 0.1 |
| rcp45$_L$ | 3.4 ± 0.1 | 1.9 ± 0.2 |

[a]Hamsters, in groups of eight, were administered 10$^{6.0}$ TCID$_{50}$ of virus intranasally in a 0.1 ml inoculum. Lungs and nasal turbinates were harvested four days later and virus titer was determined at 32° C.
[b]S.E.: Standard error.

Evaluation of the Level of Temperature Sensitivity of GU and NCR Insertions

The efficiency of plaquing (EOP) at permissive and non-permissive temperatures of rPIVs was determined on LLC-MK2 monolayers as described above (Table 28). At 32° C., viruses bearing GU insertions ranging in size from 168 nt up to 3918 nt and NCR insertions ranging in size from 258 nt up to 3894 nt had a plaque morphology that was similar to that of rPIV3 wt. However, at 39° C. and at higher temperatures all of the viruses bearing insertion mutations had a small plaque phenotype (Table 28). The GU insertions ranging in size from 996 nt up to 3918 nt yielded viruses that were not ts at 40° C. However, viruses bearing HN gene NCR insertions of 1404 nts or greater yielded viruses that were slightly ts at 40° C. with a gradient of temperature sensitivity proportional to the size of the insertion. Addition of the 1908 nt GU insertion to the cp45$_L$ backbone yielded a virus that was almost 100-fold more ts at 38° C. compared to rcp45$_L$, demonstrating that the ts phenotype specified by the 1908 nt GU insertion and by the L gene ts mutations is additive.

TABLE 28

Efficiency of plaque formation of rPIV3 GU and NCR insertion mutants at permissive and non-permissive temperatures

| Virus | Virus titer at indicated temperature ($\log_{10}$PFU/ml) | | | | |
|---|---|---|---|---|---|
| | 32° C. | 37° C. | 38° C. | 39° C. | 40° C. |
| rPIV3 wt | 7.8 | ND | ND | 7.4 | 7.5 |
| r168 nt GU ins | 7.8 | ND | ND | 7.5[a] | 6.7[a] |
| r678 nt GU ins | 7.9 | ND | ND | 7.3[a] | 7.0[a] |
| r996 nt GU ins | 7.7 | ND | ND | 7.0[a] | 6.3[a] |
| r1428 nt GU ins | 7.8 | ND | ND | 7.4[a] | 6.4[a] |
| r1908 nt GU ins | 7.6 | ND | ND | 6.5[a] | 6.0[a] |
| r3918 nt GU ins | 6.3 | ND | ND | 5.7[a] | 5.0[a] |
| r258 nt NCR ins | 8.1 | ND | ND | 7.4[a] | 7.5[a] |
| r972 nt NCR ins | 8.2 | ND | ND | 7.8[a] | 7.8[a] |
| r1404 nt NCR ins | 6.7 | ND | ND | 5.2[a] | <u>≤3.7</u> |
| r3126 nt NCR ins | 7.4 | ND | ND | 6.4[a] | <u>4.5[a]</u> |
| r3894 nt NCR ins | 7.4 | ND | ND | <u>5.3[a]</u> | 5.0[a] |
| rcp45$_L$ | 7.8 | 7.3 | 6.0 | <u>≤0.7</u> | ND |
| r1908 nt GU ins/cp45$_L$ | 6.7 | 5.0[a] | <u>3.0[a]</u> | <0.7 | ND |
| rcp45 | 8.1 | 6.7 | <u>5.7[a]</u> | 2.0[a] | ND |

[a]Plaques were enumerated by immunoperoxidase staining after incubation for 6 days at the indicated temperature. Values which are underlined and in bold type represent the lowest restrictive temperature at which there was at least a 100-fold reduction of plaquing efficiency compared to the titer at 32° C., which is defined as the shut-off temperature of plaque formation.

Since the r3918 nt GU insertion mutant as well as the r3126 nt and r3894 nt NCR insertion mutants replicated efficiently in vitro but were restricted in replication in the respiratory tract of hamsters, these recombinants exhibit a novel, host-range attenuation phenotype.

EXAMPLE XXII

A Single rHPIV3 Expressing Up to Three Supernumerary Foreign Viral Glycoproteins Induces Protective Antibodies Against Up to Three Viruses Modification of a single recombinant vaccine virus to induce immunity against multiple pathogens has several advantages. It is much more feasible and expeditious to develop a single attenuated backbone expressing antigens against multiple pathogens than it is to develop a separate attenuated vaccine against each pathogen. Each pathogen offers different challenges for manipulation, attenuation and demonstration of safety and efficacy, and it would be a daunting task to attempt to develop an attenuated version of each of a series of pathogens. It is also simpler and easier to prepare, handle, and administer a single vaccine virus than to undertake these activities with several different attenuated viruses. Reducing the number of vaccine viruses also will help simplify the crowded schedule of pediatric immunizations. Several attenuated viruses can be administered as a mixture, but this complicates vaccine development, since each component must be shown to be safe separately, and then shown to be safe and efficacious as a mixture. One particular problem with the administration of mixtures of viruses is the common phenomenon of viral interference, in which one or more of the viruses in the mixture interferes with the replication of one or more of the other components. This may result in reduced replication and immunogenicity for one or more components. This common problem is obviated by the use of a single vector backbone. Also, since some viruses such as measles virus have particular safety concerns, it would be safer to use a single, comparatively benign virus such as PIV as a vector bearing multiple supernumerary antigens, as opposed to a mixture of separately-attenuated viruses, each of which must be developed and validated separately.

In the present example recombinant HPIVs are constructed and shown to serve as vectors for more than one supernumerary gene with satisfactory characteristics of replication and immunogenicity for development of vaccine viruses. In particular, this example describes the design, construction, recovery, and characterization of rHPIV3s expressing one, two or three supernumerary genes from the following list: (i) the hemagglutinin-neuraminidase (HN) of HPIV1 (Washington/20993/1964 strain); (ii) the HN of HPIV2 (V9412 strain); (iii) the hemagglutinin (HA) of the wild type Edmonston strain of measles virus; and (iv) a 3918-nt translationally-silent synthetic gene called gene unit (GU) (see above). The added genes were inserted into rHPIV3 between the nucleoprotein (N) and phosphoprotein (P) genes, between the P and membrane protein (M) genes, or between the HN and large polymerase (L) genes. Thus, the disclosure demonstrates the successful use of an HPIV3 vector modified into a bivalent, trivalent, or quadrivalent vaccine recombinant capable of inducing multivalent immunity, e.g., against the vector itself and one or two additional pathogens.

Insertion of the HPIV1 HN and HPIV2 HN genes between the N/P and P/M genes was performed as follows: Plasmid pUC119(AfIII N-P), a subclone of the HPIV3 antigenomic cDNA (Durbin, *J. Virol.* 74:6821-31, 2000, incorporated herein by reference), was modified by site directed mutagenesis to insert a unique Af/II site into (i) the downstream noncoding region of the HPIV3 N gene (CTAAAT to CTTAAG, HPIV3 nts 1677-1682), or (ii) the downstream noncoding region of the HPIV3 P gene (TCAATC to CTTAAG, HPIV3 nts 3693-3698). Each Af/II site was then modified by the insertion of an oligonucleotide duplex, creating the intermediate plasmids pUC(GE/GS-N-H)$_{N-P}$ and pUC(GE/GS-N-H)$_{P-M}$, respectively. The inserted duplex contained an HPIV3 gene-end (GE) sequence, the conserved intergenic (IG) trinucleotide sequence, and an HPIV3 gene-start (GS) sequence, which are cis-acting signals that direct transcriptional termination and initiation, respectively (FIG. 10). Additional unique restriction endonuclease sites were included in the multiple cloning region to facilitate subsequent subcloning and screening, including NcoI and HindIII sites for addition of the HPIV1 and HPIV2 HN ORFs. Thus, a foreign ORF inserted into the multiple cloning site would be under the control of a set of HPIV3 transcription signals and expressed as a separate mRNA by the HPIV3 polymerase. The multiple cloning site also contained an Mlu I site for inserting oligonucleotides of varying lengths as necessary to make the entire inserted sequence conform to the rule of six (Calain et al., *J. Virol.* 67:4822-30, 1993; Durbin et al., *Virology* 234:74-83, 1997b; 1999a Skiadopoulos et al., *Virology* 272:225-34, 2000).

The HPIV1 HN ORF, available as an NcoI to HindIII restriction fragment of p38'Δ31 hc #6 (Tao et al., *J. Virol.* 72:2955-2961, 1998), was inserted into the NcoI to HindIII sites of pUC(GE/GS-N-H)$_{N-P}$ and pUC(GE/GS-N-H)$_{P-M}$ to generate pUC 1HN$_{N-P}$ and pUC 1HN$_{P-M}$, respectively. Short oligonucleotide duplexes were inserted in the unique MluI restriction site to adjust the sequence to conform to the rule of six. These chimeric subgenomic cDNAs were then cloned into the full-length HPIV3 antigenomic cDNA p3/7(131) 2G+, referred to here as pFLC HPIV3 wt, to yield pFLC HPIV3 1HN$_{N-P}$ and pFLC HPIV3 1HN$_{P-M}$, respectively (FIG. 11, the plasmids from which the second and third recombinant viruses from the top were isolated).

The HPIV2 HN ORF, available within an NcoI to HindIII restriction fragment of p32Hnhc#3 31hc (Tao et al., *J. Virol.* 72:2955-2961, 1998, incorporated herein by reference), was inserted into the NcoI to HindIII sites of pUC(GE/GS-H-N)$_{N-P}$ and pUC(GE/GS-H-N)$_{P-M}$ to generate pUC 2HN$_{N-P}$ and pUC 2HN$_{P-M}$, respectively. Short oligonucleotide duplexes were inserted in the unique MluI restriction site to adjust the sequence to conform to the rule of six. Inadvertently, the inserted oligonucleotide was one nucleotide shorter that that required to specify that the genome of the recovered virus would conform to the rule of six. Therefore, all cDNAs bearing the HIV2 HN gene insertion did not conform to the rule of six. Nonetheless, virus was recovered from each of these cDNAs. These chimeric subgenomic cDNAs were cloned into the full-length PIV3 antigenomic cDNA pFLC HPIV3 wt to yield pFLC PIV3 2HN$_{(N-P)}$ and pFLC PIV3 2HN$_{(P-M)}$, respectively (FIG. 11, plasmids from which the fourth and fifth recombinant viruses from the top were isolated).

Additional recombinant HPIV3 antigenomic cDNAs were assembled that contained up to three supernumerary foreign genes in various combinations and locations in the HPIV3 backbone (FIG. 11). These antigenomic cDNAs were assembled from the subgenomic cDNAs described above in which the HN of HPIV1 or HPIV2 was inserted between the N and P genes or the P and M genes. Other subclones used for assembly contained the measles virus HA gene between the P/M genes or HN/L genes as described above. Another subclone used in assembly contained the 3918-nt GU between the HN and L genes, as described above.

The recombinants containing two or three supernumerary inserts were as follows: rHPIV3 1HN$_{N-P}$ 2HN$_{P-M}$ (FIG. 11, sixth recombinant from the top) contained the HPIV1 HN and HPIV2 HN genes inserted between the N/P and P/M genes, respectively; rHPIV3 1HN$_{N-P}$ 2HN$_{P-M}$ HA$_{HN-L}$ (FIG. 11, seventh recombinant) contained the HPIV1 HN, HPIV2 HN, and measles virus HA inserted between the N/P, P/M, and HN/L genes, respectively; and rPIV3 1HN$_{N-P}$ 2HN$_{P-M}$ 3918GU$_{HN-L}$ (FIG. 11, bottom), contained the HPIV1 HN and HPIV2 HN genes inserted between the N/P and P/M genes, respectively, and in addition contained the 3918-nt GU insert between the HN and L genes.

It is noteworthy that the penultimate of these constructs, rHPIV3 1HN$_{N-P}$ 2HN$_{P-M}$ HA$_{HN-L}$ (FIG. 11, seventh construct from the top), contained protective antigens for four pathogens: HPIV3 (HN and F), HPIV1 (HN), HPIV2 (HN), and measles virus (HA). The total length of foreign sequence inserted into this recombinant was about 5.5 kb, which is 36% of the total HPIV3 genome length of 15,462 nt. The last recombinant, rHPIV3-1 HN$_{N-P}$2HN$_{P-M}$GU$_{HN-L}$ (FIG. 11, bottom), was approximately 23 kb in length. This is 50% longer than wild-type HPIV3, and longer than any previously described biologically derived or recombinant paramyxovirus.

Recovery and Replication In Vitro of Recombinant rHPIV3 Bearing One, Two, or Three Supernumerary Gene Inserts The full length HPIV3 antigenomic cDNAs bearing single or multiple supernumerary genes of heterologous paramyxovirus protective antigens were separately transfected into HEp-2 monolayer cultures on six-well plates (Costar, Cambridge, Mass.) together with the support plasmids pTM(N), pTM(P no C), and pTM(L) and LipofectACE (Life Technologies, Gaithersburg, Md.) and the cells were simultaneously infected with MVA-T7, a replication-defective vaccinia virus recombinant encoding the bacteriophage T7 polymerase protein using techniques previously described (Durbin et al., *Virology* 235:323-332, 1997a; Skiadopoulos et al., *Virology*

272:225-34, 2000, each incorporated herein by reference). After incubation at 32° C. for up to four days, the transfection harvest was passaged onto LLC-MK2 monolayer cultures in a 25 cm² flask and the cells were incubated for 5 days at 32° C. The virus recovered from the cell supernatant was further passaged on LLC-MK2 cells at 32° C. to amplify the virus. rHPIV3s bearing single or multiple foreign gene inserts were biologically-cloned by plaque purification on LLC-MK2 cells as previously described (Skiadopoulos et al., *J. Virol.* 73:1374-81, 1999a, incorporated herein by reference). Viral suspensions derived from biologically cloned virus were amplified on LLC-MK2 cells and yielded final titers of $10^7$ and $10^9$ TCID$_{50}$/ml, similar to the range of titers typically obtained for wt rHPIV3. Recombinant viruses were assayed for their ability to grow at 39° C. Surprisingly several rHPIV3s bearing single or multiple foreign gene insertions two or more supernumerary genes and retain the ability to replicate efficiently in vitro and in vivo and to induce protective immune responses against both the vector and the expressed supernumerary antigens. The present example indicates that this is indeed possible.

Hamsters in groups of eight were inoculated intranasally with $10^6$ TCID$_{50}$ of each rHPIV3 bearing single or multiple supernumerary foreign gene inserts or with control viruses (Table 13). Nasal turbinates and lungs were harvested four days post infection and the virus present in tissue homogenates was quantified by serial dilution on LLC-MK2 monolayer cultures at 32° C. as described above (see also, Skiadopoulos et al., *J. Virol.* 73:1374-81, 1999a). Virus was detected by hemadsorption with guinea pig erythrocytes, and the mean virus titer for each group is expressed as log$_{10}$ TCID$_{50}$(50% tissue culture infectious dose/gram tissue±SE).

TABLE 29

Replication of recombinant HPIV3s containing single or multiple supernumerary gene inserts expressing the HPIV1, HPIV2 or measles virus glycoprotein genes in the upper and lower respiratory tract of hamsters

| Group[a] no. | Virus[b] | Nasal Turbinates | titer reduction (log$_{10}$)[d] | Mean virus titer[c] (log$_{10}$ TCID$_{50}$/g ± S.E.) in: Lungs | titer reduction (log$_{10}$)[d] |
|---|---|---|---|---|---|
| 1 | rHPIV3 1HN$_{(N-P)}$ | 4.5 ± 0.2 | 1.8 | 3.9 ± 0.2 | 3.0 |
| 2 | rHPIV3 1HN$_{(P-M)}$ | 3.5 ± 0.2 | 2.8 | 4.3 ± 0.2 | 2.3 |
| 3 | rHPIV3 2HN$_{(N-P)}$ | 5.4 ± 0.2 | 0.9 | 5.3 ± 0.3 | 1.6 |
| 4 | rHPIV3 2HN$_{(P-M)}$ | 6.3 ± 0.1 | 0.0 | 6.3 ± 0.5 | 0.6 |
| 5 | rHPIV3 HA$_{(N-P)}$ | 5.3 ± 0.2 | 1.0 | 5.8 ± 0.4 | 1.1 |
| 6 | rHPIV3 HA$_{(P-M)}$ | 6.0 ± 0.2 | 0.3 | 7.3 ± 0.2 | −0.4 |
| 7 | rHPIV3 HA$_{(HN-L)}$ | 6.0 ± 0.1 | 0.3 | 6.6 ± 0.2 | 0.3 |
| 8 | rHPIV3 1HN$_{(N-P)}$ 2HN$_{(P-M)}$ | 5.2 ± 0.1 | 1.1 | 5.0 ± 0.3 | 1.9 |
| 9 | rHPIV3 1HN$_{(N-P)}$ 2HN$_{(N-P)}$ HA$_{(HN-L)}$ | 1.6 ± 0.1 | 4.7 | 2.5 ± 0.1 | 4.4 |
| 10 | rHPIV3 1HN$_{(N-P)}$ 2HN$_{(N-P)}$ 3918 GU$_{(HN-L)}$ | 2.0 ± 0.3 | 4.3 | 1.8 ± 0.2 | 5.1 |
| 11 | rHPIV3 cp45 | 4.6 ± 0.1 | 1.7 | 2.1 ± 0.2 | 4.8 |
| 12 | rHPIV3 wt | 6.3 ± 0.1 | — | 6.9 ± 0.1 | — |

[a]8 hamsters per group.
[b]Each hamster was inoculated with $10^6$ TCID$_{50}$ of virus in a 0.1 ml inoculum.
[c]Virus was titered by serial dilution on LLC-MK2 monolayer cultures at 32° C.
[d]Reduction in virus replication compared to rHPIV3 wt (group 12).

(rHPIV3 1HN$_{N-P}$, rHPIV3 1HN$_{N-P}$2HN$_{P-M}$HA$_{HN-L}$, and rHPIV3 1HN$_{N-P}$ 2HN$_{P-M}$ 3918 GU$_{HN-L}$) were 100 to 1000-fold restricted for replication at 39° C. compared to the replication at the permissive temperature.

Viral RNA (vRNA) was isolated from biologically cloned recombinant chimeric viruses as described above (see also, Skiadopoulos et al., *J. Virol.* 73:1374-81, 1999a, incorporated herein by reference). This was used as the template for reverse transcription and polymerase chain reaction (RT-PCR) using specific primers that border the insertion sites. The amplified products were analyzed by restriction endonuclease digestion and partial DNA sequencing of the junction regions to confirm the presence and identity of each foreign insert. In all cases, the expected, correct sequence was confirmed.

Replication in the Respiratory Tract of Hamsters of rHPIV3s Expressing One, Two, or Three Supernumerary Foreign Protective Antigens It was previously shown that rHPIV3 or rHPIV3-1 viruses expressing one supernumerary viral protective antigen gene replicated efficiently in vitro and in vivo and induced protective immune responses against both the vector virus and the virus represented by the supernumerary antigen gene. However, it was unknown whether a rHPIV could accommodate It was shown above that a rHPIV3 expressing measles virus HA from a supernumerary gene insert between the HPIV3 HN and L genes, between the N and P genes, or between the P and M genes was modestly (about 10 to 20-fold) restricted in replication in the upper and lower respiratory tract of hamsters. This was confirmed in the present experiment, in which rHPIV3 containing measles virus HA as a single supernumerary gene between the N/P, P/M or HN/L genes was attenuated up to 10-fold (Table 13, groups 5, 6, and 7). Similarly, insertion of the HPIV2 HN gene between the HPIV3 N and P genes or between the P and M genes also exhibited a modest reduction (about 10 to 20-fold) in replication in the respiratory tract of hamsters (Table 13 groups 3 and 4). In contrast, insertion of the HPIV1 HN gene between the P and M genes or between the N and P, resulted in over approximately 100-fold reduction of replication in the upper and lower respiratory tract of hamsters (Table 13, groups 1 and 2). Since the HPIV1 HN, HPIV2 HN, and measles virus HA gene insertions are all of approximately the same size (1794 nt, 1781 nt, and 1926 nt, respectively), this was unlikely to be due to insert length. Therefore, the greater level of attenuation conferred by the introduction the HPIV1 HN gene likely is due to an additional attenuating effect that is specific to the expression of the HPIV1 HN protein on replication of the HPIV3 vector. Thus, in some cases, such as with HPIV1 HN, a supernumerary antigen can attenuate rHPIV3 for hamsters above and beyond the modest attenuation due to inserting an additional gene.

Inspection of the data in Table 13 indicates that the site of insertion also plays a role in the level of restriction of replication of the chimeric rHPIV3 in the respiratory tract of hamsters. Insertion of the measles virus HA gene or the HPIV2 HN gene between the rHPIV3 N and P genes resulted in a greater reduction of replication in the upper and lower respiratory tract of hamsters than did insertion between the P and M genes (Table 13, compare groups 3 versus 4 and 5 versus 6). This site-specific attenuation effect on replication of the HPIV3 vector was not evident for insertions of the HPIV1 HN gene, presumably because it was masked by the more substantial attenuating effect specific to HPIV1 HN.

The rHPIV3 chimeric recombinant viruses exhibited a gradient of attenuation that was a function of the number of supernumerary gene inserts. The viruses bearing three added genes exhibited the greatest effect, and were reduced approximately 10,000-108,000 fold in replication in the upper and lower respiratory tract of the infected hamsters (Table 13, groups 9 and 10). The rHPIV3 chimeric recombinant virus bearing two gene inserts exhibited an intermediate level of attenuation, and was reduced approximately 12-80 fold (Table 13, group 8). rHPIV3 chimeric recombinant viruses bearing one supernumerary gene (except those bearing the HPIV1 HN gene) were reduced only approximately 10-25 fold (groups 3-7 in Table 13). Importantly, rHPIV3 chimeric recombinant viruses bearing one, two, or three supernumerary gene inserts replicated in all animals. The most attenuated of these viruses, namely those bearing three supernumerary genes, were substantially more attenuated than rcp45 (group 11) with respect to replication in the upper and lower respiratory tract.

Immunogenicity in Hamsters of rHPIV3s Expressing One, Two, or Three Supernumerary Foreign Protective Antigens Hamsters were infected with HPIV1 wt, HPIV2 wt, rHPIV3 wt, or rHPIV3s bearing single, double or triple supernumerary gene inserts as described above. Serum samples were collected 3 days pre-immunization and 28 days post-immunization and were assayed for HPIV1, HPIV2, HPIV3 or measles virus-specific antibodies by virus neutralizing assay specific for either HPIV1 or measles virus, or by the hemagglutination inhibition (HAI) assay for HPIV3 or HPIV2 HN-specific antibodies (Table 14). All rHPIV3 viruses elicited a strong immune response to the HPIV3 backbone with the exception of the viruses bearing the three supernumerary gene insertions. The reduced or absent immune response in hamsters infected with either the rHPIV3 $1HN_{N-P}$ $2HN_{N-P}$ $HA_{HN-L}$ or rHPIV3 1 $HN_{N-P}$ $2HN_{N-P}$ $3918GU_{HN-L}$ was likely a result of these viruses being overly attenuated for replication in hamsters. Likewise the immune response to the vectored antigens in the viruses bearing three foreign genes was also low or undetectable. In contrast, viruses bearing single or double foreign gene insertions induced an immune response against each of the additional antigens, demonstrating that the vectored foreign genes are immunogenic in hamsters, and as in the example of rHPIV3 $1HN_{N-P}$ $2HN_{N-P}$ (Table 14; group 11) can be used to induce a strong immune response to three different viruses: HPIV1, HPIV2 and HPIV3.

TABLE 30

Immune response in hamsters to immunization with rHPIV3 vectors expressing single or multiple supernumerary protective antigens of HPIV1, HPIV2, or measles virus[a]

| Group no. | Virus | Serum[b] antibody titer (mean $\log_2$ ± SE) to the indicated virus | | | |
|---|---|---|---|---|---|
| | | HPIV3[c] | HPIV1[d] | HPIV2[e] | Measles virus[f] |
| 1 | rHPIV3 wt | 10.0 ± 0 | — | — | — |
| 2 | HPIV2 wt | <2.0 ± 0 | — | 8.0 ± 0.0 | — |
| 3 | HPIV1 wt | <2.0 ± 0 | 5.4 ± 0.3 | — | — |
| 4 | rHPIV3 $HA_{(N-P)}$ | 9.5 ± 0.2 | — | — | 12.4 ± 0.4 |
| 5 | rHPIV3 $HA_{(P-M)}$ | 8.7 ± 1.4 | — | — | 11.8 ± 0.2 |
| 6 | rHPIV3 $HA_{(HN-L)}$ | 9.0 ± 0 | — | — | 8.1 ± 0.6 |
| 7 | rHPIV3 $1HN_{(N-P)}$ | 9.5 ± 0.2 | 3.4 ± 0.6 | — | — |
| 8 | rHPIV3 $1HN_{(P-M)}$ | 7.2 ± 0.8 | 2.7 ± 0.3 | — | — |
| 9 | rHPIV3 $2HN_{(N-P)}$ | 9.8 ± 0.5 | — | 9.3 ± 0.8 | — |
| 10 | rHPIV3 $2HN_{(P-M)}$ | 10.0 ± 0.5 | — | 8.3 ± 1.1 | — |
| 11 | rHPIV3 $1HN_{(N-P)} 2HN_{(N-P)}$ | 9.6 ± 0.7 | 5.5 ± 0.4 | 8.3 ± 0.8 | — |
| 12 | rHPIV3 $1HN_{(N-P)} 2HN_{(N-P)} HA_{(HN-L)}$ | <2.0 ± 0 | 1.0 ± 0.3 | <2.0 ± 0.0 | <3 |
| 13 | rHPIV3 $1HN_{(N-P)} 2HN_{(N-P)} 3918 GU_{(HN-L)}$ | 4.3 ± 0.7 | 2.3 ± 0.6 | <2.0 ± 0.0 | — |
| 14 | rHPIV3 cp45 | 7.7 ± 0.2 | — | — | — |

[a]Mean antibody response in groups of hamsters (n = 6) inoculated intranasally with $10^6$ TCID$_{50}$ rHPIV3s expressing the hemagglutinin-neuraminidase protein of HPIV1 (1HN), HPIV2 (2HN) or measles virus hemagglutination (HA) inserted between the N and P genes (N-P), the P and M genes (P-M) or the HN and L genes (HN-L) of rHPIV3.
[b]Sera were collected 3 days before and 28 days after immunization.
[c]Mean hemagglutination inhibiting antibody (HAI) titer to HPIV3.
[d]Mean neutralizing antibody titer to HPIV1.
[e]Mean HAI antibody titer to HPIV2.
[f]Mean neutralizing antibody titer to measles virus (60% plaque reduction neutralization, PRN).

EXAMPLE XXIII

Use of rHPIV3-$N_B$ as an Attenuated Vector for the Measles Virus HA Protein

The use of an animal virus that is attenuated in humans because of a host range restriction as a vaccine against an antigenically-related human counterpart is the basis of the Jennerian approach to vaccine development. The Kansas (Ka) strain of bovine parainfluenza virus type 3 (BPIV3) was found to be 100- to 1000-fold restricted in replication in rhesus monkeys compared to human parainfluenza virus type 3 (HPIV3), and was also shown to be attenuated in humans (Coelingh et al., *J. Infect. Dis.* 157:655-62, 1988; Karron et al., *J. Infect. Dis.* 171:1107-14, 1995b, each incorporated herein by reference). A viable chimeric recombinant human parainfluenza virus type 3 (HPIV3) virus was previously produced containing the nucleoprotein (N) open reading frame (ORF) from BPIV3 Ka in place of the HPIV3 N ORF. This chimeric recombinant was previously designated cKa-N (Bailly et al., *J. Virol.* 74:3188-3195, 2000a, incorporated herein by reference) and is referred to here as rHPIV3-$N_B$. This previous study was initiated with an exchange of the N ORF because, among the PIV3 proteins, the BPIV3 and HPIV3 N proteins possess an intermediate level of amino acid sequence identity (85%) (Bailly et al., *Virus Genes* 20:173-82, 2000b, incorporated herein by reference), and it was shown that such a BPIV3/HPIV3 N recombinant is viable (Bailly et al., *J. Virol.* 74:3188-3195, 2000a, incorporated herein by reference). This represents a "modified Jennerian" approach, in which only a subset of the genes in the vaccine virus is derived from the animal counterpart. rHPIV3-$N_B$ grew to a titer comparable to that of the rHPIV3 and BPIV3 parent viruses in LLC-MK2 monkey kidney and Madin Darby bovine kidney cells (Bailly et al., *J. Virol.* 74:3188-3195, 2000a). Thus, the heterologous nature of the N protein did not impede replication of rHPIV3-$N_B$ in vitro. However, rHPIV3-$N_B$ was restricted in replication in rhesus monkeys to a similar extent as its BPIV3 parent virus (Bailly et al., *J. Virol.* 74:3188-3195, 2000a). This identified the BPIV3 N protein as a determinant of the host range restriction of replication of BPIV3 in primates.

The rHPIV3-$N_B$ chimeric virus thus combines the antigenic determinants of HPIV3 with the host range restriction and attenuation phenotype of BPIV3. There are 79 differences out of a total of 515 amino acids between the N proteins of HPIV3 and BPIV3 (Bailly et al., *Virus Genes* 20:173-82, 2000b). Many of these 79 amino acid differences likely contribute to the host-range attenuation phenotype of rHPIV3-$N_B$. Because the host range restriction is anticipated to be based on numerous amino acid differences, it is anticipated that the attenuation phenotype of rHPIV3-$N_B$ will be stable genetically even following prolonged replication in vivo. Despite its restricted replication in rhesus monkeys, rHPIV3-$N_B$ induced a high level of resistance to challenge of the monkeys with wild type (wt) HPIV3, and this level of resistance was indistinguishable from that conferred by immunization with wt rHPIV3. The infectivity, attenuation, and immunogenicity of rHPIV3-$N_B$ suggest that this novel chimeric virus is an excellent candidate as a HPIV3 vaccine (Bailly et al., *J. Virol.* 74:3188-3195, 2000a). Furthermore, as described below, it is shown herein that such chimeric viruses are excellent candidates to serve as an attenuated vector for the expression of supernumerary protective antigens, such as the HA of measles virus. The vector component of the resulting chimeric virus induces an immune response against HPIV3, and the added supernumerary genes induce immune responses against their respective heterologous pathogens. In this specific example, a bivalent attenuated vaccine virus is made that simultaneously induces immune response to HPIV3 and measles virus.

It is shown above that rHPIV3 can be used as a vector for expression of the measles virus hemagglutinin (HA) protein. In two examples, rcp45$_L$ HA(N-P) and rcp45 HA(HN-L), attenuated vectors expressing the measles virus HA gene possessed three attenuating amino acid point mutations in the vector backbone. The rHPIV3-$N_B$ vector of the present invention will likely be even more stable than vectors having an attenuation phenotype based on three amino acid point mutations. Also above, it was shown that the insertion of HA as a supernumerary gene into rHPIV3 conferred some attenuation on replication of both wt HPIV3 and attenuated HPIV3 cp45$_L$ for hamsters. In addition, the insertion of a 1908-nt gene insert into HPIV3 did not attenuate the wild type backbone, but did increase the level of attenuation of a backbone bearing the cp45$_L$ mutations for replication in hamsters. Therefore, the insertion of the measles virus HA gene into the host-range restricted rHPIV3-$N_B$ virus is projected to further attenuate its growth in vitro and/or in vivo. Inserts that affect replication in vitro or in vivo can be problematic for development of specific vaccines such as rHPIV3-$N_B$. Specifically, a candidate virus that is highly restricted in replication in vitro would be difficult to manufacture, and one that is highly restricted in replication in vivo could be overattenuated and not useful as a vaccine. It was also not known whether the rHPIV3-$N_B$ chimeric virus expressing the measles virus HA glycoprotein, designated rHPIV3-$N_B$ HA$_{(P-M)}$, would be satisfactorily immunogenic in primates against both HPIV3 and measles virus since all previous studies with HPIV3 expressing HA were conducted in a rodent model.

The present example, which details the generation of rHPIV3-$N_B$ HA$_{(P-M)}$ using reverse genetic techniques, indicates, surprisingly, that insertion of the HA gene into rHPIV3-$N_B$ did not further restrict its replication in rhesus monkeys. Presumably the attenuating effect of insertion is masked by the genetic elements present in the $N_B$ gene that specify the host range restriction of replication in primates. Rather, rHPIV3-$N_B$ HA$_{(P-M)}$ was satisfactorily attenuated in rhesus monkeys. Immunization of rhesus monkeys with rHPIV3-$N_B$ HA$_{(P-M)}$ induced resistance to the replication of wt HPIV3 challenge virus and stimulated high levels of neutralizing antibodies to the measles virus, levels that are known to be protective in humans (Chen et al., *J. Infect. Dis.* 162:1036-42, 1990, incorporated herein by reference).

Figure 31:
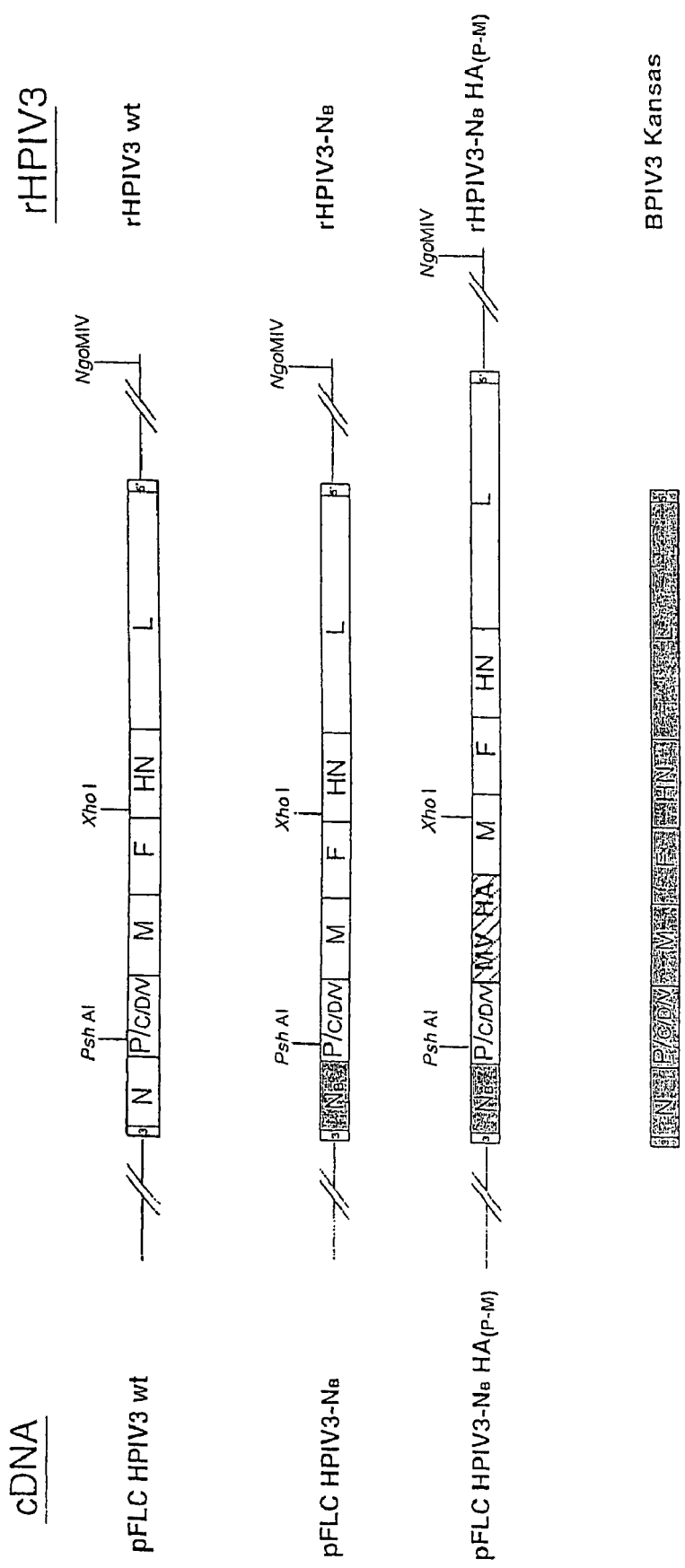

Construction of a pFLC HPIV3-$N_B$ HA$_{(P-M)}$, a Chimeric Bovine/Human PIV3 Antigenomic cDNA Encoding the BPIV3 N Gene ORF in Place of the rHPIV3 N Gene ORF and the HA Gene of Measles Virus as a Supernumerary Gene Inserted Between the rHPIV3 P and M Genes The full length antigenomic cDNA plasmid pFLC HPIV3-$N_B$ HA$_{(P-M)}$ (FIG. 31) was constructed in two steps. First, the previously-constructed pLeft-$N_B$ plasmid contains the 3' half of the HPIV3 antigenomic cDNA (HPIV3 nts 1-7437, the latter position being an XhoI site within the HN gene) with the HPIV3 N ORF replaced by that of BPIV3 (Bailly et al., *J. Virol.* 74:3188-3195, 2000a, incorporated herein by reference). The PshAI-NgoMIV fragment was excised from this plasmid. Note that the PshAI site is at position 2147 in the HPIV3 antigenome sequence (see FIG. 12) and the NgoMIV site occurs in the vector sequence, and so this removes all of the HPIV3 sequence downstream of the PshAI site. This fragment was replaced by the PshAI-NgoMIV fragment from the previously-constructed plasmid pLeft HA$_{(P-M)}$, which contains the measles virus HA ORF under the control of HPIV3 transcription signals and inserted between the HPIV3 N and P genes (Durbin, *J. Virol.* 74:6821-31, 2000, incorporated herein by reference). This yielded pLeft-$N_B$ HA$_{P-M}$. Next, the 11899 nt NgoMIV to Xho I fragment of pLeft $N_B$ HA$_{P-M}$, containing the 3' half of the HPIV3 antigenomic cDNA including the BPIV3 N gene ORF and the measles virus HA gene insert, was cloned into the NgoMIV to Xho I window of pRight, a plasmid encoding the 5' half of the HPIV3 antigenomic cDNA (PIV3 nts 7462-15462) (Durbin et al., *Virology* 235:323-332, 1997a). This yielded pFLC HPIV3-$N_B$ HA$_{P-M}$, a plasmid bearing the full length antigenomic cDNA of HPIV3 containing the BPIV3 N ORF in place of the HPIV3 N ORF, and containing measles virus HA gene as a supernumerary gene inserted between the P and M genes of HPIV3.

Recovery of Chimeric rHPIV3 Expressing the Bovine N Gene and the Measles Virus HA Gene rHPIV3-$N_B$ $HA_{P-M}$ was recovered from HEp-2 cells transfected with pFLC HPIV3-$N_B$ $HA_{P-M}$. To accomplish this, pFLC HPIV3-$N_B$ $HA_{P-M}$ was transfected into HEp-2 cells on six-well plates (Costar, Cambridge, Mass.) together with the support plasmids pTM(N), pTM(P no C), and pTM(L) and LipofectACE (Life Technologies, Gaithersburg, Md.), and the cells were simultaneously infected with MVA-T7, a replication-defective vaccinia virus recombinant encoding the bacteriophage T7 polymerase protein, as described above. After incubation at 32° C. for four days, the transfection harvest was passaged onto LLC-MK2 cells in a 25 cm² flask, and the cells were incubated for 5 days at 32° C. The virus recovered from the cell supernatant was amplified by a further passage on LLC-MK2 cells at 32° C. rHPIV3-$N_B$ $HA_{P-M}$ was biologically cloned by plaque purification on LLC-MK2 monolayer cultures as described above. Viral suspensions derived from biologically cloned virus were amplified on LLC-MK2 monolayer cultures at 32° C. Viral RNA (vRNA) was isolated from biologically cloned recombinant chimeric viruses as described above. RT-PCR was performed using specific oligonucleotide primer pairs spanning the BPIV3 N ORF or the measles virus HA gene, and the amplified cDNAs were analyzed by restriction endonuclease digestion and partial DNA sequencing as described above. This confirmed the presence of the BPIV3 N ORF substitution and the measles virus HA supernumerary gene insert.

Expression of the measles virus HA protein was initially confirmed by immunostaining plaques formed on LLC-MK2 monolayer cultures infected with rHPIV3-$N_B$ $HA_{P-M}$ using mouse monoclonal antibodies specific to the measles virus HA protein and goat anti-mouse peroxidase-conjugated antibodies, as described previously (Durbin, *J. Virol.* 74:6821-31, 2000, incorporated herein by reference).

rHPIV3-$N_B$ $HA_{P-M}$ Replicates to the Same Level as rHPIV3-$N_B$ in the Respiratory Tract of Rhesus Monkeys.

It was next determined whether the acquisition of the measles virus HA insert significantly decreased the replication of rHPIV3-$N_B$ in the upper and lower respiratory tract, as was observed when a supernumerary gene was inserted into an attenuated HPIV3 backbone lacking a bovine chimeric component. It was also determined whether rHPIV3-$N_B$ $HA_{P-M}$ replicated sufficiently to induce an immune response against both HPIV3 and measles virus in vivo. The replication of rHPIV3-$N_B$ $HA_{P-M}$ in the upper and lower respiratory tract of rhesus monkeys was compared to that of its rHPIV3-$N_B$ parent as well as wt HPIV3 and wt BPIV3 (Table 15). Rhesus monkeys that were seronegative for both HPIV3 and measles virus were inoculated simultaneously by the intranasal (IN) and intratracheal (IT) routes with one milliliter per site of L15 medium containing $10^5$ $TCID_{50}$ of virus suspension, as described previously (Bailly et al., *J. Virol.* 74:3188-3195, 2000a). Nasopharyngeal (NP) swab samples were collected on days 1 through 10 post-infection, and tracheal lavage (TL) samples were collected on days 2, 4, 6, 8, and 10 post-infection. Virus present in the NP and TL specimens was quantified by serial dilution on LLC-MK2 cell monolayers at 32° C., and the titer obtained was expressed as $\log_{10}$ $TCID_{50}$/ml (Table 31).

This comparison showed that the rHPIV3-$N_B$ $HA_{(P-M)}$ chimeric virus replicated to the same level in the upper and lower respiratory tract of rhesus monkeys as its rHPIV3-$N_B$ parent virus. This level of replication was also comparable to that of the BPIV3 virus parent, demonstrating that rHPIV3-$N_B$ $HA_{(P-M)}$ retains the attenuation phenotype of rHPIV3-$N_B$ and BPIV3 and, unexpectedly, that the insertion of the measles virus HA gene into the rHPIV3-$N_B$ genome does not further attenuate this virus for replication in the respiratory tract of rhesus monkeys.

TABLE 31

A chimeric human/bovine PIV3 containing the measles virus hemagglutinin gene is satisfactorily attenuated for replication in the upper and lower respiratory tract of rhesus monkeys, induces antibodies to both HPIV3 and measles virus, and protects against HPIV3 wild type virus challenge

| | | | Response to immunization | | | | Response to challenge with HPIV3 wt on day 28 or 31 | | Serum antibody response | Response to administration of measles virus vaccine |
|---|---|---|---|---|---|---|---|---|---|---|
| | | | Virus Replication Mean peak virus titer[c] ($\log_2$ ± $TCID_{50}$/ml ± SE) | | Serum HAI antibody titer (mean reciprocal $\log_2$ ± S.E.) for | Mean antibody titer to measles virus (60% PRN, mean reciprocal $\log_2$ ± SE) | Virus replication Mean peak HPIV3 virus titer[g] ($\log_{10}$ $TCID_{50}$/ml ± SE) | | HAI antibody titer (mean reciprocal $\log_2$ ± SE) for HPIV3 | (Moraten) on day 59 Serum antibody response Mean antibody titer to measles virus (60% PRN, mean reciprocal |
| Group no. | Immunizing virus[a] | No. of animals[a] | NP swab | Tracheal lavage | HPIV3 on day 28/31[d,e] | (day 31 post immunization)[f] | NP swap | Tracheal lavage | on day 56/59[h] | $\log_2$ ± SE) (day 87 post first immunization)[f] |
| 1 | rHPIV3 wt | 6 | 4.9 ± 0.4 | 3.2 ± 0.6 | 9.3 ± 0.6 | <5.5 ± 0.0 | 0.5 ± 0.0 | 0.5 ± 0.0 | 12.0 ± 0.0 | 8.2 ± 0.8 |
| 2 | rHPIV3-$N_B$ | 8 | 2.6 ± 0.6 | 2.0 ± 0.4 | 7.3 ± 0.3 | <5.5 ± 0.0 | 1.4 ± 0.9 | 0.5 ± 0.0 | 9 ± 1.0 | 10.1 ± 0.4 |
| 3 | rHPIV3-$N_B$ $HA_{(P-M)}$ | 4 | 2.2 ± 0.6 | 2.8 ± 0.6 | 6.8 ± 0.3 | 9.6 ± 0.5 | 1.2 ± 0.7 | 2.3 ± 0.2 | 11.5 ± 0.3 | 10.2 ± 0.4 |

TABLE 31-continued

A chimeric human/bovine PIV3 containing the measles virus hemagglutinin gene is satisfactorily attenuated for replication in the upper and lower respiratory tract of rhesus monkeys, induces antibodies to both HPIV3 and measles virus, and protects against HPIV3 wild type virus challenge

| | | | Response to immunization | | | | Response to challenge with HPIV3 wt on day 28 or 31 | | | Response to administration of measles virus vaccine (Moraten) on day 59 Serum antibody response Mean antibody titer to measles virus (60% PRN, mean reciprocal $\log_2 \pm$ SE) (day 87 post first immunization)[f] |
|---|---|---|---|---|---|---|---|---|---|---|
| | | | Virus Replication Mean peak virus titer[c] ($\log_2 \pm$ TCID$_{50}$/ml $\pm$ SE) | | Serum antibody response | | Virus replication Mean peak HPIV3 virus titer[g] ($\log_{10}$ TCID$_{50}$/ml $\pm$ SE) | | Serum antibody response HAI antibody titer (mean reciprocal $\log_2 \pm$ SE) for HPIV3 on day 56/59[h] | |
| | | | | | Serum HAI antibody titer (mean reciprocal $\log_2 \pm$ S.E.) for | Mean antibody titer to measles virus (60% PRN, mean reciprocal $\log_2 \pm$ SE) | | | | |
| Group no. | Immu- nizing virus[a] | No. of animals[a] | NP swab | Tracheal lavage | HPIV3 on day 28/31[d,e] | (day 31 post immunization)[f] | NP swap | Tracheal lavage | | |
| 4 | BPIV3 Ka | 8 | 2.3 ± 0.2 | 1.9 ± 0.2 | 5.0 ± 0.4 | ND | 2.9 ± 0.3 | 2.0 ± 0.5 | 11.5 ± 0.3 | ND |
| 5 | none[b] | 4 | ND | ND | <2 | ND | 4.5 ± 0.3 | 4.5 ± 0.2 | 12.0 ± 0.6 | ND |

[a]The present study included 4 monkeys that received rHPIV3-N$_B$ HA$_{(P-M)}$ and two monkeys in each of the groups that received rHPIV3 wt, rHPIV3-N$_B$, or BPIV3 Ka. With the exception of the group that received rHPIV3-N$_B$ HA$_{(P-M)}$, the data presented includes historical data from studies reported in Bailey et al., J. Virol. 74: 3188-3195, 2000, and Schmidt et al., J. Virol. 74: 8922-8929, 2000.
[b]Historical data from Schmidt et al., J. Virol. 74: 8922-8929, 2000.
[c]Monkeys were inoculated intranasally and intratracheally with $10^5$ TCID$_{50}$ of virus in a 1 ml inoculum at each site. Nasopharyngeal (NP) swab samples were collected on days 1 to 10 post-infection. Tracheal lavage (TL) samples were collected on days 2, 4, 6, 8, and 10 post-infection. Mean of the peak virus titers for each animal in its group irrespective of sampling day. S.E. = standard error. Virus titrations were performed on LLC-MK2 cells at 32° C. The limit of detection of virus titer was 10 TCID$_{50}$/ml.
[d]In the present study sera were collected from monkeys on day 31 post immunization and animals were then challenged with HPIV3. In the two previous studies, monkeys were sampled and challenged on day 28 post immunization.
[e]Sera collected for the present study and from the two previous studies were assayed at the same time. Serum HAI titer is expressed as the mean reciprocal $\log_2 \pm$ standard error, SE.
[f]Animals were immunized on day 59 with $10^6$ pfu of the measles virus Moraten vaccine strain administered parenterally (IM). Serum was collected 28 days later (i.e., 87 days after the first immunization). Data shown was obtained from samples collected only from animals in the present study. Mean neutralizing antibody titer to wt measles virus is expressed as the mean reciprocal $\log_2$ standard error. PRN, plaque reduction neutralizing.
[g]28 or 31 days after immunization monkeys were inoculated intranasally and intratracheally with $10^6$ TCID$_{50}$ of wt HPIV3 in a 1 ml inoculum at each site. NP and TL samples were collected on days 0, 2, 4, 6 and 8 post challenge. The titers obtained for NP and TL samples on day 0 were <2.0 $\log_{10}$ TCID$_{50}$/ml.
[h]With the exception of group 5, data shown are from the present study.

Immunization of Rhesus Monkeys with rHPIV3-N$_B$ HA$_{(P-M)}$ Induces High Titers of Antibodies Against Both HPIV3 and Measles Virus and Protects the Monkeys from Challenge with HPIV3

Rhesus monkeys immunized with rHPIV3-N$_B$ HA$_{P-M}$ developed high levels of serum antibodies against both HPIV3 and measles virus (Table 31). Serum HPIV3 antibodies were quantified by hemagglutination inhibition assay (HAI) using guinea pig erythrocytes as described previously (Durbin, J. Virol. 74:6821-31, 2000, incorporated herein by reference), and the titers are expressed as mean reciprocal $\log_2 \pm$ SE. High levels of serum HAI antibodies to HPIV3 were induced by both rHPIV3-N$_B$ HA$_{P-M}$ and rHPIV3-N$_B$, demonstrating that these attenuated recombinants can induce a strong immune response against the backbone antigens of the HPIV3 vector. It was also found that rhesus monkeys immunized with rHPIV3-N$_B$ HA$_{P-M}$ developed high levels of serum measles virus neutralizing antibodies 31 days after immunization, levels that are in excess of those needed to protect humans against infection with measles virus (Chen et al., J. Infect. Dis. 162:1036-42, 1990, incorporated herein by reference). Serum neutralizing antibody titers against wild type measles virus were quantified as described previously (Durbin, J. Virol. 74:6821-31, 2000), and the titers are expressed as reciprocal mean $\log_2 \pm$ SE (Table 15).

To compare the ability of infection with the live attenuated rHPIV3-N$_B$ HA$_{P-M}$ and rHPIV3-N$_B$ virus vaccine candidates to protect against wt HPIV3, the monkeys were challenged IN and IT with $10^6$ TCID$_{50}$ of wt HPIV3 31 days after the initial infection (Table 31). Nasopharyngeal swab and tracheal lavage samples were collected on days 2, 4, 6, and 8 post-challenge. Virus present in the specimens was quantified by serial dilution on LLC-MK2 monolayer cultures as described above. rHPIV3-N$_B$ HA$_{P-M}$ and rHPIV3-N$_B$ conferred a comparable, high level of protection against challenge with wt HPIV3 as indicated by a 100 to 1000-fold reduction in wt HPIV3 replication in the respiratory tract of immunized monkeys. This demonstrated that insertion of the measles virus HA gene into the chimeric bovine/human PIV3 did not diminish the level of protection induced by the HPIV3 glycoproteins present in the backbone of the attenuated virus vector.

Immunogenicity of rHPIV3-N$_B$ HA$_{P-M}$ was then compared with that of the licensed Moraten strain of live attenuated measles virus vaccine in rhesus monkeys, a species in which both PIV3 and measles virus replicate efficiently. Rhesus monkeys previously infected with a rHPIV3 virus or with rHPIV3-N$_B$ HA$_{P-M}$ were immunized parenterally (IM) with $10^6$ pfu of the Moraten strain of live-attenuated measles virus vaccine on day 59, and serum samples were taken on day 87 and analyzed for neutralizing antibodies against measles virus (Table 31). In animals that were naive for measles virus before receiving the Moraten vaccine (Table 31, groups 1 and 2), the titer of measles-specific antibodies induced by the Moraten vaccine was approximately the same as that observed in rHPIV3-N$_B$ HA$_{P-M}$-immunized animals (Table 31, group 2). Thus, rHPIV3-N$_B$ HA$_{P-M}$ vector expressing the HA glycoprotein measles virus was equivalent to the Moraten vaccine in the ability to induce virus-neutralizing antibodies in this primate model.

An important advantage of rHPIV3-N$_B$ HA$_{P-M}$ as a vaccine for measles virus over the Moraten vaccine is that the PIV vector can be administered by the intranasal route, whereas live-attenuated measles virus vaccines are not consistently infectious by this route, probably as a consequence of their attenuation and adaptation to cell culture. This makes it possible to immunize with rHPIV3-N$_B$ HA$_{P-M}$ in early infancy, an age group that cannot be immunized with a current live attenuated measles virus vaccine such as the Moraten strain because of the neutralizing and immunosuppressive effects of maternal antibodies (Durbin, *J. Virol.* 74:6821-31, 2000, incorporated herein by reference). Other advantages are also described above, including the superior growth of the PIV vector in cell culture and the lack of incorporation of measles virus HA in the virions, which should preclude changing the tropism of the PIV vector and should preclude measles virus-induced immunosuppression.

The lack of effective vaccination against measles virus infection results in the deaths of over 2700 children every day worldwide. The rHPIV3-$N_B$ $HA_{(P-M)}$ candidate vaccine offers a unique opportunity to immunize against two major causes of severe pediatric disease, namely, HPIV3 and measles virus. Unlike the currently licensed measles virus vaccines, we expect that chimeric rHPIV3-$N_B$ $HA_{(P-M)}$ and other human-bovine chimeric vector constructs, expressing the major antigenic determinant of measles virus or other heterologous pathogens, can be used to induce a strong immune response to, e.g., measles virus, in infants and children younger than six months of age (Durbin, *J. Virol.* 74:6821-31, 2000). An effective immunization strategy for infants and children will be required to meet the World Health Organization goal to eradicate measles by the year 2010. In particular, it would be advantageous for eradication to use a measles virus vaccine that does not involve infectious measles virus.

EXAMPLE XXIV

Use of a Recombinant Bovine-Human Parainfluenza Virus Type 3 (rB/H PIV3) as a Vector for RSV Glycoprotein Supernumerary Genes For use within the present invention, a recombinant chimeric human-bovine PIV was constructed in which the BPIV3 F and HN genes were replaced with those of HPIV3. This recombinant chimeric bovine-human virus rB/HPIV3 was shown to be fully competent for replication in cell culture, whereas in rhesus monkeys it displayed the host range-restricted, attenuated phenotype characteristic of BPIV3 and was highly immunogenic and protective (U.S. patent application Ser. No. 09/586,479, filed Jun. 1, 2000 by Schmidt et al.; Schmidt et al., *J. Virol.* 74:8922-9, 2000, each incorporated herein by reference). This is another example of a "modified Jennerian" approach that is useful within the compositions and methods of the invention, but in this case the entire set of viral "internal" genes is derived from BPIV3, with the antigenic determinants alone derived from HPIV3.

As noted above, there are numerous practical and safety considerations that favor vaccines based on a single PIV3 backbone, as opposed to a complex mixture of different viruses each of which must be separately attenuated and verified and which can interact in unpredictable ways. In addition, the host range restriction of BPIV3 confers an attenuation phenotype that should be very highly stable. In the present example, a recombinant chimeric human-bovine PIV3 (rB/HPIV3) was designed, rescued and characterized that encodes the respiratory syncytial virus (RSV) G or F glycoprotein, which are the major RSV neutralization and protective antigens. This example shows that rB/HPIV3 readily accepted the foreign RSV genes without a significant reduction of its replicative efficiency in vitro or in vivo and thus is a promising candidate vaccine and vector. This vector will be free of the problems of poor growth in vitro and instability that are otherwise characteristic of RSV.

Figure 32:
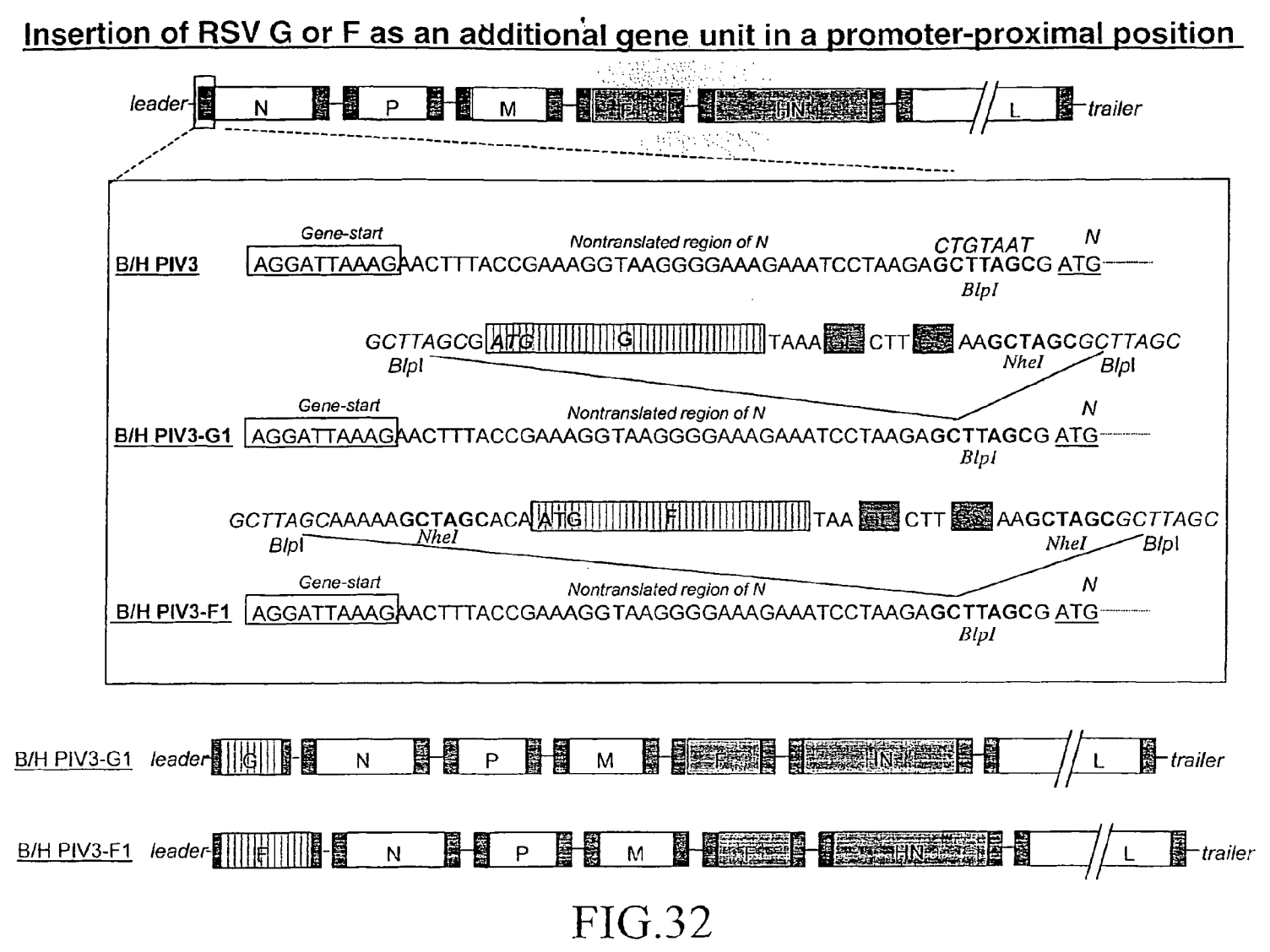

Construction of Antigenomic cDNAs Encoding Recombinant Chimeric rB/HPIV3 Viruses Bearing an RSV Subgroup A G or F ORF as an Additional, Supernumerary Gene A full length cDNA of the BPIV3 Kansas strain was constructed in which the F and HN glycoprotein genes of the bovine virus had been replaced with the corresponding genes of the HPIV3 JS strain (rB/HPIV3) (U.S. patent application Ser. No. 09/586,479, filed Jun. 1, 2000 by Schmidt et al.; Schmidt et al., *J. Virol.* 74:8922-9, 2000, each incorporated herein by reference). For use within the present invention, this cDNA was modified to contain three additional unique restriction enzyme recognition sites. Specifically, a BlpI site was introduced preceding the N ORF (nucleotide (nt) 103-109), an AscI site was introduced preceding the N gene end sequence and a NotI site was introduced preceding the P gene end sequence. These restriction enzyme recognition sites were introduced to facilitate the insertion of foreign, supernumerary genes into the genome of the chimeric B/HPIV3 virus genome. The sites were designed so that they did not disrupt any of the BPIV3 replication and transcription cis-acting elements. This specific example will describe insertion into the BlpI site (FIG. 32).

The previously described RSV subgroup A glycoprotein genes G and F (GenBank accession no. M74568) were modified for insertion into the promoter-proximal BlpI site of B/HPIV3 (FIG. 32). The strategy was to express each heterologous ORF as an additional, separate mRNA, and hence it was important that it be introduced into the rB/HPIV3 genome so that it was preceded by a BPIV3 gene start signal and followed by a BPIV3 gene end signal. The BlpI insertion site followed the gene start signal of the N gene (FIG. 32). Hence, for insertion at this site, the RSV ORF needed to be modified by insertion of a BlpI site at its upstream end and addition of a BPIV3 gene end signal, intergenic region, gene start signal, and BlpI site at its downstream end. For the RSV A G ORF, the forward PCR primer used was (5' to 3') AATTC GCTTAGCGATGTCCAAAAACAAGGACCAACGCACC-GC (SEQ ID NO. 144),
the reverse primer was (5' to 3') AAAAAGC-TAAGCGCTAGCCTTTAATCCTAAGTTTTTCTTACTT-TTTTTACTACTGGCGTGGTGTGTTGGGTGGAGATG-AAGGTTGTGATGGG (SEQ ID NO. 145) (Blp I site underlined, ORF translational initiation and termination triplets in bold). For the RSV A F ORF, the forward PCR primer used was (5' to 3') AAAGGCCTGCTTAGCAAAAAGCTAGCACAATGGA-GTTGCTAATCCTCAAAGCAAATGCAATTACC (SEQ ID NO. 146), and the reverse primer was (5' to 3') AAAAGCTAAGCGCTAGCTTCTTTAATCCTAAGTTTT-TCTTACTTTTATTAGTTACTAAATGCAATATTATTTAT-ACCACTCAGTTGATC (SEQ ID NO. 147) (Blp I site underlined, ORF translational initiation and termination triplets in bold).

The PCR products were digested with BlpI and cloned into the modified full length cDNA clone using standard molecular cloning techniques. The resulting full length cDNA containing the RSV A G ORF was designated pB/HPIV3-$G_A$1 and the plasmid containing the F ORF was designated pB/HPIV3-$F_A$1. The nucleotide sequence of each inserted gene was confirmed by restriction enzyme digestion and automated sequencing. All constructs were designed so that the final genome nucleotide length was a multiple of six, which has been shown to be a requirement for efficient RNA replication (Calain et al., *J. Virol.* 67:4822-30, 1993, incorporated herein by reference).

Recovery of rB/HPIV3-G1 and rB/HPIV3-F1 Chimeric Viruses from cDNA.

rB/HPIV3-G1 and rB/HPIV3-F1 viruses were recovered from the cDNAs pB/HPIV3-$G_A$1 and pB/HPIV3-$F_A$1, respectively. This was accomplished by the previously-described method in which HEp-2 cells were transfected with the respective antigenomic cDNA together with BPIV3 N, P and L support plasmids. The cells were simultaneously infected with a recombinant vaccinia virus, strain MVA, expressing the T7 RNA polymerase gene. The recovered recombinant viruses were cloned biologically by sequential terminal dilution in Vero cells. The presence of the inserted RSV G or F gene in the backbone of each recovered recombinant virus was confirmed by RT-PCR of viral RNA isolated from infected cells followed by restriction enzyme digestion and DNA sequencing. The sequence of the inserted gene and flanking regions in the recovered recombinant viruses was identical to that of the starting antigenomic cDNA.

rB/HPIV3-G1 and rB/HPIV3-F1 Viruses Replicate Efficiently in Cell Culture.

Figure 33:
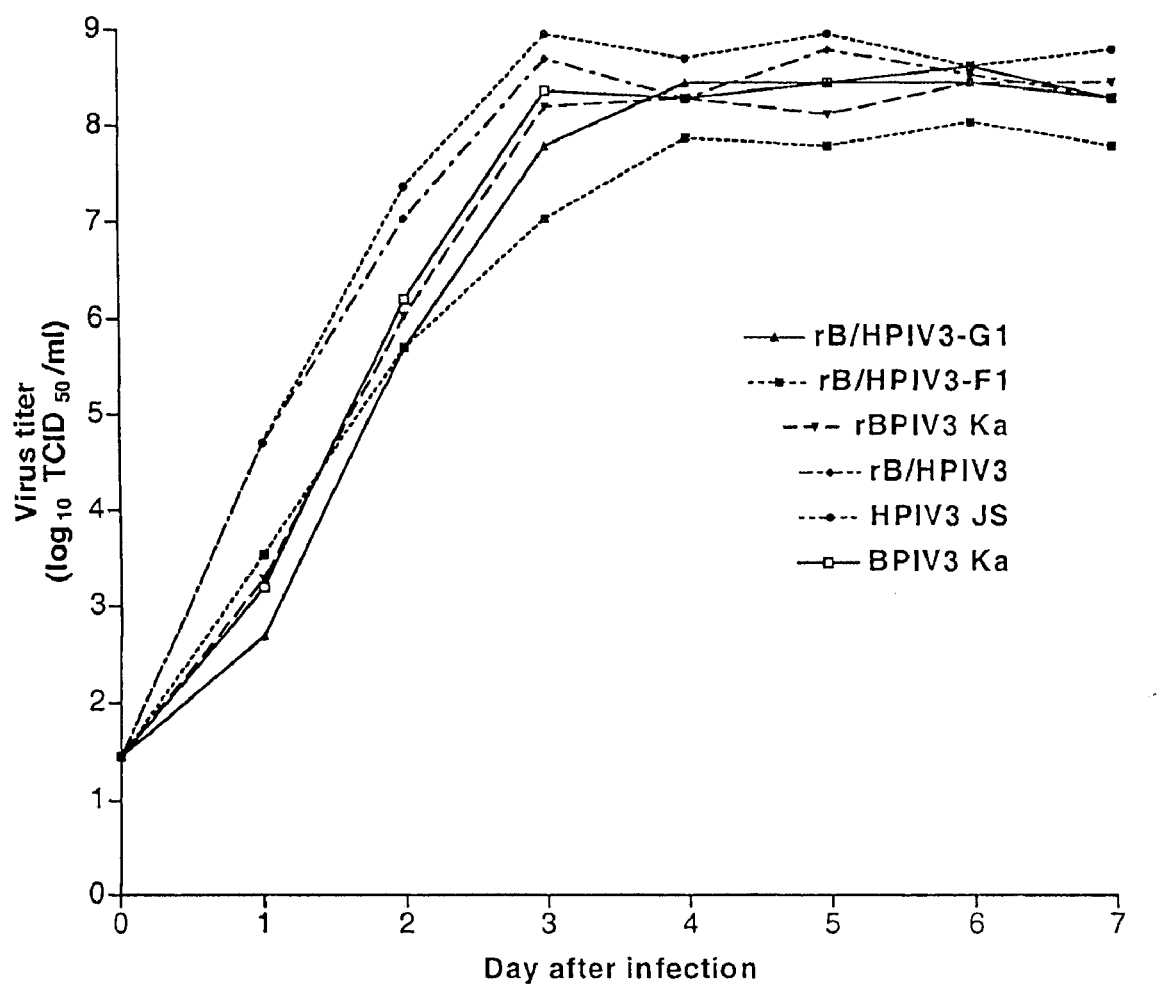

The multicycle growth kinetics of rB/HPIV3-G1 and rB/HPIV3-F1 in LLC-MK2 cells were determined by infecting LLC-MK2 cell monolayers in triplicate at a multiplicity of infection (MOI) of 0.01 and harvesting samples at 24-hour intervals over a seven day period, as previously described (Bailly et al., *J. Virol.* 74:3188-3195, 2000a, incorporated herein by reference). These two viruses were compared with BPIV3 Ka, HPIV3 JS, rBIV3 Ka, and rB/HPIV3 (FIG. 33). The two parental viruses bearing HPIV3 glycoproteins, namely HPIV3 and rB/HPIV3, appeared to replicate somewhat more rapidly than the others. However, the final titer achieved for each of the six viruses were similar with one exception: rB/HPIV3-F1 was approximately 8-fold reduced in its replicative capacity compared to the other viruses (FIG. 33). This might be an effect of having this large gene in a promoter-proximal position, or might be an effect of the expression of a second fusogenic protein, or both. This latter possibility was suggested by the observation that rB/HPIV3-F1 induced massive syncytia, comparable to what is observed with wild type RSV infection and greater than that observed with rB/HPIV3 or the other parental viruses. In comparison, rB/HPIV3-G1 induced less cytopathic effect and few syncytia in LLC-MK2 cells, comparable to rB/HPIV3. Nonetheless, rB/HPIV3-F1 and rB/HPIV3-G1 grew to a final titer of at least $10^7$ TCID$_{50}$/ml in LLC-MK2 cells and in Vero cells. This indicates that each virus is fully-permissive for growth which will allow cost-efficient vaccine manufacture.

The rB/HPIV3-G1 and rB/HPIV3-F1 Viruses Replicate Efficiently in the Respiratory Tract of Hamsters rB/HPIV3-G1 and rB/HPIV3-F1 were evaluated for their ability to replicate in the upper and lower respiratory tract of hamsters. The rB/HPIV3 parental virus, as well as the BPIV3 and HPIV3 biologically-derived viruses, were compared in parallel as controls (Table 32). Each virus was administered intranasally at a dose of $10^6$ TCID$_{50}$, and one group received both rB/HPIV3-G1 and rB/HPIV3-F1. Animals from each group were sacrificed on days 4 and 5 post infection, and the virus titer in the nasal turbinates and lungs were determined by serial dilution. The level of replication of rB/HPIV3-G1 in the respiratory tract was very similar to, and statistically indistinguishable from, that of HPIV3 JS and BPIV3 Ka. Replication of rB/HPIV3-F1 appeared to be somewhat reduced on days 4 and 5 relative to the others, but this difference was not statistically significant in comparison with the biological BPIV3 virus, which in previous primate and clinical studies replicated sufficiently well to induce a protective immune response (Coelingh et al., *Virology* 162:137-143, 1988; Karron et al., *Pediatr. Infect. Dis. J.* 15:650-654, 1996, each incorporated herein by reference). Also, the titer of virus from the mixed infection of rB/HPIV3-G1 and rB/HPIV3-F1 appeared to be somewhat reduced in the lower respiratory tract on day 4, but this was not statistically significant. Replication of one of the control viruses, BPIV3 Ka, was somewhat reduced in the lower respiratory tract on day 5: this also was not statistically significant, and indicates that these small differences likely are not important. Thus, the rB/HPIV3-G1 and rB/HPIV3-F1 viruses appeared to be fully competent for replication in vivo, despite the presence of the 0.9 kb G or 1.8 kb F supernumerary gene next to the promoter.

TABLE 32 rB/HPIV3 bearing the RSV G or F ORF as a supernumerary gene in the promoter proximal position replicates efficiently in the respiratory tract of hamsters.

| Immunizing virus[a] | Number of animals | Mean virus titer on day 4[b] ($log_{10}TCID_{50}/g \pm$ S.E.)[c] Nasal turbinates | Lungs | Mean virus titer on day 5[b] ($log_{10}TCID_{50}/g \pm$ S.E.)[c] Nasal turbinates | Lungs |
|---|---|---|---|---|---|
| rB/HPIV3-G1 | 6 | 5.9 ± 0.1 (AB) | 5.1 ± 0.6 (A) | 5.5 ± 0.2 (A) | 5.6 ± 0.4 (AC) |
| rB/HPIV3-F1 | 6 | 5.1 ± 0.3 (B) | 4.6 ± 0.2 (A) | 5.7 ± 0.2 (AB) | 3.6 ± 0.2 (BD) |
| rB/HPIV3-G1 & rB/HPIV3-F1 | 6 | 5.7 ± 0.3 (BC) | 4.3 ± 0.8 (A) | 5.6 ± 0.2 (A) | 5.9 ± 0.2 (A) |
| rB/H PIV3 | 6 | 6.2 ± 0.2 (AC) | 5.2 ± 0.6 (A) | 6.5 ± 0.1 (B) | 5.7 ± 0.6 (AC) |
| HPIV3 JS wild type | 6 | 6.6 ± 0.1 (A) | 6.5 ± 0.1 (A) | 6.0 ± 0.2 (AB) | 6.0 ± 0.4 (A) |
| BPIV3 Ka wild type | 6 | 5.8 ± 0.1 (AB) | 6.1 ± 0.2 (A) | 5.3 ± 0.2 (A) | 4.2 ± 0.5 (CD) |

[a]Hamsters were inoculated intranasally with $10^6$ $TCID_{50}$ of virus in a 0.1 ml inoculum.

[b]Animals were sacrificed on day 4 or 5 post inoculation, as indicated, and virus titers in the nasal turbinates and lungs were determined by titration on LLC-MK2 (PIV3) or HEp-2 (RSV) cells at 32° C. The limit of detectability of virus was $10^{2.45}$ $TCID_{50}$/g tissue. S.E. = standard error.

[c]Mean virus titers were assigned to similar groups (A, B, C, D) by the Tukey-Kramer test. Within each column, mean titers with different letters are statistically different ($p < 0.05$). Titers indicated with two letters are not significantly different from those indicated with either letter.

The rB/HPIV3-G1 and rB/HPIV3-F1 Viruses Induce Serum Antibodies to Both HPIV3 and RSV Hamsters were infected with rB/HPIV3-G1, rB/HPIV3-F1, or rB/HPIV3 as described above. An additional group received both rB/HPIV3-G1 and rB/HPIV3-F1, and another group was infected intranasally with RSV. Serum samples were collected 5 days post infection and assayed for RSV-specific antibodies by an ELISA test specific for the RSV F protein or RSV G protein (Table 33), and for HPIV3 HN-specific antibodies by the hemagglutination inhibiting (HAI) antibody assay (Table 34). The titer of F-specific or G-specific antibodies induced by the rB/HPIV3-F1 or rB/HPIV3-G1 virus, respectively, was 2- to 4-fold higher than that induced by wild type RSV. Animals inoculated with both rB/HPIV3-F1 and rB/HPIV3-G1 also had high titers of F-specific and G-specific antibodies. In addition to high ELISA titers against RSV G and F, rB/HPIV3-G1 and rB/HPIV3-F1 also induced RSV-neutralizing serum antibody titers that were higher than those induced by wt RSV (Table 34). Each of the viruses induced a titer of PIV3-specific antibody that was indistinguishable from that of their parent virus rB/HPIV3 (Table 34). Thus, the rB/HPIV3 vector bearing the F or G gene of RSV induced strong immune responses against both the RSV insert and the PIV vector.

TABLE 33

Immunization of hamsters with rB/HPIV3 expressing the RSV G or F ORF as a supernumerary gene induces an antibody response against the RSV G or F protein.

| Immunizing virus[a] | Animals per group | Serum IgG ELISA titer against RSV G protein[b] (mean recip. $\log_2$ ± S.E.) | | $\log_2$-fold increase | Serum IgG ELISA titer against RSV F protein[b] (mean recip. $\log_2$ ± S.E.) | | $\log_2$ fold increase |
|---|---|---|---|---|---|---|---|
| | | Pre | Day 26 | | Pre | Day 26 | |
| rB/HPIV3-G1 | 12 | 6.0 ± 0.4[c] | 12.5 ± 0.5 | 6.5 | 6.7 ± 0.5[c] | 7.5 ± 0.5 | 0.8 |
| rB/HPIV3-F1 | 12 | 6.3 ± 0.3 | 7.2 ± 0.3 | 0.9 | 6.8 ± 0.3 | 16.2 ± 0.5 | 9.4 |
| rB/HPIV3-G1 & rB/HPIV3-F1 | 12 | 6.5 ± 0.6 | 12.0 ± 0.9 | 5.5 | 7.3 ± 0.5 | 14.7 ± 0.4 | 7.4 |
| rB/HPIV3 | 12 | 6.5 ± 0.4 | 8.0 ± 0.4 | 1.5 | 7.3 ± 0.7 | 8.3 ± 0.8 | 1.0 |
| RSV | 12 | 6.8 ± 0.3 | 10.8 ± 0.4 | 4.0 | 7.3 ± 0.5 | 15.7 ± 0.4 | 8.2 |

[a]Hamsters were inoculated intranasally with $10^6$ TCID$_{50}$ of the virus in a 0.1 ml inoculum.
[b]Serum samples were taken on day 26 post inoculation and analyzed by glycoprotein-specific ELISA for antibodies against FSV G or F protein, as indicated.
[c]Titers in the pre serum specimen represent non-specific background levels of antibody in this sensitive ELISA.

TABLE 34

Immunization of hamsters with rB/HPIV3s expressing the RSV G or F ORF induces neutralizing antibodies against RSV as well as hemagglutination-inhibiting (HAI) antibodies against HPIV3.

| Immunizing virus[a] | Animals per group | Serum neutralizing antibody response to RSV[b] (mean recip. $\log_2$ ± S.E.)[d] | | Serum HAI antibody response to HPIV3[c] (mean recip. $\log_2$ ± S.E.)[d] | |
|---|---|---|---|---|---|
| | | Pre | Day 26 | Pre | Day 26 |
| rB/HPIV3-G1 | 12 | ≦3.3 | 10.0 ± 0.3 (A) | ≦2 | 10.0 ± 0.5 (A) |
| rB/HPIV3-F1 | 12 | ≦3.3 | 9.3 ± 0.5 (A) | ≦2 | 8.8 ± 0.1 (A) |
| rB/HPIV3-G1 & rB/HPIV3-F1 | 12 | ≦3.3 | 10.8 ± 0.4 (A) | ≦2 | 8.8 ± 0.3 (A) |
| rB/HPIV3 | 12 | ≦3.3 | 0.8 ± 0.8 (B) | ≦2 | 9.5 ± 0.8 (A) |
| RSV | 12 | ≦3.3 | 8.1 ± 1.2 (A) | ≦2 | ≦2 (B) |

[a]Hamsters were inoculated intranasally with $10^6$ TCID$_{50}$ of the indicated PIV3 or $10^6$ PFU of RSV in a 0.1 ml inoculum.
[b]Serum samples were taken on day 26 post inoculation and antibody titers were determined by 60% plaque reduction neutralization test.
[c]Serum samples were taken on day 26 post inoculation and antibody titers were determined by hemagglutination inhibition test.
[d]Mean virus titers were assigned to similar groups (A, B) by the Tukey-Kramer test. Within each column, mean titers with different letters are statistically different (p < 0.05).

The rB/HPIV3-G1 and rB/HPIV3-F1 Viruses Induce Resistance to Replication of HPIV3 and RSV Challenge Virus.

Hamsters immunized with rB/HPIV3, rB/HPIV3-G1, rB/HPIV3-F1, or rB/HPIV3-G1 plus rB/HPIV3-F1 vaccine candidates were challenged 28 days later by the intranasal inoculation of $10^6$ TCID$_{50}$ of HPIV3 or $10^6$ PFU of RSV. The animals were sacrificed five days later and the nasal turbinates and lungs were harvested and virus titers determined (Table 35). Animals that had received the parental rB/HPIV3 virus or the G1 and F1 derivatives exhibited a high level of resistance to the replication of the HPIV3 challenge virus, and there were no significant differences between experimental groups. Animals that received rB/HPIV3-G1, or rB/HPIV3-F1, or both viruses, exhibited a high level of resistance to replication of the RSV challenge virus. The level of protective efficacy of the rB/HPIV3-F1 virus against the RSV challenge appeared to be marginally less than that of the rB/HPIV3-G1 virus or of the RSV control. However, this difference was not significantly different. Thus, the rB/HPIV3 vector bearing either the F or G gene of RSV induced a level of protective efficacy that was comparable to that of complete infectious RSV.

TABLE 35

Immunization of hamsters with rB/HPIV3-G1 and or rB/HPIV3-F1 induces resistance to challenge with HPIV3 and RSV 28 days post infection.

| Immunizing virus[a] | No. of Animals | Mean HPIV3 titer[b] ($\log_{10}$TCID$_{50}$/g ± S.E.)[d] | | Mean RSV titer[c] ($\log_{10}$PFU/g ± S.E.)[d] | |
|---|---|---|---|---|---|
| | | Nasal turb. | Lungs | Nasal turb. | Lungs |
| rB/HPIV3-G1 | 6 | 2.3 ± 0.1 (A) | 3.1 ± 0.2 (A) | 1.9 ± 0.2 (AB) | ≦1.7 (A) |
| rB/HPIV3-F1 | 6 | 2.6 ± 0.2 (A) | 3.1 ± 0.1 (A) | 2.9 ± 0.4 (BC) | 2.1 ± 0.2 (A) |
| rB/HPIV3-G1 & rB/HPIV3-F1 | 6 | 2.8 ± 0.2 (A) | 2.8 ± 0.3 (A) | 1.8 ± 0.1 (A) | 1.9 ± 0.4 (A) |

TABLE 35-continued

Immunization of hamsters with rB/HPIV3-G1 and or rB/HPIV3-F1 induces resistance to challenge with HPIV3 and RSV 28 days post infection.

| Immunizing virus[a] | No. of Animals | Mean HPIV3 titer[b] ($\log_{10}TCID_{50}/g \pm S.E.$)[d] | | Mean RSV titer[c] ($\log_{10}PFU/g \pm S.E.$)[d] | |
|---|---|---|---|---|---|
| | | Nasal turb. | Lungs | Nasal turb. | Lungs |
| rB/HPIV3 | 6 | 2.3 ± 0.5 (A) | 3.6 ± 0.4 (A) | 4.1 ± 0.5 (C) | 3.5 ± 0.4 (B) |
| RSV | 6 | 5.6 ± 0.2 (B) | 5.2 ± 0.2 (B) | 1.9 ± 0.3 (AB) | ≦1.7 (A) |

[a]Groups of 6 hamsters were inoculated intranasally with $10^6$ $TCID_{50}$ of the indicated PIV3 or $10^6$ PFU of RSV in a 0.1 ml inoculum.
[b]HPIV3 titrations were performed on LLC-MK2 cells. The limit of detectability of virus was $10^{1.7}$ $TCID_{50}$/g tissue.
[c]Quantitation of RSV was determined by plaque numeration on HEp-2 cells. The limit of detectability of virus was $10^{1.7}$ PFU/g tissue.
[d]Mean virus titers were assigned to similar groups (A, B, C) by the Tukey-Kramer test. Within each column, mean titers with different letters are statistically different (p < 0.05). Titers indicated with two letters are not significantly different from those indicated with either letter.

EXAMPLE XXV

Use of rB/HPIV3.1 as a Vector for the Hemagglutinin HN and F Proteins of PIV2

The chimeric rHPIV3-1 virus, which has a HPIV3 backbone in which the HPIV3 HN and F genes have been replaced by their HPIV1 counterparts, serves as a useful vector for the HPIV2 HN protein as a supernumerary gene. This chimeric vector, rHPIV3-1.2HN, is demonstrated herein to induce resistance to replication of both HPIV1 and HPIV2 in hamsters. These findings illustrate the surprising flexibility of the PIV expression system. For example, the rHPIV3-1.2HN recombinant virus contains elements from each of the three serotypes of HPIV that cause significant disease: the internal genes of serotype 3 combined with the HN and F glycoprotein genes of serotype 1, and the HN protective antigen of serotype 2 as a supernumerary gene.

The present example provides yet another approach to deriving a PIV-based vector vaccine to protect against both PIV1 and PIV2. In this example, the rB/HPIV3 was modified by the substitution of the human PIV3 HN and F proteins by those of HPIV1. This virus, designated rB/HPIV3.1, contains the PIV1 HN and F glycoproteins as part of the vector backbone, intended to induce neutralizing antibodies and immunity to HPIV1. This virus was used in the present example as a vector to express the HN and F proteins of HPIV2 singly or together as supernumerary gene(s). Three viruses were recovered and shown to be fully viable: rB/HPIV3.1-2F; rB/HPIV3.1-2HN; or rB/HPIV3.1-2F,2HN, and each expressed the PIV2 F and/or HN gene as a supernumerary gene or genes. rB/HPIV3.1-2F,2HN, which expresses both the PIV2 F and/or HN proteins from two supernumerary genes and the PIV1 F and HN genes from the vector backbone, thus expresses both major protective antigens, i.e., the F and HN of glycoproteins, of PIV1 and PIV2 from a single virus. This approach optimizes the vaccine's protective efficacy and minimizes manufacturing costs since it accomplishes this increased immunogenicity using only one virus. It also likely will be simpler, safer and more effective to immunize infants and children with a single multivalent virus compared to a mixture of several viruses.

Construction of Antigenomic cDNAs Encoding Recombinant Chimeric rB/HPIV3.1 Viruses Bearing the HPIV2 F and HN Genes as Additional, Supernumerary Genes A full length cDNA of the BPIV3 Kansas strain in which the F and HN glycoprotein genes of the bovine virus had been replaced with the corresponding genes of the HPIV3 JS strain (rB/HPIV3) was constructed as previously described (Schmidt et al., *J. Virol.* 74:8922-9, 2000, incorporated herein by reference). This cDNA was modified to contain three additional unique restriction enzyme recognition sites (FIG. 34). Specifically, a BlpI site was introduced preceding the N ORF (nucleotide (nt) 103-109), an AscI site (nt 1676-83) was introduced preceding the N gene end sequence and a NotI site (nt 3674-3681) was introduced preceding the P gene end sequence. Next, the F and HN glycoprotein genes of rB/HPIV3 were substituted with the corresponding genes of HPIV1. To achieve this, the sub-clone 3.1hcR6 of the previously described rHPIV3-1 full length cDNA (Tao et al., *J. Virol.* 72:2955-2961, 1998, incorporated herein by reference), which contained the ORFs of the F and HN glycoprotein genes of HPIV1 under the control of HPIV3 transcription signals was modified by PCR mutagenesis to create a SgrAI restriction enzyme recognition site preceding the F gene and a BsiWI site preceding the HN gene end sequence, analogous to the position of the SgrAI and BsiWI sites that had been introduced previously into rB/HPIV3 (Schmidt et al., *J. Virol.* 74:8922-9, 2000). The mutagenic forward primer used to create the SgrAI site was (5' to 3') CGGCCGT-GACGCGTCTCCGCACCGGTGTATTAAGCCGAAGCA-AA (SEQ ID NO. 148) (SgrAI site underlined), and the mutagenic reverse primer was (5' to 3) CCCGAG-CACGCTTTGCTCCTAAGTTTTTTATATTTCCCGTAC-GTCTATTGTCTGATTGC (SEQ ID NO. 149) (BsiWI site underlined). The SgrAI and BsiWI sites were used to replace, as a single DNA fragment, the HPIV3 F and HN genes in rB/HPIV3 with the HPIV1 F and HN genes from the modified 3.1hcR6 plasmid. This yielded the full length antigenomic cDNA pB/HPIV3.1, consisting of HPIV1 F and HN open reading frames under the control of HPIV3 transcription signals in a background that is derived from BPIV3.

In the following step, the previously described HPIV2 F and HN open reading frames (GenBank accession numbers AF213351 and AF213352) were modified for insertion into the NotI and AscI sites, respectively, of pB/HPIV3.1 (FIG. 34). The strategy was to express each PIV2 F and HN ORF as an additional, separate mRNA, and hence it was important that it be introduced into the rB/HPIV3 genome so that it was preceded by a PIV3 gene start signal and followed by a PIV3 gene end signal. The NotI insertion site precedes the gene end signal of the P gene (FIG. 34). Hence, for insertion at this site, the HPIV2 F ORF needed to be modified by insertion of a NotI site and addition of a BPIV3 gene end signal, intergenic region and gene start signal at its upstream end, and a NotI site at its downstream end. For the HPIV2 F ORF, the forward PCR primer used was (5' to 3') AAAATATAGC-GGCCGCAAGTAAGAAAAACTTAGGATTAAAGGCG-GATGGATCACCTGCATCCAATGATAGTATGCATTTT-TGTTATGTACACTGG (SEQ ID NO. 150) and the reverse primer was (5' to 3') AAAATATAGCGGCCG-CTTTTACTAAGATATCCCATATATGTTTCCATGATTG-TTCTTGGAAAAGACGGCAGG (SEQ ID NO. 151) (NotI site underlined, ORF translational initiation and termination triplets in bold). For the HPIV2 HN ORF, the same cis-acting elements as described above for HPIV2 F were added, but instead of NotI, an AscI site was added on either side of the insert to facilitate cloning into the N-P gene junction. The forward PCR primer used was (5' to 3') GGAAA GGCGCGCCAAAGTAAGAAAAACTTAGGATTAAAGG-CGGATGGAAGATTACAGCAATCTATCTCTTAAATCA-ATTCC (SEQ ID NO. 152), the reverse primer was (5' to 3') GGAAAGGCGCGCCAAAATTAAAGCATTAGTTCCCT-TAAAAATGGTATTATTTGG (SEQ ID NO. 153).

The PCR products were digested with NotI (HPIV2 F insert) or AscI (HPIV2 HN insert) and cloned into the modified full length cDNA clone using standard molecular cloning techniques. The resulting full length cDNA containing the HPIV2 F ORF was designated pB/HPIV3.1-2F, the full length cDNA containing the HPIV2 HN ORF was designated pB/HPIV3.1-2HN, and the plasmid containing both the F and HN inserts was designated pB/HPIV3.1-2F,2HN. The nucleotide sequence of each inserted gene was confirmed by restriction enzyme digestion and automated sequencing. All constructs were designed so that the final genome nucleotide length was a multiple of six, which has been shown to be a requirement for efficient RNA replication (Calain et al., *J. Virol.* 67:4822-30, 1993, incorporated herein by reference). The genome nucleotide length of the recovered chimeric viruses is as follows: pB/HPIV3.1: 15492; pB/HPIV3.1-2HN: 17250; pB/HPIV3.1-2F: 17190; pB/HPIV3.1-2HN,2F: 18948.

Recovery of rB/HPIV3.1, rB/HPIV3.1-2F, rB/HPIV3.1-2HN, and rB/HPIV3.1-2F,2HN Chimeric Viruses from cDNA rB/HPIV3.1, rB/HPIV3.1-2F, rB/HPIV3.1-2HN, and rB/HPIV3.1-2F,2HN chimeric viruses were recovered from the cDNAs pB/HPIV3.1, pB/HPIV3.1-2F, pB/HPIV3.1-2HN, and pB/HPIV3.1-2F,2HN, respectively. This was accomplished by the previously-described method in which HEp-2 cells were transfected with the respective antigenomic cDNA together with BPIV3 N, P and L support plasmids. The cells were simultaneously infected with a recombinant vaccinia virus, strain MVA, expressing the T7 RNA polymerase gene. Porcine trypsin was added to the cell culture medium to activate the HPIV1 F protein, as previously described (Tao et al., *J. Virol.* 72:2955-2961, 1998). The recovered recombinant viruses were cloned biologically by sequential terminal dilution in Vero cells. All of the recombinant viruses replicated efficiently, induced CPE in Vero cells within 5 days and rendered the cell monolayer positive for hemadsorption. The presence of the inserted HPIV2 F and HN gene in the backbone of each recovered recombinant virus was confirmed by RT-PCR of viral RNA isolated from infected cells followed by restriction enzyme digestion and DNA sequencing. The sequence of the inserted gene and flanking regions in the recovered recombinant viruses was identical to that of the starting antigenomic cDNA.

EXAMPLE XXVI

Use of rHPIV3-1 cp45$_L$ as a Vector for the Measles Virus Hemagglutinin (HA) Protein: Development of a Sequential Immunization Strategy The chimeric rHPIV3-1 virus, which has a HPIV3 backbone in which the HPIV3 HN and F genes have been replaced by their HPIV1 counterparts, was shown above to serve as a useful vector for the HPIV2 HN protein as a supernumerary gene. This chimeric vector, rHPIV3-1.2HN, was able to induce resistance to replication of both HPIV1 and HPIV2 in hamsters. This finding illustrates the surprising flexibility of the PIV expression system. For example, this particular virus, rHPIV3-1.2HN, contained elements from each of the three serotypes of HPIV: the internal genes of serotype 3 combined with the HN and F glycoprotein genes of serotype 1, and the HN protective antigen of serotype 2 as a supernumerary gene. A further derivative, rHPIV3-1.2HNcp45$_L$, was also made that contained attenuating mutations from the cp45 HPIV3 vaccine candidate.

Thus, a PIV vector can be represented as comprising three components: the internal vector backbone genes, which can contain attenuating mutations as desired; the vector glycoprotein genes, which can be of the same or of a heterologous serotype; and one or more supernumerary genes encoding protective antigens for additional pathogens. In most cases, these supernumerary antigens are not incorporated into the virion and hence do not change the neutralization or tropism characteristics of the virus. Thus, each PIV vector is a bivalent or multivalent vaccine in which the vector itself induces immunity against an important human pathogen and each supernumerary antigen induces immunity against an additional pathogen.

In the present example, the flexibility of the PIV vector system is further demonstrated by using the rHPIV3-1 virus, as well as its attenuated rHPIV3-1 cp45$_L$ derivative, as vectors to express measles virus HA as a supernumerary gene. This provides a new bivalent vaccine candidate for HPIV1 and measles virus. Thus, measles virus HA can be vectored by rHPIV3 and attenuated derivatives thereof, bearing the serotype 3 antigenic determinants, or by rHPIV3-1 and attenuated derivatives thereof, bearing the serotype 1 antigenic determinants.

It is noteworthy that the three serotypes of HPIV (1, 2 and 3) do not confer significant cross-protection, and that each represents a significant human pathogen for which a vaccine is needed. This raises the possibility that the three serotypes might be used to sequentially immunize the infant against the PIVs as well as vectored protective antigens against heterologous pathogens. Specifically, immunization with a PIV vector containing the antigenic determinants of one serotype should be affected minimally or not at all by prior immunization with a vector or vectors containing the antigenic determinants of a heterologous serotype. This provides the opportunity to perform sequential immunizations and boosts (preferentially at intervals of 4-6 weeks or more) against supernumerary antigens as well as against the three HPIV serotypes, whose genes can be expressed either in the vector backbone or as supernumerary genes.

The present example details the use of the techniques of reverse genetics to develop a live-attenuated HPIV1 candidate vaccine, rPIV3-1 HA$_{P-M}$ cp45$_L$, expressing as a supernumerary gene the major measles virus protective antigen, the HA glycoprotein (Durbin, *J. Virol.* 74:6821-31, 2000, incorporated herein by reference), for use in infants and young children to induce an immune response against both measles virus and HPIV1. Also, a sequential immunization schedule was developed in which immunization with the attenuated rHPIV3 HA$_{P-M}$ cp45$_L$ candidate vaccine (bearing the serotype 3 antigenic determinants) was followed by the rHPIV3-1 HA$_{P-M}$ cp45$_L$ candidate vaccine (bearing the serotype 1 antigenic determinants). Hamsters immunized with these viruses developed antibodies to the HPIV3 and HPIV1 antigens present in the backbone of the vectors and also maintained high titers of antibodies to the vectored antigen, the measles virus HA expressed as a supernumerary antigen from both the HPIV3 and HPIV1 candidate vaccine viruses. Construction of rHPIV3-1 HA$_{(P-M)}$ and rHPIV3-1 HA$_{(P-M)}$ cp45$_L$, Wild Type and Attenuated Versions of rHPIV3-1 Expressing Measles Virus HA as a Supernumerary Gene.

Two full-length plasmids were constructed, pFLC HPIV3-1 HA$_{(P-M)}$ and pFLC HPIV3-1 HA$_{(P-M)}$ cp45$_L$ (FIG. 35) as described above (see also, Durbin, J. Virol. 74:6821-31, 2000; Skiadopoulos et al., J. Virol. 72:1762-8, 1998; Tao et al., J. Virol. 72:2955-2961, 1998, each incorporated herein by reference). pFLC HPIV3-1 HA$_{(P-M)}$ was constructed using the above-described pFLC HPIV3 HA$_{(P-M)}$ in which the wild type measles virus Edmonston strain HA gene ORF was inserted as a supernumerary gene between the P and M genes of rHPIV3. pFLC HPIV3 HA$_{(P-M)}$ was digested with BspEI to SphI and the cDNA fragment lacking the 6487 bp BspEI to SphI sequence was isolated. Next, pFLC 2G+.hc, a full-length antigenomic cDNA plasmid bearing the F and HN ORFs of PIV1 in place of those of HPIV3 (Tao et al., J. Virol. 72:2955-2961, 1998) was digested with BspEI and SphI, and the 6541 bp fragment (plasmid nts 4830-11371) containing the HPIV1 glycoprotein genes in the HPIV3 backbone was inserted into the BspEI to SphI window of pFLC HPIV3 HA$_{P-M}$ to give pFLC HPIV3-1 HA$_{P-M}$ (FIG. 35). The cp45 L mutations present in the L gene ORF (point mutations encoding amino acid substitutions Ser-942 to His, Leu-992 to Phe and Thr-1558 to Ile) are the major ts and att determinants of the HPIV3 cp45 candidate vaccine (Skiadopoulos et al., J. Virol. 72:1762-8, 1998) and were previously shown to confer attenuation of replication to the rHPIV3-1 cp45$_L$ in the respiratory tract of hamsters (Tao et al., Vaccine 17:1100-8, 1999). The pFLC HPIV3-1 HA$_{P-M}$ was then modified to encode these three ts mutations to yield pFLC HPIV3-1 HA$_{P-M}$ cp45$_L$ (FIG. 34). This was accomplished by inserting the SphI to NgoMIV restriction endonuclease fragment of pFLC HPIV3 cp45L (plasmid nts 11317-15929) (Skiadopoulos et al., J. Virol. 72:1762-8, 1998) into the SphI to NgoMIV window of pFLC HPIV3-1 HA$_{P-M}$.

Recovery of rHPIV3-1 HA$_{(P-M)}$ and rHPIV3-1 HA$_{(P-M)}$ cp45$_L$ pFLC HPIV3-1 HA$_{(P-M)}$ or pFLC HPIV3-1 HA$_{(P-M)}$ cp45$_L$ was transfected separately into HEp-2 cells on six-well plates (Costar, Cambridge, Mass.) together with the support plasmids pTM(N), pTM(P no C), and pTM(L) and LipofectACE (Life Technologies, Gaithersburg, Md.) and the cells were simultaneously infected with MVA-T7, a replication-defective vaccinia virus recombinant encoding the bacteriophage T7 polymerase protein as previously described (Skiadopoulos et al., Vaccine 18:503-10, 1999b, incorporated herein by reference). After incubation at 32° C. for four days in medium containing trypsin, the transfection harvest was passaged onto LLC-MK2 cells in a 25 cm$^2$ flask, and the cells were incubated for 5 days at 32° C. The virus recovered from the cell supernatant was further passaged on LLC-MK2 monolayer cultures with trypsin at 32° C. to amplify the virus. rPIV3-1 HA$_{P-M}$ and rPIV3-1 HA$_{P-M}$ cp45$_L$ were biologically cloned by terminal dilution on LLC-MK2 monolayer cultures at 32° C. as previously described (Skiadopoulos et al., Vaccine 18:503-10, 1999b). Viral suspensions derived from biologically cloned virus were amplified on LLC-MK2 monolayer cultures.

Viral RNA (vRNA) was isolated from biologically cloned recombinant chimeric viruses as described above. RT-PCR was performed using rHPIV3-1 HA$_{P-M}$ or rHPIV3-1 HA$_{P-M}$ cp45$_L$ vRNA as template and specific oligonucleotide primers that spanned the HA gene insert or the cp45 mutations in the L gene. The RT-PCR products were analyzed by restriction endonuclease digestion and partial DNA sequencing of the PCR products as described above. This confirmed the presence of the measles virus HA gene inserted between the P and M genes of rHPIV3-1 and the presence of the cp45 L gene mutations in its attenuated derivative.

Demonstration of the Attenuation Phenotype of rHPIV3-1 HA$_{(P-M)}$ cp45$_L$ in Hamsters Golden Syrian hamsters in groups of six were inoculated intranasally with 10$^6$ TCID$_{50}$ of rHPIV3-1, rHPIV3-1 HA$_{P-M}$, rHPIV3-1 cp45$_L$, or rHPIV3-1 HA$_{P-M}$ cp45$_L$. Four days after inoculation the lungs and nasal turbinates were harvested and titers of virus were determined as described previously (Skiadopoulos et al., Vaccine 18:503-10, 1999b). The titers are expressed as mean log$_{10}$ TCID$_{50}$/gram tissue (Table 36). The recombinant rHPIV3-1 HA$_{P-M}$ and its parent rHPIV3-1 wt replicated to comparable levels, indicating that insertion of an additional transcription unit encoding the HA gene ORF did not further attenuate this virus for hamsters. The rHPIV3-1 HA$_{P-M}$ cp45$_L$ and its rHPIV3-1 cp45$_L$ parent replicated to similar levels in the upper and lower respiratory tract indicating that rHPIV3-1 HA$_{P-M}$ cp45$_L$ was satisfactorily attenuated for replication in hamsters and that the insertion of the measles virus HA gene ORF did not further attenuate the chimeric rHPIV3-1 cp45$_L$ parent virus.

TABLE 36

Replication of wild type and attenuated versions of the rPIV3-1 and rPIV3-1 HA viruses in the respiratory tract of hamsters

| Virus[a] | Mean virus titer[b] (log$_{10}$ TCID$_{50}$/g ± S.E.) in: | |
|---|---|---|
| | Nasal Turbinates | Lungs |
| rPIV3-1 wt | 6.3 ± 0.1 | 6.6 ± 0.2 |
| rPIV3-1 HA$_{P-M}$ | 6.0 ± 0.1 | 5.7 ± 0.7 |
| rPIV3-1 cp45$_L$ | 4.1 ± 0.2 | 1.8 ± 0.2 |
| rPIV3-1 HA$_{P-M}$ cp45$_L$ | 4.4 ± 0.2 | 1.9 ± 0.2 |

[a]Groups of 6 hamsters each were inoculated with 10$^6$ TCID$_{50}$ of the indicated virus intranasally.
[b]Lungs and nasal turbinates were harvested four days later. Virus present in tissue homogenates was titered by serial dilution on LLC-MK2 monolayer cultures at 32° C. Guinea pig erythrocytes were used for hemadsorbtion.

A Sequential Immunization Schedule Employing Immunization with the Attenuated rHPIV3 HA$_{P-M}$cp45$_L$ Chimeric Vaccine Candidate Followed by the Attenuated rHPIV3-1 HA$_{P-M}$ cp45$_L$ Vaccine Candidate Induces Antibodies to the HPIV3 and HPIV1 Antigens of the Vector Backbones and Induces and Maintains High Titers of Antibodies to the Shared Vectored Antigen, the Measles Virus HA.

Immunization of a group of hamsters with rHPIV3-1 HA$_{P-M}$ cp45$_L$ induced a strong immune response to both the HPIV1 and to the measles virus (Table 37, group 6) indicating that rHPIV3-1, like rHPIV3, can be an efficient vector for the measles virus HA.

The feasibility of sequential immunization of hamsters with rHPIV3 HA$_{P-M}$cp45$_L$ and rHPIV3-1 HA$_{P-M}$ cp45$_L$ was next examined. Groups of hamsters were immunized with 10$^6$ TCID$_{50}$ of rHPIV3 HA$_{P-M}$ cp45$_L$ (Table 37, groups 1, 2 and 3), rHPIV3 cp45$_L$ (group 4) or L15 medium control (group 5) (Table 37). 59 days after the first immunization, groups of hamsters were immunized with 10$^6$ TCID$_{50}$ of rHPIV3-1 HA$_{P-M}$ cp45$_L$ (group 1 and 4), rHPIV3-1 cp45$_L$ (group 2 and 5), or L15 medium control (group 3). Serum samples were collected before the first immunization, 58 days after the first immunization, and 35 days after the second immunization. Animals immunized with rHPIV3 cp45$_L$ (Table 37, group 4) developed a strong antibody response to HPIV3, and animals immunized with rHPIV3 HA$_{P-M}$ cp45$_L$ (groups 1, 2 and 3) developed a strong antibody response to both HPIV3 and measles virus. Animals in Group 4, which had been previously immunized with rHPIV3 cp45$_L$, were subsequently immunized with rHPIV3-1 HA$_{P-M\ cp}$45$_L$ on day 59. When assayed on day 94, these animals had high titers of antibodies against HPIV3 and measles virus and a low to moderate level of antibodies to HPIV1. This showed that the HPIV3-1 chimeric vaccine virus was able to induce an immune response to both the HPIV1 antigens of the vector and to the vectored HA protein even in the presence of immunity to HPIV3, but there was some diminution of its immunogenicity in animals immune to HPIV3. The rHPIV3-1 HA$_{P-M}$ cp45$_L$ vaccine was clearly immunogenic in animals previously immune to HPIV3 as indicated by the response of hamsters in Group 4. These animals, which were immunized with rHPIV3 cp45$_L$ on day 0, developed a moderately high titer of neutralizing antibodies to measles virus on day 94, 35 days following immunization with rHPIV3-1 HA$_{P-M}$ cp45$_L$ on day 59. Significantly, hamsters that were first immunized with rHPIV3 HA$_{P-M}$ cp45$_L$ and were then immunized with rHPIV3-1 HA$_{P-M}$ cp45$_L$ (Group 1, Table 37) achieved a higher measles virus serum neutralizing antibody titer on day 94 than groups of hamsters that were immunized with rHPIV3 HA$_{P-M}$ cp45$_L$ alone (Group 3), suggesting that rHPIV3-1 HA$_{P-M}$ cp45$_L$ can be used to maintain high titers of serum neutralizing antibodies to measles following immunization with rHPIV3 HA$_{P-M}$ cp45$_L$. Since hamsters in Group 1 developed such a high titer of antibody to the measles virus HA following first immunization with rHPIV3 HA$_{P-M}$ cp45$_L$, it was not possible to detect a four-fold or greater rise of these titers following immunization with rHPIV3-1 HA$_{P-M}$ cp45$_L$.

In humans, it is likely that an HPIV3 vaccine such as rHPIV3 HA$_{P-M}$ cp45$_L$ will be given within the first four months of life followed two months later by an HPIV1 vaccine such as rHPIV3-1 HA$_{P-M}$ cp45$_L$ (Skiadopoulos et al., Vaccine 18:503-10, 1999b, incorporated herein by reference). In contrast to rodents, human infants characteristically develop low titers of antibodies to viral glycoprotein antigens administered within the first six months of life, due to immunologic immaturity, immunosuppression by maternal antibodies, and other factors (Karron et al., Pediatr. Infect. Dis. J. 14:10-6, 1995a; Karron et al., J. Infect. Dis. 172:1445-1450, 1995b; Murphy et al., J. Clin. Microbiol. 24:894-8, 1986, each incorporated herein by reference). It therefore is very likely that a boosting effect of rPIV3-1 HA$_{P-M}$ cp45$_L$ on the antibody titers to measles virus HA will be needed and will be readily observed in those infants immunized with rPIV3 HA$_{P-M}$ cp45$_L$ within the first six months of life. The present example indicates that it is possible to sequentially immunize animals with two serologically distinct live attenuated PIV vaccines, each of which expresses the measles virus HA, to develop antibodies to the HPIV3 and HPIV1 antigens of the vector backbone, and to maintain high titers of antibodies to the vectored antigen, the measles virus HA.

TABLE 37

Sequential immunization of hamsters with rPIV3 HA$_{(P-M)}$ cp45$_L$ followed by rPIV3-1 HA$_{(P-M)}$ cp45$_L$ induces immunity to three viruses, namely, HPIV1, HPIV3 and measles virus, and maintains the measles virus antibody titer at high levels

| | | | Immune response to first immunization | | | | Immune response to second immunization[a] | | |
| --- | --- | --- | --- | --- | --- | --- | --- | --- | --- |
| Group no. | Group size | Virus given in first immunization (day 0) | Serum HAI antibody titer to HPIV3 ($\log_2$ ± SE)[b] (day 58) | Serum antibody titer to HPIV1[c] ($\log_2$ ± SE) (day 58) | Serum antibody titer to measles virus[d] (60% PRN, $\log_2$ ± SE) (day 58) | Virus given in second immunization (day 59) | Serum HAI antibody titer to HPIV3[b] ($\log_2$ ± SE) (day 94) | Serum neutralizing antibody titer to HPIV1[c] ($\log_2$ ± SE) (day 94) | Serum antibody titer to measles virus[d] (60% PRN, $\log_2$ ± SE) (day 94) |
| 1 | 8 | rPIV3 HA$_{(P-M)}$ cp45$_L$ | 10.8 ± 0.4 | ≦0.5 ± 0.0 | 12.5 ± 0.4 | rPIV3-1 HA$_{(P-M)}$ cp45$_L$ | 11.5 ± 0.5 | 0.9 ± 0.2 | 13.1 ± 0.3 |
| 2 | 8 | rPIV3 HA$_{(P-M)}$ cp45$_L$ | 10.9 ± 0.4 | ≦0.5 ± 0.0 | 13.2 ± 0.4 | rPIV3-1 cp45$_L$ | 10.5 ± 0.5 | 1.2 ± 0.3 | 12.8 ± 0.4 |
| 3 | 6 | rPIV3 HA$_{(P-M)}$ cp45$_L$ | 9.3 ± 0.3 | ≦0.5 ± 0.0 | 12.7 ± 0.4 | none | 9.6 ± 0.9 | 1.1 ± 0.4 | 12.3 ± 0.2 |
| 4 | 8 | rPIV3 cp45$_L$ | 9.6 ± 0.6 | ≦0.5 ± 0.0 | <3.3 | rPIV3-1 HA$_{(P-M)}$ cp45$_L$ | 9.0 ± 0.7 | 0.9 ± 0.3 | 7.3 ± 0.3 |
| 5 | 6 | none | <2 ± 0.0 | ≦0.5 ± 0.0 | <3.3 | rPIV3-1 cp45$_L$ | <2 ± 0.0 | 4.8 ± 0.6 | <3.3 |
| 6 | 8 | rPIV3-1 HA$_{(P-M)}$ cp45$_L$ | | 3.0 ± 0.4 | 10.5 ± 0.4 | | | | |

[a]Sera were collected 5 days before and 58 days after the first immunization. The second immunization was given 59 days after the first, and serum was collected again 35 days later (day 94).
[b]Mean serum PIV3 HAI antibody titer is expressed as the reciprocal mean $\log_2$ ± standard error, SE.
[c]Mean serum neutralizing antibody titer to HPIV1 is expressed as the reciprocal mean $\log_2$ ± S.E.
[d]Mean serum neutralizing antibody titer to wild type measles virus is expressed as the reciprocal mean $\log_2$ ± standard error, PRN, plaque reduction neutralization.

EXAMPLE XXVII

Construction and Characterization of Chimeric HPIV3-2 Vaccine Recombinants Expressing Chimeric Glycoproteins The present example details development of a live attenuated PIV2 candidate vaccine virus for use in infants and young children using reverse genetic techniques. Preliminary efforts to recover recombinant chimeric PIV3-PIV2 virus carrying full-length PIV2 glycoproteins in a wild type PIV3 backbone, as described above for HPIV3-1 chimeric constructs, did not yield infectious virus. However, viable PIV2-PIV3 chimeric viruses were recovered when chimeric HN and F ORFs rather than full-length PIV2 ORFs were used to construct the full-length cDNA. The recovered viruses, designated rPIV3-2CT in which the PIV2 ectodomain and transmembrane domain was fused to the PIV3 cytoplasmic domain and rPIV3-2TM in which the PIV2 ectodomain was fused to the PIV3 transmembrane and cytoplasmic tail domain, possessed similar, although not identical, in vitro and in vivo phenotypes. Thus, it appears that only the cytoplasmic tail of the HN or F glycoprotein of PIV3 is required for successful recovery of PIV2-PIV3 chimeric viruses.

The rPIV3-2 recombinant chimeric viruses exhibit a strong host range phenotype, i.e. they replicate efficiently in vitro but are strongly restricted in replication in vivo. This attenuation in vivo occurs in the absence of any added mutations from cp45. Although rPIV3-2CT and rPIV3-2TM replicated efficiently in vitro, they were highly attenuated in both the upper and the lower respiratory tract of hamsters and African green monkeys (AGMs), indicating that chimerization of the HN and F proteins of PIV2 and PIV3 itself specified an attenuation phenotype in vivo. A phenotype including efficient replication in vitro and highly restricted growth in vivo is greatly desired for vaccine candidates. Despite this attenuation, they were highly immunogenic and protective against challenge with PIV2 wild type virus in both species. rPIV3-2CT and rPIV3-2TM were further modified by the introduction of the 12 PIV3 cp45 mutations located outside of the HN and F coding sequences to derive rPIV3-2CTcp45 and rPIV3-2TMcp45. These derivatives replicated efficiently in vitro but were even further attenuated in hamsters and AGMs indicating that the attenuation specified by the glycoprotein chimerization and by the cp45 mutations was additive. These findings identify the rPIV3-2CT and rPIV3-2TM recombinants as preferred candidates for use in live attenuated PIV2 vaccines.

Viruses and Cells

The wild type PIV1 strain used in this study, PIV1/Washington/20993/1964 (PIV1/Wash64) (Murphy et al., *Infect. Immun.* 12:62-68, 1975, incorporated herein by reference), was propagated in LLC-MK2 cells (ATCC CCL 7.1) as previously described (Tao et al., *J. Virol.* 72:2955-2961, 1998, incorporated herein by reference). The PIV wild type virus, strain V9412-6, designated PIV2/V94, was isolated in qualified Vero cells from a nasal wash of a sick child in 1994. PIV2/V94 was plaque purified three times on Vero cells before being amplified twice on Vero cells using OptiMEM without FBS. The wild type cDNA-derived recombinant PIV3/JS strain (rPIV3/JS) was propagated as previously described (Durbin et al., *Virology* 235:323-332, 1997, incorporated herein by reference). The modified vaccinia Ankara virus (MVA) recombinant that expresses the bacteriophage T7 RNA polymerase was generously provided by Drs. L. Wyatt and B. Moss (Wyatt et al., *Virology* 210:202-205, 1995, incorporated herein by reference).

HEp-2 cells (ATCC CCL 23) were maintained in MEM (Life Technologies, Gaithersburg, Md.) with 10% fetal bovine serum, 50 µg/ml gentamicin sulfate, and 2 mM glutamine. Vero cells below passage 150 were maintained in serum-free medium VP-SFM (Formula No. 96-0353SA, Life Technologies) with 50 µg/ml gentamicin sulfate and 2 mM glutamine.

Virion RNA Isolation, Reverse Transcription and PCR Amplification of Viral Genes, and Automated Sequencing To clone viral genes or to verify genetic markers of recombinant chimeric viruses, viruses were amplified on cultured cells and concentrated by polyethylene glycol precipitation as previously described (Mbiguino et al., *J. Virol. Methods* 31:161-170, 1991, incorporated herein by reference). Virion RNA was extracted from the virus pellet using Trizol reagent (Life Technologies) and used as template for reverse transcription (RT) with the Superscript Preamplification system (Life Technologies). The cDNA was further PCR amplified using the Advantage cDNA kit (Clontech, Palo Alto, Calif.). For cloning or sequencing purposes, the RT-PCR amplified DNA was purified from agarose gels using NA45 DEAE membrane as suggested by the manufacturer (Schleicher & Schuell, Keene, N. H.). Sequencing was performed with the dRhodamine dye terminator cycling squencing kit (Perkin Elmer, Forster City, Calif.) and an ABI 310 Gene Analyzer (Perkin Elmer, Forster City, Calif.).

Construction of the Chimeric PIV3-PIV2 Antigenomic cDNAs Encoding the Complete PIV2 F and HN Proteins or Chimeric F and HN Proteins Containing a PIV2-Derived Ectodomain and PIV3-Derived Cytoplasmic Tail Domain A DNA encoding a full-length PIV3 antigenomic RNA was constructed in which the PIV3 F and HN ORFs were replaced by their PIV2 counterparts following the strategy described previously (Tao et al., *J. Virol.* 72:2955-2961, 1998) for PIV3-PIV1. Details of this construction are presented in FIG. 36. PIV2/V94 propagated in Vero cells was concentrated and virion RNA (vRNA) was extracted from the virus pellet using Trizol reagent. The F and HN ORFs of PIV2/V94 were reverse transcribed from vRNA using random hexamer primers and the SuperScript Preamplification System before being amplified by PCR using the cDNA Advantage kit and primer pairs specific to PIV2 F and HN genes, respectively (1, 2 and 3, 4; Table 38). The amplified cDNA fragment of PIV2 F ORF was digested with NcoI plus BamHI and ligated into the NcoI-BamHI window of pLit.PIV31.Fhc (Tao et al., *J. Virol.* 72:2955-2961, 1998, incorporated herein by reference) to generate pLit.PIV32Fhc. The BspEI site in the PIV3 full-length cDNA is unique and we planned to use it to exchange segments between cDNAs (see FIGS. 36-38). Therefore, a BspEI site that was found in the PIV2 F ORF was removed by site-directed mutagenesis without affecting the amino acid sequence. The cDNA fragment of PIV2 HN ORF was digested with NcoI plus HindIII and ligated into the NcoI-HindIII window of pLit.PIV31.HNhc (Tao et al., *J. Virol.* 72:2955-2961, 1998) to generate pLit.PIV32HNhc. The PIV2 ORFs in pLit.PIV32Fhc and pLit.PIV32HNhc were sequenced, and the sequence was found to be as designed. The nucleotide sequences for the PIV2 F and HN ORFs are submitted in the GenBank. pLit.PIV32Fhc and pLit.PIV32HNhc were each digested with PpuMI plus SpeI and assembled to generate pLit.PIV32hc. The 4 kb BspEI-SpeI fragment of pLit.PIV32hc was introduced into the BspEI-SpeI window of p38'ΔPIV31hc (Skiadopoulos et al., *Vaccine* 18:503-510, 1999, incorporated herein by reference) to generate p38'ΔPIV32hc. The 6.5 kb fragment, generated by BspEI and SphI digestion of p38'ΔPIV32hc, containing the PIV2 full-length F and HN ORFs was introduced into the BspEI-SphI window of pFLC.2G+.hc (Tao et al., *J. Virol.* 72:2955-2961, 1998) to generate pFLC.PIV32hc (FIG. 36; Table 39=SEQ ID NO: 154).

TABLE 38

Primers used in construction of PIV3-2 full-length chimeric antigenomic cDNAs

| Primer No. | Gene | Direction | Position Beginning | End | Used in the construction or characterization of: | Sequence[a] |
|---|---|---|---|---|---|---|
| 1 | PIV2 F | sense | PIV2 F start codon 5070[b] | 20 bp down stream 5091 | pFLC.PIV32hc | gtaccATGgATCACCTGCATCCAAT (SEQ ID NO. 155) |

TABLE 38-continued

Primers used in construction of PIV3-2 full-length chimeric antigenomic cDNAs

| Primer No. | Gene | Direction | Position Beginning | End | Used in the construction or characterization of: | Sequence[a] |
|---|---|---|---|---|---|---|
| 2 | F | PIV2 antisense | PIV2 F stop codon 6732[b] | 20 bp upstream 6705[b] | pFLC.PIV32hc | tgtggatccTAAGATATCCCATATATGTTTC (SEQ ID NO. 156) |
| 3 | HN | PIV2 sense | PIV2 HN start codon 6837[b] | 18 bp down stream 6856[b] | pFLC.PIV32hc | gggccATGGAAGATTACAGCAAT (SEQ ID NO. 133) |
| 4 | HN | PIV2 antisense | PIV2 HN stop codon 8558[b] | 17 bp upstream 8538[b] | pFLC.PIV32hc | caataagcTTAAAGCATTAGTTCCC (SEQ ID NO. 134) |
| 5 | F | PIV2 sense | 5069[c] | 5088[c] | pFLC.PIV32TM | ATGCATCACCTGCATCCAAT (SEQ ID NO. 157) |
| 6 | F | PIV2 antisense | 6538[c] | 6517[c] | pFLC.PIV32TM | TAGTGAATAAAGTGTCTTGGCT (SEQ ID NO. 158) |
| 7 | HN | PIV2 sense | 6962[c] | 6985[c] | pFLC.PIV32TM | CATGAGATAATTCATCTTGATGTT (SEQ ID NO. 159) |
| 8 | HN | PIV2 antisense | 8560[c] | 8537[c] | pFLC.PIV32TM | agcTTAAAGCATTAGTTCCCTTAA (SEQ ID NO. 160) |
| 9 | F | PIV3 sense | 6539[c] | 6566[c] | pFLC.PIV32TM | ATCATAATTATTTTGATAATGATCATTA (SEQ ID NO. 161) |
| 10 | F | PIV3 antisense | 5068[c] | 5050[c] | pFLC.PIV32TM | GTTCAGTGCTTGTTGTGTT (SEQ ID NO. 162) |
| 11 | HN | PIV3 sense | 8561[c] | 8587[c] | pFLC.PIV32TM | TCATAATTAACCATAATATGCATCAAT (SEQ ID NO. 163) |
| 12 | HN | PIV3 antisense | 6961[c] | 6938[c] | pFLC.PIV32TM | GATGGAATTAATTAGCACTATGAT (SEQ ID NO. 164) |
| 13 | F | PIV2 sense | 5069[d] | 5088[d] | pFLC.PIV32CT | ATGCATCACCTGCATCCAAT (SEQ ID NO. 157) |
| 14 | F | PIV2 antisense | 6607[d] | 6589[d] | pFLC.PIV32CT | GATGATGTAGGCAATCAGC (SEQ ID NO. 165) |
| 15 | HN | PIV2 sense | 6887[d] | 6904[d] | pFLC.PIV32CT | ACTGCCACAATTCTTGGC (SEQ ID NO. 166) |
| 16 | HN | PIV2 antisense | 8536[d] | 8511[d] | pFLC.PIV32CT | TTAAAGCATTAGTTCCCTTAAAAATG (SEQ ID NO. 167) |
| 17 | F | PIV3 sense | 6620[d] | 6642[d] | pFLC.PIV32CT | AAGTATTACAGAATTCAAAGAG (SEQ ID NO. 168) |
| 18 | F | PIV3 antisense | 5068[d] | 5050[d] | pFLC.PIV32CT | GTTCAGTGCTTGTTGTGTT (SEQ ID NO. 162) |
| 19 | HN | PIV3 sense | 8525[d] | 8551[d] | pFLC.PIV32CT | TCATAATTAACCATAATATGCATCAAT (SEQ ID NO. 163) |
| 20 | HN | PIV3 antisense | 6898[d] | 6879[d] | pFLC.PIV32CT | CTTATTAGTGAGCTTGTTGC (SEQ ID NO. 169) |
| 21 | F | PIV2 Sense | 6608[c, d] | 6630[c, d] | Chimera confirmation | ACCGCAGCTGTAGCAATAGT (SEQ ID NO. 170) |
| 22 | HN | PIV2 antisense | 7522[c] 7501[d] | 7502[c] 7481[d] | Chimera confirmation | GATTCCATCACTTAGGTAAAT (SEQ ID NO. 171) |
| 23 | M | PIV3 sense | 4759[c, d] | 4780[c, d] | Chimera confirmation | GATACTATCCTAATATTATTGC (SEQ ID NO. 172) |

TABLE 38-continued

Primers used in construction of PIV3-2 full-length chimeric antigenomic cDNAs

| Primer No. | Gene | Direction | Position Beginning | End | Used in the construction or characterization of: | Sequence[a] |
|---|---|---|---|---|---|---|
| 24 | L | PIV3 antisense | 9100[c]<br>9176[d] | 9081[c]<br>9057[d] | Chimera confirmation | GCTAATTTTGATAGCACATT<br>(SEQ ID NO. 173) |

[a] All the primers are anotated in that the PIV specific sequences are in uppercase, non-PIV sequences in lowercase, start and stop codons in bold, and restriction sites underlined.
[b] The numbers are the nt positions in the full-length antigenomic cDNA construct pFLC.P1V32hc.
[c] The numbers are the nt positions in the full-length antigenomic cDNA construct pFLC.PIV32TM and pFLC.PIV32TMcp45.
[d] The numbers are the nt positions in the full-length antigenomic cDNA construct pFLC.PIV32CT and pFLC.PIV32CTcp45.###

TABLE 39

(SEQ ID NO. 154)
Sequence of pFLC.P1V32, 15492 bp in sense orientation
(only the insert is shown)

```
   1 ACCAAACAAG AGAAGAAACT TGTCTGGGAA TATAAATTTA ACTTTAAATT AACTTAGGAT
  61 TAAAGACATT GACTAGAAGG TCAAGAAAAG GGAACTCTAT AATTTCAAAA ATGTTGAGCC
 121 TATTTGATAC ATTTAATGCA CGTAGGCAAG AAAACATAAC AAAATCAGCC GGTGGAGCTA
 181 TCATTCCTGG ACAGAAAAAT ACTGTCTCTA TATTCGCCCT TGGACCGACA ATAACTGATG
 241 ATAATGAGAA AATGACATTA GCTCTTCTAT TTCTATCTCA TTCACTAGAT AATGAGAAAC
 301 AACATGCACA AAGGGCAGGG TTCTTGGTGT CTTTATTGTC AATGGCTTAT GCCAATCCAG
 361 AGCTCTACCT AACAACAAAT GGAAGTAATG CAGATGTCAA GTATGTCATA TACATGATTG
 421 AGAAAGATCT AAAACGGCAA AAGTATGGAG GATTTGTGGT TAAGACGAGA GAGATGATAT
 481 ATGAAAAGAC AACTGATTGG ATATTTGGAA GTGACCTGGA TTATGATCAG GAAACTATGT
 541 TGCAGAACGG CAGGAACAAT TCAACAATTG AAGACCTTGT CCACACATTT GGGTATCCAT
 601 CATGTTTAGG AGCTCTTATA ATACAGATCT GGATAGTTCT GGTCAAAGCT ATCACTAGTA
 661 TCTCAGGGTT AAGAAAAGGC TTTTTCACCC GATTGGAAGC TTTCAGACAA GATGGAACAG
 721 TGCAGGCAGG GCTGGTATTG AGCGGTGACA CAGTGGATCA GATTGGGTCA ATCATGCGGT
 781 CTCAACAGAG CTTGGTAACT CTTATGGTTG AAACATTAAT AACAATGAAT ACCAGCAGAA
 841 ATGACCTCAC AACCATAGAA AAGAATATAC AAATTGTTGG CAACTACATA AGAGATGCAG
 901 GTCTCGCTTC ATTCTTCAAT ACAATCAGAT ATGGAATTGA GACCAGAATG GCAGCTTTGA
 961 CTCTATCCAC TCTCAGACCA GATATCAATA GATTAAAAGC TTTGATGGAA CTGTATTTAT
1021 CAAAGGGACC ACGCGCTCCT TTCATCTGTA TCCTCAGAGA TCCTATACAT GGTGAGTTCG
1081 CACCAGGCAA CTATCCTGCC ATATGGAGCT ATGCAATGGG GGTGGCAGTT GTACAAAATA
1141 GAGCCATGCA ACAGTATGTG ACGGGAAGAT CATATCTAGA CATTGATATG TTCCAGCTAG
1201 GACAAGCAGT AGCACGTGAT GCCGAAGCTC AAATGAGCTC AACACTGGAA GATGAACTTG
1261 GAGTGACACA CGAATCTAAA GAAAGCTTGA AGAGACATAT AAGGAACATA AACAGTTCAG
1321 AGACATCTTT CCACAAACCG ACAGGTGGAT CAGCCATAGA GATGGCAATA GATGAAGAGC
1381 CAGAACAATT CGAACATAGA GCAGATCAAG AACAAAATGG AGAACCTCAA TCATCCATAA
1441 TTCAATATGC CTGGGCAGAA GGAAATAGAA GCGATGATCA GACTGAGCAA GCTACAGAAT
1501 CTGACAATAT CAAGACCGAA CAACAAAACA TCAGAGACAG ACTAAACAAG AGACTCAACG
1561 ACAAGAAGAA ACAAAGCAGT CAACCACCCA CTAATCCCAC AAACAGAACA AACCAGGACG
1621 AAATAGATGA TCTGTTTAAC GCATTTGGAA GCAACTAATC GAATCAACAT TTTAATCTAA
1681 ATCAATAATA AATAAGAAAA ACTTAGGATT AAAGAATCCT ATCATACCGG AATATAGGGT
```

TABLE 39-continued (SEQ ID NO. 154)
Sequence of pFLC.P1V32, 15492 bp in sense orientation
(only the insert is shown)

```
1741  GGTAAATTTA GAGTCTGCTT GAAACTCAAT CAATAGAGAG TTGATGGAAA GCGATGCTAA
1801  AAACTATCAA ATCATGGATT CTTGGGAAGA GGAATCAAGA GATAAATCAA CTAATATCTC
1861  CTCGGCCCTC AACATCATTG AATTCATACT CAGCACCGAC CCCCAAGAAG ACTTATCGGA
1921  AAACGACACA ATCAACACAA GAACCCAGCA ACTCAGTGCC ACCATCTGTC AACCAGAAAT
1981  CAAACCAACA GAAACAAGTG AGAAAGATAG TGGATCAACT GACAAAATA DACAGTCCGG
2041  GTCATCACAC GAATGTACAA CAGAAGCAAA AGATAGAAAT ATTGATCAGG AAACTGTACA
2101  GAGAGGACCT GGGAGAAGAA GCAGCTCAGA TAGTAGAGCT GAGACTGTGG TCTCTGGAGG
2161  AATCCCCAGA AGCATCACAG ATTCTAAAAA TGGAACCCAA AACACGGAGG ATATTGATCT
2221  CAATGAAATT AGAAAGATGG ATAAGGACTC TATTGAGGGG AAAATGCGAC AATCTGCAAA
2281  TGTTCCAAGC GAGATATCAG GAAGTGATGA CATATTTACA ACAGAACAAA GTAGAAACAG
2341  TGATCATGGA AGAAGCCTGG AATCTATCAG TACACCTGAT ACAAGATCAA TAAGTGTTGT
2401  TACTGCTGCA ACACCAGATG ATGAAGAAGA AATACTAATG AAAAATAGTA GGACAAAGAA
2461  AAGTTCTTCA ACACATCAAG AAGATGACAA AGAATTAAA AAAGGGGGAA AAGGGAAAGA
2521  CTGGTTTAAG AAATCAAAAG ATACCGACAA CCAGATACCA ACATCAGACT ACAGATCCAC
2581  ATCAAAAGGG CAGAAGAAAA TCTCAAAGAC AACAACCACC AACACCGACA CAAAGGGGCA
2641  AACAGAAATA CAGACAGAAT CATCAGAAAC ACAATCCTCA TCATGGAATC TCATCATCGA
2701  CAACAACACC GACCGGAACG AACAGACAAG CACAACTCCT CCAACAACAA CTTCCAGATC
2761  AACTTATACA AAAGAATCGA TCCGAACAAA CTCTGAATCC AAACCCAAGA CACAAAAGAC
2821  AAATGGAAAG GAAAGGAAGG ATACAGAAGA GAGCAATCGA TTTACAGAGA GGGCAATTAC
2881  TCTATTGCAG AATCTTGGTG TAATTCAATC CACATCAAAA CTAGATTTAT ATCAAGACAA
2941  ACGAGTTGTA TGTGTAGCAA ATGTACTAAA CAATGTAGAT ACTGCATCAA AGATAGATTT
3001  CCTGGCAGGA TTAGTCATAG GGGTTTCAAT GGACAACGAC ACAAAATTAA CACAGATACA
3061  AAATGAAATG CTAAACCTCA AGCAGATCT AAAGAAAATG GACGAATCAC ATAGAAGATT
3121  GATAGAAAAT CAAAGAGAAC AACTGTCATT GATCACGTCA CTAATTTCAA ATCTCAAAAT
3181  TATGACTGAG AGAGGAGGAA AGAAAGACCA AAATGAATCC AATGAGAGAG TATCCATGAT
3241  CAAACAAAA TTGAAAGAAG AAAAGATCAA GAAGACCAGG TTTGACCCAC TTATGGAGGC
3301  ACAAGGCATT GACAAGAATA TACCCGATCT ATATCGACAT GCAGGAGATA CACTAGAGAA
3361  CGATGTACAA GTTAAATCAG AGATATTAAG TTCATACAAT GAGTCAAATG CAACAAGACT
3421  AATACCCAAA AAAGTGAGCA GTACAATGAG ATCACTAGTT GCAGTCATCA ACAACAGCAA
3481  TCTCTCACAA AGCACAAAAC AATCATACAT AAACGAACTC AAACGTTGCA AAAATGATGA
3541  AGAAGTATCT GAATTAATGG ACATGTTCAA TGAAGATGTC AACAATTGCC AATGATCCAA
3601  CAAAGAAACG ACACCGAACA AACAGACAAG AAACAACAGT AGATCAAAAC CTGTCAACAC
3661  ACACAAAATC AAGCAGAATG AAACAACAGA TATCAATCAA TATACAAATA AGAAAAACTT
3721  AGGATTAAAG AATAAATTAA TCCTTGTCCA AAATGAGTAT AACTAACTCT GCAATATACA
3781  CATTCCCAGA ATCATCATTC TCTGAAAATG GTCATATAGA ACCATTACCA CTCAAAGTCA
3841  ATGAACAGAG GAAAGCAGTA CCCCACATTA GAGTTGCCAA GATCGGAAAT CCACCAAAAC
3901  ACGGATCCCG GTATTTAGAT GTCTTCTTAC TCGGCTTCTT CGAGATGGAA CGAATCAAAG
3961  ACAAATACGG GAGTGTGAAT GATCTCGACA GTGACCCGAG TTACAAAGTT TGTGGCTCTG
```

TABLE 39-continued (SEQ ID NO. 154)
Sequence of pFLC.P1V32, 15492 bp in sense orientation
(only the insert is shown)

```
4021  GATCATTACC AATCGGATTG GCTAAGTACA CTGGGAATGA CCAGGAATTG TTACAAGCCG

4081  CAACCAAACT GGATATAGAA GTGAGAAGAA CAGTCAAAGC GAAAGAGATG GTTGTTTACA

4141  CGGTACAAAA TATAAAACCA GAACTGTACC CATGGTCCAA TAGACTAAGA AAAGGAATGC

4201  TGTTCGATGC CAACAAAGTT GCTCTTGCTC CTCAATGTCT TCCACTAGAT AGGAGCATAA

4261  AATTTAGAGT AATCTTCGTG AATTGTACGG CAATTGGATC AATAACCTTG TTCAAAATTC

4321  CTAAGTCAAT GGCATCACTA TCTCTACCCA ACACAATATC AATCAATCTG CAGGTACACA

4381  TAAAAACAGG GGTTCAGACT GATTCTAAAG GGATAGTTCA AATTTTGGAT GAGAAAGGCG

4441  AAAAATCACT GAATTTCATG GTCCATCTCG GATTGATCAA AGAAAAGTA GGCAGAATGT

4501  ACTCTGTTGA ATACTGTAAA CAGAAAATCG AGAAATGAG ATTGATATTT TCTTTAGCAC

4561  TAGTTGGAGG AATCAGTCTT CATGTCAATG CAACTGGGTC ATATCAAAA ACACTAGCAA

4621  GTCAGCTGGT ATTCAAAAGA GAGATTTGTT ATCCTTTAAT GGATCTAAAT CCGCATCTCA

4681  ATCTAGTTAT CTGGGCTTCA TCAGTAGAGA TTACAAGAGT GGATGCAATT TTCCAACCTT

4741  CTTTACCTGG CGAGTTCAGA TACTATCCTA ATATTATTGC AAAAGGAGTT GGGAAAATCA

4801  AACAATGGAA CTAGTAATCT CTATTTTAGT CCGGACGTAT CTATTAAGCC GAAGCAAATA

4861  AAGGATAATC AAAAACTTAG GACAAAGAG GTCAATACCA ACAACTATTA GCAGTCACAC

4921  TCGCAAGAAT AAGAGAGAAG GGACCAAAAA AGTCAAATAG GAGAAATCAA AACAAAAGGT

4981  ACAGAACACC AGAACAACAA AATCAAAACA TCCAACTCAC TCAAACAAA AATTCCAAAA

5041  GAGACCGGCA ACACAACAAG CACTGAACAC CATGGATCAC CTGCATCCAA TGATAGTATG

5101  CATTTTTGTT ATGTACACTG GAATTGTAGG TTCAGATGCC ATTGCTGGAC ATCAACTCCT

5161  CAATGTAGGG GTCATTCAAT CAAAGATAAG ATCACTCATG TACTACACTG ATGGTGGCGC

5221  TAGCTTTATT GTTGTAAAAT TACTACCCAA TCTTCCCCCA AGCAATGGAA CATGCAACAT

5281  CACCAGTCTA GATGCATATA ATGTTACCCT ATTTAAGTTG CTAACACCCC TGATTGAGAA

5341  CCTGAGCAAA ATTTCTGCTG TTACAGATAC CAAACCCCGC CGAGAACGAT TTGCAGGAGT

5401  CGTTATTGGG CTTGCTGCAC TAGGAGTAGC TACAGCTGCA CAAATAACCG CAGCTGTAGC

5461  AATAGTAAAA GCCAATGCAA ATGCTGCTGC GATAAACAAT CTTGCATCTT CAATTCAATC

5521  CACCAACAAG GCAGTATCCG ATGTGATAAC TGCATCAAGA ACAATTGCAA CCGCAGTTCA

5581  AGCGATTCAG GATCACATCA ATGGAGCCAT TGTCAACGGG ATAACATCTG CATCATGCCG

5641  TGCCCATGAT GCACTAATTG GGTCAATATT AAATTTGTAT CTCACTGAGC TTACTACAAT

5701  ATTTCATAAT CAAATAACAA ACCCTGCGCT GACACCACTT TCCATCCAAC CTTTAAGAAT

5761  CCTCCTCGGT AGCACCTTGC CAATTGTCAT TGAATCCAAA CTCAACACAA AACTCAACAC

5821  AGCAGAGCTG CTCAGTAGCG GACTGTTAAC TGGTCAAATA ATTTCCATTT CCCCAATGTA

5881  CATGCAAATG CTAATTCAAA TCAATGTTCC GACATTTATA ATGCAACCCC GTGCGAAGGT

5941  AATTGATCTA ATTGCTATCT CTGCAAACCA TAAATTACAA GAAGTAGTTG TACAAGTTCC

6001  TAATAGAATT CTAGAATATG CAAATGAACT ACAAAACTAC CCAGCCAATG ATTGTTTCGT

6061  GACACCAAAC TCTGTATTTT GTAGATACAA TGAGGGTTCC CCGATCCCTG AATCACAATA

6121  TCAATGCTTA AGGGGGAATC TTAATTCTTG CACTTTTACC CCTATTATCC GGAACTTTCT

6181  CAAGCGATTC GCATTTGCCA ATGGTGTGCT CTATGCCAAC TGCAATCTT TGCTATGTAA

6241  GTGTGCCGAC CCTCCCCATG TTGTGTCTCA AGATGACAAC CAAGGCATCA GCATAATTGA
```

TABLE 39-continued (SEQ ID NO. 154)
Sequence of pFLC.P1V32, 15492 bp in sense orientation
(only the insert is shown)

```
6301  TATTAAGAGG TGCTCTGAGA TGATGCTTGA CACTTTTTCA TTTAGGATCA CATCTACATT

6361  CAATGCTACA TACGTGACAG ACTTCTCAAT GATTAATGCA AATATTGTAC ATCTAAGTCC

6421  TCTAGACTTG TCAAATCAAA TCAATTCAAT AAACAAATCT CTTAAAAGTG CTGAGGATTG

6481  GATTGCAGAT AGCAACTTCT TCGCTAATCA AGCCAGAACA GCCAAGCACA TTTATTCACT

6541  AAGTGCAATC GCATTAATAC TATCAGTGAT TACTTTGGTT GTTGTGGGAT TGCTGATTGC

6601  CTACATCATC AAGCTGGTTT CTCAAATCCA TCAATTCAGA GCACTAGCTG CTACAACAAT

6661  GTTCCACAGG GAGAATCCTG CCGTCTTTTC CAAGAACAAT CATGGAAACA TATATGGGAT

6721  ATCTTAGGAT CCCTACAGAT CATTAGATAT TAAAATTATA AAAACTTAG GAGTAAAGTT

6781  ACGCAATCCA ACTCTACTCA TATAATTGAG GAAGGACCCA ATAGACAAAT CCAAATCCAT

6841  GGAAGATTAC AGCAATCTAT CTCTTAAATC AATTCCTAAA AGGACATGTA GAATCATTTT

6901  CCGAACTGCC ACAATTCTTG GCATATGCAC ATTAATTGTG CTATGTTCAA GTATTCTTCA

6961  TGAGATAATT CATCTTGATG TTTCCTCTGG TCTTATGAAT CTGATGAGT CACAGCAAGG

7021  CATTATTCAG CCTATCATAG AATCATTAAA ATCATTGATT GCTTTGGCCA ACCAGATTCT

7081  ATATAATGTT GCAATAGTAA TTCCTCTTAA AATTGACAGT ATCGAAACTG TAATACTCTC

7141  TGCTTTAAAA GATATGCACA CCGGGAGTAT GTCCAATGCC AACTGCACGC AGGAAATCT

7201  GCTTCTGCAT GATGCAGCAT ACATCAATGG AATAAACAAA TTCCTTGTAC TTGAATCATA

7261  CAATGGGACG CCTAAATATG GACCTCTCCT AAATATACCC AGCTTTATCC CCTCAGCAAC

7321  ATCTCCCCAT GGGTGTACTA GAATACCATC ATTTTCACTC ATCAAGACCC ATTGGTGTTA

7381  CACTCACAAT GTAATGCTTG GAGATTGTCT TGATTTCACG GCATCTAACC AGTATTTATC

7441  AATGGGGATA ATACAACAAT CTGCTGCAGG GTTTCCAATT TTCAGGACTA TGAAAACCAT

7501  TTACCTAAGT GATGGAATCA ATCGCAAAAG CTGTTCAGTC ACTGCTATAC CAGGAGGTTG

7561  TGTCTTGTAT TGCTATGTAG CTACAAGGTC TGAAAAAGAA GATTATGCCA CGACTGATCT

7621  AGCTGAACTG AGACTTGCTT TCTATTATTA TAATGATACC TTTATTGAAA GAGTCATATC

7681  TCTTCCAAAT ACAACAGGGC AGTGGGCCAC AATCAACCCT GCAGTCGGAA GCGGGATCTA

7741  TCATCTAGGC TTTATCTTAT TTCCTGTATA TGGTGGTCTC ATAAATGGGA CTACTTCTTA

7801  CAATGAGCAG TCCTCACGCT ATTTTATCCC AAAACATCCC AACATAACTT GTGCCGGTAA

7861  CTCCAGCAAA CAGGCTGCAA TAGCACGGAG TTCCTATGTC ATCCGTTATC ACTCAAACAG

7921  GTTAATTCAG AGTGCTGTTC TTATTTGTCC ATTGTCTGAC ATGCATACAG AAGAGTGTAA

7981  TCTAGTTATG TTTAACAATT CCCAAGTCAT GATGGGTGCA GAAGGTAGGC TCTATGTTAT

8041  TGGTAATAAT TTGTATTATT ATCAACGCAG TTCCTCTTGG TGGTCTGCAT CGCTCTTTTA

8101  CAGGATCAAT ACAGATTTTT CTAAAGGAAT TCCTCCGATC ATTGAGGCTC AATGGGTACC

8161  GTCCTATCAA GTTCCTCGTC CTGGAGTCAT GCCATGCAAT GCAACAAGTT TTTGCCCTGC

8221  TAATTGCATC ACAGGGGTGT ACGCAGATGT GTGGCCGCTT AATGATCCAG AACTCATGTC

8281  ACGTAATGCT CTGAACCCCA ACTATCGATT TGCTGGAGCC TTTCTCAAAA ATGAGTCCAA

8341  CCGAACTAAT CCCACATTCT ACACTGCATC GGCTAACTCC CTCTTAAATA CTACCGGATT

8401  CAACAACACC AATCACAAAG CAGCATATAC ATCTTCAACC TGCTTTAAAA ACACTGGAAC

8461  CCAAAAAATT TATTGTTTAA TAATAATTGA AATGGGCTCA TCTCTTTTAG GGGAGTTCCA

8521  AATAATACCA TTTTTAAGGG AACTAATGCT TTAAGCTTAA TTAACCATAA TATGCATCAA
```

TABLE 39-continued (SEQ ID NO. 154)
Sequence of pFLC.P1V32, 15492 bp in sense orientation
(only the insert is shown)

```
 8581 TCTATCTATA ATACAAGTAT ATGATAAGTA ATCTGCAATC AGACAATAGA CAAAAGGGAA
 8641 ATATAAAAAA CTTAGGAGCA AAGCGTGCTC GGGAAATGGA CACTGAATCT AACAATGGCA
 8701 CTGTATCTGA CATACTCTAT CCTGAGTGTC ACCTTAACTC TCCTATCGTT AAAGGTAAAA
 8761 TAGCACAATT ACACACTATT ATGAGTCTAC CTCAGCCTTA TGATATGGAT GACGACTCAA
 8821 TACTAGTTAT CACTAGACAG AAAATAAAAC TTAATAAATT GGATAAAAGA CAACGATCTA
 8881 TTAGAAGATT AAAATTAATA TTAACTGAAA AAGTGAATGA CTTAGGAAAA TACACATTTA
 8941 TCAGATATCC AGAAATGTCA AAAGAAATGT TCAAATTATA TATACCTGGT ATTAACAGTA
 9001 AAGTGACTGA ATTATTACTT AAAGCAGATA GAACATATAG TCAAATGACT GATGGATTAA
 9061 GAGATCTATG GATTAATGTG CTATCAAAAT TAGCCTCAAA AAATGATGGA AGCAATTATG
 9121 ATCTTAATGA AGAAATTAAT AATATATCGA AAGTTCACAC AACCTATAAA TCAGATAAAT
 9181 GGTATAATCC ATTCAAAACA TGGTTTACTA TCAAGTATGA TATGAGAAGA TTACAAAAAG
 9241 CTCGAAATGA GATCACTTTT AATGTTGGGA AGGATTATAA CTTGTTAGAA GACCAGAAGA
 9301 ATTTCTTATT GATACATCCA GAATTGGTTT TGATATTAGA TAAACAAAAC TATAATGGTT
 9361 ATCTAATTAC TCCTGAATTA GTATTGATGT ATTGTGACGT AGTCGAAGGC CGATGGAATA
 9421 TAAGTGCATG TGCTAAGTTA GATCCAAAAT TACAATCTAT GTATCAGAAA GGTAATAACC
 9481 TGTGGGAAGT GATAGATAAA TTGTTTCCAA TTATGGGAGA AAAGACATTT GATGTGATAT
 9541 CGTTATTAGA ACCACTTGCA TTATCCTTAA TTCAAACTCA TGATCCTGTT AAACAACTAA
 9601 GAGGAGCTTT TTTAAATCAT GTGTTATCCG AGATGGAATT AATATTTGAA TCTAGAGAAT
 9661 CGATTAAGGA ATTTCTGAGT GTAGATTACA TTGATAAAAT TTTAGATATA TTTAATAAGT
 9721 CTACAATAGA TGAAATAGCA GAGATTTTCT CTTTTTTTAG AACATTTGGG CATCCTCCAT
 9781 TAGAAGCTAG TATTGCAGCA GAAAAGGTTA GAAAATATAT GTATATTGGA AAACAATTAA
 9841 AATTTGACAC TATTAATAAA TGTCATGCTA TCTTCTGTAC AATAATAATT AACGGATATA
 9901 GAGAGAGGCA TGGTGGACAG TGGCCTCCTG TGACATTACC TGATCATGCA CACGAATTCA
 9961 TCATAAATGC TTACGGTTCA AACTCTGCGA TATCATATGA AAATGCTGTT GATTATTACC
10021 AGAGCTTTAT AGGAATAAAA TTCAATAAAT TCATAGAGCC TCAGTTAGAT GAGGATTTGA
10081 CAATTTATAT GAAAGATAAA GCATTATCTC CAAAAAAATC AAATTGGGAC ACAGTTTATC
10141 CTGCATCTAA TTTACTGTAC CGTACTAACG CATCCAACGA ATCACGAAGA TTAGTTGAAG
10201 TATTTATAGC AGATAGTAAA TTTGATCCTC ATCAGATATT GGATTATGTA GAATCTGGGG
10261 ACTGGTTAGA TGATCCAGAA TTTAATATTT CTTATAGTCT TAAAGAAAAA GAGATCAAAC
10321 AGGAAGGTAG ACTCTTTGCA AAAATGACAT ACAAAATGAG AGCTACACAA GTTTTATCAG
10381 AGACCCTACT TGCAAATAAC ATAGGAAAAT TCTTTCAAGA AAATGGGATG TGAAGGGAG
10441 AGATTGAATT ACTTAAGAGA TTAACAACCA TATCAATATC AGGAGTTCCA CGGTATAATG
10501 AAGTGTACAA TAATTCTAAA AGCCATACAG ATGACCTTAA AACCTACAAT AAAATAAGTA
10561 ATCTTAATTT GTCTTCTAAT CAGAAATCAA AGAAATTTGA ATTCAAGTCA ACGGATATCT
10621 ACAATGATGG ATACGAGACT GTGAGCTGTT TCCTAACAAC AGATCTCAAA AAATACTGTC
10681 TTAATTGGAG ATATGAATCA ACAGCTCTAT TTGGAGAAAC TTGCAACCAA ATATTTGGAT
10741 TAAATAAATT GTTTAATTGG TTACACCCTC GTCTTGAAGG AAGTACAATC TATGTAGGTG
10801 ATCCTTACTG TCCTCCATCA GATAAAGAAC ATATATCATT AGAGGATCAC CCTGATTCTG
```

TABLE 39-continued (SEQ ID NO. 154)
Sequence of pFLC.P1V32, 15492 bp in sense orientation
(only the insert is shown)

```
10861 GTTTTTACGT TCATAACCCA AGAGGGGGTA TAGAAGGATT TTGTCAAAAA TTATGGACAC

10921 TCATATCTAT AAGTGCAATA CATCTAGCAG CTGTTAGAAT AGGCGTGAGG GTGACTGCAA

10981 TGGTTCAAGG AGACAATCAA GCTATAGCTG TAACCACAAG AGTACCCAAC AATTATGACT

11041 ACAGAGTTAA GAAGGAGATA GTTTATAAAG ATGTAGTGAG ATTTTTTGAT TCATTAAGAG

11101 AAGTGATGGA TGATCTAGGT CATGAACTTA AATTAAATGA AACGATTATA AGTAGCAAGA

11161 TGTTCATATA TAGCAAAAGA ATCTATTATG ATGGGAGAAT TCTTCCTCAA GCTCTAAAAG

11221 CATTATCTAG ATGTGTCTTC TGGTCAGAGA CAGTAATAGA CGAAACAAGA TCAGCATCTT

11281 CAAATTTGGC AACATCATTT GCAAAAGCAA TTGAGAATGG TTATTCACCT GTTCTAGGAT

11341 ATGCATGCTC AATTTTTAAG AATATTCAAC AACTATATAT TGCCCTTGGG ATGAATATCA

11401 ATCCAACTAT AACACAGAAT ATCAGAGATC AGTATTTTAG GAATCCAAAT TGGATGCAAT

11461 ATGCCTCTTT AATACCTGCT AGTGTTGGGG GATTCAATTA CATGGCCATG TCAAGATGTT

11521 TTGTAAGGAA TATTGGTGAT CCATCAGTTG CCGCATTGGC TGATATTAAA AGATTTATTA

11581 AGGCGAATCT ATTAGACCGA AGTGTTCTTT ATAGGATTAT GAATCAAGAA CCAGGTGAGT

11641 CATCTTTTTT GGACTGGGCT TCAGATCCAT ATTCATGCAA TTTACCACAA TCTCAAAATA

11701 TAACCACCAT GATAAAAAAT ATAACAGCAA GGAATGTATT ACAAGATTCA CCAAATCCAT

11761 TATTATCTGG ATTATTCACA AATACAATGA TAGAAGAAGA TGAAGAATTA GCTGAGTTCC

11821 TGATGGACAG GAAGGTAATT CTCCCTAGAG TTGCACATGA TATTCTAGAT AATTCTCTCA

11881 CAGGAATTAG AAATGCCATA GCTGGAATGT TAGATACGAC AAAATCACTA ATTCGGGTTG

11941 GCATAAATAG AGGAGGACTG ACATATAGTT TGTTGAGGAA AATCAGTAAT TACGATCTAG

12001 TACAAATATGA AACACTAAGT AGGACTTTGC GACTAATTGT AAGTGATAAA ATCAAGTATG

12061 AAGATATGTG TTCGGTAGAC CTTGCCATAG CATTGCGACA AAAGATGTGG ATTCATTTAT

12121 CAGGAGGAAG GATGATAAGT GGACTTGAAA CGCCTGACCC ATTAGAATTA CTATCTGGGG

12181 TAGTAATAAC AGGATCAGAA CATTGTAAAA TATGTTATTC TTCAGATGGC ACAAACCCAT

12241 ATACTTGGAT GTATTTACCC GGTAATATCA AAATAGGATC AGCAGAAACA GGTATATCGT

12301 CATTAAGAGT TCCTTATTTT GGATCAGTCA CTGATGAAAG ATCTGAAGCA CAATTAGGAT

12361 ATATCAAGAA TCTTAGTAAA CCTGCAAAAG CCGCAATAAG AATAGCAATG ATATATACAT

12421 GGGCATTTGG TAATGATGAG ATATCTTGGA TGGAAGCCTC ACAGATAGCA CAAACACGTG

12481 CAAATTTTAC ACTAGATAGT CTCAAAATTT TAACACCGGT AGCTACATCA ACAAATTTAT

12541 CACACAGATT AAAGGATACT GCAACTCAGA TGAAATTCTC CAGTACATCA TTGATCAGAG

12601 TCAGCAGATT CATAACAATG TCCAATGATA ACATGTCTAT CAAAGAAGCT AATGAAACCA

12661 AAGATACTAA TCTTATTTAT CAACAAATAA TGTTAACAGG ATTAAGTGTT TTCGAATATT

12721 TATTTAGATT AAAAGAAACC ACAGGACACA ACCCTATAGT TATGCATCTG CACATAGAAG

12781 ATGAGTGTTG TATTAAAGAA AGTTTTAATG ATGAACATAT TAATCCAGAG TCTACATTAG

12841 AATTAATTCG ATATCCTGAA AGTAATGAAT TTATTTATGA TAAAGACCCA CTCAAAGATG

12901 TGGACTTATC AAAACTTATG GTTATTAAAG ACCATTCTTA CACAATTGAT ATGAATTATT

12961 GGGATGATAC TGACATCATA CATGCAATTT CAATATGTAC TGCAATTACA ATAGCAGATA

13021 CTATGTCACA ATTAGATCGA GATAATTTAA AAGAGATAAT AGTTATTGCA AATGATGATG

13081 ATATTAATAG CTTAATCACT GAATTTTTGA CTCTTGACAT ACTTGTATTT CTCAAGACAT
```

TABLE 39-continued (SEQ ID NO. 154)
Sequence of pFLC.P1V32, 15492 bp in sense orientation
(only the insert is shown)

```
13141 TTGGTGGATT ATTAGTAAAT CAATTTGCAT ACACTCTTTA TAGTCTAAAA ATAGAAGGTA

13201 GGGATCTCAT TTGGGATTAT ATAATGAGAA CACTGAGAGA TACTTCCCAT TCAATATTAA

13261 AAGTATTATC TAATGCATTA TCTCATCCTA AAGTATTCAA GAGGTTCTGG GATTGTGGAG

13321 TTTTAAACCC TATTTATGGT CCTAATACTG CTAGTCAAGA CCAGATAAAA CTTGCCCTAT

13381 CTATATGTGA ATATTCACTA GATCTATTTA TGAGAGAATG GTTGAATGGT GTATCACTTG

13441 AAATATACAT TTGTGACAGC GATATGGAAG TTGCAAATGA TAGGAAACAA GCCTTTATTT

13501 CTAGACACCT TTCATTTGTT TGTTGTTTAG CAGAAATTGC ATCTTTCGGA CCTAACCTGT

13561 TAAACTTAAC ATACTTGGAG AGACTTGATC TATTGAAACA ATATCTTGAA TTAAATATTA

13621 AAGAAGACCC TACTCTTAAA TATGTACAAA TATCTGGATT ATTAATTAAA TCGTTCCCAT

13681 CAACTGTAAC ATACGTAAGA AAGACTGCAA TCAAATATCT AAGGATTCGC GGTATTAGTC

13741 CACCTGAGGT AATTGATGAT TGGGATCCGG TAGAAGATGA AAATATGCTG GATAACATTG

13801 TCAAAACTAT AAATGATAAC TGTAATAAAG ATAATAAAGG GAATAAAATT AACAATTTCT

13861 GGGGACTAGC ACTTAAGAAC TATCAAGTCC TTAAAATCAG ATCTATAACA AGTGATTCTG

13921 ATGATAATGA TAGACTAGAT GCTAATACAA GTGGTTTGAC ACTTCCTCAA GGAGGGAATT

13981 ATCTATCGCA TCAATTGAGA TTATTCGGAA TCAACAGCAC TAGTTGTCTG AAAGCTCTTG

14041 AGTTATCACA AATTTTAATG AAGGAAGTCA ATAAAGACAA GGACAGGCTC TTCCTGGGAG

14101 AAGGAGCAGG AGCTATGCTA GCATGTTATG ATGCCACATT AGGACCTGCA GTTAATTATT

14161 ATAATTCAGG TTTGAATATA ACAGATGTAA TTGGTCAACG AGAATTGAAA ATATTTCCTT

14221 CAGAGGTATC ATTAGTAGGT AAAAAATTAG GAAATGTGAC ACAGATTCTT AACAGGGTAA

14281 AAGTACTGTT CAATGGGAAT CCTAATTCAA CATGGATAGG AAATATGGAA TGTGAGAGCT

14341 TAATATGGAG TGAATTAAAT GATAAGTCCA TTGGATTAGT ACATTGTGAT ATGGAAGGAG

14401 CTATCGGTAA ATCAGAAGAA ACTGTTCTAC ATGAACATTA TAGTGTTATA AGAATTACAT

14461 ACTTGATTGG GGATGATGAT GTTGTTTTAG TTTCCAAAAT TATACCTACA ATCACTCCGA

14521 ATTGGTCTAG AATACTTTAT CTATATAAAT TATATTGGAA AGATGTAAGT ATAATATCAC

14581 TCAAAACTTC TAATCCTGCA TCAACAGAAT TATATCTAAT TTCGAAAGAT GCATATTGTA

14641 CTATAATGGA ACCTAGTGAA ATTGTTTTAT CAAAACTTAA AAGATTGTCA CTCTTGGAAG

14701 AAAATAATCT ATTAAAATGG ATCATTTTAT CAAAGAAGAG GAATAATGAA TGGTTACATC

14761 ATGAAATCAA AGAAGGAGAA AGAGATTATG GAATCATGAG ACCATATCAT ATGGCACTAC

14821 AAATCTTTGG ATTTCAAATC AATTTAAATC ATCTGGCGAA AGAATTTTTA TCAACCCCAG

14881 ATCTGACTAA TATCAACAAT ATAATCCAAA GTTTTCAGCG AACAATAAAG GATGTTTTAT

14941 TTGAATGGAT TAATATAACT CATGATGATA AGAGACATAA ATTAGGCGGA ACATATAACA

15001 TATTCCCACT GAAAAATAAG GGAAAGTTAA GACTGCTATC GAGAAGACTA GTATTAAGTT

15061 GGATTTCATT ATCATTATCG ACTCGATTAC TTACAGGTCG CTTTCCTGAT GAAAAATTTG

15121 AACATAGAGC ACAGACTGGA TATGTATCAT TAGCTGATAC TGATTTAGAA TCATTAAAGT

15181 TATTGTCGAA AACATCATT AAGAATTACA GAGAGTGTAT AGGATCAATA TCATATTGGT

15241 TTCTAACCAA AGAAGTTAAA ATACTTATGA AATTGATCGG TGGTGCTAAA TTATTAGGAA

15301 TTCCCAGACA ATATAAAGAA CCCGAAGACC AGTTATTAGA AAACTACAAT CAACATGATG

15361 AATTTGATAT CGATTAAAAC ATAAATACAA TGAAGATATA TCCTAACCTT TATCTTTAAG
```

TABLE 39-continued (SEQ ID NO. 154)
Sequence of pFLC.P1V32, 15492 bp in sense orientation
(only the insert is shown)

```
15421 CCTAGGAATA GACAAAAAGT AAGAAAAACA TGTAATATAT ATATACCAAA CAGAGTTCTT

15481 CTCTTGTTTG GT
```

In a second strategy (FIG. 37), chimeric PIV3-PIV2 F and HN ORFs rather than the complete ORF exchange were constructed in which regions of the PIV2 F and HN ORFs encoding the ectodomains were amplified from pLit.PIV32Fhc and pLit.PIV32HNhc, respectively, using PCR, Vent DNA polymerase (NEB, Beverly, Mass.), and primer pairs specific to PIV2 F (5, 6 in Table 38) and HN (7, 8 in Table 38). In parallel, the regions of PIV3 F and HN ORFs encoding the ectodomains were deleted from their cDNA subclones pLit.PIV3.F3a and pLit.PIV3.HN4 (Tao et al., J. Virol. 72:2955-2961, 1998, incorporated herein by reference), respectively, using PCR, Vent DNA polymerase, and primer pairs specific to PIV3 F (9, 10 in Table 38) and HN (11, 12 in Table 38). The amplified F and HN cDNA fragments of PIV2 and PIV3 were purified from agarose gels and ligated to generate pLit.PIV32FTM and pLit.PIV32HNTM, respectively. The chimeric F and HN constructs were digested with PpuMI plus SpeI and assembled together to generate pLit.PIV32TM, which was subsequently sequenced with the dRhodamine dye terminator sequencing kit across its PIV specific region in its entirety and found to be as designed. The 4 kb BspEI-SpeI fragment from pLit.PIV32TM was then introduced into the BspEI-SpeI window of p38'ΔPIV31hc to generate p38'ΔPIV32TM. The 6.5 kb BspEI-SphI fragment from p38'ΔPIV32TM, containing the PIV3-PIV2 chimeric F and HN genes, was introduced into the BspEI-SphI window of pFLC.2G+.hc and pFLCcp45 (Skiadopoulos et al., J. Virol. 73:1374-81, 1999, incorporated herein by reference) to generate pFLC.PIV32TM (Table 40; SEQ ID NO. 174) and pFLC.PIV32TMcp45, respectively. The nucleotide sequence of the BspEI-SpeI fragment, containing the chimeric PIV3-PIV2 F and HN genes, is submitted in the GenBank.

TABLE 40

(SEQ ID NO. 174)
Sequence of pFLC.PIV32TM, 15498 bp in sense orientation
(only the antigenome is shown)

```
   1 ACCAAACAAG AGAAGAAACT TGTCTGGGAA TATAAATTTA ACTTTAAATT AACTTAGGAT

61 TAAAGACATT GACTAGAAGG TCAAGAAAAG GGAACTCTAT AATTTCAAAA ATGTTGAGCC

121 TATTTGATAC ATTTAATGCA CGTAGGCAAG AAAACATAAC AAAATCAGCC GGTGGAGCTA

181 TCATTCCTGG ACAGAAAAAT ACTGTCTCTA TATTCGCCCT TGGACCGACA ATAACTGATG

241 ATAATGAGAA AATGACATTA GCTCTTCTAT TTCTATCTCA TTCACTAGAT AATGAGAAAC

301 AACATGCACA AAGGGCAGGG TTCTTGGTGT CTTTATTGTC AATGGCTTAT GCCAATCCAG

361 AGCTCTACCT AACAACAAAT GGAAGTAATG CAGATGTCAA GTATGTCATA TACATGATTG

421 AGAAAGATCT AAAACGGCAA AAGTATGGAG GATTTGTGGT TAAGACGAGA GAGATGATAT

481 ATGAAAAGAC AACTGATTGG ATATTTGGAA GTGACCTGGA TTATGATCAG GAAACTATGT

541 TGCAGAACGG CAGGAACAAT TCAACAATTG AAGACCTTGT CCACACATTT GGGTATCCAT

601 CATGTTTAGG AGCTCTTATA ATACAGATCT GGATAGTTCT GGTCAAAGCT ATCACTAGTA

661 TCTCAGGGTT AAGAAAAGGC TTTTTCACCC GATTGGAAGC TTTCAGACAA GATGGAACAG

721 TGCAGGCAGG GCTGGTATTG AGCGGTGACA CAGTGGATCA GATTGGGTCA ATCATGCGGT

781 CTCAACAGAC CTTGGTAACT CTTATGGTTG AAACATTAAT AACAATGAAT ACCAGCAGAA

841 ATGACCTCAC AACCATAGAA AAGAATATAC AAATTGTTGG CAACTACATA AGAGATGCAG

901 GTCTCGCTTC ATTCTTCAAT ACAATCGAT ATGGAATTGA GACCAGAATG GCAGCTTTGA

961 CTCTATCCAC TCTCAGACCA GATATCAATA GATTAAAAGC TTTGATGGAA CTGTATTTAT

1021 CAAAGGGACC ACGCGCTCCT TTCATCTGTA TCCTCAGAGA TCCTATACAT GGTGAGTTCG

1081 CACCAGGCAA CTATCCTGCC ATATGGAGCT ATGCAATGGG GGTGGCAGTT GTACAAAATA

1141 GAGCCATGCA ACAGTATGTG ACGGGAAGAT CATATCTAGA CATTGATATG TTCCAGCTAG

1201 GACAAGCAGT AGCACGTGAT GCCGAAGCTC AAATGAGCTC AACACTGGAA GATGAACTTG

1261 GAGTGACACA CGAATCTAAA GAAAGCTTGA AGAGACATAT AAGGAACATA AACAGTTCAG
```

TABLE 40-continued (SEQ ID NO. 174)
Sequence of pFLC.PIV32TM, 15498 bp in sense orientation
(only the antigenome is shown)

```
1321 AGACATCTTT CCACAAACCG ACAGGTGGAT CAGCCATAGA GATGGCAATA GATGAAGAGC

1381 CAGAACAATT CGAACATAGA GCAGATCAAG AACAAAATGG AGAACCTCAA TCATCCATAA

1441 TTCAATATGC CTGGGCAGAA GGAAATAGAA GCGATGATCA GACTGAGCAA GCTACAGAAT

1501 CTGACAATAT CAAGACCGAA CAACAAAACA TCAGAGACAG ACTAAACAAC AGACTCAACG

1561 ACAAGAAGAA ACAAAGCAGT CAACCACCCA CTAATCCCAC AAACAGAACA AACCAGGACG

1621 AAATAGATGA TCTGTTTAAC GCATTTGGAA GCAACTAATC GAATCAACAT TTTAATCTAA

1681 ATCAATAATA AATAAGAAAA ACTTAGGATT AAAGAATCCT ATCATACCGG AATATAGGGT

1741 GGTAAATTTA GAGTCTGCTT GAAACTCAAT CAATAGAGAG TTGATGGAAA GCGATGCTAA

1801 AAACTATCAA ATCATGGATT CTTGGGAAGA GGAATCAAGA GATAAATCAA CTAATATCTC

1861 CTCGGCCCTC AACATCATTG AATTCATACT CAGCACCGAC CCCCAAGAAG ACTTATCGGA

1921 AAACGACACA ATCAACACAA GAACCCAGCA ACTCAGTGCC ACCATCTGTC AACCAGAAAT

1981 CAAACCAACA GAAACAAGTG AGAAAGATAG TGGATCAACT GACAAAAATA GACAGTCCGG

2041 GTCATCACAC GAATGTACAA CAGAAGCAAA AGATAGAAAT ATTGATCAGG AAACTGTACA

2101 GAGAGGACCT GGGAGAAGAA GCAGCTCAGA TAGTAGAGCT GAGACTGTGG TCTCTGGAGG

2161 AATCCCCAGA AGCATCACAG ATTCTAAAAA TGGAACCCAA AACACGGAGG ATATTGATCT

2221 CAATGAAATT AGAAAGATGG ATAAGGACTC TATTGAGGGG AAAATGCGAC AATCTGCAAA

2281 TGTTCCAAGC GAGATATCAG GAAGTGATGA CATATTTACA ACAGAACAAA GTAGAAACAG

2341 TGATCATGGA AGAAGCCTGG AATCTATCAG TACACCTGAT ACAAGATCAA TAAGTGTTGT

2401 TACTGCTGCA ACACCAGATG ATGAAGAAGA AATACTAATG AAAAATAGTA GGACAAAGAA

2461 AAGTTCTTCA ACACATCAAG AAGATGACAA AGAATTAAA AAAGGGGGAA AAGGGAAAGA

2521 CTGGTTTAAG AAATCAAAAG ATACCGACAA CCAGATACCA ACATCAGACT ACAGATCCAC

2581 ATCAAAAGGG CAGAAGAAAA TCTCAAAGAC AACAACCACC AACACCGACA CAAAGGGGCA

2641 AACAGAAATA CAGACAGAAT CATCAGAAAC ACAATCCTCA TCATGGAATC TCATCATCGA

2701 CAACAACACC GACCGGAACG AACAGACAAG CACAACTCCT CCAACAACAA CTTCCAGATC

2761 AACTTATACA AAAGAATCGA TCCGAACAAA CTCTGAATCC AAACCCAAGA CACAAAAGAC

2821 AAATGGAAAG GAAAGGAAGG ATACAGAAGA GAGCAATCGA TTTACAGAGA GGGCAATTAC

2881 TCTATTGCAG AATCTTGGTG TAATTCAATC CACATCAAAA CTAGATTTAT ATCAAGACAA

2941 ACGAGTTGTA TGTGTAGCAA ATGTACTAAA CAATGTAGAT ACTGCATCAA AGATAGATTT

3001 CCTGGCAGGA TTAGTCATAG GGGTTTCAAT GGACAACGAC ACAAAATTAA CACACATACA

3061 AAATGAAATG CTAAACCTCA AGCAGATCT AAAGAAAATG GACGAATCAC ATAGAAGATT

3121 GATAGAAAAT CAAAGAGAAC AACTGTCATT GATCACGTCA CTAATTTCAA ATCTCAAAAT

3181 TATGACTGAG AGAGGAGGAA AGAAAGACCA AAATGAATCC AATGAGAGAG TATCCATGAT

3241 CAAAACAAAA TTGAAAGAAG AAAAGATCAA GAAGACCAGG TTTGACCCAC TTATGGAGGC

3301 ACAAGGCATT GACAAGAATA TACCCGATCT ATATCGACAT GCAGGAGATA CACTAGAGAA

3361 CGATGTACAA GTTAAATCAG AGATATTAAG TTCATACAAT GAGTCAAATG CAACAAGACT

3421 AATACCCAAA AAGTGAGCA GTACAATGAG ATCACTAGTT GCAGTCATCA ACAACAGCAA

3481 TCTCTCACAA AGCACAAAAC AATCATACAT AAACGAACTC AAACGTTGCA AAAATGATGA

3541 AGAAGTATCT GAATTAATGG ACATGTTCAA TGAAGATGTC AACAATTGCC AATGATCCAA
```

TABLE 40-continued (SEQ ID NO. 174)
Sequence of pFLC.PIV32TM, 15498 bp in sense orientation
(only the antigenome is shown)

```
3601 CAAAGAAACG ACACCGAACA ACAGACAAG AAACAACAGT AGATCAAAAC CTGTCAACAC

3661 ACACAAAATC AAGCAGAATG AAACAACAGA TATCAATCAA TATACAAATA AGAAAAACTT

3721 AGGATTAAAG AATAAATTAA TCCTTGTCCA AAATGAGTAT AACTAACTCT GCAATATACA

3781 CATTCCCAGA ATCATCATTC TCTGAAAATG GTCATATAGA ACCATTACCA CTCAAAGTCA

3841 ATGAACAGAG GAAAGCAGTA CCCCACATTA GAGTTGCCAA GATCGGAAAT CCACCAAAAC

3901 ACGGATCCCG GTATTTAGAT GTCTTCTTAC TCGGCTTCTT CGAGATGGAA CGAATCAAAG

3961 ACAAATACGG GAGTGTGAAT GATCTCGACA GTGACCCGAG TTACAAAGTT TGTGGCTCTG

4021 GATCATTACC AATCGGATTG GCTAAGTACA CTGGGAATGA CCAGGAATTG TTACAAGCCG

4081 CAACCAAACT GGATATAGAA GTGAGAAGAA CAGTCAAAGC GAAAGAGATG GTTGTTTACA

4141 CGGTACAAAA TATAAAACCA GAACTGTACC CATGGTCCAA TAGACTAAGA AAAGGAATGC

4201 TGTTCGATGC CAACAAAGTT GCTCTTGCTC CTCAATGTCT TCCACTAGAT AGGAGCATAA

4261 AATTTAGAGT AATCTTCGTG AATTGTACGG CAATTGGATC AATAACCTTG TTCAAAATTC

4321 CTAAGTCAAT GGCATCACTA TCTCTACCCA ACACAATATC AATCAATCTG CAGGTACACA

4381 TAAAAACAGG GGTTCAGACT GATTCTAAAG GGATAGTTCA AATTTTGGAT GAGAAAGGCG

4441 AAAAATCACT GAATTTCATG GTCCATCTCG GATTGATCAA AGAAAAGTA GGCAGAATGT

4501 ACTCTGTTGA ATACTGTAAA CAGAAAATCG AGAAAATGAG ATTGATATTT TCTTTAGGAC

4561 TAGTTGGAGG AATCAGTCTT CATGTCAATG CAACTGGGTC CATATCAAAA ACACTAGCAA

4621 GTCAGCTGGT ATTCAAAAGA GAGATTTGTT ATCCTTTAAT GGATCTAAAT CCGCATCTCA

4681 ATCTAGTTAT CTGGGCTTCA TCAGTAGAGA TTACAAGAGT GGATGCAATT TTCCAACCTT

4741 CTTTACCTGG CGAGTTCAGA TACTATCCTA ATATTATTGC AAAAGGAGTT GGGAAAATCA

4801 AACAATGGAA CTAGTAATCT CTATTTTAGT CCGGACGTAT CTATTAAGCC GAAGCAAATA

4861 AAGGATAATC AAAAACTTAG GACAAAAGAG GTCAATACCA ACAACTATTA GCAGTCACAC

4921 TCGCAAGAAT AAGAGAGAAG GGACCAAAAA AGTCAAATAG GAGAAATCAA AACAAAAGGT

4981 ACAGAACACC AGAACAACAA AATCAAAACA TCCAACTCAC TCAAAACAAA AATTCCAAAA

5041 GAGACCGGCA ACACAACAAG CACTGAACAT GCATCACCTG CATCCAATGA TAGTATGCAT

5101 TTTTGTTATG TACACTGGAA TTGTAGGTTC AGATGCCATT GCTGGAGATC AACTCCTCAA

5161 TGTAGGGGTC ATTCAATCAA AGATAAGATC ACTCATGTAC TACACTGATG GTGGCGCTAG

5221 CTTTATTGTT GTAAAATTAC TACCCAATCT TCCCCCAAGC AATGGAACAT GCAACATCAC

5281 CAGTCTAGAT GCATATAATG TTACCCTATT TAAGTTGCTA ACACCCCTGA TTGAGAACCT

5341 GAGCAAAATT TCTGCTGTTA CAGATACCAA ACCCCGCCGA GAACGATTTG CAGGAGTCGT

5401 TATTGGGCTT GCTGCACTAG GAGTAGCTAC AGCTGCACAA ATAACCGCAG CTGTAGCAAT

5461 AGTAAAAGCC AATGCAAATG CTGCTGCGAT AAACAATCTT GCATCTTCAA TTCAATCCAC

5521 CAACAAGGCA GTATCCGATG TGATAACTGC ATCAAGAACA ATTGCAACCG CAGTTCAAGC

5581 GATTCAGGAT CACATCAATG GAGCCATTGT CAACGGGATA ACATCTGCAT CATGCCGTGC

5641 CCATGATGCA CTAATTGGGT CAATATTAAA TTTGTATCTC ACTGAGCTTA CTACAATATT

5701 TCATAATCAA ATAACAAACC CTGCGCTGAC ACCACTTTCC ATCCAAGCTT TAAGAATCCT

5761 CCTCGGTAGC ACCTTGCCAA TTGTCATTGA ATCCAAACTC AACACAAAAC TCAACACAGC

5821 AGAGCTGCTC AGTAGCGGAC TGTTAACTGG TCAAATAATT CCATTTCCC CAATGTACAT
```

TABLE 40-continued (SEQ ID NO. 174)
Sequence of pFLC.PIV32TM, 15498 bp in sense orientation
(only the antigenome is shown)

```
5881  GCAAATGCTA ATTCAAATCA ATGTTCCGAC ATTTATAATG CAACCCGGTG CGAAGGTAAT

5941  TGATCTAATT GCTATCTCTG CAAACCATAA ATTACAAGAA GTAGTTGTAC AAGTTCCTAA

6001  TAGAATTCTA GAATATGCAA ATGAACTACA AAACTACCCA GCCAATGATT GTTTCGTGAC

6061  ACCAAACTCT GTATTTTGTA GATACAATGA GGGTTCCCCG ATCCCTGAAT CACAATATCA

6121  ATGCTTAAGG GGGAATCTTA ATTCTTGCAC TTTTACCCCT ATTATCGGGA ACTTTCTCAA

6181  GCGATTCGCA TTTGCCAATG GTGTGCTCTA TGCCAACTGC AAATCTTTGC TATGTAAGTG

6241  TGCCGACCCT CCCCATGTTG TGTCTCAAGA TGACAACCAA GGCATCAGCA TAATTGATAT

6301  TAAGAGGTGC TCTGAGATGA TGCTTGACAC TTTTTCATTT AGGATCACAT CTACATTCAA

6361  TGCTACATAC GTGACAGACT TCTCAATGAT TAATGCAAAT ATTGTACATC TAAGTCCTCT

6421  AGACTTGTCA ATCAAATCA ATTCAATAAA CAAATCTCTT AAAAGTGCTG AGGATTGGAT

6481  TGCAGATAGC AACTTCTTCG CTAATCAAGC CAGAACAGCC AAGACACTTT ATTCACTAAT

6541  CATAATTATT TTGATAATGA TCATTATATT GTTTATAATT AATATAACGA TAATTACAAT

6601  TGCAATTAAG TATTACAGAA TTCAAAGAG AAATCGAGTG GATCAAAATG ACAAGCCATA

6661  TGTACTAACA AACAAATAAC ATATCTACAG ATCATTAGAT ATTAAAATTA TAAAAACTT

6721  AGGAGTAAAG TTACGCAATC CAACTCTACT CATATAATTG AGGAAGGACC CAATAGACAA

6781  ATCCAAATTC GAGATGGAAT ACTGGAAGCA TACCAATCAC GGAAAGGATG CTGGTAATGA

6841  GCTGGAGACG TCTATGGCTA CTCATGGCAA CAAGCTCACT AATAAGATAA TATACATATT

6901  ATGGACAATA ATCCTGGTGT TATTATCAAT AGTCTTCATC ATAGTGCTAA TTAATTCCAT

6961  CCATGAGATA ATTCATCTTG ATGTTTCCTC TGGTCTTATG AATTCTGATG AGTCACAGCA

7021  AGGCATTATT CAGCCTATCA TAGAATCATT AAAATCATTG ATTGCTTTGG CCAACCAGAT

7081  TCTATATAAT GTTGCAATAG TAATTCCTCT TAAAATTGAC AGTATCGAAA CTGTAATACT

7141  CTCTGCTTTA AAAGATATGC ACACCGGGAG TATGTCCAAT GCCAACTGCA CGCCAGGAAA

7201  TCTGCTTCTG CATGATGCAG CATACATCAA TGGAATAAAC AAATTCCTTG TACTTGAATC

7261  ATACAATGGG ACGCCTAAAT ATGGACCTCT CCTAAATATA CCCAGCTTTA TCCCCTCAGC

7321  AACATCTCCC CATGGGTGTA CTAGAATACC ATCATTTTCA CTCATCAAGA CCCATTGGTG

7381  TTACACTCAC AATGTAATGC TTGGAGATTG TCTTGATTTC ACGGCATCTA ACCAGTATTT

7441  ATCAATGGGG ATAATACAAC AATCTGCTGC AGGGTTTCCA ATTTTCAGGA CTATGAAAAC

7501  CATTTACCTA AGTGATGGAA TCAATCGCAA AAGCTGTTCA GTCACTGCTA TACCAGGAGG

7561  TTGTGTCTTG TATTGCTATG TAGCTACAAG GTCTGAAAAA GAAGATTATG CCACGACTGA

7621  TCTAGCTGAA CTGAGACTTG CTTTCTATTA TTATAATGAT ACCTTTATTG AAAGAGTCAT

7681  ATCTCTTCCA AATACAACAG GGCAGTGGGC CACAATCAAC CCTGCAGTCG GAAGCGGGAT

7741  CTATCATCTA GGCTTTATCT TATTTCCTGT ATATGGTGGT CTCATAAATG GGACTACTTC

7801  TTACAATGAG CAGTCCTCAC GCTATTTTAT CCCAAAACAT CCCAACATAA CTTGTGCCGG

7861  TAACTCCAGC AAACAGGCTG CAATAGCACG GAGTTCCTAT GTCATCCGTT ATCACTCAAA

7921  CAGGTTAATT CAGAGTGCTG TTCTTATTTG TCCATTGTCT GACATGCATA CAGAAGAGTG

7981  TAATCTAGTT ATGTTTAACA ATTCCCAAGT CATGATGGGT GCAGAAGGTA GGCTCTATGT

8041  TATTGGTAAT AATTTGTATT ATTATCAACG CAGTTCCTCT TGGTGGTCTG CATCGCTCTT

8101  TTACAGGATC AATACAGATT TTTCTAAAGG AATTCCTCCG ATCATTGAGG CTCAATGGGT
```

TABLE 40-continued (SEQ ID NO. 174)
Sequence of pFLC.PIV32TM, 15498 bp in sense orientation
(only the antigenome is shown)

```
 8161 ACCGTCCTAT CAAGTTCCTC GTCCTGGAGT CATGCCATGC AATGCAACAA GTTTTTGCCC
 8221 TGCTAATTGC ATCACAGGGG TGTACGCAGA TGTGTGGCCG CTTAATGATC CAGAACTCAT
 8281 GTCACGTAAT GCTCTGAACC CCAACTATCG ATTTGCTGGA GCCTTTCTCA AAAATGAGTC
 8341 CAACCGAACT AATCCCACAT TCTACACTGC ATCGGCTAAC TCCCTCTTAA ATACTACCGG
 8401 ATTCAACAAC ACCAATCACA AGCAGCATA TACATCTTCA ACCTGCTTTA AAACACTGG
 8461 AACCCAAAAA ATTTATTGTT TAATAATAAT TGAAATGGGC TCATCTCTTT TAGGGGAGTT
 8521 CCAAATAATA CCATTTTTAA GGGAACTAAT GCTTTAAGCT TCATAATTAA CCATAATATG
 8581 CATCAATCTA TCTATAATAC AAGTATATGA TAAGTAATCA GCAATCAGAC AATAGACAAA
 8641 AGGGAAATAT AAAAAACTTA GGAGCAAAGC GTGCTCGCCA AATGGACACT GAATCTAACA
 8701 ATGGCACTGT ATCTGACATA CTCTATCCTG AGTGTCACCT TAACTCTCCT ATCGTTAAAG
 8761 GTAAAATAGC ACAATTACAC ACTATTATGA GTCTACCTCA GCCTTATGAT ATGGATCACG
 8821 ACTCAATACT AGTTATCACT AGACAGAAAA TAAACTTAA TAAATTGGAT AAAAGACAAC
 8881 GATCTATTAG AAGATTAAAA TTAATATTAA CTGAAAAAGT GAATGACTTA GGAAAATACA
 8941 CATTTATCAG ATATCCAGAA ATGTCAAAAG AAATGTTCAA ATTATATATA CCTGGTATTA
 9001 ACAGTAAAGT GACTGAATTA TTACTTAAAG CAGATAGAAC ATATAGTCAA ATGACTGATG
 9061 GATTAAGAGA TCTATGGATT AATGTGCTAT CAAAATTAGC CTCAAAAAAT GATGGAAGCA
 9121 ATTATGATCT TAATGAAGAA ATTAATAATA TATCGAAAGT TCACACAACC TATAAATCAG
 9181 ATAAATGGTA TAATCCATTC AAAAACATGGT TTACTATCAA GTATGATATG AGAAGATTAC
 9241 AAAAAGCTCG AAATGAGATC ACTTTTAATG TTGGGAAGGA TTATAACTTG TTAGAAGACC
 9301 AGAAGAATTT CTTATTGATA CATCCAGAAT TGGTTTTGAT ATTAGATAAA CAAACTATA
 9361 ATGGTTATCT AATTACTCCT GAATTAGTAT TGATGTATTG TGACGTAGTC GAAGGCCGAT
 9421 GGAATATAAG TGCATGTGCT AAGTTAGATC CAAAATTACA ATCTATGTAT CAGAAAGGTA
 9481 ATAACCTGTG GGAAGTGATA GATAAATTGT TTCCAATTAT GGGAGAAAAG ACATTTGATG
 9541 TGATATCGTT ATTAGAACCA CTTGCATTAT CCTTAATTCA AACTCATGAT CCTGTTAAAC
 9601 AACTAAGAGG AGCTTTTTTA AATCATGTGT TATCCGAGAT GGAATTAATA TTTGAATCTA
 9661 GAGAATCGAT TAAGGAATTT CTGAGTGTAG ATTACATTGA TAAAATTTTA GATATATTTA
 9721 ATAAGTCTAC AATAGATGAA ATAGCAGAGA TTTTCTCTTT TTTTAGAACA TTTGGGCATC
 9781 CTCCATTAGA AGCTAGTATT GCAGCAGAAA AGGTTAGAAA ATATATGTAT ATTGGAAAAC
 9841 AATTAAAATT TGACACTATT AATAAATGTC ATGCTATCTT CTGTACAATA ATAATTAACG
 9901 GATATAGAGA GAGGCATGGT GGACAGTGGC CTCCTGTGAC ATTACCTGAT CATGCACACG
 9961 AATTCATCAT AAATGCTTAC GGTTCAAACT CTGCGATATC ATATGAAAAT GCTGTTGATT
10021 ATTACCAGAG CTTTATAGGA ATAAAATTCA ATAAATTCAT AGAGCCTCAG TTAGATGAGG
10081 ATTTGACAAT TTATATGAAA GATAAAGCAT TATCTCCAAA AAAATCAAAT TGGGACACAG
10141 TTTATCCTGC ATCTAATTTA CTGTACCGTA CTAACGCATC CAACGAATCA CGAAGATTAG
10201 TTGAAGTATT TATAGCAGAT AGTAAATTTG ATCCTCATCA GATATTGGAT TATGTAGAAT
10261 CTGGGGACTG GTTAGATGAT CCAGAATTTA ATATTTCTTA TAGTCTTAAA GAAAAAGAGA
10321 TCAAACAGGA AGGTAGACTC TTTGCAAAAA TGACATACAA AATGAGAGCT ACACAAGTTT
10381 TATCAGAGAC CCTACTTGCA AATAACATAG GAAATTCTT TCAAGAAAAT GGGATGGTGA
```

TABLE 40-continued (SEQ ID NO. 174)
Sequence of pFLC.PIV32TM, 15498 bp in sense orientation
(only the antigenome is shown)

```
10441 AGGGAGAGAT TGAATTACTT AAGAGATTAA CAACCATATC AATATCAGGA GTTCCACGGT

10501 ATAATGAAGT GTACAATAAT TCTAAAAGCC ATACAGATGA CCTTAAAACC TACAATAAAA

10561 TAAGTAATCT TAATTTGTCT TCTAATCAGA AATCAAAGAA ATTTGAATTC AAGTCAACGG

10621 ATATCTACAA TGATGGATAC GAGACTGTGA GCTGTTTCCT AACAACAGAT CTCAAAAAAT

10681 ACTGTCTTAA TTGGAGATAT GAATCAACAG CTCTATTTGG AGAAACTTGC AACCAAATAT

10741 TTGGATTAAA TAAATTGTTT AATTGGTTAC ACCCTCGTCT TGAAGGAAGT ACAATCTATG

10801 TAGGTGATCC TTACTGTCCT CCATCAGATA AGAACATAT ATCATTAGAG GATCACCCTG

10861 ATTCTGGTTT TTACGTTCAT AACCCAAGAG GGGGTATAGA AGGATTTTGT CAAAAATTAT

10921 GGACACTCAT ATCTATAAGT GCAATACATC TAGCAGCTGT TAGAATAGGC GTGAGGGTGA

10981 CTGCAATGGT TCAAGGAGAC AATCAAGCTA TAGCTGTAAC CACAAGAGTA CCCAACAATT

11041 ATGACTACAG AGTTAAGAAG GAGATAGTTT ATAAAGATGT AGTGAGATTT TTTGATTCAT

11101 TAAGAGAAGT GATGGATGAT CTAGGTCATG AACTTAAATT AAATGAAACG ATTATAAGTA

11161 GCAAGATGTT CATATATAGC AAAAGAATCT ATTATGATGG GAGAATTCTT CCTCAAGCTC

11221 TAAAAGCATT ATCTAGATGT GTCTTCTGGT CAGAGACAGT AATAGACGAA ACAAGATCAG

11281 CATCTTCAAA TTTGGCAACA TCATTTGCAA AAGCAATTGA GAATGGTTAT TCACCTGTTC

11341 TAGGATATGC ATGCTCAATT TTTAAGAATA TTCAACAACT ATATATTGCC CTTGGGATGA

11401 ATATCAATCC AACTATAACA CAGAATATCA GAGATCAGTA TTTTAGGAAT CCAAATTGGA

11461 TGCAATATGC CTCTTTAATA CCTGCTAGTG TTGGGGGATT CAATTACATG GCCATGTCAA

11521 GATGTTTTGT AAGGAATATT GGTGATCCAT CAGTTGCCGC ATTGGCTGAT ATTAAAAGAT

11581 TTATTAAGGC GAATCTATTA GACCGAAGTG TTCTTTATAG GATTATGAAT CAAGAACCAG

11641 GTGAGTCATC TTTTTTGGAC TGGGCTTCAG ATCCATATTC ATGCAATTTA CCACAATCTC

11701 AAAATATAAC CACCATGATA AAAAATATAA CAGCAAGGAA TGTATTACAA GATTCACCAA

11761 ATCCATTATT ATCTGGATTA TTCACAAATA CAATGATAGA AGAAGATGAA GAATTAGCTG

11821 AGTTCCTGAT GGACAGGAAG GTAATTCTCC CTAGAGTTGC ACATGATATT CTAGATAATT

11881 CTCTCACAGG AATTAGAAAT GCCATAGCTG GAATGTTAGA TACGACAAAA TCACTAATTC

11941 GGGTTGGCAT AAATAGAGGA GGACTGACAT ATAGTTTGTT GAGGAAAATC AGTAATTACG

12001 ATCTAGTACA ATATGAAACA CTAAGTAGGA CTTTGCGACT AATTGTAAGT GATAAAATCA

12061 AGTATGAAGA TATGTGTTCG GTAGACCTTG CCATAGCATT GCGACAAAAG ATGTGGATTC

12121 ATTTATCAGG AGGAAGGATG ATAAGTGGAC TTGAAACGCC TGACCCATTA GAATTACTAT

12181 CTGGGGTAGT AATAACAGGA TCAGAACATT GTAAATATG TTATTCTTCA GATGGCACAA

12241 ACCCATATAC TTGGATGTAT TTACCCGGTA ATATCAAAAT AGGATCAGCA GAAACAGGTA

12301 TATCGTCATT AAGAGTTCCT TATTTTGGAT CAGTCACTGA TGAAAGATCT GAAGCACAAT

12361 TAGGATATAT CAAGAATCTT AGTAAACCTG CAAAAGCCGC AATAAGAATA GCAATGATAT

12421 ATACATGGGC ATTTGGTAAT GATGAGATAT CTTGGATGGA AGCCTCACAG ATAGCACAAA

12481 CACGTGCAAA TTTTACACTA GATAGTCTCA AAATTTTAAC ACCGGTAGCT ACATCAACAA

12541 ATTTATCACA CAGATTAAAG GATACTGCAA CTCAGATGAA ATTCTCCAGT ACATCATTGA

12601 TCAGAGTCAG CAGATTCATA ACAATGTCCA ATGATAACAT GTCTATCAAA GAAGCTAATG

12661 AAACCAAAGA TACTAATCTT ATTTATCAAC AAATAATGTT AACAGGATTA AGTGTTTTCG
```

TABLE 40-continued (SEQ ID NO. 174)
Sequence of pFLC.PIV32TM, 15498 bp in sense orientation
(only the antigenome is shown)

```
12721 AATATTTATT TAGATTAAAA GAAACCACAG GACACAACCC TATAGTTATG CATCTGCACA

12781 TAGAAGATGA GTGTTGTATT AAAGAAAGTT TTAATGATGA ACATATTAAT CCAGAGTCTA

12841 CATTAGAATT AATTCGATAT CCTGAAAGTA ATGAATTTAT TTATGATAAA GACCCACTCA

12901 AAGATGTGGA CTTATCAAAA CTTATGGTTA TTAAAGACCA TTCTTACACA ATTGATATGA

12961 ATTATTGGGA TGATACTGAC ATCATACATG CAATTTCAAT ATGTACTGCA ATTACAATAG

13021 CAGATACTAT GTCACAATTA GATCGAGATA ATTTAAAAGA GATAATAGTT ATTGCAAATG

13081 ATGATGATAT TAATAGCTTA ATCACTGAAT TTTTGACTCT TGACATACTT GTATTTCTCA

13141 AGACATTTGG TGGATTATTA GTAAATCAAT TTGCATACAC TCTTTATAGT CTAAAAATAG

13201 AAGGTAGGGA TCTCATTTGG GATTATATAA TGAGAACACT GAGAGATACT TCCCATTCAA

13261 TATTAAAAGT ATTATCTAAT GCATTATCTC ATCCTAAAGT ATTCAAGAGG TTCTGGGATT

13321 GTGGAGTTTT AAACCCTATT TATGGTCCTA ATACTGCTAG TCAAGACCAG ATAAAACTTG

13381 CCCTATCTAT ATGTGAATAT TCACTAGATC TATTTATGAG AGAATGGTTG AATGGTGTAT

13441 CACTTGAAAT ATACATTTGT GACAGCGATA TGGAAGTTGC AAATGATAGG AAACAAGCCT

13501 TTATTTCTAG ACACCTTTCA TTTGTTTGTT GTTTAGCAGA AATTGCATCT TTCGGACCTA

13561 ACCTGTTAAA CTTAACATAC TTGGAGAGAC TTGATCTATT GAAACAATAT CTTGAATTAA

13621 ATATTAAAGA AGACCCTACT CTTAAATATG TACAAATATC TGGATTATTA ATTAAATCGT

13681 TCCCATCAAC TGTAACATAC GTAAGAAAGA CTGCAATCAA ATATCTAAGG ATTCGCGGTA

13741 TTAGTCCACC TGAGGTAATT GATGATTGGG ATCCGGTAGA AGATGAAAAT ATGCTGGATA

13801 ACATTGTCAA AACTATAAAT GATAACTGTA ATAAGATAA TAAAGGGAAT AAAATTAACA

13861 ATTTCTGGGG ACTAGCACTT AAGAACTATC AAGTCCTTAA AATCAGATCT ATAACAAGTG

13921 ATTCTGATGA TAATGATAGA CTAGATGCTA ATACAAGTGG TTTGACACTT CCTCAAGGAG

13981 GGAATTATCT ATCGCATCAA TTGAGATTAT TCGGAATCAA CAGCACTAGT TGTCTGAAAG

14041 CTCTTGAGTT ATCACAAATT TTAATGAAGG AAGTCAATAA AGACAAGGAC AGGCTCTTCC

14101 TGGGAGAAGG AGCAGGAGCT ATGCTAGCAT GTTATGATGC CACATTAGGA CCTGCAGTTA

14161 ATTATTATAA TTCAGGTTTG AATATAACAG ATGTAATTGG TCAACGAGAA TTGAAAATAT

14221 TTCCTTCAGA GGTATCATTA GTAGGTAAAA AATTAGGAAA TGTGACACAG ATTCTTAACA

14281 GGGTAAAAGT ACTGTTCAAT GGGAATCCTA ATTCAACATG GATAGGAAAT ATGGAATGTG

14341 AGAGCTTAAT ATGGAGTGAA TTAAATGATA AGTCCATTGG ATTAGTACAT TGTGATATGG

14401 AAGGAGCTAT CGGTAAATCA GAAGAAACTG TTCTACATGA ACATTATAGT GTTATAAGAA

14461 TTACATACTT GATTGGGGAT GATGATGTTG TTTTAGTTTC CAAAATTATA CCTACAATCA

14521 CTCCGAATTG GTCTAGAATA CTTTATCTAT ATAAATTATA TTGGAAAGAT GTAAGTATAA

14581 TATCACTCAA AACTTCTAAT CCTGCATCAA CAGAATTATA TCTAATTTCG AAAGATGCAT

14641 ATTGTACTAT AATGGAACCT AGTGAAATTG TTTTATCAAA ACTTAAAAGA TTGTCACTCT

14701 TGGAAGAAAA TAATCTATTA AAATGGATCA TTTATCAAA GAAGAGGAAT AATGAATGGT

14761 TACATCATGA AATCAAAGAA GGAGAAAGAG ATTATGGAAT CATGAGACCA TATCATATGG

14821 CACTACAAAT CTTTGGATTT CAAATCAATT TAAATCATCT GGCGAAAGAA TTTTTATCAA

14881 CCCCAGATCT GACTAATATC AACAATATAA TCCAAAGTTT TCAGCGAACA ATAAAGGATG

14941 TTTTATTTGA ATGGATTAAT ATAACTCATG ATGATAAGAG ACATAAAATTA GGCGGAAGAT
```

TABLE 40-continued (SEQ ID NO. 174)
Sequence of pFLC.PIV32TM, 15498 bp in sense orientation
(only the antigenome is shown)

```
15001 ATAACATATT CCCACTGAAA AATAAGGGAA AGTTAAGACT GCTATCGAGA AGACTAGTAT

15061 TAAGTTGGAT TTCATTATCA TTATCGACTC GATTACTTAC AGGTCGCTTT CCTGATGAAA

15121 AATTTGAACA TAGAGCACAG ACTGGATATG TATCATTAGC TGATACTGAT TTAGAATCAT

15181 TAAAGTTATT GTCGAAAAAC ATCATTAAGA ATTACAGAGA GTGTATAGGA TCAATATCAT

15241 ATTGGTTTCT AACCAAAGAA GTTAAAATAC TTATGAAATT GATCGGTGGT GCTAAATTAT

15301 TAGGAATTCC CAGACAATAT AAAGAACCCG AAGACCAGTT ATTAGAAAAC TACAATCAAC

15361 ATGATGAATT TGATATCGAT TAAAACATAA ATACAATGAA GATATATCCT AACCTTTATC

15421 TTTAAGCCTA GGAATAGACA AAAAGTAAGA AAAACATGTA ATATATATAT ACCAAACAGA

15481 GTTCTTCTCT TGTTTGGT
```

In a third strategy (FIG. 38), chimeric PIV3-PIV2 F and HN genes were constructed in which regions of the PIV2 F and HN ORFs encoding the ectodomains and the transmembrane domains were amplified from pLit.PIV32Fhc and pLit.PIV32HNhc, respectively, using PCR, Vent DNA polymerase, and primer pairs specific to PIV2 F (13, 14 in Table 38) and PIV2 HN (15, 16 in Table 38). In parallel, the partial ORFs of PIV3 F and HN genes encoding the ectodomains plus transmembrane domains were deleted from their cDNA subclones pLit.PIV3.F3a and pLit.PIV3.HN4 (Tao et al., *J. Virol.* 72:2955-2961, 1998, incorporated herein by reference), respectively, using PCR, Vent DNA polymerase, and primer pairs specific to PIV3 F (17, 18 in Table 38) and PIV3 HN (19, 20 in Table 38). The F and HN cDNA fragments of PIV2 and PIV3 were gel purified and ligated to generate pLit.PIV32FCT and pLit.PIV32HNCT, respectively. The chimeric F and HN constructs were digested with PpuMI plus SpeI and assembled together to generate pLit.PIV32CT, which was sequenced across the PIV specific region in its entirety and found to be as designed. The 4 kb BspEI-SpeI fragment from pLit.PIV32CT was introduced into the BspEI-SpeI window of p38'ΔPIV31hc to generate p38'ΔPIV32CT. The 6.5 kb BspEI-SphI fragment from p38'ΔPIV32CT, containing the PIV3-PIV2 F and HN chimeric genes, was introduced into the BspEI-SphI window of pFLC.2G+.hc and pFLCcp45, to generate pFLC.PIV32CT (Table 41, SEQ ID NO. 175) and pFLC.PIV32CTcp45, respectively. The nucleotide sequence of this BspEI-SpeI fragment is submitted in the GenBank.

TABLE 41

| (SEQ ID NO. 175) Sequence of pFLC.PIV32CT, 15474 bp in sense orientation (only the insert is shown) |
|---|
| 1 ACCAAACAAG AGAAGAAACT TGTCTGGGAA TATAAATTTA ACTTTAAATT AACTTAGGAT |
| 61 TAAAGACATT GACTAGAAGG TCAAGAAAAG GGAACTCTAT AATTTCAAAA ATGTTGAGCC |
| 121 TATTTGATAC ATTTAATGCA CGTAGGCAAG AAAACATAAC AAAATCAGCC GGTGGAGCTA |
| 181 TCATTCCTGG ACAGAAAAAT ACTGTCTCTA TATTCGCCCT TGGACCGACA ATAACTGATG |
| 241 ATAATGAGAA AATGACATTA GCTCTTCTAT TTCTATCTCA TTCACTAGAT AATGAGAAAC |
| 301 AACATGCACA AAGGGCAGGG TTCTTGGTGT CTTTATTGTC AATGGCTTAT GCCAATCCAG |
| 361 AGCTCTACCT AACAACAAAT GGAAGTAATG CAGATGTCAA GTATGTCATA TACATGATTG |
| 421 AGAAAGATCT AAAACGGCAA AAGTATGGAG GATTTGTGGT TAAGACGAGA GAGATGATAT |
| 481 ATGAAAAGAC AACTGATTGG ATATTTGGAA GTGACCTGGA TTATGATCAG GAAACTATGT |
| 541 TGCAGAACGG CAGGAACAAT TCAACAATTG AAGACCTTGT CCACACATTT GGGTATCCAT |
| 601 CATGTTTAGG AGCTCTTATA ATACAGATCT GGATAGTTCT GGTCAAAGCT ATOACTACTA |
| 661 TCTCAGGGTT AAGAAAAGGC TTTTTCACCC GATTGGAAGC TTTCAGACAA GATGGAACAG |
| 721 TGCAGGCAGG GCTGGTATTG AGCGGTGACA CAGTGGATCA GATTGGGTCA ATCATGCCGT |
| 781 CTCAACAGAG CTTGGTAACT CTTATGGTTG AAACATTAAT AACAATGAAT ACCAGCACAA |
| 841 ATGACCTCAC AACCATAGAA AAGAATATAC AAATTGTTGG CAACTACATA AGAGATGCAG |

TABLE 41-continued (SEQ ID NO. 175)
Sequence of pFLC.PIV32CT, 15474 bp in sense orientation
(only the insert is shown)

```
 901 GTCTCGCTTC ATTCTTCAAT ACAATCAGAT ATGGAATTGA GACCAGAATG GCAGCTTTGA
 961 CTCTATCCAC TCTCAGACCA GATATCAATA GATTAAAAGC TTTGATGGAA CTGTATTTAT
1021 CAAAGGGACC ACGCGCTCCT TTCATCTGTA TCCTCAGAGA TCCTATACAT GGTGAGTTCG
1081 CACCAGGCAA CTATCCTGCC ATATGGAGCT ATGCAATGGG GGTGGCAGTT GTACAAAATA
1141 GAGCCATGCA ACAGTATGTG ACGGAAGAT CATATCTAGA CATTGATATC TTCCAGCTAG
1201 GACAAGCAGT AGCACGTGAT GCCGAAGCTC AAATGAGCTC AACACTGGAA GATGAACTTG
1261 GAGTGACACA CGAATCTAAA GAAAGCTTGA AGAGACATAT AAGGAACATA AACAGTTCAG
1321 AGACATCTTT CCACAAACCG ACAGGTGGAT CAGCCATAGA GATGGCAATA GATGAAGAGC
1381 CAGAACAATT CGAACATAGA GCAGATCAAG AACAAAATGG AGAACCTCAA TCATCCATAA
1441 TTCAATATGC CTGGGCAGAA GGAAATAGAA GCGATGATCA GACTGAGCAA GCTACAGAAT
1501 CTGACAATAT CAAGACCGAA CAACAAAACA TOAGAGACAG ACTAAACAAG AGACTCAACG
1561 ACAAGAAGAA ACAAAGCAGT CAACCACCCA CTAATCCCAC AAACAGAACA ACCAGGACG
1621 AAATAGATGA TCTGTTTAAC GCATTTGGAA GCAACTAATC GAATCAACAT TTTAATCTAA
1681 ATCAATAATA AATAAGAAAA ACTTAGGATT AAAGAATCCT ATCATACCGG AATATAGGGT
1741 GGTAAATTTA GAGTCTGCTT GAAACTCAAT CAATAGAGAG TTGATGGAAA GCGATGCTAA
1801 AAACTATCAA ATCATGGATT CTTGGGAAGA GGAATCAAGA GATAAATCAA CTAATATCTC
1861 CTCGGCCCTC AACATCATTG AATTCATACT CAGCACCGAC CCCCAAGAAG ACTTATCGGA
1921 AAACGACACA ATCAACACAA GAACCCAGCA ACTCAGTGCC ACCATCTGTC AACCAGAAAT
1981 CAAACCAACA GAAACAAGTG AGAAAGATAG TGGATCAACT GACAAAAATA GACAGTCCGG
2041 GTCATCACAC GAATGTACAA CAGAAGCAAA AGATAGAAAT ATTGATCAGG AAACTGTACA
2101 GAGAGGACCT GGGAGAAGAA GCAGCTCAGA TAGTAGAGCT GAGACTGTGG TCTCTGGAGG
2161 AATCCCCAGA AGCATCACAG ATTCTAAAAA TGGAACCCAA AACACGGAGG ATATTGATCT
2221 CAATGAAATT AGAAAGATGG ATAAGGACTC TATTGAGGGG AAAATGCGAC AATCTGCAAA
2281 TGTTCCAAGC GAGATATCAG GAAGTGATGA CATATTTACA ACAGAACAAA GTAGAAACAG
2341 TGATCATGGA AGAAGCCTGG AATCTATCAG TACACCTGAT ACAAGATCAA TAAGTGTTGT
2401 TACTGCTGCA ACACCAGATG ATGAAGAAGA AATACTAATG AAAAATAGTA GGACAAAGAA
2461 AAGTTCTTCA ACACATCAAG AAGATGACAA AGAATTAAA AAAGGGGGAA AAGGGAAAGA
2521 CTGGTTTAAG AAATCAAAAG ATACCGACAA CCAGATACCA ACATCAGACT ACAGATCCAC
2581 ATCAAAAGGG CAGAAGAAAA TCTCAAAGAC AACAACCACC AACACCGACA CAAAGGGGCA
2641 AACAGAAATA CAGACAGAAT CATCAGAAAC ACAATCCTCA TCATGGAATC TCATCATCGA
2701 CAACAACACC GACCGGAACG AACAGACAAG CACAACTCCT CCAACAACAA CTTCCAGATC
2761 AACTTATACA AAAGAATCGA TCCGAACAAA CTCTGAATCC AAACCCAAGA CACAAAAGAC
2821 AAATGGAAAG GAAAGGAAGG ATACAGAAGA GAGCAATCGA TTTACAGAGA GGGCAATTAC
2881 TCTATTGCAG AATCTTGGTG TAATTCAATC CACATCAAAA CTAGATTTAT ATCAAGACAA
2941 ACGAGTTGTA TGTGTAGCAA ATGTACTAAA CAATGTAGAT ACTGCATCAA AGATAGATTT
3001 CCTGGCAGGA TTAGTCATAG GGGTTTCAAT GGACAACGAC ACAAAATTAA CACAGATACA
3061 AAATGAAATG CTAAACCTCA AGCAGATCT AAAGAAAATG GACGAATCAC ATAGAAGATT
3121 GATAGAAAAT CAAAGAGAAC AACTGTCATT GATCACGTCA CTAATTTCAA ATCTCAAAAT
```

TABLE 41-continued (SEQ ID NO. 175)
Sequence of pFLC.PIV32CT, 15474 bp in sense orientation
(only the insert is shown)

```
3181 TATGACTGAG AGAGGAGGAA AGAAAGACCA AAATGAATCC AATGAGAGAG TATCCATGAT

3241 CAAAACAAAA TTGAAAGAAG AAAAGATCAA GAAGACCAGG TTTGACCCAC TTATGGAGGC

3301 ACAAGGCATT GACAAGAATA TACCCGATCT ATATCGACAT GCAGGAGATA CACTAGAGAA

3361 CGATGTACAA GTTAAATCAG AGATATTAAG TTCATACAAT GAGTCAAATG CAACAAGACT

3421 AATACCCAAA AAAGTGAGCA GTACAATGAG ATCACTAGTT GCAGTCATCA ACAACAGCAA

3481 TCTCTCACAA AGCACAAAAC AATCATACAT AAACGAACTC AAACGTTGCA AAAATGATGA

3541 AGAAGTATCT GAATTAATGG ACATGTTCAA TGAAGATGTC AACAATTGCC AATGATCCAA

3601 CAAAGAAACG ACACCGAACA AACAGACAAG AAACAACAGT AGATCAAAAC CTGTCAACAC

3661 ACACAAAATC AAGCAGAATG AAACAACAGA TATCAATCAA TATACAAATA GAAAAACTT

3721 AGGATTAAAG AATAAATTAA TCCTTGTCCA AAATGAGTAT AACTAACTCT GCAATATACA

3781 CATTCCCAGA ATCATCATTC TCTGAAAATG GTCATATAGA ACCATTACCA CTCAAAGTCA

3841 ATGAACAGAG GAAAGCAGTA CCCCACATTA GAGTTGCCAA GATCGGAAAT CCACCAAAAC

3901 ACGGATCCCG GTATTTAGAT GTCTTCTTAC TCGGCTTCTT CGAGATGGAA CGAATCAAAG

3961 ACAAATACGG GAGTGTGAAT GATCTCGACA GTGACCCGAG TTACAAAGTT TGTGGCTCTG

4021 GATCATTACC AATCGGATTG CTAAGTACA CTGGGAATGA CCAGGAATTG TTACAAGCCG

4081 CAACCAAACT GGATATAGAA GTGAGAAGAA CAGTCAAAGC GAAAGAGATG GTTGTTTACA

4141 CGGTACAAAA TATAAAACCA GAACTGTACC CATGGTCCAA TAGACTAAGA AAAGGAATGC

4201 TGTTCGATGC CAACAAAGTT GCTCTTGCTC CTCAATGTCT TCCACTAGAT AGGAGCATAA

4261 AATTTAGAGT AATCTTCGTG AATTGTACGG CAATTGGATC AATAACCTTG TTCAAAATTC

4321 CTAAGTCAAT GGCATCACTA TCTCTACCCA ACACAATATC AATCAATCTG CAGGTACACA

4381 TAAAAACAGG GGTTCAGACT GATTCTAAAG GGATAGTTCA AATTTTGGAT GAGAAAGGCG

4441 AAAAATCACT GAATTTCATG GTCCATCTCG GATTGATCAA AGAAAAGTA GGCAGAATGT

4501 ACTCTGTTGA ATACTGTAAA CAGAAAATCG AGAAAATGAG ATTGATATTT TCTTTAGGAC

4561 TAGTTGGAGG AATCAGTCTT CATGTCAATG CAACTGGGTC CATATCAAAA ACACTAGCAA

4621 GTCAGCTGGT ATTCAAAAGA GAGATTTGTT ATCCTTTAAT GGATCTAAAT CCGCATCTCA

4681 ATCTAGTTAT CTGGGCTTCA TCAGTAGAGA TTACAAGAGT GGATGCAATT TTCCAACCTT

4741 CTTTACCTGG CGAGTTCAGA TACTATCCTA ATATTATTGC AAAAGGAGTT GGGAAAATCA

4801 AACAATGGAA CTAGTAATCT CTATTTTAGT CCGGACGTAT CTATTAAGCC GAAGCAAATA

4861 AAGGATAATC AAAAACTTAG GACAAAAGAG GTCAATACCA ACAACTATTA GCAGTCACAC

4921 TCGCAAGAAT AAGAGAGAAG GGACCAAAAA AGTCAAATAG GAGAAATCAA AACAAAAGGT

4981 ACAGAACACC AGAACAACAA AATCAAAACA TCCAACTCAC TCAAAACAAA AATTCCAAAA

5041 GAGACCGGCA ACACAACAAG CACTGAACAT GCATCACCTG CATCCAATGA TAGTATGCAT

5101 TTTTGTTATG TACACTGGAA TTGTAGGTTC AGATGCCATT GCTGGAGATC AACTCCTCAA

5161 TGTAGGGGTC ATTCAATCAA AGATAAGATC ACTCATGTAC TACACTGATG GTGGCGCTAG

5221 CTTTATTGTT GTAAAATTAC TACCCAATCT TCCCCCAAGC AATGGAACAT GCAACATCAC

5281 CAGTCTAGAT GCATATAATG TTACCCTATT TAAGTTGCTA ACACCCCTGA TTGAGAACCT

5341 GAGCAAAATT TCTGCTGTTA CAGATACCAA ACCCCGCCGA GAACGATTTG CAGGAGTCGT

5401 TATTGGGCTT GCTGCACTAG GAGTAGCTAC AGCTGCACAA ATAACCGCAG CTGTAGCAAT
```

TABLE 41-continued (SEQ ID NO. 175)
Sequence of pFLC.PIV32CT, 15474 bp in sense orientation
(only the insert is shown)

```
5461 AGTAAAAGCC AATGCAAATG CTGCTGCGAT AAACAATCTT GCATCTTCAA TTCAATCCAC

5521 CAACAAGGCA GTATCCGATG TGATAACTGC ATCAAGAACA ATTGCAACCG CAGTTCAAGC

5581 GATTCAGGAT CACATCAATG GAGCCATTGT CAACGGGATA ACATCTGCAT CATGCCGTGC

5641 CCATGATGCA CTAATTGGGT CAATATTAAA TTTGTATCTC ACTGAGCTTA CTACAATATT

5701 TCATAATCAA ATAACAAACC CTGCGCTGAC ACCACTTTCC ATCCAAGCTT AAGAATCCT

5761 CCTCGGTAGC ACCTTGCCAA TTGTCATTGA ATCCAAACTC AACACAAAAC TCAACACAGC

5821 AGAGCTGCTC AGTAGCGGAC TGTTAACTGG TCAAATAATT TCCATTTCCC CAATGTACAT

5881 GCAAATGCTA ATTCAAATCA ATGTTCCGAC ATTTATAATG CAACCCGGTG CGAAGGTAAT

5941 TGATCTAATT GCTATCTCTG CAAACCATAA ATTACAAGAA GTAGTTGTAC AAGTTCCTAA

6001 TAGAATTCTA GAATATGCAA ATGAACTACA AAACTACCCA GCCAATGATT GTTTCGTGAC

6061 ACCAAACTCT GTATTTTGTA GATACAATGA GGGTTCCCCG ATCCCTGAAT CACAATATCA

6121 ATGCTTAAGG GGGAATCTTA ATTCTTGCAC TTTTACCCCT ATTATCGGGA ACTTTCTCAA

6181 GCGATTCGCA TTTGCCAATG GTGTGCTCTA TGCCAACTGC AAATCTTTGC TATGTAAGTG

6241 TGCCGACCCT CCCCATGTTG TGTCTCAAGA TGACAACCAA GGCATCAGCA TAATTGATAT

6301 TAAGAGGTGC TCTGAGATGA TGCTTGACAC TTTTTCATTT AGGATCACAT CTACATTCAA

6361 TGCTACATAC GTGACAGACT CTCAATGAT TAATGCAAAT ATTGTACATC TAAGTCCTCT

6421 AGACTTGTCA AATCAAATCA ATTCAATAAA CAAATCTCTT AAAAGTGCTG AGGATTGGAT

6481 TGCAGATAGC AACTTCTTCG CTAATCAAGC CAGAACAGCC AAGCACTTT ATTCACTAAG

6541 TGCAATCGCA TTAATACTAT CAGTGATTAC TTTGGTTGTT GTGGGATTGC TGATTGCCTA

6601 CATCATCAAG TATTACAGAA TTCAAAAGAG AAATCGAGTG GATCAAAATG ACAAGCCATA

6661 TGTACTAACA AACAAATAAC ATATCTACAG ATCATTAGAT ATTAAAATTA TAAAAACTT

6721 AGGAGTAAAG TTACGCAATC CAACTCTACT CATATAATTG AGGAAGGACC AATAGACAA

6781 ATCCAAATTC GAGATGGAAT ACTGGAAGCA TACCAATCAC GGAAAGGATG CTGGTAATGA

6841 GCTGGAGACG TCTATGGCTA CTCATGGCAA CAAGCTCACT AATAAGACTG CCACAATTCT

6901 TGGCATATGC ACATTAATTG TGCTATGTTC AAGTATTCTT CATGAGATAA TTCATCTTGA

6961 TGTTTCCTCT GGTCTTATGA ATTCTGATGA GTCACAGCAA GGCATTATTC AGCCTATCAT

7021 AGAATCATTA AAATCATTGA TTGCTTTGGC CAACCAGATT CTATATAATG TTGCAATAGT

7081 AATTCCTCTT AAAATTGACA GTATCGAAAC TGTAATACTC TCTGCTTTAA AGATATGCA

7141 CACCGGGAGT ATGTCCAATG CCAACTGCAC GCCAGGAAAT CTGCTTCTGC ATGATGCAGC

7201 ATACATCAAT GGAATAAACA AATTCCTTGT ACTTGAATCA TACAATGGGA CGCCTAAATA

7261 TGGACCTCTC CTAAATATAC CCAGCTTTAT CCCCTCAGCA ACATCTCCCC ATGGGTGTAC

7321 TAGAATACCA TCATTTTCAC TCATCAAGAC CCATTGGTGT TACACTCACA ATGTAATCCT

7381 TGGAGATTGT CTTGATTTCA CGGCATCTAA CCAGTATTTA TCAATGGGGA TAATACAACA

7441 ATCTGCTGCA GGGTTTCCAA TTTTCAGGAC TATGAAAACC ATTTACCTAA GTGATGGAAT

7501 CAATCGCAAA AGCTGTTCAG TCACTGCTAT ACCAGGAGGT TGTGTCTTGT ATTGCTATGT

7561 AGCTACAAGG TCTGAAAAAG AAGATTATGC CACGACTGAT CTAGCTGAAC TGAGACTTGC

7621 TTTCTATTAT TATAATGATA CCTTTATTGA AAGAGTCATA TCTCTTCCAA ATACAACAGG

7681 GCAGTGGGCC ACAATCAACC CTGCAGTCGG AAGCGGGATC TATCATCTAG GCTTTATCTT
```

TABLE 41-continued (SEQ ID NO. 175)
Sequence of pFLC.PIV32CT, 15474 bp in sense orientation
(only the insert is shown)

```
7741 ATTTCCTGTA TATGGTGGTC TCATAAATGG GACTACTTCT TACAATGAGC AGTCCTCACG

7801 CTATTTTATC CCAAAACATC CCAACATAAC TTGTGCCGGT AACTCCAGCA AACAGGCTGC

7861 AATAGCACGG AGTTCCTATG TCATCCGTTA TCACTCAAAC AGGTTAATTC AGAGTGCTGT

7921 TCTTATTTGT CCATTGTCTG ACATGCATAC AGAAGAGTGT AATCTAGTTA TGTTTAACAA

7981 TTCCCAAGTC ATGATGGGTG CAGAAGGTAG GCTCTATGTT ATTGGTAATA ATTTGTATTA

8041 TTATCAACGC AGTTCCTCTT GGTGGTCTGC ATCGCTCTTT TACAGGATCA ATACAGATTT

8101 TTCTAAAGGA ATTCCTCCGA TCATTGAGGC TCAATGGGTA CCGTCCTATC AAGTTCCTCG

8161 TCCTGGAGTC ATGCCATGCA ATGCAACAAG TTTTTGCCCT GCTAATTGCA TCACAGGGGT

8221 GTACGCAGAT GTGTGGCCGC TTAATGATCC AGAACTCATG TCACGTAATG CTCTCAACCC

8281 CAACTATCGA TTTGCTGGAG CCTTTCTCAA AAATGAGTCC AACCGAACTA ATCCCACATT

8341 CTACACTGCA TCGGCTAACT CCCTCTTAAA TACTACCGGA TTCAACAACA CCAATCACAA

8401 AGCAGCATAT ACATCTTCAA CCTGCTTTAA AAACACTGGA ACCCAAAAAA TTTATTGTTT

8461 AATAATAATT GAAATGGGCT CATCTCTTTT AGGGGAGTTC CAAATAATAC CATTTTTAAG

8521 GGAACTAATG CTTTAATCAT AATTAACCAT AATATGCATC AATCTATCTA TAATACAAGT

8581 ATATGATAAG TAATCAGCAA TCAGACAATA GACAAAAGGG AAATATAAAA AACTTAGGAG

8641 CAAAGCGTGC TCGGGAAATG GACACTGAAT CTAACAATGG CACTGTATCT GACATACTCT

8701 ATCCTGAGTG TCACCTTAAC TCTCCTATCG TTAAAGGTAA AATAGCACAA TTACACACTA

8761 TTATGAGTCT ACCTCAGCCT TATGATATGG ATGACGACTC AATACTAGTT ATCACTAGAC

8821 AGAAAATAAA ACTTAATAAA TTGGATAAAA GACAACGATC TATTAGAAGA TTAAAATTAA

8881 TATTAACTGA AAAAGTGAAT GACTTAGGAA ATACACATT TATCAGATAT CCAGAAATGT

8941 CAAAGAAAT GTTCAAATTA TATATACCTG GTATTAACAG TAAAGTGACT GAATTATTAC

9001 TTAAAGCAGA TAGAACATAT AGTCAAATGA CTGATGGATT AAGAGATCTA TGGATTAATG

9061 TGCTATCAAA ATTAGCCTCA AAAAATGATG GAAGCAATTA TGATCTTAAT GAAGAAATTA

9121 ATAATATATC GAAAGTTCAC ACAACCTATA AATCAGATAA ATGGTATAAT CCATTCAAAA

9181 CATGGTTTAC TATCAAGTAT GATATGAGAA GATTACAAAA AGCTCGAAAT GAGATCACTT

9241 TTAATGTTGG GAAGGATTAT AACTTGTTAG AAGACCAGAA GAATTTCTTA TTGATACATC

9301 CAGAATTGGT TTTGATATTA GATAAACAAA ACTATAATGG TTATCTAATT ACTCCTGAAT

9361 TAGTATTGAT GTATTGTGAC GTAGTCGAAG GCCGATGGAA TATAAGTGCA TGTGCTAAGT

9421 TAGATCCAAA ATTACAATCT ATGTATCAGA AAGGTAATAA CCTGTGGGAA GTGATAGATA

9481 AATTGTTTCC AATTATGGGA GAAAAGACAT TGATGTGAT ATCGTTATTA GAACCACTTG

9541 CATTATCCTT AATTCAAACT CATGATCCTG TTAAACAACT AAGAGGAGCT TTTTTAAATC

9601 ATGTGTTATC CGAGATGGAA TTAATATTTG AATCTAGAGA ATCGATTAAG GAATTTCTGA

9661 GTGTAGATTA CATTGATAAA ATTTTAGATA TATTTAATAA GTCTACAATA GATGAAATAG

9721 CAGAGATTTT CTCTTTTTTT AGAACATTTG GCATCCTCC ATTAGAAGCT AGTATTGCAG

9781 CAGAAAAGGT TAGAAAATAT ATGTATATTG GAAAACAATT AAAATTTGAC ACTATTAATA

9841 AATGTCATGC TATCTTCTGT ACAATAATAA TTAACGGATA TAGAGAGAGG CATGGTGGAC

9901 AGTGGCCTCC TGTGACATTA CCTGATCATG CACACGAATT CATCATAAAT GCTTACGGTT

9961 CAAACTCTGC GATATCATAT GAAAATGCTG TTGATTATTA CCAGAGCTTT ATAGGAATAA
```

TABLE 41-continued (SEQ ID NO. 175)
Sequence of pFLC.PIV32CT, 15474 bp in sense orientation
(only the insert is shown)

```
10021 AATTCAATAA ATTCATAGAG CCTCAGTTAG ATGAGGATTT GACAATTTAT ATGAAAGATA
10081 AAGCATTATC TCCAAAAAAA TCAAATTGGG ACACAGTTTA TCCTGCATCT AATTTACTGT
10141 ACCGTACTAA CGCATCCAAC GAATCACGAA GATTAGTTGA AGTATTTATA GCAGATAGTA
10201 AATTTGATCC TCATCAGATA TTGGATTATG TAGAATCTGG GGACTGGTTA GATGATCCAG
10261 AATTTAATAT TTCTTATAGT CTTAAAGAAA AAGAGATCAA ACAGGAAGGT AGACTCTTTG
10321 CAAAAATGAC ATACAAATG AGAGCTACAC AAGTTTTATC AGAGACACTA CTTGCAAATA
10381 ACATAGGAAA ATTCTTTCAA GAAAATGGGA TGGTGAAGGG AGAGATTGAA TTACTTAAGA
10441 GATTAACAAC CATATCAATA TCAGGAGTTC CACGGTATAA TGAAGTGTAC AATAATTCTA
10501 AAAGCCATAC AGATGACCTT AAAACCTACA ATAAAATAAG TAATCTTAAT TTGTCTTCTA
10561 ATCAGAAATC AAAGAAATTT GAATTCAAGT CAACGGATAT CTACAATGAT GGATACGAGA
10621 CTGTGAGCTG TTTCCTAACA ACAGATCTCA AAAAATACTG TCTTAATTGG AGATATGAAT
10681 CAACAGCTCT ATTTGGAGAA ACTTGCAACC AAATATTTGG ATTAAATAAA TTGTTTAATT
10741 GGTTACACCC TCGTCTTGAA GGAAGTACAA TCTATGTAGG TGATCCTTAC TGTCCTCCAT
10801 CAGATAAAGA ACATATATCA TTAGAGGATC ACCCTGATTC TGGTTTTTAC GTTCATAACC
10861 CAAGAGGGGG TATAGAAGGA TTTTGTCAAA AATTATGGAC ACTCATATCT ATAAGTGCAA
10921 TACATCTAGC AGCTGTTAGA ATAGGCGTGA GGGTGACTGC AATGGTTCAA GGAGACAATC
10981 AAGCTATAGC TGTAACCACA AGAGTACCCA ACAATTATGA CTACAGAGTT AAGAAGGAGA
11041 TAGTTTATAA AGATGTAGTG AGATTTTTTG ATTCATTAAG AGAAGTGATG GATGATCTAG
11101 GTCATGAACT TAAATTAAAT GAAACGATTA TAAGTAGCAA GATGTTCATA TATAGCAAAA
11161 GAATCTATTA TGATGGGAGA ATTCTTCCTC AAGCTCTAAA AGCATTATCT AGATGTGTCT
11221 TCTGGTCAGA GACAGTAATA GACGAAACAA GATCAGCATC TTCAAATTTG GCAACATCAT
11281 TTGCAAAAGC AATTGAGAAT GGTTATTCAC CTGTTCTAGG ATATGCATGC TCAATTTTTA
11341 AGAATATTCA ACAACTATAT ATTGCCCTTG GGATGAATAT CAATCCAACT ATAACACAGA
11401 ATATCAGAGA TCAGTATTTT AGGAATCCAA ATTGGATGCA ATATGCCTCT TTAATACCTG
11461 CTAGTGTTGG GGGATTCAAT TACATGGCCA TGTCAAGATG TTTTGTAAGG AATATTGGTG
11521 ATCCATCAGT TGCCGCATTG GCTGATATTA AAGATTTAT TAAGGCGAAT CTATTAGACC
11581 GAAGTGTTCT TTATAGGATT ATGAATCAAG AACCAGGTGA GTCATCTTTT TTGGACTGGG
11641 CTTCAGATCC ATATTCATGC AATTTACCAC AATCTCAAAA TATAACCACC ATGATAAAAA
11701 ATATAACAGC AAGGAATGTA TTACAAGATT CACCAAATCC ATTATTATCT GGATTATTCA
11761 CAAATACAAT GATAGAAGAA GATGAAGAAT TAGCTGAGTT CCTGATGGAC AGGAAGGTAA
11821 TTCTCCCTAG AGTTGCACAT GATATTCTAG ATAATTCTCT CACAGGAATT AGAAATGCCA
11881 TAGCTGGAAT GTTAGATACG ACAAAATCAC TAATTCGGGT TGGCATAAAT AGAGGAGGAC
11941 TGACATATAG TTTGTTGAGG AAAATCAGTA ATTACGATCT AGTACAATAT GAAACACTAA
12001 GTAGGACTTT GCGACTAATT GTAAGTGATA AAATCAAGTA TGAAGATATG TGTTCGGTAG
12061 ACCTTGCCAT AGCATTGCGA CAAAAGATGT GGATTCATTT ATCAGGAGGA AGGATGATAA
12121 GTGGACTTGA AACGCCTGAC CCATTAGAAT TACTATCTGG GGTAGTAATA ACAGGATCAG
12181 AACATTGTAA AATATGTTAT TCTTCAGATG GCACAAACCC ATATACTTGG ATGTATTTAC
12241 CCGGTAATAT CAAAATAGGA TCAGCAGAAA CAGGTATATC GTCATTAAGA GTTCCTTATT
```

TABLE 41-continued (SEQ ID NO. 175)
Sequence of pFLC.PIV32CT, 15474 bp in sense orientation
(only the insert is shown)

```
12301 TTGGATCAGT CACTGATGAA AGATCTGAAG CACAATTAGG ATATATCAAG AATCTTAGTA
12361 AACCTGCAAA AGCCGCAATA AGAATAGCAA TGATATATAC ATGGGCATTT GGTAATGATG
12421 AGATATCTTG GATGGAAGCC TCACAGATAG CACAAACACG TGCAAATTTT ACACTAGATA
12481 GTCTCAAAAT TTTAACACCG GTAGCTACAT CAACAAATTT ATCACACAGA TTAAAGGATA
12541 CTGCAACTCA GATGAAATTC TCCAGTACAT CATTGATCAG AGTCAGCAGA TTCATAACAA
12601 TGTCCAATGA TAACATGTCT ATCAAAGAAG CTAATGAAAC CAAAGATACT AATCTTATTT
12661 ATCAACAAAT AATGTTAACA GGATTAAGTG TTTTCGAATA TTTATTTAGA TTAAAAGAAA
12721 CCACAGGACA CAACCCTATA GTTATGCATC TGCACATAGA AGATGAGTGT TGTATTAAAG
12781 AAAGTTTTAA TGATGAACAT ATTAATCCAG AGTCTACATT AGAATTAATT CGATATCCTG
12841 AAAGTAATGA ATTTATTTAT GATAAAGACC CACTCAAAGA TGTGGACTTA TCAAAACTTA
12901 TGGTTATTAA AGACCATTCT TACACAATTG ATATGAATTA TTGGGATGAT ACTGACATCA
12961 TACATGCAAT TTCAATATGT ACTGCAATTA CAATAGCAGA TACTATGTCA CAATTAGATC
13021 GAGATAATTT AAAAGAGATA ATAGTTATTG CAAATGATGA TGATATTAAT AGCTTAATCA
13081 CTGAATTTTT GACTCTTGAC ATACTTGTAT TTCTCAAGAC ATTTGGTGGA TTATTAGTAA
13141 ATCAATTTGC ATACACTCTT TATAGTCTAA AAATAGAAGG TAGGGATCTC ATTTGGGATT
13201 ATATAATGAG AACACTGAGA GATACTTCCC ATTCAATATT AAAAGTATTA TCTAATGCAT
13261 TATCTCATCC TAAAGTATTC AAGAGGTTCT GGGATTGTGG AGTTTTAAAC CCTATTTATG
13321 GTCCTAATAC TGCTAGTCAA GACCAGATAA AACTTGCCCT ATCTATATGT GAATATTCAC
13381 TAGATCTATT TATGAGAGAA TGGTTGAATG GTGTATCACT TGAAATATAC ATTTGTGACA
13441 GCGATATGGA AGTTGCAAAT GATAGGAAAC AAGCCTTTAT TTCTAGACAC CTTTCATTTG
13501 TTTGTTGTTT AGCAGAAATT GCATCTTTCG GACCTAACCT GTTAAACTTA ACATACTTGG
13561 AGAGACTTGA TCTATTGAAA CAATATCTTG AATTAAATAT TAAAGAAGAC CCTACTCTTA
13621 AATATGTACA AATATCTGGA TTATTAATTA AATCGTTCCC ATCAACTGTA ACATACGTAA
13681 GAAAGACTGC AATCAAATAT CTAAGGATTC GCGGTATTAG TCCACCTGAG GTAATTGATG
13741 ATTGGGATCC GGTAGAAGAT GAAAATATGC TGGATAACAT TTCAAAAACT ATAAATGATA
13801 ACTGTAATAA AGATAATAAA GGGAATAAAA TTAACAATTT CTGGGGACTA GCACTTAAGA
13861 ACTATCAAGT CCTTAAAATC AGATCTATAA CAAGTGATTC TGATGATAAT GATAGACTAG
13921 ATGCTAATAC AAGTGGTTTG ACACTTCCTC AAGGAGGGAA TTATCTATCG CATCAATTGA
13981 GATTATTCGG AATCAACAGC ACTAGTTGTC TGAAAGCTCT TGAGTTATCA CAAATTTTAA
14041 TGAAGGAAGT CAATAAAGAC AAGGACAGGC TCTTCCTGGG AGAAGGAGCA GGAGCTATGC
14101 TAGCATGTTA TGATGCCACA TTAGGACCTG CAGTTAATTA TTATAATTCA GGTTTGAATA
14161 TAACAGATGT AATTGGTCAA CGAGAATTGA AAATATTTCC TTCAGAGGTA TCATTAGTAG
14221 GTAAAAAATT AGGAAATGTG ACACAGATTC TTAACAGGGT AAAAGTACTG TTCAATGGGA
14281 ATCCTAATTC AACATGGATA GGAAATATGG AATGTGAGAG CTTAATATGG AGTGAATTAA
14341 ATGATAAGTC CATTGGATTA GTACATTGTG ATATGGAAGG AGCTATCGGT AAATCAGAAG
14401 AAACTGTTCT ACATGAACAT TATAGTGTTA TAAGAATTAC ATACTTGATT GGGGATGATG
14461 ATGTTGTTTT AGTTTCCAAA ATTATACCTA CAATCACTCC GAATTGGTCT AGAATACTTT
14521 ATCTATATAA ATTATATTGG AAAGATGTAA GTATAATATC ACTCAAAACT TCTAATCCTG
```

TABLE 41-continued (SEQ ID NO. 175)
Sequence of pFLC.PIV32CT, 15474 bp in sense orientation
(only the insert is shown)

```
14581 CATCAACAGA ATTATATCTA ATTTCGAAAG ATGCATATTG TACTATAATG GAACCTAGTG

14641 AAATTGTTTT ATCAAAACTT AAAAGATTGT CACTCTTGGA AGAAAATAAT CTATTAAAAT

14701 GGATCATTTT ATCAAAGAAG AGGAATAATG AATGGTTACA TCATGAAATC AAAGAAGGAG

14761 AAAGAGATTA TGGAATCATG AGACCATATC ATATGGCACT ACAAATCTTT GGATTTCAAA

14821 TCAATTTAAA TCATCTGGCG AAAGAATTTT TATCAACCCC AGATCTGACT AATATCAACA

14881 ATATAATCCA AAGTTTTCAG CGAACAATAA AGGATGTTTT ATTTGAATGG ATTAATATAA

14941 CTCATGATGA TAAGAGACAT AAATTAGGCG GAAGATATAA CATATTCCCA CTGAAAAATA

15001 AGGGAAAGTT AAGACTGCTA TCGAGAAGAC TAGTATTAAG TTGGATTTCA TTATCATTAT

15061 CGACTCGATT ACTTACAGGT CGCTTTCCTG ATGAAAAATT TGAACATAGA GCACAGACTG

15121 GATATGTATC ATTAGCTGAT ACTGATTTAG AATCATTAAA GTTATTGTCG AAAAACATCA

15181 TTAAGAATTA CAGAGAGTGT ATAGGATCAA TATCATATTG GTTTCTAACC AAAGAAGTTA

15241 AAATACTTAT GAAATTGATC GGTGGTGCTA AATTATTAGG AATTCCCAGA CAATATAAAG

15301 AACCCGAAGA CCAGTTATTA GAAAACTACA ATCAACATGA TGAATTTGAT ATCGATTAAA

15361 ACATAAATAC AATGAAGATA TATCCTAACC TTTATCTTTA AGCCTAGGAA TAGACAAAAA

15421 GTAAGAAAAA CATGTAATAT ATATATACCA AACAGAGTTC TTCTCTTGTT TGGT
```

The cDNA engineering was designed so that the final PIV3-2 antigenomes conformed to the rule of six (Calain et al., J. Virol. 67:4822-30, 1993; Durbin et al., Virology 234: 74-83, 1997, each incorporated herein by reference). The PIV3-2 insert in pFLC.PIV32TM is 15498 nt in length, and that in pFLC.PIV32CT is 15474 nt in length. These total lengths do not include two 5'-terminal G residues contributed by the T7 promoter, because it is assumed that they are removed during recovery.

Transfection and Recovery of Recombinant Chimeric PIV3-PIV2 Viruses

HEp-2 cell monolayers were grown to confluence in six-well plates, and transfections were performed essentially as described (Tao et al., 72:2955-2961, 1998, incorporated herein by reference). The HEp-2 monolayer in one well was transfected with 5 μg PIV3-PIV2 antigenomic cDNA and three support plasmids, 0.2 μg pTM(N), 0.2 μg pTM(PnoC), 0.1 μg pTM(L) in 0.2 ml of MEM containing 12 μl LipofectACE (Life Technologies). The cells were infected simultaneously with MVA-T7 at a multiplicity of infection (MOI) of 3 in 0.8 ml of serum-free MEM containing 50 μg/ml gentamicin and 2 mM glutamine. The chimeric antigenomic cDNA pFLC.2G+.hc (Tao et al., *J. Virol.* 72:2955-2961, 1998), was transfected in parallel as a positive control. After incubation at 32° C. for 12 hours, the transfection medium was replaced with 1.5 ml of fresh serum-free MEM supplemented with 50 μg/ml gentamicin and 2 mM glutamine. Transfected cells were incubated at 32° C. for two additional days. Gamma-irradiated porcine trypsin (p-trypsin; T1311, Sigma, St Louis, Mo.) was added to a final concentration of 0.5 μg/ml on day 3 post transfection. Cell culture supernatants were harvested and passaged (referred to as passage 1) onto fresh Vero cell monolayers in T25 flasks. After overnight adsorption, the transfection harvest was replaced with fresh VP-SFM supplemented with 0.5 μg/ml p-trypsin. Cultures from passage 1 were incubated at 32° C. for 4 days, and the amplified virus was harvested and further passaged on Vero cells (referred to as passage 2) for another 4 days at 32° C. in the presence of 0.5 μg/ml p-trypsin. The presence of viruses in the passage 2 cultures was determined by hemadsorption with 0.2% guinea pig red blood cells (RBCs). Viruses were further purified by three consecutive terminal dilutions performed using Vero cells maintained in VP-SFM supplemented with 2 mM glutamine, 50 μg/ml gentamicin, and 0.5 μg/ml p-trypsin. Following the third terminal dilution, virus was further amplified three times on Vero cells, and this virus suspension was used for further characterization in vitro and in vivo.

Confirmation of the Chimeric Nature of vRNA Using Sequencing and Restriction Analysis of PCR Products For analysis of the genetic structure of vRNAs, the recombinant PIVs were amplified on LLC-MK2 cells and concentrated. vRNA was extracted from the viral pellets and reverse transcribed using the Superscript Preamplification System. RT-PCR was performed using the Advantage cDNA synthesis kit and primer pairs specific to PIV2 or PIV3 (21, 22 or 23, 24 in Table 38). RT-PCR products were either analyzed by restriction digestion or gel purified and analyzed by sequencing.

Replication of PIVs in LLC-MK2 Cells

Growth of the PIV viruses in tissue culture was evaluated by infecting confluent LLC-MK2 cell monolayers on six-well plates in triplicate at an MOI of 0.01. The inoculum was removed after absorption for 1 hour at 32° C. Cells were washed 3 times with serum-free OptiMEM I, fed with 2 ml/well of OptiMEM I supplemented with 50 μg/ml gentamicin and 0.5 μg/ml p-trypsin, and incubated at 32° C. At each 24 hour interval, a 0.5 ml aliquot of medium was removed from each well and flash-frozen, and 0.5 ml fresh medium with p-trypsin was added to the cultures. The virus in the aliquots was titrated at 32° C. on LLC-MK2 cell monolayers using fluid overlay as previously described (Tao et al., *J. Virol.* 72:2955-2961, 1998, incorporated herein by reference), and the endpoint of the titration was determined by hemadsorption, and the titers are expressed as $\log_{10}$ TCID$_{50}$/ml.

Replication of Recombinant Chimeric PIV3-PIV2 Viruses at Various Temperatures

Viruses were serially diluted in 1×L15 supplemented with 2 mM glutamine and 0.5 µg/ml p-trypsin. Diluted viruses were used to infect LLC-MK2 monolayers in 96 well plates. Infected plates were incubated at various temperatures for 7 days as described (Skiadopoulos et al., Vaccine 18:503-510, 1999, incorporated herein by reference). Virus titers were determined as above.

Replication, Immunogenicity, and Protective Efficacy of Recombinant Chimeric PIV3-PIV2 Viruses in the Respiratory Tract of Hamsters Golden Syrian hamsters in groups of six were inoculated intranasally with $10^{5.3}$ TCID$_{50}$ of recombinant or biologically-derived viruses. Four days after inoculation, hamsters were sacrificed and their lungs and nasal turbinates were harvested and prepared for quantitation of virus (Skiadopoulos et al., Vaccine 18:503-510, 1999, incorporated herein by reference). The titers are expressed as mean $\log_{10}$ TCID$_{50}$/gram of tissue for each group of six hamsters.

Hamsters in groups of 12 were infected intranasally with $10^{5.3}$ TCID$_{50}$ of viruses on day 0, and six hamsters from each group were challenged four weeks later with $10^6$ TCID$_{50}$ of PIV1 or $10^6$ TCID$_{50}$ of PIV2. Hamsters were sacrificed 4 days after challenge and their lungs and nasal turbinates were harvested. Challenge virus titers in the harvested tissue was determined as previously described (Tao et al., J. Virol. 72:2955-2961, 1998, incorporated herein by reference). The virus titers are expressed as mean $\log_{10}$ TCID$_{50}$/gram of tissue for each group of six hamsters. Serum samples were collected three days prior to inoculation and on day 28, and hemagglutination-inhibition antibody (HAI) titers against PIV1, PIV2, and PIV3 were determined as previously described (van Wyke Coelingh et al., Virology 143:569-582, 1985, incorporated herein by reference). The titers are expressed as reciprocal mean $\log_2$.

Replication, Immunogenicity, and Protective Efficacy of Recombinant Chimeric PIV3-PIV2 Viruses in African Green Monkeys (AGMs)

AGMs in groups of 4 were infected intranasally and intratracheally with $10^5$ TCID$_{50}$ of virus at each site on day 0. Nasal/throat (NT) swab specimens and tracheal lavages were collected for 12 and 5 days, respectively, as previously described (van Wyke Coelingh et al., Virology 143:569-582, 1985). On day 29, immunized AGMs were challenged intranasally and intratracheally with $10^5$ TCID$_{50}$ of PIV2/V94 at each site. NT swab specimens and tracheal lavages were collected for 10 and 5 days, respectively. Pre-immunization, post-immunization, and post challenge serum samples were collected on days −3, 28, and 60, respectively. Virus titers in the NT swab specimens and in tracheal lavages were determined as previously described (Tao et al., J. Virol. 72:2955-2961, 1998). Titers are expressed as $\log_{10}$ TCID$_{50}$/ml. Serum neutralizing antibody titers against PIV1 and PIV2 were determined as previously described (van Wyke Coelingh et al., Virology 143:569-582, 1985), and the titers are expressed as reciprocal mean Replication and Immunogenicity of Recombinant Chimeric PIV3-PIV2 Viruses in Chimpanzees Chimpanzees in groups of 4 were infected intranasally and intratracheally with $10^5$ TCID$_{50}$ of PIV2/V94 or rPIV3-2TM on day 0 as previously described (Whitehead et al., J. Virol. 72:4467-4471, 1998, incorporated herein by reference). NT swab specimens were collected daily for 12 days and tracheal lavages were obtained on days 2, 4, 6, 8, and 10. Virus titers in the specimens were determined as previously described (Tao et al., J. Virol. 72:2955-2961, 1998, incorporated herein by reference). The peak virus titers are expressed as mean $\log_{10}$ TCID$_{50}$/ml. Pre-immunization and post-immunization serum samples were collected on days −3 and 28, respectively. Serum neutralizing antibody titers against PIV1 and PIV2 were determined as previously described (van Wyke Coelingh et al., Virology 143:569-582, 1985, incorporated herein by reference), and the titers are expressed as reciprocal mean $\log_2$.

Viable Recombinant Chimeric Virus was not Recovered from PIV3-PIV2 Chimeric cDNA Encoding the Complete PIV2 F and HN Proteins The construction of the PIV3-PIV2 chimeric cDNA, in which the F and HN ORFs of the JS wild type PIV3 were replaced by those of PIV2/V94, is described above and summarized in FIG. 36. The final plasmid construct, pFLC.PIV32hc (FIG. 36), encodes a PIV3-PIV2 chimeric antigenomic RNA of 15492 nt, which conforms to the rule of six.

HEp-2 cell monolayers were transfected with pFLC.PIV32hc along with the three support plasmids pTM (N), pTM(PnoC), and pTM(L) using LipofectACE, and the cells were simultaneously infected with MVA-T7 as previously described (Tao et al., J. Virol. 72:2955-2961, 1998, incorporated herein by reference). Virus was not recovered from several initial transfections using pFLC.PIV32hc, while chimeric viruses were recovered from all the transfections using control plasmid pFLC.2G+.hc.

Consistent with these results is the possibility that a mutation occurred outside of the 4 kb BspEI-SpeI segment of pFLC.PIV32hc that prevented the recovery of rPIV3-2 virus from cells transfected with this cDNA clone. To examine this possibility, the BspEI-SpeI fragments of p38'ΔPIV31hc and p38'ΔPIV32hc were exchanged. The regenerated p38'ΔPIV31hc and p38'ΔPIV32hc were identical to those in FIG. 36 except that the SpeI-SphI fragments containing PIV3 L gene sequences were exchanged. The BspEI-SphI fragments of these two regenerated cDNAs were introduced into the BspEI-SphI window of a PIV3 full-length clone, p3/7-(131)2G+, in five separate independent ligations to give 10 pFLC.2G+.hc and pFLC.PIV32hc clones (2 clones selected from each ligation), respectively. (Note that the PIV3 sequences outside of the BspEI-SphI window of p3/7-(131) 2G+, pFLC.2G+.hc, and pFLC.PIV32hc are identical). Thus, this would have replaced any PIV3 bacbone sequence which might have acquired a spurious mutation with sequence known to be functional. Furthermore, the functionality of the backbone was reevaluauated in parallel. None of the 10 pFLC.PIV32hc cDNA clones yielded viable virus, but each of the 10 pFLC.2G+.hc cDNA clones yielded viable virus. Virus was not recovered from pFLC.PIV32hc despite passaging the transfection harvest in a fashion similar to that used successfully to recover the highly defective PIV3 C-knock out recombinant (Durbin et al., Virology 261:319-30, 1999, incorporated herein by reference). Since each of the unique components used to generate the pFLC.PIV32hc was used to successfully generate other recombinant viruses except the cytoplasmic tail domains of F and HN, it is highly unlikely that errors in the cDNA account for the failure to yield recombinant virus in this case. Rather, the favored interpretation is that the full-length PIV2 F and HN glycoproteins are not compatible with one or more of the PIV3 proteins needed for virus growth.

Recovery of Chimeric Viruses from PIV3-PIV2 Chimeric cDNAs Encoding the Chimeric PIV3-PIV2 F and HN Proteins Using two other strategies, new chimeric PIV3-PIV2 antigenomic cDNAs were constructed, in which the ectodomain or the ectodomain and the transmembrane domain of PIV3 F and HN glycoproteins were replaced by their PIV2 counterparts. The construction of the four full-length cDNAs, namely pFLC.PIV32TM, pFLC.PIV32TMcp45, pFLC.PIV32CT, and pFLC.PIV32CTcp45, is described above and summarized in FIGS. 37, 38, and 39. The PIV3-2 inserts in the final plasmids pFLC.PIV32TM and pFLC.PIV32CT, in which the F and HN genes encoded chimeric glycoproteins, were 15498 nt and 15474 nt in length, respectively, and conformed to the rule of six (Calain et al., J. Virol. 67:4822-30, 1993; Durbin et al., Virology 234:74-83, 1997, each incorporated herein by reference). The authenticity of those four constructs was confirmed by sequencing of the BspEI-SphI region and by restriction analysis.

Recombinant chimeric viruses were recovered from full-length clones pFLC.PIV32TM, pFLC.PIV32CT, pFLC.PIV32TMcp45, or pFLC.PIV32CTcp45 and were designated rPIV3-2TM, rPIV3-2CT, rPIV3-2TMcp45, and rPIV3-2CTcp45, respectively. These viruses were biologically cloned by 3 consecutive terminal dilutions on Vero cells and then amplified three times in Vero cells.

Genetic Characterization of Recombinant Chimeric PIV3-PIV2 Viruses

The biologically-cloned chimeric PIV3-PIV2 viruses, rPIV3-2TM, rPIV3-2CT, rPIV3-2TMcp45, and rPIV3-2CTcp45, were propagated on LLC-MK2 cells and then concentrated. Viral RNAs extracted from pelleted viruses were used in RT-PCR amplification of specific gene segments using primer pairs specific to PIV2 or PIV3 (21, 22 or 23, 24 in Table 38). The restriction enzyme digestion patterns of the RT-PCR products amplified with PIV2 specific primer pairs from rPIV3-2TM, rPIV3-2CT, rPIV3-2TMcp45, and rPIV3-2CTcp45, were each distinct from that derived from PIV2/V94, and their patterns, using EcoRI, MfeI, NcoI, or PpuMI, were those expected from the designed cDNA. Nucleotide sequences for the 8 different PIV3-PIV2 junctions in F and HN genes of rPIV3-2TM and rPIV3-2CT are given in FIG. 39. Also, the cp45 markers present in rPIV3-2TMcp45 and rPIV3-2CTcp45, except those in the 3'-leader region and the gene start of NP, were verified with RT-PCR and restriction enzyme digestion as previously described (Skiadopoulos et al., J. Virol. 73:1374-81, 1999, incorporated herein by reference). These results confirmed the chimeric nature of the recovered PIV3-PIV2 viruses as well as the presence of the introduced cp45 mutations.

PIV3-PIV2 Recombinant Chimeric Viruses Replicate Efficiently in LLC-MK2 Cells In Vitro The kinetics and magnitude of replication in vitro of the PIV3-PIV2 recombinant chimeric viruses were assessed by multicycle replication in LLC-MK2 cells (FIG. 40). LLC-MK2 cell monolayer cultures in six-well plates were infected in triplicate with rPIV3-2TM, rPIV3-2CT, rPIV3-2TMcp45, or rPIV3-2CTcp45 at an MOI of 0.01 in the presence of p-trypsin (0.5 μg/ml). Samples were removed from culture supernate at 24 hour intervals for 6 days. Each of the recombinant chimeric viruses, except rPIV3-2CTcp45 (clone 2A1), replicated at the same rate and to a similar level as their PIV2/V94 parent virus indicating that PIV3-PIV2 chimerization of F and HN proteins did not alter the rates of growth of the recombinant chimeric viruses, and all reached a titer of 107 TCID$_{50}$/ml or higher. Only the rPIV3-2CTcp45 grew slightly faster in each of two experiments and reached its peak titer earlier than PIV2/V94. This accelerated growth pattern was likely a result of an unidentified mutation in this clone since a sister clone failed to exhibit this growth pattern. rPIV3-2CTcp45 clone 2A1 was used in the studies described below.

The Level of Temperature Sensitivity of rPIV3-2 Chimeric Viruses and their cp45 Derivatives The level of temperature sensitivity of replication of PIV3-PIV2 recombinant chimeric viruses was tested to determine if rPIV3-2TM and rPIV3-2CT viruses exhibit a ts phenotype and to determine if the acquisition of the 12 cp45 mutations by these viruses specified a level of temperature sensitivity characteristic of cp45 derivatives bearing these 12 PIV3 cp45 mutations (Skiadopoulos et al., J. Virol. 73:1374-81, 1999, incorporated herein by reference). The level of temperature sensitivity of the virus was determined in LLC-MK2 cell monolayers as previously described (Skiadopoulos et al., Vaccine 18:503-510, 1999, incorporated herein by reference) (Table 42). The titer of rPIV3-2TM and rPIV3-2CT was fairly constant at permissive temperature (32° C.) and the various restrictive temperatures tested indicating these recombinants were ts+. In contrast, their cp45 derivatives, rPIV3-2TMcp45 and rPIV3-2CTcp45, were ts and the level of temperature sensitivity was similar to that of rPIV3-1 cp45, the chimeric PIV3-PIV1 virus carrying the complete PIV1 F and HN glycoproteins and the same set of 12 cp45 mutations. Thus the in vitro properties of rPIV3-2TM and rPIV3-2CT viruses and their cp45 derivative are similar to those of rPIV3-1 and rPIV3-1 cp45, respectively, suggesting that the in vivo properties of the rPIV3-2 and rPIV3-1 viruses would also be similar, but surprisingly this was not the case.

TABLE 42

The replication of rPIV3-2CT and rPIV3-2TM are not temperature sensitive in LLC-MK2 cells, whereas the inclusion of the cp45 mutations confers the cp45 temperature sensitive phenotype

| Virus | Titer at 32° C[a] (log$_{10}$ TCID$_{50}$) | Change in titer (log$_{10}$) at various temperatures compared to that at 32°[a, b] | | | | | |
|---|---|---|---|---|---|---|---|
| | | 35°[c] | 36° | 37° | 38° | 39° | 40° |
| rPIV3/JS | 7.9 | 0.3[b] | 0.1 | 0.1 | (0.3)[b] | (0.4) | 0.4 |
| PIV3cp45[e] | 7.8 | 0.5 | 0.3 | 1.3 | 3.4[d] | 6.8 | 6.9 |
| PIV1/Wash64[e] | 8.5 | 1.5 | 1.1 | 1.4 | 0.6 | 0.5 | 0.9 |
| rPIV3-1 | 8.0 | 0.8 | 0.5 | 0.6 | 0.9 | 1.1 | 2.6 |
| rPIV3-1cp45 | 8.0 | 0.5 | 0.4 | 3.4[d] | 4.8 | 6.6 | 7.5 |
| PIV2/V9412[e] | 7.8 | 0.3 | (0.1) | 0.0 | (0.4) | (0.4) | 0.0 |
| rPIV3-2CT | 6.9 | 0.3 | 0.3 | 0.6 | (0.1) | 0.6 | 0.4 |
| rPIV3-2TM | 8.3 | 0.3 | (0.1) | 0.3 | 0.6 | 1.0 | 2.1[d] |
| rPIV3-2CTcp45 | 8.0 | 0.8 | (0.4) | 2.0[d] | 4.3 | 7.5 | ≧7.6 |
| rPIV3-2TMcp45 | 8.0 | 0.3 | 0.6 | 2.4[d] | 5.4 | 7.5 | ≧7.6 |

[a]Data presented are means of two experiments.
[b]Numbers not in parentheses represent titer decrease; numbers in parentheses represent titer increase.
[c]Data at 35° were from one experiment only.
[d]Values which are underlined represent the lowest temperature at which there was a 100-fold reduction of virus titer compared to the titer at permissive temperature (32° C.). This restrictive temperature is referred to as the shut-off temperature.
[e]Biologically-derived viruses.

rPIV3-2TM and rPIV3-2CT are Attenuated, Immunogenic, and Highly Protective in Hamsters, and Introduction of cp45 Mutations Results in Highly Attenuated and Less Protective Viruses Hamsters in groups of six were inoculated intranasally with 10$^{5.3}$ TCID$_{50}$ of rPIV3-2TM, rPIV3-2CT, rPIV3-2TMcp45, rPIV3-2CTcp45, or control viruses. It was previously seen that rPIV3-1 virus replicated in the upper and lower respiratory tract of hamsters like that of its PIV3 and PIV1 parents (Skiadopoulos et al., *Vaccine* 18:503-510, 1999; Tao et al., *J. Virol.* 72:2955-2961, 1998, each incorporated herein by reference). PIV2 virus replicates efficiently in hamsters, but rPIV3-2TM and rPIV3-2CT viruses each replicated to a 50- to 100-fold lower titer than their PIV2 and PIV3 parents in the upper respiratory tract and to a 320- to 2000-fold lower titer in the lower respiratory tract (Table 43). This indicates that the chimeric PIV3-PIV2 F and HN glycoproteins specify an unexpected attenuation phenotype in hamsters. rPIV3-2TMcp45 and rPIV3-2CTcp45, the derivatives carrying the cp45 mutations, were 50- to 100-fold more attenuated than their respective rPIV3-2 parents, with only barely detectable replication in the nasal turbinates, and none in the lungs. These rPIV3-2 cp45 viruses were clearly more attenuated than rPIV3-1 cp45, exhibiting an additional 50-fold reduction of replication in the nasal turbinates. Thus, the attenuating effects of the chimerization of F and HN glycoproteins and that specified by cp45 mutations were additive.

TABLE 43

The rPIV3-2TM and rPIV3-2CT viruses, in contrast to rPIV3-1, are attenuated in the respiratory tract of hamsters and importation of the cp45 mutations resulted in further attenuation.

| | Virus titers in the indicated tissue ($\log_{10}TCID_{50}/g \pm S.E.$)[b] [Duncan Group][e] | | | |
|---|---|---|---|---|
| Virus[a] | NT | $\log_{10}$ titer reduction | Lung | $\log_{10}$ titer reduction |
| rPIV3/JS | 5.9 ± 0.1[AB] | 0 | 6.5 ± 0.1[A] | 0 |
| rPIV3cp45 | 4.5 ± 0.2[C] | 1.4[c] | 1.8 ± 0.2[E] | 4.7[c] |
| PIV1/Wash64[d] | 5.7 ± 0.1[B] | — | 5.5 ± 0.1[B] | — |
| rPIV3-1 | 6.4 ± 0.2[A] | 0 | 6.6 ± 0.2[A] | 0 |
| rPIV3-1cp45 | 3.1 ± 0.1[D] | 3.3[c] | 1.2 ± 0.0[F] | 5.4[c] |
| PIV2/V94[d] | 6.2 ± 0.2[A] | 0 | 6.4 ± 0.2[A] | 0 |
| rPIV3-2CT | 4.5 ± 0.4[C] | 1.7[c] | 3.1 ± 0.1[D] | 3.3[c] |
| rPIV3-2TM | 3.9 ± 0.3[C] | 2.3[c] | 3.9 ± 0.4[C] | 2.5[c] |
| rPIV3-2CTcp45 | 1.4 ± 0.1[E] | 4.8[c] | 1.5 ± 0.2[E] | 4.9[c] |
| rPIV3-2TMcp45 | 1.6 ± 0.2[E] | 4.6[c] | 1.4 ± 0.1[E] | 5.0[c] |

[a]Hamsters in group of six were inoculated intranasally with $10^{5.3}$ TCID$_{50}$ of indicated virus on day 0.
[b]Hamsters were sacrificed and their tissue samples harvested on day 4. The virus titer in hamster tissues was determined and the results are expressed as $\log_{10}TCID_{50}/g \pm$ standard error (SE). NT = nasal turbinates.
[c]The $\log_{10}$ titer reduction values are derived by comparing: rPIV3cp45 against rPIV3/JS; rPIV3-1 cp45 against rPIV3-1; each of the PIV3-PIV2 chimeras against PIV2/V94.
[d]Biologically-derived viruses.
[e]Grouping as analyzed by Duncan mult:range test.

To determine the immunogenicity and protective efficacy of the PIV3-PIV2 chimeric viruses, hamsters in groups of twelve were immunized with $10^{5.3}$ TCID$_{50}$ of rPIV3-2TM, rPIV3-2CT, rPIV3-2TMcp45, rPIV3-2CTcp45, or control viruses on day O, Six of the hamsters from each group were challenged with $10^6$ TCID$_{50}$ of PIV1 on day 29, and the remaining half were challenged with PIV2 on day 32. Hamsters were sacrificed 4 days after challenge and the lungs and nasal turbinates harvested. Serum samples were collected on day −3 and day 28, and their HAI antibody titer against PIV1, PIV2, and PIV3 was determined. As shown in Table 28, despite their attenuated growth in hamsters, immunization with rPIV3-2TM or rPIV3-2CT each elicited a level of serum HAI antibody against PIV2 that was comparable to that induced by infection with wild type PIV2N94. Immunization of hamsters with rPIV3-2TM and rPIV3-2CT resulted in complete restriction of the replication of PIV2 challenge virus. rPIV3-2TMcp45 and rPIV3-2CTcp45 failed to elicit a detectable serum antibody response, and immunization of hamsters with either of these two viruses resulted in only a 10- to 100-fold reduction of replication of the PIV2 challenge virus in the lower respiratory tract (Table 44).

TABLE 44

The rPIV3-2CT and rPIV3-2TM viruses are highly protective in hamsters against challenge with wild type PIV2, but not against PIV1

| | HAI antibody titer[b] against indicated virus | | | Challenge virus titer[c] in indicated tissue ($\log_{10}TCID_{50}/g \pm SE$) | | | |
|---|---|---|---|---|---|---|---|
| | (reciprocal mean $\log_2 \pm SE$) | | | PIV1 | | PIV2 | |
| Immunizing virus[a] | PIV1 | PIV2 | PIV3 | NT | Lung | NT | Lung |
| rPIV3/JS | ≤1 | ≤1 | 10.2 ± 0.1 | 6.2 ± 0.2 | 5.8 ± 0.1 | 5.9 ± 0.2 | 5.7 ± 0.2 |
| rPIV3cp45 | ≤1 | ≤1 | 8.6 ± 0.2 | 5.9 ± 0.3 | 5.1 ± 0.3 | 5.6 ± 0.2 | 4.5 ± 0.7 |
| PIV1 | 6.7 ± 0.2 | ≤1 | ≤1 | 1.3 ± 0.1 | ≤1.2 ± 0.0 | 6.1 ± 0.2 | 6.2 ± 0.3 |
| rPIV3-1 | 6.4 ± 0.2 | ≤1 | ≤1 | ≤1.2 ± 0.0 | ≤1.2 ± 0.0 | 6.5 ± 0.2 | 5.0 ± 0.6 |
| rPIV3-1cp45 | 1.8 ± 0.6 | ≤1 | ≤1 | 3.9 ± 0.4 | 1.6 ± 0.3 | 6.2 ± 0.2 | 4.5 ± 0.6 |
| PIV2 | ≤1 | 4.0 ± 0.0 | ≤1 | 5.9 ± 0.2 | 5.5 ± 0.1 | ≤1.2 ± 0.0 | ≤1.2 ± 0.0 |
| rPIV3-2CT | ≤1 | 3.6 ± 0.8 | ≤1 | 5.3 ± 0.1 | 5.2 ± 0.3 | ≤1.2 ± 0.0 | ≤1.2 ± 0.0 |
| rPIV3-2TM | ≤1 | 4.5 ± 0.2 | ≤1 | 5.9 ± 0.2 | 4.4 ± 0.3 | ≤1.2 ± 0.0 | ≤1.2 ± 0.0 |
| rPIV3-2CT.cp45 | ≤1 | ≤1 | ≤1 | 6.2 ± 0.2 | 5.7 ± 0.1 | 5.3 ± 0.2 | 3.3 ± 0.8 |
| rPIV3-2TM.cp45 | ≤1 | ≤1 | ≤1 | 5.8 ± 0.3 | 4.4 ± 0.3 | 5.5 ± 0.2 | 3.7 ± 0.7 |

[a]Hamsters in groups of 12 were immunized intranasally with $10^{5.3}$ TCID$_{50}$ of the indicated virus on day 0.
[b]Serum samples were collected two days before immunization and 28 days after immunization. They were tested for HAI antibody titer against the three PIVs, and the antibody titers are presented as reciprocal mean $\log_2 \pm$ standard error (SE).
[c]Six hamsters from each group were challenged intranasally with $10^6$ TCID$_{50}$ of PIV1 (on day 29) or PIV2 (on day 32). Hamster tissues were harvested 4 days after challenge, and the virus titer in indicated tissues are expressed as $\log_{10}TCID_{50}/g \pm SE$.

rPIV3-2TM and rPIV3-2CT are Attenuated, Immunogenic, and Highly Protective in AGMs, whereas Introduction of cp45 Mutations Results in Highly Attenuated and Poorly Protective Viruses Certain recombinant PIV3 and RSV viruses may exhibit different levels of attenuation in rodents and primates (Skiadopoulos et al., Vaccine 18:503-510, 1999; Skiadopoulos et al., J. Virol. 73:1374-81, 1999a; Skiadopoulos et al., Virology 272:225-34, 2000; Whitehead et al., J. Virol. 73:9773-9780, 1999, each incorporated herein by reference), indicating that attenuation can be somewhat species specific. Therefore, the rPIV3-2 viruses were evaluated for their level of replication and immunogenicity in AGMs. AGMs in groups of four were intranasally and intratracheally administered $10^5$ TCID$_{50}$ per site of rPIV3-2TM, rPIV3-2CT, rPIV3-2TMcp45, rpiv3-2CTcp45, PIV2/V94, or rPIV3-1 on day 0. Virus in the NT swab specimens (collected day 1 to 12) and tracheal lavages (collected on day 2, 4, 5, 8, and 10) were titered as previously described (van Wyke Coelingh et al., Virology 143:569-582, 1985, incorporated herein by reference). As shown in Table 45, rPIV3-2TM and rPIV3-2CT were clearly attenuated in the respiratory tract of AGMs as indicated by a peak titer of virus shedding lower in both the upper and lower respiratory tract than their PIV2/V94 parent virus.

rPIV3-2TMcp45 and rPIV3-2CTcp45, the derivatives carrying cp45 mutations, were detected at very low levels, if at all, in the NT swab and tracheal lavage specimens suggesting that the attenuating effects of chimerization of the F and HN glycoproteins and that specified by the cp45 mutations were additive for AGMs as well as for hamsters.

To determine whether immunization of AGMs with the PIV3-PIV2 chimeric viruses is protective against PIV2 challenge, AGMs previously infected with a rPIV3-2 virus were challenged with $10^5$ TCID$_{50}$ of PIV2 on day 28 (Table 45). Virus present in the NT swab specimens (collected day 29 to 38) and tracheal lavages fluids (collected on day 30, 32, 34, 36, and 38) was titered as previously described (Durbin et al., Virology 261:319-30, 1999, incorporated herein by reference). As shown in Table 45, immunization with rPIV3-2TM and rPIV3-2CT induced a high level of restriction of the replication of PIV2/V94 challenge virus. In contrast, immunization of AGMs with rPIV3-2TMcp45 and rPIV3-2CTcp45 failed to restrict the replication of PIV2/V94 challenge virus and these animals developed very low levels of pre-challenge serum neutralizing antibody to PIV2. The complete restriction of replication of PIV2/V94 challenge virus in rPIV3-2CT immunized AGMs was associated with a 2.5-fold greater level of pre-challenge serum antibody to PIV2 than that of rPIV3-2TM immunized AGMs which provided incomplete protection.

TABLE 45

The rPIV3-2CT or rPIV3-2TM viruses are attenuated for replication in the respiratory tract of African green monkeys, yet still induce resistance to challenge with wild type PIV2

| Immunizing[a] virus | Mean peak titer[b] of immunizing virus in indicated site ($\log_{10}$TCID$_{50}$/ml ± SE) | | Serum neutralization antibody titer[c] against indicated virus (mean reciprocal $\log_2$ ± SE) | | Mean peak titer[d] of PIV2/V94 challenge virus in indicated site ($\log_{10}$TCID$_{50}$/ml ± SE) | |
|---|---|---|---|---|---|---|
| | NT | TL | PIV1 | PIV2 | NT | TL |
| rPIV3-1 | 2.6 ± 0.5 | 3.2 ± 0.1 | 6.3 ± 0.4 | 3.1 ± 0.3 | 3.6 ± 0.2 | 3.3 ± 0.7 |
| PIV2/V94 | 2.8 ± 0.7 | 5.0 ± 0.3 | 3.8 ± 0.0 | 7.1 ± 0.7 | ≤0.2 | ≤0.2 |
| rPIV3-2CT | 1.5 ± 0.4 | 0.5 ± 0.2 | 2.9 ± 0.1 | 7.2 ± 0.1 | ≤0.2 | ≤0.2 |
| rPIV3-2TM | 1.4 ± 0.1 | 1.6 ± 0.7 | 4.1 ± 0.1 | 5.9 ± 0.2 | 1.6 ± 0.6 | 1.3 ± 0.9 |
| rPIV3-2CTcp45 | 1.0 ± 0.2 | ≤0.2 | 4.1 ± 0.1 | 5.3 ± 0.0 | 3.3 ± 0.4 | 3.5 ± 0.3 |
| rPIV3-2TMcp45 | 0.6 ± 0.3 | ≤0.2 | 3.4 ± 0.2 | 4.6 ± 0.6 | 3.0 ± 0.5 | 4.1 ± 0.2 |

[a]African green monkeys in group of 4 were inoculated with $10^5$ TCID$_{50}$ of indicated virus intranasally and intratracheally on day 0.
[b]Combined nasal wash and throat swab (NT) samples were collected on days 1 to 12. Tracheal lavage (TL) samples were collected on days 2, 4, 6, 8, and 10. The virus titers were determined on LLC-MK2 monolayers and expressed as $\log_{10}$TCID$_{50}$/ml ± standard error (SE).
[c]Serum samples collected on day 28 were assayed for their neutralizing antibody titers against PIV1 and PIV2. The titers were expressed as reciprocal mean $\log_2$ ± SE.
[d]NT specimens were collected on days 29 to 38. TL specimens were collected on days 30, 32, 34, 36, and 38.

rPIV3-2TM is Attenuated in its Replication in the Respiratory Tract of Chimpanzees Chimpanzees in groups of 4 were inoculated intranasally and intratracheally with $10^5$ TCID$_{50}$ of rPIV3-2TM or PIV2/V94 on day 0. NT swab specimens (day 1 to 12) and tracheal lavage (days 2, 4, 6, 8, and 10) samples were collected. Virus titer was determined as previously described (Durbin et al., Virology 261:319-30, 1999, incorporated herein by reference), and results are expressed as $\log_{10}$ TCID$_{50}$/ml. As shown in Table 46, rPIV3-2TM had a lower peak titer than it wild type parent PIV2/V94 and was shed for a significantly shorter duration than PIV2/94, indicating that rPIV3-2TM is attenuated in chimpanzees. PIV2/94 wt virus replicates to low levels in chimpanzees compared to hamsters and AFGs, whereas rPIV3-2TM virus was attenuated in each of these model hosts.

TABLE 46 rPIV3-2TM is attenuated in the respiratory tract of chimpanzees and yet still elicits a strong serum immune response to PIV2

| Inoculated virus[a] | Mean peak titer[b] of virus shed in indicated site ($\log_{10}TCID_{50}$/ml ± SE) | | Mean days of virus shedding in the upper respiratory tract (days ± SE) | Serum neutralizing antibody titer[c] against indicated virus (recirpocal mean $\log_2$ ± SE) | |
|---|---|---|---|---|---|
| | NT | TL | | PRE | POST |
| PIV2/V94 | 2.9 ± 0.6 | 1.2 ± 0.5 | 8.8 ± 1.1[d] | ≦2.8 ± 0.0 | 6.2 ± 0.5 |
| rPIV3-2TM | 2.0 ± 0.3 | ≦0.5 ± 0.0 | 2.5 ± 0.7[d] | 3.3 ± 0.2 | 4.3 ± 0.4 |

[a]Chimpanzees in group of four were inoculated intranasally and intratracheally with $10^5$ TCID50 of indicated virus.
[b]Nose/throat (NT) swab specimens and tracheal lavages (TL) were collected for 12 and 10 days, respectively, and virus titer were determined. The peak titers are expressed as $\log_{10}TCID_{50}$/ml ± standard error (SE).
[c]Serum samples collected 3 days prior and 28 days after virus inoculation were assayed for their neutralizing antibody titer against indicated virus. The titers are expressed as recirpocal mean $\log_2$ ± SE.
[d]Significant difference in duration of shedding, p ≦ 0.005, Student T test.

As noted above, the major protective antigens of PIVs are their HN and F glycoproteins. Thus, in examplary embodiments of the invention, live attenuated PIV candidate vaccine viruses for use in infants and young children include chimeric HPIV3-1 and HPIV3-2 viruses carrying full-length PIV1 and partial PIV2 glycoproteins, respectively in a PIV3 background genome or antigenome. In the latter case, chimeric HN and F ORFs rather than full-length PIV2 ORFs are used to construct the full-length cDNA. The recovered viruses, designated rPIV3-2CT in which the PIV2 ectodomain and transmembrane domain is fused to the PIV3 cytoplasmic domain and rPIV3-2TM in which the PIV2 ectodomain was fused to the PIV3 transmembrane and cytoplasmic tail domain, possessed similar in vitro and in vivo phenotypes. In particular, the rPIV3-2 recombinant chimeric viruses exhibit a host range phenotype, i.e. they replicate efficiently in vitro but are restricted in replication in vivo. This attenuation in vivo occurs in the absence of any added mutations from cp45. This is an unexpected host range effect which is highly desirable for vaccine purposes, in part because the phenotype is not specified by point mutations which may refert to wt. At the same time, the unrestricted growth in vitro is highly advantageous for efficient vaccine production.

Although rPIV3-2CT and rPIV3-2TM replicate efficiently in vitro, they are highly attenuated in both the upper and the lower respiratory tract of hamsters and African green monkeys (AGMs), indicating that chimerization of the HN and F proteins of PIV2 and PIV3 itself specified an attenuation phenotype in vivo. Despite this attenuation, they are highly immunogenic and protective against challenge with PIV2 wild virus in both species. rPIV3-2CT and rPIV3-2TM were further modified by the introduction of the 12 PIV3 cp45 mutations located outside of the HN and F coding sequences to derive rPIV3-2CTcp45 and rPIV3-2TMcp45 which replicated efficiently in vitro but were even further attenuated in hamsters and AGMs indicating that the attenuation specified by the glycoprotein chimerization and by the cp45 mutations was additive.

The development of antigenic chimeric viruses possessing protective antigens of one virus and attenuating mutations from another virus has been reported by others for influenza viruses (Belshe et al., N. Engl. J. Med. 338:1405-1, 1998; Murphy et al., Infectious Diseases in Clinical Practice 2:174-181, 1993) and for rotaviruses (Perez-Schael et al., N. Engl. J. Med. 337:1181-7, 1997). Attenuated antigenic chimeric vaccines are more readily generated for these viruses which have segmented genomes, since genome segment reassortment occurs with high frequency during coinfection. Live attenuated influenza virus vaccine candidates are antigenically updated annually by replacement of the HA and NA genes of the attenuated donor virus with those of a new epidemic or pandemic virus. Recombinant DNA technology is also actively being used to construct live attenuated antigenic chimeric virus vaccines for flaviviruses and for paramyxoviruses. For flaviviruses, a live attenuated virus vaccine candidate for Japanese encephalitis virus (JEV) has been made by the replacement of the premembrane (prM) and envelope (E) regions of the attenuated yellow fever virus (YFV) with those from an attenuated strain of JEV (Guirakhoo et al., Virology 257:363-72, 1999). The JEV-YFV antigenic chimeric recombinant vaccine candidate was attenuated and immunogenic in vivo (Guirakhoo et al., Virology 257:363-72, 1999). Both the structural and the non-structural proteins of this chimeric virus came from a live attenuated vaccine virus. Antigenic chimeric vaccines have also been made between a naturally attenuated tick-borne flavivirus (Langat virus) and a wild type mosquito-borne dengue 4 virus, and the resulting recombinant was found to be significantly more attenuated for mice than its tick-borne parent virus (Pletnev et al., Proc. Natl. Acad. Sci. USA. 95:1746-51, 1998), but this chimeric virus was highly restricted in replication in Vero cells in vitro. This is an example of an attenuating effect that stems from partial incompatibility between the evolutionarily divergent structural proteins specified by the Langat virus and the non-structural proteins of the dengue virus. A third strategy is being pursued for the production of a quadrivalent dengue virus vaccine in which a dengue 4 backbone containing an attenuating deletion mutation in the 3' non-coding region is used to construct antigenic chimeric viruses containing the protective antigens of dengue 1, 2 or 3 viruses (Bray et al., Proc. Natl. Acad. Sci. USA 88:10342-6, 1991; J. Virol. 70:3930-7, 1996).

Antigenic chimeric viruses have also been produced for single-stranded, negative-sense RNA viruses. For example, antigenic chimeric PIV1 vaccine candidates can be constructed according to the methods disclosed herein by substituting the full-length HN and F proteins of parainfluenza virus type 1 for those of PIV3 in an attenuated PIV3 vaccine candidate, and this recombinant is attenuated and protective against PIV1 challenge in experimental animals. Similarly, exemplary antigenic chimeric respiratory syncytial virus (RSV) vaccine candidates can be made in which one or more of the RSV F and G protective antigens, or antigenic determinant(s) thereof, of subgroup B virus are substituted for those in an attenuated RSV subgroup A virus yielding attenuated RSV subgroup B vaccine candidates. (See also, International Publication No. WO 97/06270; Collins et al., *Proc. Natl. Acad. Sci. USA* 92:11563-11567 (1995); U.S. patent application Ser. No. 08/892,403, filed Jul. 15, 1997 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); U.S. patent application Ser. No. 09/291,894, filed by Collins et al. on Apr. 13, 1999; U.S. Provisional Patent Application Ser. No. 60/129, 006, filed Apr. 13, 1999; U.S. Provisional Patent Application Ser. No. 60/143,132, filed by Bucholz et al. on Jul. 9, 1999; and Whitehead et al., *J. Virol.* 73:9773-9780, 1999, each incorporated herein by reference). When the glycoprotein exchanges between the PIV1 and PIV3 viruses and between the RSV subgroup A and RSV subgroup B viruses were performed in a wild type virus background, the antigenic chimeric viruses replicated to wild type virus levels in vitro and in vivo. These findings indicate that a high level of compatibility exists between recipient and donor viruses and that only very little, if any, attenuation was achieved as a result of the process of chimerization. These findings with the PIV1 and PIV3 and the RSV A and B glycoprotein exchanges contrast strikingly in several ways with those between PIV2 and PIV3 disclosed herein.

In the present disclosure, viable recombinant virus in which the full-length PIV2 HN or F protein was used to replace those of PIV3 was not recovered in this instance, evidently attributable to incidental mutations introduced during cDNA construction, whereas this was successfully achieved for the PIV1-PIV3 glycoprotein exchange. This suggests that the PIV2 HN or F glycoprotein is poorly compatible with one or more of the PIV3 proteins encoded in the cDNA. Two viable PIV2-PIV3 chimeric viruses were obtained when chimeric HN and F ORFs rather than full-length PIV2 ORF were used to construct the full-length cDNA. One of these chimeric viruses contained chimeric HN and F glycoproteins in which the PIV2 ectodomain was fused to the PIV3 transmembrane and cytoplasmic tail region, and the other contained chimeric HN and F glycoproteins in which the PIV2 ectodomain and transmembrane region was fused to the PIV3 cytoplasmic tail region. Both rPIV3-2 recombinants possessed similar, although not identical, in vitro and in vivo phenotypes. Thus, it appeared that only the cytoplasmic tail of the HN or F glycoprotein of PIV3 was required for successful recovery of the PIV2-PIV3 chimeric viruses.

In previous studies directed to protein structure-function analysis, chimeric HN or F proteins have been constructed and expressed in vitro and have been used to map various functional domains of the proteins (Bousse et al., *Virology* 204:506-14, 1994; Deng et al., *Arch. Virol. Suppl.* 13:115-30, 1997; Deng, et al., *Virology* 253:43-54, 1999; Deng et al., *Virology* 209:457-69, 1995; Mebatsion et al., *J. Virol.* 69:1444-1451, 1995; Takimoto et al., *J. Virol.* 72:9747-54, 1998; Tanabayashi et al., *J. Virol.* 70:6112-6118, 1996; Tsurudome et al., *J. Gen. Virol.* 79:279-89, 1998; Tsurudome et al., *Virology* 213:190-203, 1995; Yao et al., *J. Virol.* 69:7045-53, 1995). In one report, a chimeric glycoprotein consisting of a measles virus F cytoplasmic tail fused to the transmembrane and ectodomains of the vesicular stomatitis virus G protein was inserted into a measles virus infectious clone in place of the measles virus F and HN virus glycoproteins (Spielhofer et al., *J. Virol.* 72:2150-9, 1998). A chimeric virus was obtained that was replication competent, but highly restricted in replication in vitro as indicated by delayed growth and by low virus yields indicating a high degree of attenuation in vitro. This finding is in marked contrast to the phenotype exhibited by recombinant PIV of the invention expressing chimeric glycoproteins, e.g., a PIV2-PIV3 chimera, which replicate efficiently in vitro.

The efficient replication of rPIV3-2 and other chimeric PIV viruses of the invention in vitro is an important property for a live attenuated vaccine candidate that is needed for large scale vaccine production. In contrast to rPIV3-2CT and rPIV3-2TM, rPIV3-1 was not attenuated in vivo. Thus, the chimerization of the HN and F proteins of PIV2 and PIV3 itself resulted in attenuation of replication in vivo, a novel finding for single-stranded, negative-sense RNA viruses. The mechanism for this host range restriction of replication in vivo is not known. Importantly, infection with these attenuated rPIV3-2CT and rPIV3-2TM vaccine candidates induced a high level of resistance to challenge with PIV2 indicating that the antigenic structure of the chimeric glycoproteins was largely or completely intact. Thus rPIV3-2CT and rPIV3-2TM function as live attenuated PIV2 candidate vaccine viruses, exhibiting a desirable balance between attenuation and immunogenicity in both AGMs and hamsters.

The attenuating effects of the PIV3-PIV2 chimerization of the F and HN glycoprotein are additive with that specified by the cp45 mutations. rPIV3-2 recombinants containing the cp45 mutations were highly attenuated in vivo and provided incomplete protection in hamsters against challenge with PIV2 and little protection in AGMs. This is in contrast to the finding with rPIV3-1 cp45 which was satisfactorily attenuated in vivo and protected animals against challenge with PIV1. The combination of the independent, additive attenuating effects of the chimerization of PIV3-PIV2 glycoproteins and the 12 cp45 mutations appeared too attenuating in vivo. Clearly, if the rPIV3-2CT and rPIV3-2TM vaccine candidates are found to be insufficiently attenuated in humans, the cp45 attenuating mutations should be added incrementally rather than as a set of 12 to achieve a desired balance between attenuation and immunogenicity needed for a live attenuated PIV2 vaccine for use in humans. The findings presented herein thus identify a novel means to attenuate a paramyxovirus and provide the basis for evaluation of these PIV3-PIV2 chimeric live attenuated PIV2 vaccine candidates in humans. Importantly, the rPIV3-2CT or rPIV3-2TM viruses can also be used as vectors for other PIV antigens or for other viral protective antigens, e.g., the measles virus HA protein or immunogenic portions thereof.

At any given time in a vaccination schedule, it is possible to coadminister several PIV vector-based vaccine viruses that each expresses a different protective antigen from one or more additional gene units. In this way, it is possible to develop a multivalent vaccine against many human pathogens.

Briefly summarizing the foregoing description and examples, recombinant chimeric PIVs constructed as vectors bearing heterologous viral genes or genome segments have been made and characterized using a cDNA-based virus recovery system. Recombinant viruses made from cDNA replicate independently and can be propagated in the same manner as if they were biologically-derived viruses. In preferred embodiments, recombinant chimeric human PIV (HPIV) vaccine candidates bear one or more major antigenic determinant(s) of a HPIV, preferably in a background that is attenuated by one or more nucleotide modifications. Preferably, chimeric PIVs of the invention also express one or more protective antigens of another pathogen, for example a microbial pathogen. In these cases, the HPIV acts as an attenuated virus vector and is used with the dual purpose of inducing a protective immune response against one or more HPIVs as well as against the pathogen(s) from which the foreign protective antigen(s) was/were derived. As mentioned above, the major protective antigens of PIVs are their HN and F glycoproteins. The major protective antigens of other enveloped viruses, for example viruses that infect the respiratory tract of humans, that can be expressed by the HPIV vector from one or more extra transcriptional units, also referred to as gene units, are their attachment proteins, e.g., the G protein of RSV, the HA protein of measles virus, the HN protein of mumps virus, or their fusion (F) proteins, e.g., the F protein of RSV, measles virus or mumps virus. It is also be possible to express the protective antigens of non-enveloped viruses such as the L1 protein of human papillomaviruses which could form virus-like particles in the infected hosts (Roden et al., *J. Virol.* 70:5875-83, 1996). In accordance with these teachings, a large array of protective antigens and their constituent antigenic determinants from diverse pathogens can be integrated within chimeric PIV of the invention to generate novel, effective immune responses.

Based on the foregoing examples, it is demonstrated that recombinant HPIV3 (rHPIV3) provides an effective vector for foreign viral protective antigens expressed as additional, supernumerary genes, as exemplified by the measles virus hemagglutinin (HA) glycoprotein gene. In another embodiment, the rHPIV3-1 antigenic chimeric virus, a recombinant HPIV3 in which the PIV3 F and HN genes were replaced by their HPIV1 counterparts, provides an effective vector the HPIV2 hemagglutinin-neuraminidase (HN) glycoprotein. In each case, the foreign coding sequence was designed and constructed to be under the control of a set of HPIV3 gene start and gene end transcription signals, inserted into the vector genome as an additional, supernumerary gene, and expressed as a separate mRNA by the HPIV3 polymerase.

Expression of the measles virus HA or the HPIV2 HN glycoprotein from a supernumerary gene insert by the rHPIV3 or rHPIV3-1 vector was determined to be stable over multiple rounds of replication. Hamsters infected with the rHPIV3 vector expressing the measles virus HA or the rHPIV3-1 vector expressing the HPIV2 HN glycoprotein induced a protective immune response to HPIV3 and measles virus, or to HPIV1 and HPIV2, respectively. Thus, a single rHPIV3 vector expressing the protective antigen of measles virus induced a protective immune response against two human pathogens, namely, HPIV3 via an immune response to the glycoproteins present in the vector backbone and measles virus via the HA protective antigen expressed from the extra gene inserted into rHPIV3. The measles virus glycoprotein was not incorporated into the infectious HPIV3 vector virus, and hence its expression would not be expected to alter the tropism of the vector nor render it susceptible to neutralization with measles virus-specific antibodies. Similarly, a single rHPIV3-1 vector expressing the protective HN antigen of HPIV2 induced a protective immune response against two human pathogens, namely, HPIV1 via an immune response to the glycoproteins present in the vector backbone and HPIV2 via the HN protective antigen expressed from the extra gene inserted into rHPIV3-1.

The present invention overcomes the difficulties inherent in prior approaches to vector based vaccine development and provides unique opportunities for immunization of infants during the first year of life against a variety of human pathogens. Previous studies in developing live-attenuated PIV vaccines indicate that, unexpectedly, rPIVs and their attenuated and chimeric derivatives have properties which make them uniquely suited among the nonsegmented negative strand RNA viruses as vectors to express foreign proteins as vaccines against a variety of human pathogens. The skilled artisan would not have predicted that the human PIVs, which tend to grow substantially less well than the model nonsegmented negative strand viruses and which typically have been underrepresented with regard to molecular studies, would prove to have characteristics which are highly favorable as vectors. It is also surprising that the intranasal route of administration of these vaccines has proven a very efficient means to stimulate a robust local and systemic immune response against both the vector and the expressed heterologous antigen. Furthermore, this route provides additional advantages for immunization against heterologous pathogens which infect the respiratory tract or elsewhere.

These properties of PIV vectors are described herein above using examples of rPIV3 vectors which bear (i) a major neutralization antigen of measles virus expressed as a separate gene in wild type and attenuated backgrounds or (ii) major neutralization antigens of HPIV1 in place of the PIV3 neutralization antigens which express in addition a major neutralization antigen of HPIV2. These rPIV vectors were constructed using wild type and attenuated backgrounds. In addition, the description herein demonstrates the ability to readily modify the level of attenuation of the PIV vector backbone. According to one of these methods, varying the length of genome inserts in a chimeric PIV of the invention allows for adjustment of the attenuation phenotype, which is only apparent in wild type derivatives using very long inserts.

The present invention provides six major advantages over previous attempts to immunize the young infant against measles virus or other microbial pathogens. First, the PIV recombinant vector into which the protective antigen or antigens of measles virus or of other microbial pathogens is inserted is an attenuated rPIV bearing one or more attenuating genetic elements that are known to attenuate virus for the respiratory tract of the very young human infant (Karron et al., *Pediatr. Infect. Dis. J.* 15:650-654, 1996; Karron et al., *J. Infect. Dis.* 171:1107-1114, 1995a; Karron et al., *J. Infect. Dis.* 172:1445-1450, 1995b). This extensive history of prior clinical evaluation and practice greatly facilitates evaluation of derivatives of these recombinants bearing foreign protective antigens in the very young human infant.

The second advantage is that the rPIV backbone carrying the measles HA or other protective antigen of another human pathogen will induce a dual protective immune response against (1) the PIV, for which there is a compelling independent need for a vaccine as indicated above, and (2) the heterologous virus or other microbial pathogen whose protective antigen is expressed by the vector. This contrasts with the VSV-measles virus HA recombinant described above which will induce immunity to only one human pathogen, i.e., the measles virus, and in which the immune response to the vector itself is at best irrelevant or is potentially disadvantageous. The coding sequences of the foreign genes inserted into various members of the Mononegavirales Order of viruses have remained intact in the genomes of the most of the recombinant viruses following multiple cycles of replication in tissue culture cells, indicating that members of this group of viruses are excellent candidates for use as vectors (Bukreyev et al., *J. Virol.* 70:6634-41, 1996; Schnell et al., *Proc. Natl. Acad. Sci. U.S.A.* 93:11359-65, 1996a; Singh et al., *J. Gen. Virol.* 80:101-6; Yu et al., *Genes Cells* 2:457-66, 1997).

Another advantage provided by the invention is that use of a human pathogen backbone, for which there is a need for a vaccine, will favor the introduction of such a live attenuated virus vector into an already crowded early childhood immunization schedule. In addition, immunization via the mucosal surface of the respiratory tract offers various advantages. A live attenuated PIV3 was shown to replicate in the respiratory tract of rhesus monkeys and to induce a protective immune response against itself in the presence of high quantities of maternally-acquired PIV3 antibodies. The ability of two candidate PIV3 vaccines to infect and to replicate efficiently in the upper respiratory tract of the very young human infant who possess maternally-acquired antibodies has also been demonstrated (Karron et al., *Pediatr. Infect. Dis. J.* 15:650-654, 1996; Karron et al., *J. Infect. Dis.* 171:1107-1114, 1995a; Karron et al., *J. Infect. Dis.* 172:1445-1450, 1995b). This is in contrast to the currently licensed measles virus vaccine which is poorly infectious when administered to the upper respiratory tract of humans and which is highly sensitive to neutralization when administered parenterally to young children (Black et al., *New Eng. J. Med.* 263:165-169, 1960; Kok et al., *Trans. R. Soc. Trop. Med. Hyg.* 77:171-6, 1983; Simasathien et al., *Vaccine* 15:329-34, 1997). The replication of the HPIV vector in the respiratory tract will stimulate the production of both mucosal IgA and systemic immunity to the HPIV vector and to the expressed foreign antigen. Upon subsequent natural exposure to wild type virus, e.g., measles virus, the existence of vaccine-induced local and systemic immunity should serve to restrict its replication at both its portal of entry, i.e., the respiratory tract, as well as at systemic sites of replication.

Yet another advantage of the invention is that chimeric HPIVs bearing heterologous sequences replicate efficiently in vitro demonstrating the feasibility for large scale production of vaccine. This is in contrast to the replication of some single-stranded, negative-sense RNA viruses which can be inhibited in vitro by the insertion of a foreign gene (Bukreyev et al., *J. Virol.* 70:6634-41, 1996). Also, the presence of three antigenic serotypes of HPIV, each of which causes significant disease in humans and hence can serve simultaneously as vector and vaccine, presents a unique opportunity to sequentially immunize the infant with antigenically distinct variants of HPIV each bearing the same foreign protein. In this manner the sequential immunization will permit the development of a primary immune response to the foreign protein which can be boosted during subsequent infections with the antigenically distinct HPIV also bearing the same or a different foreign protein or proteins, i.e., the protective antigen of measles virus or of another microbial pathogen. It is also likely that readministration of homologous HPIV vectors will also boost the response to both HPIV and the foreign antigen since the ability to cause multiple reinfections in humans is an unusual but characteristic attribute of the HPIVs (Collins et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1205-1243. Lippincott-Raven Publishers, Philadelphia, 1996).

Yet another advantage is that the introduction of a gene unit into a PIV vector has several unexpected, but highly desirable effects, for the production of attenuated viruses. First, the insertion of gene units expressing, for example, the HA of measles virus or the HN of PIV2 can specify a host range phenotype on the PIV vector that has not been previously recognized, i.e., the resulting PIV vector replicates efficiently in vitro but is restricted in replication in vivo in both the upper and lower respiratory tracts. These findings identify the insertion of a gene unit expressing a viral protective antigen as an attenuating factor for the PIV vector, a desirable property in live attenuated virus vaccines of the invention.

The PIV vector system has unique advantages over all other members of the single-stranded, negative-sense viruses of the Order Mononegavirales. First, most other mononegaviruses that have been used as vectors are not derived from human pathogens (e.g., murine HPIV1 (Sendai virus) (Sakai et al., *FEBS Lett.* 456:221-6, 1999), vesicular stomatitis virus (VSV) which is a bovine pathogen (Roberts et al., *J. Virol.* 72:4704-11, 1998), and canine PIV2 (SV5) He et al., *Virology* 237:249-60, 1997)). For these nonhuman viruses, little or only weak immunity would be conferred against any human virus by antigens present in the vector backbone. Thus, a nonhuman virus vector expressing a supernumerary gene for a human pathogen would induce resistance only against that single human pathogen. In addition, use of viruses such as VSV, SV5, rabies, or Sendai virus as vector would expose vaccinees to viruses that they likely would not otherwise encounter during life. Infection with, and immune responses against, such nonhuman viruses would be of marginal benefit and would pose safety concerns, because there is little experience of infection with these viruses in humans.

An important and specific advantage of the PIV vector system is that its preferred, intranasal route of administration, mimicking natural infection, induces both mucosal and systemic immunity and reduces the neutralizing and immunosuppressive effects of maternally-derived serum IgG that is present in infants. While these same advantages theoretically are possible for using RSV as a vector, for example, we have found that RSV replication is strongly inhibited by inserts of greater than approximately 500 bp (Bukreyev et al., *Proc. Natl. Acad. Sci. USA* 96:2367-72, 1999). In contrast, as described herein, HPIV3 can readily accommodate several large gene inserts. The finding that recombinant RSV is unsuitable for bearing large inserts, whereas recombinant PIVs are highly suitable, represents unexpected results.

It might be proposed that some other viral vector could be given intranasally to obtain similar benefits as shown for PIV vectors, but this has not been successful to date. For example, the MVA strain of vaccinia virus expressing the protective antigens of HPIV3 was evaluated as a live attenuated intranasal vaccine against HPIV3. Although this vector appeared to be a very efficient expression system in cell culture, it was inexplicably inefficient in inducing resistance in the upper respiratory tract of primates (Durbin et al., *Vaccine* 16:1324-30, 1998) and was inexplicably inefficient in inducing a protective response in the presence of passive serum antibodies (Durbin et al., *J. Infect. Dis.* 179:1345-51, 1999). In contrast, PIV3 and RSV vaccine candidates have been found to be protective in the upper and lower respiratory tract of non-human primates, even in the presence of passive serum antibodies (Crowe et al., *Vaccine* 13:847-855, 1995; Durbin et al., *J. Infect. Dis.* 179:1345-51, 1999).

The use of PIV3 in particular as a vector offers yet additional advantages. For example, conditions have been established to obtain high titers of PIV3 in microcarrier culture that are 10 to 1000 times greater than can be achieved with viruses such as RSV and measles virus. Also, RSV infectivity is unstable, which complicates propagation, transport, storage and handling. These problems will be obviated by development of a PIV-vectored RSV vaccine.

Importantly, two versions of PIV3 have undergone extensive clinical evaluation as candidate vaccines administered intranasally, namely BPIV3 and the attenuated HPIV3 cp45 strain. Each was found to be safe, immunogenic, and phenotypically stable in children and infants. No other candidate engineered vector has been evaluated in children and infants, and in particular no other available vector has been evaluated for intranasal administration in this age group.

Another advantage of the PIV vector system is that, using HPIV3 as a model, a number attenuating mutations have been identified that can be introduced into the vector backbone singly and in combination to obtain the desired degree of attenuation. For example, the specific mutations that confer the HPIV3 cp45 attenuation phenotype have been identified directly by sequence analysis and introduction into wild type recombinant virus. Additional attenuating mutations were developed by "importing" attenuating point mutations from Sendai virus and RSV. In some cases, it was possible to introduce certain point mutations into recombinant virus using two nucleotide changes rather than one, which stabilizes the mutation against reversion to wild type. Ablation of expression of the C, D and V ORFs was shown to attenuate the virus. In addition, chimeric viruses of HPIV3 and bovine (B)PIV3 were developed to use the natural host range restriction of BPIV3 in primates as a means of attenuation. It also was found that certain sequence combinations were attenuating, such as replacement of the HPIV3 HN and F ectodomains with their counterparts from HPIV2. Thus, a large menu of PIV attenuating mutations exists that can be used to attenuate the vector backbone as desired.

Thus, one aspect of the invention disclosed herein relates to a method of using selected recombinant PIVs as vectors to express one or multiple protective antigens of a heterologous pathogen as supernumerary genes. The heterologous pathogens described herein include heterologous PIVs, measles virus, and RSV. In the examples above, rHPIV3 was engineered as a vector to express up to three separate supernumerary gene inserts each expressing a different viral protective antigen. Furthermore, rHPIV3 readily accommodated a total aggregate insert length of at least 50% that of the wild type genome. Constructs were made with several different PIV vector backbones, namely: wild type HPIV3; an attenuated version of HPIV3 in which the N ORF was replaced by that of BPIV3; the HPIV3-1 chimeric virus, in which the HN and F ORFs of HPIV3 were replaced by their counterparts from HPIV1; a version of HPIV3-1 that was attenuated by the presence of three independent attenuating cp45 point mutations in the L gene; and a version of BPIV3 in which the HN and F genes were replaced by their counterparts from HPIV3. These vectors bearing one or more supernumerary genes replicated efficiently in vitro, demonstrating feasibility for their commercial development, and they replicated and induced strong immune responses in vivo against both the vector and the inserts. In this way it is possible to construct a single recombinant PIV-based virus that is capable of inducing an immune response against at least four human pathogens, namely the PIV vector itself and the pathogens represented by the supernumerary genes.

A second aspect of the invention is to use the superior characteristics of PIV as a vaccine and as a vector to make a vaccine against RSV. RSV is a pathogen that grows less well than PIV, is unstable, and tends to induce immune responses that are poorly protective for reasons that are not completely understood. The development of a live-attenuated RSV vaccine has been underway for more than 35 years, indicating the difficulty of achieving an appropriate balance between immunogenicity and attenuation for this human pathogen. Thus, there are compelling reasons for developing a live attenuated RSV vaccine that is not based on infectious RSV. The RSV major protective F and G antigens were expressed as supernumerary genes from a PIV vector, in this case BPIV3, obviating the need to produce a live-attenuated vaccine based on infectious RSV.

A third aspect of the invention described herein has been to develop PIV-based vectors bearing the antigenic determinants of different PIV serotypes. Since there is essentially no cross protection between serotypes, this makes it possible to develop a method for sequential immunizations with a common PIV vector in which the protective antigenic determinants are changed. Thus, a single attenuated PIV vector backbone such as derived from rHPIV3, bearing supernumerary genes as desired, can be used for an initial immunization. A subsequent immunization, which preferably follows the first by 4-6 or more weeks, can be achieved using a version of the same PIV vector in which the vector glycoprotein genes have been replaced with those of a heterologous PIV serotype, such as in rHPIV3-1. This vector can contain the same supernumerary genes, which would then provide a "boost" against the supernumerary antigens, or can contain a different set. Because the second immunization is done with a version of the vector containing the glycoproteins of a heterologous PIV serotype, there is some interference by vector-specific immunity induced by the initial immunization. Alternatively, the second immunization can be performed with a PIV vector in which all of the vector genes are of a different serotype, such as HPIV1 or HPIV2. However, the advantage of using a common set of internal genes, such as in the rPIV3 and rPIV3-1 vectors that are based on HPIV3, is that a single set of attenuating mutation can be employed in each construct, and there is no need to separately develop attenuated strains for each PIV serotype. Importantly, sequential immunization follows a multivalent strategy: in each immunization, the vector itself induces immunity against an important human pathogen and each supernumerary insert induces immunity against an additional pathogen.

Although the foregoing invention has been described in detail by way of example for purposes of clarity of understanding, it will be apparent to the artisan that certain changes and modifications may be practice within the scope of the appended claims which are presented by way of illustration not limitation. In this context, various publications and other references have been cited within the foregoing disclosure for economy of description. Each of these references are incorporated herein by reference in its entirety for all purposes.

Deposit of Biological Material

The following materials have been deposited with the American Type Culture Collection, 10801 University Boulevard, Manassas, Va. 20110-2209, under the terms of the Budapest Treaty.

| Virus | Accession No. | Deposit Date |
| --- | --- | --- |
| p3/7(131)2G | (ATCC 97989) | Apr. 18, 1997 |
| p3/7(131) | (ATCC 97990) | Apr. 18, 1997 |
| p218(131) | (ATCC 97991) | Apr. 18, 1997 |
| HPIV3 JS cp45 | (ATCC PTA-2419) | Aug. 24, 2000 |

EXAMPLE XXVIII

Construction of cDNAs Encoding a Chimeric HPIV3/BPIV3 Antigenome and Recovery of Infectious Virus The following three examples document studies to identify which of the proteins of BPIV3 contribute to its host range restriction in primates. To illustrate these methods, the N protein of the wild type HPIV3 virus was replaced with its counterpart from BPIV3. This exchange was accomplished using a reverse genetics system for recovery of infectious PIV from cDNA as described above. The studies were initiated with the N gene of BPIV3 because this protein possesses an intermediate level of amino acid sequence difference from its HPIV3 counterpart compared to other HPIV3 and BPIV3 proteins (see Example XXVII).

A chimeric recombinant virus was constructed in which the N ORF of the JS strain of HPIV3 was replaced by that of either the Ka or SF strain of BPIV3 (FIG. 41). These chimeric viruses possess the HN and F glycoproteins of the HPIV3 parent and will induce a high level of immunity to HPIV3 in primates. Both chimeric viruses were successfully recovered. Both grew to high titer in cell culture and both were found to be attenuated in rhesus monkeys. Thus, the N protein was identified as an exemplary protein that contributes to the host range phenotype of BPIV3. Immunization of rhesus monkeys with either the Ka or SF chimeric recombinant virus induced a high level of resistance to the replication of HPIV3 used as a wild type challenge.

The present invention, therefore, establishes the usefulness of reverse genetics methods to generate chimeric human-bovine PIV virus that combines the host range attenuation properties of BPIV3 and the immunogenicity of the HPIV3 HN and F protective antigens. Immunization of humans with such a chimeric recombinant will redress the problem of suboptimal immunogenicity of the BPIV3 vaccine previously observed in humans.

The complete consensus nucleotide sequence for each of the Ka or SF BPIV3 strains was determined from RT-PCR products generated from virion RNA. These sequences are set forth in FIGS. 46A-46G (SEQ ID NO. 41), and FIGS. 47A-47G (SEQ ID NO: 42), respectively. The full length cDNA encoding a complete 15456 nucleotide (nt) antigenomic RNA of BPIV3 Ka is set forth in FIGS. 46A-46G herein (see also GenBank accession #AF178654). The GenBank sequence for BPIV3 kansas strain differs from the sequence of the exemplary cDNA in two positions at nucleotide 21 and 23. Both, the published sequence and the sequence in the exemplary cDNA occur naturally in kansas strain virus population with similar frequencies. The former cDNA contains a sequence beginning at nucleotide 18, ACTGGTT, whereas the corresponding published sequence (GenBank accession #AF178654; FIGS. 46A-46G) reads ACTTGCT (differing nucleotides at positions 21 and 23 are underscored).

To construct consensus nucleotide sequences for the Ka and SF BPIV3 strains, virion RNA was subjected to reverse transcription using the Superscript II Preamplification System (Life Technologies, Gaithersburg, Md.) and 200 ng of random hexamer primers. PCR was carried out on the first strand product using the Advantage cDNA PCR kit (Clontech Laboratories, Palo Alto, Calif.). Ka and SF genomes were each amplified by PCR in 3 or 4 overlapping fragments using primers homologous to regions of RNA conserved among previously-published paramyxovirus sequences. Each primer pair was constructed to include matching restriction enzyme sites (not represented in the sequence targeted for amplification).

A separate random library was generated for each amplicon by digesting a set of PCR products with the appropriate restriction enzyme, followed by gel-purification, ligation of the products into tandem arrays and sonication. A random library was generated from this pool of sheared cDNA sequences by cloning a subset (approx. 500 bp fragments) into M13. The nucleotide sequences of cDNA inserts were determined by automated DNA sequencing using the Taq DYE Deoxy Terminator cycle sequencing kit (ABI, Foster City, Calif.). A continuous sequence (contig) was assembled for each of the original large RT-PCR fragments with sufficient redundancy that each nucleotide position was confirmed by a minimum 3 independent M13 clones. The 5' and 3' terminal genomic sequences of Ka and SF were converted to cDNA using the system for Rapid Amplification of cDNA Ends (Life Technologies, Gaithersburg, Md.) and sequenced by automated sequencing.

These sequences are set forth in FIGS. 46A-46G (Ka) and FIGS. 47A-47G (SF), respectively. Analysis of these sequences revealed that the percent amino acid identity between HPIV3 and BPIV3 for each of the following proteins is: N (86%), P (65%), M (93%), F (83%), HN (77%), and L (91%). Thus sequence divergence was found distributed over many genes. The deduced amino acid sequence of the N genes of these two viruses is presented in GenBank #Af178654 (Ka) and #AF178655 (SF), not included. The position of the N ORF in the BPIV3 genome is indicated in the respective BenBank reports and included herein by reference. In the example below, the N ORF of the Ka or SF virus was initially selected for replacement of the corresponding gene in the HPIV3 virus because the N gene represents a gene with an intermediate level of sequence divergence among the six HPIV3 and BPIV3 proteins. In this study the N ORF, but not the 3' or 5, noncoding N gene sequences, was exchanged, which permitted us to assign an observed attenuation phenotype of cKa and cSF to the protein encoded by the N gene.

Human-bovine chimeric full-length PIV3 genomes were constructed by introducing the BPIV3 Ka or SF N coding region as a replacement for its HPIV3 counterpart into the rJS cDNA p3/7(131)2G which encodes a complete copy of HPIV3 positive-sense antigenomic RNA (see, e.g., Durbin et al., 1997a, supra; Hoffman et al., 1997, supra; Skiadopoulos et al., 1998, supra; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997; each incorporated herein by reference). BPIV3 and HPIV3 N coding regions with flanking sequences were first subcloned and further modified to permit an exchange of just the N ORF. pUC119JSN bearing the HPIV3 N gene and the plasmids with a BPIV3 N Ka or SF gene (pBSKaN and pBSSFN) were subjected to mutagenesis using the method of Kunkel (*Proc. Natl. Acad. Sci. USA* 82:488-492, 1985, incorporated herein by reference) to introduce NcoI and AflIII restriction enzyme recognition sites at translational start and stop sites, respectively (FIG. 41A). Following NcoI/AflIII digestion of pUC119KaN-NcoI/AflIII, the BPIV3 N coding region was introduced as an NcoI/AflIII fragment into pUC119JSN-NcoI/AflIII as a replacement for the HPIV3 N coding region (FIG. 41 B). The chimeric N genes, which contain the HPIV3 3' and 5' noncoding sequences and the BPIV3 ORF, were modified by site-directed mutagensis to restore the original HPIV3 noncoding sequence and BPIV3 coding sequence. This chimeric N gene was then introduced into the 5' half of the rJS antigenome, pLeft, in exchange for its corresponding HPIV3 sequence (FIGS. 42A and 42B) using existing MluI and EcoRI sites present in the human sequence. In each case parallel reactions were carried out for the SF N ORF. The chimeric pLeft plasmid was combined with the XhoI/NgoMI fragment from pRight containing the 3' half of the rJS antigenome flanked by the delta ribozyme and the T7 terminator at its 3' end (FIG. 42). The resulting chimeric PIV3 plasmids designated pB/HPIV3NKa or pB/HPIV3NSF, contained the full-length rJS antigenome in which the N ORF encoded the BPIV3 Ka or SF N protein.

Chimeric antigenomic HPIV3/BPIV3 cDNAs were transfected individually into HEp-2 cells grown to near-confluence in 6-well plates along with two previously-described support plasmids, pTM(P no C) and pTM(L), Lipofectace (Life Technologies, Gaithersburg, Md.), and infected with a modified vaccinia virus recombinant that expresses bacteriophage T7 RNA polymerase (MVA-T7) as previously described (Durbin et al., *Virology* 234:74-83, 1997b). An N support plasmid used in previous work was omitted because the antigenomic plasmid expressed sufficient levels of the N protein. The cultures were maintained for 3.5 days at 32° C. after which supernatants were harvested, passaged in LLC-MK2 cells and plaque-purified 3 times in LLC-MK2 cells. The identities of the chimeric viruses incorporating a human PIV 3 background genome or antigenome and a BPIV3 N protein (designated as rHPIV3-$N_B$ chimeric recombinants or, more specifically, as "cKa" and "cSF" chimeric viruses) recovered from the transfections were confirmed by sequencing RT-PCR products containing the regions of the N ORF start and stop codons from virion RNA isolated after amplification of triply plaque-purified virus (FIG. 43). This amplified product and the corresponding amplified HPIV3 rJS and BPIV3 Ka or SF sequences were also subjected to TaqI digestion to confirm the chimeric identity of cKa and cSF viruses (FIG. 44). TaqI digestion profiles were distinct for the 3 parental and 2 chimeric viruses, and each parental profile included TaqI fragments of unique size, allowing the contribution of sequence of rJS, Ka and SF parents to the chimeric viruses to be verified. The recovered cKa and cSF chimeric recombinants each contained the expected sequences as designed.

EXAMPLE XXIX

Replication of HPIV3/BPIV3 Chimeric Viruses in Cell Culture

Efficient replication of live attenuated virus vaccines in tissue culture cells is a feature of human-bovine chimeric PIV of the invention that permits efficient manufacture of the recombinant vaccine materials. The multicycle replication of rJS parent, cKa, Ka parent, cSF, and SF parent in a bovine cell line (MDBK) and in a simian cell line (LLC-MK2) was determined by infecting cells with virus at a multiplicity of infection of 0.01 and harvesting samples (in triplicate) over a five day period of time (FIG. 45) as previously described (Tao et al., 1998, supra, incorporated herein by reference). The chimeric viruses replicated efficiently in both cell lines like their human or bovine parent viruses without significant delay in replication or a significant reduction in the titer of virus achieved. In each case, the chimeric viruses replicated to over $10^{7.0}$ TCID$_{50}$/ml which is well above the $10^{4.0}$ or $10^{5.0}$ dose of live attenuated human or bovine PIV vaccines currently being used in human clinical trials (Karron et al., 1996, supra; Karron et al., 1995a, supra; and Karron et al., 1995b, supra).

EXAMPLE XXX

Evaluation of Attenuation and Protective Efficacy of the HPIV3/BPIV3 Chimeric Viruses in Rhesus Monkeys Both the SF and Ka BPIV3s are attenuated for the upper and the lower respiratory tract of the rhesus monkey (van Wyke Coelingh et al., 1988, supra). This attenuation phenotype correlates with attenuation in humans (Karron et al., 1995a, supra) as indicated by the fact that Ka is highly restricted in replication in the upper respiratory tract of fully susceptible seronegative infants and children. The absence of cough, croup, bronchiolitis, or pneumonia in the BPIV3-infected vaccinees suggests that the Ka BPIV3 virus is attenuated for the lower respiratory tract as well. Therefore, the rhesus monkey is widely accepted as a reasonably correlative model to evaluate attenuation of candidate PIV vaccine viruses and their efficacy against challenge with wild type PIV.

The rJS, cKa, Ka parent, cSF, and SF parent were administered intranasally and intratracheally at a dose of $10^{5.0}$ TCID$_{50}$ per site to rhesus monkeys. Replication was monitored using previously described procedures for obtaining samples from the upper (nasopharyngeal swab specimens) and lower (tracheal lavage specimens) respiratory tract and for titering the virus in LLC-MK2 cells (Hall et al., 1992, supra). The cKa and cSF recombinants were significantly attenuated for the upper respiratory tract (Table 47) exhibiting, respectively, a 63-fold or a 32-fold reduction in mean peak virus titer compared to that of the rJS HPIV3 parent. Both cKa and cSF were also attenuated for the lower respiratory tract, but this difference was only statistically significant for cSF. The low level of replication of rJS in the lower respiratory tract made it difficult to demonstrate in a statistically-significant fashion further restriction of replication due to an attenuation phenotype at this site.

TABLE 47

Replication of cKa and cSFis restricted relative to HPIV3 in the upper and lower respiratory tracts of rhesus monkeys.

| | | Virus Replication | | | | | |
|---|---|---|---|---|---|---|---|
| | | Mean titers $Log_{10}TCID_{50}$/ml ± standard error [Duncan grouping]2 | | | | Mean peak titers $Log_{10}TCID_{50}$/ml ± standard error [Duncan grouping] | |
| Immunizing virus[1] | No. of animals | Nasopharynx | | Trachea | | | |
| | | day 6 | day 7 | day 4 | day 6 | Nasopharynx | Trachea |
| rJS | 4 | 5.3 ± 0.59 [A] | 3.9 ± 0.36 [A] | 1.7 ± 0.45 [A] | 1.7 ± 0.29 [A] | 5.3 ± 0.59 [A] | 2.5 ± 50.51 [A] |
| cKa | 4 | 3.0 ± 0.58 [B] | 2.9 ± 0.42 [AB] | 1.5 ± 0.40 [A] | 1.0 ± 0.19 [A] | 3.5 ± 0.54 [B] | 1.5 ± 0.18 [AB] |
| Ka | 4 | 2.0 ± 0.27 [B] | 2.4 ± 0.30 [B] | 1.3 ± 0.26 [A] | 1.3 ± 0.21 [A] | 2.5 ± 0.30 [B] | 1.6 ± 0.15 [AB] |
| cSF | 4 | 3.3 ± 0.40 [B] | 3.7 ± 0.57 [A] | 1.1 ± 0.25 [A] | 1.1 ± 0.24 [A] | 3.8 ± 0.46 [B] | 1.4 ± 0.26 [B] |
| SF | 4 | 2.8 ± 0.48 [B] | 2.6 ± 0.40 [AB] | 1.6 ± 0.46 [A] | 1.5 ± 0.40 [A] | 3.3 ± 0.28 [B] | 1.8 ± 0.41 [AB] |

[1]Monkeys were inoculated intranasally and intratracheally with $10^{5.0}$ TCID$^{50}$ in 1 ml at each site.
[2]Mean viral titers in each column were assigned to statistically similar groups (designated with a letter) using a Duncan Multiple Range test ($\alpha = 0.05$). Mean titers in each column with different letters are statistically different.

The level of replication of each chimeric virus, cKa and cSF, was not significantly different from its bovine parent in the upper or the lower respiratory tract, although the chimeric viruses each replicated somewhat better than their BPIV3 parents in the upper respiratory tract. Thus, the acquisition of the N gene of either the Ka or SF BPIV3 by rJS HPIV3 attenuated the human virus for rhesus monkeys to a level approximately equivalent to that of the BPIV parent. Since the HPIV3/BPIV3 chimeric recombinants replicated efficiently in tissue culture cells in vitro, it is clear that the phenotype of host range restricted replication manifested by the two bovine parental viruses was transferred to HPIV3 by the N ORF. It is possible, but unknown and unpredictable, that substitution of other BPIV3 genes, such as M, P, or L, for their HPIV3 counterpart in rJS will give similar or greater levels of attenuation as observed upon substitution of the BPIV3 N gene for the HPIV3 N gene. The observation that the level of replication of cKa and cSF is slightly greater than that of their BPIV3 parents in the upper respiratory tract suggests that additional bovine genes contribute to the host range attenuation phenotype of the BPIV3 parent virus at this site.

Uninoculated monkeys and monkeys that were previously infected with a human or bovine PIV3 parental virus, or with the cKa or cSF chimeric virus, were challenged 42 days after the initial inoculation with $10^{6.0}$ $TCID_{50}$ of rJS intranasally and intratracheally in a 1 ml inoculum at each site. The nasopharynx and the trachea were sampled as described previously on the days indicated in Table 48. The titer of virus present at each site was determined for each monkey on LLC-MK2 cell monolayers, and the titers presented are mean peak titers (Hall et al., 1992, supra). Previous infection with either chimeric virus induced a high level of resistance to replication of the rJS challenge virus in both the upper and lower respiratory tract. Monkeys previously infected with cKa manifested a 300-fold reduction of replication of wild type HPIV3 (rJS) in the upper respiratory tract and a 1000-fold reduction in the lower tract compared to uninoculated control monkeys. Monkeys previously infected with cSF manifested a 2000-fold reduction of replication of rJS in the upper respiratory tract and a 1000-fold reduction in the lower tract compared to uninoculated control monkeys. The level of reduction of replication of rJS challenge virus in monkeys previously-inoculated with cKa or cSF was comparable to that of monkeys previously infected with either the bovine or the human PIV parent. Thus, infection with either HPIV3/BPIV3 chimeric virus provided a high level of protection in the upper and lower respiratory tract of monkeys, and both chimeric viruses represent promising vaccine candidates.

Serum collected from monkeys on days 0 and 28 was tested by HAI assay using HPIV3 (JS strain) and BPIV3 (Ka strain) as antigen as previously described (Coelingh et al., *J. Infect. Dis.* 157:655-662, 1988). Although cKa-N and cSF-N were highly attenuated in the upper and lower respiratory tract of rhesus monkeys relative to rJS, each chimeric virus induced a hemagglutination-inhibiting (HAI) antibody response to HPIV3 that was 2.5 to 5-fold greater in magnitude than that induced by immunization with its respective BPIV3 patent. This likely is due to the presence of HPIV3 HN protein in the chimeric viruses. Furthermore, the HPIV3-specific HAI-responses induced by the chimeric viruses were statistically indistinguishable from that induced by immunization with rJS. An additional unexpected result demonstrated herein is that, following challenge of the monkeys with HPIV3, the level of HAI antibody in monkeys initially immunized with cKa-N or cSF-N was significantly greater than levels observed in animals immunized with rJS, Ka or SF.

EXAMPLE XXXI

Construction and Characterization of Chimeric HPIV3/BPIV3 Vaccine Candidates Having Heterologous Fusion And Hemagglutinin-Neuraminidase Glycoproteins In the preceding example, the basis of host range restriction of replication of BPIV3 for the respiratory tract of primates was examined by the generation and characterization of a recombinant human PIV3 (rHPIV3) in which the N open reading frame (ORF) was replaced by that of its BPIV3 counterpart. The resulting chimeric virus, rHPIV3-$N_B$, also referred to as cKa or cSF, efficiently replicated in vitro but was restricted in replication in the upper respiratory tract of rhesus monkeys, identifying the N protein as an independent determinant of the host range restriction of BPIV3 in rhesus monkeys (Bailly et al., *J. Virol.* 74:3188-3195, 2000).

In the present example, the contribution of the fusion (F) and hemagglutinin-neuraminidase (HN) glycoprotein genes of bovine parainfluenza virus type 3 (BPIV3) to its restricted replication in the respiratory tract of non-human primates was examined by generating and characterizing two reciprocal chimeric BPIV3/HPIV3 viruses. A chimeric HPIV3 containing heterologous BPIV3 F and HN glycoprotein genes in place of its own, and the reciprocal recombinant comprising a BPIV3 "backbone" bearing the HPIV3 F and HN genes substituted for the counterpart BPIV3 glycoprotein genes, were generated to assess the effect of glycoprotein substitution on replication of HPIV3 and BPIV3 in the upper and lower respiratory tract of rhesus monkeys. Thus, in one chimeric virus, the F and HN genes of HPIV3 were replaced with their BPIV3 counterparts, resulting in a chimeric recombinant designated rHPIV3-$F_B HN_B$. The reciprocal chimeric recombinant PIV3 (rBPIV3-$F_H HN_H$) was constructed by replacing the F and HN genes of a recombinant BPIV3 (rBPIV3) with their HPIV3 counterparts. In the latter virus, the introduction of the HPIV3 F and HN ORFs into the BPIV3 backbone combines the antigenic determinants of HPIV3 with the backbone of BPIV3 and thus provides an improved vaccine candidate compared with parental BPIV3. The F and HN genes were exchanged as pairs in view of the proposed requirement for homologous HN and F proteins for parainfluenza viruses for full functional activity (Deng et al., *Virology* 209:457-469, 1995; and Tanabayashi et al., *J. Virol.* 70:6112-6118, 1996; each incorporated herein by reference).

The foregoing chimeric viruses were readily recovered and exhibited kinetics of replication in simian LLC-MK2 cells that were comparable to those of their parent viruses, suggesting that the heterologous glycoproteins were compatible with the PIV3 internal proteins. The distinctive features of cytopathology of BPIV3 versus HPIV3 cosegregated with their respective F and HN genes. HPIV3 bearing the BPIV3 F and HN genes was attenuated for replication in rhesus monkeys to a level similar to that of its BPIV3 parent virus, indicating that the glycoprotein genes of BPIV3 are major determinants of its host range restriction of replication in rhesus monkeys. BPIV3 bearing the HPIV3 F and HN genes (rBPIV3-$F_H HN_H$) replicated in rhesus monkeys to a level intermediate between that of HPIV3 and BPIV3.

These results indicate that the F and HN genes make a significant contribution to the overall attenuation of BPIV3. Furthermore, they demonstrate that BPIV3 sequences outside the F and HN region also contribute to the attenuation phenotype in primates. This latter finding is consistent with the demonstration in the preceding example that the nucleoprotein coding sequence of BPIV3 is a determinant of its attenuation for primates. Despite its restricted replication in the respiratory tract of rhesus monkeys, rBPIV3-$F_H HN_H$ conferred a level of protection against challenge with wild type HPIV3 that was indistinguishable from that conferred by previous infection with wild type HPIV3. From these and related findings, the usefulness of rBPIV3-$F_H HN_H$ as a vaccine candidate against HPIV3 is readily apparent.

Viruses and Cells

HEp-2 and simian LLC-MK2 monolayer cell cultures were maintained in MEM medium (Life Technologies, Gaithersburg, Md.) supplemented with 5% fetal bovine serum (Summit Biotechnology, Ft. Collins, Colo.), 50 ug/ml gentamicin sulfate, and 4 mM glutamine (Life Technologies, Gaithersburg, Md.).

The wild type BPIV3 strain Kansas/15626/84 (Clone 5-2-4, Lot BPI3-1) (BPIV3 Ka), the HPIV3 JS wild type, its recombinant version (rHPIV3), and the rHPIV3 virus containing the BPIV3 Ka N ORF in place of the HPIV3-N ORF (rHPIV3-$N_B$) are each described above (see also, Clements et al., 1991, supra; Karron et al., 1995a, supra; Bailly et al., 2000, supra; and Durbin et al., 1997, supra). PIVs were propagated at 32° C. in LLC-MK2 cells (ATCC CCL-7), as previously described (Hall et al., 1992, supra). The modified vaccinia strain Ankara (MVA) recombinant virus that expresses bacteriophage T7 RNA polymerase is described by Wyatt et al. (1995, supra).

Construction of Antigenomic cDNAs Encoding Recombinant BPIV3/HPIV3 Viruses.

a) Construction of cDNA to Recover rBPIV3

A full length cDNA was constructed to encode the complete 15456 nucleotide (nt) antigenomic RNA of BPIV3 Ka, as described above. The cDNA was assembled from 4 subclones derived from reverse transcription (RT) of viral RNA using the SuperScript II Pre-amplification System (Life Technologies, Gaithersburg, Md.) and polymerase chain reaction (PCR) amplification with a High Fidelity PCR kit (Clontech Laboratories, Palo Alto, Calif.). The RT-PCR products were cloned into modified pUC19 plasmids (New England Biolabs, Beverly, Mass.) using the following naturally occurring internal restriction enzyme recognition sites: Sma I (BPIV3 Ka sequence position nt186), Pst I (nt 2896), Mlu I (nt 6192), Sac II (nt 10452) and Bsp LU11 (nt 15412). Multiple subclones of the antigenomic cDNA were sequenced using a Perkin Elmer ABI 310 sequencer with dRhodamine Terminator Cycle Sequencing (Perkin Elmer Applied Biosystems, Warrington, UK), and only those matching the consensus sequence of BPIV3 Ka were used for assembly of the full length clone. The 3' and 5' ends of BPIV3 Ka were cloned and the assembly of the full length cDNA took place in the previously described p(Right) vector (Durbin et al., 1997, supra), which we modified to contain a new polylinker with restriction enzyme recognition sites for Xho I, Sma I, Mlu I, Sac II, Eco RI, Hind III and RsrII. The full length cDNA clone pBPIV3(184) contained the following elements in 3' to 5' order: a T7 promoter followed by 2 non-viral guanosine residues, the complete antigenomic sequence of BPIV3 Ka, a hepatitis delta virus ribozyme and a T7 polymerase transcription terminator (Bailly et al., 2000, supra; and Durbin et al., 1997a, supra).

b) Construction of rHPIV3-$F_B HN_B$ and rBPIV3-$F_H HN_H$

Unique restriction enzyme recognition sites were introduced into the BPIV3 antigenomic cDNA and into the previously described HPIV3 antigenomic cDNA p3/7(131)2G (Durbin et al., 1997a, supra) to facilitate the exchange of the F and HN genes between BPIV3 and HPIV3 cDNAs. Using the transformer site-directed mutagenesis protocol from Clontech (Clontech Laboratories, Palo Alto, Calif.), SgrAI restriction sites were introduced in the downstream non-coding region of the M gene at position 4811 of the rBPIV3 sequence and position 4835 of the rHPIV3 JS sequence (GenBank accession # Z11575). The nucleotide number given for the position of restriction enzyme recognition sites indicates the nucleotide after which the enzyme cuts, not the first nucleotide of the restriction enzyme recognition site. The sequence was changed from TCCAACATTGCA (SEQ. ID. NO. 45) to TCCACCGGTGCA (SEQ. ID. NO. 49) in rBPIV3 and from CGGACGTATCTA (SEQ. ID. NO. 43) to CGCACCGGTGTA (SEQ. ID. NO. 47) in rHPIV3 (recognition sites underlined). BsiWI restriction sites were introduced in the downstream non-coding region of the HN gene at nt 8595 of the rBPIV3 sequence and at nt 8601 of the rHPIV3 JS sequence. The sequence was changed from GATATAAAGA (SEQ. ID. NO. 176) to GACGTACGGA (SEQ. ID. NO. 177) in rBPIV3 to give pBPIVs(107) and from GACAAAAGGG (SEQ. ID. NO. 178) to GACGTACGGG (SEQ. ID. NO. 179) in rHPIV3 to give pHPIVs(106). The F and HN genes were exchanged between pBPIVs(107) and pHPIV3s(106) by digestion of each with SgrAI and BsiWI, gel purification of the fragments, and assembly of the appropriate fragments into the two full length cDNAs. The HPIV3 backbone bearing the BPIV3 F and HN genes, designated pHPIV(215), encoded 15480 nts of viral sequence, of which nts 4835 to 8619 came from BPIV3, and it was used to derive rHPIV3-$F_B HN_B$ (FIGS. 48A-48C). The BPIV3 backbone bearing the HPIV3 F and HN genes, designated pBPIV(215), encoded 15438 nts of viral sequence, of which nts 4811 to 8577 came from HPIV3, and it was used to derive rBPIV3-$F_H HN_H$ (FIG. 48A-48C).

BPIV3 Support Plasmids for Recovery of Virus from cDNA.

Support plasmids encoding the BPIV3 Ka N, P and L genes were assembled in modified pUC19 vectors and then cloned into the previously described pTM-1 vector (Durbin et al., 1997a, supra). In order to place the individual genes immediately downstream of the T7 promoter in the pTM vector, an Nco I site was introduced at the start codon of the N, P and L open reading frames (ORFs) using site-directed mutagenesis. The Nco I restriction site and a naturally occurring restriction site downstream of each ORF (Spe I for N, HincII for P and Bsp LU11I for L) was used for cloning into pTM. After cloning, the Nco I site in pTM(N) was mutagenized back to the original sequence to restore the correct amino acid assignment in the second codon. In pTM(P) and pTM(L) the amino acid sequence encoded by the ORF was not altered by the introduction of Nco I sites.

Transfection.

HEp-2 cells (approximately $1.5 \times 10^6$ cells per well of a six-well plate) were grown to 90% confluence and transfected with 0.2 µg each of the BPIV3 support plasmids pTM(N) and pTM(P), and 0.1 µg of pTM(L), along with 5 µg of the full length antigenomic cDNA and 12 µl LipofectACE (Life Technologies, Gaithersburg, Md.). Each transfection mixture also contained $1.5 \times 10^7$ plaque forming units (PFU) of MVA-T7, as previously described (Durbin et al., 1997, supra). The cultures were incubated at 32° C. for 12 hrs before the medium was replaced with MEM (Life Technologies, Gaithersburg, Md.) containing 10% fetal bovine serum. The supernatants were harvested after incubation at 32° C. for an additional three days, and were passaged onto LLC-MK2 cell monolayers in 25 $cm^2$ flasks and incubated for 5 days at 32° C.

Virus present in the supernatant was plaque-purified three times prior to amplification and characterization.

Molecular Characterization of Recovered Chimeric Recombinants.

The presence of the heterologous F and HN genes in the bovine or human PIV3 backbone was confirmed in plaque-purified recombinant viruses by RT-PCR of viral RNA isolated from infected cells or supernatant, which was performed using a primer pair that recognizes conserved sequences in rBPIV3 and rHPIV3. This yielded similarly sized fragments (nts 4206-9035 in rBPIV3, nts 4224-9041 in rHPIV3, nts 4206-9017 in rBPIV3-$F_H HN_H$, and nts 4224-9059 in rHPIV3-$F_B HN_B$) which were then digested with Eco RI and analyzed by electrophoresis on a 1% agarose gel (FIG. 49). The nucleotide sequence flanking the introduced SgrAI and BsiWI restriction sites in each virus was confirmed by sequencing the respective RT-PCR product.

Replication of HPIV3/BPIV3 Chimeric Viruses in Cell Culture.

The multicycle growth kinetics of BPIV3 Ka, rHPIV3-$F_B HN_B$, rBPIV3-$F_H HN_H$, rHPIV3-$N_B$ and rHPIV3 in LLC-MK2 cells were determined by infecting cells in triplicate at a multiplicity of infection (MOI) of 0.01 and harvesting samples at 24 hr intervals over a six day period, as previously described (Tao et al., 1998, supra). Samples were flash-frozen and titered in a single assay on LLC-MK2 cell monolayers in 96 well plates at 32° C., as described (Durbin et al., *Virology* 261:319-330, 1999b, incorporated herein by reference).

Primate Model Studies.

Rhesus monkeys seronegative for PIV3 as determined by hemagglutination-inhibition (HAI) assay (van Wyke Coelingh et al., 1988, supra) were inoculated intranasally and intratracheally in groups of 2 or 4 animals with $10^5$ tissue culture infectious dose$_{50}$ (TCID$_{50}$) per ml of BPIV3 Ka, rHPIV3-$F_B HN_B$, rBPIV3-$F_H HN_H$, rHPIV3-$N_B$ or rHPIV3. Nasopharyngeal swabs were collected daily on days 1 to 11 and on day 13. Tracheal lavage samples were collected on days 2, 4, 6, 8, and 10 post-infection. Individual samples were flash-frozen and stored at −70° C. until all samples were available for titration. Virus in the specimens was titered on LLC-MK2 cell monolayers in 24 and 96 well plates as previously described (Durbin et al., 1999b, supra). Sera collected from monkeys on days 0 and 28 was tested by HAI assay using HPIV3 JS and BPIV3 Ka as antigens, as previously described (van Wyke Coelingh et al., 1988, supra). On day 28 post inoculation, the monkeys were challenged intranasally and intratracheally with $10^6$ TCID$_{50}$ per site of HPIV3 JS. Nasopharyngeal swab samples were collected on days 3, 4, 5, 6, 7 and 8, and tracheal lavage samples on days 4, 6 and 8 post challenge. Samples were titered in a single assay as described above. Serum was collected on day 28 post challenge.

Recovery of rBPIV3 and BPIV3/HPIV3 Chimeric Viruses (rHPIV3-$F_B HN_B$ and rBPIV3-$F_H HN_H$) from cDNA.

A complete BPIV3 antigenomic cDNA, designated pBPIV (184), was constructed to encode the consensus sequence of BPIV3 Ka. This BPIV3 antigenomic cDNA was further modified by the introduction of unique SgrAI and BsiWI sites into the downstream noncoding region of the M and HN genes, respectively (FIG. 48C). The same restriction sites were introduced into the downstream noncoding region of the M and HN genes of a previously described complete HPIV3 antigenomic cDNA, p3/7(131)2G (Durbin et al., 1997a, supra). The F and HN glycoprotein genes of HPIV3 and BPIV3 were swapped by exchanging this SgrAI-BsiWI restriction fragment. A direct exchange of entire genes was anticipated to be well-tolerated because of the high level of sequence conservation between the cis-acting signals of BPIV3 and HPIV3. The HPIV3 antigenomic cDNA bearing the BPIV3 F and HN genes was designated pHPIV(215), and the BPIV3 antigenomic cDNA bearing the HPIV3 F and HN genes was designated pBPIV(215).

The antigenomic cDNAs pBPIV(184), pHPIV(215), pBPIV(215) and p3/7(131)2G were separately transfected into HEp-2 cells along with the three BPIV3 support plasmids pTM(N), pTM(P) and pTM(L), and the cells were simultaneously infected with recombinant MVA expressing the T7 RNA polymerase. To confirm that the recovered viruses indeed were the expected rBPIV3, rHPIV3-$F_B HN_B$, rBPIV3-$F_H HN_H$ and rHPIV3 viruses, intracellular RNA or RNA from supernatant from each cloned virus was analyzed by RT-PCR using a primer pair that recognized identical sequences in HPIV3 JS and BPIV3 Ka. The primer pair amplified a 4.8 kb fragment of DNA corresponding to the downstream end of the M gene, the F and HN genes, and the upstream end of the L gene (nts 4206-9035 in rBPIV3, nts 4224-9041 in rHPIV3, nts 4206-9017 in rBPIV3-$F_H HN_H$, and nts 4224-9059 in rHPIV3-$F_B HN_B$). The generation of each PCR product was dependent upon the inclusion of reverse transcriptase, indicating that each was derived from viral RNA and not from contaminating cDNA (data not shown). The PCR products were then digested with Eco RI, which would be predicted to yield a different, unique restriction enzyme digest pattern for each of the four viruses (FIG. 9). In each case, the predicted pattern was observed, confirming the identity of the backbone and the inserted F and HN genes. In addition, nucleotide sequencing was performed on the RT-PCR products to confirm the presence of the introduced restriction sites and flanking sequences.

The cytopathic effect (CPE) caused by rBPIV3-$F_H HN_H$ in LLC-MK2 cells was indistinguishable from that of HPIV3 JS (condensed, rounded-up cells and small syncytia) but different from BPIV3 (large multicellular syncytia), whereas the CPE caused by rHPIV3-$F_B HN_B$ was identical to that caused by the BPIV3. This indicates that the cytopathology of the chimeric PIVs cosegregated with the parental origin of the F and HN genes.

BPIV3/HPIV3 Chimeric Viruses Replicate Efficiently in Cell Culture.

The growth kinetics of rHPIV3-$F_B HN_B$ and rBPIV3-$F_H HN_H$ were compared with that of their parental viruses by infecting LLC-MK2 monolayers at an MOI of 0.01 and monitoring the production of infectious virus. The kinetics and magnitude of replication of the two chimeric viruses were comparable to those of their HPIV3 or BPIV3 parental viruses (FIG. 50). This suggested that BPIV3 and HPIV3 glycoproteins were compatible with the heterologous PIV3 internal proteins. This is an important property because it will be possible to efficiently prepare vaccine virus.

The F and HN Genes of the BPIV3/HPIV3 Chimeric Viruses are Determinants of the Host Range Restriction of Replication of BPIV3 Ka in the Respiratory Tract of Rhesus Monkeys.

rHPIV3-$F_B HN_B$ and rBPIV3-$F_H HN_H$ were evaluated for their ability to replicate in the upper and lower respiratory tract of rhesus monkeys. In particular, the effects of introduction of the BPIV3 F and HN genes into HPIV3 on attenuation of replication in rhesus monkeys was demonstrated, as described above for the BPIV3 N protein (see also, Bailly et al., 2000, supra). In addition, the effects of introduction of the HPIV3 F and HN genes into BPIV3 on replication in rhesus monkeys was determined. If the predominant attenuating mutations of BPIV3 were in genes other than the F and HN, then one would expect little overall effect of the HPIV3-BPIV3 glycoprotein exchange on replication of BPIV3 in rhesus monkeys.

Each chimeric virus was administered intranasally and intratracheally to rhesus monkeys at a dose of $10^5$ TCID$_{50}$ per site. The level of replication of the chimeric viruses was compared to that of the rHPIV3 and BPIV3 parental viruses and to that of rHPIV3-$N_B$ (Table 49). Since the rHPIV3 parental virus replicated to a low to moderate level in the lower respiratory tract, meaningful comparisons between groups could only be made for replication in the upper respiratory tract. The level of replication of rHPIV3-$F_B HN_B$ was similar to that of its BPIV3 parent and substantially lower than that of its HPIV3 parent (Table 49; FIG. 51, panel A). This showed that the BPIV3 glycoprotein genes contained one or more major determinants of the host range attenuation phenotype of BPIV3 for rhesus monkeys. The magnitude and pattern of replication of rHPIV3-$F_B HN_B$ and rHPIV3-$N_B$ were very similar, indicating that each of the two bovine genetic elements, namely the N gene versus the F and HN genes, attenuate HPIV3 to a similar extent.

tency of ranks (Sprent, P., "A Generalization Of The Sign Test," *Applied Nonparametric Statistical Methods*, pp. 123-126, Chapman and Hall, London, 1989, incorporated herein by reference), which indicated that the median titers of HPIV3, rBPIV3-$F_H HN_H$, and BPIV3 between day 3 and day 8 post infection are significantly different (d.f.2,8; p<0.05). The observation that the introduction of the HPIV3 F and HN proteins resulted in an increase in the replication of BPIV3 in rhesus monkeys indicates (i) that F and HN contain one or more determinants of host range restriction and (ii) that one or more genetic elements of BPIV3 that lie outside of the F and HN genes, e.g. the N protein, attenuate the virus for rhesus monkeys. This confirms that the genetic basis for host range restriction can involve multiple genes.

The Chimeric BPIV3 Bearing HPIV3 Glycoprotein Genes Induces Serum HAI Antibody to HPIV3 and a High Level of Resistance to wt HPIV3 Challenge.

rBPIV3-$F_H HN_H$ has important features that make it a candidate live attenuated virus vaccine against HPIV3, including attenuating genes from BPIV3 and the antigenic specificity of HPIV3, i.e. the F and HN glycoproteins, which are the major protective antigens. Therefore, its immunogenicity and protective efficacy against challenge with HPIV3 were documented. Rhesus monkeys were immunized by infection with BPIV3 Ka, rHPIV3-$F_B HN_B$, rBPIV3-$F_H HN_H$, rHPIV3-$N_B$, or rHPIV3. They were challenged 28 days later with HPIV3 JS wild type virus. Serum samples were taken prior to the initial infection on day 0 and prior to the challenge. BPIV3 and rHPIV3-$F_B HN_B$ induced serum HAI antibodies that reacted more efficiently with BPIV3 than HPIV3, whereas the converse was the case for HPIV3 and rBPIV3-$F_H HN_H$. Thus, the origin of the glycoprotein genes in each virus determined whether the HAI antibody response was directed predominantly against HPIV3 or against BPIV3. The replication of challenge HPIV3 virus was significantly reduced in the

TABLE 49

The F and HN glycoprotein genes of BPIV3 contribute to its restricted replication in the respiratory tract of rhesus monkeys.

| Immunizing virus[1] | Number of animals[2] | Mean peak virus titer[3] ($\log_{10}$TCID$_{50}$/ml ± S.E.) [Duncan Grouping][4] | | Serum HAI antibody titer (mean recip. $\log_2$ ± S.E.) for HPIV3 on day 28[7] | Serum HAI antibody titer (mean recip. $\log_2$ ± S.E.) for BPIV3 on day 28[7] |
|---|---|---|---|---|---|
| | | NP swab[5] | Tracheal lavage[6] | | |
| rHPIV3 | 6 | 4.7 ± 0.54 [A] | 2.4 ± 0.37 [A] | 9.5 ± 0.72 [A] | 6.8 ± 1.03 [B] |
| rBPIV3-$F_H HN_H$ | 4 | 3.1 ± 0.58 [B] | 1.6 ± 0.05 [A] | 6.8 ± 0.63 [BC] | 3.8 ± 0.63 [C] |
| rHPIV3-$N_B$ | 6 | 3.0 ± 0.60 [B] | 1.4 ± 0.19 [A] | 8.2 ± 0.48 [AB] | 6.5 ± 0.62 [B] |
| rHPIV3-$F_B HN_B$ | 4 | 2.9 ± 0.28 [B] | 2.0 ± 0.24 [A] | 4.5 ± 0.29 [D] | 9.5 ± 0.65 [A] |
| BPIV3 Ka | 6 | 2.6 ± 0.26 [B] | 1.6 ± 0.10 [A] | 5.5 ± 0.62 [CD] | 9.2 ± 0.60 [A] |

[1]Monkeys were inoculated intranasally and intratracheally with $10^5$ TCID$_{50}$ of virus in a 1 ml inoculum at each site.
[2]The groups with 6 animals contain 4 animals each from a previous rhesus study (Bailly et al., 2000, supra).
[3]Mean of the peak virus titers for each animal in its group irrespective of sampling day. S.E. = standard error.
[4]Virus titrations were performed on LLC-MK2 cells at 32° C. The limit of detectability of virus titer was 10 TCID$_{50}$/ml. Mean viral titers were compared using a Duncan Multiple Range test ($\alpha$ = 0.05). Within each column, mean titers with different letters are statistically different. Titers indicated with two letters are not significantly different from those indicated with either letter.
[5]Nasopharyngeal swab samples were collected on days 1 to 11 and on day 13.
[6]Tracheal lavage samples were collected on days 2, 4, 6, 8 and 10 post-infection.
[7]The titers on day 0 were <2.0. Day 28 was the day of challenge with wild type HPIV3.
**Two of the animals in the fHPIV3 group were infected with rHPIV3s, the virus containing two restriction enzyme recognition sites for the glycoprotein swap.

The rBPIV3-$F_H HN_H$ chimeric virus replicated significantly less well than rHPIV3 (Table 49), and it grouped with BPIV3 in a Duncan multiple range test. However, inspection of its pattern of replication in FIG. 51B suggested that rBPIV3-$F_H HN_H$ replicated to a level intermediate between that of its HPIV3 and BPIV3 parents. The interpretation that rBPIV3-$F_H HN_H$ replicates to a level intermediate between that of its parents is supported by Friedman's test of consisupper and lower respiratory tract of previously immunized monkeys (Table 50). Although the level of protective efficacy against HPIV3 was not significantly different among the different viruses, viruses bearing HPIV3 F and HN were consistently more protective in the upper respiratory tract than were viruses bearing BPIV3 F and HN. This is in accordance with the higher level of HPIV3-specific serum HAI antibodies induced by viruses bearing HPIV3 F and HN.

TABLE 50

Immunization of rhesus monkeys with BPIV3/HPIV3 chimeric recombinant virus induces resistance to challenge with wild type HPIV3

| Immunizing virus[1] | Number of animals[2] | Mean peak virus titer[3] ($\log_{10}TCID_{50}$/ml ± S.E.) [Duncan Grouping][4] | | Serum HAI antibody titer (mean recip. $\log_2$ ± S.E.) for HPIV3 on the day of challenge | Serum HAI antibody titer (mean recip. $\log_2$ ± S.E.) for HPIV3 28 days after challenge |
|---|---|---|---|---|---|
| | | Nasopharyngeal swab[5] | Tracheal lavage[6] | | |
| none | 4 | 4.5 ± 0.33 [A] | 4.5 ± 0.19 [A] | <2 | 12.0 ± 0.58 [A] |
| rHPIV3 | 6 | 2.3 ± 0.14 [B] | 1.2 ± 0.20 [B] | 9.5 ± 0.72 [A] | 11.7 ± 0.21 [A] |
| rBPIV3-$F_HHN_H$ | 4 | 2.5 ± 0.25 [B] | 1.0 ± 0.48 [B] | 6.8 ± 0.63 [BC] | 10.5 ± 0.29 [AB] |
| rHPIV3-$N_B$ | 6 | 2.3 ± 0.41 [B] | 1.4 ± 0.08 [B] | 8.2 ± 0.48 [AB] | 11.5 ± 0.22 [A] |
| rHPIV3-$F_BHN_B$ | 4 | 3.0 ± 0.14 [B] | 1.0 ± 0.0 [B] | 4.5 ± 0.29 [D] | 9.5 ± 0.87 [B] |
| BPIV3 Ka | 6 | 2.9 ± 0.26 [B] | 1.3 ± 0.20 [B] | 5.5 ± 0.62 [CD] | 9.3 ± 0.76 [B] |

[1]Each previously immunized monkey and non-immunized controls were challenged with $10^6$ $TCID_{50}$ of HPIV3 JS in a 1 ml inoculum at each site 28 days after immunization.
[2]The groups with 6 animals contain 4 animals each from a previous rhesus study (Bailly et al., 2000, supra).
[3]Mean of the peak virus titers for each animal in its group irrespective of sampling day.
[4]Virus titrations were performed on LLC-MK2 cells. The limit of detectability of virus titer was 10 $TCID_{50}$/ml. Mean viral titers were compared using a Duncan Multiple Range test ($\alpha$ = 0.05). Within each column, mean titers with different letters are statistically different. Titers indicated with two letters are not significantly different from those indicated with either letter. The group of unimmunized animals were not included in theDuncan analysis at the day of challenge.
[5]Nasopharyngeal swab samples were collected on days 3 to 8 post challenge.
[6]Trachael lavage samples were collected on days 4, 6 and 8 post challenge.
**Two animals in the rHPIV3 group were infected with rHPIV3s.

Based on the foregoing examples, the invention provides for importation of BPIV genes into a virulent HPIV backbone and visa versa to yield novel, human-bovine chimeric PIV vaccine candidates. In exemplary chimeric recombinants disclosed in the present example, rBPIV3-$F_HHN_H$ and its rHPIV3-$F_BHN_B$ counterpart, replicated in vitro as well as the respective parental viruses. It was also confirmed that the F and HN exchange between the BPIV3 and HPIV3 is compatible since the considerably more divergent HPIV1 F and HN proteins were highly functional in a HPIV3 background (Tao et al., *J. Virol.* 72:2955-2961, 1998), which was evinced by the undiminished capacity of the chimeric viruses for replication in vitro. rBPIV3-$F_HHN_H$ replicated in the upper respiratory tract of rhesus monkeys to a level intermediate between that of its HPIV3 and BPIV3 parents indicating that the BPIV3 F and HN genes make an independent contribution to the overall attenuation of BPIV3 for primates. The overall attenuation of BPIV3 virus thus is the sum of two or more genetic elements, one of which is the set of F and HN genes and one of the others is indicated to be N.

Although BPIV3 itself is being evaluated as a vaccine virus for HPIV3 (Karron et al., *Pediatr. Infect. Dis. J.* 15:650-654, 1996; and Karron et al., *J. Infect. Dis.* 171:1107-1114, 1995), it is only 25% related antigenically to HPIV3 (Coelingh et al., *J. Infect. Dis.* 157:655-662, 1988). Thus, the immunogenicity of BPIV3 against HPIV3 will be improved if it is modified according to the present invention to express the protective F and HN antigens of HPIV3. rBPIV3-$F_HHN_H$ represents such a virus, and, in the present example, immunization of rhesus monkeys with rBPIV3-$F_HHN_H$ induced a higher level of antibody to HPIV3 than did immunization with BPIV3. Furthermore, rBPIV3-$F_HHN_H$ conferred a level of protection against replication of HPIV3 challenge in the upper and lower respiratory tract that was statistically indistinguishable from that conferred by a previous infection with rHPIV3. Similarly, rHPIV3-$N_B$, which is attenuated by the BPIV3 N protein but possesses HPIV3 protective antigens, also induced a high level of resistance to HPIV3 challenge. Despite replicating to similar levels in rhesus monkeys, rHPIV3-$N_B$ induced higher levels of antibodies to HPIV3 than rBPIV3-$F_HHN_H$.

rBPIV3-$F_HHN_H$ replicates to higher levels in rhesus monkeys than BPIV3, although it is significantly attenuated compared to HPIV3. Since the level of replication of BPIV3 in humans is low (Karron et al., *J. Infect. Dis.* 171:1107-1114, 1995), this increase is expected to be well tolerated among vaccinees. Alternatively, additional methods to attenuate human-bovine chimeric viruses of the invention are disclosed herein to ensure that the vaccine viruses replicate only to moderate levels, for example in human infants, to prevent unacceptable respiratory tract illness among vaccinees. Within other aspects of the invention, the slight increase in replication of rBPIV3-$F_HHN_H$ in primates offers an opportunity to use rBPIV3-$F_HHN_H$ as a vector for heterologous viral antigens such as glycoproteins of other PIVs (e.g., HPIV1 and HPIV2), the RSV F and G glycoproteins, and the measles HA glycoprotein, which can be incorporated as added or substituted gene(s) or genome segment(s) into the attenuated HPIV3 vaccine candidate. In various alternative embodiments disclosed herein, the slight increase in replication of rBPIV3-$F_HHN_H$ in monkeys over that of BPIV3 can be offset by the addition of foreign viral protective antigens, e.g., RSV glycoproteins, whose addition provides a selected level of attenuation. The data presented here further defined the basis for the host range restriction of BPIV3 for primates and identify rBPIV3-$F_HHN_H$ as a potential vaccine candidate against HPIV3 and as a vector for heterologous viral antigens.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation.

SEQUENCE LISTING

<160> NUMBER OF SEQ ID NOS: 188

<210> SEQ ID NO 1
<211> LENGTH: 42
<212> TYPE: DNA
<213> ORGANISM: Artificial Sequence
<220> FEATURE:
<223> OTHER INFORMATION: Flanking sequence of measles HA gene insert
      for N-P and P-M junctions.  Nucleotide insert to conform inserted
      sequence to rule of six.
<220> FEATURE:
<221> NAME/KEY: misc_feature
<222> LOCATION: (1)..(42)
<223> OTHER INFORMATION: Part of Parent Appln No 09/733,692 as SEQ ID
      NO: 01; Part of Parent Appln No 09/458,813 as SEQ ID NO: 01;
      Part of Parent Appln No 09/459,062 as SEQ ID NO: 01

<400> SEQUENCE: 1
cttaagaata tacaaataag aaaaacttag gattaaagag cg                         42

<210> SEQ ID NO 2
<211> LENGTH: 36
<212> TYPE: DNA
<213> ORGANISM: Artificial Sequence
<220> FEATURE:
<223> OTHER INFORMATION: Flanking sequence of Measles HA gene insert
      for N-P and P-M junctions. Nucleotide insert to conform inserted
      sequence to rule of six.
<220> FEATURE:
<221> NAME/KEY: misc_feature
<222> LOCATION: (1)..(36)
<223> OTHER INFORMATION: Part of Parent Appln No 09/733,692 as SEQ ID
      NO: 02; Part of Parent Appln No 09/458,813 as SEQ ID NO: 02;
      Part of Parent Appln No 09/459,062 as SEQ ID NO: 02

<400> SEQUENCE: 2
gatccaacaa agaaacgaca ccgaacaaac cttaag                               36

<210> SEQ ID NO 3
<211> LENGTH: 101
<212> TYPE: DNA
<213> ORGANISM: Artificial Sequence
<220> FEATURE:
<223> OTHER INFORMATION: Flanking sequence of Measles HA gene insert
      for HN-L junction.  Nucleotide insert to conform inserted
      sequence to rule of six.
<220> FEATURE:
<221> NAME/KEY: misc_feature
<222> LOCATION: (1)..(101)
<223> OTHER INFORMATION: Part of Parent Appln No 09/733,692 as SEQ ID
      NO: 03; Part of Parent Appln No 09/458,813 as SEQ ID NO: 03;
      Part of Parent Appln No 09/459,062 as SEQ ID NO: 03

<400> SEQUENCE: 3
aggcctaaaa gggaaatata aaaaacttag gagtaaagtt acgcaatcca actctactca      60
tataattgag gaaggaccca atagacaaat ccaaattcga g                        101

<210> SEQ ID NO 4
<211> LENGTH: 79
<212> TYPE: DNA
<213> ORGANISM: Artificial Sequence
<220> FEATURE:
<223> OTHER INFORMATION: Flanking sequence of Measles HA gene insert
      for HN-L junction.
<220> FEATURE:
<221> NAME/KEY: misc_feature
<222> LOCATION: (1)..(79)
<223> OTHER INFORMATION: Part of Parent Appln No 09/733,692 as SEQ ID
      NO: 04; Part of Parent Appln No 09/458,813 as SEQ ID NO: 04;
      Part of Parent Appln No 09/459,062 as SEQ ID NO: 04

-continued

```
<400> SEQUENCE: 4
tcataattaa ccataatatg catcaatcta tctataatac aagtatatga taagtaatca      60
gcaatcagac aataggcct                                                  79

<210> SEQ ID NO 5
<211> LENGTH: 64
<212> TYPE: DNA
<213> ORGANISM: Artificial Sequence
<220> FEATURE:
<223> OTHER INFORMATION: Cloning site for GU insertion
<220> FEATURE:
<221> NAME/KEY: misc_feature
<222> LOCATION: (1)..(64)
<223> OTHER INFORMATION: Part of Parent Appln No 09/733,692 as SEQ ID
      NO: 05

<400> SEQUENCE: 5
aggaaaaggg aaatataaaa aacttaggag taaagttacg cgtgttaact tcgaagagct      60
ccct                                                                  64

<210> SEQ ID NO 6
<211> LENGTH: 38
<212> TYPE: DNA
<213> ORGANISM: Artificial Sequence
<220> FEATURE:
<223> OTHER INFORMATION: Cloning site for NCR insertion.  Nucleotide
      insert to conform inserted sequence to rule of six.
<220> FEATURE:
<221> NAME/KEY: misc_feature
<222> LOCATION: (1)..(38)
<223> OTHER INFORMATION: Part of Parent Appln No 09/733,692 as SEQ ID
      NO: 06; Part of Parent Appln No 09/458,813 as SEQ ID NO: 06

<400> SEQUENCE: 6
aggaaaaggg aacgcgtgtt aacttcgaag agctccct                             38

<210> SEQ ID NO 7
<211> LENGTH: 63
<212> TYPE: DNA
<213> ORGANISM: Artificial Sequence
<220> FEATURE:
<223> OTHER INFORMATION: Cloning site for supernumerary gene insert
      between the P and M genes of rHPIV3
<220> FEATURE:
<221> NAME/KEY: misc_feature
<222> LOCATION: (1)..(63)
<223> OTHER INFORMATION: Part of Parent Appln No 09/733,692 as SEQ ID
      NO: 07

<400> SEQUENCE: 7
ttaacaatat acaaataaga aaaacttagg attaaagagc catggcgtac gaagcttacg      60
cgt                                                                   63

<210> SEQ ID NO 8
<211> LENGTH: 12
<212> TYPE: DNA
<213> ORGANISM: Artificial Sequence
<220> FEATURE:
<223> OTHER INFORMATION: PIV3 gene end(GE) sequence.
      Chemically synthesized sequence.
<220> FEATURE:
<221> NAME/KEY: misc_feature
<222> LOCATION: (1)..(12)
<223> OTHER INFORMATION: Part of Parent Appln No 09/733,692 as SEQ ID
      NO: 08
```

```
<400> SEQUENCE: 8
aagtaagaaa aa                                                            12

<210> SEQ ID NO 9
<211> LENGTH: 58
<212> TYPE: DNA
<213> ORGANISM: Artificial Sequence
<220> FEATURE:
<223> OTHER INFORMATION: Cloning site for RSV G and F
      gene inserts in B/H PI

```
<210> SEQ ID NO 13
<211> LENGTH: 10
<212> TYPE: DNA
<213> ORGANISM: Artificial Sequence
<220> FEATURE:
<223> OTHER INFORMATION: Chemically synthesized sequence

<400> SEQUENCE: 13
aggattaaag                                                                10

<210> SEQ ID NO 14
<211> LENGTH: 24
<212> TYPE: DNA
<213> ORGANISM: Artificial Sequence
<220> FEATURE:
<223> OTHER INFORMATION: Sequence spanning PIV2 F ectodomain and PIV3
      F transmembrane/cytoplasmic domains.
<220> FEATURE:
<221> NAME/KEY: mis -continued

```
<400> SEQUENCE: 17

Leu Tyr Ser Leu Ile Ile Ile Ile
1               5

<210> SEQ ID NO 18
<211> LENGTH: 21
<212> TYPE: DNA
<213> ORGANISM: Artificial Sequence
<220> FEATURE:
<223> OTHER INFORMATION: Sequence spanning PIV3 HN 5' ntr and PIV3 HN
      transmembrane/cytoplasmic domains.
<220> FEATURE:
<221> NAME/KEY: misc_feature
<222> LOCATION: (1)..(21)
<223> OTHER INFORMATION: Part of Parent Appln No 09/459,062 as SEQ ID
      NO: 47

<400> SEQUENCE: 18
tccaaattcg agatggaata c                                              21

<210> SEQ ID NO 19
<211> LENGTH: 27
<212> TYPE: DNA
<213> ORGANISM: Artificial Sequence
<220> FEATURE:
<223> OTHER INFORMATION: Sequence spanning PIV3 HN
      transmembrane/cytoplasmic domains and PIV2 HN ectodomain.
<220> FEATURE:
<221> NAME/KEY: misc_feature
<222> LOCATION: (1)..(27)
<223> OTHER INFORMATION: Part of Parent Appln No 09/459,062 as SEQ ID
      NO: 48

<400> SEQUENCE: 19
attaattcca tccatgagat aattcat                                        27

<210> SEQ ID NO 20
<211> LENGTH: 33
<212> TYPE: DNA
<213> ORGANISM: Artificial Sequence
<220> FEATURE:
<223> OTHER INFORMATION: Sequence spanning PIV2 HN ectodomain and PIV3
      HN 3' ntr, with extra nucleotides.
<220> FEATURE:
<221> NAME/KEY: misc_feature
<222> LOCATION: (1)..(33)
<223> OTHER INFORMATION: Part of Parent Appln No 09/459,062 as SEQ ID
      NO: 49

<400> SEQUENCE: 20
gaactaatgc tttaagcttc ataattaacc ata                                 33

<210> SEQ ID NO 21
<211> LENGTH: 9
<212> TYPE: PRT
<213> ORGANISM: Artificial Sequence
<220> FEATURE:
<223> OTHER INFORMATION: Terminal amino acids bridging fused PIV3 HN
      transmembrane/cytoplasmic domains and PIV2 HNectodomain.
<220> FEATURE:
<221> NAME/KEY: misc_feature
<222> LOCATION: (1)..(9)
<223> OTHER INFORMATION: Part of Parent Appln No 09/459,062 as SEQ ID
      NO: 50

<400> SEQUENCE: 21

Ile Asn Ser Ile His Glu Leu Ile His
1               5
```

```
<210> SEQ ID NO 22
<211> LENGTH: 4
<212> TYPE: PRT
<213> ORGANISM: Artificial Sequence
<220> FEATURE:
<223> OTHER INFORMATION: Terminal amino acids of PIV2 HN ectodomain.
<220> FEATURE:
<221> NAME/KEY: misc_feature
<222> LOCATION: (1)..(4)
<223> OTHER INFORMATION: Part of Parent Appln No 09/459,062 as SEQ ID
      NO: 51

<400> SEQUENCE: 22

Glu Leu Met Leu
1

<210> SEQ ID NO 23
<211> LENGTH: 21
<212> TYPE: DNA
<213> ORGANISM: Artificial Sequence
<220> FEATURE:
<223> OTHER INFORMATION: Sequence spanning PIV2 F
      ectodomain/transmembrane domain and PIV3 F cytoplasmic domain.
<220> FEATURE:
<221> NA

```
<220> FEATURE:
<221> NAME/KEY: misc_feature
<222> LOCATION: (1)..(24)
<223> OTHER INFORMATION: Part of Parent Appln No 09/459,062 as SEQ ID
      NO: 55

<400> SEQUENCE: 26
ctcactaata agactgccac aatt                                              24

<210> SEQ ID NO 27
<211> LENGTH: 30
<212> TYPE: DNA
<213> ORGANISM: Artificial Sequence
<220> FEATURE:
<223> OTHER INFORMATION: Sequence spanning PIV2 HN
      transmembrane/ectodomains and PIV3 HN 3' ntr.
<220> FEATURE:
<221> NAME/KEY: misc_feature
<222> LOCATION: (1)..(30)
<223> OTHER INFORMATION: Part of Parent Appln No 09/459,062 as SEQ ID
      NO: 56

<400> SEQUENCE: 27
gaactaatgc tttaatcata attaaccata                                        30

<210> SEQ ID NO 28
<211> LENGTH: 8
<212> TYPE: PRT
<213> ORGANISM: Artificial Sequence
<220> FEATURE:
<223> OTHER INFORMATION: Terminal amino acids bridging fused PIV3 HN
      cytoplasmic domain and PIV2 HN transmembrane/ectodomains.
<220> FEATURE:
<221> NAME/KEY: misc_feature
<222> LOCATION: (1)..(8)
<223> OTHER INFORMATION: Part of Parent Appln No 09/459,062 as SEQ ID
      NO: 57

<400> SEQUENCE: 28

Leu Thr Asn Lys Thr Ala Thr Ile
1               5

<210> SEQ ID NO 29
<211> LENGTH: 11
<212> TYPE: DNA
<213> ORGANISM: Artificial Sequence
<220> FEATURE:
<223> OTHER INFORMATION: Sequence flanking N gene start codon
<220> FEATURE:
<221> NAME/KEY: misc_feature
<222> LOCATION: (1)..(11)
<223> OTHER INFORMATION: Part of Parent Appln No 09/586,479 as SEQ ID
      NO: 10

<400> SEQUENCE: 29
caaaaatgtt g                                                            11

<210> SEQ ID NO 30
<211> LENGTH: 12
<212> TYPE: DNA
<213> ORGANISM: Artificial Sequence
<220> FEATURE:
<223> OTHER INFORMATION: Sequence flanking N gene stop codon
<220> FEATURE:
<221> NAME/KEY: misc_feature
<222> LOCATION: (1)..(12)
<223> OTHER INFORMATION: Part of Parent Appln No 09/586,479 as SEQ ID
      NO: 11

<400> SEQUENCE: 30
gcaactaatc ga                                                           12
```

```
<210> SEQ ID NO 31
<211> LENGTH: 12
<212> TYPE: DNA
<213> ORGANISM: Artificial Sequence
<220> FEATURE:
<223> OTHER INFORMATION: Sequence flanking introduced restriction site
      at N gene start codon
<220> FEATURE:
<221> NAME/KEY: misc_feature
<222> LOCATION: (1)..(12)
<223> OTHER INFORMATION: Part of Parent Appln No 09/586,479 as SEQ ID
      NO: 12

<400> SEQUENCE: 31
taaccatggt ga                                                          12

<210> SEQ ID NO 32
<211> LENGTH: 12
<212> TYPE: DNA
<213> ORGANISM: Artificial Sequence
<220> FEATURE:
<223> OTHER INFORMATION: Sequence flanking introduced restriction site
      at N gene stop codon
<220> FEATURE:
<221> NAME/KEY: misc_feature
<222> LOCATION: (1)..(12)
<223> OTHER INFORMATION: Part of Parent Appln No 09/586,479 as SEQ ID
      NO: 13

<400> SEQUENCE: 32
gcacttaagc ac                                                          12

<210> SEQ ID NO 33
<211> LENGTH: 12
<212> TYPE: DNA
<213> ORGANISM: Artificial Sequence
<220> FEATURE:
<223> OTHER INFORMATION: Sequence flanking mutation to restore context
      for N gene start codon
<220> FEATURE:
<221> NAME/KEY: misc_feature
<222> LOCATION: (1)..(12)
<223> OTHER INFORMATION: Part of Parent Appln No 09/586,479 as SEQ ID
      NO: 14

<400> SEQUENCE: 33
caaaaatgtt ga                                                          12

<210> SEQ ID NO 34
<211> LENGTH: 12
<212> TYPE: DNA
<213> ORGANISM: Artificial Sequence
<220> FEATURE:
<223> OTHER INFORMATION: Sequence flanking mutation to restore context
      for N gene stop codon
<220> FEATURE:
<221> NAME/KEY: misc_feature
<222> LOCATION: (1)..(12)
<223> OTHER INFORMATION: Part of Parent Appln No 09/586,479 as SEQ ID
      NO: 15

<400> SEQUENCE: 34
gcaactagtc ga                                                          12

<210> SEQ ID NO 35
<211> LENGTH: 40
<212> TYPE: DNA
<213> ORGANISM: Artificial Sequence
<220> FEATURE:
<223> OTHER INFORMATION: Sequence flanking N gene start codon in rJS
```

```
<220> FEATURE:
<221> NAME/KEY: misc_feature
<222> LOCATION: (1)..(40)
<223> OTHER INFORMATION: Part of Parent Appln No 09/586,479 as SEQ ID
      NO: 16

<400> SEQUENCE: 35
ggaactctat aatttcaaaa atgttgagcc tatttgatac                                40

<210> SEQ ID NO 36
<211> LENGTH: 40
<212> TYPE: DNA
<213> ORGANISM: Artificial Sequence
<220> FEATURE:
<223> OTHER INFORMATION: Sequence flanking N gene start codon in cKa
      and cSF
<220> FEATURE:
<221> NAME/KEY: misc_feature
<222> LOCATION: (1)..(40)
<223> OTHER INFORMATION: Part of Parent Appln No 09/586,479 as SEQ ID
      NO: 17

<400> SEQUENCE: 36
ggaactctat aatttcaaaa atgttgagtc tattcgacac                                40

<210> SEQ ID NO 37
<211> LENGTH: 40
<212> TYPE: DNA
<213> ORGANISM: Artificial Sequence
<220> FEATURE:
<223> OTHER INFORMATION: Sequence flanking N gene start codon in Ka
      and SF
<220> FEATURE:
<221> NAME/KEY: misc_feature
<222> LOCATION: (1)..(40)
<223> OTHER INFORMATION: Part of Parent Appln No 09/586,479 as SEQ ID
      NO: 18

<400> SEQUENCE: 37
gaaatcctaa gactgtaatc atgttgagtc tattcgacac                                40

<210> SEQ ID NO 38
<211> LENGTH: 40
<212> TYPE: DNA
<213> ORGANISM: Artificial Sequence
<220> FEATURE:
<223> OTHER INFORMATION: Sequence flanking N gene stop codon in rJS
<220> FEATURE:
<221> NAME/KEY: misc_feature
<222> LOCATION: (1)..(40)
<223> OTHER INFORMATION: Part of Parent Appln No 09/586,479 as SEQ ID
      NO: 19

<400> SEQUENCE: 38
ttaacgcatt tggaagcaac taatcgaatc aacattttaa                                40

<210> SEQ ID NO 39
<211> LENGTH: 40
<212> TYPE: DNA
<213> ORGANISM: Artificial Sequence
<220> FEATURE:
<223> OTHER INFORMATION: Sequence flanking N gene stop codon in cKa
      and cSF
<220> FEATURE:
<221> NAME/KEY: misc_feature
<222> LOCATION: (1)..(40)
<223> OTHER INFORMATION: Part of Parent Appln No 09/586,479 as SEQ ID
      NO: 20

<400> SEQUENCE: 39
tcagtgcatt cggaagcaac tagtcgaatc aacattttaa                                40
```

-continued

```
<210> SEQ ID NO 40
<211> LENGTH: 40
<212> TYPE: DNA
<213> ORGANISM: Artificial Sequence
<220> FEATURE:
<223> OTHER INFORMATION: Sequence flanking N gene stop codon in Ka
      and SF
<220> FEATURE:
<221> NAME/KEY: misc_feature
<222> LOCATION: (1)..(40)
<223> OTHER INFORMATION: Part of Parent Appln No 09/586,479 as SEQ ID
      NO: 21

<400> SEQUENCE: 40
tcagtgcatt cggaagcaac tagtcacaaa gagatgacca                    40

<210> SEQ ID NO 41
<211> LENGTH: 15456
<212> TYPE: DNA
<213> ORGANISM: Bovine Parainfluenza Virus 3
<220> FEATURE:
<221> NAME/KEY: misc_feature
<222> LOCATION: (1)..(15456)
<223> OTHER INFORMATION: Part of Parent Appln No 09/586,479 as SEQ ID
      NO: 23

<400> SEQUENCE: 41
accaaacaag agaagagact tgcttgggaa tattaattca ataaaaatt aacttaggat    60 taaagaactt taccgaaagg taaggggaaa gaaatcctaa gactgtaatc atgttgagtc   120
tattcgacac attcagtgcg cgtaggcagg agaacataac aaaatcagct ggtgggctg    180 ttattcccgg gcaaaaaac actgtgtcta tatttgctct tggaccatca ataacagatg    240
acaatgacaa aatgcattg gctcttctct ttttgtctca ttctttagac aatgaaaagc    300
agcatgcgca aagagctgga tttttagttt ctctgttatc aatggcttat gccaacccag   360
aattatattt aacatcaaat ggtagtaatg cagatgttaa atatgtcatc tacatgatag   420
agaaagaccc aggaagacag aaatatggtg ggtttgtcgt caagactaga gagatggttt   480
atgaaaagac aactgactgg atgtttggga gtgatcttga gtatgatcaa gacaatatgt   540
tgcaaaatgg tagaagcact tctacaatcg aggatcttgt tcatactttt ggatatccat   600
cgtgtcttgg agcccttata atccaggttt ggataatact tgttaaggct ataaccagta   660
tatcaggatt gaggaaagga ttctttactc ggttagaagc atttcgacaa gatggaacag   720
ttaaatccag tctagtgttg agcggtgatg cagtagaaca aattggatca attatgaggt   780
cccaacagag cttggtaaca ctcatggttg aaacactgat aacaatgaac acaggcagga   840
atgacctgac aacaatagaa aagaatatac agattgtagg aaactacatc agagatgcag   900
gtcttgcttc attttcaac acaatcagat atggcattga actagaatg gcagctctaa    960 ctctgtctac ccttagaccg gacatcaaca gactcaaggc actgatagag ctatatctat   1020 caaagggcc acgtgctcct tttatatgca ttttgagaga tcctgtgcat ggtgagtttg   1080
caccaggcaa ctatcctgcc ctctggagtt atgcgatggg tgtagcagtt gtacaaaaca   1140
aggccatgca acagtatgta acaggaaggt cctatctgga tattgaaatg ttccaactgg   1200
gtcaagcagt ggcacgtgac gccgagtcgc agatgagttc aatattagag gatgaactgg   1260
gggtcacaca agaagccaag caaagcttga agaaacacat gaagaacatc agcagttcag   1320
atacaacctt ctataagcct acaggggat cagccataga aatggcaata gatgaggaag   1380
cagagcagcc cgaatccaga gggagaccaag accaaggaga tgaacctcgg tcatccatag   1440
ttccttatgc atgggcagac gaaaccggga atgacaacca aactgaatca accacagaaa   1500
```

```
ttgacagcat caaaactgaa caaagaaaca tcagagacag gctgaacaaa agactcaacg    1560
agaaaaggaa acagagtaac ccgggatcaa ctgacatcac aaacaacaca aatcaaactg    1620
aaatagatga tttattcagt gcattcggaa gcaactagtc acaaagagat gaccaccatc    1680
atcagcaaca agtaagaaaa acttaggatt aatggaaatt atccaatccg agacggaag     1740 gacaaatcca gaatccaacc acaactcaat caaccaaaga ttcatggaag acaatgttca    1800
aaacaatcaa atcatggatt cttgggaaga gggatcagga gataaatcat ctgacatctc    1860
atcggccctc gacatcattg aattcatact caacaccgac tcccaagaga cacggcaga    1920 cagcaatgaa atcaacacag gagccacaag acttagcacg acaatctacc aacttgagtc    1980
caaaacaaca gaaacaagca aggaaaatag tggaccagct aacaaaaatc gacagtttgg    2040
ggcatcacac gaacgtgcca cagagacaaa agatagaaat gttaatcaga agactgtaca    2100
gggaggatat aggagaggaa gcagcccaga tagtagaact gagactatgg tcactcgagg    2160
aatctccaga agcagcccag atcctaacaa tggaacccaa atccaggaag atattgatta    2220
caatgaagtt ggagagatgg ataaggactc tactaagagg gaaatgcgac aatttaaaga    2280
tgttccagtc aaggtatcag gaagtgatgc cattcctcca acaaaacaag atggagacgg    2340
tgatgatgga agaggcctgg aatctatcag tacatctgat tcaggatata ccagtatagt    2400
gactgccgca acactagatg acgaagaaga actccttatg aagaacaaca ggccaagaaa    2460
gtatcaatca acacccagaa acagtgacaa gggaattaaa aaagggagtg aaggccaaa     2520 agacacagac aaacaatcac caatattgga ctacgaactc aactccaaag gatcgaagaa    2580
gagccagaaa atcctcaaag ccagcacgaa tacaggagaa ccaacaagat cacagagtgg    2640
atcccagggg aagagaatca catcctggaa catcctcaac agcgagagcg gcaatcgagc    2700
agaatcaaca aaccaaaccc atcagacatc aatctcggga cagaaccaca caatgggacc    2760
aagcagaaca acctcagaac caaggaccaa gacacaaaag acggatggaa aggaaagaga    2820
ggacacagaa gagagcactc gatttacaga aagggcgatt acattattac agaatcttgg    2880
tgtaatccaa tctgcagcaa aattagacct ataccaagac aagagagttg tgtgtgtggc    2940
gaatgtccta acaatgcag  atactgcatc aaagatagac ttcctagcag gtttgatgat    3000
aggagtgtca atggatcatg atgtcaaatt aaatcagatt cagaacgaga tattaagttt    3060
aaaaactgat cttaagaaga tggatgaatc acatagaaga ctaattgaga atcaaaaaga    3120
acaattatca ctgatcacat cattaatctc aaatcttaaa atcatgacag agagaggagg    3180
gaagaaggac caaccagaac ctagcgggag gacatccatg atcaagacaa aggcaaaaga    3240
agagagaata aagaaagtca ggtttgaccc tcttatggaa acacagggca tcgagaaaaa    3300
catccctgac ctctacagat caatagaaaa acaccagaaa acgacacac  agatcaaatc    3360 agaaataaac agattgaatg atgaatccaa tgccactaga ttagtaccta agagaataag    3420
cagtacaatg agatcactaa taataatcat caacaacagc aatttatcat caaaagcaaa    3480
gcaatcatac atcaacgaac tcaagctctg caagagtgat gaggaagtgt ctgagttgat    3540
ggacatgttc aatgaggatg tcagctccca gtaaaccgcc aaccaagggt caacaccaag    3600
aaaaccaaca gcacaaaaca gccaataaga gaccatccca acacaccgaa ccaatcaaca    3660
cataacaaag atctttagat catagatgac taagaaaaac ttaggatgaa aggactgatc    3720
aatcctccaa aacaatgagc atcaccagct ccacaatcta cacattccca gaatcctctt    3780
tctccgagaa tggcaacata gagccgttac cactcaaggt caatgaacag agaaaggcca    3840
tacctcatat tagggttgtc aagataggag atccgcccaa acatggatcc agatatctgg    3900
```

```
atgtcttttt actgggcttc tttgaaatgg aaaggtcaaa agacaggtat gggagcataa    3960
gtgatctaga tgatgatcca agttacaagg tttgtggctc tggatcattg ccacttgggt    4020
tggctagata cactggaaat gatcaggaac tcctacaggc tgcaaccaag ctcgatatag    4080
aagtaagaag aactgtaaag gctacggaga tgatagttta cactgtgcaa acatcaaac     4140 ctgaactata tccatggtcc agtagattaa gaaaagggat gttatttgac gctaacaagg    4200
ttgcacttgc tcctcaatgt cttccactag atagagggat aaaattcagg gtgatatttg    4260
tgaactgcac agcaattgga tcaataactc tattcaaaat ccccaagtcc atggcattgt    4320
tatcattgcc taatacaata tcaataaatc tacaagtaca tatcaaaaca ggaattcaga    4380
cagattccaa aggagtagtt cagattctag atgaaaaagg tgaaaaatca ctaaatttca    4440
tggttcatct cggggttgatc aaaaggaaga tgggtagaat gtactcagtt gaatattgta    4500
agcagaagat tgagaagatg agattattat tctcattggg attagttgga gggatcagct    4560
tccacgtcaa cgcaactggc tctatatcaa agacattagc aagtcaatta gcatttaaaa    4620
gagaaatctg ctatccccta atggatctga atccacactt aaatttagtt atatgggcat    4680
catcagttga aattacaaga gtagatgcaa ttctccagcc ttcattacct ggcgaattca    4740
gatactaccc aaacatcata gcaaaagggg tcgggaaaat cagacagtaa aaccaacaac    4800
cctgacatcc aacactgcaa atcaggctac ccacaggaga aaaatcaaaa acttaggatc    4860
aaagggatca ccacaaaccc cgggaaacag ccaaaccaac aacacacaa atcacagaca     4920 aaaaggaaaa ggcactgcaa agaccgagaa caagcagaac gcacacaacc aagcagagga    4980
aagccaaagc ccgccattca caaacacacc aacaatccta caaacaagca ccaaaataga    5040
ggtcaaaaga caaagagcat cagatatgac catcacaacc ataatcatag ccatactact    5100
aataccccta tcattctgtc aaatagacat aacaaaactg caacgtgtag gtgtattagt    5160
caacaatccc aaaggcatga aaatttcaca aaattttgaa acgagatacc tgatattaag    5220
tctgataccc aaaatagaga attcacactc atgtggggat caacagataa accaatacaa    5280
gaagttattg atagattga taattcctct atatgatgga ttaaaattac aaaaagatgt      5340
aatagtagta agtcatgaaa cccataataa tactaatctt aggacaaaac gattctttgg    5400
agagataatt gggacaattg cgatagggat agccacctca gcgcaaatca ccgcagcagt    5460
cgctcttgtc gaagctaaac aggcaaggtc agacatagaa aaactcaaag aagctataag    5520
agacacaaac aaggcagtac aatcgattca aagttctgta ggtaacctaa ttgttgcagt    5580
taaatcagtt caagactatg tcaacaatga aattgtacct tcaatcacaa gattaggctg    5640
tgaagcagca gggttacaat tgggaattgc actgacacaa cattactcag aattaacaaa    5700
tatatttggt gataatatag gaacactgaa agaaaagggg ataaaattac aggggatagc    5760
atcgttatat catacaaaca aacagaaat atttactact tcaacagttg accaatatga    5820
tatttatgac ctattattca ctgaatcaat caagatgaga gtgatagatg ttgatttgag    5880
tgattactca attactcttc aagttagact tccttattta actaaactat caaatactca    5940
gatttataaa gtagattcta tatcatacaa catccagggc aaagagtggt atattcctct    6000
tcccaatcac atcatgacaa aaggggcttt tctaggtggt gctgatatta agaatgcat     6060 agaggcattc agcagttata tatgtccttc tgatccaggt tatatattaa atcacgagat    6120 agagaaattgt ttatcaggga acataacaca gtgtcctaag actgttgtta catcagatgt    6180
ggtaccacga tacgcgtttg tgaatggtgg attaattgca aactgcataa caactacatg    6240
tacatgcaat ggaattgaca atagaattaa tcaatcacct gatcaaggaa ttaagatcat    6300
```

```
aacacataaa gaatgccagg taataggtat aaacggaatg ttattcaata ctaatagaga    6360
agggacatta gcaacttata catttgatga cattatatta ataactctg ttgcacttaa    6420 tccaattgat atatctatgg aacttaacaa ggcaaaacta gaattagaag aatcgaagga    6480
atggataaag aaatcaaatc aaaagttaga ttccgttgga agttggtatc aatctagtgc    6540
aacaatcacc ataatcatag tgatgataat aattctattt ataatcaata taacaattat    6600
tgtagtcata atcaaattct atagaattaa ggggaaaat caaaacgaca aaaacagtga    6660
gccgtatata ctgacaaata gacaataaga ctatacacga tcaaatatag aaagtacaaa    6720
aaacttagga acaaagttgt tcaacacagc agcagcgaac agacccaaag gcagcgcaga    6780
ggcgacaccg aacccaaaaa tggaatattg gaaacacaca aacagcacaa aaaacaccaa    6840
caatgaaacc gaaacaacca gaggcaaaca cagtagcaag gttacaaata tcataatgta    6900
caccttctgg acaataacat caacaatatt attagtcatt tttataatga tattgacaaa    6960
cttaattcaa gagaacaatc ataataaatt aatgttgcag gaaataagaa aagaattcgc    7020
ggcaatagac accaagattc agaggacctc ggatgacatt ggaacctcaa tacagtcagg    7080
aataaataca agacttctca caattcagag tcatgttcaa aactatatcc cactatcact    7140
aacacaacaa atgtcagatc tcagaaaatt tatcaatgat ctaacaaata aaagagaaca    7200
tcaagaagtg ccaatacaga gaatgactca tgatagaggt atagaaccc taaatccaga    7260 caagttctgg aggtgtacat ctggtaaccc atctctaaca agtagtccta agataaggtt    7320
aataccaggg ccaggtttat tagcaacatc tactacagta aatggctgta ttagaatccc    7380
atcgttagca atcaatcatt taatctacgc ttacacctct aatcttatca cccagggctg    7440
tcaaaatata gggaaatctt accaagtact acaaataggg ataattacta taaattcgga    7500
cctagtacct gatttaaatc ccagagtcac acatacattt aatattgatg ataataggaa    7560
atcttgctct ctggcactat tgaatacaga tgtttatcag ttatgctcaa caccaaaagt    7620
tgatgagaga tccgattatg catcaacagg tattgaggat attgtacttg acattgtcac    7680
taataatgga ttaattataa caacaaggtt tacaaataat aatataactt ttgataaacc    7740
gtatgcagca ttgtatccat cagtaggacc aggaatctat tataagggta agttatatt    7800 tctcggatat ggaggtctag agcatgaaga aaacggagac gtaatatgta atacaactgg    7860
ttgtcctggc aaaacacaga gagactgtaa tcaggcttct tatagcccat ggttctcaaa    7920
taggagaatg gtaaactcta ttattgttgt tgataaaggc atagatgcaa cttttagctt    7980
gagggtgtgg actattccaa tgagccaaaa ttattgggga tcagaaggaa gattacttt    8040 attaggtgac agaatataca tatatactag atccacaagt tggcacagta aattacagtt    8100 agggtaatt gatatttctg attataataa tataagaata aattggactt ggcataatgt    8160
actatcacgg ccaggaaatg atgaatgtcc atggggtcat tcatgcccag acggatgtat    8220
aacaggagtt tacactgatg catatccgct aaacccatcg gggagtgttg tatcatcagt    8280
aattcttgac tcacaaaagt ctagagaaaa cccaatcatt acctactcaa cagctacaaa    8340
tagaataaat gaattagcta tatataacag aacacttcca gctgcatata caacaacaaa    8400
ttgtatcaca cattatgata aagggtattg ttttcatata gtagaaataa atcacagaag    8460
tttgaatacg tttcaaccta tgttattcaa aacagaagtt ccaaaaaact gcagctaaat    8520
tgatcatcgc atatcggatg ccagatgaca ttaaaagaga ccaccagaca gacaacacag    8580
gagatgatgc aagatataaa ggaataataa aaaacttagg agaaaagtgt gcaagaaaaa    8640
tggacactga atcccacagc ggcacaacat ctgacattct gtaccctgaa tgtcacctca    8700
```

```
attctcctat agttaaagga aaaatagcac aactgcatac aataatgagt ttgccccaac    8760
cctacgatat ggatgatgat tcaatactga ttattactag acaaaaaatc aaactcaata    8820
aattagataa aagacaacgg tcaattagga aattaagatc agtcttaatg gaaagagtaa    8880
atgatcttgg taaatacacc tttatcagat atccagaaat gtctagtgaa atgttccaat    8940
tatgtatacc cggaattaat aataaaataa atgaattgct aagtaaagca agtaaaacat    9000
ataatcaaat gactgatgga ttaagagatc tatgggttac tgtactatcg aagttagcat    9060
cgaaaaatga tggaagtaat tatgatatca atgaagatat tagcaatata tcaaatgttc    9120
acatgactta ccaatcagac aaatggtata atccattcaa gacatggttt actattaagt    9180
atgacatgag gagattacaa aaagccaaaa atgagattac attcaatagg cataaagatt    9240
ataatctatt agaagaccaa aagaatatat tgctgataca tccagaactc gtcttaatat    9300
tagataaaca aaattacaat gggtatataa tgactcctga attggtacta atgtattgtg    9360
atgtagttga agggaggtgg aatataagtt catgtgcaaa attggatcct aaattacaat    9420
caatgtatta taaggtaac aatttatggg aaataataga tggactattc ctgaccttag    9480
gagaaagaac atttgacata atatcactat tagaaccgct tgcattatcg ctcattcaaa    9540
ctcatgaccc ggttaaacag ctcagagggg ctttttttaaa tcacgtgtta tcagaaatgg    9600
aatcaatatt cgcagctgag tgtacaacag aggaaatacc taatgtggat tatatagata    9660
aaattttaga tgtattcaaa gaatcaacaa tagatgaaat agcagaaatt ttctctttct    9720
tccgaacttt tggacaccct ccattagagg cgagtatagc agcagagaaa gttgaaaagt    9780
atatgtacac tgagaaatgt ttgaaatttg atactatcaa taaatgtcat gctatttttt    9840
gtacaataat tataaatgga tatagagaaa gacatggtgg tcaatggcct ccagttacat    9900
tacctattca tgcacatgaa tttatcataa atgcgtacgg atcaaattct gccatatcat    9960
atgaaaatgc tgtagattat tataagagct tcataggaat aaaatttgac aagtttatag    10020
agcctcaatt ggatgaagac ttaactattt atatgaaaga taaagcatta tccccaaaga    10080
aatctaactg ggacacagtc tatccagctt caaacctgtt ataccgcact aatgtgtctc    10140
atgattcacg aagattggtt gaagtattta tagcagatag taaatttgat ccccaccaag    10200
tattagatta cgtagaatca ggatattggc tagatgatcc tgaatttaat atctcatata    10260
gtttaaaaga gaaagaaata aaacaagaag gtagactttt tgcaaaaatg acatacaaga    10320
tgagagctac acaagtatta tcagaaacat tattggcgaa taatataggg aaatccttcc    10380
aagagaatgg gatggttaaa ggagaaattg aattactcaa gagactgaca acaatatcta    10440
tgtctggggt tccgcggtat aatgaggtat acaataattc aaaaagtcac acagaggaac    10500
ttcaagctta taatgcaatt agcagttcca atttatcttc taatcagaag tcaaagaagt    10560
ttgaatttaa atcaacagat atatacaatg atggatacga aaccgtaagc tgcttcttaa    10620
cgacagatct taaaaatat tgttttaaatt ggaggtatga atcaacagct ttattcggtg    10680
atacttgtaa tcagatattt gggttaaagg aattatttaa ttggctgcac cctcgccttg    10740
aaaagagtac aatatatgtt ggagatcctt attgcccgcc atcagatatt gaacatttac    10800
cacttgatga ccatcctgat tcaggatttt atgttcataa tcctaaagga ggaatagaag    10860
ggttttgcca aaagttatgg acactcatat ctatcagtgc catacattta gcagctgtca    10920
aaatcggtgt aagagttact gcaatggttc aaggggataa tcaagccata gctgttacca    10980
ccagagtacc taataattat gattataagg ttaagaaaga gattgtttat aaagatgtgg    11040
taagattttt tgattctttg agagaggtta tggatgatct gggtcatgag ctcaaactaa    11100
```

```
atgaaactat aataagtagt aaaatgttta tatatagcaa aaggatatac tatgacggaa  11160
gaatccttcc tcaggcgtta aaagcattgt ctagatgtgt tttttggtct gaaacaatca  11220
tagatgagac aagatcagca tcctcaaatc tggcgacatc gtttgcaaag gccattgaga  11280
atggctactc acctgtattg ggatatgtat gctcaatctt caaaaatatc caacagttgt  11340
atatagcact tggaatgaat ataaatccaa ctataaccca aaatattaaa gatcaatatt  11400
tcaggaatat tcattggatg caatatgcat ctctaatccc tgctagtgtc ggaggattta  11460
attatatggc catgtcaagg tgttttgtca gaaacattgg agatcctaca gtcgctgcat  11520
tagctgatat taaaagattt ataaaagcaa atttgttaga tcgaggtgtc ctttacagaa  11580
ttatgaatca ggaaccaggc gagtcctcct ttttagactg ggcttcagac ccctattcat  11640
gtaacttacc acaatctcaa aatataacca ccatgataaa gaatataact gcaagaaatg  11700
tactacagga ctcaccaaac ccattactat ctggattatt tacaagtaca atgatagaag  11760
aggatgagga attagctgag ttcctaatgg acaggagaat aattctccca agggttgcgc  11820
atgacatttt agataattct cttactggaa ttaggaatgc tatagctggt atgttggata  11880
caacaaaatc actaattcga gtagggataa acagaggagg attaacctat aacttattaa  11940
gaaagataag caactatgat cttgtacaat atgagacact tagtaaaact ttaagactaa  12000
tagtcagtga caagattaag tatgaagata tgtgctcagt agacctagcc atatcattaa  12060
gacaaaaaat gtggatgcat ttatcaggag gaagaatgat aaatggactt gaaactccag  12120
atcctttaga gttactgtct ggagtaataa taacaggatc tgagcattgt aggatatgtt  12180
attcaactga aggtgaaagc ccatatacat ggatgtattt accaggcaat cttaatatag  12240
gatcagctga aacaggaata gcatcattaa gggtccctta cttttggatca gttacggatg  12300 agagatctga agcacaattg gggtatatca aaaatctaag caaaccagct aaggctgcta  12360
taagaatagc aatgatatat acttgggcat ttgggaatga cgaaatatct tggatggaag  12420
catcacagat tgcacaaaca cgtgcgaact ttacattaga tagcttaaag attttgacac  12480
cagtgacaac atcaacaaat ctatcacata ggttaaaaga tactgctact cagatgaaat  12540
tttctagtac atcacttatt agagtaagca ggttcatcac aatatctaat gataaatgt  12600 ctattaaaga ggcaaatgaa actaaagata caaatcttat ttatcaacag gtaatgttaa  12660
cagggttaag tgtatttgaa tatctatttta ggttagagga gagtacagga cataacccta  12720
tggtcatgca tctacatata gaggatggat gttgtatcaa agagagttac aatgatgagc  12780
atatcaatcc ggagtctaca ttagagttaa ttaaataccc tgagagtaat gaatttatat  12840
atgataagga ccctttaaag gatatagatc tatcaaaatt aatggttata agagatcatt  12900
cttatacaat tgacatgaat tactgggacg acacagatat tgtacatgca atatcaatat  12960
gtactgcagt tacaatagca gatacaatgt cgcagctaga tcgggataat cttaaggagc  13020
tggttgtaat tgcaaatgat gatgatatta acagtctgat aactgaattt ctgaccctag  13080
atatactagt gttctctcaaa acatttggag ggttactcgt gaatcaattt gcatataccc  13140
tttatggatt gaaaatagaa ggaagggatc ccatttggga ttatataatg agaacattaa  13200 aagcacctc acattcagta cttaaagtat tatctaatgc actatctcat ccaaaagtgt  13260
ttaagagatt ttgggattgt ggagttttga atcctatttta tggtcctaat actgctagtc  13320
aggaccaagt taagcttgct ctctcaattt gcgagtactc cttggatcta tttatgagag  13380
aatggctgaa tggagcatca cttgagatct atatctgtga tagtgacatg gaaatagcaa  13440
atgatagaag acaagcattt ctctcaagac accttgcctt tgtgtgttgt ttagcagaga  13500
```

```
tagcatctttt tggaccaaat ttattaaatc taacatatct agagagactt gacgaattaa    13560
aacaatactt ggatctgaac atcaaagaag atcctactct taaatatgtg caagtatcag    13620
gactgttaat taaatcattc ccctcaactg ttacgtatgt gaggaaaact gcgattaagt    13680
atctgaggat tcgtggcatt aatccgcctg aaacgattga agattgggat cccatagaag    13740
atgagaatat cttagacaat attgttaaaa ctgtaaatga caattgcagt gataatcaaa    13800
agagaaataa aagtagttat ttctggggat tagctctaaa gaattatcaa gtcgtaaaaa    13860
taagatccat aacgagtgat tctgaagtta atgaagcttc gaatgttact acacatggaa    13920
tgacacttcc tcagggagga agttatctat cacatcagct gaggttattt ggagtaaaca    13980
gtacaagttg tctgaaagct cttgaattgt cacaaatttt aatgagggaa gttaaaaaag    14040
ataaagatag actctttttta ggagaaggag caggagctat gttagcatgt tatgatgcta    14100
cactcggtcc tgcaataaat tattacaatt ctggtttaaa tattacagat gtaattggtc    14160
aacgggaatt aaaaatcttc ccatcagaag tatcattagt aggtaaaaaa ctaggaaatg    14220
taacacagat tcttaatcgg gtgagggtgt tatttaatgg gaatcccaat tcaacatgga    14280
taggaaatat ggaatgtgag agtttaatat ggagtgaatt aaatgataag tcaattggtt    14340
tagtacattg tgacatggag ggagcgatag gcaaatcaga agaaactgtt ttacatgaac    14400
attatagtat tattaggatt acatatttaa tcggggatga tgatgttgtc ctagtatcaa    14460
aaattatacc aactattact ccgaattggt ctaaaatact ctatctatac aagttgtatt    14520
ggaaggatgt aagtgtagtg tcccttaaaa catccaatcc tgcctcaaca gagctttatt    14580
taatttcaaa ggatgcttac tgtactgtaa tggaacccag taatcttgtt ttatcaaaac    14640
ttaaaaggat atcatcagta gaagaaaata atctattaaa atggataatc ttatcaaaaa    14700
ggaagaacaa cgaatggtta cagcatgaaa tcaaagaagg agaaagggat tatgggataa    14760
tgaggccata tcatacagca ctgcaaattt ttggattcca aattaactta aatcacttag    14820
ctaaagaatt tttatcaact cctgatttaa ccaacattaa taatataatt caaagtttta    14880
caagaacaat taaagatgtt atgttcgaat gggtcaatat cactcatgac aataaaagac    14940
ataaattagg aggaagatat aatctattcc cgcttaaaaa taaggggaag ttaagattac    15000
tatcacgaag attagtacta agctggatat cattatcttt atcaaccaga ttactgacag    15060
gccgtttccc agatgaaaaa tttgaaaata gggcacagac cggatatgta tcattggctg    15120
atactgattt agaatcttta aagttattat caagaaatat tgtcaaaagt tacaaagaac    15180
acataggatt aatatcatac tggttttttaa ccaaagaggt caaaatacta atgaaactta    15240
tagggggagt caaactacta ggaattccca aacagtacaa agagttagag gatcgatcat    15300
ttcagggtta tgaatatgat aatgaatttg atattgatta atacataaaa acaaaaaata    15360
aaacacctaa tcctctccca ttcacttcca acaaaatgaa aagtaagaaa acatatataat    15420 atacatatac caaacagagt ttttctcttg tttggt                              15456
```

<210> SEQ ID NO 42
<211> LENGTH: 15456
<212> TYPE: DNA
<213> ORGANISM: Bovine Parainfluenza Virus 3
<220> FEATURE:
<221> NAME/KEY: misc_feature
<222> LOCATION: (1)..(15456)
<223> OTHER INFORMATION: Part of Parent Appln No 09/586,479 as SEQ ID
      NO: 22

```
<400> SEQUENCE: 42
accaaacaag agaagagact ggtttgggaa tattaattca aataaaaatt aacttaggat      60
taaagaactt taccgaaagg taaggggaaa gaaatcctaa gactgtaatc atgttgagtc     120
tattcgacac attcagtgcg cgtaggcagg agaacataac gaaatcagct ggtggggctg     180
ttattcccgg gcaaaaaaac actgtgtcta tatttgctct tggaccatca ataacagatg     240
acaatgataa aatgacattg gctcttctct ttttgtctca ttctttagac aatgaaaagc     300
agcatgcgca aagagctgga tttttagttt ctctgttatc aatggcttat gccaacccag     360
aattatattt aacatcaaat ggtagtaatg cagatgttaa atatgttatc tacatgatag     420
agaaagaccc aggaagacag aaatatggtg ggtttgtcgt caagactaga gagatggttt     480
atgaaaagac aactgattgg atgttcggga gtgatcttga gtatgatcaa gacaatatgt     540
tgcaaaatgg tagaagcact tctacaatcg aggatcttgt tcatactttt ggatatccat     600
cgtgtcttgg agcccttata atccaagttt ggataatact tgttaaggct ataaccagta     660
tatcaggatt gaggaaagga ttctttactc ggttagaagc atttcgacaa gatggaacag     720
ttaaatccag tctagtgttg agcggtgatg cagtagaaca aattggatca attatgaggt     780
cccaacagag cttggtaaca ctcatggttg aaacactgat aacaatgaac acaggcagga     840
atgatctgac aacaatagaa aagaatatac agattgtagg aaactacatc agagatgcag     900
gtcttgcttc attttcaac acaatcagat atggcattga gactagaatg gcagctctaa     960
ctctgtctac ccttagaccg gatatcaaca gactcaaggc actgatcgag ttatatctat    1020
caaaggggcc acgtgctcct tttatatgca ttttgagaga tcccgtgcat ggtgagtttg    1080
caccaggcaa ctatcctgcc ctctggagtt atgcgatggg tgtagcagtt gtacaaaaca    1140
aggccatgca acagtatgta acaggaaggt cttatctgga tattgaaatg ttccaacttg    1200
gtcaagcagt ggcacgtgat gccgagtcgc agatgagttc aatattagag gatgaactgg    1260
gggtcacaca agaagccaag caaagcttga agaaacacat gaagaacatc agcagttcag    1320
atacaaccct tcataagcct acaggggat cagccataga aatggcgata gatgaagaag    1380
cagggcagcc tgaatccaga ggagatcagg atcaaggaga tgagcctcgg tcatccatag    1440
ttccttatgc atgggcagac gaaaccggga atgacaatca aactgaatca actacagaaa    1500
ttgacagcat caaaactgaa caaagaaaca tcagagacag gctgaacaaa agactcaacg    1560
agaaaaggaa acagagtgac ccgagatcaa ctgacatcac aaacaacaca aatcaaactg    1620
aaatagatga tttgttcagt gcattcggaa gcaactagtc acaaagagat gaccactatc    1680
accagcaaca agtaagaaaa acttaggatt aatggaaatt atccaatcca gagacggaag    1740
gacaaatcca gaatccaacc acaactcaat caaccaaaga ttcatggaag acaatgttca    1800
aaacaatcaa atcatggatt cttgggaaga gggatcagga gataaatcat ctgacatctc    1860
atcggccctc gacatcattg aattcatact cagcaccgac tcccaagaga cacggcaga    1920 cagcaatgaa atcaacacag gaaccacaag acttagcacg acaatctacc aacctgaatc    1980
caaaacaaca gaaacaagca aggaaaatag tggaccagct aacaaaaatc gacagtttgg    2040
ggcatcacac gaacgtgcca cagagacaaa agatagaaat gttaatcagg agactgtaca    2100
gggaggatat aggagaggaa gcagcccaga tagtagaact gagactatgg tcactcgaag    2160
aatctccaga agcagcccag atcctaacaa tggaacccaa atccaggaag atattgatta    2220
caatgaagtt ggagagatgg ataaggactc tactaagagg gaaatgcgac aatttaaaga    2280
tgttccagtc aaggtatcag gaagtgatgc cattcctcca acaaaacaag atggagacgg    2340
```

```
tgatgatgga agaggcctgg aatctatcag tacatttgat tcaggatata ccagtatagt   2400
gactgccgca acactagatg acgaagaaga actccttatg aagaacaaca ggccaagaaa   2460
gtatcaatca acaccccaga acagtgacaa gggaattaaa aaaggggttg aaggccaaa    2520
agacacagac aaacaatcat caatattgga ctacgaactc aacttcaaag gatcgaagaa   2580
gagccagaaa atcctcaaag ccagcacgaa tacaggagaa ccaacaagac cacagaatgg   2640
atcccagggg aagagaatca catcctggaa catcctcaac agcgagagcg gcaatcgaac   2700
agaatcaaca aaccaaaccc atcagacatc aacctcggga cagaaccaca caatgggacc   2760
aagcagaaca acctccgaac caaggatcaa gacacaaaag acggatggaa aggaaagaga   2820
ggacacagaa gagagcactc gatttacaga aagggcgatt acattattac agaatcttgg   2880
tgtaatccaa tctgcagcaa aattagacct ataccaagac aagagagttg tgtgtgtggc   2940
gaatgtccta acaatgcag atactgcatc aaagatagac ttcctagcag gtttgatgat   3000
aggagtgtca atggatcatg ataccaaatt aaatcagatt cagaacgaga tattaagttt   3060
gaaaactgat cttaaaaaga tggatgaatc acatagaaga ctaattgaga atcaaaaaga   3120
acaattatca ctgatcacat cattaatctc aaatcttaaa attatgacag agagaggagg   3180
gaagaaggac caaccagaac ctagcgggag gacatccatg atcaagacaa aagcaaaaga   3240
agagaaaata aagaaagtca ggtttgaccc tcttatggaa acacagggca tcgagaaaaa   3300
catccctgac ctctatagat caatagagaa acaccagaa aacgacacac agatcaaatc    3360
agaaataaac agattgaatg atgaatccaa tgccactaga ttagtaccta aagaataag   3420
cagtacaatg agatcattaa taataatcat taacaacagc aatttatcat caaaagcaaa   3480
gcaatcatac atcaacgaac tcaagctctg caagagtgac gaggaagtgt ctgagttgat   3540
ggacatgttc aatgaggatg tcagctccca gtaaaccgcc aaccaagggt caacaccaag   3600
aaaaccaata gcacaaaaca gccaatcaga gaccaccca atacaccaaa ccaatcaaca    3660
cataacaaag atctccagat catagatgat taagaaaaac ttaggatgaa aggactaatc   3720
aatcctccga aacaatgagc atcaccaact ccacaatcta cacattccca gaatcctctt   3780
tctccgagaa tggcaacata gagccgttac cactcaaggt caatgaacag agaaaggcca   3840
tacctcatat tagggttgtc aagataggag atccgcccaa acatggatcc agatatctgg   3900
atgtcttttt actgggcttc tttgagatgg aaaggtcaaa agacaggtat gggagcataa   3960
gtgatctaga tgatgatcca agttacaagg tttgtggctc tggatcattg ccacttgggt   4020
tggctagata caccggaaat gatcaggaac tcctacaggc tgcaaccaag ctcgatatag   4080
aagtaagaag aactgtaaag gctacggaga tgatagttta cactgtacaa aacatcaaac   4140
ctgaactata tccatggtcc agtagattaa gaaaagggat gttatttgac gctaataagg   4200
ttgcacttgc tcctcaatgt cttccactag atagagggat aaaattcagg gtgatatttg   4260
tgaactgcac agcaattgga tcaataactc tattcaaaat ccctaagtcc atggcattgt   4320
tatcattgcc taatacaata tcaataaatc tacaagtaca tcaaaaca ggagttcaga    4380
cagattccaa aggagtagtt cagattctag atgaaaaagg tgaaaatca ctaaatttca    4440
tggttcatct cggggttgatc aaaaggaaga tgggcagaat gtactcagtt gaatattgta   4500
agcagaagat cgagaagatg agattattat tctcattggg attagttgga gggatcagct   4560
tccacgtcaa cgcaactggc tctatatcaa agacattagc aagtcaatta gcattcaaaa   4620
gagaaatctg ctatccccta atggatctga atccacactt aaattcagtt atatgggcat   4680
catcagttga aattacaagg gtagatgcag ttctccagcc ttcattacct ggcgaattca   4740
```

```
gatactaccc aaacatcata gcaaaagggg tcgggaaaat cagacagtaa aatcaacaac    4800
cctgatatcc aacattgcaa atcaggctac ccacaggaga aaaatcaaaa acttaggatc    4860
aaagggatca ccacgaaccc cggaaaacag ccaaacaaac caacacacaa atcacagaca    4920
aaaaggagaa ggcactgcaa agaccgagaa aaaacagaac gcacacaacc aagcagagaa    4980
aagccaaagc ccgccattca caaacacacc aacaatcctg caaacaagca ccaaaacaga    5040
ggtcaaaaga caaagagcac cagatatgac catcacaacc acaatcatag ccatattact    5100
aataccccca tcattttgtc aaatagacat aacaaaactg caacgtgtag gtgtgttagt    5160
caacaatcct aaaggcatga agatttcaca aaatttcgaa acgagatacc tgatattaag    5220
tttgataccc aaaatagaga attcacactc atgtggggat caacagataa accaatacaa    5280
gaagttattg gatagattga taattcctct atatgatgga ttaaaattac aaaaagatgt    5340
aatagtagta agtcatgaaa cccacaacaa tactaatctt aggacaaaac gattctttgg    5400
agagataatt gggacaattg cgatagggat agccacttca gcacaaatca ccgcagcagt    5460
cgctcttgtc gaagctaaac aggcaaagtc agacatagaa aaactcaaag aggctataag    5520
agacacaaac aaggcagtac aatcgattca aagttctgta ggtaacctaa ttgttgcagt    5580
taaatcagtt caagactatg tcaacaatga aattatacct tcaatcacaa gattaggctg    5640
tgaagcagca gggttacaat gggaattgc attgacacaa cattactcag aattaacaaa    5700
tatatttggt gataatatag gaacactgaa agaaaaaggg ataaaattac aagggatagc    5760
atcattatat cacacaaaca taacggaaat atttactact tcaacagttg ccaatatga    5820 tatttatgac ctattattca ctgagtcaat caagatgaga gtgatagatg ttgatttgag    5880
tgattactca attactcttc aagttagact tccttatta actaaactat caaatactca    5940
aatttataaa gtagattcta tatcatacaa catccagggc aaagagtggt atattcctct    6000
tcccaatcac atcatgacaa aaggggcttt tctaggtggt gctgatatta agaatgcat    6060 agaggcattc agcagttata tatgtccttc tgatccaggt tacatattaa atcacgagat    6120
agagaattgt ttatcaggga acataacaca gtgtcctaag actgttgtta catcagatgt    6180
ggtaccacga tacgcgtttg tgaatggtgg attaattgca aactgcataa caactacatg    6240
tacatgcaat ggaattgaca atagaattaa tcaatcacct gatcaaggaa ttaagatcat    6300
aacacataaa gaatgccagg taataggtat aaacggaatg ttattcaata ctaatagaga    6360
agggacatta gcaacttata catttgatga catcatatta ataactctg ttgcacttaa     6420 tccaattgat atatctatgg aactcaacaa ggcaaaacta gaattagaag aatcgaagga    6480
atggataaag aaatcaaatc aaaagttaga ttccgttgga agttggtatc aatctagtgc    6540
aacaatcacc ataatcatag tgatgataat aattctagtt ataatcaata taacaattat    6600
tgtagtcata atcaaattcc atagaattca ggggaaagat caaaacgaca aaacagtga    6660 gccgtatata ctgacaaata gacaataaga ctatacacga tcaaatataa aaagtacaaa    6720
aaacttagga acaaagttgt tcaacacagc agcaccgaat agaccaaaag gcagcgcaga    6780
ggcgacacca aactcaaaaa tggaatattg gaaacacaca aacagcataa ataacaccaa    6840
caatgaaacc gaaacagcca gaggcaaaca tagtagcaag gttacaaata tcataatgta    6900 cacccttctgg acaataacat taacaatatt atcagtcatt tttataatga tattgacaaa    6960
cttaattcaa gagaacaatc ataataaatt aatgttgcag gaaataagaa aagaattcgc    7020
ggcaatagac accaagattc agaggacttc ggatgacatt ggaacctcaa tacagtcagg    7080
aataaataca agacttctca caattcagag tcatgttcaa aactatatcc cactatcatt    7140
```

```
aacacaacaa atgtcagatc tcagaaaatt tatcaatgat ctaacaaata aaagagaaca    7200
tcaagaagtg ccaatacaga gaatgactca tgatagaggt atagaacccc taaatccaaa    7260
caagttctgg aggtgtacat ctggtaaccc atctctaaca agtagtccta agataaggtt    7320
aataccagga ccaggtttat tagcaacatc tactacagta aatggctgta ttagaattcc    7380
atcgttagta atcaatcatc taatctatgc ttacacctct aatcttatta cccagggctg    7440
tcaagatata gggaaatctt accaagtact acaaataggg ataattacta taaattcgga    7500
cctagtacct gatttaaacc ccagagtcac acatacattt aatattgatg ataatagaag    7560
atcttgctct ctggcactat tgaatacaga tgtttatcag ttatgctcaa caccaaaagt    7620
tgatgaaaga tccgattatg catcaacagg tattgaggat attgtacttg acattgtcac    7680
taataatgga ttaattataa caacaaggtt tacaaataat aatataactt ttgataaacc    7740
gtatgcagca ttgtatccat cagtgggacc aggaatctat tataaggata agttatatt    7800 tctcggatat ggaggtctag agcatgaaga aaacggagac gtaatatgta atacaactgg    7860
ttgtcctggc aaaacacaga gagactgtaa tcaggcttct tatagcccat ggttctcaaa    7920
taggagaatg gtaaactcta ttattgttgt tgataaaggc atagatgcaa cttttagctt    7980
gagggtgtgg actattccaa tgagccaaaa ttattgggga tcagaaggaa gattactttt    8040
attaggtgac agaatataca tatatactag atccacaagt tggcacagta aattacagtt    8100
aggggtaatt gatatttctg attatactaa tataagaata aattggactt ggcataatgt    8160
actatcacgg ccagggaatg atgaatgtcc atggggtcat tcatgcccag acggatgtat    8220
aacaggagtt tacactgatg catatccgct aaacccatcg gggagtgttg tatcatcagt    8280
aattcttgat tcacaaaagt ctagagaaaa cccaatcatt acttactcaa cagctacaaa    8340
tagaataaat gaattagcta tatataacag aacacttcca gctgcatata caacaacaaa    8400
ttgtatcaca cattatgata aagggtattg ttttcatata gtagaaataa atcacagaag    8460
tttgaatacg tttcaaccta tgttattcaa aacagaagtt ccaaaaaact gcagctaaat    8520
tgatcatcgc atatcggatg caagatgaca ttaaaagaga ccaccagaca gacaacacag    8580
gagacgatgc aagatataaa gaaataataa aaaacttagg agaaaagtgt gcaagaaaaa    8640
tggacaccga gtcccacagc ggcacaacat ctgacattct gtaccctgaa tgtcacctca    8700
attctcctat agttaaagga aagatagcac aactgcatac aataatgagt ttgcctcagc    8760
cctacgatat ggatgatgat tcaatactga ttattactag acaaaaaatt aaactcaata    8820
aattagataa aagacaacgg tcaattagga aattaagatc agtcttaatg gaaagagtaa    8880
gtgatctagg taaatatacc tttatcagat atccagagat gtctagtgaa atgttccaat    8940
tatgtatacc cggaattaat aataaaataa atgaattgct aagtaaagca agtaaaacat    9000
ataatcaaat gactgatgga ttaagagatc tatgggttac tatactatcg aagttagcat    9060
cgaaaaatga tggaagtaat tatgatatca atgaagatat tagcaatata tcaaatgttc    9120
acatgactta tcaatcagac aaatggtata atccattcaa gacatggttt actattaagt    9180
atgacatgag aagattacaa aaagccaaaa atgagattac attcaatagg cataaagatt    9240
ataatctatt agaagaccaa aagaatatat tgctgataca tccagaactc gtcttaatat    9300
tagataaaca aaattacaat gggtatataa tgactcctga attggtacta atgtattgtg    9360
atgtagttga agggaggtgg aatataagtt catgtgcaaa attggatcct aagttacaat    9420
caatgtatta taagggtaac aatttatggg aaataatagg tggactattc tcgaccttag    9480
gagaaagaac atttgacata atatcactat tagaaccact tgcattatcg ctcattcaaa    9540
```

```
cttatgaccc ggttaaacag ctcagggggg cttttttaaa tcacgtgtta tcagaaatgg      9600
aattaatatt tgcagctgag tgtacaacag aggaaatacc taatgtggat tatatagata      9660
aaattttaga tgtgttcaaa gaatcaacaa tagatgaaat agcagaaatt ttctctttct      9720
tccgaacttt tggacaccct ccattagagg cgagtatagc agcagagaaa gttagaaagt      9780
atatgtatac tgagaaatgc ttgaaatttg atactatcaa taaatgtcat gctattttt       9840
gtacaataat tataaatgga tatagagaaa gacatggtgg tcaatggcct ccagttacat      9900
tacctgtcca tgcacatgaa tttatcataa atgcatacgg atcaaattct gccatatcat      9960
atgagaatgc tgtagattat tataagagct tcataggaat aaaatttgac aagtttatag     10020
agcctcaatt ggatgaagac ttaactattt atatgaaaga taaagcatta tccccaaaga     10080
aatcaaactg gcacacagtc tatccagctt caaacctgtt ataccgcact aatgtgtctc     10140
atgattcacg aagattggtt gaagtattta tagcagatag taaatttgat ccccaccaag     10200
tattagatta cgtagaatca ggatattggc tggatgatcc tgaatttaat atctcatata     10260
gtttaaaaga gaaagaaata aaacaagaag gtagactttt tgcaaaaatg acatacaaga     10320
tgagggctac acaagtatta tcagaaacat tattggcgaa taatataggg aaattcttcc     10380
aagagaatgg gatggttaaa ggagaaattg aattactcaa gagactaaca acaatatcta     10440
tgtctggagt tccgcggtat aatgaggtat acaataattc aaaaagtcac acagaagaac     10500
ttcaagctta taatgcaatt agcagttcca atttatcttc taatcagaag tcaaagaagt     10560
ttgaatttaa atctcagat atatacaatg atggatacga aaccgtaagc tgcttcttaa      10620
cgacagatct taaaaaatat tgtttaaatt ggaggtatga atcaacagct ttattcggtg     10680
atacttgtaa tcagatattt gggttaaagg aattatttaa ttggctgcac cctcgccttg     10740
aaaagagtac aatatatgtt ggagatcctt attgcccgcc atcagatatt gaacatttac     10800
cacttgatga ccatcctgat tcaggatttt atgttcataa tcctaaagga ggaatagaag     10860
ggttttgcca aaagttatgg acactcatat ctatcagtgc aatacattta gcagctgtca     10920
aaatcggtgt aagagttact gcaatggttc aaggggataa tcaagccata gctgttacca     10980
caagagtacc taataattat gattataaag ttaagaaaga gattgtttat aaagatgtgg     11040
taagattttt tgattccttg agagaggtga tggatgatct gggtcatgag ctcaaactaa     11100
atgaaactat aataagtagt aaaatgttta tatatagcaa aaggatatac tatgacggaa     11160
gaatccttcc tcaggcatta aaagcattgt ctagatgtgt tttttggtct gaaacaatca     11220
tagatgagac aagatcagca tcctcaaatc tggctacatc gtttgcaaag gccattgaga     11280
atggctactc acctgtattg ggatatgtat gctcaatctt caaaaatatc caacagttgt     11340
atatagcgct tggaatgaat ataaacccaa ctataaccca aaatattaaa gatcaatatt     11400
tcaggaatat tcattggatg caatatgcct ccttaatccc tgctagtgtc ggaggattta     11460
attatatggc catgtcaagg tgttttgtca gaaacattgg agatcctaca gtcgctgcgt     11520
tagccgatat taaaagattt ataaaagcaa atttgttaga tcgaggtgtc ctttacagaa     11580
ttatgaatca agaaccaggc gagtcttctt ttttagactg ggcctcagat ccctattcat     11640
gtaacttacc acaatctcaa aatataacca ccatgataaa gaatataact gcaagaaatg     11700
tactacagga ctcaccaaac ccattactat ctggattatt tacaagtaca atgatagaag     11760
aggatgagga attagctgag ttcctaatgg acaggagaat aatcctccca agagttgcac     11820
atgacatttt agataattct cttactggaa ttaggaatgc tatagctggt atgttggata     11880
caacaaaatc actaattcga gtagggataa gcagaggagg attaacctat aacttattaa     11940
```

```
gaaagataag caactatgat cttgtacaat atgagacact tagtaaaact ttaagactaa    12000
tagtcagtga caagattaag tatgaagata tgtgctcagt agacctagcc atatcattaa    12060
gacaaaaaat gtggatgcat ttatcaggag gaagaatgat aaatggactt gaaactccag    12120
atcctttaga gttactgtct ggagtaataa taacaggatc tgaacattgt aggatatgtt    12180
attcaactga aggtgaaagc ccatatacat ggatgtattt accaggcaat cttaatatag    12240
gatcagctga gacaggaata gcatcattaa gggtccctta ctttggatca gttacagatg    12300
agagatctga agcacaatta gggtatatca aaaatctaag caaaccagct aaggctgcta    12360
taagaatagc aatgatatat acttgggcat ttgggaatga cgaaatatct tggatggaag    12420
catcacagat tgcacaaaca cgtgcaaact ttacattgga tagcttaaag attttgacac    12480
cagtgacaac atcaacaaat ctatcacaca ggttaaaaga tactgctact cagatgaaat    12540
tttctagtac atcacttatt agagtaagca ggttcatcac aatatctaat gataatatgt    12600
ctattaaaga agcaaatgaa actaaagata caaatcttat ttatcaacag gtaatgttaa    12660
caggattaag tgtatttgaa tatctatttta ggttagagga gagtacagga cataacccta    12720
tggtcatgca tctacatata gaggatggat gttgtataaa agagagttac aatgatgagc    12780
atatcaatcc ggagtctaca ttagagttaa tcaaataccc tgagagtaat gaatttatat    12840
atgataagga ccctttaaag gatatagatc tatcaaaatt aatggttata agagatcatt    12900
cttatacaat tgacatgaat tactgggatg acacagatat tgtacatgca atatcaatat    12960
gtactgcagt tacaatagca gatacaatgt cgcagctaga tcgggataat cttaaggagc    13020
tggttgtgat tgcaaatgat gatgatatta acagtctgat aactgaattt ctgacctag    13080 atatactagt gtttctcaaa acatttggag ggttactcgt gaatcaattt gcatataccc    13140
tttatggatt gaaaatagaa ggaagggatc ccatttggga ttatataatg agaacattaa    13200
aagacacctc acattcagta cttaaagtat tatctaatgc actatctcat ccaaaagtgt    13260
ttaagagatt ttgggattgt ggagttttga atcctatttta tggtcctaat actgctagtc    13320
aagatcaagt taagcttgct ctctcgattt gcgagtactc cttggatcta tttatgagag    13380
aatggttgaa tggagcatca cttgagatct atatctgtga tagtgacatg gaaatagcaa    13440
atgacagaag acaagcattt ctctcaagac atcttgcctt tgtgtgttgt ttagcagaga    13500
tagcatcttt tggaccaaat ttattaaatc taacatatct agagagactt gatgaattaa    13560
aacaatactt agatctgaac atcaaagaag atcctactct taaatatgtg caagtatcag    13620
gactgttaat taaatcattc ccctcaactg ttacgtatgt aaggaaaact gcgattaagt    13680
atctgaggat tcgtggtatt aatccgcctg aaacgattga agattgggat cccatagaag    13740
atgagaatat cttagacaat attgttaaaa ctgtaaatga caattgcagt gataatcaaa    13800
agagaaataa aagtagttat ttctggggat tagctctaaa gaattatcaa gtcgtgaaaa    13860
taagatccat aacgagtgat tctgaagtta atgaagcttc gaatgttact acacatggaa    13920
tgacacttcc tcagggagga agttatctat cacatcagct gaggttattt ggagtaaaca    13980
gtacaagttg tcttaaagct cttgaattat cacaaatctt aatgagggaa gttaaaaaag    14040
ataaagatag actcttttta ggagaaggag caggagctat gttagcatgt tatgatgcta    14100
cactcggtcc tgcaataaat tattataatt ctggtttaaa tattacagat gtaattggtc    14160
aacgggaatt aaaaatcttc ccatcagaag tatcattagt aggtaaaaaa ctaggaaatg    14220
taacacagat tcttaatcgg gtgagggtgt tatttaatgg gaatcccaat tcaacatgga    14280
taggaaatat ggaatgtgag agtttaatat ggagtgaatt aaatgataag tcaattggtt    14340
```

```
tagtacattg tgacatggag ggagcgatag gcaaatcaga agaaactgtt ctacatgaac    14400
attatagtat tattaggatt acatatttaa tcggggatga tgatgttgtc ctagtatcaa    14460
aaattatacc aactattact ccgaattggt ctaaaatact ctatctatac aagttgtatt    14520
ggaaggatgt aagtgtagtg tcccttaaaa catccaatcc tgcctcaaca gagctttatt    14580
taatttcaaa agatgcttac tgtactgtaa tggaacccag taatcttgtt ttatcaaaac    14640
ttaaaaggat atcatcaata gaagaaaata atctattaaa gtggataatc ttatcaaaaa    14700
ggaagaataa cgagtggtta cagcatgaaa tcaagaagg agaaagggat tatgggataa     14760
tgaggccata tcatacagca ctgcaaattt ttggattcca aattaactta aatcacttag    14820
ctagagaatt tttatcaact cctgatttaa ccaacattaa taatataatt caagtttta     14880 caagaacaat taaagatgtt atgttcgaat gggtcaatat cactcatgac aataaaagac    14940
ataaattagg aggaagatat aatctattcc cgcttaaaaa taagggggaaa ttaagattat   15000 tatcacgaag attagtacta agctggatat cattatcctt atcaaccaga ttactgacgg    15060
gccgttttcc agatgaaaaa tttgaaaata gggcacagac cggatatgta tcattggctg    15120
atattgattt agaatcctta aagttattat caagaaatat tgtcaaaaat tacaaagaac    15180
acataggatt aatatcatac tggttttga ccaaagaggt caaaatacta atgaagctta     15240
taggaggagt caaactacta ggaattccta acagtacaa agagttagag gatcgatcat     15300
ctcagggtta tgaatatgat aatgaatttg atattgatta atacataaaa acataaaata    15360
aaacacctat tcctcaccca ttcacttcca acaaaatgaa aagtaagaaa aacatgtaat    15420
atatatatac caaacagagt ttttctcttg tttggt                              15456

<210> SEQ ID NO 43
<211> LENGTH: 12
<212> TYPE: DNA
<213> ORGANISM: Artificial Sequence
<220> FEATURE:
<223> OTHER INFORMATION: Chemically synthesized sequence

<400> SEQUENCE: 43
cggacgtatc ta                                                             12

<210> SEQ ID NO 44
<211> LENGTH: 12
<212> TYPE: DNA
<213> ORGANISM: Artificial Sequence
<220> FEATURE:
<223> OTHER INFORMATION: Sequence flanking site for introduction of
      Bsi W1 site for rHPIV3 JS
<220> FEATURE:
<221

```
<220> FEATURE:
<221> NAME/KEY: misc_feature
<222> LOCATION: (1)..(12)
<223> OTHER INFORMATION: Part of Parent Appln No 09/586,479 as SEQ ID
      NO: 02

<400> SEQUENCE: 45
tccaacattg ca                                                          12

<210> SEQ ID NO 46
<211> LENGTH: 12
<212> TYPE: DNA
<213> ORGANISM: Artificial Sequence
<220> FEATURE:
<223> OTHER INFORMATION: Sequence flanking site for introduction of
      Bsi W1 site for rBPIV3 Ka
<220> FEATURE:
<221> NAME/KEY: misc_feature
<222> LOCATION: (1)..(12)
<223> OTHER INFORMATION: Part of Parent Appln No 09/586,479 as SEQ ID
      NO: 25

<400> SEQUENCE: 46
aagatataaa ga                                                          12

<210> SEQ ID NO 47
<211> LENGTH: 12
<212> TYPE: DNA
<213> ORGANISM: Artificial Sequence
<220> FEATURE:
<223> OTHER INFORMATION: Sequence flanking site for introduction of
      Sgr A1 site for rHPIV3 s.
<220> FEATURE:
<221> NAME/KEY: misc_feature
<222> LOCATION: (1)..(12)
<223> OTHER INFORMATION: Part of Parent Appln No 09/586,479 as SEQ ID
      NO: 05

<400> SEQUENCE: 47
cgcaccggtg ta                                                          12

<210> SEQ ID NO 48
<211> LENGTH: 12
<212> TYPE: DNA
<213> ORGANISM: Artificial Sequence
<220> FEATURE:
<223> OTHER INFORMATION: Sequence flanking site for introduction of
      Bsi W1 site for rHPIV3 s
<220> FEATURE:
<221> NAME/KEY: misc_feature
<222> LOCATION: (1)..(12)
<223> OTHER INFORMATION: Part of Parent Appln No 09/586,479 as SEQ ID
      NO: 26

<400> SEQUENCE: 48
tagacgtacg gg                                                          12

<210> SEQ ID NO 49
<211> LENGTH: 12
<212> TYPE: DNA
<213> ORGANISM: Artificial Sequence
<220> FEATURE:
<223> OTHER INFORMATION: Sequence flanking site for introduction of Sgr
      A1 site for rBPIV3 s and for introduction of Sgr A1 site for
      rHPIV3 JS.
<220> FEATURE:
<221> NAME/KEY: misc_feature
<222> LOCATION: (1)..(12)
<223> OTHER INFORMATION: Part of Parent Appln No 09/586,479 as SEQ ID
      NO: 03; Part of Parent Appln No 09/586,479 as SEQ ID NO: 04
```

-continued

```
<400> SEQUENCE: 49
tccaccggtg ca                                                          12

<210> SEQ ID NO 50
<211> LENGTH: 12
<212> TYPE: DNA
<213> ORGANISM: Artificial Sequence
<220> FEATURE:
<223> OTHER INFORMATION: Sequence flanking site for introduction of
      Bsi W1 site for rBPIV3 s
<220> FEATURE:
<221> NAME/KEY: misc_feature
<222> LOCATION: (1)..(12)
<223> OTHER INFORMATION: Part of Parent Appln No 09/586,479 as SEQ ID
      NO: 27

<400> SEQUENCE: 50
aagacgtacg ga                                                          12

<210> SEQ ID NO 51
<211> LENGTH: 12
<212> TYPE: DNA
<213> ORGANISM: Artificial Sequence
<220> FEATURE:
<223> OTHER INFORMATION: Sequence flanking Sgr A1 site in rHPIV3
      sFBHNB
<220> FEATURE:
<221> NAME/KEY: misc_feature
<222> LOCATION: (1)..(12)
<223> OTHER INFORMATION: Part of Parent Appln No 09/586,479 as SEQ ID
      NO: 28

<400> SEQUENCE: 51
cgcaccggtg ca                                                          12

<210> SEQ ID NO 52
<211> LENGTH: 12
<212> TYPE: DNA
<213> ORGANISM: Artificial Sequence
<220> FEATURE:
<223> OTHER INFORMATION: Sequence flanking Bsi W1 site in rHPIV3
      sFBHNB
<220> FEATURE:
<221> NAME/KEY: misc_feature
<222> LOCATION: (1)..(12)
<223> OTHER INFORMATION: Part of Parent Appln No 09/586,479 as SEQ ID
      NO: 29

<400> SEQUENCE: 52
aagacgtacg gg                                                          12

<210> SEQ ID NO 53
<211> LENGTH: 12
<212> TYPE: DNA
<213> ORGANISM: Artificial Sequence
<220> FEATURE:
<223> OTHER INFORMATION: Sequence flanking Sgr A1 site in rBPIV3
      sFHHNH
<220> FEATURE:
<221> NAME/KEY: misc_feature
<222> LOCATION: (1)..(12)
<223> OTHER INFORMATION: Part of Parent Appln No 09/586,479 as SEQ ID
      NO: 30

<400> SEQUENCE: 53
tccaccggtg ta                                                          12
```

```
<210> SEQ ID NO 54
<211> LENGTH: 12
<212> TYPE: DNA
<213> ORGANISM: Artificial Sequence
<220> FEATURE:
<223> OTHER INFORMATION: Sequence flanking Bsi W1 site in rBPIV3 of
      sFHHNH
<220> FEATURE:
<221> NAME/KEY: misc_feature
<222> LOCATION: (1)..(12)
<223> OTHER INFORMATION: Part of Parent Appln No 09/586,479 as SEQ ID
      NO: 31

<400> SEQUENCE: 54
tagacgtacg ga                                                          12

<210> SEQ ID NO 55
<211> LENGTH: 31
<212> TYPE: DNA
<213> ORGANISM: Artificial Sequence
<220> FEATURE:
<223> OTHER INFORMATION: Synethic Primer.
<220> FEATURE:
<221> NAME/KEY: misc_feature
<222> LOCATION: (1)..(31)
<223> OTHER INFORMATION: Part of Parent Appln No 09/083,793 as SEQ ID
      NO: 02

<400> SEQUENCE: 55
aatacgactc actataacca aacaagagaa c                                     31

<210> SEQ ID NO 56
<211> LENGTH: 24
<212> TYPE: DNA
<213> ORGANISM: Artificial Sequence
<220> FEATURE:
<223> OTHER INFORMATION: Synethic Primer

<400> SEQUENCE: 56
ccaagtacta tgagatgctt gatt                                             24

<210> SEQ ID NO 57
<211> LENGTH: 31
<212> TYPE: DNA
<213> ORGANISM: Artificial Sequence
<220> FEATURE:
<223> OTHER INFORMATION: Synethic Primer.
<220> FEATURE:
<221> NAME/KEY: misc_feature
<222> LOCATION: (1)..(31)
<223> OTHER INFORMATION: Part of Parent Appln No 09/083,793 as SEQ ID
      NO: 04

<400> SEQUENCE: 57
ccctataatt tcaacatgtt gagcctattt g                                     31

<210> SEQ ID NO 58
<211> LENGTH: 31
<212> TYPE: DNA
<213> ORGANISM: Artificial Sequence
<220> FEATURE:
<223> OTHER INFORMATION: Chemically synthesized primer.
<220> FEATURE:
<221> NAME/KEY: misc_feature
<222> LOCATION: (1)..(31)
<223> OTHER INFORMATION: Part of Parent Appln No 09/083,793 as SEQ ID
      NO: 05

<400> SEQUENCE: 58
gattaaaatg ttggtcgact tagttgcttc c                                     31
```

```
<210> SEQ ID NO 59
<211> LENGTH: 38
<212> TYPE: DNA
<213> ORGANISM: Artificial Sequence
<220> FEATURE:
<223> OTHER INFORMATION: Chemically synthesized sequence.

<400> SEQUENCE: 59
ccatagagag tccatggaaa gcgatgctaa aaactatc                              38

<210> SEQ ID NO 60
<211> LENGTH: 37
<212> TYPE: DNA
<213> ORGANISM: Artificial Sequence
<220> FEATURE:
<223> OTHER INFORMATION: Synethic Primer.
<220> FEATURE:
<221> NAME/KEY: misc_feature
<222> LOCATION: (1)..(37)
<223> OTHER INFORMATION: Part of Parent Appln No 09/083,793 as SEQ ID
      NO: 07

<400> SEQUENCE: 60
cggtgtcgtt tctttgtcga ctcattggca attgttg                               37

<210> SEQ ID NO 61
<211> LENGTH: 38
<212> TYPE: DNA
<213> ORGANISM: Artificial Sequence
<220> FEATURE:
<223> OTHER INFORMATION: Synethic Primer.
<220> FEATURE:
<221> NAME/KEY: misc_feature
<222> LOCATION: (1)..(38)
<223> OTHER INFORMATION: Part of Parent Appln No 09/083,793 as SEQ ID
      NO: 06; Part of Parent Appln No 09/083,793 as SEQ ID NO: 74

<400> SEQUENCE: 61
ccatagagag tccatggaaa gcgacgctaa aaactatc                              38

<210> SEQ ID NO 62
<211> LENGTH: 42
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(42)
<223> OTHER INFORMATION: Part of Parent Appln No 09/083,793 as SEQ ID
      NO: 08

<400> SEQUENCE: 62
gcaaagcgtg cccgggccat ggacactgaa tctaacaatg gc                         42

<210> SEQ ID NO 63
<211> LENGTH: 28
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(28)
<223> OTHER INFORMATION: Part of Parent Appln No 09/083,793 as SEQ ID
      NO: 09

<400> SEQUENCE: 63
gaaattcctt aatcgattct ctagattc                                         28
```

```
<210> SEQ ID NO 64
<211> LENGTH: 30
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(30)
<223> OTHER INFORMATION: Part of Parent Appln No 09/083,793 as SEQ ID
      NO: 10

<400> SEQUENCE: 64
cccatcaact gtaacatacg taagaaagac                                        30

<210> SEQ ID NO 65
<211> LENGTH: 29
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(29)
<223> OTHER INFORMATION: Part of Parent Appln No 09/083,793 as SEQ ID
      NO: 11

<400> SEQUENCE: 65
ggttaggata tgtcgacatt gtatttatg                                         29

<210> SEQ ID NO 66
<211> LENGTH: 6843
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(6843)
<223> OTHER INFORMATION: Part of Parent Appln No 09/083,793 as SEQ ID
      NO: 20

<400> SEQUENCE: 66
atgttgagcc tatttgatac atttaatgca cgtaggcaag aaaacataac aaaatcagcc       60
ggtggagcta tcattcctgg acagaaaaat actgtctcta tattcgccct tggaccgaca      120
ataactgatg ataatgagaa aatgacatta gctcttctat ttctatctca ttcactagat      180
aatgagaaac aacatgcaca aagggcaggg ttcttggtgt ctttattgtc aatggcttat      240
gccaatccag agctctacct aacaacaaat ggaagtaatg cagatgtcaa gtatgtcata      300
tacatgattg agaaagatct aaaacggcaa aagtatggag gatttgtggt taagacgaga      360
gagatgatat atgaaaagac aactgattgg atatttggaa gtgacctgga ttatgatcag      420
gaaactatgt tgcagaacgg caggaacaat tcaacaattg aagaccttgt ccacacattt      480
gggtatccat catgtttagg agctcttata atacagatct ggatagttct ggtcaaagct      540
atcactagta tctcagggtt aagaaaaggc tttttcaccc gattggaagc tttcagacaa      600
gatggaacag tgcaggcagg gctggtattg agcggtgaca cagtggatca gattgggtca      660
atcatgcggt ctcaacagag cttggtaact cttatggttg aaacattaat aacaatgaat      720
accagcagaa atgacctcac aaccatagaa aagaatatac aaattgttgg caactacata      780
agagatgcag gtctcgcttc attcttcaat acaatcagat atggaattga gaccagaatg      840
gcagctttga ctctatccac tctcagacca gatatcaata gattaaaagc tttgatggaa      900
ctgtatttat caaagggacc acgcgctcct ttcatctgta tcctcagaga tcctatacat      960
```

```
ggtgagttcg caccaggcaa ctatcctgcc atatggagct atgcaatggg ggtggcagtt    1020
gtacaaaata gagccatgca acagtatgtg acgggaagat catatctaga cattgatatg    1080
ttccagctag acaagcagt agcacgtgat gccgaagctc aaatgagctc aacactggaa     1140
gatgaacttg gagtgacaca cgaatctaaa gaaagcttga agagacatat aaggaacata    1200
aacagttcag agacatcttt ccacaaaccg acaggtggat cagccataga gatggcaata    1260
gatgaagagc cagaacaatt cgaacataga gcagatcaag aacaaaatgg agaacctcaa    1320
tcatccataa ttcaatatgc ctgggcagaa ggaaatagaa gcgatgatca gactgagcaa    1380
gctacagaat ctgacaatat caagaccgaa caacaaaaca tcagagacag actaaacaag    1440
agactcaacg acaagaagaa acaaagcagt caaccaccca ctaatcccac aaacagaaca    1500
aaccaggacg aaatagatga tctgtttaac gcatttggaa gcaactaagt cgacgatccg    1560
gctgctaaca aagcccgaaa ggaagctgag ttggctgctg ccaccgctga gcaataacta    1620
gcataacccc ttggggcctc taaacgggtc ttgagggggt ttttgctgaa aggaggaact    1680
atatccggat cgagatcaat tctgtgagcg tatggcaaac gaaggaaaaa tagttatagt    1740
agccgcactc gatgggacat ttcaacgtaa accgtttaat aatatttga atcttattcc     1800 attatctgaa atggtggtaa aactaactgc tgtgtgtatg aaatgcttta aggaggcttc    1860
cttttctaaa cgattgggtg aggaaaccga gatagaaata ataggaggta atgatatgta    1920
tcaatcggtg tgtagaaagt gttacatcga ctcataatat tatattttt atctaaaaaa     1980 ctaaaaataa acattgatta aatttttaata taatacttaa aaatggatgt tgtgtcgtta   2040
gataaaccgt ttatgtattt tgaggaaatt gataatgagt tagattacga accagaaagt    2100
gcaaatgagg tcgcaaaaaa actgccgtat caaggacagt taaaactatt actaggagaa    2160 ttatttttttc ttagtaagtt acagcgacac ggtatattag atggtgccac cgtagtgtat   2220
ataggatctg ctcccggtac acatatacgt tatttgagag atcatttcta aatttagga    2280 gtgatcatca aatggatgct aattgacggc cgccatcatg atcctatttt aaatggattg    2340
cgtgatgtga ctctagtgac tcggttcgtt gatgaggaat atctacgatc catcaaaaaa    2400
caactgcatc cttctaagat tattttaatt tctgatgtga gatccaaacg aggaggaaat    2460
gaacctagta cggcggattt actaagtaat tacgctctac aaaatgtcat gattagtatt    2520
ttaaaccccg tggcgtctag tcttaaatgg agatgcccgt ttccagatca atggatcaag    2580
gactttatta tcccacacgg taataaaatg ttacaacctt ttgctccttc atattcaggg   2640
ccgtcgtttt acaacgtcgt gactgggaaa accctggcgt tacccaactt aatcgccttg   2700
cagcacatcc cccttttcgcc agctggcgta atagcgaaga ggcccgcacc gatcgccctt   2760
cccaacagtt gcgcagcctg aatggcgaat ggcgcgacgc gccctgtagc ggcgcattaa   2820
gcgcggcggg tgtggtggtt acgcgcagcg tgaccgctac acttgccagc gccctagcgc   2880
ccgctccttt cgctttcttc ccttcctttc tcgccacgtt cgccggcttt ccccgtcaag   2940
ctctaaatcg ggggctccct ttagggttcc gatttagtgc tttacggcac ctcgacccca   3000 aaaacttga ttagggtgat ggttcacgta gtgggccatc gccctgatag acggtttttc    3060
gccctttgac gttggagtcc acgttcttta atagtggact cttgttccaa actggaacaa   3120
cactcaaccc tatctcggtc tattcttttg atttataagg gattttgccg atttcggcct   3180
attggttaaa aaatgagctg atttaacaaa aatttaacgc gaattttaac aaaatattaa   3240
cgtttacaat ttcccaggtg gcacttttcg gggaaatgtg cgcggaaccc ctatttgttt   3300 attttttctaa atacattcaa atatgtatcc gctcatgaga caataaccct gataaatgct   3360
```

```
tcaataatat tgaaaaagga agagtatgag tattcaacat ttccgtgtcg cccttattcc    3420
cttttttgcg gcattttgcc ttcctgtttt tgctcaccca gaaacgctgg tgaaagtaaa    3480
agatgctgaa gatcagttgg gtgcacgagt gggttacatc gaactggatc tcaacagcgg    3540
taagatcctt gagagttttc gccccgaaga acgttttcca atgatgagca cttttaaagt    3600
tctgctatgt ggcgcggtat tatcccgtat tgacgccggg caagagcaac tcggtcgccg    3660
catacactat tctcagaatg acttggttga gtactcacca gtcacagaaa agcatcttac    3720
ggatggcatg acagtaagag aattatgcag tgctgccata accatgagtg ataacactgc    3780
ggccaactta cttctgacaa cgatcggagg accgaaggag ctaaccgctt ttttgcacaa    3840
catgggggat catgtaactc gccttgatcg ttgggaaccg gagctgaatg aagccatacc    3900
aaacgacgag cgtgacacca cgatgcctgt agcaatggca acaacgttgc gcaaactatt    3960
aactggcgaa ctacttactc tagcttcccg gcaacaatta atagactgga tggaggcgga    4020
taaagttgca ggaccacttc tgcgctcggc ccttccggct ggctggttta ttgctgataa    4080
atctggagcc ggtgagcgtg ggtctcgcgg tatcattgca gcactggggc cagatggtaa    4140
gccctcccgt atcgtagtta tctacacgac ggggagtcag gcaactatgg atgaacgaaa    4200
tagacagatc gctgagatag gtgcctcact gattaagcat tggtaactgt cagaccaagt    4260
ttactcatat atactttaga ttgatttaaa acttcatttt taatttaaaa ggatctaggt    4320
gaagatcctt tttgataatc tcatgaccaa aatcccttaa cgtgagtttt cgttccactg    4380
agcgtcagac cccgtagaaa agatcaaagg atcttcttga gatcctttt ttctgcgcgt    4440 aatctgctgc ttgcaaacaa aaaaaccacc gctaccagcg gtggtttgtt tgccggatca    4500
agagctacca actcttttc cgaaggtaac tggcttcagc agagcgcaga taccaaatac    4560
tgtccttcta gtgtagccgt agttaggcca ccacttcaag aactctgtag caccgcctac    4620
atacctcgct ctgctaatcc tgttaccagt ggctgctgcc agtggcgata agtcgtgtct    4680
taccgggttg gactcaagac gatagttacc ggataaggcg cagcggtcgg gctgaacggg    4740
gggttcgtgc acacagccca gcttggagcg aacgacctac accgaactga gatacctaca    4800
gcgtgagcta tgagaaagcg ccacgcttcc cgaagggaga aaggcggaca ggtatccggt    4860
aagcggcagg gtcggaacag gagagcgcac gagggagctt ccagggggaa acgcctggta    4920
tctttatagt cctgtcgggt ttcgccacct ctgacttgag cgtcgatttt tgtgatgctc    4980 gtcaggggg cggagcctat ggaaaaacgc cagcaacgcg gcctttttac ggttcctggc    5040
cttttgctgg ccttttgctc acatgttctt tcctgcgtta tcccctgatt ctgtggataa    5100
ccgtattacc gcctttgagt gagctgatac cgctcgccgc agccgaacga ccgagcgcag    5160
cgagtcagtg agcgaggaag cggaagagcg cccaatacgc aaaccgcctc tccccgcgcg    5220
ttggccgatt cattaatgca gctggcacga caggtttccc gactggaaag cgggcagtga    5280
gcgcaacgca attaatgtga gttagctcac tcattaggca ccccaggctt tacactttat    5340
gcttccggct cgtatgttgt gtggaattgt gagcggataa caatttcaca caggaaacag    5400
ctatgaccat gattacgcca agcttttgcg atcaataaat ggatcacaac cagtatctct    5460
taacgatgtt cttcgcagat gatgattcat tttttaagta tttggctagt caagatgatg    5520
aatcttcatt atctgatata ttgcaaatca ctcaatatct agactttctg ttattattat    5580
tgatccaatc aaaaaataaa ttagaagccg tgggtcattg ttatgaatct ctttcagagg    5640
aatacagaca attgacaaaa ttcacagact ttcaagattt taaaaactg tttaacaagg    5700 tccctattgt tacagatgga agggtcaaac ttaataaagg atatttgttc gactttgtga    5760
```

-continued

```
ttagtttgat gcgattcaaa aaagaatcct ctctagctac caccgcaata gatcctgtta      5820
gatacataga tcctcgtcgc aatatcgcat tttctaacgt gatggatata ttaaagtcga      5880
ataaagtgaa caataattaa ttctttattg tcatcatgaa cggcggacat attcagttga      5940
taatcggccc catgttttca ggtaaaagta cagaattaat tagacgagtt agacgttatc      6000
aaatagctca atataaatgc gtgactataa aatattctaa cgataataga tacggaacgg      6060
gactatggac gcatgataag aataattttg aagcattgga agcaactaaa ctatgtgatg      6120
tcttggaatc aattacagat ttctccgtga taggtatcga tgaaggacag ttcttttccag     6180 acattgttga attgatctcg atcccgcgaa attaatacga ctcactatag ggagaccaca      6240
acggtttccc tctagcggga tcaattccgc ccctctccct cccccccccc taacgttact      6300
ggccgaagcc gcttggaata aggccggtgt gcgtttgtct atatgttatt ttccaccata     6360
ttgccgtctt ttggcaatgt gagggcccgg aaacctggcc ctgtcttctt gacgagcatt     6420
cctaggggtc tttcccctct cgccaaagga atgcaaggtc tgttgaatgt cgtgaaggaa     6480
gcagttcctc tggaagcttc ttgaagacaa acaacgtctg tagcgaccct ttgcaggcag     6540
cggaaccccc cacctggcga caggtgcctc tgcggccaaa agccacgtgt ataagataca     6600
cctgcaaagg cggcacaacc ccagtgccac gttgtgagtt ggatagttgt ggaaagagtc     6660
aaatggctct cctcaagcgt attcaacaag gggctgaagg atgcccagaa ggtaccccat     6720
tgtatgggat ctgatctggg gcctcggtgc acatgcttta catgtgttta gtcgaggtta     6780
aaaaacgtct aggccccccg aaccacgggg acgtggtttt cctttgaaaa acacgataat     6840
acc                                                                   6843
```

<210> SEQ ID NO 67
<211> LENGTH: 7107
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(7107)
<223> OTHER INFORMATION: Part of Parent Appln No 09/083,793 as SEQ ID
       NO: 21

<400> SEQUENCE: 67

```
atggaaagcg acgctaaaaa ctatcaaatc atggattctt gggaagagga atcaagagat        60
aaatcaacta atatctcctc ggccctcaac atcattgaat tcatactcag caccgacccc       120
caagaagact tatcggaaaa cgacacaatc aacacaagaa cccagcaact cagtgccacc       180
atctgtcaac cagaaatcaa accaacagaa acaagtgaga aagatagtgg atcaactgac       240
aaaaatagac agtccgggtc atcacacgaa tgtacaacag aagcaaaaga tagaaatatt       300
gatcaggaaa ctgtacagag aggacctggg agaagaagca gctcagatag tagagctgag       360
actgtggtct ctggaggaat ccccagaagc atcacagatt ctaaaaatgg aacccaaaac       420
acggaggata ttgatctcaa tgaaattaga aagatggata aggactctat tgagggggaaa       480 atgcgacaat ctgcaaatgt tccaagcgag atatcaggaa gtgatgacat atttacaaca       540
gaacaaagta gaaacagtga tcatggaaga agcctggaat ctatcagtac acctgataca       600
agatcaataa gtgttgttac tgctgcaaca ccagatgatg aagaagaaat actaatgaaa       660
aatagtagga caaagaaaag ttcttcaaca catcaagaag atgacaaaag aattaaaaaa       720
gggggaaaag ggaagactg gtttaagaaa tcaaagata ccgacaacca gataccaaca        780
tcagactaca gatccacatc aaaagggcag aagaaatct caaagacaac aaccaccaac       840
```

```
accgacacaa agggcaaac agaaatacag acagaatcat cagaaacaca atcctcatca       900
tggaatctca tcatcgacaa caacaccgac cggaacgaac agacaagcac aactcctcca       960
acaacaactt ccagatcaac ttatacaaaa gaatcgatcc gaacaaactc tgaatccaaa      1020
cccaagacac aaaagacaaa tggaaaggaa aggaaggata cagaagagag caatcgattt      1080
acagagaggg caattactct attgcagaat cttggtgtaa ttcaatccac atcaaaacta      1140
gatttatatc aagacaaacg agttgtatgt gtagcaaatg tactaaacaa tgtagatact      1200
gcatcaaaga tagatttcct ggcaggatta gtcataggg tttcaatgga caacgacaca       1260
aaattaacac agatacaaaa tgaaatgcta aacctcaaag cagatctaaa gaaaatggac      1320
gaatcacata gaagattgat agaaaatcaa agagaacaac tgtcattgat cacgtcacta      1380
atttcaaatc tcaaaattat gactgagaga ggaggaaaga aagaccaaaa tgaatccaat      1440
gagagagtat ccatgatcaa aacaaaattg aaagaagaaa agatcaagaa gaccaggttt      1500
gacccactta tggaggcaca aggcattgac aagaatatac ccgatctata tcgacatgca      1560
ggagatacac tagagaacga tgtacaagtt aaatcagaga tattaagttc atacaatgag      1620
tcaaatgcaa caagactaat acccaaaaaa gtgagcagta caatgagatc actagttgca      1680
gtcatcaaca acagcaatct ctcacaaagc acaaacaat catacataaa cgaactcaaa       1740
cgttgcaaaa atgatgaaga agtatctgaa ttaatggaca tgttcaatga agatgtcaac      1800
aattgccaat gagtcgacga tccggctgct aacaaagccc gaaaggaagc tgagttggct      1860
gctgccaccg ctgagcaata actagcataa cccctttgggg cctctaaacg ggtcttgagg     1920
ggttttttgc tgaaaggagg aactatatcc ggatcgagat caattctgtg agcgtatggc      1980
aaacgaagga aaaatagtta tagtagccgc actcgatggg acatttcaac gtaaaccgtt      2040
taataatatt ttgaatctta ttccattatc tgaaatggtg gtaaaactaa ctgctgtgtg      2100
tatgaaatgc tttaaggagg cttccttttc taaacgattg ggtgaggaaa ccgagataga      2160
aataatagga ggtaatgata tgtatcaatc ggtgtgtaga aagtgttaca tcgactcata      2220
atattatatt ttttatctaa aaaactaaaa ataaacattg attaaatttt aatataatac      2280
ttaaaaatgg atgttgtgtc gttagataaa ccgtttatgt attttgagga aattgataat      2340
gagttagatt acgaaccaga aagtgcaaat gaggtcgcaa aaaaactgcc gtatcaagga      2400
cagttaaaac tattactagg agaattattt tttcttagta agttacagcg acacggtata      2460
ttagatggtg ccaccgtagt gtatatagga tctgctcccg gtacacatat acgttatttg      2520
agagatcatt tctataattt aggagtgatc atcaaatgga tgctaattga cggccgccat      2580
catgatccta ttttaaatgg attgcgtgat gtgactctag tgactcggtt cgttgatgag      2640
gaatatctac gatccatcaa aaaacaactg catccttcta agattatttt aatttctgat      2700
gtgagatcca aacgaggagg aaatgaacct agtacggcgg atttactaag taattacgct      2760
ctacaaaatg tcatgattag tattttaaac cccgtggcgt ctagtcttaa atggagatgc      2820
ccgtttccag atcaatggat caaggacttt tatatcccac acggtaataa aatgttacaa      2880
cctttgctc cttcatattc agggccgtcg ttttacaacg tcgtgactgg gaaaaccctg       2940
gcgttaccca acttaatcgc cttgcagcac atccccctt cgccagctgg cgtaatagcg       3000
aagaggcccg caccgatcgc ccttcccaac agttgcgcag cctgaatggc gaatggcgcg      3060
acgcgccctg tagcggcgca ttaagcgcgg cgggtgtggt ggttacgcgc agcgtgaccg      3120
ctacacttgc cagcgcccta gcgcccgctc ctttcgcttt cttcccttcc tttctcgcca      3180
cgttcgccgg ctttccccgt caagctctaa atcgggggct ccctttaggg ttccgattta      3240
```

```
gtgctttacg gcacctcgac cccaaaaaac ttgattaggg tgatggttca cgtagtgggc    3300
catcgccctg atagacggtt tttcgccctt tgacgttgga gtccacgttc tttaatagtg    3360
gactcttgtt ccaaactgga acaacactca accctatctc ggtctattct tttgatttat    3420
aagggatttt gccgatttcg gcctattggt taaaaatga gctgatttaa caaaaattta    3480
acgcgaattt taacaaaata ttaacgttta caatttccca ggtggcactt tcggggaaa    3540
tgtgcgcgga accccatttt gtttattttt ctaaatacat tcaaatatgt atccgctcat    3600
gagacaataa ccctgataaa tgcttcaata atattgaaaa aggaagagta tgagtattca    3660
acatttccgt gtcgccctta ttcccttttt tgcggcattt tgccttcctg ttttttgctca   3720
cccagaaacg ctggtgaaag taaaagatgc tgaagatcag ttgggtgcac gagtgggtta    3780
catcgaactg gatctcaaca gcggtaagat ccttgagagt tttcgccccg aagaacgttt    3840
tccaatgatg agcacttttta aagttctgct atgtggcgcg gtattatccc gtattgacgc    3900
cgggcaagag caactcggtc gccgcataca ctattctcag aatgacttgg ttgagtactc    3960
accagtcaca gaaaagcatc ttacggatgg catgacagta agagaattat gcagtgctgc    4020
cataaccatg agtgataaca ctgcggccaa cttacttctg acaacgatcg gaggaccgaa    4080
ggagctaacc gcttttttgc acaacatggg ggatcatgta actcgccttg atcgttggga    4140
accggagctg aatgaagcca taccaaacga cgagcgtgac accacgatgc ctgtagcaat    4200
ggcaacaacg ttgcgcaaac tattaactgg cgaactactt actctagctt cccggcaaca    4260
attaatagac tggatggagg cggataaagt tgcaggacca cttctgcgct cggcccttcc    4320
ggctggctgg tttattgctg ataaatctgg agccggtgag cgtgggtctc gcggtatcat    4380
tgcagcactg gggccagatg gtaagccctc ccgtatcgta gttatctaca cgacggggag    4440
tcaggcaact atggatgaac gaaatagaca gatcgctgag ataggtgcct cactgattaa    4500
gcattggtaa ctgtcagacc aagtttactc atatatactt tagattgatt taaaacttca    4560
ttttttaattt aaaaggatct aggtgaagat cctttttgat aatctcatga ccaaaatccc    4620
ttaacgtgag ttttcgttcc actgagcgtc agacccgta gaaaagatca aaggatcttc    4680
ttgagatcct ttttttctgc gcgtaatctg ctgcttgcaa acaaaaaaac caccgctacc    4740
agcggtggtt tgtttgccgg atcaagagct accaactctt tttccgaagg taactggctt    4800
cagcagagcg cagataccaa atactgtcct tctagtgtag ccgtagttag gccaccactt    4860
caagaactct gtagcaccgc ctacatacct cgctctgcta atcctgttac cagtggctgc    4920
tgccagtggc gataagtcgt gtcttaccgg gttggactca agacgatagt taccggataa    4980
ggcgcagcgg tcgggctgaa cggggggttc gtgcacacag cccagcttgg agcgaacgac    5040
ctacaccgaa ctgagatacc tacagcgtga gctatgagaa agcgccacgc ttcccgaagg    5100
gagaaaggcg gacaggtatc cggtaagcgg cagggtcgga acaggagagc gcacgaggga    5160
gcttccaggg ggaaacgcct ggtatcttta tagtcctgtc gggtttcgcc acctctgact    5220
tgagcgtcga tttttgtgat gctcgtcagg gggcggagc ctatggaaaa acgccagcaa    5280
cgcggccttt ttacggttcc tggccttttg ctggcctttt gctcacatgt tctttcctgc    5340
gttatcccct gattctgtgg ataaccgtat taccgccttt gagtgagctg ataccgctcg    5400
ccgcagccga acgaccgagc gcagcgagtc agtgagcgag gaagcggaag agcgcccaat    5460
acgcaaaccg cctctccccg cgcgttggcc gattcattaa tgcagctggc acgacaggtt    5520
tcccgactgg aaagcgggca gtgagcgcaa cgcaattaat gtgagttagc tcactcatta    5580
ggcaccccag gctttacact ttatgcttcc ggctcgtatg ttgtgtggaa ttgtgagcgg    5640
```

```
ataacaattt cacacaggaa acagctatga ccatgattac gccaagcttt tgcgatcaat      5700
aaatggatca caaccagtat ctcttaacga tgttcttcgc agatgatgat tcattttta      5760 agtatttggc tagtcaagat gatgaatctt cattatctga tatattgcaa atcactcaat      5820
atctagactt tctgttatta ttattgatcc aatcaaaaaa taaattagaa gccgtgggtc      5880
attgttatga atctctttca gaggaataca gacaattgac aaaattcaca gactttcaag      5940 atttaaaaa actgtttaac aaggtcccta ttgttacaga tggaagggtc aaacttaata      6000
aaggatattt gttcgactt gtgattagtt tgatgcgatt caaaaagaa tcctctctag       6060 ctaccaccgc aatagatcct gttagataca tagatcctcg tcgcaatatc gcattttcta    6120
acgtgatgga tatattaaag tcgaataaag tgaacaataa ttaattcttt attgtcatca    6180
tgaacggcgg acatattcag ttgataatcg gccccatgtt ttcaggtaaa agtacagaat    6240
taattagacg agttagacgt tatcaaatag ctcaatataa atgcgtgact ataaaatatt    6300
ctaacgataa tagatacgga acgggactat ggacgcatga taagaataat tttgaagcat    6360
tggaagcaac taaactatgt gatgtcttgg aatcaattac agatttctcc gtgataggta    6420
tcgatgaagg acagttcttt ccagacattg ttgaattgat ctcgatcccg cgaaattaat    6480
acgactcact atagggagac cacaacggtt tccctctagc gggatcaatt ccgcccctct    6540 ccctccccc ccctaacgt tactggccga agccgcttgg aataaggccg gtgtgcgttt      6600
gtctatatgt tattttccac catattgccg tcttttggca atgtgagggc ccggaaacct    6660
ggccctgtct tcttgacgag cattcctagg ggtctttccc ctctcgccaa aggaatgcaa    6720
ggtctgttga atgtcgtgaa ggaagcagtt cctctggaag cttcttgaag acaaacaacg    6780
tctgtagcga cccttgcag gcagcggaac cccccacctg gcgacaggtg cctctgcggc    6840
caaaagccac gtgtataaga tacacctgca aaggcggcac aaccccagtg ccacgttgtg    6900
agttggatag ttgtggaaag agtcaaatgg ctctcctcaa gcgtattcaa caaggggctg    6960
aaggatgccc agaaggtacc ccattgtatg ggatctgatc tggggcctcg gtgcacatgc    7020
tttacatgtg tttagtcgag gttaaaaaac gtctaggccc cccgaaccac ggggacgtgg    7080
ttttcctttg aaaaacacga taatacc                                       7107
```

<210> SEQ ID NO 68
<211> LENGTH: 12011
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12011)
<223> OTHER INFORMATION: Part of Parent Appln No 09/083,793 as SEQ ID
      NO: 22

<400> SEQUENCE: 68

```
atggacactg aatctaacaa tggcactgta tctgacatac tctatcctga gtgtcacctt       60
aactctccta tcgttaaagg taaaatagca caattacaca ctattatgag tctacctcag      120
ccttatgata tggatgacga ctcaatacta gttatcacta gacagaaaat aaaacttaat      180
aaattggata aaagcaacg atctattaga agattaaaat taatattaac tgaaaaagtg      240
aatgacttag gaaaatacac atttatcaga tatccagaaa tgtcaaaaga atgttcaaa      300 ttatatatac ctggtattaa cagtaaaagtg actgaattat tacttaaagc agatagaaca    360
tatagtcaaa tgactgatgg attaagagat ctatggatta atgtgctatc aaaattagcc     420
tcaaaaaatg atggaagcaa ttatgatctt aatgaagaaa ttaataatat atcgaaagtt     480
```

-continued

```
cacacaacct ataaatcaga taaatggtat aatccattca aaacatggtt tactatcaag    540
tatgatatga gaagattaca aaaagctcga aatgagatca cttttaatgt tgggaaggat    600
tataacttgt tagaagacca gaagaatttc ttattgatac atccagaatt ggttttgata    660
ttagataaac aaaactataa tggttatcta attactcctg aattagtatt gatgtattgt    720
gacgtagtcg aaggccgatg gaatataagt gcatgtgcta agttagatcc aaaattacaa    780
tctatgtatc agaaaggtaa taacctgtgg gaagtgatag ataaattgtt tccaattatg    840
ggagaaaaga catttgatgt gatatcgtta ttagaaccac ttgcattatc cttaattcaa    900
actcatgatc ctgttaaaca actaagagga gcttttttaa atcatgtgtt atccgagatg    960
gaattaatat ttgaatctag agaatcgatt aaggaatttc tgagtgtaga ttacattgat   1020
aaaattttag atatatttaa taagtctaca atagatgaaa tagcagagat tttctctttt   1080
tttagaacat ttgggcatcc tccattagaa gctagtattg cagcagaaaa ggttagaaaa   1140
tatatgtata ttggaaaaca attaaaattt gacactatta ataaatgtca tgctatcttc   1200
tgtacaataa taattaacgg atatagagag aggcatggtg gacagtggcc tcctgtgaca   1260
ttacctgatc atgcacacga attcatcata aatgcttacg gttcaaactc tgcgatatca   1320
tatgaaaatg ctgttgatta ttaccagagc tttataggaa taaaattcaa taaattcata   1380
gagcctcagt tagatgagga tttgacaatt tatatgaaag ataaagcatt atctccaaaa   1440
aaatcaaatt gggacacagt ttatcctgca tctaatttac tgtaccgtac taacgcatcc   1500
aacgaatcac gaagattagt tgaagtattt atagcagata gtaaatttga tcctcatcag   1560
atattggatt atgtagaatc tggggactgg ttagatgatc cagaatttaa tatttcttat   1620
agtcttaaag aaaagagat caaacaggaa ggtagactct tgcaaaaat gacatacaaa   1680 atgagagcta cacaagtttt atcagagaca ctacttgcaa ataacatagg aaaattcttt   1740
caagaaaatg ggatggtgaa gggagagatt gaattactta agagattaac aaccatatca   1800
atatcaggag ttccacggta taatgaagtg tacaataatt ctaaaagcca tacagatgac   1860
cttaaaacct acaataaaat aagtaatctt aatttgtctt ctaatcagaa atcaaagaaa   1920
tttgaattca agtcaacgga tatctacaat gatggatacg agactgtgag ctgtttccta   1980
acaacagatc tcaaaaaata ctgtcttaat tggagatatg aatcaacagc tctatttgga   2040
gaaacttgca accaaatatt tggattaaat aaattgttta attggttaca ccctcgtctt   2100
gaaggaagta caatctatgt aggtgatcct tactgtcctc catcagataa agaacatata   2160
tcattagagg atcaccctga ttctggtttt tacgttcata acccaagagg gggtatagaa   2220
ggattttgtc aaaaattatg gacactcata tctataagtg caatacatct agcagctgtt   2280
agaataggcg tgagggtgac tgcaatggtt caaggagaca atcaagctat agctgtaacc   2340
acaagagtac ccaacaatta tgactacaga gttaagaagg agatagtta taaagatgta   2400 gtgagatttt ttgattcatt aagagaagtg atggatgatc taggtcatga acttaaatta   2460
aatgaaacga ttataagtag caagatgttc atatatagca aaagaatcta ttatgatggg   2520
agaattcttc ctcaagctct aaaagcatta tctagatgtg tcttctggtc agagacagta   2580
atagacgaaa caagatcagc atcttcaaat ttggcaacat catttgcaaa agcaattgag   2640
aatggttatt cacctgttct aggatatgca tgctcaattt ttaagaacat tcaacaacta   2700
tatattgccc ttgggatgaa tatcaatcca actataacac agaatatcag agatcagtat   2760
tttaggaatc caaattggat gcaatatgcc tcttaaatac ctgctagtgt tggggattc   2820 aattacatgg ccatgtcaag atgttttgta aggaatattg gtgatccatc agttgccgca   2880
```

```
ttggctgata ttaaaagatt tattaaggcg aatctattag accgaagtgt tctttatagg    2940
attatgaatc aagaaccagg tgagtcatct tttttggact gggcttcaga tccatattca    3000
tgcaatttac cacaatctca aaatataacc accatgataa aaatataac agcaaggaat     3060 gtattacaag attcaccaaa tccattatta tctggattat tcacaaatac aatgatagaa    3120
gaagatgaag aattagctga gttcctgatg gacaggaagg taattctccc tagagttgca    3180
catgatattc tagataattc tctcacagga attagaaatg ccatagctgg aatgttagat    3240
acgacaaaat cactaattcg ggttggcata aatagaggag gactgacata tagtttgttg    3300
aggaaaatca gtaattacga tctagtacaa tatgaaacac taagtaggac tttgcgacta    3360
attgtaagtg ataaaatcaa gtatgaagat atgtgttcgg tagaccttgc catagcattg    3420
cgacaaaaga tgtggattca tttatcagga ggaaggatga aagtggact tgaaacgcct     3480 gacccattag aattactatc tggggtagta ataacaggat cagaacattg taaaatatgt    3540
tattcttcag atggcacaaa cccatatact tggatgtatt tacccggtaa tatcaaaata    3600
ggatcagcag aaacaggtat atcgtcatta agagttcctt attttggatc agtcactgat    3660
gaaagatctg aagcacaatt aggatatatc aagaatctta gtaaacctgc aaaagccgca    3720
ataagaatag caatgatata tacatgggca tttggtaatg atgagatatc ttggatggaa    3780
gcctcacaga tagcacaaac acgtgcaaat tttacactag atagtctcaa aattttaaca    3840
ccggtagcta catcaacaaa tttatcacac agattaaagg atactgcaac tcagatgaaa    3900
ttctccagta catcattgat cagagtcagc agattcataa caatgtccaa tgataacatg    3960
tctatcaaag aagctaatga aaccaaagat actaatctta tttatcaaca aataatgtta    4020
acaggattaa gtgttttcga atatttattt agattaaaag aaaccacagg acacaaccct    4080
atagttatgc atctgcacat agaagatgag tgttgtatta agaaagttt taatgatgaa      4140 catattaatc cagagtctac attagaatta attcgatatc ctgaaagtaa tgaatttatt    4200
tatgataaag acccactcaa agatgtggac ttatcaaaac ttatggttat taaagaccat    4260
tcttacacaa ttgatatgaa ttattgggat gatactgaca tcatacatgc aatttcaata    4320
tgtactgcaa ttacaatagc agatactatg tcacaattag atcgagataa tttaaaagag    4380
ataatagtta ttgcaaatga tgatgatatt aatagcttaa tcactgaatt tttgactctt    4440
gacatacttg tatttctcaa gacatttggt ggattattag taaatcaatt tgcatacact    4500
ctttatagtc taaaaataga aggtagggat ctcatttggg attatataat gagaacactg    4560
agagatactt cccattcaat attaaaagta ttatctaatg cattatctca tcctaaagta    4620
ttcaagaggt tctgggattg tggagtttta aaccctattt atggtcctaa tactgctagt    4680
caagaccaga taaaacttgc cctatctata tgtgaatatt cactagatct atttatgaga    4740
gaatggttga atggtgtatc acttgaaata tacatttgtg acagcgatat ggaagttgca    4800
aatgatagga aacaagcctt tatttctaga cacctttcat ttgtttgttg tttagcagaa    4860
attgcatctt tcggacctaa cctgttaaac ttaacatact tggagagact tgatctattg    4920
aaacaatatc ttgaattaaa tattaaagaa gaccctactc ttaaatatgt acaaatatct    4980
ggattattaa ttaaatcgtt cccatcaact gtaacatacg taagaaagac tgcaatcaaa    5040
tatctaagga ttcgcggtat tagtccacct gaggtaattg atgattggga tccggtagaa    5100
gatgaaaata tgctggataa cattgtcaaa actataaatg ataactgtaa taagataat     5160 aaagggaata aaattaacaa tttctgggga ctagcactta agaactatca agtcccttaaa   5220 atcagatcta taacaagtga ttctgatgat aatgatagac tagatgctaa tacaagtggt    5280
```

-continued

```
ttgacacttc ctcaaggagg gaattatcta tcgcatcaat tgagattatt cggaatcaac    5340
agcactagtt gtctgaaagc tcttgagtta tcacaaattt taatgaagga agtcaataaa    5400
gacaaggaca ggctcttcct gggagaagga gcaggagcta tgctagcatg ttatgatgcc    5460
acattaggac ctgcagttaa ttattataat tcaggtttga atataacaga tgtaattggt    5520
caacgagaat tgaaaatatt tccttcagag gtatcattag taggtaaaaa attaggaaat    5580
gtgacacaga ttcttaacag ggtaaaagta ctgttcaatg ggaatcctaa ttcaacatgg    5640
ataggaaata tggaatgtga gagcttaata tggagtgaat taaatgataa gtccattgga    5700
ttagtacatt gtgatatgga aggagctatc ggtaaatcag aagaaactgt tctacatgaa    5760
cattatagtg ttataagaat tacatacttg attggggatg atgatgttgt tttagtttcc    5820
aaaattatac ctacaatcac tccgaattgg tctagaatac tttatctata taaattatat    5880
tggaaagatg taagtataat atcactcaaa acttctaatc ctgcatcaac agaattatat    5940
ctaatttcga aagatgcata ttgtactata atggaaccta gtgaaattgt tttatcaaaa    6000
cttaaaagat tgtcactctt ggaagaaaat aatctattaa aatggatcat tttatcaaag    6060
aagaggaata atgaatggtt acatcatgaa atcaaagaag gagaaagaga ttatggaatc    6120
atgagaccat atcatatggc actacaaatc tttggatttc aaatcaattt aaatcatctg    6180
gcgaaagaat ttttatcaac cccagatctg actaatatca acaatataat ccaaagtttt    6240
cagcgaacaa taaaggatgt tttatttgaa tggattaata taactcatga tgataagaga    6300 cataaaattag gcggaagata taacatattc ccactgaaaa ataagggaaa gttaagactg    6360
ctatcgagaa gactagtatt aagttggatt tcattatcat tatcgactcg attacttaca    6420
ggtcgctttc ctgatgaaaa atttgaacat agagcacaga ctggatatgt atcattagct    6480
gatactgatt tagaatcatt aaagttattg tcgaaaaaca tcattaagaa ttacagagag    6540
tgtataggat caatatcata ttggtttcta accaagaag ttaaaatact tatgaaattg    6600
attggtggtg ctaaattatt aggaattccc agacaatata aagaacccga agaccagtta    6660
ttagaaaact acaatcaaca tgatgaattt gatatcgatt aaaacataaa tacaatgtcg    6720
acgatccggc tgctaacaaa gcccgaaagg aagctgagtt ggctgctgcc accgctgagc    6780
aataactagc ataaccccctt ggggcctcta acgggtctt gagggttttt tgctgaaag    6840 gaggaactat atccggatcg agatcaattc tgtgagcgta tggcaaacga aggaaaata    6900 gttatagtag ccgcactcga tgggacattt caacgtaaac cgtttaataa tatttttgaat    6960 cttattccat tatctgaaat ggtggtaaaa ctaactgctg tgtgtatgaa atgctttaag    7020
gaggcttcct tttctaaacg attgggtgag gaaaccgaga tagaaataat aggaggtaat    7080
gatatgtatc aatcggtgtg tagaaagtgt tacatcgact cataatatta tattttttat    7140
ctaaaaaact aaaaataaac attgattaaa ttttaatata atacttaaaa atggatgttg    7200
tgtcgttaga taaaccgttt atgtattttg aggaaattga taatgagtta gattacgaac    7260
cagaaagtgc aaatgaggtc gcaaaaaaac tgccgtatca aggacagtta aaactattac    7320
taggagaatt atttttttctt agtaagttac agcgacacgg tatattagat ggtgccaccg    7380
tagtgtatat aggatctgct cccgtacac atatacgtta tttgagagat catttctata    7440
atttaggagt gatcatcaaa tggatgctaa ttgacggccg ccatcatgat cctattttaa    7500
atggattgcg tgatgtgact ctagtgactc ggttcgttga tgaggaatat ctacgatcca    7560
tcaaaaaaca actgcatcct tctaagatta ttttaatttc tgatgtgaga tccaaacgag    7620
gaggaaatga acctagtacg gcggatttac taagtaatta cgctctacaa aatgtcatga    7680
```

```
ttagtatttt aaacccgtg gcgtctagtc ttaaatggag atgcccgttt ccagatcaat    7740
ggatcaagga cttttatatc ccacacggta ataaaatgtt acaaccttt gctccttcat    7800
attcagggcc gtcgttttac aacgtcgtga ctgggaaaac cctggcgtta cccaacttaa    7860
tcgccttgca gcacatcccc ctttcgccag ctggcgtaat agcgaagagg cccgcaccga    7920
tcgcccttcc caacagttgc gcagcctgaa tggcgaatgg cgcgacgcgc cctgtagcgg    7980
cgcattaagc gcggcgggtg tggtggttac gcgcagcgtg accgctacac ttgccagcgc    8040
cctagcgccc gctcctttcg ctttcttccc ttcctttctc gccacgttcg ccggctttcc    8100
ccgtcaagct ctaaatcggg ggctcccttt agggttccga tttagtgctt tacggcacct    8160
cgaccccaaa aaacttgatt agggtgatgg ttcacgtagt gggccatcgc cctgatagac    8220
ggttttcgc cctttgacgt tggagtccac gttctttaat agtggactct tgttccaaac    8280
tggaacaaca ctcaacccta tctcggtcta ttcttttgat ttataaggga ttttgccgat    8340
ttcggcctat tggttaaaaa atgagctgat ttaacaaaaa tttaacgcga attttaacaa    8400
aatattaacg tttacaattt cccaggtggc acttttcggg gaaatgtgcg cggaacccct    8460
atttgtttat ttttctaaat acattcaaat atgtatccgc tcatgagaca ataaccctga    8520
taaatgcttc aataatattg aaaaaggaag agtatgagta ttcaacattt ccgtgtcgcc    8580
cttattccct tttttgcggc attttgcctt cctgttttg ctcacccaga aacgctggtg    8640
aaagtaaaag atgctgaaga tcagttgggt gcacgagtgg gttacatcga actggatctc    8700
aacagcggta agatccttga gttttcgc cccgaagaac gttttccaat gatgagcact    8760
tttaaagttc tgctatgtgg cgcggtatta tcccgtattg acgccgggca agagcaactc    8820
ggtcgccgca tacactattc tcagaatgac ttggttgagt actcaccagt cacagaaaag    8880
catcttacgg atggcatgac agtaagagaa ttatgcagtg ctgccataac catgagtgat    8940
aacactgcgg ccaacttact tctgacaacg atcggaggac cgaaggagct aaccgctttt    9000
ttgcacaaca tgggggatca tgtaactcgc cttgatcgtt gggaaccgga gctgaatgaa    9060
gccataccaa acgacgagcg tgacaccacg atgcctgtag caatggcaac aacgttgcgc    9120
aaactattaa ctggcgaact acttactcta gcttcccggc aacaattaat agactggatg    9180
gaggcggata agttgcagg accacttctg cgctcggccc ttccggctgg ctggtttatt    9240
gctgataaat ctggagccgg tgagcgtggg tctcgcggta tcattgcagc actggggcca    9300
gatggtaagc cctcccgtat cgtagttatc tacacgacgg ggagtcaggc aactatggat    9360
gaacgaaata gacagatcgc tgagataggt gcctcactga ttaagcattg gtaactgtca    9420
gaccaagttt actcatatat actttagatt gatttaaaac ttcatttta atttaaaagg    9480
atctaggtga agatcctttt tgataatctc atgaccaaaa tcccttaacg tgagttttcg    9540
ttccactgag cgtcagaccc cgtagaaaag atcaaaggat cttcttgaga tccttttttt    9600
ctgcgcgtaa tctgctgctt gcaaacaaaa aaaccaccgc taccagcggt ggtttgtttg    9660
ccggatcaag agctaccaac tcttttccg aaggtaactg gcttcagcag agcgcagata    9720
ccaaatactg tccttctagt gtagccgtag ttaggccacc acttcaagaa ctctgtagca    9780
ccgcctacat acctcgctct gctaatcctg ttaccagtgg ctgctgccag tggcgataag    9840
tcgtgtctta ccgggttgga ctcaagacga tagttaccgg ataaggcgca gcggtcgggc    9900
tgaacggggg gttcgtgcac acagcccagc ttggagcgaa cgacctacac cgaactgaga    9960
tacctacagc gtgagctatg agaaagcgcc acgcttcccg aagggagaaa ggcggacagg   10020
tatccggtaa gcggcagggt cggaacagga gagcgcacga gggagcttcc agggggaaac   10080
```

-continued

```
gcctggtatc tttatagtcc tgtcgggttt cgccacctct gacttgagcg tcgattttg    10140
tgatgctcgt caggggggcg gagcctatgg aaaaacgcca gcaacgcggc cttttttacgg  10200
ttcctggcct tttgctggcc ttttgctcac atgttctttc ctgcgttatc ccctgattct   10260
gtggataacc gtattaccgc ctttgagtga gctgataccg ctcgccgcag ccgaacgacc   10320
gagcgcagcg agtcagtgag cgaggaagcg gaagagcgcc caatacgcaa accgcctctc   10380
cccgcgcgtt ggccgattca ttaatgcagc tggcacgaca ggtttcccga ctggaaagcg   10440
ggcagtgagc gcaacgcaat taatgtgagt tagctcactc attaggcacc ccaggcttta   10500
cactttatgc ttccggctcg tatgttgtgt ggaattgtga gcggataaca atttcacaca   10560
ggaaacagct atgaccatga ttacgccaag cttttgcgat caataaatgg atcacaacca   10620
gtatctctta acgatgttct tcgcagatga tgattcattt tttaagtatt tggctagtca   10680
agatgatgaa tcttcattat ctgatatatt gcaaatcact caatatctag actttctgtt   10740
attattattg atccaatcaa aaaataaatt agaagccgtg ggtcattgtt atgaatctct   10800
ttcagaggaa tacagacaat tgacaaaatt cacagacttt caagatttta aaaaactgtt   10860
taacaaggtc cctattgtta cagatggaag ggtcaaactt aataaaggat atttgttcga   10920
cttttgtgatt agtttgatgc gattcaaaaa agaatcctct ctagctacca ccgcaataga   10980
tcctgttaga tacatagatc ctcgtcgcaa tatcgcattt tctaacgtga tggatatatt   11040
aaagtcgaat aaagtgaaca ataattaatt ctttattgtc atcatgaacg gcggacatat   11100
tcagttgata atcggcccca tgttttcagg taaaagtaca gaattaatta gacgagttag   11160
acgttatcaa atagctcaat ataaatgcgt gactataaaa tattctaacg ataatagata   11220
cggaacggga ctatggacgc atgataagaa taattttgaa gcattggaag caactaaact   11280
atgtgatgtc ttggaatcaa ttacagattt ctccgtgata ggtatcgatg aaggacagtt   11340
cttttccagac attgttgaat tgatctcgat cccgcgaaat taatacgact cactataggg   11400
agaccacaac ggtttccctc tagcgggatc aattccgccc ctctccctcc ccccccccta   11460
acgttactgg ccgaagccgc ttggaataag gccggtgtgc gtttgtctat atgttatttt   11520
ccaccatatt gccgtctttt ggcaatgtga gggcccggaa acctggccct gtcttcttga   11580
cgagcattcc tagggggtctt tcccctctcg ccaaaggaat gcaaggtctg ttgaatgtcg   11640
tgaaggaagc agttcctctg gaagcttctt gaagacaaac aacgtctgta gcgacccttt   11700
gcaggcagcg gaaccccca cctggcgaca ggtgcctctg cggccaaaag ccacgtgtat    11760
aagatacacc tgcaaaggcg gcacaacccc agtgccacgt tgtgagttgg atagttgtgg   11820
aaagagtcaa atggctctcc tcaagcgtat tcaacaaggg gctgaaggat gcccagaagg   11880
taccccattg tatgggatct gatctggggc ctcggtgcac atgctttaca tgtgtttagt    11940
cgaggttaaa aaacgtctag gccccccgaa ccacggggac gtggttttcc tttgaaaaac   12000
acgataatac c                                                        12011
```

<210> SEQ ID NO 69
<211> LENGTH: 43
<212> TYPE: DNA
<213> ORGANISM: Artificial Sequence
<220> FEATURE:
<223> OTHER INFORMATION: Synthetic primer.
<220> FEATURE:
<221> NAME/KEY: misc_feature
<222> LOCATION: (1)..(43)
<223> OTHER INFORMATION: Part of Parent Appln No 09/083,793 as SEQ ID
      NO: 12

-continued

```
<400> SEQUENCE: 69
ggggttatgc tactgcaggc ttttttctc ccttagccat ccg                          43

<210> SEQ ID NO 70
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(13)
<223> OTHER INFORMATION: n is a, c, g, t, unknown or other
<220> FEATURE:
<221> NAME/KEY: misc_feature
<222> LOCATION: (1)..(35)
<223> OTHER INFORMATION: Part of Parent Appln No 09/083,793 as SEQ ID
      NO: 13

<400> SEQUENCE: 70
ctccattcta ganttataaa aattatagag ttccc                                  35

<210> SEQ ID NO 71
<211> LENGTH: 15669
<212> TYPE: DNA
<213> ORGANISM: Artificial Sequence
<220> FEATURE:
<223> OTHER INFORMATION: Chemically synthesized cDNA clone p218(131).
<220> FEATURE:
<221> NAME/KEY: misc_feature
<222> LOCATION: (1)..(15669)
<223> OTHER INFORMATION: Part of Parent Appln No 09/083,793 as SEQ ID
      NO: 01

<400> SEQUENCE: 71
gctgggtacc gggcccgtcg acgcgtatat agttcctcct ttcagcaaaa aacccctcaa       60
gacccgttta gaggcoccaa ggggttatgc tactgcaggc tctcccttag ccatccgagt      120
ggacgtgcgt cctccttcgg atgcccaggt cggaccgcga ggaggtggag atgccatgcc     180
gacccaccaa acaagagaag aaacttgtct gggaatataa atttaacttt aaattaactt     240
aggattaaag acattgacta gaaggtcaag aaaagggaac tctataattt caaaaatgtt     300
gagcctattt gatacattta atgcacgtag gcaagaaaac ataacaaaat cagccggtgg     360
agctatcatt cctggacaga aaaatactgt ctctatattc gcccttggac cgacaataac     420
tgatgataat gagaaaatga cattagctct tctatttcta tctcattcac tagataatga     480
gaaacaacat gcacaaggg cagggttctt ggtgtcttta ttgtcaatgg cttatgccaa     540
tccagagctc tacctaacaa caaatggaag taatgcagat gtcaagtatg tcatatacat     600
gattgagaaa gatctaaaac ggcaaaagta tggaggattt gtggttaaga cgagagagat     660
gatatatgaa aagacaactg attggatatt tggaagtgac ctggattatg atcaggaaac     720
tatgttgcag aacggcagga acaattcaac aattgaagac cttgtccaca catttgggta     780
tccatcatgt ttaggagctc ttataataca gatctggata gttctggtca aagctatcac     840
tagtatctca gggttaagaa aaggctttt cacccgattg gaagctttca gacaagatgg     900
aacagtgcag gcagggctgg tattgagcgg tgacacagtg gatcagattg ggtcaatcat     960
gcggtctcaa cagagcttgg taactcttat ggttgaaaca ttaataacaa tgaataccag    1020
cagaaatgac ctcacaacca tagaaaagaa tatacaaatt gttggcaact acataagaga    1080
tgcaggtctc gcttcattct tcaatacaat cagatatgga attgagacca gaatggcagc    1140
tttgactcta tccactctca gaccagatat caatagatta aaagctttga tggaactgta    1200
```

```
tttatcaaag ggaccacgcg ctcctttcat ctgtatcctc agagatccta tacatggtga    1260
gttcgcacca ggcaactatc ctgccatatg gagctatgca atgggggtgg cagttgtaca    1320
aaatagagcc atgcaacagt atgtgacggg aagatcatat ctagacattg atatgttcca    1380
gctaggacaa gcagtagcac gtgatgccga agctcaaatg agctcaacac tggaagatga    1440
acttggagtg acacacgaat ctaaagaaag cttgaagaga catataagga acataaacag    1500
ttcagagaca tctttccaca aaccgacagg tggatcagcc atagagatgg caatagatga    1560
agagccagaa caattcgaac atagagcaga tcaagaacaa aatggagaac ctcaatcatc    1620
cataattcaa tatgcctggg cagaaggaaa tagaagcgat gatcagactg agcaagctac    1680
agaatctgac aatatcaaga ccgaacaaca aaacatcaga gacagactaa acaagagact    1740
caacgacaag aagaaacaaa gcagtcaacc acccactaat cccacaaaca gaacaaacca    1800
ggacgaaata gatgatctgt ttaacgcatt tggaagcaac taatcgaatc aacattttaa    1860
tctaaatcaa taataaataa gaaaaactta ggattaaaga atcctatcat accgaatat    1920 agggtggtaa atttagagtc tgcttgaaac tcaatcaata gagagttgat ggaaagcgat    1980
gctaaaaact atcaaatcat ggattcttgg gaagaggaat caagagataa atcaactaat    2040
atctcctcgg ccctcaacat cattgaattc atactcagca ccgaccccca agaagactta    2100
tcggaaaacg acacaatcaa cacaagaacc cagcaactca gtgccaccat ctgtcaacca    2160
gaaatcaaac caacagaaac aagtgagaaa gatagtggat caactgacaa aaatagacag    2220
tctgggtcat cacacgaatg tacaacgaaa gcaaagata gaaatattga tcaggaaact    2280
gtacagagag gacctgggag aagaagcagc tcagatagta gagctgagac tgtggtctct    2340
ggaggaatcc ccagaagcat cacagattct aaaaatggaa cccaaaacac ggaggatatt    2400
gatctcaatg aaattagaaa gatggataag gactctattg aggggaaaat gcgacaatct    2460
gcaaatgttc caagcgagat atcaggaagt gatgacatat ttacaacaga acaaagtaga    2520
aacagtgatc atgaagaag cctggaatct atcagtacac ctgatacaag atcaataagt    2580
gttgttactg ctgcaacacc agatgatgaa gaagaaatac taatgaaaaa tagtaggaca    2640
aagaaaagtt cttcaacaca tcaagaagat gacaaaagaa ttaaaaaggg gggaaagggg    2700
aaagactggt ttaagaaatc aaaagatacc gacaaccaga taccaacatc agactacaga    2760
tccacatcaa aagggcagaa gaaaatctca aagacaacaa ccaccaacac cgacacaaag    2820
gggcaaacag aaatacagac agaatcatca gaaacacaat cctcatcatg gaatctcatc    2880
atcgacaaca acaccgaccg gaacgaacag acaagcacaa ctcctccaac aacaacttcc    2940
agatcaactt atacaaaaga atcgatccga acaaactctg aatccaaacc caagacacaa    3000
aagacaaatg gaaggaaag gaaggataca gaagagagca atcgatttac agagagggca    3060
attactctat tgcagaatct tggtgtaatt caatccacat caaaactaga tttatatcaa    3120
gacaaacgag ttgtatgtgt agcaaatgta ctaaacaatg tagatactgc atcaaagata    3180
gatttcctgg caggattagt cataggggtt tcaatggaca acgacacaaa attaacacag    3240
atacaaaatg aaatgctaaa cctcaaagca gatctaaaga aatggacga atcacataga    3300 agattgatag aaaatcaaag agaacaactg tcattgatca cgtcactaat ttcaaatctc    3360
aaaattatga ctgagagagg aggaaagaaa gaccaaaatg aatccaatga gagtatcc    3420 atgatcaaaa caaattgaa agaagaaaag atcaagaaga ccaggtttga cccacttatg    3480
gaggcacaag gcattgacaa gaatataccc gatctatatc gacatgcagg agatacacta    3540
gagaacgatg tacaagttaa atcagagata ttaagttcat acaatgagtc aaatgcaaca    3600
```

```
agactaatac ccaaaaaagt gagcagtaca atgagatcac tagttgcagt catcaacaac   3660
agcaatctct cacaaagcac aaaacaatca tacataaacg aactcaaacg ttgcaaaaat   3720
gatgaagaag tatctgaatt aatggacatg ttcaatgaag atgtcaacaa ttgccaatga   3780
tccaacaaag aaacgacacc gaacaaacag acaagaaaca acagtagatc aaaacctgtc   3840
aacacacaca aaatcaagca gaatgaaaca acagatatca atcaatatac aaataagaaa   3900
aacttaggat taaagaataa attaatcctt gtccaaaatg agtataacta actctgcaat   3960
atacacattc ccagaatcat cattctctga aaatggtcat atagaaccat taccactcaa   4020
agtcaatgaa cagaggaaag cagtacccca cattagagtt gccaagatcg gaaatccacc   4080
aaaacacgga tcccggtatt tagatgtctt cttactcggc ttcttcgaga tggaacgaat   4140
caaagacaaa tacgggagtg tgaatgatct cgacagtgac ccgagttaca agtttgtgg    4200 ctctggatca ttaccaatcg gattggctaa gtacactggg aatgaccagg aattgttaca   4260
agccgcaacc aaactggata tagaagtgag aagaacagtc aaagcgaaag agatggttgt   4320
ttacacggta caaatataa  aaccagaact gtacccatgg tccaatagac taagaaaagg    4380
aatgctgttc gatgccaaca agttgctctt gctcctcaa  tgtcttccac tagataggag    4440
cataaaattt agagtaatct cgtgaattg  tacggcaatt ggatcaataa ccttgttcaa    4500
aattcctaag tcaatggcat cactatctct acccaacaca atatcaatca atctgcaggt   4560
acacataaaa acaggggttc agactgattc taaagggata gttcaaattt tggatgagaa   4620
aggcgaaaaa tcactgaatt tcatggtcca tctcggattg atcaaaagaa aagtaggcag   4680
aatgtactct gttgaatact gtaaacagaa aatcgagaaa atgagattga tattttcttt   4740
aggactagtt ggaggaatca gtcttcatgt caatgcaact gggtccatat caaaaacact   4800
agcaagtcag ctggtattca aaagagagat ttgttatcct ttaatggatc taaatccgca   4860
tctcaatcta gttatctggg cttcatcagt agagattaca agagtggatg caatttccca   4920
accttcttta cctggcgagt tcagatacta tcctaatatt attgcaaaag gagttgggaa   4980
aatcaaacaa tggaactagt aatctctatt ttagtccgga cgtatctatt aagccgaagc   5040
aaataaagga taatcaaaaa cttaggacaa aagaggtcaa taccaacaac tattagcagt   5100
cacactcgca agaataagag agaagggacc aaaaaagtca aataggagaa atcaaaacaa   5160
aaggtacaga acaccagaac aacaaaatca aaacatccaa ctcactcaaa acaaaaattc   5220
caaaagagac cggcaacaca acaagcactg aacacaatgc caacttcaat actgctaatt   5280
attcaaccca tgatcatggc atctttctgc caaatagata tcacaaaact acagcacgta   5340
ggtgtattgg tcaacagtcc caaagggatg aagatatcac aaaactttga aacaagatat   5400
ctaattttga gcctcatacc aaaaatagaa gactctaact cttgtggtga ccaacagatc   5460
aagcaataca agaagttatt ggatagactg atcatcccytt tatatgatgg attaagatta   5520
cagaaagatg tgatagtaac caatcaagaa tccaatgaaa acactgatcc cagaacaaaa   5580
cgattctttg gagggtaat  tggaaccatt gctctgggag tagcaacctc agcacaaatt    5640
acagcggcag ttgctctggt tgaagccaag caggcaagat cagacatcga aaaactcaaa   5700
gaagcaatta gggacacaaa caaagcagtg cagtcagttc agagctccat aggaaattta   5760
atagtagcaa ttaaatcagt ccaggattat gttaacaaag aaatcgtgcc atcgattgcg   5820
aggctaggtt gtgaagcagc aggacttcaa ttaggaattg cattaacaca gcattactca   5880
gaattaacaa acatatttgg tgataacata ggatcgttac aagaaaaagg aataaaatta   5940
caaggtatag catcattata ccgcacaaat atcacagaaa tattcacaac atcaacagtt   6000
```

```
gataaatatg atatctatga tctgttattt acagaatcaa taaaggtgag agttatagat    6060
gttgacttga atgattactc aatcaccctc caagtcagac tcccttatt aactaggctg     6120
ctgaacactc agatctacaa agtagattcc atatcatata acatccaaaa cagagaatgg    6180
tatatccctc ttcccagcca tatcatgacg aaaggggcat ttctaggtgg agcagacgtc    6240
aaagaatgta tagaagcatt cagcagctat atatgcccctt ctgatccagg atttgtatta   6300
aaccatgaaa tagagagctg cttatcagga aacatatccc aatgtccaag aacaacggtc    6360
acatcagaca ttgttccaag atatgcattt gtcaatggag gagtggttgc aaactgtata    6420
acaaccacct gtacatgcaa cggaattggt aatagaatca atcaaccacc tgatcaagga    6480
gtaaaaatta taacacataa agaatgtagt acaataggta tcaacggaat gctgttcaat    6540
acaaataaag aaggaactct tgcattctat acaccaaatg atataacact aaacaattct    6600
gttgcacttg atccaattga catatcaatc gagctcaaca aggccaaatc agatctagaa    6660
gaatcaaaag aatggataag aaggtcaaat caaaaactag attctattgg aaattggcat    6720
caatctagca ctacaatcat aattatttttg ataatgatca ttatattgtt tataattaat   6780
ataacgataa ttcaattgc aattaagtat tacagaattc aaaagagaaa tcgagtggat     6840
caaaatgaca agccatatgt actaacaaac aaataacata tctacagatc attagatatt    6900
aaaattataa aaaacttagg agtaaagtta cgcaatccaa ctctactcat ataattgagg    6960
aaggacccaa tagacaaatc caaattcgag atggaatact ggaagcatac caatcacgga    7020
aaggatgctg gtaatgagct ggagacgtct atggctactc atggcaacaa gctcactaat    7080
aagataatat acatattatg gacaataatc ctggtgttat tatcaatagt cttcatcata    7140
gtgctaatta attccatcaa aagtgaaaag gcccacgaat cattgctgca agacataaat    7200
aatgagttta tggaaattac agaaaagatc caaatggcat cggataatac caatgatcta    7260
atacagtcag gagtgaatac aaggcttctt acaattcaga gtcatgtcca gaattacata    7320
ccaatatcat tgacacaaca gatgtcgat cttaggaaat tcattagtga aattacaatt     7380
agaaatgata tcaagaagt gctgccacaa agaataacac atgatgtagg tataaaaccct    7440
ttaaatccag atgattttg gagatgcacg tctggtcttc catctttaat gaaaactcca    7500
aaaataaggt taatgccagg gccgggatta ttagctatgc caacgactgt tgatggctgt    7560
gttagaactc cgtctttagt tataaatgat ctgatttatg cttatacctc aaatctaatt    7620
actcgaggtt gtcaggatat aggaaaatca tatcaagtct tacagatagg gataataact    7680
gtaaactcag acttggtacc tgacttaaat cctaggatct ctcatacctt taacataaat    7740
gacaatagga agtcatgttc tctagcactc ctaaatatag atgtatatca actgtgttca    7800
actcccaaag ttgatgaaag atcagattat gcatcatcag gcatagaaga tattgtactt    7860
gatattgtca attatgatgg ttcaatctca acaacaagat ttaagaataa taacataagc    7920
tttgatcaac catatgctgc actataccca tctgttggac cagggatata ctacaaaggc    7980
aaaataatat ttctcgggta tggaggtcttt gaacatccaa taaatgagaa tgtaatctgc    8040
aacacaactg ggtgccccgg gaaaacacag agagactgta atcaagcatc tcatagtact    8100
tggttttcag ataggaggat ggtcaactcc atcattgttg ttgacaaagg cttaaactca    8160
attccaaaat tgaaagtatg gacgatatct atgcgacaaa attactgggg gtcagaagga    8220
aggttacttc tactaggtaa caagatctat atatacaa gatctacaag ttggcatagc      8280
aagtttacaat taggaataat tgatattact gattacagtg atataaggat aaaatggaca    8340
tggcataatg tgctatcaag accaggaaac aatgaatgtc catgggaca ttcatgtcca      8400
```

```
gatggatgta taacaggagt atatactgat gcatatccac tcaatcccac agggagcatt   8460
gtgtcatctg tcatattaga ctcacaaaaa tcgagagtga acccagtcat aacttactca   8520
acagcaaccg aaagagtaaa cgagctggcc atcctaaaca gaacactctc agctggatat   8580
acaacaacaa gctgcattac acactataac aaaggatatt gttttcatat agtagaaata   8640
aatcataaaa gcttaaacac atttcaaccc atgttgttca aaacagagat tccaaaaagc   8700
tgcagttaat cataattaac cataatatgc atcaatctat ctataataca agtatatgat   8760
aagtaatcag caatcagaca atagacaaaa gggaaatata aaaaacttag gagcaaagcg   8820
tgctcgggaa atggacactg aatctaacaa tggcactgta tctgacatac tctatcctga   8880
gtgtcacctt aactctccta tcgttaaagg taaaatagca caattacaca ctattatgag   8940
tctacctcag ccttatgata tggatgacga ctcaatacta gttatcacta gacagaaaat   9000
aaaacttaat aaattggata aaagacaacg atctattaga agattaaaat taatattaac   9060
tgaaaaagtg aatgacttag gaaaatacac atttatcaga tatccagaaa tgtcaaaaga   9120
aatgttcaaa ttatatatac ctggtattaa cagtaaagtg actgaattat acttaaagc    9180 agatagaaca tatagtcaaa tgactgatgg attaagagat ctatggatta atgtgctatc   9240
aaaattagcc tcaaaaaatg atggaagcaa ttatgatctt aatgaagaaa ttaataatat   9300
atcgaaagtt cacacaacct ataaatcaga taaatggtat aatccattca aaacatggtt   9360
tactatcaag tatgatatga agagattaca aaaagctcga aatgagatca cttttaatgt   9420
tgggaaggat tataacttgt tagaagacca gaagaatttc ttattgatac atccagaatt   9480
ggttttgata ttagataaac aaaactataa tggttatcta attactcctg aattagtatt   9540
gatgtattgt gacgtagtcg aaggccgatg gaatataagt gcatgtgcta agttagatcc   9600
aaaattacaa tctatgtatc agaaaggtaa taacctgtgg gaagtgatag ataaattgtt   9660
tccaattatg ggagaaaaga catttgatgt gatatcgtta ttagaaccac ttgcattatc   9720
cttaattcaa actcatgatc ctgttaaaca actaagagga gcttttttaa atcatgtgtt   9780
atccgagatg gaattaatat ttgaatctag agaatcgatt aaggaatttc tgagtgtaga   9840
ttacattgat aaaatttttag atatatttaa taagtctaca atagatgaaa tagcagagat   9900
tttctctttt tttagaacat ttgggcatcc tccattagaa gctagtattg cagcagaaaa   9960
ggttagaaaa tatatgtata ttggaaaaca attaaaattt gacactatta ataaatgtca   10020
tgctatcttc tgtacaataa taattaacgg atatagagag aggcatggtg gacagtggcc   10080
tcctgtgaca ttacctgatc atgcacacga attcatcata aatgcttacg gttcaaactc   10140
tgcgatatca tatgaaaatg ctgttgatta ttaccagagc tttataggaa taaaattcaa   10200
taaattcata gagcctcagt tagatgagga tttgacaatt tatatgaaag ataaagcatt   10260
atctccaaaa aaatcaaatt gggacacagt ttatcctgca tctaatttac tgtaccgtac   10320
taacgcatcc aacgaatcac gaagattagt tgaagtattt atagcagata gtaaatttga   10380
tcctcatcag atattggatt atgtagaatc tggggactgg ttagatgatc cagaatttaa   10440
tatttcttat agtcttaaag aaaaagagat caaacaggaa ggtagactct ttgcaaaaat   10500
gacatacaaa atgagagcta cacaagtttt atcagagacc ctacttgcaa ataacatagg   10560
aaaattcttt caagaaaatg ggatggtgaa gggagagatt gaattactta agagattaac   10620
aaccatatca atatcaggag ttccacggta taatgaagtg tacaataatt ctaaaagcca   10680
tacagatgac cttaaaaacct acaataaaat aagtaatctt aatttgtctt ctaatcgaa    10740 atcaaagaaa tttgaattca agtcaacgga tatctacaat gatggatacg agactgtgag   10800
```

```
ctgtttccta acaacagatc tcaaaaaata ctgtcttaat tggagatatg aatcaacagc    10860
tctatttgga gaaacttgca accaaatatt tggattaaat aaattgttta attggttaca    10920
ccctcgtctt gaaggaagta caatctatgt aggtgatcct tactgtcctc catcagataa    10980
agaacatata tcattagagg atcaccctga ttctggtttt tacgttcata acccaagagg    11040
gggtatagaa ggattttgtc aaaaattatg gacactcata tctataagtg caatacatct    11100
agcagctgtt agaataggcg tgagggtgac tgcaatggtt caaggagaca atcaagctat    11160
agctgtaacc acaagagtac ccaacaatta tgactacaga gttaagaagg atagagttta    11220
taaagatgta gtgagatttt ttgattcatt aagagaagtg atggatgatc taggtcatga    11280
acttaaatta aatgaaacga ttataagtag caagatgttc atatatagca aaagaatcta    11340
ttatgatggg agaattcttc ctcaagctct aaaagcatta tctagatgtg tcttctggtc    11400
agagacagta atagacgaaa caagatcagc atcttcaaat ttggcaacat catttgcaaa    11460
agcaattgag aatggttatt cacctgttct aggatatgca tgctcaattt ttaagaatat    11520
tcaacaacta tatattgccc ttgggatgaa tatcaatcca actataacac agaatatcag    11580
agatcagtat tttaggaatc caaattggat gcaatatgcc tctttaatac ctgctagtgt    11640
tgggggattc aattacatgg ccatgtcaag atgttttgta aggaatattg gtgatccatc    11700
agttgccgca ttggctgata ttaaaagatt tattaaggcg aatctattag accgaagtgt    11760
tctttatagg attatgaatc aagaaccagg tgagtcatct tttttggact gggcttcaga    11820
tccatattca tgcaatttac cacaatctca aaatataacc accatgataa aaatataaac    11880
agcaaggaat gtattacaag attcaccaaa tccattatta tctggattat tcacaaatac    11940
aatgatagaa gaagatgaag aattagctga gttcctgatg gacaggaagg taattctccc    12000
tagagttgca catgatattc tagataattc tctcacagga attagaaatg ccatagctgg    12060
aatgttagat acgacaaaat cactaattcg ggttggcata aatagaggag gactgacata    12120
tagtttgttg aggaaaatca gtaattacga tctagtacaa tatgaaacac taagtaggac    12180
tttgcgacta attgtaagtg ataaaatcaa gtatgaagat atgtgttcgg tagaccttgc    12240
catagcattg cgacaaaaga tgtggattca tttatcagga ggaaggatga aagtggact    12300 tgaaacgcct gacccattag aattactatc tggggtagta ataacaggat cagaacattg    12360
taaaatatgt tattcttcag atggcacaaa cccatatact tggatgtatt tacccggtaa    12420
tatcaaaata ggatcagcag aaacaggtat atcgtcatta agagttcctt attttggatc    12480
agtcactgat gaaagatctg aagcacaatt aggatatatc aagaatctta gtaaacctgc    12540
aaaagccgca ataagaatag caatgatata tacatgggca tttggtaatg atgagatatc    12600
ttggatggaa gcctcacaga tagcacaaac acgtgcaaat tttacactag atagtctcaa    12660
aattttaaca ccggtagcta catcaacaaa tttatcacac agattaaagg atactgcaac    12720
tcagatgaaa ttctccagta catcattgat cagagtcagc agattcataa caatgtccaa    12780
tgataacatg tctatcaaag aagctaatga accaaagat actaatctta tttatcaaca    12840
aataatgtta acaggattaa gtgttttcga atatttattt agattaaaag aaaccacagg    12900
acacaaccct atagtatgc atctgcacat agaagatgag tgttgtatta agaaagtttt    12960
taatgatgaa catattaatc cagagtctac attagaatta attcgatatc ctgaaagtaa    13020
tgaatttatt tatgataaag acccactcaa agatgtggac ttatcaaaac ttatggttat    13080
taaagaccat tcttacacaa ttgatatgaa ttattgggat gatactgaca tcatacatgc    13140
aatttcaata tgtactgcaa ttacaatagc agatactatg tcacaattag atcgagataa    13200
```

```
tttaaaagag ataatagtta ttgcaaatga tgatgatatt aatagcttaa tcactgaatt  13260
tttgactctt gacatacttg tatttctcaa gacatttggt ggattattag taaatcaatt  13320
tgcatacact ctttatagtc taaaaataga aggtagggat ctcatttggg attatataat  13380
gagaacactg agagatactt cccattcaat attaaaagta ttatctaatg cattatctca  13440
tcctaaagta ttcaagaggt tctgggattg tggagtttta aaccctattt atggtcctaa  13500
tactgctagt caagaccaga taaaacttgc cctatctata tgtgaatatt cactagatct  13560
atttatgaga gaatggttga atggtgtatc acttgaaata tacatttgtg acagcgatat  13620
ggaagttgca aatgatagga aacaagcctt tatttctaga cacctttcat ttgtttgttg  13680
tttagcagaa attgcatctt tcggacctaa cctgttaaac ttaacatact tggagagact  13740
tgatctattg aaacaatatc ttgaattaaa tattaaagaa gaccctactc ttaaatatgt  13800
acaaatatct ggattattaa ttaaatcgtt cccatcaact gtaacatacg taagaaagac  13860
tgcaatcaaa tatctaagga ttcgcggtat tagtccacct gaggtaattg atgattggga  13920
tccggtagaa gatgaaaata tgctggataa cattgtcaaa actataaatg ataactgtaa  13980
taaagataat aaagggaata aaattaacaa tttctgggga ctagcactta agaactatca  14040
agtccttaaa atcagatcta taacaagtga ttctgatgat aatgatagac tagatgctaa  14100
tacaagtggt ttgacacttc ctcaaggagg gaattatcta tcgcatcaat tgagattatt  14160
cggaatcaac agcactagtt gtctgaaagc tcttgagtta tcacaaattt taatgaagga  14220
agtcaataaa gacaaggaca ggctcttcct gggagaagga gcaggagcta tgctagcatg  14280
ttatgatgcc acattaggac ctgcagttaa ttattataat tcaggtttga atataacaga  14340
tgtaattggt caacgagaat tgaaaatatt tccttcagag gtatcattag taggtaaaaa  14400
attaggaaat gtgacacaga ttcttaacag ggtaaaagta ctgttcaatg ggaatcctaa  14460
ttcaacatgg ataggaaata tggaatgtga gagcttaata tggagtgaat taaatgataa  14520
gtccattgga ttagtacatt gtgatatgga aggagctatc ggtaaatcag aagaaactgt  14580
tctacatgaa cattatagtg ttataagaat tacatacttg attggggatg atgatgttgt  14640
tttagttttcc aaaattatac ctacaatcac tccgaattgg tctagaatac tttatctata  14700
taaattatat tggaaagatg taagtataat atcactcaaa acttctaatc ctgcatcaac  14760
agaattatat ctaatttcga aagatgcata ttgtactata atggaaccta gtgaaattgt  14820
tttatcaaaa cttaaaagat tgtcactctt ggaagaaaat aatctattaa aatggatcat  14880
tttatcaaag aagaggaata atgaatggtt acatcatgaa atcaaagaag gagaaagaga  14940
ttatggaatc atgagaccat atcatatggc actacaaatc tttggatttc aaatcaattt  15000
aaatcatctg gcgaaagaat ttttatcaac cccagatctg actaatatca acaatataat  15060
ccaaagtttt cagcgaacaa taaggatgt tttatttgaa tggattaata taactcatga  15120
tgataagaga cataaaattag gcggaagata acatattc ccactgaaaa ataagggaaa  15180
gttaagactg ctatcgagaa gactagtatt aagttggatt tcattatcat tatcgactcg  15240
attacttaca ggtcgctttc ctgatgaaaa atttgaacat agagcacaga ctggatatgt  15300
atcattagct gatactgatt tagaatcatt aaagttattg tcgaaaaaca tcattaagaa  15360
ttacagagag tgtataggat caatatcata ttggtttcta accaagaag ttaaaatact  15420
tatgaaattg atcggtggtg ctaaattatt aggaattccc agacaatata agaacccga  15480
agaccagtta ttagaaaact acaatcaaca tgatgaattt gatatcgatt aaaacataaa  15540
tacaatgaag atatatccta acctttatct ttaagcctag gaatagacaa aaagtaagaa  15600
```

-continued

```
aaacatgtaa tatatatata ccaaacagag ttcttctctt gtttggttat agtgagtcgt    15660
attacaatc                                                            15669
```

<210> SEQ ID NO 72
<211> LENGTH: 15660
<212> TYPE: DNA
<213> ORGANISM: Artificial Sequence
<220> FEATURE:
<223> OTHER INFORMATION: Chemically synthesized cDNA clone p3/7(131).
<220> FEATURE:
<221> NAME/KEY: misc_feature
<222> LOCATION: (1)..(15660)
<223> OTHER INFORMATION: Part of Parent Appln No 09/083,793 as SEQ ID
      NO: 14

<400> SEQUENCE: 72

```
taatacgact cactataacc aaacaagaga agaaacttgt ctgggaatat aaatttaact      60
ttaaattaac ttaggattaa agacattgac tagaaggtca agaaaaggga actctataat     120
ttcaaaaatg ttgagcctat ttgatacatt taatgcacgg aggcaagaaa acataacaaa    180
atcagccggt ggagctatca ttcctggaca gaaaatact gtctctatat tcgcccttgg     240
accgacaata actgatgata atgagaaaat gacattagct cttctatttc tatctcattc    300
actagataat gagaaacaac atgcacaaag gcagggttc ttggtgtctt tattgtcaat     360
ggcttatgcc aatccagagc tctacctaac aacaaatgga agtaatgcag atgtcaagta    420
tgtcatatac atgattgaga agatctaaa acggcaaaag tatggaggat ttgtggttaa     480
gacgagagag atgatatatg aaaagacaac tgattggata tttggaagtg acctggatta    540
tgatcaggaa actatgttgc agaacggcag gaacaattca acaattgaag accttgtcca    600
cacatttggg tatccatcat gtttaggagc tcttataata cagatctgga tagttctggt    660
caaagctatc actagtatct cagggttaag aaaaggcttt ttcacccgat tggaagcttt    720
cagacaagat ggaacagtgc aggcagggct ggtattgagc ggtgacacag tggatcagat    780
tgggtcaatc atgcggtctc aacagagctt ggtaactctt atggttgaaa cattaataac    840
aatgaatacc agcagaaatg acctcacaac catagaaaag aatatacaaa ttgttggcaa    900
ctacataaga gatgcaggtc tcgcttcatt cttcaataca atcagatatg gaattgagac    960
cagaatggca gctttgactc tatccactct cagaccagat atcaatagat taaaagcttt   1020
gatggaactg tatttatcaa agggaccacg cgctcctttc atctgtatcc tcagagatcc   1080
tatacatggt gagttcgcac caggcaacta tcctgccata tggagctatg caatgggggt   1140
ggcagttgta caaaatagag ccatgcaaca gtatgtgacg ggaagatcat atctagacat   1200
tgatatgttc cagctaggac aagcagtagc acgtgatgcc gaagctcaaa tgagctcaac   1260 actgaagat gaacttggag tgacacacga atctaaagaa agcttgaaga gacatataag     1320
gaacataaac agttcagaga catctttcca caaccgaca ggtggatcag ccatagagat    1380
ggcaatagat gaagagccag aacaattcga acatagagca gatcaagaac aaaatggaga   1440
acctcaatca tccataattc aatatgcctg gcagaagga aatagaagcg atgatcagac     1500
tgagcaagct acagaatctg acaatatcaa gaccgaacaa caaaacatca gagacagact   1560
aaacaagaga ctcaacgaca gaagaaaca aagcagtcaa ccacccacta atcccacaaa    1620
cagaacaaac caggacgaaa tagatgatct gtttaacgca tttggaagca actaatcgaa   1680
tcaacatttt aatctaaatc aataataaat aagaaaaact taggattaaa gaatcctatc   1740
ataccggaat atagggtggt aaatttagag tctgcttgaa actcaatcaa tagagagttg   1800
atggaaagcg atgctaaaaa ctatcaaatc atggattctt gggaagagga atcaagagat   1860
```

-continued

```
aaatcaacta atatctcctc ggccctcaac atcattgaat tcatactcag caccgacccc    1920
caagaagact tatcggaaaa cgacacaatc aacacaagaa cccagcaact cagtgccacc    1980
atctgtcaac cagaaatcaa accaacagaa acaagtgaga agatagtgg  atcaactgac    2040 aaaaatagac agtctgggtc atcacacgaa tgtacaacag aagcaaaaga tagaaatatt    2100
gatcaggaaa ctgtacagag aggacctggg agaagaagca gctcagatag tagagctgag    2160
actgtggtct ctggaggaat ccccagaagc atcacagatt ctaaaaatgg aacccaaaac    2220
acggaggata ttgatctcaa tgaaattaga agatggata  aggactctat tgagggaaa     2280 atgcgacaat ctgcaaatgt tccaagcgag atatcaggaa gtgatgacat atttacaaca    2340
gaacaaagta gaaacagtga tcatggaaga agcctggaat ctatcagtac acctgataca    2400
agatcaataa gtgttgttac tgctgcaaca ccagatgatg aagaagaaat actaatgaaa    2460
aatagtagga caaagaaaag ttcttcaaca catcaagaag atgacaaaag aattaaaaaa    2520
gggggaaaag ggaaagactg gtttaagaaa tcaaaagata ccgacaacca gataccaaca    2580
tcagactaca gatccacatc aaaagggcag aagaaaatct caaagacaac aaccaccaac    2640
accgacacaa aggggcaaac agaaatacag acagaatcat cagaaacaca atcctcatca    2700
tggaatctca tcatcgacaa caacaccgac cggaacgaac agacaagcac aactcctcca    2760
acaacaactt ccagatcaac ttatacaaaa gaatcgatcc gaacaaactc tgaatccaaa    2820
cccaagacac aaaagacaaa tggaaaggaa aggaaggata cagaagagag caatcgattt    2880
acagagaggg caattactct attgcagaat cttggtgtaa ttcaatccac atcaaaacta    2940
gatttatatc aagacaaacg agttgtatgt gtagcaaatg tactaaacaa tgtagatact    3000
gcatcaaaga tagatttcct ggcaggatta gtcataggg  tttcaatgga caacgacaca    3060
aaattaacac agatacaaaa tgaaatgcta aacctcaaag cagatctaaa gaaaatggac    3120
gaatcacata gaagattgat agaaaatcaa agagaacaac tgtcattgat cacgtcacta    3180
atttcaaatc tcaaaattat gactgagaga ggaggaaaga aagaccaaaa tgaatccaat    3240
gagagagtat ccatgatcaa aacaaaattg aaagaagaaa agatcaagaa gaccaggttt    3300
gacccactta tggaggcaca aggcattgac aagaatatac ccgatctata tcgacatgca    3360
ggagatacac tagagaacga tgtacaagtt aaatcagaga tattaagttc atacaatgag    3420
tcaaatgcaa caagactaat acccaaaaaa gtgagcagta caatgagatc actagttgca    3480
gtcatcaaca acagcaatct ctcacaaagc acaaaacaat catacataaa cgaactcaaa    3540
cgttgcaaaa atgatgaaga agtatctgaa ttaatggaca tgttcaatga agatgtcaac    3600
aattgccaat gatccaacaa agaaacgaca ccgaacaaac agacaagaaa caacagtaga    3660
tcaaaacctg tcaacacaca caaatcaag  cagaatgaaa caacagatat caatcaatat    3720
acaaataaga aaaacttagg attaaagaat aaattaatcc ttgtccaaaa tgagtataac    3780
taactctgca atatacacat tcccagaatc atcattctct gaaaatggtc atatagaacc    3840
attaccactc aaagtcaatg aacagaggaa agcagtaccc cacattagag ttgccaagat    3900
cggaaatcca ccaaaacacg gatcccggta tttagatgtc ttcttactcg gcttcttcga    3960
gatggaacga atcaaagaca aatacgggag tgtgaatgat ctcgacagtg acccgagtta    4020
caaagtttgt ggctctggat cattaccaat cggattggct aagtacactg gaatgaccca    4080
ggaattgtta caagccgcaa ccaaactgga tatagaagtg agaagaacag tcaaagcgaa    4140
agagatggtt gtttacacgg tacaaaatat aaaaccagaa ctgtacccat ggtccaatag    4200
actaagaaaa ggaatgctgt tcgatgccaa caaagttgct cttgctcctc aatgtcttcc    4260
```

```
actagatagg agcataaaat ttagagtaat cttcgtgaat tgtacggcaa ttggatcaat    4320
aaccttgttc aaaattccta agtcaatggc atcactatct ctacccaaca caatatcaat    4380
caatctgcag gtacacataa aaacagggt tcagactgat tctaaaggga tagttcaaat    4440
tttggatgag aaaggcgaaa aatcactgaa tttcatggtc catctcggat tgatcaaaag    4500
aaaagtaggc agaatgtact ctgttgaata ctgtaaacag aaaatcgaga aaatgagatt    4560
gatattttct ttaggactag ttggaggaat cagtcttcat gtcaatgcaa ctgggtccat    4620
atcaaaaaca ctagcaagtc agctggtatt caaaagagag atttgttatc ctttaatgga    4680
tctaaatccg catctcaatc tagttatctg ggcttcatca gtagagatta caagagtgga    4740
tgcaattttc caaccttctt tacctggcga gttcagatac tatcctaata ttattgcaaa    4800
aggagttggg aaaatcaaac aatgaaacta gtaatctcta ttttagtccg gacgtatcta    4860
ttaagccgaa gcaaataaag gataatcaaa aacttaggac aaaagaggtc aataccaaca    4920
actattagca gtcacactcg caagaataag agagaaggga ccaaaaaagt caaataggag    4980
aaatcaaaac aaaaggtaca gaacaccaga acaacaaaat caaaacatcc aactcactca    5040
aaacaaaaat tccaaaagag accggcaaca caacaagcac tgaacacaat gccaacttca    5100
atactgctaa ttattacaac catgatcatg gcatctttct gccaaataga tatcacaaaa    5160
ctacagcacg taggtgtatt ggtcaacagt cccaaaggga tgaagatatc acaaaacttt    5220
gaaacaagat atctaatttt gagcctcata ccaaaaatag aagactctaa ctcttgtggt    5280
gaccaacaga tcaagcaata caagaagtta ttggatagac tgatcatccc tttatatgat    5340
ggattaagat tacagaaaga tgtgatagta accaatcaag aatccaatga aaacactgat    5400
cccagaacaa aacgattctt tggaggggta attggaacca ttgctctggg agtagcaacc    5460
tcagcacaaa ttacagcggc agttgctctg gttgaagcca agcaggcaag atcagacatc    5520
gaaaaactca aagaagcaat tagggacaca aacaaagcag tgcagtcagt tcagagctcc    5580
ataggaaatt taatagtagc aattaaatca gtccaggatt atgttaacaa agaaatcgtg    5640
ccatcgattg cgaggctagg ttgtgaagca gcaggacttc aattaggaat tgcattaaca    5700
cagcattact cagaattaac aaacatattt ggtgataaca taggatcgtt acaagaaaaa    5760
ggaataaaat tacaaggtat agcatcatta taccgcacaa atatcacaga atattcaca     5820 acatcaacag ttgataaata tgatatctat gatctgttat ttacagaatc aataaaggtg    5880
agagttatag atgttgactt gaatgattac tcaatcaccc tccaagtcag actcccttta    5940
ttaactaggc tgctgaacac tcagatctac aaagtagatt ccatatcata taacatccaa    6000
aacagagaat ggtatatccc tcttcccagc catatcatga cgaaaggggc atttctaggt    6060
ggagcagacg tcaagaatg tatagaagca ttcagcagct atatgcccc ttctgatcca     6120 ggatttgtat taaaccatga aatagagagc tgcttatcag gaaacatatc ccaatgtcca    6180
agaacaacgg tcacatcaga cattgttcca gatatgcat ttgtcaatgg aggagtggtt     6240
gcaaactgta taacaaccac ctgtacatgc aacggaattg gtaatagaat caatcaacca    6300
cctgatcaag gagtaaaaat tataacacat aaagaatgta gtacaatagg tatcaacgga    6360
atgctgttca atacaaataa agaaggaact cttgcattct atacaccaaa tgatataaca    6420
ctaaacaatt ctgttgcact tgatccaatt gacatatcaa tcgagctcaa caaggccaaa    6480
tcagatctag aagaatcaaa agaatggata agaaggtcaa atcaaaaact agattctatt    6540
ggaaattggc atcaatctag cactacaatc ataattattt tgataatgat cattatattg    6600
tttataatta atataacgat aattacaatt gcaattaagt attacagaat tcaaaagaga    6660
```

```
aatcgagtgg atcaaaatga caagccatat gtactaacaa acaaataaca tatctacaga   6720
tcattagata ttaaaattat aaaaaactta ggagtaaagt tacgcaatcc aactctactc   6780
atataattga ggaaggaccc aatagacaaa tccaaattcg agatggaata ctggaagcat   6840
accaatcacg gaaaggatgc tggtaatgag ctggagacgt ctatggctac tcatggcaac   6900
aagctcacta ataagataat atacatatta tggacaataa tcctggtgtt attatcaata   6960
gtcttcatca tagtgctaat taattccatc aaaagtgaaa aggcccacga atcattgctg   7020
caagacataa ataatgagtt tatggaaatt acagaaaaga tccaaatggc atcggataat   7080
accaatgatc taatacagtc aggagtgaat acaaggcttc ttacaattca gagtcatgtc   7140
cagaattaca taccaatatc attgacacaa cagatgtcag atcttaggaa attcattagt   7200
gaaattacaa ttagaaatga taatcaagaa gtgctgccac aaagaataac acatgatgta   7260
ggtataaaac ctttaaatcc agatgatttt tggagatgca cgtctggtct tccatcttta   7320
atgaaaactc caaaaataag gttaatgcca gggccgggat tattagctat gccaacgact   7380
gttgatggct gtgttagaac tccgtctttt gttataaatg atctgatttt tgcttatacc   7440
tcaaatctaa ttactcgagg ttgtcaggat ataggaaaat catatcaagt cttacagata   7500
gggataataa ctgtaaactc agacttggta cctgacttaa atcctaggat ctctcatacc   7560
tttaacataa atgacaatag gaagtcatgt tctctagcac tcctaaatat agatgtatat   7620
caactgtgtt caactcccaa agttgatgaa agatcagatt atgcatcatc aggcatagaa   7680
gatattgtac ttgatattgt caattatgat ggttcaatct caacaacaag atttaagaat   7740
aataacataa gctttgatca accatatgct gcactatacc catctgttgg accagggata   7800
tactacaaag gcaaaataat atttctcggg tatggaggtc ttgaacatcc aataaatgag   7860
aatgtaatct gcaacacaac tgggtgcccc gggaaaacac agagagactg taatcaagca   7920
tctcatagta cttggttttc agataggagg atggtcaact ccatcattgt tgttgacaaa   7980
ggcttaaact caattccaaa attgaaagta tggacgtatt ctatgcgaca aaattactgg   8040
gggtcagaag gaaggttact tctactaggt aacaagatct atatatatac aagatctaca   8100
agttggcata gcaagttaca attaggaata attgatatta ctgattacag tgatataagg   8160
ataaaatgga catggcataa tgtgctatca agaccaggaa acaatgaatg tccatgggga   8220
cattcatgtc cagatggatg tataacagga gtatatactg atgcatatcc actcaatccc   8280
acagggagca ttgtgtcatc tgtcatatta gactcacaaa atcgagagt gaacccagtc   8340 ataacttact caacagcaac cgaaagagta aacgagctgg ccatcctaaa cagaacactc   8400
tcagctggat atacaacaac aagctgcatt acacactata caaaggata ttgttttcat   8460 atagtagaaa taaatcataa aagcttaaac acatttcaac ccatgttgtt caaaacagag   8520
attccaaaaa gctgcagtta atcataatta accataatat gcatcaatct atctataata   8580
caagtatatg ataagtaatc agcaatcaga caatagacaa aagggaaata taaaaaactt   8640
aggagcaaag cgtgctcggg aaatggacac tgaatctaac aatggcactg tatctgacat   8700
actctatcct gagtgtcacc ttaactctcc tatcgttaaa ggtaaaatag cacaattaca   8760 cactatatg agtctacctc agccttatga tatggatgac gactcaatac tagttatcac   8820
tagacagaaa ataaaactta ataaattgga taaaagacaa cgatctatta aagattaaa   8880 attaatatta actgaaaaag tgaatgactt aggaaaatac acatttatca gatatccaga   8940
aatgtcaaaa gaaatgttca attatatat acctggtatt aacagtaaag tgactgaatt   9000
attacttaaa gcagatagaa catatagtca aatgactgat ggattaagag atctatggat   9060
```

-continued

```
taatgtgcta tcaaaattag cctcaaaaaa tgatggaagc aattatgatc ttaatgaaga    9120
aattaataat atatcgaaag ttcacacaac ctataaatca gataaatggt ataatccatt    9180
caaaacatgg tttactatca agtatgatat gagaagatta caaaaagctc gaaatgagat    9240
cacttttaat gttgggaagg attataactt gttagaagac cagaagaatt tcttattgat    9300
acatccagaa ttggttttga tattagataa acaaaactat aatggttatc taattactcc    9360
tgaattagta ttgatgtatt gtgacgtagt cgaaggccga tggaatataa gtgcatgtgc    9420
taagttagat ccaaaattac aatctatgta tcagaaaggt aataacctgt gggaagtgat    9480
agataaattg tttccaatta tgggagaaaa gacatttgat gtgatatcgt tattagaacc    9540
acttgcatta tccttaattc aaactcatga tcctgttaaa caactaagag gagcttttt    9600 aaatcatgtg ttatccgaga tggaattaat atttgaatct agagaatcga ttaaggaatt    9660
tctgagtgta gattacattg ataaaatttt agatatattt aataagtcta caatagatga    9720
aatagcagag atttctcttt tttttagaac atttgggcat cctccattag aagctagtat    9780
tgcagcagaa aaggttagaa aatatatgta tattggaaaa caattaaaat ttgacactat    9840
taataaatgt catgctatct tctgtacaat aataattaac ggatatagag agaggcatgg    9900
tggacagtgg cctcctgtga cattacctga tcatgcacac gaattcatca taaatgctta    9960
cggttcaaac tctgcgatat catatgaaaa tgctgttgat tattaccaga gctttatagg   10020
aataaaattc aataaattca tagagcctca gttagatgag gatttgacaa tttatatgaa   10080
agataaagca ttatctccaa aaaaatcaaa ttgggacaca gtttatcctg catctaattt   10140
actgtaccgt actaacgcat ccaacgaatc acgaagatta gttgaagtat ttatagcaga   10200
tagtaaattt gatcctcatc agatattgga ttatgtagaa tctggggact ggttagatga   10260
tccagaattt aatatttctt atagtcttaa agaaaaagag atcaaacagg aaggtagact   10320
ctttgcaaaa atgacataca aaatgagagc tacacaagtt ttatcagaga ccctacttgc   10380
aaataacata ggaaaattct ttcaagaaaa tgggatggtg aagggagaga ttgaattact   10440
taagagatta acaaccatat caatatcagg agttccacgg tataatgaag tgtacaataa   10500
ttctaaaagc catacagatg accttaaaac ctacaataaa ataagtaatc ttaatttgtc   10560
ttctaatcag aaatcaaaga aatttgaatt caagtcaacg gatatctaca atgatggata   10620
cgagactgtg agctgtttcc taacaacaga tctcaaaaaa tactgtctta attggagata   10680
tgaatcaaca gctctatttg gagaaacttg caaccaaata tttggattaa ataaattgtt   10740
taattggtta caccctcgtc ttgaaggaag tacaatctat gtaggtgatc cttactgtcc   10800
tccatcagat aaagaacata tatcattaga ggatcaccct gattctggtt tttacgttca   10860
taacccaaga gggggtatag aaggattttg tcaaaaatta tggacactca tatctataag   10920
tgcaatacat ctagcagctg ttagaatagg cgtgagggtg actgcaatgg ttcaaggaga   10980
caatcaagct atagctgtaa ccacaagagt acccaacaat tatgactaca gagttaagaa   11040
ggagatagtt tataaagatg tagtgagatt ttttgattca ttaagagaag tgatggatga   11100
tctaggtcat gaacttaaat taaatgaaac gattataagt agcaagatgt tcatatatag   11160
caaaagaatc tattatgatg ggagaattct tcctcaagct ctaaaagcat tatctagatg   11220
tgtcttctgg tcagagacag taatagacga aacaagatca gcatcttcaa atttggcaac   11280
atcatttgca aaagcaattg agaatggtta ttcacctgtt ctaggatatg catgctcaat   11340
ttttaagaat attcaacaac tatatattgc ccttgggatg aatatcaatc caactataac   11400
acagaatatc agagatcagt attttaggaa tccaaattgg atgcaatatg cctctttaat   11460
```

```
acctgctagt gttgggggat tcaattacat ggccatgtca agatgttttg taaggaatat    11520
tggtgatcca tcagttgccg cattggctga tattaaaaga tttattaagg cgaatctatt    11580
agaccgaagt gttctttata ggattatgaa tcaagaacca ggtgagtcat cttttttgga    11640
ctgggcttca gatccatatt catgcaattt accacaatct caaaatataa ccaccatgat    11700
aaaaaatata acagcaagga atgtattaca agattcacca aatccattat tatctggatt    11760
attcacaaat acaatgatag aagaagatga agaattagct gagttcctga tggacaggaa    11820
ggtaattctc cctagagttg cacatgatat tctagataat tctctcacag gaattagaaa    11880
tgccatagct ggaatgttag atacgacaaa atcactaatt cggttggca taaatagagg     11940
aggactgaca tatagtttgt tgaggaaaat cagtaattac gatctagtac aatatgaaac    12000
actaagtagg actttgcgac taattgtaag tgataaaatc aagtatgaag atatgtgttc    12060
ggtagacctt gccatagcat tgcgacaaaa gatgtggatt catttatcag gaggaaggat    12120
gataagtgga cttgaaacgc ctgacccatt agaattacta tctggggtag taataacagg    12180
atcagaacat tgtaaaatat gttattcttc agatggcaca aacccatata cttggatgta    12240
tttacccggt aatatcaaaa taggatcagc agaaacaggt atatcgtcat taagagttcc    12300
ttattttgga tcagtcactg atgaaagatc tgaagcacaa ttaggatata tcaagaatct    12360
tagtaaacct gcaaaagccg caataagaat agcaatgata tatacatggg catttggtaa    12420
tgatgagata tcttggatgg aagcctcaca gatagcacaa acacgtgcaa attttacact    12480
agatagtctc aaaattttaa caccggtagc tacatcaaca aatttatcac acagattaaa    12540
ggatactgca actcagatga aattctccag tacatcattg atcagagtca gcagattcat    12600
aacaatgtcc aatgataaca tgtctatcaa agaagctaat gaaaccaaag atactaatct    12660
tatttatcaa caaataatgt taacaggatt aagtgttttc gaatatttat ttagattaaa    12720
agaaaccaca ggacacaacc ctatagttat gcatctgcac atagaagatg agtgttgtat    12780
taaagaaagt tttaatgatg aacatattaa tccagagtct acattagaat taattcgata    12840
tcctgaaagt aatgaattta tttatgataa agacccactc aaagatgtgg acttatcaaa    12900
acttatggtt attaaagacc attcttacac aattgatatg aattattggg atgatactga    12960
catcatacat gcaattcaa tatgtactgc aattacaata gcagatacta tgtcacaatt     13020
agatcgagat aatttaaaag agataatagt tattgcaaat gatgatgata ttaatagctt    13080
aatcactgaa tttttgactc ttgacatact tgtatttctc aagacatttg gtggattatt    13140
agtaaatcaa tttgcataca ctctttatag tctaaaaata gaaggtaggg atctcatttg    13200
ggattatata atgagaacac tgagagatac ttcccattca atattaaaag tattatctaa    13260
tgcattatct catcctaaag tattcaagag gttctgggat tgtggagttt taaaccctat    13320
ttatggtcct aatactgcta gtcaagacca gataaaactt gccctatcta tatgtgaata    13380
ttcactagat ctatttatga gagaatggtt gaatggtgta tcacttgaaa tatacatttg    13440
tgacagcgat atggaagttg caaatgatag gaaacaagcc tttatttcta gacacctttc    13500
atttgtttgt tgtttagcag aaattgcatc tttcggacct aacctgttaa acttaacata    13560
cttggagaga cttgatctat tgaaacaata tcttgaatta aatattaaag aagacccta  c  13620
tcttaaatat gtacaaatat ctggattatt aattaaatcg ttcccatcaa ctgtaacata    13680
cgtaagaaag actgcaatca aatatctaag gattcgcggt attagtccac ctgaggtaat    13740
tgatgattgg gatccggtag aagatgaaaa tatgctggat aacattgtca aaactataaa    13800
tgataactgt aataaagata ataaagggaa taaaattaac aatttctggg gactagcact    13860
```

```
taagaactat caagtcctta aaatcagatc tataacaagt gattctgatg ataatgatag    13920
actagatgct aatacaagtg gtttgacact tcctcaagga gggaattatc tatcgcatca    13980
attgagatta ttcggaatca acagcactag ttgtctgaaa gctcttgagt tatcacaaat    14040
tttaatgaag gaagtcaata aagacaagga caggctcttc ctgggagaag gagcaggagc    14100
tatgctagca tgttatgatg ccacattagg acctgcagtt aattattata attcaggttt    14160
gaatataaca gatgtaattg gtcaacgaga attgaaaata tttccttcag aggtatcatt    14220
agtaggtaaa aaattaggaa atgtgacaca gattcttaac agggtaaaag tactgttcaa    14280
tgggaatcct aattcaacat ggataggaaa tatggaatgt gagagcttaa tatggagtga    14340
attaaatgat aagtccattg gattagtaca ttgtgatatg gaaggagcta tcggtaaatc    14400
agaagaaact gttctacatg aacattatag tgttataaga attacatact tgattgggga    14460
tgatgatgtt gttttagttt ccaaaattat acctacaatc actccgaatt ggtctagaat    14520
actttatcta tataaattat attggaaaga tgtaagtata atatcactca aaacttctaa    14580
tcctgcatca acagaattat atctaatttc gaaagatgca tattgtacta taatggaacc    14640
tagtgaaatt gttttatcaa aacttaaaag attgtcactc ttggaagaaa ataatctatt    14700
aaaatggatc attttatcaa agaagaggaa taatgaatgg ttacatcatg aaatcaaaga    14760
aggagaaaga gattatggaa tcatgagacc atatcatatg gcactacaaa tctttggatt    14820
tcaaatcaat ttaaatcatc tggcgaaaga attttttatca accccagatc tgactaatat    14880
caacaatata atccaaagtt ttcagcgaac aataaaggat gttttatttg aatggattaa    14940
tataactcat gatgataaga gacataaaatt aggcggaaga tataacatat tcccactgaa    15000
aaataaggga aagttaagac tgctatcgag aagactagta ttaagttgga tttcattatc    15060
attatcgact cgattactta caggtcgctt tcctgatgaa aaatttgaac atagagcaca    15120
gactggatat gtatcattag ctgatactga tttagaatca ttaaagttat tgtcgaaaaa    15180
catcattaag aattacagag agtgtatagg atcaatatca tattggtttc taaccaaaga    15240
agttaaaata cttatgaaat tgatcggtgg tgctaaatta ttaggaattc ccagacaata    15300
taaagaaccc gaagaccagt tattagaaaa ctacaatcaa catgatgaat tgatatcga    15360 ttaaaacata aatacaatga agatatatcc taacctttat ctttaagcct aggaatagac    15420
aaaaagtaag aaaaacatgt aatatatata taccaaacag agttcttctc ttgtttggtg    15480
ggtcggcatg gcatctccac ctcctcgcgg tccggacctg gcatccgaa ggaggacgca    15540 cgtccactcg gatggctaag ggagagcctg cagtagcata accccttggg gcctctaaac    15600
gggtcttgag gggttttttg ctgaaaggag gaactatata cgcgtcgacg ggccccgcgc    15660
```

<210> SEQ ID NO 73
<211> LENGTH: 15666
<212> TYPE: DNA
<213> ORGANISM: Artificial Sequence
<220> FEATURE:
<223> OTHER INFORMATION: Chemically synthesized cDNA clone p3/7(131)2G.
<220> FEATURE:
<221> NAME/KEY: misc_feature
<222> LOCATION: (1)..(15666)
<223> OTHER INFORMATION: Part of Parent Appln No 09/083,793 as SEQ ID
      NO: 15

<400> SEQUENCE: 73

```
taatacgact cactatagga ccaaacaaga gaagaaactt gtctgggaat ataaatttaa      60
ctttaaatta actaggatt aaagacattg actagaaggt caagaaaagg gaactctata     120
atttcaaaaa tgttgagcct atttgataca tttaatgcac gtaggcaaga aaacataaca     180
```

```
aaatcagccg gtggagctat cattcctgga cagaaaaata ctgtctctat attcgccctt      240
ggaccgacaa taactgatga taatgagaaa atgacattga ctcttctatt tctatctcat      300
tcactagata atgagaaaca acatgcacaa agggcagggt tcttggtgtc tttattgtca      360
atggcttatg ccaatccaga gctctaccta acaacaaatg gaagtaatgc agatgtcaag      420
tatgtcatat acatgattga gaaagatcta aaacggcaaa agtatggagg atttgtggtt      480
aagacgagag agatgatata tgaaaagaca actgattgga tatttggaag tgacctggat      540
tatgatcagg aaactatgtt gcagaacggc aggaacaatt caacaattga agaccttgtc      600
cacacatttg ggtatccatc atgtttagga gctcttataa tacagatctg gatagttctg      660
gtcaaagcta tcactagtat ctcagggtta agaaaaggct ttttcacccg attggaagct      720
ttcagacaag atggaacagt gcaggcaggg ctggtattga gcggtgacac agtggatcag      780
attgggtcaa tcatgcggtc tcaacagagc ttggtaactc ttatggttga aacattaata      840
acaatgaata ccagcagaaa tgacctcaca accatagaaa agaatataca aattgttggc      900
aactacataa gagatgcagg tctcgcttca ttcttcaata caatcagata tggaattgag      960
accagaatgg cagctttgac tctatccact ctcagaccag atatcaatag attaaaagct     1020
ttgatggaac tgtatttatc aaagggacca cgcgctcctt tcatctgtat cctcagagat     1080
cctatacatg gtgagttcgc accaggcaac tatcctgcca tatggagcta tgcaatgggg     1140
gtggcagttg tacaaaatag agccatgcaa cagtatgtga cgggaagatc atatctagac     1200
attgatatgt ccagctagg acaagcagta gcacgtgatg ccgaagctca aatgagctca     1260
acactggaag atgaacttgg agtgacacac gaatctaaag aaagcttgaa gagacatata     1320
aggaacataa acagttcaga gacatctttc cacaaaccga caggtggatc agccatagag     1380
atggcaatag atgaagagcc agaacaattc gaacatagag cagatcaaga acaaaatgga     1440
gaacctcaat catccataat tcaatatgcc tgggcagaag gaatagaag cgatgatcag     1500 actgagcaag ctacagaatc tgacaatatc aagaccgaac aacaaaacat cagagacaga     1560
ctaaacaaga gactcaacga caagaagaaa caaagcagtc aaccacccac taatcccaca     1620
aacagaacaa accaggacga aatagatgat ctgtttaacg catttggaag caactaatcg     1680
aatcaacatt ttaatctaaa tcaataataa ataagaaaaa cttaggatta aagaatccta     1740
tcataccgga atatagggtg gtaaatttag agtctgcttg aaactcaatc aatagagagt     1800
tgatggaaag cgatgctaaa aactatcaaa tcatggattc ttgggaagag gaatcaagag     1860
ataaatcaac taatatctcc tcggccctca acatcattga attcatactc agcaccgacc     1920
cccaagaaga cttatcggaa aacgacacaa tcaacacaag aacccagcaa ctcagtgcca     1980
ccatctgtca accagaaatc aaaccaacag aaacaagtga aaagatagt ggatcaactg     2040 acaaaaatag acagtctggg tcatcacacg aatgtacaac agaagcaaaa gatagaaata     2100
ttgatcagga aactgtacag agaggacctg ggagaagaag cagctcagat agtagagctg     2160
agactgtggt ctctggagga atccccagaa gcatcacaga ttctaaaaat ggaacccaaa     2220
acacggagga tattgatctc aatgaaatta gaaagatgga taaggactct attgagggga     2280
aaatgcgaca atctgcaaat gttccaagcg agatatcagg aagtgatgac atatttacaa     2340
cagaacaaag tagaaacagt gatcatggaa gaagcctgga atctatcagt acacctgata     2400
caagatcaat aagtgttgtt actgctgcaa caccagatga tgaagaagaa atactaatga     2460
aaaatagtag gacaaagaaa agttcttcaa cacatcaaga agatgacaaa agaattaaaa     2520
aagggggaaa agggaaagac tggtttaaga aatcaaaaga taccgacaac cagataccaa     2580
```

```
catcagacta cagatccaca tcaaaagggc agaagaaaat ctcaaagaca acaaccacca    2640
acaccgacac aaaggggcaa acagaaatac agacagaatc atcagaaaca caatcctcat    2700
catggaatct catcatcgac aacaaccacg accggaacga acagacaagc acaactcctc    2760
caacaacaac ttccagatca acttatacaa aagaatcgat ccgaacaaac tctgaatcca    2820
aacccaagac acaaaagaca aatggaaagg aaaggaagga tacagaagag agcaatcgat    2880
ttacagagag ggcaattact ctattgcaga atcttggtgt aattcaatcc acatcaaaac    2940
tagatttata tcaagacaaa cgagttgtat gtgtagcaaa tgtactaaac aatgtagata    3000
ctgcatcaaa gatagatttc ctggcaggat tagtcatagg ggtttcaatg gacaacgaca    3060
caaaattaac acagatacaa aatgaaatgc taaacctcaa agcagatcta aagaaaatgg    3120
acgaatcaca tagaagattg atagaaaatc aaagagaaca actgtcattg atcacgtcac    3180
taatttcaaa tctcaaaatt atgactgaga gaggaggaaa gaaagaccaa aatgaatcca    3240
atgagagagt atccatgatc aaaacaaaat tgaaagaaga aaagatcaag aagaccaggt    3300
ttgacccact tatggaggca caaggcattg acaagaatat acccgatcta tatcgacatg    3360
caggagatac actagagaac gatgtacaag ttaaatcaga gatattaagt tcatacaatg    3420
agtcaaatgc aacaagacta atacccaaaa aagtgagcag tacaatgaga tcactagttg    3480
cagtcatcaa caacagcaat ctctcacaaa gcacaaaaca atcatacata aacgaactca    3540
aacgttgcaa aaatgatgaa gaagtatctg aattaatgga catgttcaat gaagatgtca    3600
acaattgcca atgatccaac aaagaaacga caccgaacaa acagacaaga aacaacagta    3660
gatcaaaacc tgtcaacaca cacaaaatca agcagaatga aacaacagat atcaatcaat    3720
atacaaataa gaaaaactta ggattaaaga ataaattaat ccttgtccaa aatgagtata    3780
actaactctg caatatacac attcccagaa tcatcattct ctgaaaatgg tcatatagaa    3840
ccattaccac tcaaagtcaa tgaacagagg aaagcagtac cccacattag agttgccaag    3900
atcggaaatc caccaaaaca cggatcccgg tatttagatg tcttcttact cggcttcttc    3960
gagatggaac gaatcaaaga caaatacggg agtgtgaatg atctcgacag tgacccgagt    4020
tacaaagttt gtggctctgg atcattacca atcggattgg ctaagtacac tgggaatgac    4080
caggaattgt tacaagccgc aaccaaactg gatatagaag tgagaagaac agtcaaagcg    4140
aaagagatgg ttgtttacac ggtacaaaat ataaaaccag aactgtaccc atggtccaat    4200
agactaagaa aaggaatgct gttcgatgcc aacaagttg ctcttgctcc tcaatgtctt    4260
ccactagata ggagcataaa atttagagta atccttcgtga attgtacggc aattggatca    4320
ataaccttgt tcaaaattcc taagtcaatg gcatcactat ctctacccaa cacaatatca    4380
atcaatctgc aggtacacat aaaaacaggg gttcagactg attctaaagg gatagttcaa    4440
attttggatg agaaaggcga aaaatcactg aatttcatgg tccatctcgg attgatcaaa    4500
agaaaagtag gcagaatgta ctctgttgaa tactgtaaac agaaaatcga gaaaatgaga    4560
ttgatatttt ctttaggact agttggagga atcagtcttc atgtcaatgc aactgggtcc    4620
atatcaaaaa cactagcaag tcagctggta ttcaaaagag agatttgtta tccttttaatg    4680 gatctaaatc cgcatctcaa tctagttatc tgggcttcat cagtgagat tacaagagtg    4740 gatgcaattt tccaaccttc tttacctggc gagttcagat actatcctaa tattattgca    4800
aaaggagttg ggaaaatcaa acaatggaac tagtaatctc tattttagtc cggacgtatc    4860
tattaagccg aagcaaataa aggataatca aaaacttagg acaaaagagg tcaataccaa    4920
caactattag cagtcacact cgcaagaata agagagaagg gaccaaaaaa gtcaaatagg    4980
```

```
agaaatcaaa acaaaaggta cagaacacca gaacaacaaa atcaaaacat ccaactcact   5040
caaaacaaaa attccaaaag agaccggcaa cacaacaagc actgaacaca atgccaactt   5100
caatactgct aattattaca accatgatca tggcatcttt ctgccaaata gatatcacaa   5160
aactacagca cgtaggtgta ttggtcaaca gtcccaaagg gatgaagata tcacaaaact   5220
ttgaaacaag atatctaatt ttgagcctca taccaaaaat agaagactct aactcttgtg   5280
gtgaccaaca gatcaagcaa tacaagaagt tattggatag actgatcatc cctttatatg   5340
atggattaag attacagaaa gatgtgatag taaccaatca agaatccaat gaaaacactg   5400
atcccagaac aaaacgattc tttggagggg taattggaac cattgctctg ggagtagcaa   5460
cctcagcaca aattacagcg gcagttgctc tggttgaagc caagcaggca agatcagaca   5520
tcgaaaaact caaagaagca attagggaca caaacaaagc agtgcagtca gttcagagct   5580
ccataggaaa tttaatagta gcaattaaat cagtccagga ttatgttaac aaagaaatcg   5640
tgccatcgat tgcgaggcta ggttgtgaag cagcaggact tcaattagga attgcattaa   5700
cacagcatta ctcagaatta acaaacatat tggtgataa cataggatcg ttacaagaaa   5760
aaggaataaa attacaaggt atagcatcat tataccgcac aaatatcaca gaaatattca   5820
caacatcaac agttgataaa tatgatatct atgatctgtt atttacagaa tcaataaagg   5880
tgagagttat agatgttgac ttgaatgatt actcaatcac cctccaagtc agactccctt   5940
tattaactag gctgctgaac actcagatct acaaagtaga ttccatatca tataacatcc   6000
aaaacagaga atggtatatc cctcttccca gccatatcat gacgaaaggg gcatttctag   6060
gtggagcaga cgtcaaagaa tgtatagaag cattcagcag ctatatatgc ccttctgatc   6120
caggatttgt attaaaccat gaaatagaga gctgcttatc aggaaacata tcccaatgtc   6180
caagaacaac ggtcacatca gacattgttc caagatatgc atttgtcaat ggaggagtgg   6240
ttgcaaactg tataacaacc acctgtacat gcaacggaat tggtaataga atcaatcaac   6300
cacctgatca aggagtaaaa attataacac ataaagaatg tagtacaata ggtatcaacg   6360
gaatgctgtt caatacaaat aaagaaggaa ctcttgcatt ctatacacca aatgatataa   6420
cactaaacaa ttctgttgca cttgatccaa ttgacatatc aatcgagctc aacaaggcca   6480
aatcagatct agaagaatca aaagaatgga taagaaggtc aaatcaaaaa ctagattcta   6540
ttggaaattg gcatcaatct agcactacaa tcataattat tttgataatg atcattatat   6600 tgtttatat aatataacg ataattacaa ttgcaattaa gtattacaga attcaaaaga   6660
gaaatcgagt ggatcaaaat gacaagccat atgtactaac aaacaaataa catatctaca   6720
gatcattaga tattaaaatt ataaaaaact taggagtaaa gttacgcaat ccaactctac   6780
tcatataatt gaggaaggac ccaatagaca aatccaaatt cgagatggaa tactggaagc   6840
ataccaatca cggaaaggat gctggtaatg agctggagac gtctatggct actcatggca   6900
acaagctcac taataagata atatacatat tatggacaat aatcctggtg ttattatcaa   6960
tagtcttcat catagtgcta attaattcca tcaaaagtga aaaggccca gaatcattgc   7020 tgcaagacat aaataatgag tttatggaaa ttacagaaaa gatccaaatg gcatcggata   7080
ataccaatga tctaatacag tcaggagtga atacaaggct tcttacaatt cagagtcatg   7140
tccagaatta cataccaata tcattgacac aacagatgtc agatcttagg aaattcatta   7200
gtgaaattac aattagaaat gataatcaag aagtgctgcc acaaagaata acacatgatg   7260
taggtataaa acctttaaat ccagatgatt tttggagatg cacgtctggt cttccatctt   7320
taatgaaaac tccaaaaata aggttaatgc cagggccggg attattagct atgccaacga   7380
```

```
ctgttgatgg ctgtgttaga actccgtctt tagttataaa tgatctgatt tatgcttata   7440
cctcaaatct aattactcga ggttgtcagg atataggaaa atcatatcaa gtcttacaga   7500
tagggataat aactgtaaac tcagacttgg tacctgactt aaatcctagg atctctcata   7560
cctttaacat aaatgacaat aggaagtcat gttctctagc actcctaaat atagatgtat   7620
atcaactgtg ttcaactccc aaagttgatg aaagatcaga ttatgcatca tcaggcatag   7680
aagatattgt acttgatatt gtcaattatg atggttcaat ctcaacaaca agatttaaga   7740
ataataacat aagctttgat caaccatatg ctgcactata cccatctgtt ggaccaggga   7800
tatactacaa aggcaaaata atatttctcg ggtatggagg tcttgaacat ccaataaatg   7860
agaatgtaat ctgcaacaca actgggtgcc ccgggaaaac acagagagac tgtaatcaag   7920
catctcatag tacttggttt tcagatagga ggatggtcaa ctccatcatt gttgttgaca   7980
aaggcttaaa ctcaattcca aaattgaaag tatggacgat atctatgcga caaaattact   8040
gggggtcaga aggaaggtta cttctactag gtaacaagat ctatatatat acaagatcta   8100
caagttggca tagcaagtta caattaggaa taattgatat tactgattac agtgatataa   8160
ggataaaatg gacatggcat aatgtgctat caagaccagg aaacaatgaa tgtccatggg   8220
gacattcatg tccagatgga tgtataacag gagtatatac tgatgcatat ccactcaatc   8280
ccacagggag cattgtgtca tctgtcatat tagactcaca aaaatcgaga gtgaacccag   8340
tcataactta ctcaacagca accgaaagag taaacgagct ggccatccta aacagaacac   8400
tctcagctgg atatacaaca acaagctgca ttacacacta taacaaagga tattgttttc   8460
atatagtaga aataaatcat aaaagcttaa acacatttca acccatgttg ttcaaaacag   8520
agattccaaa aagctgcagt taatcataat taaccataat atgcatcaat ctatctataa   8580
tacaagtata tgataagtaa tcagcaatca gacaatagac aaaagggaaa tataaaaaac   8640
ttaggagcaa agcgtgctcg ggaaatggac actgaatcta acaatggcac tgtatctgac   8700
atactctatc ctgagtgtca ccttaactct cctatcgtta aaggtaaaat agcacaatta   8760
cacactatta tgagtctacc tcagccttat gatatggatg acgactcaat actagttatc   8820
actagacaga aaataaaact taataaattg gataaaagac aacgatctat tagaagatta   8880
aaattaatat taactgaaaa agtgaatgac ttaggaaaat acacatttat cagatatcca   8940
gaaatgtcaa agaaatgtt caaattatat atacctggta ttaacagtaa agtgactgaa   9000
ttattactta aagcagatag aacatatagt caaatgactg atggattaag agatctatgg   9060
attaatgtgc tatcaaaatt agcctcaaaa aatgatggaa gcaattatga tcttaatgaa   9120
gaaattaata atatatcgaa agttcacaca acctataaat cagataaatg gtataatcca   9180
ttcaaaacat ggtttactat caagtatgat atgagaagat tacaaaaagc tcgaaatgag   9240
atcactttta atgttgggaa ggattataac ttgttagaag accagaagaa tttcttattg   9300
atacatccag aattggtttt gatattagat aaacaaaact ataatggtta tctaattact   9360
cctgaattag tattgatgta ttgtgacgta gtcgaaggcc gatggaatat aagtgcatgt   9420
gctaagttag atccaaaatt acaatctatg tatcagaaag gtaataacct gtgggaagtg   9480
atagataaat tgtttccaat tatgggagaa aagacatttg atgtgatatc gttattagaa   9540
ccacttgcat tatccttaat tcaaactcat gatcctgtta acaactaag aggagctttt   9600 ttaaatcatg tgttatccga gatggaatta atatttgaat ctagagaatc gattaaggaa   9660
tttctgagtg tagattacat tgataaaatt ttagatatat ttaataagtc tacaatagat   9720
gaaatagcag agattttctc tttttttaga acatttgggc atcctccatt agaagctagt   9780
```

```
attgcagcag aaaaggttag aaaatatatg tatattggaa aacaattaaa atttgacact    9840
attaataaat gtcatgctat cttctgtaca ataataatta acggatatag agagaggcat    9900
ggtggacagt ggcctcctgt gacattacct gatcatgcac acgaattcat cataaatgct    9960
tacggttcaa actctgcgat atcatatgaa aatgctgttg attattacca gagctttata   10020
ggaataaaat tcaataaatt catagagcct cagttagatg aggatttgac aatttatatg   10080
aaagataaag cattatctcc aaaaaaatca aattgggaca cagtttatcc tgcatctaat   10140
ttactgtacc gtactaacgc atccaacgaa tcacgaagat tagttgaagt atttatagca   10200
gatagtaaat ttgatcctca tcagatattg gattatgtag aatctgggga ctggttagat   10260
gatccagaat ttaatatttc ttatagtctt aaagaaaaag agatcaaaca ggaaggtaga   10320
ctctttgcaa aaatgacata caaaatgaga gctacacaag ttttatcaga gaccctactt   10380
gcaaataaca taggaaaatt cttttcaagaa aatgggatgg tgaagggaga gattgaatta   10440
cttaagagat taacaaccat atcaatatca ggagttccac ggtataatga agtgtacaat   10500
aattctaaaa gccatacaga tgaccttaaa acctacaata aaataagtaa tcttaatttg   10560
tcttctaatc agaaatcaaa gaaatttgaa ttcaagtcaa cggatatcta caatgatgga   10620
tacgagactg tgagctgttt cctaacaaca gatctcaaaa aatactgtct taattggaga   10680
tatgaatcaa cagctctatt tggagaaact tgcaaccaaa tatttggatt aaataaattg   10740
tttaattggt tacaccctcg tcttgaagga agtacaatct atgtaggtga tccttactgt   10800
cctccatcag ataaagaaca tatatcatta gaggatcacc ctgattctgg tttttacgtt   10860
cataacccaa gagggggtat agaaggattt tgtcaaaaat tatggacact catatctata   10920
agtgcaatac atctagcagc tgttagaata ggcgtgaggg tgactgcaat ggttcaagga   10980
gacaatcaag ctatagctgt aaccacaaga gtacccaaca attatgacta cagagttaag   11040
aaggagatag tttataaaga tgtagtgaga tttttttgatt cattaagaga agtgatggat   11100
gatctaggtc atgaacttaa attaaatgaa acgattataa gtagcaagat gttcatatat   11160
agcaaaagaa tctattatga tgggagaatt cttcctcaag ctctaaaagc attatctaga   11220
tgtgtcttct ggtcagagac agtaatagac gaaacaagat cagcatcttc aaatttggca   11280
acatcatttg caaaagcaat tgagaatggt tattcacctg ttctaggata tgcatgctca   11340 attttttaaga atattcaaca actatatatt gcccttggga tgaatatcaa tccaactata   11400
acacagaata tcagagatca gtattttagg aatccaaatt ggatgcaata tgcctcttta   11460
atacctgcta gtgttggggg attcaattac atggccatgt caagatgttt tgtaaggaat   11520
attggtgatc catcagttgc cgcattggct gatattaaaa gatttattaa ggcgaatcta   11580
ttagaccgaa gtgttcttta taggattatg aatcaagaac caggtgagtc atcttttttg   11640
gactgggctt cagatccata ttcatgcaat ttaccacaat ctcaaaatat aaccaccatg   11700
ataaaaaata taacagcaag gaatgtatta caagattcac caaatccatt attatctgga   11760
ttattcacaa atacaatgat agaagaagat gaagaattag ctgagttcct gatggacagg   11820
aaggtaattc tccctagagt tgcacatgat attctagata attctctcac aggaattaga   11880
aatgccatag ctggaatgtt agatacgaca aaatcactaa ttcgggttgg cataaataga   11940
ggaggactga catatagttt gttgaggaaa atcagtaatt acgatctagt acaatatgaa   12000
acactaagta ggactttgcg actaattgta agtgataaaa tcaagtatga agatatgtgt   12060
tcggtagacc ttgccatagc attgcgacaa aagatgtgga ttcatttatc aggaggaagg   12120
atgataagtg gacttgaaac gcctgaccca ttagaattac tatctggggt agtaataaca   12180
```

```
ggatcagaac attgtaaaat atgttattct tcagatggca caaacccata tacttggatg   12240
tatttacccg gtaatatcaa aataggatca gcagaaacag gtatatcgtc attaagagtt   12300
ccttattttg gatcagtcac tgatgaaaga tctgaagcac aattaggata tatcaagaat   12360
cttagtaaac ctgcaaaagc cgcaataaga atagcaatga tatatacatg ggcatttggt   12420
aatgatgaga tatcttggat ggaagcctca cagatagcac aaacacgtgc aaattttaca   12480
ctagatagtc tcaaaatttt aacaccggta gctacatcaa caaatttatc acacagatta   12540
aaggatactg caactcagat gaaattctcc agtacatcat tgatcagagt cagcagattc   12600
ataacaatgt ccaatgataa catgtctatc aaagaagcta atgaaaccaa agatactaat   12660
cttatttatc aacaaataat gttaacagga ttaagtgttt tcgaatattt atttagatta   12720
aaagaaacca caggacacaa ccctatagtt atgcatctgc acatagaaga tgagtgttgt   12780
attaaagaaa gttttaatga tgaacatatt aatccagagt ctacattaga attaattcga   12840
tatcctgaaa gtaatgaatt tatttatgat aaagacccac tcaaagatgt ggacttatca   12900
aaacttatgg ttattaaaga ccattcttac acaattgata tgaattattg ggatgatact   12960
gacatcatac atgcaatttc aatatgtact gcaattacaa tagcagatac tatgtcacaa   13020
ttagatcgag ataatttaaa agagataata gttattgcaa atgatgatga tattaatagc   13080
ttaatcactg aattttttgac tcttgacata cttgtatttc tcaagacatt tggtggatta   13140
ttagtaaatc aatttgcata cactctttat agtctaaaaa tagaaggtag ggatctcatt   13200
tgggattata taatgagaac actgagagat acttcccatt caatattaaa agtattatct   13260
aatgcattat ctcatcctaa agtattcaag aggttctggg attgtggagt tttaaaccct   13320
atttatggtc ctaatactgc tagtcaagac cagataaaac ttgccctatc tatatgtgaa   13380
tattcactag atcatttat gagagaatgg ttgaatggtg tatcacttga aatatacatt   13440
tgtgacagcg atatggaagt tgcaaatgat aggaaacaag cctttattc tagacacctt   13500 tcatttgttt gttgtttagc agaaattgca tcttttcggac ctaacctgtt aaacttaaca   13560
tacttggaga gacttgatct attgaaacaa tatcttgaat aaatattaa agaagaccct   13620 actcttaaat atgtacaaat atctggatta ttaattaaat cgttcccatc aactgtaaca   13680
tacgtaagaa agactgcaat caaatatcta aggattcgcg gtattagtcc acctgaggta   13740
attgatgatt gggatccggt agaagatgaa aatatgctgg ataacattgt caaaactata   13800
aatgataact gtaataaaga taataaaggg aataaaatta caatttctg gggactagca   13860 cttaagaact atcaagtcct taaaatcaga tctataacaa gtgattctga tgataatgat   13920
agactagatg ctaatacaag tggtttgaca cttcctcaag gagggaatta tctatcgcat   13980
caattgagat tattcggaat caacagcact agttgtctga agctcttga gttatccacaa   14040 attttaatga aggaagtcaa taaagacaag gacaggctct tcctgggaga aggagcagga   14100
gctatgctag catgttatga tgccacatta ggacctgcag ttaattatta taattcaggt   14160
ttgaatataa cagatgtaat tggtcaacga gaattgaaaa tatttccttc agaggtatca   14220
ttagtaggta aaaaattagg aaatgtgaca cagattctta acagggtaaa agtactgttc   14280
aatgggaatc ctaattcaac atggataggga aatatggaat gtgagagctt aatatggagt   14340
gaattaaatg ataagtccat tggattagta cattgtgata tggaaggagc tatcggtaaa   14400
tcagaagaaa ctgttctaca tgaacattat agtgttataa gaattacata cttgattggg   14460
gatgatgatg ttgttttagt ttccaaaatt atacctacaa tcactccgaa ttggtctaga   14520
atactttatc tatataaatt atattggaaa gatgtaagta taatatcact caaaacttct   14580
```

-continued

```
aatcctgcat caacagaatt atatctaatt tcgaaagatg catattgtac tataatggaa    14640
cctagtgaaa ttgttttatc aaaacttaaa agattgtcac tcttggaaga aaataatcta    14700
ttaaaatgga tcattttatc aaagaagagg aataatgaat ggttacatca tgaaatcaaa    14760
gaaggagaaa gagattatgg aatcatgaga ccatatcata tggcactaca aatctttgga    14820
tttcaaatca atttaaatca tctggcgaaa gaattttat caaccccaga tctgactaat    14880
atcaacaata taatccaaag ttttcagcga acaataaagg atgttttatt tgaatggatt    14940
aatataactc atgatgataa gagacataaa ttaggcggaa gatataacat attcccactg    15000
aaaaataagg gaaagttaag actgctatcg agaagactag tattaagttg gatttcatta    15060
tcattatcga ctcgattact tacaggtcgc tttcctgatg aaaaatttga acatagagca    15120
cagactggat atgtatcatt agctgatact gatttagaat cattaaagtt attgtcgaaa    15180
aacatcatta agaattacag agagtgtata ggatcaatat catattggtt tctaaccaaa    15240
gaagttaaaa tacttatgaa attgatcggt ggtgctaaat tattaggaat tcccagacaa    15300
tataaagaac ccgaagacca gttattagaa aactacaatc aacatgatga atttgatatc    15360
gattaaaaca taaatacaat gaagatatat cctaacctt atctttaagc ctaggaatag    15420
acaaaaagta agaaaaacat gtaatatata tataccaaac agagttcttc tcttgtttgg    15480
tgggtcggca tggcatctcc acctcctcgc ggtccggacc tgggcatccg aaggaggacg    15540
cacgtccact cggatggcta agggagagcc tgcagtagca taaccccttg gggcctctaa    15600
acgggtcttg aggggttttt tgctgaaagg aggaactata tacgcgtcga cgggccccgc    15660
gctcac                                                              15666
```

```
<210> SEQ ID NO 74
<211> LENGTH: 45
<212> TYPE: DNA
<213> ORGANISM: Artificial Sequence
<220> FEATURE:
<223> OTHER INFORMATION: Synthetic primer.
<220> FEATURE:
<221> NAME/KEY: misc_feature
<222> LOCATION: (1)..(45)
<223> OTHER INFORMATION: Part of Parent Appln No 09/083,793 as SEQ ID
      NO: 18

<400> SEQUENCE: 74
ggcccgtcga cgcgtaatac gactcactat aggaccaaac aagag              45

<210> SEQ ID NO 75
<211> LENGTH: 16
<212> TYPE: DNA
<213> ORGANISM: Artificial Sequence
<220> FEATURE:
<223> OTHER INFORMATION: Synthetic primer.
<220> FEATURE:
<221> NAME/KEY: misc_feature
<222> LOCATION: (1)..(16)
<223> OTHER INFORMATION: Part of Parent Appln No 09/083,793 as SEQ ID
      NO: 19

<400> SEQUENCE: 75
cggcatcacg tgctac                                              16

<210> SEQ ID NO 76
<211> LENGTH: 28
<212> TYPE: DNA
<213> ORGANISM: Artificial Sequence
<220> FEATURE:
<223> OTHER INFORMATION: Synthetic primer.
```

```
-continued

<220> FEATURE:
<221> NAME/KEY: misc_feature
<222> LOCATION: (1)..(28)
<223> OTHER INFORMATION: Part of Parent Appln No 09/083,793 as SEQ ID
      NO: 16

<400> SEQUENCE: 76
ggatttgcgc gcaatttaaa tcatctgg                                          28

<210> SEQ ID NO 77
<211> LENGTH: 70
<212> TYPE: DNA
<213> ORGANISM: Artificial Sequence
<220> FEATURE:
<223> OTHER INFORMATION: Synthetic primer.
<220> FEATURE:
<221> NAME/KEY: misc_feature
<222> LOCATION: (1)..(70)
<223> OTHER INFORMATION: Part of Parent Appln No 09/083,793 as SEQ ID
      NO: 17

<400> SEQUENCE: 77
cccaggtcgg accgcgagga ggtggagatg ccatgccagc ccaccaaaac aagagaagaa      60
ctctgtttgg                                                              70

<210> SEQ ID NO 78
<211> LENGTH: 15
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(15)
<223> OTHER INFORMATION: Part of Parent Appln No 09/083,793 as SEQ ID
      NO: 23

<400> SEQUENCE: 78
gatcgatgct agccc                                                        15

<210> SEQ ID NO 79
<211> LENGTH: 15
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(15)
<223> OTHER INFORMATION: Part of Parent Appln No 09/083,793 as SEQ ID
      NO: 24

<400> SEQUENCE: 79
gatcgggcta gcatc                                                        15

<210> SEQ ID NO 80
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 25

<400> SEQUENCE: 80
ttacatggcc at                                                           12
```

```
<210> SEQ ID NO 81
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 26

<400> SEQUENCE: 81
tcacatggcg at                                                             12

<210> SEQ ID NO 82
<211> LENGTH: 12
<212> TYPE: DNA
<213> ORGANISM: Artificial Sequence
<220> FEATURE:
<223> OTHER INFORMATION: Chemically synthesized sequence.

<400> SEQUENCE: 82
ttttgattgg gc                                                             12

<210> SEQ ID NO 83
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 28

<400> SEQUENCE: 83
ttttgattgg gc                                                             12

<210> SEQ ID NO 84
<211> LENGTH: 14
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(14)
<223> OTHER INFORMATION: Part of Parent Appln No 09/083,793 as SEQ ID
      NO: 29

<400> SEQUENCE: 84
tggtcctaat actg                                                           14

<210> SEQ ID NO 85
<211> LENGTH: 14
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(14)
<223> OTHER INFORMATION: Part of Parent Appln No 09/083,793 as SEQ ID
      NO: 30

<400> SEQUENCE: 85
tgggcctaat atcg                                                           14
```

```
<210> SEQ ID NO 86
<211> LENGTH: 30
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(30)
<223> OTHER INFORMATION: Part of Parent Appln No 09/083,793 as SEQ ID
      NO: 32

<400> SEQUENCE: 86
cctgaattat aataattaac tgcaggtcct                                         30

<210> SEQ ID NO 87
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 46

<400> SEQUENCE: 87
ttgtctggga at                                                            12

<210> SEQ ID NO 88
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 47

<400> SEQUENCE: 88
ttgcctggga at                                                            12

<210> SEQ ID NO 89
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 48

<400> SEQUENCE: 89
ttgtttggga at                                                            12

<210> SEQ ID NO 90
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 49
```

```
<400> SEQUENCE: 90
ttgtctggta at                                                          12

<210> SEQ ID NO 91
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 50

<400> SEQUENCE: 91
aactttaaat ta                                                          12

<210> SEQ ID NO 92
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 51

<400> SEQUENCE: 92
aacttaaaat ta                                                          12

<210> SEQ ID NO 93
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 52

<400> SEQUENCE: 93
ttaaagacat tg                                                          12

<210> SEQ ID NO 94
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 53

<400> SEQUENCE: 94
tttaagacat tg                                                          12

<210> SEQ ID NO 95
<211> LENGTH: 12
<212> TYPE: DNA
<213> ORGANISM: Artificial Sequence
<220> FEATURE:
<223> OTHER INFORMATION: Chemically synthesized sequence.
```

```
<220> FEATURE:
<221> NAME/KEY: misc_feature
<222> LOCATION: (1)..(12)
<223> OTHER INFORMATION: Part of Parent Appln No 09/083,793 as SEQ ID
      NO: 54

<400> SEQUENCE: 95
gcagatgtca ag                                                            12

<210> SEQ ID NO 96
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 55

<400> SEQUENCE: 96
gcagatgcca ag                                                            12

<210> SEQ ID NO 97
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 56

<400> SEQUENCE: 97
cgaatctaaa ga                                                            12

<210> SEQ ID NO 98
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 57

<400> SEQUENCE: 98
cgaagctaaa ga                                                            12

<210> SEQ ID NO 99
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 58

<400> SEQUENCE: 99
gaaatattga tc                                                            12
```

```
<210> SEQ ID NO 100
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 59

<400> SEQUENCE: 100
gaaacattga tc                                                          12

<210> SEQ ID NO 101
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 60

<400> SEQUENCE: 101
tctctaccca ac                                                          12

<210> SEQ ID NO 102
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 61

<400> SEQUENCE: 102
tcgttaacca ac                                                          12

<210> SEQ ID NO 103
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 62

<400> SEQUENCE: 103
agtacaatag gt                                                          12

<210> SEQ ID NO 104
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 63
```

-continued

```
<400> SEQUENCE: 104
agtactgtgg gt                                                        12

<210> SEQ ID NO 105
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 64

<400> SEQUENCE: 105
gcacttgatc ca                                                        12

<210> SEQ ID NO 106
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 65

<400> SEQUENCE: 106
acactggatc ca                                                        12

<210> SEQ ID NO 107
<211> LENGTH: 19
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(19)
<223> OTHER INFORMATION: Part of Parent Appln No 09/083,793 as SEQ ID
      NO: 66

<400> SEQUENCE: 107
ccatcattgt tgttgacaa                                                 19

<210> SEQ ID NO 108
<211> LENGTH: 19
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(19)
<223> OTHER INFORMATION: Part of Parent Appln No 09/083,793 as SEQ ID
      NO: 67

<400> SEQUENCE: 108
ccatcattgt ggctgacaa                                                 19

<210> SEQ ID NO 109
<211> LENGTH: 11
<212> TYPE: DNA
<213> ORGANISM: Artificial Sequence
<220> FEATURE:
<223> OTHER INFORMATION: Chemically synthesized sequence.
```

```
<220> FEATURE:
<221> NAME/KEY: misc_feature
<222> LOCATION: (1)..(11)
<223> OTHER INFORMATION: Part of Parent Appln No 09/083,793 as SEQ ID
      NO: 68

<400> SEQUENCE: 109
ttacatggcc a                                                              11

<210> SEQ ID NO 110
<211> LENGTH: 11
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(11)
<223> OTHER INFORMATION: Part of Parent Appln No 09/083,793 as SEQ ID
      NO: 69

<400> SEQUENCE: 110
tcacatggcg a                                                              11

<210> SEQ ID NO 111
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 27; Part of Parent Appln No 09/083,793 as SEQ ID NO: 70

<400> SEQUENCE: 111
tttggactgg gc                                                             12

<210> SEQ ID NO 112
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 71

<400> SEQUENCE: 112
ttttgattgg gc                                                             12

<210> SEQ ID NO 113
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 72

<400> SEQUENCE: 113
ggtcctaata ct                                                             12
```

```
<210> SEQ ID NO 114
<211> LENGTH: 12
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(12)
<223> OTHER INFORMATION: Part of Parent Appln No 09/083,793 as SEQ ID
      NO: 73

<400> SEQUENCE: 114
gggcctaata tc                                                          12

<210> SEQ ID NO 115
<211> LENGTH: 26
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(26)
<223> OTHER INFORMATION: Part of Parent Appln No 09/083,793 as SEQ ID
      NO: 33

<400> SEQUENCE: 115
gggaaagaat ccagagacaa gaacgg                                           26

<210> SEQ ID NO 116
<211> LENGTH: 26
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(26)
<223> OTHER INFORMATION: Part of Parent Appln No 09/083,793 as SEQ ID
      NO: 34

<400> SEQUENCE: 116
ggtgaagttg tggatccatt tgattg                                           26

<210> SEQ ID NO 117
<211> LENGTH: 24
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(24)
<223> OTHER INFORMATION: Part of Parent Appln No 09/083,793 as SEQ ID
      NO: 35

<400> SEQUENCE: 117
caacctgtaa ggtaccagca tccg                                             24

<210> SEQ ID NO 118
<211> LENGTH: 27
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(27)
<223> OTHER INFORMATION: Part of Parent Appln No 09/083,793 as SEQ ID
      NO: 36
```

```
<400> SEQUENCE: 118
gatatggtgt taggccttga tctgttc                                        27

<210> SEQ ID NO 119
<211> LENGTH: 29
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(29)
<223> OTHER INFORMATION: Part of Parent Appln No 09/083,793 as SEQ ID
      NO: 37

<400> SEQUENCE: 119
cgccatggaa aaatcagaga tcctcttct                                      29

<210> SEQ ID NO 120
<211> LENGTH: 31
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(31)
<223> OTHER INFORMATION: Part of Parent Appln No 09/083,793 as SEQ ID
      NO: 38

<400> SEQUENCE: 120
ctggatccta attggagttg ttacccatgt a                                   31

<210> SEQ ID NO 121
<211> LENGTH: 23
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(23)
<223> OTHER INFORMATION: Part of Parent Appln No 09/083,793 as SEQ ID
      NO: 39

<400> SEQUENCE: 121
aaccatggct gaaaaaggga aaa                                            23

<210> SEQ ID NO 122
<211> LENGTH: 33
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(33)
<223> OTHER INFORMATION: Part of Parent Appln No 09/083,793 as SEQ ID
      NO: 40

<400> SEQUENCE: 122
ggtgaagctt aagatgtgat tttacatatt tta                                 33

<210> SEQ ID NO 123
<211> LENGTH: 35
<212> TYPE: DNA
<213> ORGANISM: Artificial Sequence
<220> FEATURE:
<223> OTHER INFORMATION: Chemically synthesized sequence.
```

-continued

```
<220> FEATURE:
<221> NAME/KEY: misc_feature
<222> LOCATION: (1)..(35)
<223> OTHER INFORMATION: Part of Parent Appln No 09/083,793 as SEQ ID
      NO: 41

<400> SEQUENCE: 123
aaataggatc cctacagatc attagatatt aaaat                                    35

<210> SEQ ID NO 124
<211> LENGTH: 24
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(24)
<223> OTHER INFORMATION: Part of Parent Appln No 09/083,793 as SEQ ID
      NO: 42

<400> SEQUENCE: 124
cgccatggtg ttcagtgctt gttg                                                24

<210> SEQ ID NO 125
<211> LENGTH: 31
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(31)
<223> OTHER INFORMATION: Part of Parent Appln No 09/083,793 as SEQ ID
      NO: 43

<400> SEQUENCE: 125
ccacaagctt aattaaccat aatatgcatc a                                        31

<210> SEQ ID NO 126
<211> LENGTH: 29
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(29)
<223> OTHER INFORMATION: Part of Parent Appln No 09/083,793 as SEQ ID
      NO: 44

<400> SEQUENCE: 126
ttccatggat ttggatttgt ctattgggt                                           29

<210> SEQ ID NO 127
<211> LENGTH: 83
<212> TYPE: DNA
<213> ORGANISM: Artificial Sequence
<220> FEATURE:
<223> OTHER INFORMATION: Forward primer for PCR of measles HA gene
      insert for N-P and P-M junctions.
<220> FEATURE:
<221> NAME/KEY: misc_feature
<222> LOCATION: (1)..( -continued
<210> SEQ ID NO 128
<211> LENGTH: 67
<212> TYPE: DNA
<213> ORGANISM: Artificial Sequence
<220> FEATURE:
<223> OTHER INFORMATION: Reverse primer for PCR of measles HA gene
      insert for N-P and P-M junctions.
<220> FEATURE:
<221> NAME/KEY: misc_feature
<222> LOCATION: (1)..(67)
<223> OTHER INFORMATION: Part of Parent Appln No 09/733,692 as SEQ ID NO: 14; Part of Parent Appln No 09/458,813 as SEQ ID NO: 11; Part of Parent Appln No 09/459,062 as SEQ ID NO: 06

<400> SEQUENCE: 128
attattgctt aaggtttgtt cggtgtcgtt tctttgttgg atcctatctg cgattggttc 60
catcttc 67

<210> SEQ ID NO 129
<211> LENGTH: 55
<212> TYPE: DNA
<213> ORGANISM: Artificial Sequence
<220> FEATURE:
<223> OTHER INFORMATION: Forward primer for PCR of measles HA gene insert for HN-L junction.
<220> FEATURE:
<221> NAME/KEY: misc_feature
<222> LOCATION: (1)..(55)
<223> OTHER INFORMATION: Part of Parent Appln No 09/733,692 as SEQ ID NO: 15; Part of Parent Appln No 09/458,813 as SEQ ID NO: 14; Part of Parent Appln No 09/459,062 as SEQ ID NO: 07

<400> SEQUENCE: 129
gacaataggc ctaaaaggga aatataaaaa acttaggagt aaagttacgc aatcc 55

<210> SEQ ID NO 130
<211> LENGTH: 68
<212> TYPE: DNA
<213> ORGANISM: Artificial Sequence
<220> FEATURE:
<223> OTHER INFORMATION: Reverse/Forward primer for PCR of measles HA gene insert for HN-L junction.
<220> FEATURE:
<221> NAME/KEY: misc_feature
<222> LOCATION: (1)..(68)
<223> OTHER INFORMATION: Part of Parent Appln No 09/733,692 as SEQ ID NO: 16; Part of Parent Appln No 09/458,813 as SEQ ID NO: 15 and 16; Part of Parent Appln No 09/459,062 as SEQ ID NO: 08

<400> SEQUENCE: 130
gtagaacgcg tttatccggt ctcgttgtgg tgacatctcg aatttggatt tgtctattgg 60
gtccttcc 68

<210> SEQ ID NO 131
<211> LENGTH: 28
<212> TYPE: DNA
<213> ORGANISM: Artificial Sequence
<220> FEATURE:
<223> OTHER INFORMATION: Reverse primer for PCR of measles HA gene insert for HN-L junction
<220> FEATURE:
<221> NAME/KEY: misc_feature
<222> LOCATION: (1)..(28)
<223> OTHER INFORMATION: Part of Parent Appln No 09/733,692 as SEQ ID NO: 17; Part of Parent Appln No 09/458,813 as SEQ ID NO: 17; Part of Parent Appln No 09/459,062 as SEQ ID NO: 10

<400> SEQUENCE: 131
ccatgtaatt gaatccccca acactagc 28

```
<210> SEQ ID NO 132
<211> LENGTH: 28
<212> TYPE: DNA
<213> ORGANISM: Artificial Sequence
<220> FEATURE:
<223> OTHER INFORMATION: Forward/Reverse primer for PCR of measles HA
      gene insert for HN-L junction.
<220> FEATURE:
<221> NAME/KEY: misc_feature
<222> LOCATION: (1)..(28)
<223> OTHER INFORMATION:

```
<220> FEATURE:
<223> OTHER INFORMATION: Chemically synthesized downstream HPIV2 HN
      primer
<220> FEATURE:
<221> NAME/KEY: misc_feature
<222> LOCATION: (1)..(30)
<223> OTHER INFORMATION: Part of Parent Appln No 09/733,692 as SEQ ID
      NO: 22; Part of Parent Appln No 09/458,813 as SEQ ID NO: 23;
      Part of Parent Appln No 09/459,062 as SEQ ID NO: 16

<400> SEQUENCE: 136
cccgggtcct gatttcccga gcacgctttg                                        30

<210> SEQ ID NO 137
<211> LENGTH: 26
<212> TYPE: DNA
<213> ORGANISM: Artificial Sequence
<220> FEATURE:
<223> OTHER INFORMATION: Chemically synthesized HPIV1 HN primer.
<220> FEATURE:
<221> NAME/KEY: misc_feature
<222> LOCATION: (1)..(26)
<223> OTHER INFORMATION: Part of Parent Appln No 09/733,692 as SEQ ID
      NO: 23; Part of Parent Appln No 09/458,813 as SEQ ID NO: 24;
      Part of Parent Appln No 09/459,062 as SEQ ID NO: 17

<400> SEQUENCE: 137
agtggctaat tgcattgcat ccacat                                            26

<210> SEQ ID NO 138
<211> LENGTH: 24
<212> TYPE: DNA
<213> ORGANISM: Artificial Sequence
<220> FEATURE:
<223> OTHER INFORMATION: Chemically synthesized HPIV1 HN primer.
<220> FEATURE:
<221> NAME/KEY: misc_feature
<222> LOCATION: (1)..(24)
<223> OTHER INFORMATION: Part of Parent Appln No 09/733,692 as SEQ ID
      NO: 24; Part of Parent Appln No 09/458,813 as SEQ ID NO: 25;
      Part of Parent Appln No 09/459,062 as SEQ ID NO: 18

<400> SEQUENCE: 138
gccgtctgca tggtgaatag caat                                              24

<210> SEQ ID NO 139
<211> LENGTH: 13
<212> TYPE: DNA
<213> ORGANISM: Artificial Sequence
<220> FEATURE:
<223> OTHER INFORMATION: Chemically synthesized oligomer insert for
      rule-of-six conformity.
<220> FEATURE:
<221> NAME/KEY: misc_feature
<222> LOCATION: (1)..(13)
<223> OTHER INFORMATION: Part of Parent Appln No 09/733,692 as SEQ ID
      NO: 25; Part of Parent Appln No 09/458,813 as SEQ ID NO: 26

<400> SEQUENCE: 139
cgcggcaggc ctg                                                          13

<210> SEQ ID NO 140
<211> LENGTH: 14
<212> TYPE: DNA
<213> ORGANISM: Artificial Sequence
<220> FEATURE:
<223> OTHER INFORMATION: Chemically synthesized oligomer insert for
      rule-of-six conformity
```

```
<220> FEATURE:
<221> NAME/KEY: misc_feature
<222> LOCATION: (1)..(14)
<223> OTHER INFORMATION: Part of Parent Appln No 09/733,692 as SEQ ID
      NO: 26; Part of Parent Appln No 09/458,813 as SEQ ID NO: 27

<400> SEQUENCE: 140
cgcggcgagg cctg                                                         14

<210> SEQ ID NO 141
<211> LENGTH: 15
<212> TYPE: DNA
<213> ORGANISM: Artificial Sequence
<220> FEATURE:
<223> OTHER INFORMATION: Chemically synthesized oligomer insert for
      rule-of-six conformity
<220> FEATURE:
<221> NAME/KEY: misc_feature
<222> LOCATION: (1)..(15)
<223> OTHER INFORMATION: Part of Parent Appln No 09/733,692 as SEQ ID
      NO: 27; Part of Parent Appln No 09/458,813 as SEQ ID NO: 28

<400> SEQUENCE: 141
cgcgaggcct ccgcg                                                        15

<210> SEQ ID NO 142
<211> LENGTH: 16
<212> TYPE: DNA
<213> ORGANISM: Artificial Sequence
<220> FEATURE:
<223> OTHER INFORMATION: Chemically synthesized oligomer insert for
      rule-of-six conformity
<220> FEATURE:
<221> NAME/KEY: misc_feature
<222> LOCATION: (1)..(16)
<223> OTHER INFORMATION: Part of Parent Appln No 09/733,692 as SEQ ID
      NO: 28; Part of Parent Appln No 09/458,813 as SEQ ID NO: 29

<400> SEQUENCE: 142
cgcgccgcgg aggcct                                                       16

<210> SEQ ID NO 143
<211> LENGTH: 17
<212> TYPE: DNA
<213> ORGANISM: Artificial Sequence
<220> FEATURE:
<223> OTHER INFORMATION: Chemically synthesized oligomer insert for
      rule-of-six conformity
<220> FEATURE:
<221> NAME/KEY: misc_feature
<222> LOCATION: (1)..(17)
<223> OTHER INFORMATION: Part of Parent Appln No 09/733,692 as SEQ ID
      NO: 29; Part of Parent Appln No 09/458,813 as SEQ ID NO: 30

<400> SEQUENCE: 143
cgcgcccgcg gaggcct                                                      17

<210> SEQ ID NO 144
<211> LENGTH: 42
<212> TYPE: DNA
<213> ORGANISM: Artificial Sequence
<220> FEATURE:
<223> OTHER INFORMATION: Forward primer for RSV A G gene insert.
      Chemically synthesized sequence.

-continued

```
<400> SEQUENCE: 144
aattcgctta gcgatgtcca aaaacaagga ccaacgcacc gc                              42

<210> SEQ ID NO 145
<211> LENGTH: 92
<212> TYPE: DNA
<213> ORGANISM: Artificial Sequence
<220> FEATURE:
<223> OTHER INFORMATION: Reverse primer for RSV A G gene insert.
      Chemically synthesized sequence.
<220> FEATURE:
<221> NAME/KEY: misc_feature
<222> LOCATION: (1)..(92)
<223> OTHER INFORMATION: Part of Parent Appln No 09/733,692 as SEQ ID
      NO: 31

<400> SEQUENCE: 145
aaaaagctaa gcgctagcct ttaatcctaa gttttttctta cttttttttac tactggcgtg         60 gtgtgttggg tggagatgaa ggttgtgatg gg                                         92

<210> SEQ ID NO 146
<211> LENGTH: 65
<212> TYPE: DNA
<213> ORGANISM: Artificial Sequence
<220> FEATURE:
<223> OTHER INFORMATION: Forward primer for RSV A F gene insert.
      Chemically synthesized sequence.
<220> FEATURE:
<221> NAME/KEY: misc_feature
<222> LOCATION: (1)..(65)
<223> OTHER INFORMATION: Part of Parent Appln No 09/733,692 as SEQ ID
      NO: 32

<400> SEQUENCE: 146
aaaggcctgc ttagcaaaaa gctagcacaa tggagttgct aatcctcaaa gcaaatgcaa          60
ttacc                                                                       65

<210> SEQ ID NO 147
<211> LENGTH: 89
<212> TYPE: DNA
<213> ORGANISM: Artificial Sequence
<220> FEATURE:
<223> OTHER INFORMATION: Reverse primer for RSV A G gene insert.
      Chemically synthesized sequence.
<220> FEATURE:
<221> NAME/KEY: misc_feature
<222> LOCATION: (1)..(89)
<223> OTHER INFORMATION: Part of Parent Appln No 09/733,692 as SEQ ID
      NO: 33

<400> SEQUENCE: 147
aaaagctaag cgctagcttc tttaatccta agttttttctt acttttatta gttactaaat         60
gcaatattat ttataccact cagttgatc                                             89

<210> SEQ ID NO 148
<211> LENGTH: 44
<212> TYPE: DNA
<213> ORGANISM: Artificial Sequence
<220> FEATURE:
<223> OTHER INFORMATION: Mutagenicforward primer for modification of
      rHPIV3-1 cDNA. Chemically synthesized sequence.
<220> FEATURE:
<221> NAME/KEY: misc_feature
<222> LOCATION: (1)..(44)
<223> OTHER INFORMATION: Part of Parent Appln No 09/733,692 as SEQ ID
      NO: 34
```

<400> SEQUENCE: 148
cggccgtgac gcgtctccgc accggtgtat taagccgaag caaa                           44

<210> SEQ ID NO 149
<211> LENGTH: 59
<212> TYPE: DNA
<213> ORGANISM: Artificial Sequence
<220> FEATURE:
<223> OTHER INFORMATION: Mutagenicreverse primer for modification of
      rHPIV3-1 cDNA. Chemically synthesized sequence.
<220> FEATURE:
<221> NAME/KEY: misc_feature
<222> LOCATION: (1)..(59)
<223> OTHER INFORMATION: Part of Parent Appln No 09/733,692 as SEQ ID
      NO: 35

<400> SEQUENCE: 149
cccgagcacg ctttgctcct aagttttta tatttcccgt acgtctattg tctgattgc           59

<210> SEQ ID NO 150
<211> LENGTH: 95
<212> TYPE: DNA
<213> ORGANISM: Artificial Sequence
<220> FEATURE:
<223> OTHER INFORMATION: Forward primer for insertion of HPIV2 F ORF
      into rB/HPIV3 genome. Chemically synthesized sequence.
<220> FEATURE:
<221> NAME/KEY: misc_feature
<222> LOCATION: (1)..(95)
<223> OTHER INFORMATION: Part of Parent Appln No 09/733,692 as SEQ ID
      NO: 36

<400> SEQUENCE: 150
aaaatatagc ggccgcaagt aagaaaaact taggattaaa ggcggatgga tcacctgcat          60
ccaatgatag tatgcatttt tgttatgtac actgg                                    95

<210> SEQ ID NO 151
<211> LENGTH: 72
<212> TYPE: DNA
<213> ORGANISM: Artificial Sequence
<220> FEATURE:
<223> OTHER INFORMATION: Reverse primer for insertion of HPIV2 F ORF
      into rB/HPIV3 genome. Chemically synthesized sequence.
<220> FEATURE:
<221> NAME/KEY: misc_feature
<222> LOCATION: (1)..(72)
<223> OTHER INFORMATION: Part of Parent Appln No 09/733,692 as SEQ ID
      NO: 37

<400> SEQUENCE: 151
aaaatatagc ggccgctttt actaagatat cccatatatg tttccatgat tgttcttgga         60
aaagacggca gg                                                             72

<210> SEQ ID NO 152
<211> LENGTH: 81
<212> TYPE: DNA
<213> ORGANISM: Artificial Sequence
<220> FEATURE:
<223> OTHER INFORMATION: Chemically synthesized forward primer for
      insertion of HPIV2 HN ORF into rB/HPIV3 genome.
<220> FEATURE:
<221> NAME/KEY: misc_feature
<222> LOCATION: (1)..(81)
<223> OTHER INFORMATION: Part of Parent Appln No 09/733,692 as SEQ ID
      NO: 38

-continued

```
<400> SEQUENCE: 152
ggaaaggcgc gccaaagtaa gaaaaactta ggattaaagg cggatggaag attacagcaa      60
tctatctctt aaatcaattc c                                                81

<210> SEQ ID NO 153
<211> LENGTH: 54
<212> TYPE: DNA
<213> ORGANISM: Artificial Sequence
<220> FEATURE:
<223> OTHER INFORMATION: Chemically synthesized reverse primer for
      insertion of HPIV2 HN ORF into rB/HPIV3 genome.
<220> FEATURE:
<221> NAME/KEY: misc_feature
<222> LOCATION: (

```
gacaagcagt agcacgtgat gccgaagctc aaatgagctc aacactggaa gatgaacttg    1260
gagtgacaca cgaatctaaa gaaagcttga agagacatat aaggaacata aacagttcag    1320
agacatcttt ccacaaaccg acaggtggat cagccataga gatggcaata gatgaagagc    1380
cagaacaatt cgaacataga gcagatcaag aacaaaatgg agaacctcaa tcatccataa    1440
ttcaatatgc ctgggcagaa ggaaatagaa gcgatgatca gactgagcaa gctacagaat    1500
ctgacaatat caagaccgaa caacaaaaca tcagagacag actaaacaag agactcaacg    1560
acaagaagaa acaaagcagt caaccaccca ctaatcccac aaacagaaca accaggacg     1620 aaatagatga tctgtttaac gcatttggaa gcaactaatc gaatcaacat tttaatctaa    1680
atcaataata aataagaaaa acttaggatt aaagaatcct atcataccgg aatataggt     1740 ggtaaattta gagtctgctt gaaactcaat caatagagag ttgatggaaa gcgatgctaa    1800
aaactatcaa atcatggatt cttgggaaga ggaatcaaga gataaatcaa ctaatatctc    1860
ctcggccctc aacatcattg aattcatact cagcaccgac ccccaagaag acttatcgga    1920
aaacgacaca atcaacacaa gaacccagca actcagtgcc accatctgtc aaccagaaat    1980
caaaccaaca gaaacaagtg agaaagatag tggatcaact gacaaaaata gacagtccgg    2040
gtcatcacac gaatgtacaa cagaagcaaa agatagaaat attgatcagg aaactgtaca    2100
gagaggacct gggagaagaa gcagctcaga tagtagagct gagactgtgg tctctggagg    2160
aatccccaga agcatcacag attctaaaaa tggaacccaa aacacggagg atattgatct    2220
caatgaaatt agaagatgg ataaggactc tattgagggg aaaatgcgac aatctgcaaa     2280
tgttccaagc gagatatcag gaagtgatga catatttaca acagaacaaa gtagaaacag    2340
tgatcatgga agaagcctgg aatctatcag tacacctgat acaagatcaa taagtgttgt    2400
tactgctgca acaccagatg atgaagaaga aatactaatg aaaaatagta ggacaaagaa    2460
aagttcttca acacatcaag aagatgacaa agaattaaa aaaggggaa aagggaaaga     2520 ctggtttaag aaatcaaaag ataccgacaa ccagatacca acatcagact acagatccac    2580
atcaaagggg cagaagaaaa tctcaaagac aacaaccacc aacaccgaca caaaggggca    2640
aacagaaata cagacagaat catcagaaac acaatcctca tcatggaatc tcatcatcga    2700
caacaacacc gaccggaacg aacagacaag cacaactcct ccaacaacaa cttccagatc    2760
aacttataca aaagaatcga tccgaacaaa ctctgaatcc aaacccaaga cacaaaagac    2820
aaatggaaag gaaaggaagg atacagaaga gagcaatcga tttacagaga gggcaattac    2880
tctattgcag aatcttggtg taattcaatc cacatcaaaa ctagatttat atcaagacaa    2940
acgagttgta tgtgtagcaa atgtactaaa caatgtagat actgcatcaa agatagattt    3000
cctggcagga ttagtcatag gggtttcaat ggacaacgac acaaaattaa cacagataca    3060
aaatgaaatg ctaaacctca agcagatct aaagaaaatg gacgaatcac atagaagatt     3120
gatagaaaat caaagagaac aactgtcatt gatcacgtca ctaatttcaa atctcaaaat    3180
tatgactgag agaggaggaa agaaagacca aaatgaatcc aatgagagag tatccatgat    3240
caaaacaaaa ttgaaagaag aaaagatcaa gaagaccagg tttgacccac ttatggaggc    3300
acaaggcatt gacaagaata taccgatct atatcgacat gcaggagata cactagaaaa     3360
cgatgtacaa gttaaatcag agatattaag ttcatacaat gagtcaaatg caacaagact    3420
aatacccaaa aaagtgagca gtacaatgag atcactagtt gcagtcatca acaacagcaa    3480
tctctcacaa agcacaaaac aatcatacat aaacgaactc aaacgttgca aaaatgatga    3540
agaagtatct gaattaatgg acatgttcaa tgaagatgtc aacaattgcc aatgatccaa    3600
```

```
caaagaaacg acaccgaaca aacagacaag aaacaacagt agatcaaaac ctgtcaacac    3660
acacaaaatc aagcagaatg aaacaacaga tatcaatcaa tatacaaata agaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac    3900
acggatcccg gtatttagat gtcttcttac tcggcttctt cgagatggaa cgaatcaaag    3960
acaaatacgg gagtgtgaat gatctcgaca gtgacccgag ttacaaagtt tgtggctctg    4020
gatcattacc aatcggattg gctaagtaca ctgggaatga ccaggaattg ttacaagccg    4080
caaccaaact ggatatagaa gtgagaagaa cagtcaaagc gaaagagatg gttgtttaca    4140
cggtacaaaa tataaaacca gaactgtacc catggtccaa tagactaaga aaaggaatgc    4200
tgttcgatgc caacaaagtt gctcttgctc ctcaatgtct tccactagat aggagcataa    4260
aatttagagt aatcttcgtg aattgtacgg caattggatc aataaccttg ttcaaaattc    4320
ctaagtcaat ggcatcacta tctctaccca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa aagaaaagta ggcagaatgt    4500
actctgttga atactgtaaa cagaaaatcg agaaaatgag attgatattt tctttaggac    4560
tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740
ctttacctgg cgagttcaga tactatccta atattattgc aaaaggagtt gggaaaatca    4800
aacaatggaa ctagtaatct ctattttagt ccggacgtat ctattaagcc gaagcaaata    4860
aaggataatc aaaaacttag gacaaaagag gtcaatacca acaactatta gcagtcacac    4920
tcgcaagaat aagagagaag ggaccaaaaa agtcaaatag gagaaatcaa aacaaaaggt    4980
acagaacacc agaacaacaa aatcaaaaca tccaactcac tcaaaacaaa aattccaaaa    5040
gagaccggca acacaacaag cactgaacac catggatcac ctgcatccaa tgatagtatg    5100 cattttgtt atgtacactg gaattgtagg ttcagatgcc attgctggag atcaactcct    5160
caatgtaggg gtcattcaat caaagataag atcactcatg tactcactg atggtggcgc    5220 tagctttatt gttgtaaaat tactacccaa tcttccccca agcaatggaa catgcaacat    5280
caccagtcta gatgcatata atgttaccct atttaagttg ctaacacccc tgattgagaa    5340
cctgagcaaa atttctgctg ttacagatac caaaccccgc cgagaacgat tgcaggagt    5400 cgttattggg cttgctgcac taggagtagc tacagctgca caaataaccg cagctgtagc    5460
aatagtaaaa gccaatgcaa atgctgctgc gataaacaat cttgcatctt caattcaatc    5520
caccaacaag gcagtatccg atgtgataac tgcatcaaga acaattgcaa ccgcagttca    5580
agcgattcag gatcacatca atggagccat tgtcaacggg ataacatctg catcatgccg    5640
tgcccatgat gcactaattg ggtcaatatt aaatttgtat ctcactgagc ttactacaat    5700
atttcataat caaataacaa accctgcgct gacaccactt tccatccaag ctttaagaat    5760
cctcctcggt agcaccttgc caattgtcat tgaatccaaa ctcaacacaa aactcaacac    5820
agcagagctg ctcagtagcg gactgttaac tggtcaaata atttccattt ccccaatgta    5880
catgcaaatg ctaattcaaa tcaatgttcc gacatttata atgcaacccg gtgcgaaggt    5940
aattgatcta attgctatct ctgcaaacca taaattacaa gaagtagttg tacaagttcc    6000
```

-continued

```
taatagaatt ctagaatatg caaatgaact acaaaactac ccagccaatg attgtttcgt    6060
gacaccaaac tctgtatttt gtagatacaa tgagggttcc ccgatccctg aatcacaata    6120
tcaatgctta aggggggaatc ttaattcttg cacttttacc cctattatcg ggaactttct   6180
caagcgattc gcatttgcca atggtgtgct ctatgccaac tgcaaatctt tgctatgtaa    6240
gtgtgccgac cctccccatg ttgtgtctca agatgacaac caaggcatca gcataattga    6300
tattaagagg tgctctgaga tgatgcttga cacttttca tttaggatca catctacatt     6360
caatgctaca tacgtgacag acttctcaat gattaatgca atattgtac atctaagtcc     6420
tctagacttg tcaaatcaaa tcaattcaat aaacaaatct cttaaaagtg ctgaggattg    6480
gattgcagat agcaacttct tcgctaatca agccagaaca gccaagacac tttattcact    6540
aagtgcaatc gcattaatac tatcagtgat tactttggtt ttgtgggat tgctgattgc     6600
ctacatcatc aagctggttt ctcaaatcca tcaattcaga gcactagctg ctacaacaat    6660
gttccacagg gagaatcctg ccgtcttttc caagaacaat catggaaaca tatatgggat    6720
atcttaggat ccctacagat cattagatat taaaattata aaaaacttag gagtaaagtt    6780
acgcaatcca actctactca tataattgag gaaggaccca atagacaaat ccaaatccat    6840
ggaagattac agcaatctat ctcttaaatc aattcctaaa aggacatgta gaatcatttt    6900
ccgaactgcc acaattcttg gcatatgcac attaattgtg ctatgttcaa gtattcttca    6960
tgagataatt catcttgatg tttcctctgg tcttatgaat tctgatgagt cacagcaagg    7020
cattattcag cctatcatag aatcattaaa atcattgatt gctttggcca accagattct    7080
atataatgtt gcaatagtaa ttcctcttaa aattgacagt atcgaaactg taatactctc    7140
tgctttaaaa gatatgcaca ccgggagtat gtccaatgcc aactgcacgc caggaaatct    7200
gcttctgcat gatgcagcat acatcaatgg aataaacaaa ttccttgtac ttgaatcata    7260
caatgggacg cctaaaatg gacctctcct aaatataccc agctttatcc cctcagcaac     7320
atctccccat gggtgtacta gaataccatc attttcactc atcaagaccc attggtgtta    7380
cactcacaat gtaatgcttg gagattgtct tgatttcacg gcatctaacc agtatttatc    7440
aatgggata atacaacaat ctgctgcagg gttttccaatt ttcaggacta tgaaaaccat    7500
ttacctaagt gatggaatca atcgcaaaag ctgttcagtc actgctatac caggaggttg    7560
tgtcttgtat tgctatgtag ctacaaggtc tgaaaagaa gattatgcca cgactgatct      7620
agctgaactg agacttgctt tctattatta taatgatacc tttattgaaa gagtcatatc    7680
tcttccaaat acaacagggc agtgggccac aatcaaccct gcagtcggaa gcggatcta    7740
tcatctaggc tttatcttat ttcctgtata tggtggtctc ataaatggga ctacttctta    7800
caatgagcag tcctcacgct attttatccc aaaacatccc aacataactt gtgccggtaa    7860
ctccagcaaa caggctgcaa tagcacggag ttcctatgtc atccgttatc actcaaacag    7920
gttaattcag agtgctgttc ttatttgtcc attgtctgac atgcatacag aagagtgtaa    7980
tctagttatg tttaacaatt cccaagtcat gatgggtgca gaaggtaggc tctatgttat    8040
tggtaataat ttgtattatt atcaacgcag ttcctcttgg tggtctgcat cgctctttta    8100
caggatcaat acagattttt ctaaaggaat tcctccgatc attgaggctc aatgggtacc    8160
gtcctatcaa gttcctcgtc ctggagtcat gccatgcaat gcaacaagtt tttgccctgc    8220
taattgcatc acagggggtgt acgcagatgt gtggccgcctt aatgatccag aactcatgtc    8280
acgtaatgct ctgaacccca actatcgatt tgctggagcc tttctcaaaa atgagtccaa    8340
ccgaactaat cccacattct acactgcatc ggctaactcc ctcttaaata ctaccggatt    8400
```

```
caacaacacc aatcacaaag cagcatatac atcttcaacc tgctttaaaa acactggaac    8460
ccaaaaaatt tattgtttaa taataattga aatgggctca tctcttttag gggagttcca    8520
aataatacca tttttaaggg aactaatgct ttaagcttaa ttaaccataa tatgcatcaa    8580
tctatctata atacaagtat atgataagta atctgcaatc agacaataga caaagggaa     8640
atataaaaaa cttaggagca aagcgtgctc gggaaatgga cactgaatct aacaatggca    8700
ctgtatctga catactctat cctgagtgtc accttaactc tcctatcgtt aaaggtaaaa    8760
tagcacaatt acacactatt atgagtctac ctcagcctta tgatatggat gacgactcaa    8820
tactagttat cactagacag aaaataaaac ttaataaatt ggataaaaga caacgatcta    8880
ttagaagatt aaaattaata ttaactgaaa aagtgaatga cttaggaaaa tacacattta    8940
tcagatatcc agaaatgtca aaagaaatgt tcaaattata tatacctggt attaacagta    9000
aagtgactga attattactt aaagcagata gaacatatag tcaaatgact gatggattaa    9060
gagatctatg gattaatgtg ctatcaaaat tagcctcaaa aaatgatgga agcaattatg    9120
atcttaatga agaaattaat aatatatcga aagttcacac aacctataaa tcagataaat    9180
ggtataatcc attcaaaaca tggtttacta tcaagtatga tatgagaaga ttacaaaaag    9240
ctcgaaatga gatcactttt aatgttggga aggattataa cttgttagaa gaccagaaga    9300
atttcttatt gatacatcca gaattggttt tgatattaga taaacaaaac tataatggtt    9360
atctaattac tcctgaatta gtattgatgt attgtgacgt agtcgaaggc cgatggaata    9420
taagtgcatg tgctaagtta gatccaaaat tacaatctat gtatcagaaa ggtaataacc    9480
tgtgggaagt gatagataaa ttgtttccaa ttatgggaga aaagacattt gatgtgatat    9540
cgttattaga accacttgca ttatccttaa ttcaaactca tgatcctgtt aaacaactaa    9600
gaggagcttt tttaaatcat gtgttatccg agatggaatt aatatttgaa tctagagaat    9660
cgattaagga atttctgagt gtagattaca ttgataaaat tttagatata tttaataagt    9720
ctacaataga tgaaatagca gagattttct cttttttag aacatttggg catcctccat     9780
tagaagctag tattgcagca gaaaaggtta gaaaatatat gtatattgga aaacaattaa    9840
aatttgacac tattaataaa tgtcatgcta tcttctgtac aataataatt aacgatata     9900
gagagaggca tggtggacag tggcctcctg tgacattacc tgatcatgca cacgaattca    9960
tcataaatgc ttacggttca aactctgcga tatcatatga aaatgctgtt gattattacc   10020
agagctttat aggaataaaa ttcaataaat tcatagagcc tcagttagat gaggatttga   10080
caattatat gaaagataaa gcattatctc caaaaaaatc aaattgggac acagtttatc    10140
ctgcatctaa tttactgtac cgtactaacg catccaacga atcacgaaga ttagttgaag   10200
tatttatagc agatagtaaa tttgatcctc atcagatatt ggattatgta aatctgggg    10260
actggttaga tgatccagaa tttaatatt cttatagtct taaagaaaaa gagatcaaac    10320
aggaaggtag actctttgca aaaatgacat acaaaatgag agctacacaa gtttatcag    10380
agaccctact tgcaaataac ataggaaaat tctttcaaga aaatgggatg gtgaagggag   10440
agattgaatt acttaagaga ttaacaacca tatcaatatc aggagttcca cggtataatg   10500
aagtgtacaa taattctaaa agccatacag atgaccttaa aacctacaat aaaataagta   10560
atcttaattt gtcttctaat cagaaatcaa agaaatttga attcaagtca acggatatct   10620
acaatgatgg atacgagact gtgagctgtt tcctaacaac agatctcaaa aaatactgtc   10680
ttaattggag atatgaatca acagctctat ttggagaaac ttgcaaccaa atatttgat    10740
taaataaatt gtttaattgg ttcacccctc gtcttgaagg aagtacaatc tatgtaggtg   10800
```

```
atccttactg tcctccatca gataaagaac atatatcatt agaggatcac cctgattctg    10860
gtttttacgt tcataaccca agaggggta  tagaaggatt ttgtcaaaaa ttatggacac    10920
tcatatctat aagtgcaata catctagcag ctgttagaat aggcgtgagg gtgactgcaa    10980
tggttcaagg agacaatcaa gctatagctg taaccacaag agtacccaac aattatgact    11040
acagagttaa gaaggagata gtttataaag atgtagtgag attttttgat tcattaagag    11100
aagtgatgga tgatctaggt catgaactta aattaaatga aacgattata agtagcaaga    11160
tgttcatata tagcaaaaga atctattatg atgggagaat tcttcctcaa gctctaaaag    11220
cattatctag atgtgtcttc tggtcagaga cagtaataga cgaaacaaga tcagcatctt    11280
caaatttggc aacatcattt gcaaaagcaa ttgagaatgg ttattcacct gttctaggat    11340
atgcatgctc aattttttaag aatattcaac aactatatat tgcccttggg atgaatatca    11400
atccaactat aacacagaat atcagagatc agtattttag gaatccaaat tggatgcaat    11460
atgcctcttt aatacctgct agtgttgggg gattcaatta catggccatg tcaagatgtt    11520
ttgtaaggaa tattggtgat ccatcagttg ccgcattggc tgatattaaa agatttatta    11580
aggcgaatct attagaccga agtgttcttt ataggattat gaatcaagaa ccaggtgagt    11640 catcttttttt ggactgggct tcagatccat attcatgcaa tttaccacaa tctcaaaata    11700
taaccaccat gataaaaaat ataacagcaa ggaatgtatt acaagattca ccaaatccat    11760
tattatctgg attattcaca aatacaatga tagaagaaga tgaagaatta gctgagttcc    11820
tgatggacag gaaggtaatt ctccctagag ttgcacatga tattctagat aattctctca    11880
caggaattag aaaatgccata gctggaatgt tagatacgac aaaatcacta attcgggttg    11940
gcataaatag aggaggactg acatatagtt tgttgaggaa aatcagtaat tacgatctag    12000
tacaatatga aacactaagt aggactttgc gactaattgt aagtgataaa atcaagtatg    12060
aagatatgtg ttcggtagac cttgccatag cattgcgaca aaagatgtgg attcattttat   12120 caggaggaag gatgataagt ggacttgaaa cgcctgaccc attagaatta ctatctgggg    12180
tagtaataac aggatcagaa cattgtaaaa tatgttattc ttcagatggc acaaacccat    12240
atacttggat gtatttaccc ggtaatatca aaataggatc agcagaaaca ggtatatcgt    12300
cattaagagt tccttatttt ggatcagtca ctgatgaaag atctgaagca caattaggat    12360
atatcaagaa tcttagtaaa cctgcaaaag ccgcaataag aatagcaatg atatatacat    12420
gggcatttgg taatgatgag atatcttgga tggaagcctc acagatagca caaacacgtg    12480 caaatttttac actagatagt ctcaaaattt taacaccggt agctacatca acaaatttat    12540
cacacagatt aaaggatact gcaactcaga tgaaattctc cagtacatca ttgatcagag    12600
tcagcagatt cataacaatg tccaatgata acatgtctat caaagaagct aatgaaacca    12660
aagatactaa tcttatttat caacaaataa tgttaacagg attaagtgtt ttcgaatatt    12720
tatttagatt aaaagaaacc acaggacaca accctatagt tatgcatctg cacatagaag    12780
atgagtgttg tattaaagaa agttttaatg atgaacatat taatccagag tctacattag    12840
aattaattcg atatcctgaa agtaatgaat ttatttatga taagacccca ctcaaagatg    12900
tggacttatc aaaacttatg gttattaaag accattctta cacaattgat atgaattatt    12960
gggatgatac tgacatcata catgcaattt caatatgtac tgcaattaca atagcagata    13020
ctatgtcaca attagatcga gataatttaa aagagataat agttattgca aatgatgatg    13080
atattaatag cttaatcact gaattttttga ctccttgacat acttgtattt ctcaagacat    13140
ttggtggatt attagtaaat caatttgcat acactcttta tagtctaaaa atagaaggta    13200
```

```
gggatctcat ttgggattat ataatgagaa cactgagaga tacttcccat tcaatattaa    13260
aagtattatc taatgcatta tctcatccta aagtattcaa gaggttctgg gattgtggag    13320
ttttaaaccc tatttatggt cctaatactg ctagtcaaga ccagataaaa cttgccctat    13380
ctatatgtga atattcacta gatctattta tgagagaatg gttgaatggt gtatcacttg    13440
aaatatacat ttgtgacagc gatatggaag ttgcaaatga taggaaacaa gcctttattt    13500
ctagacacct ttcatttgtt tgttgtttag cagaaattgc atctttcgga cctaacctgt    13560
taaacttaac atacttggag agacttgatc tattgaaaca atatcttgaa ttaaatatta    13620
aagaagaccc tactcttaaa tatgtacaaa tatctggatt attaattaaa tcgttcccat    13680
caactgtaac atacgtaaga aagactgcaa tcaaatatct aaggattcgc ggtattagtc    13740
cacctgaggt aattgatgat tgggatccgg tagaagatga aaatatgctg gataacattg    13800
tcaaaactat aaatgataac tgtaataaag ataataaagg gaataaaatt aacaatttct    13860
ggggactagc acttaagaac tatcaagtcc ttaaaatcag atctataaca agtgattctg    13920
atgataatga tagactagat gctaatacaa gtggttttgac acttcctcaa ggagggaatt    13980
atctatcgca tcaattgaga ttattcggaa tcaacagcac tagttgtctg aaagctcttg    14040
agttatcaca aattttaatg aaggaagtca ataaagacaa ggacaggctc ttcctgggag    14100
aaggagcagg agctatgcta gcatgttatg atgccacatt aggacctgca gttaattatt    14160
ataattcagg tttgaatata acagatgtaa ttggtcaacg agaattgaaa atatttcctt    14220
cagaggtatc attagtaggt aaaaaattag gaaatgtgac acagattctt aacagggtaa    14280
aagtactgtt caatgggaat cctaattcaa catggatagg aaatatgaaa tgtgagagct    14340
taatatggag tgaattaaat gataagtcca ttggattagt acattgtgat atggaaggag    14400
ctatcggtaa atcagaagaa actgttctac atgaacatta tagtgttata agaattacat    14460
acttgattgg ggatgatgat gttgttttag tttccaaaat tataccctaca atcactccga    14520 attggtctag aatactttat ctatataaat tatattggaa agatgtaagt ataatatcac    14580
tcaaaacttc taatcctgca tcaacagaat tatatctaat ttcgaaagat gcatattgta    14640
ctataatgga acctagtgaa attgttttat caaaacttaa aagattgtca ctcttggaag    14700
aaaataatct attaaaatgg atcattttat caaagaagag gaataatgaa tggttacatc    14760
atgaaatcaa agaaggagaa agagattatg gaatcatgag accatatcat atggcactac    14820
aaatctttgg atttcaaatc aatttaaatc atctggcgaa agaatttta tcaacccag    14880 atctgactaa tatcaacaat ataatccaaa gttttcagcg aacaataaag gatgttttat    14940
ttgaatggat taatataact catgatgata agagacataa attaggcgga agatataaca    15000
tattcccact gaaaaataag ggaaagttaa gactgctatc gagaagacta gtattaagtt    15060 ggattcatt atcattatcg actcgattac ttacaggtcg ctttcctgat gaaaaatttg    15120
aacatagagc acagactgga tatgtatcat tagctgatac tgatttagaa tcattaaagt    15180
tattgtcgaa aaacatcatt aagaattaca gagagtgtat aggatcaata tcatattggt    15240
ttctaaccaa agaagttaaa atacttatga aattgatcgg tggtgctaaa ttattaggaa    15300
ttcccagaca atataaagaa cccgaagacc agttattaga aaactacaat caacatgatg    15360
aatttgatat cgattaaaac ataaatacaa tgaagatata tcctaacctt tatctttaag    15420
cctaggaata gacaaaaagt aagaaaaaca tgtaatatat ataccaaaa cagagttctt    15480 ctcttgtttg gt                                                        15492
```

```
<210> SEQ ID NO 155
<211> LENGTH: 25
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2 F(sense
<220> FEATURE:
<221> NAME/KEY: misc_feature
<222> LOCATION: (1)..(25)
<223> OTHER INFORMATION: Part of Parent Appln No 09/733,692 as SEQ ID
      NO: 40; Part of Parent Appln No 09/459,062 as SEQ ID NO: 20

<400> SEQUENCE: 155
gtaccatgga tcacctgcat ccaat                                          25

<210> SEQ ID NO 156
<211> LENGTH: 31
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2 F(antisense).
<220> FEATURE:
<221> NAME/KEY: misc_feature
<222> LOCATION: (1)..(31)
<223> OTHER INFORMATION: Part of Parent Appln No 09/733,692 as SEQ ID
      NO: 41; Part of Parent Appln No 09/459,062 as SEQ ID NO: 21

<400> SEQUENCE: 156
tgtggatcct aagatatccc atatatgttt c                                   31

<210> SEQ ID NO 157
<211> LENGTH: 20
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2 F(sense).
<220> FEATURE:
<221> NAME/KEY: misc_feature
<222> LOCATION: (1)..(20)
<223> OTHER INFORMATION: Part of Parent Appln No 09/733,692 as SEQ ID
      NO: 42 and 50; Part of Parent Appln No 09/459,062 as SEQ ID NO:
      22 and 30

<400> SEQUENCE: 157
atgcatcacc tgcatccaat                                                20

<210> SEQ ID NO 158
<211> LENGTH: 22
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2(antisense).
<220> FEATURE:
<221> NAME/KEY: misc_feature
<222> LOCATION: (1)..(22)
<223> OTHER INFORMATION: Part of Parent Appln No 09/733,692 as SEQ ID
      NO: 43; Part of Parent Appln No 09/459,062 as SEQ ID NO: 23

<400> SEQUENCE: 158
tagtgaataa agtgtcttgg ct                                             22

<210> SEQ ID NO 159
<211> LENGTH: 24
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2 HN(sense).
```

```
<220> FEATURE:
<221> NAME/KEY: misc_feature
<222> LOCATION: (1)..(24)
<223> OTHER INFORMATION: Part of Parent Appln No 09/733,692 as SEQ ID
      NO: 44; Part of Parent Appln No 09/459,062 as SEQ ID NO: 24

<400> SEQUENCE: 159
catgagataa ttcatcttga tgtt                                              24

<210> SEQ ID NO 160
<211> LENGTH: 24
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2 HN(antisense).
<220> FEATURE:
<221> NAME/KEY: misc_feature
<222> LOCATION: (1)..(24)
<223> OTHER INFORMATION: Part of Parent Appln No 09/733,692 as SEQ ID
      NO: 45; Part of Parent Appln No 09/459,062 as SEQ ID NO: 25

<400> SEQUENCE: 160 agctta

<400> SEQUENCE: 163
tcataattaa ccataatatg catcaat                                        27

<210> SEQ ID NO 164
<211> LENGTH: 24
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV3 HN(sense/antisense).
<220> FEATURE:
<221> NAME/KEY: misc_feature
<222> LOCATION: (1)..(24)
<223> OTHER INFORMATION: Part of Parent Appln No 09/733,692 as SEQ ID
      NO: 49; Part of Parent Appln No 09/459,062 as SEQ ID NO: 29

<400> SEQUENCE: 164
gatggaatta attagcacta tgat 24

<210> SEQ ID NO 165
<211> LENGTH: 19
<212> TYPE: DNA
<213> ORGANISM: Artificial Sequence
<220> FEATURE:
<223> OTHER INFORMATION: Chemically synthesized primer for construction of PIV3-2 chimeric cDNAs, PIV2 F(sense).
<220> FEATURE:
<221> NAME/KEY: misc_feature
<222> LOCATION: (1)..(19)
<223> OTHER INFORMATION: Part of Parent Appln No 09/733,692 as SEQ ID NO: 51; Part of Parent Appln No 09/459,062 as SEQ ID NO: 31

<400> SEQUENCE: 165
gatgatgtag gcaatcagc 19

<210> SEQ ID NO 166
<211> LENGTH: 18
<212> TYPE: DNA
<213> ORGANISM: Artificial Sequence
<220> FEATURE:
<223> OTHER INFORMATION: Chemically synthesized primer for construction of PIV3-2 chimeric cDNAs, PIV2 HN(sense).
<220> FEATURE:
<221> NAME/KEY: misc_feature
<222> LOCATION: (1)..(18)
<223> OTHER INFORMATION: Part of Parent Appln No 09/733,692 as SEQ ID NO: 52; Part of Parent Appln No 09/459,062 as SEQ ID NO: 32

<400> SEQUENCE: 166
actgccacaa ttcttggc 18

<210> SEQ ID NO 167
<211> LENGTH: 26
<212> TYPE: DNA
<213> ORGANISM: Artificial Sequence
<220> FEATURE:
<223> OTHER INFORMATION: Chemically synthesized primer for construction of PIV3-2 chimeric cDNAs, PIV2 HN(antisense).
<220> FEATURE:
<221> NAME/KEY: misc_feature
<222> LOCATION: (1)..(26)
<223> OTHER INFORMATION: Part of Parent Appln No 09/733,692 as SEQ ID NO: 53; Part of Parent Appln No 09/459,062 as SEQ ID NO: 33

<400> SEQUENCE: 167
ttaaagcatt agttccctta aaaatg 26

```
<210> SEQ ID NO 168
<211> LENGTH: 23
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV3 F(sense).
<220> FEATURE:
<221> NAME/KEY: misc_feature
<222> LOCATION: (1)..(23)
<223> OTHER INFORMATION: Part of Parent Appln No 09/733,692 as SEQ ID
      NO: 54; Part of Parent Appln No 09/459,062 as SEQ ID NO: 34

<400> SEQUENCE: 168
aagtattaca gaattcaaaa gag                                          23

<210> SEQ ID NO 169
<211> LENGTH: 20
<212> TYPE: DNA
<213> ORGANISM: Artificial Sequence
<220> FEATURE:
<223> OTHER INFORMATION: Chemically synthesized primer for
      construction of PIV3-2 Chimeric cDNAs, PIV3 HN(antisense).
<220> FEATURE:
<221> NAME/KEY: misc_feature
<222> LOCATION: (1)..(20)
<223> OTHER INFORMATION: Part of Parent Appln No 09/733,692 as SEQ ID
      NO: 55; Part of Parent Appln No 09/459,062 as SEQ ID NO: 35

<400> SEQUENCE: 169
cttattagtg agcttgttgc                                              20

<210> SEQ ID NO 170
<211> LENGTH: 20
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2 F(sense).
<220> FEATURE:
<221> NAME/KEY: misc_feature
<222> LOCATION: (1)..(20)
<223> OTHER INFORMATION: Part of Parent Appln No 09/733,692 as SEQ ID
      NO: 56; Part of Parent Appln No 09/459,062 as SEQ ID NO: 36

<400> SEQUENCE: 170
accgcagctg tagcaatagt                                              20

<210> SEQ ID NO 171
<211> LENGTH: 21
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV2 HN(antisense).
<220> FEATURE:
<221> NAME/KEY: misc_feature
<222> LOCATION: (1)..(21)
<223> OTHER INFORMATION: Part of Parent Appln No 09/733,692 as SEQ ID
      NO: 57; Part of Parent Appln No 09/459,062 as SEQ ID NO: 37

<400> SEQUENCE: 171
gattccatca cttaggtaaa t                                            21

<210> SEQ ID NO 172
<211> LENGTH: 22
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV3 M(sense).
```

```
<220> FEATURE:
<221> NAME/KEY: misc_feature
<222> LOCATION: (1)..(22)
<223> OTHER INFORMATION: Part of Parent Appln No 09/733,692 as SEQ ID
      NO: 58; Part of Parent Appln No 09/459,062 as SEQ ID NO: 38

<400> SEQUENCE: 172
gatactatcc taatattatt gc                                              22

<210> SEQ ID NO 173
<211> LENGTH: 20
<212> TYPE: DNA
<213> ORGANISM: Artificial Sequence
<220> FEATURE:
<223> OTHER INFORMATION: Chemically synthesized primer for
      construction of PIV3-2 chimeric cDNAs, PIV3 L(antisense).
<220> FEATURE:
<221> NAME/KEY: misc_feature
<222> LOCATION: (1)..(20)
<223> OTHER INFORMATION: Part of Parent Appln No 09/733,692 as SEQ ID
      NO: 59; Part of Parent Appln No 09/459,062 as SEQ ID NO: 39

<400

-continued

```
caccaggcaa ctatcctgcc atatggagct atgcaatggg ggtggcagtt gtacaaaata      1140
gagccatgca acagtatgtg acgggaagat catatctaga cattgatatg ttccagctag      1200
gacaagcagt agcacgtgat gccgaagctc aaatgagctc aacactggaa gatgaacttg      1260
gagtgacaca cgaatctaaa gaaagcttga agagacatat aaggaacata aacagttcag      1320
agacatcttt ccacaaaccg acaggtggat cagccataga gatggcaata gatgaagagc      1380
cagaacaatt cgaacataga gcagatcaag aacaaaatgg agaacctcaa tcatccataa      1440
ttcaatatgc ctgggcagaa ggaaatagaa gcgatgatca gactgagcaa gctacagaat      1500
ctgacaatat caagaccgaa caacaaaaca tcagagacag actaaacaag agactcaacg      1560
acaagaagaa acaaagcagt caaccaccca ctaatcccac aaacagaaca aaccaggacg      1620
aaatagatga tctgtttaac gcatttggaa gcaactaatc gaatcaacat tttaatctaa      1680
atcaataata aataagaaaa acttaggatt aaagaatcct atcataccgg aatatagggt      1740
ggtaaattta gagtctgctt gaaactcaat caatagagag ttgatggaaa gcgatgctaa      1800
aaactatcaa atcatggatt cttgggaaga ggaatcaaga gataaatcaa ctaatatctc      1860
ctcggccctc aacatcattg aattcatact cagcaccgac ccccaagaag acttatcgga      1920
aaacgacaca atcaacacaa gaacccagca actcagtgcc accatctgtc aaccagaaat      1980
caaaccaaca gaaacaagtg agaaagatag tggatcaact gacaaaaata gacagtccgg      2040
gtcatcacac gaatgtacaa cagaagcaaa agatagaaat attgatcagg aaactgtaca      2100
gagaggacct gggagaagaa gcagctcaga tagtagagct gagactgtgg tctctggagg      2160
aatccccaga agcatcacag attctaaaaa tggaacccaa aacacggagg atattgatct      2220
caatgaaatt agaagatgg ataaggactc tattgagggg aaaatgcgac aatctgcaaa      2280
tgttccaagc gagatatcag gaagtgatga catatttaca acagaacaaa gtagaaacag      2340
tgatcatgga agaagcctgg aatctatcag tacacctgat acaagatcaa taagtgttgt      2400
tactgctgca acaccagatg atgaagaaga atactaatg aaaatagta ggacaaagaa      2460 aagttcttca acacatcaag aagatgacaa agaattaaa aaggggaa aagggaaaga      2520 ctggtttaag aaatcaaaag ataccgacaa ccagatacca acatcagact acagatccac      2580
atcaaagggg cagaagaaaa tctcaaagac aacaaccacc aacaccgaca caaaggggca      2640
aacagaaata cagacagaat catcagaaac acaatcctca tcatggaatc tcatcatcga      2700
caacaacacc gaccggaacg aacagacaag cacaactcct ccaacaacaa cttccagatc      2760
aacttataca aaagaatcga tccgaacaaa ctctgaatcc aaacccaaga cacaaaagac      2820
aaatggaaag gaaaggaagg atacagaaga gagcaatcga tttacagaga gggcaattac      2880
tctattgcag aatcttggtg taattcaatc cacatcaaaa ctagatttat atcaagacaa      2940
acgagttgta tgtgtagcaa atgtactaaa caatgtagat actgcatcaa agatagattt      3000
cctggcagga ttagtcatag gggtttcaat ggacaacgac acaaaattaa cacagataca      3060
aaatgaaatg ctaaacctca agcagatct aaagaaaatg gacgaatcac atagaagatt      3120
gatagaaaat caaagagaac aactgtcatt gatcacgtca ctaatttcaa atctcaaaat      3180
tatgactgag agaggaggaa agaaagacca aaatgaatcc aatgagagag tatccatgat      3240
caaaacaaaa ttgaaagaag aaaagatcaa gaagaccagg tttgacccac ttatggaggc      3300
acaaggcatt gacaagaata tacccgatct atatcgacat gcaggagata cactagaaa      3360 cgatgtacaa gttaaatcag agatattaag ttcatacaat gagtcaaatg caacaagact      3420
aatacccaaa aaagtgagca gtacaatgag atcactagtt gcagtcatca acaacagcaa      3480
```

```
tctctcacaa agcacaaaac aatcatacat aaacgaactc aaacgttgca aaaatgatga    3540
agaagtatct gaattaatgg acatgttcaa tgaagatgtc aacaattgcc aatgatccaa    3600
caaagaaacg acaccgaaca aacagacaag aaacaacagt agatcaaaac ctgtcaacac    3660
acacaaaatc aagcagaatg aaacaacaga tatcaatcaa tatacaaata agaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac    3900
acggatcccg gtatttagat gtcttcttac tcggcttctt cgagatggaa cgaatcaaag    3960
acaaatacgg gagtgtgaat gatctcgaca gtgacccgag ttacaaagtt tgtggctctg    4020
gatcattacc aatcggattg gctaagtaca ctgggaatga ccaggaattg ttacaagccg    4080
caaccaaact ggatatagaa gtgagaagaa cagtcaaagc gaaagagatg gttgtttaca    4140
cggtacaaaa tataaaacca gaactgtacc catggtccaa tagactaaga aaaggaatgc    4200
tgttcgatgc caacaaagtt gctcttgctc ctcaatgtct tccactagat aggagcataa    4260
aatttagagt aatcttcgtg aattgtacgg caattggatc aataaccttg ttcaaaattc    4320
ctaagtcaat ggcatcacta tctctaccca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa agaaaagta ggcagaatgt     4500 actctgttga atactgtaaa cagaaaatcg agaaaatgag attgatattt tctttaggac    4560
tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740
ctttacctgg cgagttcaga tactatccta atattattgc aaaaggagtt gggaaaatca    4800
aacaatggaa ctagtaatct ctattttagt ccggacgtat ctattaagcc gaagcaaata    4860
aaggataatc aaaaacttag gacaaaagag gtcaatacca acaactatta gcagtcacac    4920
tcgcaagaat aagagagaag ggaccaaaaa agtcaaatag gagaaatcaa aacaaaaggt    4980
acagaacacc agaacaacaa aatcaaaaca tccaactcac tcaaaacaaa aattccaaaa    5040
gagaccggca acacaacaag cactgaacat gcatcacctg catccaatga tagtatgcat    5100
ttttgttatg tacactggaa ttgtaggttc agatgccatt gctggagatc aactcctcaa    5160 tgtagggggtc attcaatcaa agataagatc actcatgtac tacactgatg gtggcgctag    5220
ctttattgtt gtaaaattac tacccaatct tccccccaagc aatggaacat gcaacatcac    5280
cagtctagat gcatataatg ttaccctatt taagttgcta acaccctga ttgagaacct     5340 gagcaaaatt tctgctgtta cagataccaa accccgccga gaacgatttg caggagtcgt    5400
tattgggctt gctgcactag gagtagctac agctgcacaa ataaccgcag ctgtagcaat    5460
agtaaaagcc aatgcaaatg ctgctgcgat aaacaatctt gcatcttcaa ttcaatccac    5520
caacaaggca gtatccgatg tgataactgc atcaagaaca attgcaaccg cagttcaagc    5580
gattcaggat cacatcaatg gagccattgt caacggata acatctgcat catgccgtgc     5640
ccatgatgca ctaattgggt caatattaaa tttgtatctc actgagctta ctacaatatt    5700
tcataatcaa ataacaaacc ctgcgctgac accactttcc atccaagctt taagaatcct    5760
cctcggtagc accttgccaa ttgtcattga atccaaactc aacacaaaac tcaacacagc    5820
agagctgctc agtagcggac tgttaactgg tcaaataatt tccatttccc caatgtacat    5880
```

```
gcaaatgcta attcaaatca atgttccgac atttataatg caacccggtg cgaaggtaat    5940
tgatctaatt gctatctctg caaaccataa attacaagaa gtagttgtac aagttcctaa    6000
tagaattcta gaatatgcaa atgaactaca aaactaccca gccaatgatt gtttcgtgac    6060
accaaactct gtattttgta gatacaatga gggttccccg atccctgaat cacaatatca    6120
atgcttaagg gggaatctta attcttgcac ttttacccct attatcggga actttctcaa    6180
gcgattcgca tttgccaatg gtgtgctcta tgccaactgc aaatctttgc tatgtaagtg    6240
tgccgaccct ccccatgttg tgtctcaaga tgacaaccaa ggcatcagca taattgatat    6300
taagaggtgc tctgagatga tgcttgacac ttttttcattt aggatcacat ctacattcaa    6360
tgctacatac gtgacagact tctcaatgat taatgcaaat attgtacatc taagtcctct    6420
agacttgtca aatcaaatca attcaataaa caaatctctt aaaagtgctg aggattggat    6480
tgcagatagc aacttcttcg ctaatcaagc cagaacagcc aagacacttt attcactaat    6540
cataattatt ttgataatga tcattatatt gtttataatt aatataacga taattacaat    6600
tgcaattaag tattacagaa ttcaaaagag aaatcgagtg gatcaaaatg acaagccata    6660
tgtactaaca aacaaataac atatctcag atcattagat attaaaatta taaaaaactt    6720
aggagtaaag ttacgcaatc caactctact catataattg aggaaggacc caatagacaa    6780
atccaaattc gagatggaat actggaagca taccaatcac ggaaaggatg ctggtaatga    6840
gctggagacg tctatggcta ctcatggcaa caagctcact aataagataa tatacatatt    6900
atggacaata atcctggtgt tattatcaat agtcttcatc atagtgctaa ttaattccat    6960
ccatgagata attcatcttg atgtttcctc tggtcttatg aattctgatg agtcacagca    7020
aggcattatt cagcctatca tagaatcatt aaaatcattg attgctttgg ccaaccagat    7080
tctatataat gttgcaatag taattcctct taaaattgac agtatcgaaa ctgtaatact    7140
ctctgcttta aaagatatgc acaccgggag tatgtccaat gccaactgca cgccaggaaa    7200
tctgcttctg catgatgcag catacatcaa tggaataaac aaattccttg tacttgaatc    7260
atacaatggg acgcctaaat atggacctct cctaaatata cccagctttta tcccctcagc    7320 aacatctccc catgggtgta ctagaatacc atcattttca ctcatcaaga cccattggtg    7380
ttacactcac aatgtaatgc ttggagattg tcttgatttc acggcatcta accagtattt    7440
atcaatgggg ataatacaac aatctgctgc agggtttcca attttcagga ctatgaaaac    7500
catttaccta agtgatggaa tcaatcgcaa aagctgttca gtcactgcta taccaggagg    7560
ttgtgtcttg tattgctatg tagctacaag gtctgaaaaa gaagattatg ccacgactga    7620
tctagctgaa ctgagacttg cttttctatta ttataatgat acctttattg aaagagtcat    7680
atctcttcca aatacaacag gcagtgggca cacaatcaac cctgcagtcg gaagcgggat    7740
ctatcatcta ggctttatct tatttcctgt atatggtggt ctcataaatg ggactacttc    7800
ttacaatgag cagtcctcac gctattttat cccaaaacat cccaacataa cttgtgccgg    7860
taactccagc aaacaggctg caatagcacg gagttcctat gtcatccgtt atcactcaaa    7920
caggttaatt cagagtgctg ttcttatttg tccattgtct gacatgcata cagaagagtg    7980
taatctagtt atgtttaaca attcccaagt catgatgggt gcagaaggta ggctctatgt    8040
tattggtaat aatttgtatt attatcaacg cagttcctct tggtggtctg catcgctctt    8100
ttacaggatc aatacagatt tttctaaagg aattcctccg atcattgagg ctcaatgggt    8160
accgtcctat caagttcctc gtcctggagt catgccatgc aatgcaacaa gttttttgccc    8220 tgctaattgc atcacagggg tgtacgcaga tgtgtggccg cttaatgatc cagaactcat    8280
```

```
gtcacgtaat gctctgaacc ccaactatcg atttgctgga gcctttctca aaaatgagtc      8340
caaccgaact aatcccacat tctacactgc atcggctaac tccctcttaa atactaccgg      8400
attcaacaac accaatcaca aagcagcata tacatcttca acctgcttta aaaacactgg      8460
aacccaaaaa atttattgtt taataataat tgaaatgggc tcatctcttt taggggagtt      8520
ccaaataata ccatttttaa gggaactaat gctttaagct tcataattaa ccataatatg      8580
catcaatcta tctataatac aagtatatga taagtaatca gcaatcagac aatagacaaa      8640
agggaaatat aaaaaactta ggagcaaagc gtgctcggga aatggacact gaatctaaca      8700
atggcactgt atctgacata ctctatcctg agtgtcacct taactctcct atcgttaaag      8760
gtaaaatagc acaattacac actattatga gtctacctca gccttatgat atggatgacg      8820
actcaatact agttatcact agacagaaaa taaaacttaa taaattggat aaaagacaac      8880
gatctattag aagattaaaa ttaatattaa ctgaaaaagt gaatgactta ggaaaataca      8940
catttatcag atatccagaa atgtcaaaag aaatgttcaa attatatata cctggtatta      9000
acagtaaagt gactgaatta ttacttaaag cagatagaac atatagtcaa atgactgatg      9060
gattaagaga tctatggatt aatgtgctat caaaattagc ctcaaaaaat gatggaagca      9120
attatgatct taatgaagaa attaataata tatcgaaagt tcacacaacc tataaatcag      9180
ataaatggta taatccattc aaaacatggt ttactatcaa gtatgatatg agaagattac      9240
aaaaagctcg aaatgagatc acttttaatg ttgggaagga ttataacttg ttagaagacc      9300
agaagaattt cttattgata catccagaat tggttttgat attagataaa caaaactata      9360
atggttatct aattactcct gaattagtat tgatgtattg tgacgtagtc gaaggccgat      9420
ggaatataag tgcatgtgct aagttagatc caaaattaca atctatgtat cagaaaggta      9480
ataacctgtg ggaagtgata gataaaattgt ttccaattat gggagaaaag acatttgatg      9540
tgatatcgtt attagaacca cttgcattat ccttaattca aactcatgat cctgttaaac      9600
aactaagagg agctttttta aatcatgtgt tatccgagat ggaattaata tttgaatcta      9660
gagaatcgat taaggaattt ctgagtgtag attacattga taaaattttta gatatattta      9720 ataagtctac aatagatgaa atagcagaga ttttctcttt ttttagaaca tttgggcatc      9780
ctccattaga agctagtatt gcagcagaaa aggttagaaa atatatgtat attggaaaac      9840
aattaaaatt tgcacactatt aataaatgtc atgctatctt ctgtacaata ataattaacg      9900
gatatagaga gaggcatggt ggacagtggc ctcctgtgac attacctgat catgcacacg      9960
aattcatcat aaatgcttac ggttcaaact ctgcgtatatc atatgaaaat gctgttgatt     10020
attaccagag ctttatagga ataaaattca ataaattcat agagcctcag ttagatgagg     10080
atttgacaat ttatatgaaa gataaagcat tatctccaaa aaaatcaaat tgggacacag     10140
tttatcctgc atctaatttta ctgtaccgta ctaacgcatc caacgaatca cgaagattag     10200
ttgaagtatt tatagcagat agtaaatttg atcctcatca gatattggat tatgtagaat     10260
ctggggactg gttagatgat ccagaattta atatttctta tagtcttaaa gaaaaagaga     10320
tcaaacagga aggtagactc tttgcaaaaa tgacatacaa aatgagagct acacaagttt     10380
tatcagagac cctacttgca aataacatag gaaaattctt tcaagaaaat gggatggtga     10440
agggagagat tgaattactt aagagattaa caaccatatc aatatcagga gttccacggt     10500
ataatgaagt gtacaataat tctaaaagcc atacagatga ccttaaaacc tacaataaaa     10560
taagtaatct taatttgtct tctaatcaga aatcaaagaa atttgaattc aagtcaacgg     10620
atatctacaa tgatggatac gagactgtga gctgtttcct aacaacagat ctcaaaaaat     10680
```

```
actgtcttaa ttggagatat gaatcaacag ctctatttgg agaaacttgc aaccaaatat    10740
ttggattaaa taaattgttt aattggttac accctcgtct tgaaggaagt acaatctatg    10800
taggtgatcc ttactgtcct ccatcagata aagaacatat atcattagag gatcaccctg    10860
attctggttt ttacgttcat aacccaagag ggggtataga aggattttgt caaaaattat    10920
ggacactcat atctataagt gcaatacatc tagcagctgt tagaataggc gtgagggtga    10980
ctgcaatggt tcaaggagac aatcaagcta tagctgtaac cacaagagta cccaacaatt    11040
atgactacag agttaagaag gagatagttt ataaagatgt agtgagattt tttgattcat    11100
taagagaagt gatggatgat ctaggtcatg aacttaaatt aaatgaaacg attataagta    11160
gcaagatgtt catatatagc aaaagaatct attatgatgg gagaattctt cctcaagctc    11220
taaaagcatt atctagatgt gtcttctggt cagagacagt aatagacgaa acaagatcag    11280
catcttcaaa tttggcaaca tcatttgcaa aagcaattga gaatggttat tcacctgttc    11340
taggatatgc atgctcaatt tttaagaata ttcaacaact atatattgcc cttgggatga    11400
atatcaatcc aactataaca cagaatatca gagatcagta ttttaggaat ccaaattgga    11460
tgcaatatgc ctctttaata cctgctagtg ttgggggatt caattacatg gccatgtcaa    11520
gatgttttgt aaggaatatt ggtgatccat cagttgccgc attggctgat attaaaagat    11580
ttattaaggc gaatcattta gaccgaagtg ttctttatag gattatgaat caagaaccag    11640
gtgagtcatc ttttttggac tgggcttcag atccatattc atgcaattta ccacaatctc    11700
aaaatataac caccatgata aaaaatataa cagcaaggaa tgtattacaa gattcaccaa    11760
atccattatt atctggatta ttcacaaata caatgataga agaagatgaa gaattagctg    11820
agttcctgat ggacaggaag gtaattctcc ctagagttgc acatgatatt ctagataatt    11880
ctctcacagg aattagaaat gccatagctg gaatgttaga tacgacaaaa tcactaattc    11940
gggttggcat aaatagagga ggactgcat atagtttgtt gaggaaaatc agtaattacg    12000
atctagtaca atatgaaaca ctaagtagga cttttgcgact aattgtaagt gataaaatca    12060
agtatgaaga tatgtgttcg gtagaccttg ccatagcatt gcgacaaaag atgtggattc    12120
atttatcagg aggaaggatg ataagtgac ttgaaacgcc tgacccatta gaattactat    12180
ctggggtagt aataacagga tcagaacatt gtaaaatatg ttattcttca gatggcacaa    12240
acccatatac ttgatgtat ttacccggta atatcaaaat aggatcagca gaaacaggta    12300
tatcgtcatt aagagttcct tattttggat cagtcactga tgaaagatct gaagcacaat    12360
taggatatat caagaatctt agtaaacctg caaaagccgc aataagaata gcaatgatat    12420
atacatgggc atttggtaat gatgagatat cttggatgga agcctcacag atagcacaaa    12480
cacgtgcaaa ttttacacta gatagtctca aaattttaac accggtagct acatcaacaa    12540
atttatcaca cagattaaag gatactgcaa ctcagatgaa attctccagt acatcattga    12600
tcagagtcag cagattcata acaatgtcca atgataacat gtctatcaaa gaagctaatg    12660
aaaccaaaga tactaatctt atttatcaac aaataatgtt aacaggatta agtgttttcg    12720
aatatttatt tagattaaaa gaaaccacag gacacaaccc tatagttatg catctgcaca    12780
tagaagatga gtgttgtatt aaagaaagtt taatgatga acatattaat ccagagtcta    12840
cattagaatt aattcgatat cctgaaagta atgaatttat ttatgataaa gacccactca    12900
aagatgtgga cttatcaaaa cttatggtta ttaaagacca ttcttacaca attgatatga    12960
attattggga tgatactgac atcatacatg caatttcaat atgtactgca attacaatag    13020
cagatactat gtcacaatta gatcgagata atttaaaaga gataatagtt attgcaaatg    13080
```

```
atgatgatat taatagctta atcactgaat ttttgactct tgacatactt gtatttctca    13140
agacatttgg tggattatta gtaaatcaat ttgcatacac tctttatagt ctaaaaatag    13200
aaggtaggga tctcatttgg gattatataa tgagaacact gagagatact tcccattcaa    13260
tattaaaagt attatctaat gcattatctc atcctaaagt attcaagagg ttctgggatt    13320
gtggagtttt aaaccctatt tatggtccta atactgctag tcaagaccag ataaaacttg    13380
ccctatctat atgtgaatat tcactagatc tatttatgag agaatggttg aatggtgtat    13440
cacttgaaat atacatttgt gacagcgata tggaagttgc aaatgatagg aaacaagcct    13500
ttatttctag acacctttca tttgtttgtt gtttagcaga aattgcatct ttcggaccta    13560
acctgttaaa cttaacatac ttggagagac ttgatctatt gaaacaatat cttgaattaa    13620
atattaaaga agaccctact cttaaatatg tacaaatatc tggattatta attaaatcgt    13680
tcccatcaac tgtaacatac gtaagaaaga ctgcaatcaa atatctaagg attcgcggta    13740
ttagtccacc tgaggtaatt gatgattggg atccggtaga agatgaaaat atgctggata    13800
acattgtcaa aactataaat gataactgta ataaagataa taaagggaat aaaattaaca    13860
atttctgggg actagcactt aagaactatc aagtccttaa aatcagatct ataacaagtg    13920
attctgatga taatgataga ctagatgcta atacaagtgg tttgacactt cctcaaggag    13980
ggaattatct atcgcatcaa ttgagattat tcggaatcaa cagcactagt tgtctgaaag    14040
ctcttgagtt atcacaaatt ttaatgaagg aagtcaataa agacaaggac aggctcttcc    14100
tgggagaagg agcaggagct atgctagcat gttatgatgc cacattagga cctgcagtta    14160
attattataa ttcaggtttg aatataacag atgtaattgg tcaacgagaa ttgaaaatat    14220
ttccttcaga ggtatcatta gtaggtaaaa aattaggaaa tgtgacacag attcttaaca    14280
gggtaaaagt actgttcaat gggaatccta attcaacatg gataggaaat atggaatgtg    14340
agagcttaat atggagtgaa ttaaatgata agtccattgg attagtacat tgtgatatgg    14400
aaggagctat cggtaaatca gaagaaactg ttctacatga acattatagt gttataagaa    14460
ttacatactt gattggggat gatgatgttg ttttagtttc caaaattata cctacaatca    14520
ctccgaattg gtctagaata ctttatctat ataaattata ttggaaagat gtaagtataa    14580
tatcactcaa aacttctaat cctgcatcaa cagaattata tctaatttcg aaagatgcat    14640
attgtactat aatggaacct agtgaaattg ttttatcaaa acttaaaaga ttgtcactct    14700
tggaagaaaa taatctatta aaatggatca ttttatcaaa gaagaggaat aatgaatggt    14760
tacatcatga aatcaaagaa ggagaaagag attatggaat catgagacca tatcatatgg    14820
cactacaaat ctttggattt caaatcaatt taaatcatct ggcgaaagaa ttttatcaa    14880 ccccagatct gactaatatc aacaatataa tccaaagttt tcagcgaaca ataaaggatg    14940
ttttatttga atggattaat ataactcatg atgataagag acataaatta ggcggaagat    15000
ataacatatt cccactgaaa aataagggaa agttaagact gctatcgaga agactagtat    15060
taagttggat ttcattatca ttatcgactc gattacttac aggtcgcttt cctgatgaaa    15120
aatttgaaca tagagcacag actggatatg tatcattagc tgatactgat ttagaatcat    15180
taaagttatt gtcgaaaaac atcattaaga attacagaga gtgtataggg tcaatatcat    15240
attggtttct aaccaaagaa gttaaaatac ttatgaaatt gatcggtggt gctaaattat    15300
taggaattcc cagacaatat aaagaacccg aagaccagtt attagaaaac tacaatcaac    15360
atgatgaatt tgatatcgat taaaacataa atacaatgaa gatatatcct aacctttatc    15420
```

-continued

```
tttaagccta ggaatagaca aaaagtaaga aaaacatgta atatatatat accaaacaga    15480
gttcttctct tgtttggt                                                  15498

<210> SEQ ID NO 175
<211> LENGTH: 15474
<212> TYPE: DNA
<213> ORGANISM: Artificial Sequence
<220> FEATURE:
<223> OTHER INFORMATION: Sequence of pFLC.PIV32CT, 15474 bp in sense
      orientation.
<220> FEATURE:
<221> NAME/KEY: misc_feature
<222> LOCATION: (1)..(15474)
<223> OTHER INFORMATION: Part of Parent Appln No 09/459,062 as SEQ ID
      NO: 41

<400> SEQUENCE: 175
accaaacaag agaagaaact tgtctgggaa tataaattta actttaaatt aacttaggat      60
taaagacatt gactagaagg tcaagaaaag ggaactctat aatttcaaaa atgttgagcc    120
tatttgatac atttaatgca cgtaggcaag aaaacataac aaaatcagcc ggtggagcta    180
tcattcctgg acagaaaaat actgtctcta tattcgccct tggaccgaca ataactgatg    240
ataatgagaa aatgacatta gctcttctat ttctatctca ttcactagat aatgagaaac    300
aacatgcaca aagggcaggg ttcttggtgt ctttattgtc aatggcttat gccaatccag    360
agctctacct aacaacaaat ggaagtaatg cagatgtcaa gtatgtcata tacatgattg    420
agaaagatct aaaacggcaa aagtatgag gatttgtggt taagacgaga gagatgatat    480
atgaaaagac aactgattgg atatttggaa gtgacctgga ttatgatcag gaaactatgt    540
tgcagaacgg caggaacaat tcaacaattg aagaccttgt ccacacattt gggtatccat    600
catgtttagg agctcttata atacagatct ggatagttct ggtcaaagct atcactagta    660
tctcagggtt aagaaaaggc ttttcaccc gattggaagc tttcagacaa gatggaacag    720
tgcaggcagg gctggtattg agcggtgaca cagtggatca gattgggtca atcatgcggt    780
ctcaacagag cttggtaact cttatggttg aaacattaat aacaatgaat accagcagaa    840
atgacctcac aaccatagaa aagaatatac aaattgttgg caactacata agagatgcag    900
gtctcgcttc attcttcaat acaatcagat atggaattga gaccagaatg gcagctttga    960
ctctatccac tctcagacca gatatcaata gattaaaagc tttgatggaa ctgtatttat   1020
caaagggacc acgcgctcct ttcatctgta tcctcagaga tcctatacat ggtgagttcg   1080
caccaggcaa ctatcctgcc atatggagct atgcaatggg ggtggcagtt gtacaaaata   1140
gagccatgca acagtatgtg acgggaagat catatctaga cattgatatg ttccagctag   1200
gacaagcagt agcacgtgat gccgaagctc aaatgagctc aacactggaa gatgaacttg   1260
gagtgacaca cgaatctaaa gaaagcttga agagacatat aaggaacata aacagttcag   1320
agacatcttt ccacaaaccg acaggtggat cagccataga gatggcaata gatgaagagc   1380
cagaacaatt cgaacataga gcagatcaag aacaaaatgg agaacctcaa tcatccataa   1440
ttcaatatgc ctgggcagaa ggaaatagaa gcgatgatca gactgagcaa gctacagaat   1500
ctgacaatat caagaccgaa caacaaaaca tcagagacag actaaacaag agactcaacg   1560
acaagaagaa acaaagcagt caaccaccca ctaatcccac aaacagaaca accaggacg   1620 aaatagatga tctgtttaac gcatttggaa gcaactaatc gaatcaacat tttaatctaa   1680
atcaataata aataagaaaa acttaggatt aaagaatcct atcataccgg aatatagggt   1740
ggtaaattta gagtctgctt gaaactcaat caatagagag ttgatggaaa gcgatgctaa   1800
```

```
aaactatcaa atcatggatt cttgggaaga ggaatcaaga gataaatcaa ctaatatctc    1860
ctcggccctc aacatcattg aattcatact cagcaccgac ccccaagaag acttatcgga    1920
aaacgacaca atcaacacaa gaacccagca actcagtgcc accatctgtc aaccagaaat    1980
caaaccaaca gaaacaagtg agaaagatag tggatcaact gacaaaaata gacagtccgg    2040
gtcatcacac gaatgtacaa cagaagcaaa agatagaaat attgatcagg aaactgtaca    2100
gagaggacct gggagaagaa gcagctcaga tagtagagct gagactgtgg tctctggagg    2160
aatccccaga agcatcacag attctaaaaa tggaacccaa aacacggagg atattgatct    2220
caatgaaatt agaaagatgg ataaggactc tattgagggg aaaatgcgac aatctgcaaa    2280
tgttccaagc gagatatcag gaagtgatga catatttaca acagaacaaa gtagaaacag    2340
tgatcatgga agaagcctgg aatctatcag tacacctgat acaagatcaa taagtgttgt    2400
tactgctgca acaccagatg atgaagaaga aatactaatg aaaaatagta ggacaaagaa    2460
aagttcttca acacatcaag aagatgacaa agaattaaaa aaggggaa aagggaaaga    2520 ctggtttaag aaatcaaaag ataccgacaa ccagatacca acatcagact acagatccac    2580
atcaaagggg cagaagaaaa tctcaaagac aacaaccacc aacaccgaca caaaggggca    2640
aacagaaata cagacagaat catcagaaac acaatcctca tcatggaatc tcatcatcga    2700
caacaacacc gaccggaacg aacagacaag cacaactcct ccaacaacaa cttccagatc    2760
aacttataca aagaatcga tccgaacaaa ctctgaatcc aaacccaaga cacaaaagac    2820
aaatggaaag gaaggaagg atacagaaga gagcaatcga tttacagaga gggcaattac    2880
tctattgcag aatcttggtg taattcaatc cacatcaaaa ctagatttat atcaagacaa    2940
acgagttgta tgtgtagcaa atgtactaaa caatgtagat actgcatcaa agatagattt    3000
cctggcagga ttagtcatag gggtttcaat ggacaacgac acaaaattaa cacagataca    3060
aaatgaaatg ctaaacctca aagcagatct aaagaaaatg gacgaatcac atagaagatt    3120
gatagaaaat caaagagaac aactgtcatt gatcacgtca ctaatttcaa atctcaaaat    3180
tatgactgag agaggaggaa agaaagacca aaatgaatcc aatgagagag tatccatgat    3240
caaaacaaaa ttgaaagaag aaaagatcaa gaagaccagg tttgacccac ttatggaggc    3300
acaaggcatt gacaagaata tacccgatct atatcgacat gcaggagata cactagagaa    3360
cgatgtacaa gttaaatcag agatattaag ttcatacaat gagtcaaatg caacaagact    3420
aataccccaa aaagtgagca gtacaatgag atcactagtt gcagtcatca acaacagcaa    3480
tctctcacaa agcacaaaac aatcatacat aaacgaactc aaacgttgca aaaatgatga    3540
agaagtatct gaattaatgg acatgttcaa tgaagatgtc aacaattgcc aatgatccaa    3600
caaagaaacg acaccgaaca aacagacaag aaacaacagt agatcaaaac ctgtcaacac    3660
acacaaaatc aagcagaatg aaacaacaga tatcaatcaa tatacaaata agaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac    3900
acggatcccg gtatttagat gtcttcttac tcggcttctt cgagatggaa cgaatcaaag    3960
acaaatacgg gagtgtgaat gatctcgaca gtgacccgag ttacaaagtt tgtggctctg    4020
gatcattacc aatcggattg gctaagtaca ctgggaatga ccaggaattg ttacaagccg    4080
caaccaaact ggatatagaa gtgagaagaa cagtcaaagc gaaagagatg gttgtttaca    4140
cggtacaaaa tataaaacca gaactgtacc catggtccaa tagactaaga aaaggaatgc    4200
```

```
tgttcgatgc caacaaagtt gctcttgctc ctcaatgtct tccactagat aggagcataa    4260
aatttagagt aatcttcgtg aattgtacgg caattggatc aataaccttg ttcaaaattc    4320
ctaagtcaat ggcatcacta tctctaccca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa aagaaaagta ggcagaatgt    4500
actctgttga atactgtaaa cagaaaatcg agaaatgag attgatattt tctttaggac     4560
tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740
ctttacctgg cgagttcaga tactatccta atattattgc aaaaggagtt gggaaaatca    4800
aacaatggaa ctagtaatct ctattttagt ccggacgtat ctattaagcc gaagcaaata    4860
aaggataatc aaaaacttag gacaaaagag gtcaatacca acaactatta gcagtcacac    4920
tcgcaagaat aagagagaag ggaccaaaaa agtcaaatag gagaaatcaa aacaaaaggt    4980
acagaacacc agaacaacaa aatcaaaaca tccaactcac tcaaaacaaa aattccaaaa    5040
gagaccggca acacaacaag cactgaacat gcatcacctg catccaatga tagtatgcat    5100
ttttgttatg tacactggaa ttgtaggttc agatgccatt gctggagatc aactcctcaa    5160
tgtagggctc attcaatcaa agataagatc actcatgtac tacactgatg gtggcgctag    5220
ctttattgtt gtaaaattac tacccaatct tcccccaagc aatggaacat gcaacatcac    5280
cagtctagat gcatataatg ttaccctatt taagttgcta acaccctga ttgagaacct     5340 gagcaaaatt tctgctgtta cagataccaa accccgccga gaacgatttg caggagtcgt    5400
tattgggctt gctgcactag gagtagctac agctgcacaa ataaccgcag ctgtagcaat    5460
agtaaaagcc aatgcaaatg ctgctgcgat aaacaatctt gcatcttcaa ttcaatccac    5520
caacaaggca gtatccgatg tgataactgc atcaagaaca attgcaaccg cagttcaagc    5580
gattcaggat cacatcaatg gagccattgt caacgggata acatctgcat catgccgtgc    5640
ccatgatgca ctaattgggt caatattaaa tttgtatctc actgagctta ctacaatatt    5700
tcataatcaa ataacaaacc ctgcgctgac accactttcc atccaagctt taagaatcct    5760
cctcggtagc accttgccaa ttgtcattga atccaaactc aacacaaaac tcaacacagc    5820
agagctgctc agtagcggac tgttaactgg tcaaataatt tccatttccc caatgtacat    5880
gcaaatgcta attcaaatca atgttccgac atttataatg caacccggtg cgaaggtaat    5940
tgatctaatt gctatctctg caaaccataa attacaagaa gtagttgtac aagttcctaa    6000
tagaattcta gaatatgcaa atgaactaca aaactaccca gccaatgatt gtttcgtgac    6060
accaaactct gtattttgta gatacaatga gggttccccg atccctgaat cacaatatca    6120
atgcttaagg gggaatctta attcttgcac ttttaccccct attatcggga actttctcaa    6180
gcgattcgca tttgccaatg gtgtgctcta tgccaactgc aaatctttgc tatgtaagtg    6240
tgccgaccct ccccatgttg tgtctcaaga tgacaaccaa ggcatcagca taattgatat    6300
taagaggtgc tctgagatga tgcttgacac ttttttcattt aggatcacat ctacattcaa    6360
tgctacatac gtgacagact tctcaatgat taatgcaaat attgtacatc taagtcctct    6420
agacttgtca aatcaaatca attcaataaa caaatctctt aaaagtgctg aggattggat    6480
tgcagatagc aacttcttcg ctaatcaagc cagaacagcc aagacacttt attcactaag    6540
tgcaatcgca ttaatactat cagtgattac tttggttgtt gtgggattgc tgattgccta    6600
```

```
catcatcaag tattacagaa ttcaaaagag aaatcgagtg gatcaaaatg acaagccata    6660
tgtactaaca aacaaataac atatctacag atcattagat attaaaatta taaaaaactt    6720
aggagtaaag ttacgcaatc caactctact catataattg aggaaggacc caatagacaa    6780
atccaaattc gagatggaat actggaagca taccaatcac ggaaaggatg ctggtaatga    6840
gctggagacg tctatggcta ctcatggcaa caagctcact aataagactg ccacaattct    6900
tggcatatgc acattaattg tgctatgttc aagtattctt catgagataa ttcatcttga    6960
tgtttcctct ggtcttatga attctgatga gtcacagcaa ggcattattc agcctatcat    7020
agaatcatta aaatcattga ttgctttggc caaccagatt ctatataatg ttgcaatagt    7080
aattcctctt aaaattgaca gtatcgaaac tgtaatactc tctgctttaa aagatatgca    7140
caccgggagt atgtccaatg ccaactgcac gccaggaaat ctgcttctgc atgatgcagc    7200
atacatcaat ggaataaaca aattccttgt acttgaatca tacaatggga cgcctaaata    7260
tggacctctc ctaaatatac ccagctttat cccctcagca acatctcccc atgggtgtac    7320
tagaatacca tcattttcac tcatcaagac ccattggtgt tacactcaca atgtaatgct    7380
tggagattgt cttgatttca cggcatctaa ccagtattta tcaatgggga taatacaaca    7440
atctgctgca gggtttccaa ttttcaggac tatgaaaacc atttacctaa gtgatggaat    7500
caatcgcaaa agctgttcag tcactgctat accaggaggt gtgtcttgt attgctatgt    7560 agctacaagg tctgaaaaag aagattatgc cacgactgat ctagctgaac tgagacttgc    7620
tttctattat tataatgata cctttattga aagagtcata tctcttccaa atacaacagg    7680
gcagtgggcc acaatcaacc ctgcagtcgg aagcgggatc tatcatctag ctttatctt    7740 atttcctgta tatggtggtc tcataaatgg gactacttct tacaatgagc agtcctcacg    7800
ctattttatc ccaaaacatc ccaacataac ttgtgccggt aactccagca acaggctgc    7860 aatagcacgg agttcctatg tcatccgtta tcactcaaac aggttaattc agagtgctgt    7920
tcttatttgt ccattgtctg acatgcatac agaagagtgt aatctagtta tgtttaacaa    7980
ttcccaagtc atgatgggtg cagaaggtag gctctatgtt attggtaata atttgtatta    8040
ttatcaacgc agttcctctt ggtggtctgc atcgctcttt tacaggatca atacagattt    8100
ttctaaagga attcctccga tcattgaggc tcaatgggta ccgtcctatc aagttcctcg    8160
tcctggagtc atgccatgca atgcaacaag tttttgccct gctaattgca tcacaggggt    8220
gtacgcagat gtgtggccgc ttaatgatcc agaactcatg tcacgtaatg ctctgaaccc    8280
caactatcga tttgctggag ccttttctcaa aaatgagtcc aaccgaacta atcccacatt    8340
ctacactgca tcggctaact ccctcttaaa tactaccgga ttcaacaaca ccaatcacaa    8400
agcagcatat acatcttcaa cctgctttaa aaacactgga acccaaaaaa tttattgttt    8460
aataataatt gaaatgggct catctctttt agggagttc caaataatac cattttttaag    8520 ggaactaatg ctttaatcat aattaaccat aatatgcatc aatctatcta taatacaagt    8580
atatgataag taatcagcaa tcagacaata gacaaaaggg aaatataaaa aacttaggag    8640
caaagcgtgc tcgggaaatg gacactgaat ctaacaatgg cactgtatct gacatactct    8700
atcctgagtg tcaccttaac tctcctatcg ttaaaggtaa aatagcacaa ttacacacta    8760
ttatgagtct acctcagcct tatgatatgg atgacgactc aatactagtt atcactagac    8820
agaaaataaa acttaataaa ttggataaaa gacaacgatc tattagaaga ttaaaattaa    8880
tattaactga aaaagtgaat gacttaggaa aatacacatt tatcagatat ccagaaatgt    8940
caaaagaaat gttcaaatta tatatacctg gtattaacag taaagtgact gaattattac    9000
```

-continued

```
ttaaagcaga tagaacatat agtcaaatga ctgatggatt aagagatcta tggattaatg    9060
tgctatcaaa attagcctca aaaaatgatg gaagcaatta tgatcttaat gaagaaatta    9120
ataatatatc gaaagttcac acaacctata aatcagataa atggtataat ccattcaaaa    9180
catggtttac tatcaagtat gatatgagaa gattacaaaa agctcgaaat gagatcactt    9240
ttaatgttgg gaaggattat aacttgttag aagaccagaa gaatttctta ttgatacatc    9300
cagaattggt tttgatatta gataaacaaa actataatgg ttatctaatt actcctgaat    9360
tagtattgat gtattgtgac gtagtcgaag gccgatggaa tataagtgca tgtgctaagt    9420
tagatccaaa attacaatct atgtatcaga aaggtaataa cctgtgggaa gtgatagata    9480
aattgtttcc aattatggga gaaaagacat tgatgtgat atcgttatta gaaccacttg     9540
cattatcctt aattcaaact catgatcctg ttaaacaact aagaggagct tttttaaatc    9600
atgtgttatc cgagatggaa ttaatatttg aatctagaga atcgattaag gaatttctga    9660
gtgtagatta cattgataaa attttagata tatttaataa gtctacaata gatgaaaatag   9720 cagagatttt ctcttttttt agaacatttg ggcatcctcc attagaagct agtattgcag    9780
cagaaaaggt tagaaaatat atgtatattg gaaaacaatt aaaatttgac actattaata    9840
aatgtcatgc tatcttctgt acaataataa ttaacggata tagagagagg catggtggac    9900
agtggcctcc tgtgacatta cctgatcatg cacacgaatt catcataaat gcttacggtt    9960
caaactctgc gatatcatat gaaaatgctg ttgattatta ccagagcttt ataggaataa    10020
aattcaataa attcatagag cctcagttag atgaggattt gacaatttat atgaaagata    10080
aagcattatc tccaaaaaaa tcaaattggg acacagttta tcctgcatct aatttactgt    10140
accgtactaa cgcatccaac gaatcacgaa gattagttga agtatttata gcagatagta    10200
aatttgatcc tcatcagata ttggattatg tagaatctgg ggactggtta gatgatccag    10260
aatttaatat ttcttatagt cttaaagaaa aagagatcaa acaggaaggt agactctttg    10320
caaaaatgac atacaaaatg agagctacac aagtttatc agagacacta cttgcaaata    10380
acataggaaa attctttcaa gaaaatggga tggtgaaggg agagattgaa ttacttaaga    10440
gattaacaac catatcaata tcaggagttc cacggtataa tgaagtgtac aataattcta    10500
aaagccatac agatgacctt aaaacctaca ataaaataag taatcttaat ttgtcttcta    10560
atcagaaatc aaagaaattt gaattcaagt caacggatat ctacaatgat ggatacgaga    10620
ctgtgagctg tttcctaaca acagatctca aaaaatactg tcttaattgg agatatgaat    10680
caacagctct atttggagaa acttgcaacc aaatatttgg attaaataaa ttgtttaatt    10740
ggttacaccc tcgtcttgaa ggaagtacaa tctatgtagg tgatccttac tgtcctccat    10800
cagataaaga acatatatca ttagaggatc accctgattc tggtttttac gttcataacc    10860
caagaggggg tatagaagga ttttgtcaaa aattatggac actcatatct ataagtgcaa    10920
tacatctagc agctgttaga ataggcgtga gggtgactgc aatggttcaa ggagacaatc    10980
aagctatagc tgtaaccaca agagtaccca acaattatga ctacagagtt aagaaggaga    11040
tagtttataa agatgtagtg agatttttg attcattaag agaagtgatg gatgatctag     11100
gtcatgaact taaattaaat gaaacgatta taagtagcaa gatgttcata tatagcaaaa    11160
gaatctatta tgatgggaga attcttcctc aagctctaaa agcattatct agatgtgtct    11220
tctggtcaga gacagtaata gacgaaacaa gatcagcatc ttcaaatttg gcaacatcat    11280
ttgcaaaagc aattgagaat ggttattcac ctgttctagg atatgcatgc tcaattttta    11340
agaatattca acaactatat attgcccttg ggatgaatat caatccaact ataacacaga    11400
```

```
atatcagaga tcagtatttt aggaatccaa attggatgca atatgcctct ttaatacctg   11460
ctagtgttgg gggattcaat tacatggcca tgtcaagatg tttttgtaagg aatattggtg   11520 atccatcagt tgccgcattg gctgatatta aaagatttat taaggcgaat ctattagacc   11580
gaagtgttct ttataggatt atgaatcaag aaccaggtga gtcatctttt ttggactggg   11640
cttcagatcc atattcatgc aatttaccac aatctcaaaa tataaccacc atgataaaaa   11700
atataacagc aaggaatgta ttacaagatt caccaaatcc attattatct ggattattca   11760
caaatacaat gatagaagaa gatgaagaat tagctgagtt cctgatggac aggaaggtaa   11820
ttctccctag agttgcacat gatattctag ataattctct cacaggaatt agaaatgcca   11880
tagctggaat gttagatacg acaaaatcac taattcgggt tggcataaat agaggaggac   11940
tgacatatag tttgttgagg aaaatcagta attacgatct agtacaatat gaaacactaa   12000
gtaggacttt gcgactaatt gtaagtgata aaatcaagta tgaagatatg tgttcggtag   12060
accttgccat agcattgcga caaaagatgt ggattcattt atcaggagga aggatgataa   12120
gtggacttga aacgcctgac ccattagaat tactatctgg ggtagtaata acaggatcag   12180
aacattgtaa aatatgttat tcttcagatg gcacaaaccc atatacttgg atgtatttac   12240
ccggtaatat caaaatagga tcagcagaaa caggtatatc gtcattaaga gttccttatt   12300
ttggatcagt cactgatgaa agatctgaag cacaattagg atatatcaag aatcttagta   12360
aacctgcaaa agccgcaata agaatagcaa tgatatatac atgggcattt ggtaatgatg   12420
agatatcttg gatggaagcc tcacagatag cacaaacacg tgcaaatttt acactagata   12480
gtctcaaaat tttaacaccg gtagctacat caacaaattt atcacacaga ttaaaggata   12540
ctgcaactca gatgaaattc tccagtacat cattgatcag agtcagcaga ttcataacaa   12600
tgtccaatga taacatgtct atcaaagaag ctaatgaaac caaagatact aatcttattt   12660
atcaacaaat aatgttaaca ggattaagtg ttttcgaata tttatttaga ttaaaagaaa   12720
ccacaggaca caaccctata gttatgcatc tgcacataga agatgagtgt tgtattaaag   12780
aaagttttaa tgatgaacat attaatccag agtctacatt agaattaatt cgatatcctg   12840
aaagtaatga atttatttat gataaagacc cactcaaaga tgtggactta tcaaaactta   12900
tggttattaa agaccattct tacacaattg atatgaatta ttgggatgat actgacatca   12960
tacatgcaat ttcaatatgt actgcaatta caatagcaga tactatgtca caattagatc   13020
gagataattt aaaagagata atagttattg caaatgatga tgatattaat agcttaatca   13080
ctgaattttt gactcttgac atacttgtat ttctcaagac atttggtgga ttattagtaa   13140
atcaatttgc atacactctt tatagtctaa aaatagaagg tagggatctc atttgggatt   13200
atataatgag aacactgaga gatacttccc attcaatatt aaaagtatta tctaatgcat   13260
tatctcatcc taaagtattc aagaggttct ggaattgtgg agttttaaac cctatttatg   13320
gtcctaatac tgctagtcaa gaccagataa aacttgccct atctatatgt gaatattcac   13380
tagatctatt tatgagagaa tggttgaatg gtgtatcact tgaaatatac atttgtgaca   13440
gcgatatgga agttgcaaat gataggaaac aagcctttat ttctagacac ctttcatttg   13500
tttgttgttt agcagaaatt gcatctttcg gacctaacct gttaaactta acatacttgg   13560
agagacttga tctattgaaa caatatcttg aattaaatat taagaagac cctactctta   13620 aatatgtaca aatatctgga ttattaatta atcgttccc atcaactgta acatacgtaa   13680
gaaagactgc aatcaaatat ctaaggattc gcggtattag tccacctgag gtaattgatg   13740
attgggatcc ggtagaagat gaaaatatgc tggataacat tgtcaaaact ataaatgata   13800
```

```
actgtaataa agataataaa gggaataaaa ttaacaattt ctggggacta gcacttaaga    13860
actatcaagt ccttaaaatc agatctataa caagtgattc tgatgataat gatagactag    13920
atgctaatac aagtggtttg acacttcctc aaggagggaa ttatctatcg catcaattga    13980
gattattcgg aatcaacagc actagttgtc tgaaagctct tgagttatca caaattttaa    14040
tgaaggaagt caataaagac aaggacaggc tcttcctggg agaaggagca ggagctatgc    14100
tagcatgtta tgatgccaca ttaggacctg cagttaatta ttataattca ggtttgaata    14160
taacagatgt aattggtcaa cgagaattga aaatatttcc ttcagaggta tcattagtag    14220
gtaaaaaatt aggaaatgtg acacagattc ttaacagggt aaaagtactg ttcaatggga    14280
atcctaattc aacatggata ggaaatatgg aatgtgagag cttaatatgg agtgaattaa    14340
atgataagtc cattggatta gtacattgtg atatggaagg agctatcggt aaatcagaag    14400
aaactgttct acatgaacat tatagtgtta taagaattac atacttgatt ggggatgatg    14460
atgttgtttt agtttccaaa attataccta caatcactcc gaattggtct agaatacttt    14520
atctatataa attatattgg aaagatgtaa gtataatatc actcaaaact tctaatcctg    14580
catcaacaga attatatcta atttcgaaag atgcatattg tactataatg gaacctagtg    14640
aaattgtttt atcaaaactt aaaagattgt cactcttgga agaaaataat ctattaaaat    14700
ggatcatttt atcaaagaag aggaataatg aatggttaca tcatgaaatc aagaaggag    14760
aaagagatta tggaatcatg agaccatatc atatggcact acaaatcttt ggatttcaaa    14820
tcaatttaaa tcatctggcg aaagaatttt tatcaacccc agatctgact aatatcaaca    14880
atataatcca aagttttcag cgaacaataa aggatgtttt atttgaatgg attaatataa    14940
ctcatgatga taagagacat aaattaggcg gaagatataa catattccca ctgaaaaata    15000
agggaaagtt aagactgcta tcgagaagac tagtattaag ttggatttca ttatcattat    15060
cgactcgatt acttacaggt cgcttttcctg atgaaaaatt tgaacataga gcacagactg    15120
gatatgtatc attagctgat actgatttag aatcattaaa gttattgtcg aaaaacatca    15180
ttaagaatta cagagagtgt ataggatcaa tatcatattg gtttctaacc aaagaagtta    15240
aaatacttat gaaattgatc ggtggtgcta aattattagg aattcccaga caatataaag    15300
aacccgaaga ccagttatta gaaaactaca atcaacatga tgaatttgat atcgattaaa    15360
acataaatac aatgaagata tatcctaacc tttatcttta agcctaggaa tagacaaaaa    15420
gtaagaaaaa catgtaatat atatatacca aacagagttc ttctcttgtt tggt          15474
```

<210> SEQ ID NO 176
<211> LENGTH: 10
<212> TYPE: DNA
<213> ORGANISM: Artificial Sequence
<220> FEATURE:
<223> OTHER INFORMATION: Chemically synthesized sequence flanking site
      for introduction of Bsi W1 site for rBPIV3 Ka.
<220> FEATURE:
<221> NAME/KEY: misc_feature
<222> LOCATION: (1)..(10)
<223> OTHER INFORMATION: Part of Parent Appln No 09/586,479 as SEQ ID
      NO: 06

<400> SEQUENCE: 176

```
gatataaaga                                                          10
```

<210> SEQ ID NO 177
<211> LENGTH: 10
<212> TYPE: DNA
<213> ORGANISM: Artificial Sequence

```
<220> FEATURE:
<223> OTHER INFORMATION: Chemically synthesized sequence flanking site
      for introduction of Bsi W1 site for rBPIV3 s.
<220> FEATURE:
<221> NAME/KEY: misc_feature
<222> LOCATION: (1)..(10)
<223> OTHER INFORMATION: Part of Parent Appln No 09/586,479 as SEQ ID
      NO: 07

<400> SEQUENCE: 177
gacgtacgga                                                          10

<210> SEQ ID NO 178
<211> LENGTH: 10
<212> TYPE: DNA
<213> ORGANISM: Artificial Sequence
<220> FEATURE:
<223> OTHER INFORMATION: Chemically synthesized sequence flanking site
      for introduction of Bsi W1 site forrHPIV3 JS.
<220> FEATURE:
<221> NAME/KEY: misc_feature
<222> LOCATION: (1)..(10)
<223> OTHER INFORMATION: Part of Parent Appln No 09/586,479 as SEQ ID
      NO: 08

<400> SEQUENCE: 178
gacaaaaggg                                                          10

<210> SEQ ID NO 179
<211> LENGTH: 10
<212> TYPE: DNA
<213> ORGANISM: Artificial Sequence
<220> FEATURE:
<223> OTHER INFORMATION: Chemically synthesized sequence flanking site
      for introduction of Bsi W1 site for rHPIV3 s.
<220> FEATURE:
<221> NAME/KEY: mis

```
atgaaaagac aactgattgg atatttggaa gtgacctgga ttatgatcag gaaactatgt    540
tgcagaacgg caggaacaat tcaacaattg aagaccttgt ccacacattt gggtatccat    600
catgtttagg agctcttata atacagatct ggatagttct ggtcaaagct atcactagta    660
tctcagggtt aagaaaaggc ttttcaccc gattggaagc tttcagacaa gatgaacag     720 tgcaggcagg gctggtattg agcggtgaca cagtggatca gattgggtca atcatgcggt    780
ctcaacagag cttggtaact cttatggttg aaacattaat aacaatgaat accagcagaa    840
atgacctcac aaccatagaa aagaatatac aaattgttgg caactacata agagatgcag    900
gtctcgcttc attcttcaat acaatcagat atggaattga gaccagaatg gcagctttga    960
ctctatccac tctcagacca gatatcaata gattaaaagc tttgatggaa ctgtatttat   1020
caaagggacc acgcgctcct ttcatctgta tcctcagaga tcctatacat ggtgagttcg   1080
caccaggcaa ctatcctgcc atatggagct atgcaatggg ggtggcagtt gtacaaaata   1140
gagccatgca acagtatgtg acgggaagat catatctaga cattgatatg ttccagctag   1200
gacaagcagt agcacgtgat gccgaagctc aaatgagctc aacactggaa gatgaacttg   1260
gagtgacaca cgaagctaaa gaaagcttga agagacatat aaggaacata aacagttcag   1320
agacatcttt ccacaaaccg acaggtggat cagccataga gatggcaata gatgaagagc   1380
cagaacaatt cgaacataga gcagatcaag aacaaaatgg agaacctcaa tcatccataa   1440
ttcaatatgc ctgggcagaa ggaaatagaa gcgatgatca gactgagcaa gctacagaat   1500
ctgacaatat caagaccgaa caacaaaaca tcagagacag actaaacaag agactcaacg   1560
acaagaagaa acaaagcagt caaccaccca ctaatcccac aaacagaaca accaggacg    1620 aaatagatga tctgtttaac gcatttggaa gcaactaatc gaatcaacat tttaatctaa   1680
atcaataata aataagaaaa acttaggatt aaagaatcct atcataccgg aatataggt    1740 ggtaaattta gagtctgctt gaaactcaat caatagagag ttgatggaaa gcgatgctaa   1800
aaactatcaa atcatggatt cttgggaaga ggaatcaaga gataaatcaa ctaatatctc   1860
ctcggccctc aacatcattg aattcatact cagcaccgac ccccaagaag acttatcgga   1920
aaacgacaca atcaacacaa gaacccagca actcagtgcc accatctgtc aaccagaaat   1980
caaaccaaca gaaacaagtg agaaagatag tggatcaact gacaaaaata gacagtctgg   2040
gtcatcacac gaatgtacaa cagaagcaaa agatagaaac attgatcagg aaactgtaca   2100
gagaggacct gggagaagaa gcagctcaga tagtagagct gagactgtgg tctctggagg   2160
aatccccaga agcatcacag attctaaaaa tggaacccaa acacggagg atattgatct    2220 caatgaaatt agaaagatgg ataaggactc tattgagggg aaaatgcgac aatctgcaaa   2280
tgttccaagc gagatatcag gaagtgatga catatttaca acagaacaaa gtagaaacag   2340
tgatcatgga agaagcctgg aatctatcag tacacctgat acaagatcaa taagtgttgt   2400
tactgctgca acaccagatg atgaagaaga aatactaatg aaaaatagta ggacaaagaa   2460
aagttcttca acacatcaag aagatgacaa aagaattaaa aaggggaa aagggaaaga    2520 ctggtttaag aaatcaaaag ataccgacaa ccagatacca acatcagact acagatccac   2580
atcaaagggg cagaagaaaa tctcaaagac aacaaccacc aacaccgaca caaaggggca   2640
aacagaaata cagacagaat catcagaaac acaatcctca tcatggaatc tcatcatcga   2700
caacaacacc gaccggaacg aacagacaag cacaactcct ccaacaacaa cttccagatc   2760
aacttataca aagaatcga tccgaacaaa ctctgaatcc aaaccaagaa cacaaaagac    2820
aaatggaaag gaaaggaagg atacagaaga gagcaatcga tttacagaga gggcaattac   2880
```

```
tctattgcag aatcttggtg taattcaatc cacatcaaaa ctagatttat atcaagacaa    2940
acgagttgta tgtgtagcaa atgtactaaa caatgtagat actgcatcaa agatagattt    3000
cctggcagga ttagtcatag gggtttcaat ggacaacgac acaaaattaa cacagataca    3060 aaaatgaaatg ctaaacctca aagcagatct aaagaaaatg gacgaatcac atagaagatt    3120
gatagaaaat caaagagaac aactgtcatt gatcacgtca ctaatttcaa atctcaaaat    3180
tatgactgag agaggaggaa agaaagacca aaatgaatcc aatgagagag tatccatgat    3240
caaaacaaaa ttgaaagaag aaaagatcaa gaagaccagg tttgacccac ttatggaggc    3300
acaaggcatt gacaagaata tacccgatct atatcgacat gcaggagata cactagagaa    3360
cgatgtacaa gttaaatcag agatattaag ttcatacaat gagtcaaatg caacaagact    3420
aatacccaaa aaagtgagca gtacaatgag atcactagtt gcagtcatca acaacagcaa    3480
tctctcacaa agcacaaaac aatcatacat aaacgaactc aaacgttgca aaaatgatga    3540
agaagtatct gaattaatgg acatgttcaa tgaagatgtc aacaattgcc aatgatccaa    3600
caaagaaacg acaccgaaca acagacaag aaacaacagt agatcaaaac ctgtcaacac    3660
acacaaaatc aagcagaatg aaacaacaga tatcaatcaa tatacaaata gaaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac    3900
acggatcccg gtatttagat gtcttcttac tcggcttctt cgagatggaa cgaatcaaag    3960
acaaatacgg gagtgtgaat gatctcgaca gtgacccgag ttacaaagtt tgtggctctg    4020
gatcattacc aatcggattg gctaagtaca ctgggaatga ccaggaattg ttacaagccg    4080
caaccaaact ggatatagaa gtgagaagaa cagtcaaagc gaaagagatg gttgtttaca    4140
cggtacaaaa tataaaacca gaactgtacc catggtccaa tagactaaga aaaggaatgc    4200
tgttcgatgc caacaaagtt gctcttgctc ctcaatgtct tccactagat aggagcataa    4260
aatttagagt aatcttcgtg aattgtacgg caattggatc aataaccttg ttcaaaattc    4320
ctaagtcaat ggcatcacta tcgttaacca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa aagaaaagta ggcagaatgt    4500
actctgttga atactgtaaa cagaaaatcg agaaaatgag attgatattt tctttaggac    4560
tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740
ctttacctgg cgagttcaga tactatccta atattattgc aaaaggagtt gggaaaatca    4800
aacaatggaa ctagtaatct ctattttagt ccggacgtat ctattaagcc gaagcaaata    4860
aaggataatc aaaaacttag gacaaaagag gtcaatacca caactatta gcagtcacac    4920 tcgcaagaat aagagagaag ggaccaaaaa agtcaaatag gagaaatcaa aacaaaaggt    4980
acagaacacc agaacaacaa aatcaaaaca tccaactcac tcaaaacaaa attccaaaa    5040 gagaccggca acacaacaag cactgaacac aatgccaact tcaatactgc taattattac    5100
aaccatgatc atggcatctt tctgccaaat agatatcaca aaactacagc acgtaggtgt    5160
attggtcaac agtcccaaag ggatgaagat atcacaaaac tttgaaacaa gatatctaat    5220
tttgagcctc ataccaaaaa tagaagactc taactcttgt ggtgaccaac agatcaagca    5280
```

```
atacaagaag ttattggata gactgatcat ccctttatat gatggattaa gattacagaa    5340
agatgtgata gtaaccaatc aagaatccaa tgaaaacact gatcccagaa caaaacgatt    5400
ctttggaggg gtaattggaa ccattgctct gggagtagca acctcagcac aaattacagc    5460
ggcagttgct ctggttgaag ccaagcaggc aagatcagac atcgaaaaac tcaaagaagc    5520
aattagggac acaaacaaag cagtgcagtc agttcagagc tccataggaa atttaatagt    5580
agcaattaaa tcagtccagg attatgttaa caaagaaatc gtgccatcga ttgcgaggct    5640
aggttgtgaa gcagcaggac ttcaattagg aattgcatta acacagcatt actcagaatt    5700
aacaaacata tttggtgata acataggatc gttacaagaa aaaggaataa aattacaagg    5760
tatagcatca ttataccgca caaatatcac agaaatattc acaacatcaa cagttgataa    5820
atatgatatc tatgatctgt tatttacaga atcaataaag gtgagagtta tagatgttga    5880
cttgaatgat tactcaatca ccctccaagt cagactccct ttattaacta ggctgctgaa    5940
cactcagatc tacaaagtag attccatatc atataacatc caaaacagag aatggtatat    6000
ccctcttccc agccatatca tgacgaaagg ggcatttcta ggtggagcag acgtcaaaga    6060
atgtatagaa gcattcagca gctatatatg cccttctgat ccaggatttg tattaaacca    6120
tgaaatagag agctgcttat caggaaacat atcccaatgt ccaagaacaa cggtcacatc    6180
agacattgtt ccaagatatg catttgtcaa tggaggagtg gttgcaaact gtataacaac    6240
cacctgtaca tgcaacggaa ttggtaatag aatcaatcaa ccacctgatc aaggagtaaa    6300
aattataaca cataaagaat gtagtactgt gggtatcaac ggaatgctgt tcaatacaaa    6360
taaagaagga actcttgcat tctatacacc aaatgatata acactaaaca attctgttac    6420
actggatcca attgacatat caatcgagct caacaaggcc aaatcagatc tagaagaatc    6480
aaaagaatgg ataagaaggt caaatcaaaa actagattct attggaaatt ggcatcaatc    6540
tagcactaca atcataatta ttttgataat gatcattata ttgtttataa ttaatataac    6600
gataattaca attgcaatta agtattacag aattcaaaag agaaatcgag tggatcaaaa    6660
tgacaagcca tatgtactaa caaacaaata acatatctac agatcattag atattaaaat    6720
tataaaaaac ttaggagtaa agttacgcaa tccaactcta ctcatataat tgaggaagga    6780
cccaatagac aaatccaaat tcgagatgga atactggaag cataccaatc acggaaagga    6840
tgctggtaat gagctggaga cgtctatggc tactcatggc aacaagctca ctaataagat    6900
aatatacata ttatggacaa taatcctggt gttattatca atagtcttca tcatagtgct    6960
aattaattcc atcaaaagtg aaaaggccca cgaatcattg ctgcaagaca taaataatga    7020
gtttatggaa attacagaaa agatccaaat ggcatcggat aataccaatg atctaataca    7080
gtcaggagtg aatacaaggc ttcttacaat tcagagtcat gtccagaatt acataccaat    7140
atcattgaca caacagatgt cagatcttag gaaattcatt agtgaaatta caattagaaa    7200
tgataatcaa gaagtgctgc cacaaagaat aacacatgat gtaggtataa aacctttaaa    7260
tccagatgat tttggagat  gcacgtctgg tcttccatct ttaatgaaaa ctccaaaaat    7320
aaggttaatg ccagggccgg gattattagc tatgccaacg actgttgatg gctgtgttag    7380
aactccgtct ttagttataa atgatctgat ttatgcttat acctcaaatc taattactcg    7440
aggttgtcag gatataggaa aatcatatca agtcttacag ataggataaa taactgtaaa    7500
ctcagacttg gtacctgact taaatcctag gatctctcat accttaacaa taaatgacaa    7560
taggaagtca tgttctctag cactcctaaa tatagatgta tatcaactgt gttcaactcc    7620
caaagttgat gaaagatcag attatgcatc atcaggcata gaagatattg tacttgatat    7680
```

```
tgtcaattat gatggttcaa tctcaacaac aagatttaag aataataaca taagctttga    7740
tcaaccatat gctgcactat acccatctgt tggaccaggg atatactaca aaggcaaaat    7800
aatatttctc gggtatggag gtcttgaaca tccaataaat gagaatgtaa tctgcaacac    7860
aactgggtgc cccgggaaaa cacagagaga ctgtaatcaa gcatctcata gtacttggtt    7920
ttcagatagg aggatggtca actccatcat tgtggctgac aaaggcttaa actcaattcc    7980
aaaattgaaa gtatggacga tatctatgcg acaaaattac tgggggtcag aaggaaggtt    8040
acttctacta ggtaacaaga tctatatata tacaagatct acaagttggc atagcaagtt    8100
acaattagga ataattgata ttactgatta cagtgatata aggataaaat ggacatggca    8160
taatgtgcta tcaagaccag gaaacaatga atgtccatgg ggacattcat gtccagatgg    8220
atgtataaca ggagtatata ctgatgcata tccactcaat cccacaggga gcattgtgtc    8280
atctgtcata ttagactcac aaaaatcgag agtgaaccca gtcataactt actcaacagc    8340
aaccgaaaga gtaaacgagc tggccatcct aaacagaaca ctctcagctg gatatacaac    8400
aacaagctgc attacacact ataacaaagg atattgtttt catatagtag aaataaatca    8460
taaaagctta aacacatttc aacccatgtt gttcaaaaca gagattccaa aaagctgcag    8520
ttaatcataa ttaaccataa tatgcatcaa tctatctata atacaagtat atgataagta    8580
atcagcaatc agacaataga caaaagggaa atataaaaaa cttaggagca aagcgtgctc    8640
gggaaatgga cactgaatct aacaatggca ctgtatctga catactctat cctgagtgtc    8700
accttaactc tcctatcgtt aaaggtaaaa tagcacaatt acacactatt atgagtctac    8760
ctcagcctta tgatatggat gacgactcaa tactagttat cactagacag aaaataaaac    8820
ttaataaatt ggataaaaga caacgatcta ttagaagatt aaaattaata ttaactgaaa    8880
aagtgaatga cttaggaaaa tacacatttta tcagatatcc agaaatgtca aaagaaatgt    8940
tcaaattata tatcctggt attaacagta aagtgactga attattactt aaagcagata    9000
gaacatatag tcaaatgact gatggattaa gagatctatg gattaatgtg ctatcaaaat    9060
tagcctcaaa aaatgatgga agcaattatg atcttaatga agaaattaat aatatatcga    9120
aagttcacac aacctataaa tcagataaat ggtataatcc attcaaaaca tggtttacta    9180
tcaagtatga tatgagaaga ttacaaaaag ctcgaaatga gatcactttt aatgttggga    9240
aggattataa cttgttagaa gaccagaaga atttcttatt gatacatcca gaattggttt    9300
tgatattaga taaacaaaac tataatggtt atctaattac tcctgaatta gtattgatgt    9360
attgtgacgt agtcgaaggc cgatggaata taagtgcatg tgctaagtta gatcaaaat    9420 tacaatctat gtatcagaaa ggtaataacc tgtgggaagt gatagataaa ttgtttccaa    9480
ttatgggaga aaagacattt gatgtgatat cgttattaga accacttgca ttatccttaa    9540
ttcaaactca tgatcctgtt aaacaactaa gaggagcttt tttaaatcat gtgttatccg    9600
agatggaatt aatatttgaa tctagagaat cgattaagga atttctgagt gtagattaca    9660
ttgataaaat tttagatata tttaataagt ctacaataga tgaaatagca gagatttct    9720 cttttttag aacatttggg catcctccat tagaagctag tattgcagca gaaaaggtta    9780
gaaaatatat gtatattgga aaacaattaa aatttgacac tattaataaa tgtcatgcta    9840
tcttctgtac aataataatt aacggatata gagagaggca tggtggacag tggcctcctg    9900
tgacattacc tgatcatgca cacgaattca tcataaatgc ttcggttca aactctgcga    9960 tatcatatga aaatgctgtt gattattacc agagctttat aggaataaaa ttcaataaat    10020
tcatagagcc tcagttagat gaggatttga caatttatat gaaagataaa gcattatctc    10080
```

```
caaaaaaatc aaattgggac acagtttatc ctgcatctaa tttactgtac cgtactaacg    10140
catccaacga atcacgaaga ttagttgaag tatttatagc agatagtaaa tttgatcctc    10200
atcagatatt ggattatgta gaatctgggg actggttaga tgatccagaa tttaatattt    10260
cttatagtct taaagaaaaa gagatcaaac aggaaggtag actctttgca aaaatgacat    10320
acaaaatgag agctacacaa gttttatcag agaccctact tgcaaataac ataggaaaat    10380
tctttcaaga aaatgggatg gtgaagggag agattgaatt acttaagaga ttaacaacca    10440
tatcaatatc aggagttcca cggtataatg aagtgtacaa taattctaaa agccatacag    10500
atgaccttaa aacctacaat aaaataagta atcttaattt gtcttctaat cagaaatcaa    10560
agaaatttga attcaagtca acggatatct acaatgatgg atacgagact gtgagctgtt    10620
tcctaacaac agatctcaaa aaatactgtc ttaattggag atatgaatca acagctctat    10680
ttggagaaac ttgcaaccaa atatttggat taaataaatt gtttaattgg ttacaccctc    10740
gtcttgaagg aagtacaatc tatgtaggtg atccttactg tcctccatca gataaagaac    10800
atatatcatt agaggatcac cctgattctg ttttttacgt tcataaccca agaggggta    10860 tagaaggatt ttgtcaaaaa ttatggacac tcatatctat aagtgcaata catctagcag    10920
ctgttagaat aggcgtgagg gtgactgcaa tggttcaagg agacaatcaa gctatagctg    10980
taaccacaag agtacccaac aattatgact acagagttaa gaaggagata gtttataaag    11040
atgtagtgag atttttttgat tcattaagag aagtgatgga tgatctaggt catgaactta    11100
aattaaatga aacgattata agtagcaaga tgttcatata tagcaaaaga atctattatg    11160
atgggagaat tcttcctcaa gctctaaaag cattatctag atgtgtcttc tggtcagaga    11220
cagtaataga cgaaacaaga tcagcatctt caaatttggc aacatcattt gcaaaagcaa    11280
ttgagaatgg ttattcacct gttctaggat atgcatgctc aatttttaag aatattcaac    11340
aactatatat tgcccttggg atgaaatca atccaactat aacacagaat atcagagatc    11400 agtatttag gaatccaaat tggatgcaat atgcctcttt aatacctgct agtgttgggg    11460
gattcaatca catggcgatg tcaagatgtt ttgtaaggaa tattggtgat ccatcagttg    11520
ccgcattggc tgatattaaa agattttatta aggcgaatct attagaccga agtgttcttt    11580
ataggattat gaatcaagaa ccaggtgagt catcttttt tgattgggct tcagatccat    11640
attcatgcaa tttaccacaa tctcaaaata taaccaccat gataaaaat ataacagcaa    11700 ggaatgtatt acaagattca ccaaatccat tattatctgg attattcaca aatacaatga    11760
tagaagaaga tgaagaatta gctgagttcc tgatggacag gaaggtaatt ctccctagag    11820
ttgcacatga tattctagat aattctctca caggaattag aaatgccata gctggaatgt    11880
tagatacgac aaaatcacta attccgggttg gcataaatag aggaggactg acatatagtt    11940
tgttgaggaa aatcagtaat tacgatctag tacaatatga aacactaagt aggactttgc    12000
gactaattgt aagtgataaa atcaagtatg aagatatgtg ttcggtagac cttgccatag    12060
cattgcgaca aaagatgtgg attcatttat caggaggaag gatgataagt ggacttgaaa    12120
cgcctgaccc attagaatta ctatctgggg tagtaataac aggatcagaa cattgtaaaa    12180
tatgttattc ttcagatggc acaaacccat atacttggat gtatttaccc ggtaatatca    12240
aaataggatc agcagaaaca ggtatatcgt cattaagagt tccttatttt ggatcagtca    12300
ctgatgaaag atctgaagca caattaggat atatcaagaa tcttagtaaa cctgcaaaag    12360
ccgcaataag aatagcaatg atatatcat gggcatttgg taatgatgag atatcttgga    12420
tggaagcctc acagatagca caaacacgtg caaatttac actagatagt ctcaaaattt    12480
```

```
taacaccggt agctacatca acaaatttat cacacagatt aaaggatact gcaactcaga   12540
tgaaattctc cagtacatca ttgatcagag tcagcagatt cataacaatg tccaatgata   12600
acatgtctat caaagaagct aatgaaacca aagatactaa tcttatttat caacaaataa   12660
tgttaacagg attaagtgtt ttcgaatatt tatttagatt aaaagaaacc acaggacaca   12720
accctatagt tatgcatctg cacatagaag atgagtgttg tattaaagaa agttttaatg   12780
atgaacatat taatccagag tctacattag aattaattcg atatcctgaa agtaatgaat   12840
ttatttatga taaagaccca ctcaaagatg tggacttatc aaaacttatg gttattaaag   12900
accattctta cacaattgat atgaattatt gggatgatac tgacatcata catgcaattt   12960
caatatgtac tgcaattaca atagcagata ctatgtcaca attagatcga gataatttaa   13020
aagagataat agttattgca aatgatgatg atattaatag cttaatcact gaattttga   13080 ctcttgacat acttgtattt ctcaagacat ttggtggatt attagtaaat caatttgcat   13140
acactcttta tagtctaaaa atagaaggta gggatctcat ttgggattat ataatgagaa   13200
cactgagaga tacttcccat tcaatattaa aagtattatc taatgcatta tctcatccta   13260
aagtattcaa gaggttctgg gattgtggag ttttaaaccc tatttatggg cctaatatcg   13320
ctagtcaaga ccagataaaa cttgccctat ctatatgtga atattcacta gatctattta   13380
tgagagaatg gttgaatggt gtatcacttg aaatatacat ttgtgacagc gatatggaag   13440
ttgcaaatga taggaaacaa gccttttattt ctagacacct ttcatttgtt tgttgtttag   13500
cagaaattgc atcttttcgga cctaacctgt taaacttaac atacttggag agacttgatc   13560
tattgaaaca atatcttgaa ttaaatatta agaagaccc tactcttaaa tatgtacaaa   13620
tatctggatt attaattaaa tcgttcccat caactgtaac atacgtaaga aagactgcaa   13680
tcaaatatct aaggattcgc ggtattagtc cacctgaggt aattgatgat tgggatccgg   13740
tagaagatga aaatatgctg gataacattg tcaaaactat aaatgataac tgtaataaag   13800
ataataaagg gaataaaatt aacaatttct ggggactagc acttaagaac tatcaagtcc   13860
ttaaaatcag atctataaca agtgattctg atgataatga tagactagat gctaatacaa   13920
gtggtttgac acttcctcaa ggagggaatt atctatcgca tcaattgaga ttattcggaa   13980
tcaacagcac tagttgtctg aaagctcttg agttatcaca aattttaatg aaggaagtca   14040
ataaagacaa ggacaggctc ttcctgggag aaggagcagg agctatgcta gcatgttatg   14100
atgccacatt aggacctgca gttaattatt ataattcagg tttgaatata acagatgtaa   14160
ttggtcaacg agaattgaaa atatttcctt cagaggtatc attagtaggt aaaaaattag   14220
gaaatgtgac acagattctt aacagggtaa aagtactgtt caatgggaat cctaattcaa   14280 catggatagaa aaatatggaa tgtgagagct taatatggag tgaattaaat gataagtcca   14340
ttggattagt acattgtgat atggaaggag ctatcggtaa atcagaagaa actgttctac   14400
atgaacatta tagtgttata agaattacat acttgattgg ggatgatgat gttgttttag   14460
tttccaaaat tatacctaca atcactccga attggtctag aatactttat ctatataaat   14520
tatattggaa agatgtaagt ataatatcac tcaaaacttc taatcctgca tcaacagaat   14580
tatatctaat ttcgaaagat gcatattgta ctataatgga acctagtgaa attgttttat   14640
caaaacttaa aagattgtca ctcttggaag aaaataatct attaaaatgg atcattttat   14700
caaagaagag gaataatgaa tggttacatc atgaaatcaa agaaggagaa agagattatg   14760
gaatcatgag accatatcat atggcactac aaatctttgg atttcaaatc aatttaaatc   14820
atctggcgaa agaatttta tcaaccccag atctgactaa tatcaacaat ataatccaaa   14880
```

```
gttttcagcg aacaataaag gatgttttat ttgaatggat taatataact catgatgata      14940
agagacataa attaggcgga agatataaca tattcccact gaaaaataag ggaaagttaa      15000
gactgctatc gagaagacta gtattaagtt ggatttcatt atcattatcg actcgattac      15060
ttacaggtcg ctttcctgat gaaaaatttg aacatagagc acagactgga tatgtatcat      15120
tagctgatac tgatttagaa tcattaaagt tattgtcgaa aaacatcatt aagaattaca      15180
gagagtgtat aggatcaata tcatattggt ttctaaccaa agaagttaaa atacttatga      15240
aattgatcgg tggtgctaaa ttattaggaa ttcccagaca atataaagaa cccgaagacc      15300
agttattaga aaactacaat caacatgatg aatttgatat cgattaaaac ataaatacaa      15360
tgaagatata tcctaacctt tatctttaag cctaggaata gacaaaaagt aagaaaaaca      15420
tgtaatatat ataccaaa  cagagttcct ctcttgtttg gt                         15462
```

<210> SEQ ID NO 181
<211> LENGTH: 24
<212> TYPE: DNA
<213> ORGANISM: Artificial Sequence
<220> FEATURE:
<223> OTHER INFORMATION: Sequence spanning PIV3 F 5' ntr and PIV2 F
      ectodomain.
<220> FEATURE:
<221> NAME/KEY: misc_feature
<222> LOCATION: (1)..(24)
<223> OTHER INFORMATION: Part of Parent Appln No 09/459,062 as SEQ ID NO: 42

<400> SEQUENCE: 181
caagcactga acatgcatca cctg 24

<210> SEQ ID NO 182
<211> LENGTH: 30
<212> TYPE: DNA
<213> ORGANISM: Artificial Sequence
<220> FEATURE:
<223> OTHER INFORMATION: Chemically synthesized sequence.
<220> FEATURE:
<221> NAME/KEY: misc_feature
<222> LOCATION: (1)..(30)
<223> OTHER INFORMATION: Part of Parent Appln No 09/083,793 as SEQ ID NO: 31

<400> SEQUENCE: 182
gcattatcta gatgtgtctt ctggtcagag 30

<210> SEQ ID NO 183
<211> LENGTH: 15492
<212> TYPE: DNA
<213> ORGANISM: Artificial Sequence
<220> FEATURE:
<221> NAME/KEY: misc_feature
<222> LOCATION: (1)..(15492)
<223> OTHER INFORMATION: Part of Parent Appln No 09/733,692 as SEQ ID NO: 62

<400> SEQUENCE: 183
accaaacaag agaagaaact tgtctgggaa tataaattta actttaaatt aacttaggat 60
taaagacatt gactagaagg tcaagaaaag ggaactctat aatttcaaaa atgttgagcc 120
tatttgatac atttaatgca cgtaggcaag aaaacataac aaaatcagcc ggtggagcta 180
tcattcctgg acagaaaaat actgtctcta tattcgccct tggaccgaca ataactgatg 240
ataatgagaa aatgacatta gctcttctat ttctatctca ttcactagat aatgagaaac 300
aacatgcaca aagggcaggg ttcttggtgt ctttattgtc aatggcttat gccaatccag 360

-continued

```
agctctacct aacaacaaat ggaagtaatg cagatgtcaa gtatgtcata tacatgattg    420
agaaagatct aaaacggcaa aagtatggag gatttgtggt taagacgaga gagatgatat    480
atgaaaagac aactgattgg atatttggaa gtgacctgga ttatgatcag gaaactatgt    540
tgcagaacgg caggaacaat tcaacaattg aagaccttgt ccacacattt gggtatccat    600
catgtttagg agctcttata atacagatct ggatagttct ggtcaaagct atcactagta    660
tctcagggtt aagaaaaggc ttttcaccc gattggaagc tttcagacaa gatggaacag    720
tgcaggcagg gctggtattg agcggtgaca cagtggatca gattgggtca atcatgcggt    780
ctcaacagag cttggtaact cttatggttg aaacattaat aacaatgaat accagcagaa    840
atgacctcac aaccatagaa aagaatatac aaattgttgg caactacata agagatgcag    900
gtctcgcttc attcttcaat acaatcgat atggaattga gaccagaatg gcagctttga     960
ctctatccac tctcagacca gatatcaata gattaaaagc tttgatggaa ctgtatttat   1020
caaagggacc acgcgctcct ttcatctgta tcctcagaga tcctatacat ggtgagttcg   1080
caccaggcaa ctatcctgcc atatggagct atgcaatggg ggtggcagtt gtacaaaata   1140
gagccatgca acagtatgtg acgggaagat catatctaga cattgatatg ttccagctag   1200
gacaagcagt agcacgtgat gccgaagctc aaatgagctc aacactggaa gatgaacttg   1260
gagtgacaca cgaatctaaa gaaagcttga gagacatat aaggaacata aacagttcag   1320
agacatcttt ccacaaaccg acaggtggat cagccataga gatggcaata gatgaagagc   1380
cagaacaatt cgaacataga gcagatcaag aacaaaatgg agaacctcaa tcatccataa   1440
ttcaatatgc ctgggcagaa ggaaatagaa gcgatgatca gactgagcaa gctacagaat   1500
ctgacaatat caagaccgaa caacaaaaca tcagagacag actaaacaag agactcaacg   1560
acaagaagaa acaaagcagt caaccaccca ctaatcccac aaacagaaca aaccaggacg   1620
aaatagatga tctgtttaac gcatttggaa gcaactaatc gaatcaacat tttaatctaa   1680
atcaataata aataagaaaa acttaggatt aaagaatcct atcataccgg aatataggt    1740 ggtaaattta gagtctgctt gaaactcaat caatagagag ttgatggaaa gcgatgctaa   1800
aaactatcaa atcatggatt cttgggaaga ggaatcaaga gataaatcaa ctaatatctc   1860
ctcggccctc aacatcattg aattcatact cagcaccgac ccccaagaag acttatcgga   1920
aaacgacaca atcaacacaa gaacccagca actcagtgcc accatctgtc aaccagaaat   1980
caaaccaaca gaaacaagtg agaaagatag tggatcaact gacaaaaata gacagtccgg   2040
gtcatcacac gaatgtacaa cagaagcaaa agatagaaat attgatcagg aaactgtaca   2100
gagaggacct gggagaagaa gcagctcaga tagtagagct gagactgtgg tctctggagg   2160
aatccccaga agcatcacag attctaaaaa tggaacccaa aacacggagg atattgatct   2220
caatgaaatt agaaagatgg ataaggactc tattgagggg aaaatgcgac aatctgcaaa   2280
tgttccaagc gagatatcag gaagtgatga catatttaca acagaacaaa gtagaaacag   2340
tgatcatgga agaagcctgg aatctatcag tacacctgat acaagatcaa taagtgttgt   2400
tactgctgca acaccagatg atgaagaaga aatactaatg aaaaatagta ggacaaagaa   2460
aagttcttca acacatcaag aagatgacaa aagaattaaa aaggggaa aagggaaaga    2520 ctggtttaag aaatcaaaag ataccgacaa ccagatacca acatcagact acagatccac   2580
atcaaagggg cagaagaaaa tctcaaagac aacaaccacc aacaccgaca caaaggggca   2640
aacagaaata cagacagaat catcagaaac acaatcctca tcatggaatc tcatcatcga   2700
caacaacacc gaccggaacg aacagacaag cacaactcct ccaacaacaa cttccagatc   2760
```

```
aacttataca aaagaatcga tccgaacaaa ctctgaatcc aaacccaaga cacaaaagac    2820
aaatggaaag gaaaggaagg atacagaaga gagcaatcga tttacagaga gggcaattac    2880
tctattgcag aatcttggtg taattcaatc cacatcaaaa ctagatttat atcaagacaa    2940
acgagttgta tgtgtagcaa atgtactaaa caatgtagat actgcatcaa agatagattt    3000
cctggcagga ttagtcatag gggtttcaat ggacaacgac acaaaattaa cacagataca    3060
aaatgaaatg ctaaacctca aagcagatct aaagaaaatg gacgaatcac atagaagatt    3120
gatagaaaat caagagaac aactgtcatt gatcacgtca ctaatttcaa atctcaaaat    3180
tatgactgag agaggaggaa agaaagacca aaatgaatcc aatgagagag tatccatgat    3240
caaaacaaaa ttgaaagaag aaaagatcaa gaagaccagg tttgacccac ttatggaggc    3300
acaaggcatt gacaagaata tacccgatct atatcgacat gcaggagata cactagagaa    3360
cgatgtacaa gttaaatcag agatattaag ttcatacaat gagtcaaatg caacaagact    3420
aatacccaaa aaagtgagca gtacaatgag atcactagtt gcagtcatca acaacagcaa    3480
tctctcacaa agcacaaaac aatcatacat aaacgaactc aaacgttgca aaaatgatga    3540
agaagtatct gaattaatgg acatgttcaa tgaagatgtc aacaattgcc aatgatccaa    3600
caaagaaacg acaccgaaca acagacaag aaacaacagt agatcaaaac ctgtcaacac    3660
acacaaaatc aagcagaatg aaacaacaga tatcaatcaa tatacaaata agaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac    3900
acggatcccg gtatttagat gtcttcttac tcggcttctt cgagatggaa cgaatcaaag    3960
acaaatacgg gagtgtgaat gatctcgaca gtgacccgag ttacaaagtt tgtggctctg    4020
gatcattacc aatcggattg gctaagtaca ctgggaatga ccaggaattg ttacaagccg    4080
caaccaaact ggatatagaa gtgagaagaa cagtcaaagc gaaagagatg gttgtttaca    4140
cggtacaaaa tataaaacca gaactgtacc catggtccaa tagactaaga aaaggaatgc    4200
tgttcgatgc caacaaagtt gctcttgctc ctcaatgtct tccactagat aggagcataa    4260
aatttagagt aatcttcgtg aattgtacgg caattggatc aataaccttg ttcaaaattc    4320
ctaagtcaat ggcatcacta tctctaccca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa aagaaaagta ggcagaatgt    4500
actctgttga atactgtaaa cagaaaatcg agaaatgag attgatattt tctttaggac    4560
tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740
ctttacctgg cgagttcaga tactatccta atattattgc aaaaggagtt gggaaaatca    4800
aacaatggaa ctagtaatct ctattttagt ccggacgtat ctattaagcc gaagcaaata    4860
aaggataatc aaaaacttag gacaaaagag gtcaatacca acaactatta gcagtcacac    4920
tcgcaagaat aagagagaag ggaccaaaaa agtcaaatag gagaaatcaa aacaaaaggt    4980
acagaacacc agaacaacaa aatcaaaaca tccaactcac tcaaaacaaa aattccaaaa    5040
gagaccggca acacaacaag cactgaacac catggatcac ctgcatccaa tgatagtatg    5100
catttttgtt atgtacactg gaattgtagg ttcagatgcc attgctggag atcaactcct    5160
```

```
caatgtaggg gtcattcaat caaagataag atcactcatg tactacactg atggtggcgc    5220
tagctttatt gttgtaaaat tactacccaa tcttccccca agcaatggaa catgcaacat    5280
caccagtcta gatgcatata atgttaccct atttaagttg ctaacacccc tgattgagaa    5340
cctgagcaaa atttctgctg ttacagatac caaaccccgc cgagaacgat ttgcaggagt    5400
cgttattggg cttgctgcac taggagtagc tacagctgca caaataaccg cagctgtagc    5460
aatagtaaaa gccaatgcaa atgctgctgc gataaacaat cttgcatctt caattcaatc    5520
caccaacaag gcagtatccg atgtgataac tgcatcaaga acaattgcaa ccgcagttca    5580
agcgattcag gatcacatca atggagccat tgtcaacggg ataacatctg catcatgccg    5640
tgcccatgat gcactaattg ggtcaatatt aaatttgtat ctcactgagc ttactacaat    5700
atttcataat caaataacaa accctgcgct gacaccactt tccatccaag ctttaagaat    5760
cctcctcggt agcaccttgc caattgtcat tgaatccaaa ctcaacacaa aactcaacac    5820
agcagagctg ctcagtagcg gactgttaac tggtcaaata atttccattt ccccaatgta    5880
catgcaaatg ctaattcaaa tcaatgttcc gacatttata atgcaacccg gtgcgaaggt    5940
aattgatcta attgctatct ctgcaaacca taaattacaa gaagtagttg tacaagttcc    6000
taatagaatt ctagaatatg caaatgaact acaaaactac ccagccaatg attgtttcgt    6060
gacaccaaac tctgtatttt gtagatacaa tgagggttcc ccgatccctg aatcacaata    6120
tcaatgctta aggggaatc ttaattcttg cacttttacc cctattatcg ggaactttct    6180
caagcgattc gcatttgcca atggtgtgct ctatgccaac tgcaaatctt tgctatgtaa    6240
gtgtgccgac cctccccatg ttgtgtctca agatgacaac caaggcatca gcataattga    6300
tattaagagg tgctctgaga tgatgcttga cacttttttca tttaggatca catctacatt    6360
caatgctaca tacgtgacag acttctcaat gattaatgca aatattgtac atctaagtcc    6420
tctagacttg tcaaatcaaa tcaattcaat aaacaaatct cttaaaagtg ctgaggattg    6480
gattgcagat agcaacttct tcgctaatca agccagaaca gccaagacac tttattcact    6540
aagtgcaatc gcattaatac tatcagtgat tactttggtt gttgtgggat tgctgattgc    6600
ctacatcatc aagctggttt ctcaaatcca tcaattcaga gcactagctg ctacaacaat    6660
gttccacagg gagaatcctg ccgtcttttc caagaacaat catggaaaca tatatgggat    6720
atcttaggat ccctacagat cattagatat taaaattata aaaaacttag gagtaaagtt    6780
acgcaatcca actctactca tataattgag gaaggaccca atagacaaat ccaaatccat    6840
ggaagattac agcaatctat ctcttaaatc aattcctaaa aggacatgta gaatcatttt    6900
ccgaactgcc acaattcttg gcatatgcac attaattgtg ctatgttcaa gtattcttca    6960
tgagataatt catcttgatg tttcctctgg tcttatgaat tctgatgagt cacagcaagg    7020
cattattcag cctatcatag aatcattaaa atcattgatt gctttggcca accagattct    7080
atataatgtt gcaatagtaa ttcctctctaa aattgacagt atcgaaactg taatactctc    7140
tgctttaaaa gatatgcaca ccgggagtat gtccaatgcc aactgcacgc caggaaatct    7200
gcttctgcat gatgcagcat acatcaatgg aataaacaaa ttccttgtac ttgaatcata    7260
caatgggacg cctaaatatg gacctctcct aaatataccc agctttatcc cctcagcaac    7320
atctccccat gggtgtacta gaataccatc attttcactc atcaagaccc attggtgtta    7380
cactcacaat gtaatgcttg gagattgtct tgatttcacg gcatctaacc agtatttatc    7440
aatggggata atacaacaat ctgctgcagg gtttccaatt ttcaggacta tgaaaaccat    7500
ttacctaagt gatggaatca atcgcaaaag ctgttcagtc actgctatac caggaggttg    7560
```

```
tgtcttgtat tgctatgtag ctacaaggtc tgaaaagaa gattatgcca cgactgatct      7620
agctgaactg agacttgctt tctattatta taatgatacc tttattgaaa gagtcatatc      7680
tcttccaaat acaacagggc agtgggccac aatcaaccct gcagtcggaa gcgggatcta      7740
tcatctaggc tttatcttat ttcctgtata tggtggtctc ataaatggga ctacttctta      7800
caatgagcag tcctcacgct attttatccc aaaacatccc aacataactt gtgccggtaa      7860
ctccagcaaa caggctgcaa tagcacggag ttcctatgtc atccgttatc actcaaacag      7920
gttaattcag agtgctgttc ttatttgtcc attgtctgac atgcatacag aagagtgtaa      7980
tctagttatg tttaacaatt cccaagtcat gatgggtgca gaaggtaggc tctatgttat      8040
tggtaataat ttgtattatt atcaacgcag ttcctcttgg tggtctgcat cgctcttta      8100 caggatcaat acagattttt ctaaaggaat tcctccgatc attgaggctc aatgggtacc      8160
gtcctatcaa gttcctcgtc ctggagtcat gccatgcaat gcaacaagtt tttgccctgc      8220
taattgcatc acaggggtgt acgcagatgt gtggccgctt aatgatccag aactcatgtc      8280
acgtaatgct ctgaaccca actatcgatt tgctggagcc tttctcaaaa atgagtccaa      8340
ccgaactaat cccacattct acactgcatc ggctaactcc ctcttaaata ctaccggatt      8400
caacaacacc aatcacaaag cagcatatac atcttcaacc tgctttaaaa acactggaac      8460
ccaaaaaatt tattgtttaa taataattga aatgggctca tctcttttag gggagttcca      8520
aataatacca tttttaaggg aactaatgct ttaagcttaa ttaaccataa tatgcatcaa      8580
tctatctata atacaagtat atgataagta atctgcaatc agacaataga caaaagggaa      8640
atataaaaaa cttaggagca aagcgtgctc gggaaatgga cactgaatct aacaatggca      8700
ctgtatctga catactctat cctgagtgtc accttaactc tcctatcgtt aaaggtaaaa      8760
tagcacaatt acacactatt atgagtctac ctcagcctta tgatatggat gacgactcaa      8820
tactagttat cactgacag aaaataaaac ttaataaatt ggataaaaga caacgatcta      8880
ttagaagatt aaaattaata ttaactgaaa aagtgaatga cttaggaaaa tacacattta      8940
tcagatatcc agaaatgtca aagaaatgt tcaaattata tatacctggt attaacagta      9000
aagtgactga attattactt aaagcagata gaacatatag tcaaatgact gatggattaa      9060
gagatctatg gattaatgtg ctatcaaaat tagcctcaaa aaatgatgga agcaattatg      9120
atcttaatga agaaattaat aatatatcga agttcacac aacctataaa tcagataaat      9180
ggtataatcc attcaaaaca tggtttacta tcaagtatga tatgagaaga ttacaaaaag      9240
ctcgaaatga gatcacttt aatgttggga aggattataa cttgttagaa gaccagaaga      9300
atttcttatt gatacatcca gaattggttt tgatattaga taaacaaaac tataatggtt      9360
atctaattac tcctgaatta gtattgatgt attgtgacgt agtcgaaggc cgatggaata      9420
taagtgcatg tgctaagtta gatccaaaat tacaatctat gtatcagaaa ggtaataacc      9480
tgtgggaagt gatagataaa ttgtttccaa ttatgggaga aaagacattt gatgtgatat      9540
cgttattaga accacttgca ttatccttaa ttcaaactca tgatcctgtt aaacaactaa      9600
gaggagcttt tttaaatcat gtgttatccg agatggaatt aatatttgaa tctagagaat      9660
cgattaagga atttctgagt gtagattaca ttgataaaat tttagatata tttaataagt      9720
ctacaataga tgaaatagca gagattttct cttttttag aacatttggg catcctccat      9780
tagaagctag tattgcagca gaaaaggtta gaaaatatat gtatattgga aaacaattaa      9840
aatttgacac tattaataaa tgtcatgcta tcttctgtac aataataatt aacgatata      9900 gagagaggca tggtggacag tggcctcctg tgacattacc tgatcatgca cacgaattca      9960
```

```
tcataaatgc ttacggttca aactctgcga tatcatatga aaatgctgtt gattattacc    10020
agagctttat aggaataaaa ttcaataaat tcatagagcc tcagttagat gaggatttga    10080
caatttatat gaaagataaa gcattatctc caaaaaaatc aaattgggac acagtttatc    10140
ctgcatctaa tttactgtac cgtactaacg catccaacga atcacgaaga ttagttgaag    10200
tatttatagc agatagtaaa tttgatcctc atcagatatt ggattatgta gaatctgggg    10260
actggttaga tgatccagaa tttaatattt cttatagtct taaagaaaaa gagatcaaac    10320
aggaaggtag actctttgca aaaatgacat acaaaatgag agctacacaa gttttatcag    10380
agaccctact tgcaaataac ataggaaaat tctttcaaga aaatgggatg gtgaagggag    10440
agattgaatt acttaagaga ttaacaacca tatcaatatc aggagttcca cggtataatg    10500
aagtgtacaa taattctaaa agccatacag atgaccttaa aacctacaat aaaataagta    10560 atcttaatttt gtcttctaat cagaaatcaa agaaatttga attcaagtca acggatatct    10620
acaatgatgg atacgagact gtgagctgtt cctaacaac agatctcaaa aaatactgtc    10680
ttaattggag atatgaatca acagctctat ttggagaaac ttgcaaccaa atatttggat    10740
taaataaatt gtttaattgg ttacacccctc gtcttgaagg aagtacaatc tatgtaggtg    10800
atccttactg tcctccatca gataaagaac atatatcatt agaggatcac cctgattctg    10860 gttttttacgt tcataaccca agaggggggta tagaaggatt ttgtcaaaaa ttatggacac    10920
tcatatctat aagtgcaata catctagcag ctgttagaat aggcgtgagg gtgactgcaa    10980
tggttcaagg agacaatcaa gctatagctg taaccacaag agtacccaac aattatgact    11040
acagagttaa gaaggagata gtttataaag atgtagtgag attttttgat tcattaagag    11100
aagtgatgga tgatctaggt catgaactta aattaaatga aacgattata agtagcaaga    11160
tgttcatata tagcaaaaga atctattatg atgggagaat tcttcctcaa gctctaaaag    11220
cattatctag atgtgtcttc tggtcagaga cagtaataga cgaaacaaga tcagcatctt    11280
caaatttggc aacatcattt gcaaaagcaa ttgagaatgg ttattcacct gttctaggat    11340
atgcatgctc aattttttaag aatattcaac aactatatat tgcccttggg atgaatatca    11400
atccaactat aacacagaat atcagagatc agtattttag gaatccaaat tggatgcaat    11460
atgcctcttt aatacctgct agtgttgggg gattcaatta catggccatg tcaagatgtt    11520
ttgtaaggaa tattggtgat ccatcagttg ccgcattggc tgatattaaa agatttatta    11580
aggcgaatct attagaccga agtgttcttt ataggattat gaatcaagaa ccaggtgagt    11640
catctttttt ggactgggct tcagatccat attcatgcaa tttaccacaa tctcaaaata    11700
taaccaccat gataaaaaat ataacagcaa ggaatgtatt acaagattca ccaaatccat    11760
tattatctgg attattcaca aatacaatga gaagaagaa tgaagaatta gctgagttcc    11820
tgatggacag gaaggtaatt ctccctagag ttgcacatga tattctagat aattctctca    11880
caggaattag aaatgccata gctggaatgt tagatacgac aaaatcacta attcgggttg    11940
gcataaatag aggaggactg acatatagtt tgttgaggaa aatcagtaat tacgatctag    12000
tacaatatga aacactaagt aggactttgc gactaattgt aagtgataaa atcaagtatg    12060
aagatatgtg ttcggtagac cttgccatag cattgcgaca aaagatgtgg attcatttat    12120
caggaggaag gatgataagt ggacttgaaa cgcctgaccc attagaatta ctatctgggg    12180
tagtaataac aggatcagaa cattgtaaaa tatgttatcc ttcagatggc acaaacccat    12240
atacttggat gtatttaccc ggtaatatca aaataggatc agcagaaaca ggtatatcgt    12300
cattaagagt tccttatttt ggatcagtca ctgatgaaag atctgaagca caattaggat    12360
```

```
atatcaagaa tcttagtaaa cctgcaaaag ccgcaataag aatagcaatg atatatacat   12420
gggcatttgg taatgatgag atatcttgga tggaagcctc acagatagca caaacacgtg   12480
caaattttac actagatagt ctcaaaattt taacaccggt agctacatca acaaatttat   12540
cacacagatt aaaggatact gcaactcaga tgaaattctc cagtacatca ttgatcagag   12600
tcagcagatt cataacaatg tccaatgata acatgtctat caaagaagct aatgaaacca   12660
aagatactaa tcttatttat caacaaataa tgttaacagg attaagtgtt ttcgaatatt   12720
tatttagatt aaaagaaacc acaggacaca accctatagt tatgcatctg cacatagaag   12780
atgagtgttg tattaaagaa agttttaatg atgaacatat taatccagag tctacattag   12840
aattaattcg atatcctgaa agtaatgaat ttatttatga taaagaccca ctcaaagatg   12900
tggacttatc aaaacttatg gttattaaag accattctta cacaattgat atgaattatt   12960
gggatgatac tgacatcata catgcaattt caatatgtac tgcaattaca atagcagata   13020
ctatgtcaca attagatcga gataatttaa aagagataat agttattgca aatgatgatg   13080
atattaatag cttaatcact gaattttga ctcttgacat acttgtattt ctcaagacat   13140
ttggtggatt attagtaaat caatttgcat acactcttta tagtctaaaa atagaaggta   13200
gggatctcat ttgggattat ataatgagaa cactgagaga tacttcccat tcaatattaa   13260
aagtattatc taatgcatta tctcatccta agtattcaa gaggtctgg gattgtggag   13320 ttttaaaccc tatttatggt cctaatactg ctagtcaaga ccagataaaa cttgccctat   13380
ctatatgtga atattcacta gatctattta tgagagaatg gttgaatggt gtatcacttg   13440
aaatatacat ttgtgacagc gatatggaag ttgcaaatga taggaaacaa gcctttattt   13500
ctagacacct ttcatttgtt tgttgtttag cagaaattgc atctttcgga cctaacctgt   13560
taaacttaac atacttggag agacttgatc tattgaaaca atatcttgaa ttaaatatta   13620
aagaagaccc tactcttaaa tatgtacaaa tatctggatt attaattaaa tcgttcccat   13680
caactgtaac atacgtaaga aagactgcaa tcaaatatct aaggattcgc ggtattagtc   13740
cacctgaggt aattgatgat tgggatccgg tagaagatga aaatatgctg gataacattg   13800
tcaaaactat aaatgataac tgtaataaag ataataaagg gaataaaatt aacaatttct   13860
ggggactagc acttaagaac tatcaagtcc ttaaaatcag atctataaca agtgattctg   13920
atgataatga tagactagat gctaatacaa gtggtttgac acttcctcaa ggagggaatt   13980
atctatcgca tcaattgaga ttattcggaa tcaacagcac tagttgtctg aaagctcttg   14040
agttatcaca aattttaatg aaggaagtca ataaagacaa ggacaggctc ttcctgggag   14100
aaggagcagg agctatgcta gcatgttatg atgccacatt aggacctgca gttaattatt   14160
ataattcagg tttgaatata acagatgaa ttggtcaacg agaattgaaa atatttcctt   14220
cagaggtatc attagtaggt aaaaaattag gaaatgtgac acagattctt aacagggtaa   14280
aagtactgtt caatgggaat cctaattcaa catggatagg aaatatgaa tgtgagagct   14340 taatatggag tgaattaaat gataagtcca ttggattagt acattgtgat atggaaggag   14400
ctatcggtaa atcagaagaa actgttctac atgaacatta tagtgttata agaattacat   14460
acttgattgg ggatgatgat gttgttttag tttccaaaat tataacctaca atcactccga   14520 attggtctag aatactttat ctatataaat tatattggaa agatgtaagt ataatatcac   14580
tcaaaacttc taatcctgca tcaacagaat tatatctaat ttcgaaagat gcatattgta   14640
ctataatgga acctagtgaa attgtttat caaaacttaa aagattgtca ctcttggaag   14700
aaaataatct attaaaatgg atcattttat caaagaagag gaataatgaa tggttacatc   14760
```

-continued

```
atgaaatcaa agaaggagaa agagattatg gaatcatgag accatatcat atggcactac    14820
aaatctttgg atttcaaatc aatttaaatc atctggcgaa agaattttta tcaacccag     14880 atctgactaa tatcaacaat ataatccaaa gttttcagcg aacaataaag gatgttttat    14940
ttgaatggat taatataact catgatgata agagacataa attaggcgga agatataaca    15000
tattcccact gaaaaataag ggaaagttaa gactgctatc gagaagacta gtattaagtt    15060
ggatttcatt atcattatcg actcgattac ttacaggtcg ctttcctgat gaaaaatttg    15120
aacatagagc acagactgga tatgtatcat tagctgatac tgatttagaa tcattaaagt    15180
tattgtcgaa aaacatcatt aagaattaca gagagtgtat aggatcaata tcatattggt    15240
ttctaaccaa agaagttaaa atacttatga aattgatcgg tggtgctaaa ttattaggaa    15300
ttcccagaca atataaagaa cccgaagacc agtattagaa aaactacaat caacatgatg    15360
aatttgatat cgattaaaac ataaatacaa tgaagatata tcctaacctt tatctttaag    15420
cctaggaata gacaaaaagt aagaaaaaca tgtaatatat ataccaaa cagagttctt      15480 ctcttgtttg gt                                                        15492
```

```
<210> SEQ ID NO 184
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Part of Parent Appln No 09/083,793 as SEQ ID
      NO: 03

<400> SEQUENCE: 184
ccaagtacta tgagatgctt catt                                           24
```

```
<210> SEQ ID NO 185
<211> LENGTH: 63
<212> TYPE: DNA
<213> ORGANISM: Artificial Sequence
<220> FEATURE:
<223> OTHER INFORMATION: Nucleotide insert to conform inserted
      sequence to rule of six.
<220> FEATURE:
<221> NAME/KEY: misc_feature
<222> LOCATION: (1)..(63)
<223> OTHER INFORMATION: Part of Parent Appln No 09/458,813 as SEQ ID
      NO: 05

<400> SEQUENCE: 185
aggaaaaggg aaatataaaa acttaggagt aaagttacgc gtgttaactt cgaagagctc    60
cct                                                                  63
```

```
<210> SEQ ID NO 186
<211> LENGTH: 28
<212> TYPE: DNA
<213> ORGANISM: Artificial Sequence
<220> FEATURE:
<223> OTHER INFORMATION: Nucleotide insert to conform inserted
      sequence to rule of six.
<220> FEATURE:
<221> NAME/KEY: misc_feature
<222> LOCATION: (1)..(28)
<223> OTHER INFORMATION: Part of Parent Appln No 09/458,813 as SEQ ID
      NO: 10

<400> SEQUENCE: 186
acaacgagac cggataaatg ccttctac                                       28
```

```
<210> SEQ ID NO 187
<211> LENGTH: 77
<212> TYPE: DNA
<213> ORGANISM: Artificial Sequence
<220> FEATURE:
<223> OTHER INFORMATION: Chemically synthesized forward primer for PCR
      of measles HA gene insert for HN-L junction.
<220> FEATURE:
<221> NAME/KEY: misc_feature
<222> L